US012446877B2

(12) United States Patent
Shelton, IV et al.

(10) Patent No.: US 12,446,877 B2
(45) Date of Patent: Oct. 21, 2025

(54) SURGICAL INSTRUMENT HAVING ARTICULATION LOCK ACTUATED BY CLOSURE TUBE DISPLACEMENT

(71) Applicant: Cilag GmbH International, Zug (CH)

(72) Inventors: Frederick E. Shelton, IV, Hillsboro, OH (US); Gregory J. Bakos, Mason, OH (US); Jason L. Harris, Lebanon, OH (US); Taylor W. Aronhalt, Loveland, OH (US)

(73) Assignee: Cilag GmbH International, Zug (CH)

( * ) Notice: Subject to any disclaimer, the term of this patent is extended or adjusted under 35 U.S.C. 154(b) by 61 days.

(21) Appl. No.: 18/125,777

(22) Filed: Mar. 24, 2023

(65) Prior Publication Data

US 2023/0301654 A1 Sep. 28, 2023

Related U.S. Application Data

(60) Continuation of application No. 16/868,218, filed on May 6, 2020, now Pat. No. 11,642,128, which is a (Continued)

(51) Int. Cl.

| | |
|---|---|
| ***A61B 17/072*** | (2006.01) |
| *A61B 17/00* | (2006.01) |
| *A61B 17/29* | (2006.01) |

(52) U.S. Cl.

CPC ...... *A61B 17/07207* (2013.01); *A61B 17/072* (2013.01); *A61B 2017/0046* (2013.01);

(Continued)

(58) Field of Classification Search

CPC ....... A61B 17/00; A61B 17/29; A61B 17/072; A61B 17/07207; A61B 17/10;

(Continued)

(56) References Cited

U.S. PATENT DOCUMENTS

| | | | |
|---|---|---|---|
| 66,052 | A | 6/1867 | Smith |
| 662,587 | A | 11/1900 | Blake |

(Continued)

FOREIGN PATENT DOCUMENTS

| | | | |
|---|---|---|---|
| AU | 2012200594 | A1 | 2/2012 |
| AU | 2012203035 | A1 | 6/2012 |

(Continued)

OTHER PUBLICATIONS

ASTM procedure D2240-00, "Standard Test Method for Rubber Property-Durometer Hardness," (Published Aug. 2000).

(Continued)

*Primary Examiner* — Vi X Nguyen

(57) ABSTRACT

A surgical instrument comprising an end effector, a closure tube, an articulation joint, an articulation driver, and an articulation lock is disclosed. The articulation driver is to rotate the end effector about the articulation joint and comprises first teeth. The articulation lock comprises a cam surface and second teeth, and the articulation lock is rotatable relative to the articulation driver between a first position, where the second teeth are demeshed from the first teeth and the articulation driver is permitted to rotate the end effector about the articulation joint, and a second position, where the second teeth are meshed with the first teeth and the articulation driver is prevented from rotating the end effector about the articulation joint. The cam is to engage the cam surface of the articulation lock and rotate the articulation lock toward the second position based on the closure tube moving toward a distal position.

13 Claims, 123 Drawing Sheets

Related U.S. Application Data division of application No. 15/635,663, filed on Jun. 28, 2017, now Pat. No. 10,765,427.

(52) U.S. Cl.
CPC ............... *A61B 2017/07271* (2013.01); *A61B 2017/07278* (2013.01); *A61B 2017/2927* (2013.01); *A61B 2017/2933* (2013.01); *A61B 2017/2946* (2013.01)

(58) Field of Classification Search
CPC .. A61B 2017/0046; A61B 2017/07271; A61B 2017/07278; A61B 2017/2946; A61B 2017/2933
See application file for complete search history.

(56) References Cited

U.S. PATENT DOCUMENTS

| | | | |
|---|---|---|---|
| 670,748 | A | 3/1901 | Weddeler |
| 719,487 | A | 2/1903 | Minor |
| 804,229 | A | 11/1905 | Hutchinson |
| 903,739 | A | 11/1908 | Lesemann |
| 951,393 | A | 3/1910 | Hahn |
| 1,075,556 | A | 10/1913 | Fenoughty |
| 1,082,105 | A | 12/1913 | Anderson |
| 1,188,721 | A | 6/1916 | Bittner |
| 1,306,107 | A | 6/1919 | Elliott |
| 1,314,601 | A | 9/1919 | McCaskey |
| 1,466,128 | A | 8/1923 | Hallenbeck |
| 1,677,337 | A | 7/1928 | Grove |
| 1,794,907 | A | 3/1931 | Kelly |
| 1,849,427 | A | 3/1932 | Hook |
| 1,912,783 | A | 6/1933 | Meyer |
| 1,944,116 | A | 1/1934 | Stratman |
| 1,954,048 | A | 4/1934 | Jeffrey et al. |
| 2,028,635 | A | 1/1936 | Wappler |
| 2,037,727 | A | 4/1936 | La Chapelle |
| 2,120,951 | A | 6/1938 | Hodgman |
| 2,132,295 | A | 10/1938 | Hawkins |
| 2,161,632 | A | 6/1939 | Nattenheimer |
| D120,434 | S | 5/1940 | Gold |
| 2,211,117 | A | 8/1940 | Hess |
| 2,214,870 | A | 9/1940 | West |
| 2,224,108 | A | 12/1940 | Ridgway |
| 2,224,882 | A | 12/1940 | Peck |
| 2,256,295 | A | 9/1941 | Schmid |
| 2,318,379 | A | 5/1943 | Davis et al. |
| 2,329,440 | A | 9/1943 | La Place |
| 2,377,581 | A | 6/1945 | Shaffrey |
| 2,406,389 | A | 8/1946 | Lee |
| 2,420,552 | A | 5/1947 | Morrill |
| 2,441,096 | A | 5/1948 | Happe |
| 2,448,741 | A | 9/1948 | Scott et al. |
| 2,450,527 | A | 10/1948 | Smith |
| 2,491,872 | A | 12/1949 | Neuman |
| 2,507,872 | A | 5/1950 | Unsinger |
| 2,526,902 | A | 10/1950 | Rublee |
| 2,527,256 | A | 10/1950 | Jackson |
| 2,578,686 | A | 12/1951 | Fish |
| 2,638,901 | A | 5/1953 | Sugarbaker |
| 2,674,149 | A | 4/1954 | Benson |
| 2,701,489 | A | 2/1955 | Osborn |
| 2,711,461 | A | 6/1955 | Happe |
| 2,724,289 | A | 11/1955 | Wight |
| 2,742,955 | A | 4/1956 | Dominguez |
| 2,804,848 | A | 9/1957 | O'Farrell et al. |
| 2,808,482 | A | 10/1957 | Zanichkowsky et al. |
| 2,825,178 | A | 3/1958 | Hawkins |
| 2,853,074 | A | 9/1958 | Olson |
| 2,856,192 | A | 10/1958 | Schuster |
| 2,887,004 | A | 5/1959 | Stewart |
| 2,957,353 | A | 10/1960 | Lewis |
| 2,959,974 | A | 11/1960 | Emrick |
| 3,026,744 | A | 3/1962 | Rouse |
| 3,032,769 | A | 5/1962 | Palmer |
| 3,035,256 | A | 5/1962 | Egbert |
| 3,060,972 | A | 10/1962 | Sheldon |
| 3,075,062 | A | 1/1963 | Iaccarino |
| 3,078,465 | A | 2/1963 | Bobrov |
| 3,079,606 | A | 3/1963 | Bobrov et al. |
| 3,080,564 | A | 3/1963 | Strekopitov et al. |
| 3,166,072 | A | 1/1965 | Sullivan, Jr. |
| 3,180,236 | A | 4/1965 | Beckett |
| 3,196,869 | A | 7/1965 | Scholl |
| 3,204,731 | A | 9/1965 | Bent et al. |
| 3,252,643 | A | 5/1966 | Strekopytov et al. |
| 3,266,494 | A | 8/1966 | Brownrigg et al. |
| 3,269,630 | A | 8/1966 | Fleischer |
| 3,269,631 | A | 8/1966 | Takaro |
| 3,275,211 | A | 9/1966 | Hirsch et al. |
| 3,315,863 | A | 4/1967 | O'Dea |
| 3,317,103 | A | 5/1967 | Cullen et al. |
| 3,317,105 | A | 5/1967 | Astafjev et al. |
| 3,357,296 | A | 12/1967 | Lefever |
| 3,359,978 | A | 12/1967 | Smith, Jr. |
| 3,377,893 | A | 4/1968 | Shorb |
| 3,480,193 | A | 11/1969 | Ralston |
| 3,490,675 | A | 1/1970 | Green et al. |
| 3,494,533 | A | 2/1970 | Green et al. |
| 3,499,591 | A | 3/1970 | Green |
| 3,503,396 | A | 3/1970 | Pierie et al. |
| 3,509,629 | A | 5/1970 | Kidokoro |
| 3,551,987 | A | 1/1971 | Wilkinson |
| 3,568,675 | A | 3/1971 | Harvey |
| 3,572,159 | A | 3/1971 | Tschanz |
| 3,583,393 | A | 6/1971 | Takahashi |
| 3,589,589 | A | 6/1971 | Akopov |
| 3,598,943 | A | 8/1971 | Barrett |
| 3,604,561 | A | 9/1971 | Mallina et al. |
| 3,608,549 | A | 9/1971 | Merrill |
| 3,616,278 | A | 10/1971 | Jansen |
| 3,618,842 | A | 11/1971 | Bryan |
| 3,635,394 | A | 1/1972 | Natelson |
| 3,638,652 | A | 2/1972 | Kelley |
| 3,640,317 | A | 2/1972 | Panfili |
| 3,643,851 | A | 2/1972 | Green et al. |
| 3,650,453 | A | 3/1972 | Smith, Jr. |
| 3,661,339 | A | 5/1972 | Shimizu |
| 3,661,666 | A | 5/1972 | Foster et al. |
| 3,662,939 | A | 5/1972 | Bryan |
| 3,685,250 | A | 8/1972 | Henry et al. |
| 3,688,966 | A | 9/1972 | Perkins et al. |
| 3,692,224 | A | 9/1972 | Astafiev et al. |
| 3,695,646 | A | 10/1972 | Mommsen |
| 3,709,221 | A | 1/1973 | Riely |
| 3,717,294 | A | 2/1973 | Green |
| 3,724,237 | A | 4/1973 | Wood |
| 3,726,755 | A | 4/1973 | Shannon |
| 3,727,904 | A | 4/1973 | Gabbey |
| 3,734,207 | A | 5/1973 | Fishbein |
| 3,740,994 | A | 6/1973 | De Carlo, Jr. |
| 3,744,495 | A | 7/1973 | Johnson |
| 3,746,002 | A | 7/1973 | Haller |
| 3,747,603 | A | 7/1973 | Adler |
| 3,747,692 | A | 7/1973 | Davidson |
| 3,751,902 | A | 8/1973 | Kingsbury et al. |
| 3,752,161 | A | 8/1973 | Bent |
| 3,797,494 | A | 3/1974 | Zaffaroni |
| 3,799,151 | A | 3/1974 | Fukaumi et al. |
| 3,808,452 | A | 4/1974 | Hutchinson |
| 3,815,476 | A | 6/1974 | Green et al. |
| 3,819,100 | A | 6/1974 | Noiles et al. |
| 3,821,919 | A | 7/1974 | Knohl |
| 3,822,818 | A | 7/1974 | Strekopytov et al. |
| 3,825,007 | A | 7/1974 | Rand |
| 3,826,978 | A | 7/1974 | Kelly |
| 3,836,171 | A | 9/1974 | Hayashi et al. |
| 3,837,555 | A | 9/1974 | Green |
| 3,841,474 | A | 10/1974 | Maier |
| 3,851,196 | A | 11/1974 | Hinds |
| 3,863,639 | A | 2/1975 | Kleaveland |
| 3,863,940 | A | 2/1975 | Cummings |
| 3,883,624 | A | 5/1975 | McKenzie et al. |

(56) References Cited

U.S. PATENT DOCUMENTS

| | | | |
|---|---|---|---|
| 3,885,491 | A | 5/1975 | Curtis |
| 3,887,393 | A | 6/1975 | La Rue, Jr. |
| 3,892,228 | A | 7/1975 | Mitsui |
| 3,894,174 | A | 7/1975 | Cartun |
| 3,899,829 | A | 8/1975 | Storm et al. |
| 3,902,247 | A | 9/1975 | Fleer et al. |
| 3,940,844 | A | 3/1976 | Colby et al. |
| 3,944,163 | A | 3/1976 | Hayashi et al. |
| 3,950,686 | A | 4/1976 | Randall |
| 3,952,747 | A | 4/1976 | Kimmell, Jr. |
| 3,955,581 | A | 5/1976 | Spasiano et al. |
| 3,959,879 | A | 6/1976 | Sellers |
| RE28,932 | E | 8/1976 | Noiles et al. |
| 3,972,734 | A | 8/1976 | King |
| 3,973,179 | A | 8/1976 | Weber et al. |
| 3,981,051 | A | 9/1976 | Brumlik |
| 3,993,072 | A | 11/1976 | Zaffaroni |
| 3,999,110 | A | 12/1976 | Ramstrom et al. |
| 4,025,216 | A | 5/1977 | Hives |
| 4,027,746 | A | 6/1977 | Kine |
| 4,034,143 | A | 7/1977 | Sweet |
| 4,038,987 | A | 8/1977 | Komiya |
| 4,047,654 | A | 9/1977 | Alvarado |
| 4,054,108 | A | 10/1977 | Gill |
| 4,060,089 | A | 11/1977 | Noiles |
| 4,066,133 | A | 1/1978 | Voss |
| 4,085,337 | A | 4/1978 | Moeller |
| 4,100,820 | A | 7/1978 | Evett |
| 4,106,446 | A | 8/1978 | Yamada et al. |
| 4,106,620 | A | 8/1978 | Brimmer et al. |
| 4,108,211 | A | 8/1978 | Tanaka |
| 4,111,206 | A | 9/1978 | Vishnevsky et al. |
| 4,127,227 | A | 11/1978 | Green |
| 4,129,059 | A | 12/1978 | Van Eck |
| 4,132,146 | A | 1/1979 | Uhlig |
| 4,135,517 | A | 1/1979 | Reale |
| 4,149,461 | A | 4/1979 | Simeth |
| 4,154,122 | A | 5/1979 | Severin |
| 4,160,857 | A | 7/1979 | Nardella et al. |
| 4,169,476 | A | 10/1979 | Hiltebrandt |
| 4,169,990 | A | 10/1979 | Lerdman |
| 4,180,285 | A | 12/1979 | Reneau |
| 4,185,701 | A | 1/1980 | Boys |
| 4,190,042 | A | 2/1980 | Sinnreich |
| 4,191,377 | A | 3/1980 | Burnside |
| 4,198,734 | A | 4/1980 | Brumlik |
| 4,198,982 | A | 4/1980 | Fortner et al. |
| 4,203,444 | A | 5/1980 | Bonnell et al. |
| 4,207,898 | A | 6/1980 | Becht |
| 4,213,562 | A | 7/1980 | Garrett et al. |
| 4,226,242 | A | 10/1980 | Jarvik |
| 4,239,431 | A | 12/1980 | Davini |
| 4,241,861 | A | 12/1980 | Fleischer |
| 4,244,372 | A | 1/1981 | Kapitanov et al. |
| 4,250,436 | A | 2/1981 | Weissman |
| 4,250,817 | A | 2/1981 | Michel |
| 4,261,244 | A | 4/1981 | Becht et al. |
| 4,272,002 | A | 6/1981 | Moshofsky |
| 4,272,662 | A | 6/1981 | Simpson |
| 4,274,304 | A | 6/1981 | Curtiss |
| 4,274,398 | A | 6/1981 | Scott, Jr. |
| 4,275,813 | A | 6/1981 | Noiles |
| 4,278,091 | A | 7/1981 | Borzone |
| 4,282,573 | A | 8/1981 | Imai et al. |
| 4,289,131 | A | 9/1981 | Mueller |
| 4,289,133 | A | 9/1981 | Rothfuss |
| 4,290,542 | A | 9/1981 | Fedotov et al. |
| D261,356 | S | 10/1981 | Robinson |
| 4,293,604 | A | 10/1981 | Campbell |
| 4,296,654 | A | 10/1981 | Mercer |
| 4,296,881 | A | 10/1981 | Lee |
| 4,304,236 | A | 12/1981 | Conta et al. |
| 4,305,539 | A | 12/1981 | Korolkov et al. |
| 4,312,363 | A | 1/1982 | Rothfuss et al. |
| 4,312,685 | A | 1/1982 | Riedl |
| 4,317,451 | A | 3/1982 | Cerwin et al. |
| 4,319,576 | A | 3/1982 | Rothfuss |
| 4,321,002 | A | 3/1982 | Froehlich |
| 4,321,746 | A | 3/1982 | Grinage |
| 4,328,839 | A | 5/1982 | Lyons et al. |
| 4,331,277 | A | 5/1982 | Green |
| 4,340,331 | A | 7/1982 | Savino |
| 4,347,450 | A | 8/1982 | Colligan |
| 4,348,603 | A | 9/1982 | Huber |
| 4,349,028 | A | 9/1982 | Green |
| 4,350,151 | A | 9/1982 | Scott |
| 4,353,371 | A | 10/1982 | Cosman |
| 4,357,940 | A | 11/1982 | Muller |
| 4,361,057 | A | 11/1982 | Kochera |
| 4,366,544 | A | 12/1982 | Shima et al. |
| 4,369,013 | A | 1/1983 | Abildgaard et al. |
| 4,373,147 | A | 2/1983 | Carlson, Jr. |
| 4,376,380 | A | 3/1983 | Burgess |
| 4,379,457 | A | 4/1983 | Gravener et al. |
| 4,380,312 | A | 4/1983 | Landrus |
| 4,382,326 | A | 5/1983 | Rabuse |
| 4,383,634 | A | 5/1983 | Green |
| 4,389,963 | A | 6/1983 | Pearson |
| 4,393,728 | A | 7/1983 | Larson et al. |
| 4,394,613 | A | 7/1983 | Cole |
| 4,396,139 | A | 8/1983 | Hall et al. |
| 4,397,311 | A | 8/1983 | Kanshin et al. |
| 4,402,445 | A | 9/1983 | Green |
| 4,406,621 | A | 9/1983 | Bailey |
| 4,408,692 | A | 10/1983 | Sigel et al. |
| 4,409,057 | A | 10/1983 | Molenda et al. |
| 4,415,112 | A | 11/1983 | Green |
| 4,416,276 | A | 11/1983 | Newton et al. |
| 4,417,890 | A | 11/1983 | Dennehey et al. |
| 4,421,264 | A | 12/1983 | Arter et al. |
| 4,423,456 | A | 12/1983 | Zaidenweber |
| 4,425,915 | A | 1/1984 | Ivanov |
| 4,428,376 | A | 1/1984 | Mericle |
| 4,429,695 | A | 2/1984 | Green |
| 4,430,997 | A | 2/1984 | DiGiovanni et al. |
| 4,434,796 | A | 3/1984 | Karapetian et al. |
| 4,438,659 | A | 3/1984 | Desplats |
| 4,442,964 | A | 4/1984 | Becht |
| 4,448,194 | A | 5/1984 | DiGiovanni et al. |
| 4,451,743 | A | 5/1984 | Suzuki et al. |
| 4,452,376 | A | 6/1984 | Klieman et al. |
| 4,454,887 | A | 6/1984 | Kruger |
| 4,459,519 | A | 7/1984 | Erdman |
| 4,461,305 | A | 7/1984 | Cibley |
| 4,467,805 | A | 8/1984 | Fukuda |
| 4,468,597 | A | 8/1984 | Baumard et al. |
| 4,469,481 | A | 9/1984 | Kobayashi |
| 4,470,414 | A | 9/1984 | Imagawa et al. |
| 4,471,780 | A | 9/1984 | Menges et al. |
| 4,471,781 | A | 9/1984 | Di Giovanni et al. |
| 4,473,077 | A | 9/1984 | Noiles et al. |
| 4,475,679 | A | 10/1984 | Fleury, Jr. |
| 4,476,864 | A | 10/1984 | Tezel |
| 4,478,220 | A | 10/1984 | Di Giovanni et al. |
| 4,480,641 | A | 11/1984 | Failla et al. |
| 4,481,458 | A | 11/1984 | Lane |
| 4,483,562 | A | 11/1984 | Schoolman |
| 4,485,816 | A | 12/1984 | Krumme |
| 4,485,817 | A | 12/1984 | Swiggett |
| 4,486,928 | A | 12/1984 | Tucker et al. |
| 4,488,523 | A | 12/1984 | Shichman |
| 4,489,875 | A | 12/1984 | Crawford et al. |
| 4,493,983 | A | 1/1985 | Taggert |
| 4,494,057 | A | 1/1985 | Hotta |
| 4,499,895 | A | 2/1985 | Takayama |
| 4,500,024 | A | 2/1985 | DiGiovanni et al. |
| D278,081 | S | 3/1985 | Green |
| 4,503,842 | A | 3/1985 | Takayama |
| 4,505,272 | A | 3/1985 | Utyamyshev et al. |
| 4,505,273 | A | 3/1985 | Braun et al. |
| 4,505,414 | A | 3/1985 | Filipi |
| 4,506,671 | A | 3/1985 | Green |
| 4,512,038 | A | 4/1985 | Alexander et al. |
| 4,514,477 | A | 4/1985 | Kobayashi |

(56) References Cited

U.S. PATENT DOCUMENTS 4,520,817 A 6/1985 Green
4,522,327 A 6/1985 Korthoff et al.
4,523,707 A 6/1985 Blake, III et al.
4,526,174 A 7/1985 Froehlich
4,527,724 A 7/1985 Chow et al.
4,530,357 A 7/1985 Pawloski et al.
4,530,453 A 7/1985 Green
4,531,522 A 7/1985 Bedi et al.
4,532,927 A 8/1985 Miksza, Jr.
4,540,202 A 9/1985 Amphoux et al.
4,548,202 A 10/1985 Duncan
4,556,058 A 12/1985 Green
4,560,915 A 12/1985 Soultanian
4,565,109 A 1/1986 Tsay
4,565,189 A 1/1986 Mabuchi
4,566,620 A 1/1986 Green et al.
4,569,346 A 2/1986 Poirier
4,569,469 A 2/1986 Mongeon et al.
4,571,213 A 2/1986 Ishimoto
4,573,468 A 3/1986 Conta et al.
4,573,469 A 3/1986 Golden et al.
4,573,622 A 3/1986 Green et al.
4,576,165 A 3/1986 Green et al.
4,576,167 A 3/1986 Noiles
4,580,712 A 4/1986 Green
4,585,153 A 4/1986 Failla et al.
4,586,501 A 5/1986 Claracq
4,586,502 A 5/1986 Bedi et al.
4,589,416 A 5/1986 Green
4,589,582 A 5/1986 Bilotti
4,589,870 A 5/1986 Citrin et al.
4,591,085 A 5/1986 Di Giovanni
RE32,214 E 7/1986 Schramm
4,597,753 A 7/1986 Turley
4,600,037 A 7/1986 Hatten
4,604,786 A 8/1986 Howie, Jr.
4,605,001 A 8/1986 Rothfuss et al.
4,605,004 A 8/1986 Di Giovanni et al.
4,606,343 A 8/1986 Conta et al.
4,607,636 A 8/1986 Kula et al.
4,607,638 A 8/1986 Crainich
4,608,980 A 9/1986 Aihara
4,608,981 A 9/1986 Rothfuss et al.
4,610,250 A 9/1986 Green
4,610,383 A 9/1986 Rothfuss et al.
4,612,933 A 9/1986 Brinkerhoff et al.
D286,180 S 10/1986 Korthoff
D286,442 S 10/1986 Korthoff et al.
4,617,893 A 10/1986 Donner et al.
4,617,914 A 10/1986 Ueda
4,617,935 A 10/1986 Cartmell et al.
4,619,262 A 10/1986 Taylor
4,619,391 A 10/1986 Sharkany et al.
4,624,401 A 11/1986 Gassner et al.
D287,278 S 12/1986 Spreckelmeier
4,628,459 A 12/1986 Shinohara et al.
4,628,636 A 12/1986 Folger
4,629,107 A 12/1986 Fedotov et al.
4,632,290 A 12/1986 Green et al.
4,633,861 A 1/1987 Chow et al.
4,633,874 A 1/1987 Chow et al.
4,634,419 A 1/1987 Kreizman et al.
4,635,638 A 1/1987 Weintraub et al.
4,641,076 A 2/1987 Linden
4,642,618 A 2/1987 Johnson et al.
4,642,738 A 2/1987 Meller
4,643,173 A 2/1987 Bell et al.
4,643,731 A 2/1987 Eckenhoff
4,646,722 A 3/1987 Silverstein et al.
4,646,745 A 3/1987 Noiles
4,651,734 A 3/1987 Doss et al.
4,652,820 A 3/1987 Maresca
4,654,028 A 3/1987 Suma
4,655,222 A 4/1987 Florez et al.
4,662,555 A 5/1987 Thornton
4,663,874 A 5/1987 Sano et al.
4,664,305 A 5/1987 Blake, III et al.
4,665,916 A 5/1987 Green
4,667,674 A 5/1987 Korthoff et al.
4,669,647 A 6/1987 Storace
4,671,278 A 6/1987 Chin
4,671,280 A 6/1987 Dorband et al.
4,671,445 A 6/1987 Barker et al.
4,672,964 A 6/1987 Dee et al.
4,675,944 A 6/1987 Wells
4,676,245 A 6/1987 Fukuda
4,679,460 A 7/1987 Yoshigai
4,679,719 A 7/1987 Kramer
4,684,051 A 8/1987 Akopov et al.
4,688,555 A 8/1987 Wardle
4,691,703 A 9/1987 Auth et al.
4,693,248 A 9/1987 Failla
4,698,579 A 10/1987 Richter et al.
4,700,703 A 10/1987 Resnick et al.
4,705,038 A 11/1987 Sjostrom et al.
4,708,141 A 11/1987 Inoue et al.
4,709,120 A 11/1987 Pearson
4,715,520 A 12/1987 Roehr, Jr. et al.
4,719,917 A 1/1988 Barrows et al.
4,721,099 A 1/1988 Chikama
4,722,340 A 2/1988 Takayama et al.
4,724,840 A 2/1988 McVay et al.
4,726,247 A 2/1988 Hormann
4,727,308 A 2/1988 Huljak et al.
4,728,020 A 3/1988 Green et al.
4,728,876 A 3/1988 Mongeon et al.
4,729,260 A 3/1988 Dudden
4,730,726 A 3/1988 Holzwarth
4,741,336 A 5/1988 Failla et al.
4,743,214 A 5/1988 Tai-Cheng
4,744,363 A 5/1988 Hasson
4,747,820 A 5/1988 Hornlein et al.
4,750,902 A 6/1988 Wuchinich et al.
4,752,024 A 6/1988 Green et al.
4,754,909 A 7/1988 Barker et al.
4,755,070 A 7/1988 Cerutti
4,761,326 A 8/1988 Barnes et al.
4,763,669 A 8/1988 Jaeger
4,767,044 A 8/1988 Green
D297,764 S 9/1988 Hunt et al.
4,773,420 A 9/1988 Green
4,777,780 A 10/1988 Holzwarth
4,781,186 A 11/1988 Simpson et al.
4,784,137 A 11/1988 Kulik et al.
4,787,387 A 11/1988 Burbank, III et al.
4,788,485 A 11/1988 Kawagishi et al.
D298,967 S 12/1988 Hunt
4,788,978 A 12/1988 Strekopytov et al.
4,790,225 A 12/1988 Moody et al.
4,790,314 A 12/1988 Weaver
4,805,617 A 2/1989 Bedi et al.
4,805,823 A 2/1989 Rothfuss
4,807,628 A 2/1989 Peters et al.
4,809,695 A 3/1989 Gwathmey et al.
4,815,460 A 3/1989 Porat et al.
4,817,643 A 4/1989 Olson
4,817,847 A 4/1989 Redtenbacher et al.
4,819,495 A 4/1989 Hormann
4,819,853 A 4/1989 Green
4,821,939 A 4/1989 Green
4,827,552 A 5/1989 Bojar et al.
4,827,911 A 5/1989 Broadwin et al.
4,828,542 A 5/1989 Hermann
4,828,944 A 5/1989 Yabe et al.
4,830,855 A 5/1989 Stewart
4,832,158 A 5/1989 Farrar et al.
4,833,937 A 5/1989 Nagano
4,834,096 A 5/1989 Oh et al.
4,834,720 A 5/1989 Blinkhorn
4,838,859 A 6/1989 Strassmann
4,844,068 A 7/1989 Arata et al.
4,848,637 A 7/1989 Pruitt
4,856,078 A 8/1989 Konopka
4,860,644 A 8/1989 Kohl et al.

(56) References Cited

U.S. PATENT DOCUMENTS 4,862,891 A 9/1989 Smith
4,863,423 A 9/1989 Wallace
4,865,030 A 9/1989 Polyak
4,868,530 A 9/1989 Ahs
4,868,958 A 9/1989 Suzuki et al.
4,869,414 A 9/1989 Green et al.
4,869,415 A 9/1989 Fox
4,870,966 A 10/1989 Dellon et al.
4,873,977 A 10/1989 Avant et al.
4,875,486 A 10/1989 Rapoport et al.
4,880,015 A 11/1989 Nierman
4,890,613 A 1/1990 Golden et al.
4,892,244 A 1/1990 Fox et al.
4,893,622 A 1/1990 Green et al.
4,894,051 A 1/1990 Shiber
4,896,584 A 1/1990 Stoll et al.
4,896,678 A 1/1990 Ogawa
4,900,303 A 2/1990 Lemelson
4,903,697 A 2/1990 Resnick et al.
4,909,789 A 3/1990 Taguchi et al.
4,915,100 A 4/1990 Green
4,919,039 A 4/1990 Nutter
4,919,679 A 4/1990 Averill et al.
4,921,479 A 5/1990 Grayzel
4,925,082 A 5/1990 Kim
4,928,699 A 5/1990 Sasai
4,930,503 A 6/1990 Pruitt
4,930,674 A 6/1990 Barak
4,931,047 A 6/1990 Broadwin et al.
4,931,737 A 6/1990 Hishiki
4,932,960 A 6/1990 Green et al.
4,933,800 A 6/1990 Yang
4,933,843 A 6/1990 Scheller et al.
D309,350 S 7/1990 Sutherland et al.
4,938,408 A 7/1990 Bedi et al.
4,941,623 A 7/1990 Pruitt
4,943,182 A 7/1990 Hoblingre
4,944,443 A 7/1990 Oddsen et al.
4,946,067 A 8/1990 Kelsall
4,948,327 A 8/1990 Crupi, Jr.
4,949,707 A 8/1990 LeVahn et al.
4,949,927 A 8/1990 Madocks et al.
4,950,268 A 8/1990 Rink
4,951,860 A 8/1990 Peters et al.
4,951,861 A 8/1990 Schulze et al.
4,954,960 A 9/1990 Lo et al.
4,955,959 A 9/1990 Tompkins et al.
4,957,212 A 9/1990 Duck et al.
4,962,681 A 10/1990 Yang
4,962,877 A 10/1990 Hervas
4,964,559 A 10/1990 Deniega et al.
4,964,863 A 10/1990 Kanshin et al.
4,965,709 A 10/1990 Ngo
4,970,656 A 11/1990 Lo et al.
4,973,274 A 11/1990 Hirukawa
4,973,302 A 11/1990 Armour et al.
4,976,173 A 12/1990 Yang
4,978,049 A 12/1990 Green
4,978,333 A 12/1990 Broadwin et al.
4,979,952 A 12/1990 Kubota et al.
4,984,564 A 1/1991 Yuen
4,986,808 A 1/1991 Broadwin et al.
4,987,049 A 1/1991 Komamura et al.
4,988,334 A 1/1991 Hornlein et al.
4,995,877 A 2/1991 Ams et al.
4,995,959 A 2/1991 Metzner
4,996,975 A 3/1991 Nakamura
5,001,649 A 3/1991 Lo et al.
5,002,543 A 3/1991 Bradshaw et al.
5,002,553 A 3/1991 Shiber
5,005,754 A 4/1991 Van Overloop
5,009,222 A 4/1991 Her
5,009,661 A 4/1991 Michelson
5,012,411 A 4/1991 Policastro et al.
D316,875 S 5/1991 Momot et al.
5,014,898 A 5/1991 Heidrich
5,014,899 A 5/1991 Presty et al.
5,015,227 A 5/1991 Broadwin et al.
5,018,515 A 5/1991 Gilman
5,018,657 A 5/1991 Pedlick et al.
5,019,077 A 5/1991 De Bastiani et al.
5,024,652 A 6/1991 Dumenek et al.
5,024,671 A 6/1991 Tu et al.
5,025,559 A 6/1991 McCullough
5,027,834 A 7/1991 Pruitt
5,030,226 A 7/1991 Green et al.
5,031,814 A 7/1991 Tompkins et al.
5,033,552 A 7/1991 Hu
5,035,040 A 7/1991 Kerrigan et al.
5,037,018 A 8/1991 Matsuda et al.
5,038,109 A 8/1991 Goble et al.
5,038,247 A 8/1991 Kelley et al.
5,040,715 A 8/1991 Green et al.
5,042,707 A 8/1991 Taheri
5,056,953 A 10/1991 Marot et al.
5,060,658 A 10/1991 Dejter, Jr. et al.
5,061,269 A 10/1991 Muller
5,062,491 A 11/1991 Takeshima et al.
5,062,563 A 11/1991 Green et al.
5,065,929 A 11/1991 Schulze et al.
5,071,052 A 12/1991 Rodak et al.
5,071,430 A 12/1991 de Salis et al.
5,074,454 A 12/1991 Peters
5,077,506 A 12/1991 Krause
5,079,006 A 1/1992 Urquhart
5,080,556 A 1/1992 Carreno
5,083,695 A 1/1992 Foslien et al.
5,084,057 A 1/1992 Green et al.
5,088,979 A 2/1992 Filipi et al.
5,088,997 A 2/1992 Delahuerga et al.
5,089,606 A 2/1992 Cole et al.
5,094,247 A 3/1992 Hernandez et al.
5,098,004 A 3/1992 Kerrigan
5,098,360 A 3/1992 Hirota
5,100,042 A 3/1992 Gravener et al.
5,100,420 A 3/1992 Green et al.
5,100,422 A 3/1992 Berguer et al.
5,104,025 A 4/1992 Main et al.
5,104,397 A 4/1992 Vasconcelos et al.
5,104,400 A 4/1992 Berguer et al.
5,106,008 A 4/1992 Tompkins et al.
5,108,368 A 4/1992 Hammerslag et al.
5,109,722 A 5/1992 Hufnagle et al.
5,111,987 A 5/1992 Moeinzadeh et al.
5,116,349 A 5/1992 Aranyi
D327,323 S 6/1992 Hunt
5,119,009 A 6/1992 McCaleb et al.
5,122,156 A 6/1992 Granger et al.
5,124,990 A 6/1992 Williamson
5,129,570 A 7/1992 Schulze et al.
5,135,483 A 8/1992 Wagner et al.
5,137,198 A 8/1992 Nobis et al.
5,139,513 A 8/1992 Segato
5,141,144 A 8/1992 Foslien et al.
5,142,932 A 9/1992 Moya et al.
5,151,102 A 9/1992 Kamiyama et al.
5,155,941 A 10/1992 Takahashi et al.
5,156,151 A 10/1992 Imran
5,156,315 A 10/1992 Green et al.
5,156,609 A 10/1992 Nakao et al.
5,156,614 A 10/1992 Green et al.
5,158,222 A 10/1992 Green et al.
5,158,567 A 10/1992 Green
D330,699 S 11/1992 Gill
5,163,598 A 11/1992 Peters et al.
5,163,842 A 11/1992 Nonomura
5,164,652 A 11/1992 Johnson et al.
5,168,605 A 12/1992 Bartlett
5,170,925 A 12/1992 Madden et al.
5,171,247 A 12/1992 Hughett et al.
5,171,249 A 12/1992 Stefanchik et al.
5,171,253 A 12/1992 Klieman
5,173,053 A 12/1992 Swanson et al.
5,173,133 A 12/1992 Morin et al.

(56) References Cited

U.S. PATENT DOCUMENTS 5,176,677 A 1/1993 Wuchinich
5,176,688 A 1/1993 Narayan et al.
5,180,375 A 1/1993 Feibus
5,181,514 A 1/1993 Solomon et al.
5,187,422 A 2/1993 Izenbaard et al.
5,188,102 A 2/1993 Idemoto et al.
5,188,111 A 2/1993 Yates et al.
5,188,126 A 2/1993 Fabian et al.
5,190,517 A 3/1993 Zieve et al.
5,190,544 A 3/1993 Chapman et al.
5,190,560 A 3/1993 Woods et al.
5,190,657 A 3/1993 Heagle et al.
5,192,288 A 3/1993 Thompson et al.
5,193,731 A 3/1993 Aranyi
5,195,505 A 3/1993 Josefsen
5,195,968 A 3/1993 Lundquist et al.
5,197,648 A 3/1993 Gingold
5,197,649 A 3/1993 Bessler et al.
5,197,966 A 3/1993 Sommerkamp
5,197,970 A 3/1993 Green et al.
5,200,280 A 4/1993 Karasa
5,201,750 A 4/1993 Hocherl et al.
5,205,459 A 4/1993 Brinkerhoff et al.
5,207,672 A 5/1993 Roth et al.
5,207,697 A 5/1993 Carusillo et al.
5,209,747 A 5/1993 Knoepfler
5,209,756 A 5/1993 Seedhom et al.
5,211,649 A 5/1993 Kohler et al.
5,211,655 A 5/1993 Hasson
5,217,457 A 6/1993 Delahuerga et al.
5,217,478 A 6/1993 Rexroth
5,219,111 A 6/1993 Bilotti et al.
5,220,269 A 6/1993 Chen et al.
5,221,036 A 6/1993 Takase
5,221,281 A 6/1993 Klicek
5,222,945 A 6/1993 Basnight
5,222,963 A 6/1993 Brinkerhoff et al.
5,222,975 A 6/1993 Crainich
5,222,976 A 6/1993 Yoon
5,223,675 A 6/1993 Taft
D337,962 S 8/1993 Avitan
D338,729 S 8/1993 Sprecklemeier et al.
5,234,447 A 8/1993 Kaster et al.
5,236,269 A 8/1993 Handy
5,236,424 A 8/1993 Imran
5,236,440 A 8/1993 Hlavacek
5,236,629 A 8/1993 Mahabadi et al.
5,239,981 A 8/1993 Anapliotis
5,240,163 A 8/1993 Stein et al.
5,242,456 A 9/1993 Nash et al.
5,242,457 A 9/1993 Akopov et al.
5,244,462 A 9/1993 Delahuerga et al.
5,246,156 A 9/1993 Rothfuss et al.
5,246,443 A 9/1993 Mai
5,251,801 A 10/1993 Ruckdeschel et al.
5,253,793 A 10/1993 Green et al.
5,258,007 A 11/1993 Spetzler et al.
5,258,008 A 11/1993 Wilk
5,258,009 A 11/1993 Conners
5,258,010 A 11/1993 Green et al.
5,258,012 A 11/1993 Luscombe et al.
5,259,366 A 11/1993 Reydel et al.
5,259,835 A 11/1993 Clark et al.
5,260,637 A 11/1993 Pizzi
5,261,135 A 11/1993 Mitchell
5,261,877 A 11/1993 Fine et al.
5,261,922 A 11/1993 Hood
5,263,629 A 11/1993 Trumbull et al.
5,263,937 A 11/1993 Shipp
5,263,973 A 11/1993 Cook
5,264,218 A 11/1993 Rogozinski
5,268,622 A 12/1993 Philipp
5,269,794 A 12/1993 Rexroth
5,271,543 A 12/1993 Grant et al.
5,271,544 A 12/1993 Fox et al.
RE34,519 E 1/1994 Fox et al.
5,275,322 A 1/1994 Brinkerhoff et al.
5,275,323 A 1/1994 Schulze et al.
5,275,608 A 1/1994 Forman et al.
5,279,416 A 1/1994 Malec et al.
5,281,216 A 1/1994 Klicek
5,281,400 A 1/1994 Berry, Jr.
5,282,806 A 2/1994 Haber et al.
5,282,826 A 2/1994 Quadri
5,282,829 A 2/1994 Hermes
5,284,128 A 2/1994 Hart
5,285,381 A 2/1994 Iskarous et al.
5,285,945 A 2/1994 Brinkerhoff et al.
5,286,253 A 2/1994 Fucci
5,289,963 A 3/1994 McGarry et al.
5,290,271 A 3/1994 Jernberg
5,290,310 A 3/1994 Makower et al.
5,291,133 A 3/1994 Gokhale et al.
5,292,053 A 3/1994 Bilotti et al.
5,293,024 A 3/1994 Sugahara et al.
5,297,714 A 3/1994 Kramer
5,300,087 A 4/1994 Knoepfler
5,302,148 A 4/1994 Heinz
5,303,606 A 4/1994 Kokinda
5,304,204 A 4/1994 Bregen
D347,474 S 5/1994 Olson
5,307,976 A 5/1994 Olson et al.
5,308,353 A 5/1994 Beurrier
5,308,358 A 5/1994 Bond et al.
5,308,576 A 5/1994 Green et al.
5,309,387 A 5/1994 Mori et al.
5,309,927 A 5/1994 Welch
5,312,023 A 5/1994 Green et al.
5,312,024 A 5/1994 Grant et al.
5,312,329 A 5/1994 Beaty et al.
5,313,935 A 5/1994 Kortenbach et al.
5,313,967 A 5/1994 Lieber et al.
5,314,424 A 5/1994 Nicholas
5,314,445 A 5/1994 Heidmueller Degwitz et al.
5,314,466 A 5/1994 Stern et al.
5,318,221 A 6/1994 Green et al.
5,318,589 A 6/1994 Lichtman
5,320,627 A 6/1994 Sorensen et al.
D348,930 S 7/1994 Olson
5,326,013 A 7/1994 Green et al.
5,329,923 A 7/1994 Lundquist
5,330,486 A 7/1994 Wilk
5,330,487 A 7/1994 Thornton et al.
5,330,502 A 7/1994 Hassler et al.
5,331,971 A 7/1994 Bales et al.
5,332,142 A 7/1994 Robinson et al.
5,333,422 A 8/1994 Warren et al.
5,333,772 A 8/1994 Rothfuss et al.
5,333,773 A 8/1994 Main et al.
5,334,183 A 8/1994 Wuchinich
5,336,130 A 8/1994 Ray
5,336,229 A 8/1994 Noda
5,336,232 A 8/1994 Green et al.
5,338,317 A 8/1994 Hasson et al.
5,339,799 A 8/1994 Kami et al.
5,341,724 A 8/1994 Vatel
5,341,807 A 8/1994 Nardella
5,341,810 A 8/1994 Dardel
5,342,380 A 8/1994 Hood
5,342,381 A 8/1994 Tidemand
5,342,385 A 8/1994 Norelli et al.
5,342,395 A 8/1994 Jarrett et al.
5,342,396 A 8/1994 Cook
5,343,382 A 8/1994 Hale et al.
5,343,391 A 8/1994 Mushabac
5,344,059 A 9/1994 Green et al.
5,344,060 A 9/1994 Gravener et al.
5,344,454 A 9/1994 Clarke et al.
5,346,504 A 9/1994 Ortiz et al.
5,348,259 A 9/1994 Blanco et al.
5,350,104 A 9/1994 Main et al.
5,350,355 A 9/1994 Sklar
5,350,388 A 9/1994 Epstein
5,350,391 A 9/1994 Iacovelli

(56) References Cited

U.S. PATENT DOCUMENTS

| | | | |
|---|---|---|---|
| 5,350,400 | A | 9/1994 | Esposito et al. |
| 5,352,229 | A | 10/1994 | Goble et al. |
| 5,352,235 | A | 10/1994 | Koros et al. |
| 5,352,238 | A | 10/1994 | Green et al. |
| 5,353,798 | A | 10/1994 | Sieben |
| 5,354,215 | A | 10/1994 | Viracola |
| 5,354,250 | A | 10/1994 | Christensen |
| 5,354,303 | A | 10/1994 | Spaeth et al. |
| 5,355,897 | A | 10/1994 | Pietrafitta et al. |
| 5,356,006 | A | 10/1994 | Alpern et al. |
| 5,356,064 | A | 10/1994 | Green et al. |
| 5,358,506 | A | 10/1994 | Green et al. |
| 5,358,510 | A | 10/1994 | Luscombe et al. |
| 5,359,231 | A | 10/1994 | Flowers et al. |
| D352,780 | S | 11/1994 | Glaeser et al. |
| 5,359,993 | A | 11/1994 | Slater et al. |
| 5,360,305 | A | 11/1994 | Kerrigan |
| 5,360,428 | A | 11/1994 | Hutchinson, Jr. |
| 5,361,902 | A | 11/1994 | Abidin et al. |
| 5,364,001 | A | 11/1994 | Bryan |
| 5,364,002 | A | 11/1994 | Green et al. |
| 5,364,003 | A | 11/1994 | Williamson, IV |
| 5,366,133 | A | 11/1994 | Geiste |
| 5,366,134 | A | 11/1994 | Green et al. |
| 5,366,479 | A | 11/1994 | McGarry et al. |
| 5,368,015 | A | 11/1994 | Wilk |
| 5,368,592 | A | 11/1994 | Stern et al. |
| 5,368,599 | A | 11/1994 | Hirsch et al. |
| 5,369,565 | A | 11/1994 | Chen et al. |
| 5,370,645 | A | 12/1994 | Klicek et al. |
| 5,372,124 | A | 12/1994 | Takayama et al. |
| 5,372,596 | A | 12/1994 | Klicek et al. |
| 5,372,602 | A | 12/1994 | Burke |
| 5,374,277 | A | 12/1994 | Hassler |
| 5,375,588 | A | 12/1994 | Yoon |
| 5,376,095 | A | 12/1994 | Ortiz |
| 5,379,933 | A | 1/1995 | Green et al. |
| 5,381,649 | A | 1/1995 | Webb |
| 5,381,782 | A | 1/1995 | DeLaRama et al. |
| 5,381,943 | A | 1/1995 | Allen et al. |
| 5,382,247 | A | 1/1995 | Cimino et al. |
| 5,383,460 | A | 1/1995 | Jang et al. |
| 5,383,738 | A | 1/1995 | Herbermann |
| 5,383,874 | A | 1/1995 | Jackson et al. |
| 5,383,880 | A | 1/1995 | Hooven |
| 5,383,881 | A | 1/1995 | Green et al. |
| 5,383,882 | A | 1/1995 | Buess et al. |
| 5,383,888 | A | 1/1995 | Zvenyatsky et al. |
| 5,383,895 | A | 1/1995 | Holmes et al. |
| 5,388,568 | A | 2/1995 | van der Heide |
| 5,388,748 | A | 2/1995 | Davignon et al. |
| 5,389,072 | A | 2/1995 | Imran |
| 5,389,098 | A | 2/1995 | Tsuruta et al. |
| 5,389,102 | A | 2/1995 | Green et al. |
| 5,389,104 | A | 2/1995 | Hahnen et al. |
| 5,391,180 | A | 2/1995 | Tovey et al. |
| 5,392,979 | A | 2/1995 | Green et al. |
| 5,395,030 | A | 3/1995 | Kuramoto et al. |
| 5,395,033 | A | 3/1995 | Byrne et al. |
| 5,395,034 | A | 3/1995 | Allen et al. |
| 5,395,312 | A | 3/1995 | Desai |
| 5,395,384 | A | 3/1995 | Duthoit et al. |
| 5,397,046 | A | 3/1995 | Savage et al. |
| 5,397,324 | A | 3/1995 | Carroll et al. |
| 5,400,267 | A | 3/1995 | Denen et al. |
| 5,403,276 | A | 4/1995 | Schechter et al. |
| 5,403,312 | A | 4/1995 | Yates et al. |
| 5,404,106 | A | 4/1995 | Matsuda |
| 5,404,870 | A | 4/1995 | Brinkerhoff et al. |
| 5,404,960 | A | 4/1995 | Wada et al. |
| 5,405,072 | A | 4/1995 | Zlock et al. |
| 5,405,073 | A | 4/1995 | Porter |
| 5,405,344 | A | 4/1995 | Williamson et al. |
| 5,405,360 | A | 4/1995 | Tovey |
| 5,407,293 | A | 4/1995 | Crainich |
| 5,408,409 | A | 4/1995 | Glassman et al. |
| 5,409,498 | A | 4/1995 | Braddock et al. |
| 5,409,703 | A | 4/1995 | McAnalley et al. |
| D357,981 | S | 5/1995 | Green et al. |
| 5,411,481 | A | 5/1995 | Allen et al. |
| 5,411,508 | A | 5/1995 | Bessler et al. |
| 5,413,107 | A | 5/1995 | Oakley et al. |
| 5,413,267 | A | 5/1995 | Solyntjes et al. |
| 5,413,268 | A | 5/1995 | Green et al. |
| 5,413,272 | A | 5/1995 | Green et al. |
| 5,413,573 | A | 5/1995 | Koivukangas |
| 5,415,334 | A | 5/1995 | Williamson et al. |
| 5,415,335 | A | 5/1995 | Knodell, Jr. |
| 5,417,203 | A | 5/1995 | Tovey et al. |
| 5,417,361 | A | 5/1995 | Williamson, IV |
| 5,419,766 | A | 5/1995 | Chang et al. |
| 5,421,829 | A | 6/1995 | Olichney et al. |
| 5,422,567 | A | 6/1995 | Matsunaga |
| 5,423,471 | A | 6/1995 | Mastri et al. |
| 5,423,809 | A | 6/1995 | Klicek |
| 5,423,835 | A | 6/1995 | Green et al. |
| 5,425,355 | A | 6/1995 | Kulick |
| 5,425,745 | A | 6/1995 | Green et al. |
| 5,427,298 | A | 6/1995 | Tegtmeier |
| 5,431,322 | A | 7/1995 | Green et al. |
| 5,431,323 | A | 7/1995 | Smith et al. |
| 5,431,645 | A | 7/1995 | Smith et al. |
| 5,431,654 | A | 7/1995 | Nic |
| 5,431,666 | A | 7/1995 | Sauer et al. |
| 5,431,668 | A | 7/1995 | Burbank, III et al. |
| 5,433,721 | A | 7/1995 | Hooven et al. |
| 5,437,681 | A | 8/1995 | Meade et al. |
| 5,438,302 | A | 8/1995 | Goble |
| 5,438,997 | A | 8/1995 | Sieben et al. |
| 5,439,155 | A | 8/1995 | Viola |
| 5,439,156 | A | 8/1995 | Grant et al. |
| 5,439,479 | A | 8/1995 | Shichman et al. |
| 5,441,191 | A | 8/1995 | Linden |
| 5,441,193 | A | 8/1995 | Gravener |
| 5,441,483 | A | 8/1995 | Avitall |
| 5,441,494 | A | 8/1995 | Ortiz |
| 5,441,499 | A | 8/1995 | Fritzsch |
| 5,443,197 | A | 8/1995 | Malis et al. |
| 5,443,198 | A | 8/1995 | Viola et al. |
| 5,443,463 | A | 8/1995 | Stern et al. |
| 5,444,113 | A | 8/1995 | Sinclair et al. |
| 5,445,155 | A | 8/1995 | Sieben |
| 5,445,304 | A | 8/1995 | Plyley et al. |
| 5,445,604 | A | 8/1995 | Lang |
| 5,445,644 | A | 8/1995 | Pietrafitta et al. |
| 5,446,646 | A | 8/1995 | Miyazaki |
| 5,447,265 | A | 9/1995 | Vidal et al. |
| 5,447,417 | A | 9/1995 | Kuhl et al. |
| 5,447,513 | A | 9/1995 | Davison et al. |
| 5,449,355 | A | 9/1995 | Rhum et al. |
| 5,449,365 | A | 9/1995 | Green et al. |
| 5,449,370 | A | 9/1995 | Vaitekunas |
| 5,452,836 | A | 9/1995 | Huitema et al. |
| 5,452,837 | A | 9/1995 | Williamson, IV et al. |
| 5,454,378 | A | 10/1995 | Palmer et al. |
| 5,454,822 | A | 10/1995 | Schob et al. |
| 5,454,824 | A | 10/1995 | Fontayne et al. |
| 5,454,827 | A | 10/1995 | Aust et al. |
| 5,456,401 | A | 10/1995 | Green et al. |
| 5,456,917 | A | 10/1995 | Wise et al. |
| 5,458,279 | A | 10/1995 | Plyley |
| 5,458,579 | A | 10/1995 | Chodorow et al. |
| 5,462,215 | A | 10/1995 | Viola et al. |
| 5,464,013 | A | 11/1995 | Lemelson |
| 5,464,144 | A | 11/1995 | Guy et al. |
| 5,464,300 | A | 11/1995 | Crainich |
| 5,465,819 | A | 11/1995 | Weilant et al. |
| 5,465,894 | A | 11/1995 | Clark et al. |
| 5,465,895 | A | 11/1995 | Knodel et al. |
| 5,465,896 | A | 11/1995 | Allen et al. |
| 5,466,020 | A | 11/1995 | Page et al. |
| 5,467,911 | A | 11/1995 | Tsuruta et al. |
| 5,468,253 | A | 11/1995 | Bezwada et al. |
| 5,470,006 | A | 11/1995 | Rodak |

(56) References Cited

U.S. PATENT DOCUMENTS

| | | | |
|---|---|---|---|
| 5,470,007 | A | 11/1995 | Plyley et al. |
| 5,470,008 | A | 11/1995 | Rodak |
| 5,470,009 | A | 11/1995 | Rodak |
| 5,470,010 | A | 11/1995 | Rothfuss et al. |
| 5,471,129 | A | 11/1995 | Mann |
| 5,472,132 | A | 12/1995 | Savage et al. |
| 5,472,442 | A | 12/1995 | Klicek |
| 5,473,204 | A | 12/1995 | Temple |
| 5,474,057 | A | 12/1995 | Makower et al. |
| 5,474,223 | A | 12/1995 | Viola et al. |
| 5,474,566 | A | 12/1995 | Alesi et al. |
| 5,474,570 | A | 12/1995 | Kockerling et al. |
| 5,474,738 | A | 12/1995 | Nichols et al. |
| 5,476,206 | A | 12/1995 | Green et al. |
| 5,476,479 | A | 12/1995 | Green et al. |
| 5,476,481 | A | 12/1995 | Schondorf |
| 5,478,003 | A | 12/1995 | Green et al. |
| 5,478,308 | A | 12/1995 | Cartmell et al. |
| 5,478,354 | A | 12/1995 | Tovey et al. |
| 5,480,089 | A | 1/1996 | Blewett |
| 5,480,409 | A | 1/1996 | Riza |
| 5,482,197 | A | 1/1996 | Green et al. |
| 5,483,630 | A | 1/1996 | Unuma et al. |
| 5,483,952 | A | 1/1996 | Aranyi |
| 5,484,095 | A | 1/1996 | Green et al. |
| 5,484,398 | A | 1/1996 | Stoddard |
| 5,484,451 | A | 1/1996 | Akopov et al. |
| 5,485,947 | A | 1/1996 | Olson et al. |
| 5,485,952 | A | 1/1996 | Fontayne |
| 5,487,377 | A | 1/1996 | Smith et al. |
| 5,487,499 | A | 1/1996 | Sorrentino et al. |
| 5,487,500 | A | 1/1996 | Knodel et al. |
| 5,489,058 | A | 2/1996 | Plyley et al. |
| 5,489,256 | A | 2/1996 | Adair |
| 5,489,290 | A | 2/1996 | Furnish |
| 5,490,819 | A | 2/1996 | Nicholas et al. |
| 5,492,671 | A | 2/1996 | Krafft |
| 5,496,312 | A | 3/1996 | Klicek |
| 5,496,317 | A | 3/1996 | Goble et al. |
| 5,497,933 | A | 3/1996 | DeFonzo et al. |
| 5,498,164 | A | 3/1996 | Ward et al. |
| 5,498,838 | A | 3/1996 | Furman |
| 5,501,654 | A | 3/1996 | Failla et al. |
| 5,503,320 | A | 4/1996 | Webster et al. |
| 5,503,635 | A | 4/1996 | Sauer et al. |
| 5,503,638 | A | 4/1996 | Cooper et al. |
| 5,505,363 | A | 4/1996 | Green et al. |
| 5,507,425 | A | 4/1996 | Ziglioli |
| 5,507,426 | A | 4/1996 | Young et al. |
| 5,507,773 | A | 4/1996 | Huitema et al. |
| 5,508,080 | A | 4/1996 | Sorimachi et al. |
| 5,509,596 | A | 4/1996 | Green et al. |
| 5,509,916 | A | 4/1996 | Taylor |
| 5,509,918 | A | 4/1996 | Romano |
| 5,510,138 | A | 4/1996 | Sanftleben et al. |
| 5,511,564 | A | 4/1996 | Wilk |
| 5,514,129 | A | 5/1996 | Smith |
| 5,514,149 | A | 5/1996 | Green et al. |
| 5,514,157 | A | 5/1996 | Nicholas et al. |
| 5,518,163 | A | 5/1996 | Hooven |
| 5,518,164 | A | 5/1996 | Hooven |
| 5,520,609 | A | 5/1996 | Moll et al. |
| 5,520,634 | A | 5/1996 | Fox et al. |
| 5,520,678 | A | 5/1996 | Heckele et al. |
| 5,520,700 | A | 5/1996 | Beyar et al. |
| 5,522,817 | A | 6/1996 | Sander et al. |
| 5,522,831 | A | 6/1996 | Sleister et al. |
| 5,527,264 | A | 6/1996 | Moll et al. |
| 5,527,320 | A | 6/1996 | Carruthers et al. |
| 5,529,235 | A | 6/1996 | Boiarski et al. |
| D372,086 | S | 7/1996 | Grasso et al. |
| 5,531,305 | A | 7/1996 | Roberts et al. |
| 5,531,744 | A | 7/1996 | Nardella et al. |
| 5,531,856 | A | 7/1996 | Moll et al. |
| 5,533,521 | A | 7/1996 | Granger |
| 5,533,581 | A | 7/1996 | Barth et al. |
| 5,533,661 | A | 7/1996 | Main et al. |
| 5,535,934 | A | 7/1996 | Boiarski et al. |
| 5,535,935 | A | 7/1996 | Vidal et al. |
| 5,535,937 | A | 7/1996 | Boiarski et al. |
| 5,540,375 | A | 7/1996 | Bolanos et al. |
| 5,540,705 | A | 7/1996 | Meade et al. |
| 5,541,376 | A | 7/1996 | Ladtkow et al. |
| 5,541,489 | A | 7/1996 | Dunstan |
| 5,542,594 | A | 8/1996 | McKean et al. |
| 5,542,945 | A | 8/1996 | Fritzsch |
| 5,542,949 | A | 8/1996 | Yoon |
| 5,543,119 | A | 8/1996 | Sutter et al. |
| 5,543,695 | A | 8/1996 | Culp et al. |
| 5,544,802 | A | 8/1996 | Crainich |
| 5,547,117 | A | 8/1996 | Hamblin et al. |
| 5,549,583 | A | 8/1996 | Sanford et al. |
| 5,549,621 | A | 8/1996 | Bessler et al. |
| 5,549,627 | A | 8/1996 | Kieturakis |
| 5,549,628 | A | 8/1996 | Cooper et al. |
| 5,549,637 | A | 8/1996 | Crainich |
| 5,551,622 | A | 9/1996 | Yoon |
| 5,553,624 | A | 9/1996 | Francese et al. |
| 5,553,675 | A | 9/1996 | Pitzen et al. |
| 5,553,765 | A | 9/1996 | Knodel et al. |
| 5,554,148 | A | 9/1996 | Aebischer et al. |
| 5,554,169 | A | 9/1996 | Green et al. |
| 5,556,020 | A | 9/1996 | Hou |
| 5,556,416 | A | 9/1996 | Clark et al. |
| 5,558,533 | A | 9/1996 | Hashizawa et al. |
| 5,558,665 | A | 9/1996 | Kieturakis |
| 5,558,671 | A | 9/1996 | Yates |
| 5,560,530 | A | 10/1996 | Bolanos et al. |
| 5,560,532 | A | 10/1996 | DeFonzo et al. |
| 5,561,881 | A | 10/1996 | Klinger et al. |
| 5,562,239 | A | 10/1996 | Boiarski et al. |
| 5,562,241 | A | 10/1996 | Knodel et al. |
| 5,562,682 | A | 10/1996 | Oberlin et al. |
| 5,562,690 | A | 10/1996 | Green et al. |
| 5,562,694 | A | 10/1996 | Sauer et al. |
| 5,562,701 | A | 10/1996 | Huitema et al. |
| 5,562,702 | A | 10/1996 | Huitema et al. |
| 5,563,481 | A | 10/1996 | Krause |
| 5,564,615 | A | 10/1996 | Bishop et al. |
| 5,569,161 | A | 10/1996 | Ebling et al. |
| 5,569,270 | A | 10/1996 | Weng |
| 5,569,284 | A | 10/1996 | Young et al. |
| 5,571,090 | A | 11/1996 | Sherts |
| 5,571,100 | A | 11/1996 | Goble et al. |
| 5,571,116 | A | 11/1996 | Bolanos et al. |
| 5,571,285 | A | 11/1996 | Chow et al. |
| 5,571,488 | A | 11/1996 | Beerstecher et al. |
| 5,573,169 | A | 11/1996 | Green et al. |
| 5,573,543 | A | 11/1996 | Akopov et al. |
| 5,574,431 | A | 11/1996 | McKeown et al. |
| 5,575,054 | A | 11/1996 | Klinzing et al. |
| 5,575,789 | A | 11/1996 | Bell et al. |
| 5,575,799 | A | 11/1996 | Bolanos et al. |
| 5,575,803 | A | 11/1996 | Cooper et al. |
| 5,575,805 | A | 11/1996 | Li |
| 5,577,654 | A | 11/1996 | Bishop |
| 5,578,052 | A | 11/1996 | Koros et al. |
| 5,579,978 | A | 12/1996 | Green et al. |
| 5,580,067 | A | 12/1996 | Hamblin et al. |
| 5,582,611 | A | 12/1996 | Tsuruta et al. |
| 5,582,617 | A | 12/1996 | Klieman et al. |
| 5,582,907 | A | 12/1996 | Pall |
| 5,583,114 | A | 12/1996 | Barrows et al. |
| 5,584,425 | A | 12/1996 | Savage et al. |
| 5,586,711 | A | 12/1996 | Plyley et al. |
| 5,588,579 | A | 12/1996 | Schnut et al. |
| 5,588,580 | A | 12/1996 | Paul et al. |
| 5,588,581 | A | 12/1996 | Conlon et al. |
| 5,591,170 | A | 1/1997 | Spievack et al. |
| 5,591,187 | A | 1/1997 | Dekel |
| 5,597,107 | A | 1/1997 | Knodel et al. |
| 5,599,151 | A | 2/1997 | Daum et al. |
| 5,599,279 | A | 2/1997 | Slotman et al. |
| 5,599,344 | A | 2/1997 | Paterson |

(56) References Cited

U.S. PATENT DOCUMENTS

| | | | |
|---|---|---|---|
| 5,599,350 | A | 2/1997 | Schulze et al. |
| 5,599,852 | A | 2/1997 | Scopelianos et al. |
| 5,601,224 | A | 2/1997 | Bishop et al. |
| 5,601,573 | A | 2/1997 | Fogelberg et al. |
| 5,601,604 | A | 2/1997 | Vincent |
| 5,602,449 | A | 2/1997 | Krause et al. |
| 5,603,443 | A | 2/1997 | Clark et al. |
| 5,605,272 | A | 2/1997 | Witt et al. |
| 5,605,273 | A | 2/1997 | Hamblin et al. |
| D378,500 | S | 3/1997 | Nakai et al. |
| 5,607,094 | A | 3/1997 | Clark et al. |
| 5,607,095 | A | 3/1997 | Smith et al. |
| 5,607,303 | A | 3/1997 | Nakamura |
| 5,607,433 | A | 3/1997 | Polla et al. |
| 5,607,436 | A | 3/1997 | Pratt et al. |
| 5,607,450 | A | 3/1997 | Zvenyatsky et al. |
| 5,607,474 | A | 3/1997 | Athanasiou et al. |
| 5,609,285 | A | 3/1997 | Grant et al. |
| 5,609,601 | A | 3/1997 | Kolesa et al. |
| 5,611,709 | A | 3/1997 | McAnulty |
| 5,611,813 | A | 3/1997 | Lichtman |
| 5,613,499 | A | 3/1997 | Palmer et al. |
| 5,613,937 | A | 3/1997 | Garrison et al. |
| 5,613,966 | A | 3/1997 | Makower et al. |
| 5,614,887 | A | 3/1997 | Buchbinder |
| 5,615,820 | A | 4/1997 | Viola |
| 5,618,294 | A | 4/1997 | Aust et al. |
| 5,618,303 | A | 4/1997 | Marlow et al. |
| 5,618,307 | A | 4/1997 | Donlon et al. |
| 5,619,992 | A | 4/1997 | Guthrie et al. |
| 5,620,289 | A | 4/1997 | Curry |
| 5,620,326 | A | 4/1997 | Younker |
| 5,620,415 | A | 4/1997 | Lucey et al. |
| 5,620,452 | A | 4/1997 | Yoon |
| 5,624,398 | A | 4/1997 | Smith et al. |
| 5,624,452 | A | 4/1997 | Yates |
| 5,626,587 | A | 5/1997 | Bishop et al. |
| 5,626,595 | A | 5/1997 | Sklar et al. |
| 5,626,979 | A | 5/1997 | Mitsui et al. |
| 5,628,446 | A | 5/1997 | Geiste et al. |
| 5,628,743 | A | 5/1997 | Cimino |
| 5,628,745 | A | 5/1997 | Bek |
| 5,630,539 | A | 5/1997 | Plyley et al. |
| 5,630,540 | A | 5/1997 | Blewett |
| 5,630,541 | A | 5/1997 | Williamson, IV et al. |
| 5,630,782 | A | 5/1997 | Adair |
| 5,631,973 | A | 5/1997 | Green |
| 5,632,432 | A | 5/1997 | Schulze et al. |
| 5,632,433 | A | 5/1997 | Grant et al. |
| 5,633,374 | A | 5/1997 | Humphrey et al. |
| 5,634,584 | A | 6/1997 | Okorocha et al. |
| 5,636,779 | A | 6/1997 | Palmer |
| 5,636,780 | A | 6/1997 | Green et al. |
| 5,637,110 | A | 6/1997 | Pennybacker et al. |
| 5,638,582 | A | 6/1997 | Klatt et al. |
| 5,639,008 | A | 6/1997 | Gallagher et al. |
| D381,077 | S | 7/1997 | Hunt |
| 5,643,291 | A | 7/1997 | Pier et al. |
| 5,643,293 | A | 7/1997 | Kogasaka et al. |
| 5,643,294 | A | 7/1997 | Tovey et al. |
| 5,643,319 | A | 7/1997 | Green et al. |
| 5,645,209 | A | 7/1997 | Green et al. |
| 5,647,526 | A | 7/1997 | Green et al. |
| 5,647,869 | A | 7/1997 | Goble et al. |
| 5,649,937 | A | 7/1997 | Bito et al. |
| 5,649,956 | A | 7/1997 | Jensen et al. |
| 5,651,491 | A | 7/1997 | Heaton et al. |
| 5,651,762 | A | 7/1997 | Bridges |
| 5,651,821 | A | 7/1997 | Uchida |
| 5,653,373 | A | 8/1997 | Green et al. |
| 5,653,374 | A | 8/1997 | Young et al. |
| 5,653,677 | A | 8/1997 | Okada et al. |
| 5,653,721 | A | 8/1997 | Knodel et al. |
| 5,653,748 | A | 8/1997 | Strecker |
| 5,655,698 | A | 8/1997 | Yoon |
| 5,656,917 | A | 8/1997 | Theobald |
| 5,657,417 | A | 8/1997 | Di Troia |
| 5,657,429 | A | 8/1997 | Wang et al. |
| 5,657,921 | A | 8/1997 | Young et al. |
| 5,658,238 | A | 8/1997 | Suzuki et al. |
| 5,658,281 | A | 8/1997 | Heard |
| 5,658,298 | A | 8/1997 | Vincent et al. |
| 5,658,300 | A | 8/1997 | Bito et al. |
| 5,658,307 | A | 8/1997 | Exconde |
| 5,662,258 | A | 9/1997 | Knodel et al. |
| 5,662,260 | A | 9/1997 | Yoon |
| 5,662,662 | A | 9/1997 | Bishop et al. |
| 5,662,667 | A | 9/1997 | Knodel |
| 5,664,404 | A | 9/1997 | Ivanov et al. |
| 5,665,085 | A | 9/1997 | Nardella |
| 5,667,517 | A | 9/1997 | Hooven |
| 5,667,526 | A | 9/1997 | Levin |
| 5,667,527 | A | 9/1997 | Cook |
| 5,667,864 | A | 9/1997 | Landoll |
| 5,669,544 | A | 9/1997 | Schulze et al. |
| 5,669,904 | A | 9/1997 | Platt, Jr. et al. |
| 5,669,907 | A | 9/1997 | Platt, Jr. et al. |
| 5,669,918 | A | 9/1997 | Balazs et al. |
| 5,672,945 | A | 9/1997 | Krause |
| 5,673,840 | A | 10/1997 | Schulze et al. |
| 5,673,841 | A | 10/1997 | Schulze et al. |
| 5,673,842 | A | 10/1997 | Bittner et al. |
| 5,674,184 | A | 10/1997 | Hassler, Jr. |
| 5,674,286 | A | 10/1997 | D'Alessio et al. |
| 5,678,748 | A | 10/1997 | Plyley et al. |
| 5,680,981 | A | 10/1997 | Mililli et al. |
| 5,680,982 | A | 10/1997 | Schulze et al. |
| 5,680,983 | A | 10/1997 | Plyley et al. |
| 5,681,330 | A | 10/1997 | Hughett et al. |
| 5,681,341 | A | 10/1997 | Lunsford et al. |
| 5,683,349 | A | 11/1997 | Makower et al. |
| 5,683,432 | A | 11/1997 | Goedeke et al. |
| 5,685,474 | A | 11/1997 | Seeber |
| 5,686,090 | A | 11/1997 | Schilder et al. |
| 5,688,270 | A | 11/1997 | Yates et al. |
| 5,690,269 | A | 11/1997 | Bolanos et al. |
| 5,690,675 | A | 11/1997 | Sawyer et al. |
| 5,692,668 | A | 12/1997 | Schulze et al. |
| 5,693,020 | A | 12/1997 | Rauh |
| 5,693,042 | A | 12/1997 | Boiarski et al. |
| 5,693,051 | A | 12/1997 | Schulze et al. |
| 5,695,494 | A | 12/1997 | Becker |
| 5,695,502 | A | 12/1997 | Pier et al. |
| 5,695,504 | A | 12/1997 | Gifford, III et al. |
| 5,695,524 | A | 12/1997 | Kelley et al. |
| 5,697,542 | A | 12/1997 | Knodel et al. |
| 5,697,543 | A | 12/1997 | Burdorff |
| 5,697,909 | A | 12/1997 | Eggers et al. |
| 5,697,943 | A | 12/1997 | Sauer et al. |
| 5,700,265 | A | 12/1997 | Romano |
| 5,700,270 | A | 12/1997 | Peyser et al. |
| 5,700,276 | A | 12/1997 | Benecke |
| 5,702,387 | A | 12/1997 | Arts et al. |
| 5,702,408 | A | 12/1997 | Wales et al. |
| 5,702,409 | A | 12/1997 | Rayburn et al. |
| 5,704,087 | A | 1/1998 | Strub |
| 5,704,534 | A | 1/1998 | Huitema et al. |
| 5,704,792 | A | 1/1998 | Sobhani |
| 5,706,997 | A | 1/1998 | Green et al. |
| 5,706,998 | A | 1/1998 | Plyley et al. |
| 5,707,392 | A | 1/1998 | Kortenbach |
| 5,709,334 | A | 1/1998 | Sorrentino et al. |
| 5,709,335 | A | 1/1998 | Heck |
| 5,709,680 | A | 1/1998 | Yates et al. |
| 5,709,706 | A | 1/1998 | Kienzle et al. |
| 5,711,472 | A | 1/1998 | Bryan |
| 5,711,960 | A | 1/1998 | Shikinami |
| 5,712,460 | A | 1/1998 | Carr et al. |
| 5,713,128 | A | 2/1998 | Schrenk et al. |
| 5,713,505 | A | 2/1998 | Huitema |
| 5,713,895 | A | 2/1998 | Lontine et al. |
| 5,713,896 | A | 2/1998 | Nardella |
| 5,713,920 | A | 2/1998 | Bezwada et al. |
| 5,715,604 | A | 2/1998 | Lanzoni |

(56) References Cited

U.S. PATENT DOCUMENTS 5,715,836 A 2/1998 Kliegis et al.
5,715,987 A 2/1998 Kelley et al.
5,715,988 A 2/1998 Palmer
5,716,352 A 2/1998 Viola et al.
5,716,366 A 2/1998 Yates
5,718,359 A 2/1998 Palmer et al.
5,718,360 A 2/1998 Green et al.
5,718,548 A 2/1998 Cotellessa
5,718,714 A 2/1998 Livneh
5,720,744 A 2/1998 Eggleston et al.
D393,067 S 3/1998 Geary et al.
5,724,025 A 3/1998 Tavori
5,725,536 A 3/1998 Oberlin et al.
5,725,554 A 3/1998 Simon et al.
5,728,110 A 3/1998 Vidal et al.
5,728,113 A 3/1998 Sherts
5,728,121 A 3/1998 Bimbo et al.
5,730,758 A 3/1998 Allgeyer
5,732,712 A 3/1998 Adair
5,732,821 A 3/1998 Stone et al.
5,732,871 A 3/1998 Clark et al.
5,732,872 A 3/1998 Bolduc et al.
5,733,308 A 3/1998 Daugherty et al.
5,735,445 A 4/1998 Vidal et al.
5,735,848 A 4/1998 Yates et al.
5,735,874 A 4/1998 Measamer et al.
5,736,271 A 4/1998 Cisar et al.
5,738,474 A 4/1998 Blewett
5,738,629 A 4/1998 Moll et al.
5,738,648 A 4/1998 Lands et al.
5,741,271 A 4/1998 Nakao et al.
5,743,456 A 4/1998 Jones et al.
5,746,770 A 5/1998 Zeitels et al.
5,747,953 A 5/1998 Philipp
5,749,889 A 5/1998 Bacich et al.
5,749,893 A 5/1998 Vidal et al.
5,749,896 A 5/1998 Cook
5,749,968 A 5/1998 Melanson et al.
5,752,644 A 5/1998 Bolanos et al.
5,752,965 A 5/1998 Francis et al.
5,752,970 A 5/1998 Yoon
5,752,973 A 5/1998 Kieturakis
5,755,717 A 5/1998 Yates et al.
5,755,726 A 5/1998 Pratt et al.
D395,645 S 6/1998 Cappa et al.
5,758,814 A 6/1998 Gallagher et al.
5,762,255 A 6/1998 Chrisman et al.
5,762,256 A 6/1998 Mastri et al.
5,762,458 A 6/1998 Wang et al.
5,765,565 A 6/1998 Adair
5,766,186 A 6/1998 Faraz et al.
5,766,188 A 6/1998 Igaki
5,766,205 A 6/1998 Zvenyatsky et al.
5,769,303 A 6/1998 Knodel et al.
5,769,640 A 6/1998 Jacobus et al.
5,769,748 A 6/1998 Eyerly et al.
5,769,791 A 6/1998 Benaron et al.
5,769,892 A 6/1998 Kingwell
5,772,099 A 6/1998 Gravener
5,772,379 A 6/1998 Evensen
5,772,578 A 6/1998 Heimberger et al.
5,772,659 A 6/1998 Becker et al.
5,773,991 A 6/1998 Chen
5,776,130 A 7/1998 Buysse et al.
5,778,939 A 7/1998 Hok-Yin
5,779,130 A 7/1998 Alesi et al.
5,779,131 A 7/1998 Knodel et al.
5,779,132 A 7/1998 Knodel et al.
5,782,396 A 7/1998 Mastri et al.
5,782,397 A 7/1998 Koukline
5,782,748 A 7/1998 Palmer et al.
5,782,749 A 7/1998 Riza
5,782,859 A 7/1998 Nicholas et al.
5,784,934 A 7/1998 Izumisawa
5,785,232 A 7/1998 Vidal et al.
5,785,647 A 7/1998 Tompkins et al.
5,787,897 A 8/1998 Kieturakis
5,791,231 A 8/1998 Cohn et al.
5,792,135 A 8/1998 Madhani et al.
5,792,162 A 8/1998 Jolly et al.
5,792,165 A 8/1998 Klieman et al.
5,792,573 A 8/1998 Pitzen et al.
5,794,834 A 8/1998 Hamblin et al.
5,796,188 A 8/1998 Bays
5,797,536 A 8/1998 Smith et al.
5,797,537 A 8/1998 Oberlin et al.
5,797,538 A 8/1998 Heaton et al.
5,797,637 A 8/1998 Ervin
5,797,900 A 8/1998 Madhani et al.
5,797,906 A 8/1998 Rhum et al.
5,797,927 A 8/1998 Yoon
5,797,941 A 8/1998 Schulze et al.
5,797,959 A 8/1998 Castro et al.
5,798,752 A 8/1998 Buxton et al.
5,799,857 A 9/1998 Robertson et al.
5,800,379 A 9/1998 Edwards
5,800,423 A 9/1998 Jensen
5,804,726 A 9/1998 Geib et al.
5,804,936 A 9/1998 Brodsky et al.
5,806,676 A 9/1998 Wasgien
5,807,241 A 9/1998 Heimberger
5,807,376 A 9/1998 Viola et al.
5,807,378 A 9/1998 Jensen et al.
5,807,393 A 9/1998 Williamson, IV et al.
5,809,441 A 9/1998 McKee
5,810,240 A 9/1998 Robertson
5,810,721 A 9/1998 Mueller et al.
5,810,811 A 9/1998 Yates et al.
5,810,846 A 9/1998 Virnich et al.
5,810,855 A 9/1998 Rayburn et al.
5,812,188 A 9/1998 Adair
5,813,813 A 9/1998 Daum et al.
5,814,055 A 9/1998 Knodel et al.
5,814,057 A 9/1998 Oi et al.
5,816,471 A 10/1998 Plyley et al.
5,817,084 A 10/1998 Jensen
5,817,091 A 10/1998 Nardella et al.
5,817,093 A 10/1998 Williamson, IV et al.
5,817,109 A 10/1998 McGarry et al.
5,817,119 A 10/1998 Klieman et al.
5,820,009 A 10/1998 Melling et al.
5,823,066 A 10/1998 Huitema et al.
5,824,333 A 10/1998 Scopelianos et al.
5,826,776 A 10/1998 Schulze et al.
5,827,271 A 10/1998 Buysse et al.
5,827,298 A 10/1998 Hart et al.
5,827,323 A 10/1998 Klieman et al.
5,829,662 A 11/1998 Allen et al.
5,830,598 A 11/1998 Patterson
5,833,690 A 11/1998 Yates et al.
5,833,695 A 11/1998 Yoon
5,833,696 A 11/1998 Whitfield et al.
5,836,503 A 11/1998 Ehrenfels et al.
5,836,960 A 11/1998 Kolesa et al.
5,839,369 A 11/1998 Chatterjee et al.
5,839,639 A 11/1998 Sauer et al.
5,841,284 A 11/1998 Takahashi
5,843,021 A 12/1998 Edwards et al.
5,843,096 A 12/1998 Igaki et al.
5,843,097 A 12/1998 Mayenberger et al.
5,843,122 A 12/1998 Riza
5,843,132 A 12/1998 Ilvento
5,843,169 A 12/1998 Taheri
5,846,254 A 12/1998 Schulze et al.
5,847,566 A 12/1998 Marritt et al.
5,849,011 A 12/1998 Jones et al.
5,849,020 A 12/1998 Long et al.
5,849,023 A 12/1998 Mericle
5,851,179 A 12/1998 Ritson et al.
5,851,212 A 12/1998 Zirps et al.
5,853,366 A 12/1998 Dowlatshahi
5,855,311 A 1/1999 Hamblin et al.
5,855,583 A 1/1999 Wang et al.
5,860,581 A 1/1999 Robertson et al.

(56) References Cited

U.S. PATENT DOCUMENTS

| | | | |
|---|---|---|---|
| 5,860,975 | A | 1/1999 | Goble et al. |
| 5,865,361 | A | 2/1999 | Milliman et al. |
| 5,865,638 | A | 2/1999 | Trafton |
| 5,868,361 | A | 2/1999 | Rinderer |
| 5,868,664 | A | 2/1999 | Speier et al. |
| 5,868,760 | A | 2/1999 | McGuckin, Jr. |
| 5,868,790 | A | 2/1999 | Vincent et al. |
| 5,871,135 | A | 2/1999 | Williamson IV et al. |
| 5,873,885 | A | 2/1999 | Weidenbenner |
| 5,876,401 | A | 3/1999 | Schulze et al. |
| 5,878,193 | A | 3/1999 | Wang et al. |
| 5,878,607 | A | 3/1999 | Nunes et al. |
| 5,878,937 | A | 3/1999 | Green et al. |
| 5,878,938 | A | 3/1999 | Bittner et al. |
| 5,881,777 | A | 3/1999 | Bassi et al. |
| 5,881,943 | A | 3/1999 | Heck et al. |
| 5,891,094 | A | 4/1999 | Masterson et al. |
| 5,891,160 | A | 4/1999 | Williamson, IV et al. |
| 5,891,558 | A | 4/1999 | Bell et al. |
| 5,893,506 | A | 4/1999 | Powell |
| 5,893,835 | A | 4/1999 | Witt et al. |
| 5,893,855 | A | 4/1999 | Jacobs |
| 5,893,863 | A | 4/1999 | Yoon |
| 5,893,878 | A | 4/1999 | Pierce |
| 5,894,979 | A | 4/1999 | Powell |
| 5,897,552 | A | 4/1999 | Edwards et al. |
| 5,897,562 | A | 4/1999 | Bolanos et al. |
| 5,899,824 | A | 5/1999 | Kurtz et al. |
| 5,899,914 | A | 5/1999 | Zirps et al. |
| 5,901,895 | A | 5/1999 | Heaton et al. |
| 5,902,312 | A | 5/1999 | Frater et al. |
| 5,903,117 | A | 5/1999 | Gregory |
| 5,904,647 | A | 5/1999 | Ouchi |
| 5,904,693 | A | 5/1999 | Dicesare et al. |
| 5,904,702 | A | 5/1999 | Ek et al. |
| 5,906,577 | A | 5/1999 | Beane et al. |
| 5,906,625 | A | 5/1999 | Bito et al. |
| 5,907,211 | A | 5/1999 | Hall et al. |
| 5,907,664 | A | 5/1999 | Wang et al. |
| 5,908,149 | A | 6/1999 | Welch et al. |
| 5,908,402 | A | 6/1999 | Blythe |
| 5,908,427 | A | 6/1999 | McKean et al. |
| 5,909,062 | A | 6/1999 | Krietzman |
| 5,911,353 | A | 6/1999 | Bolanos et al. |
| 5,915,616 | A | 6/1999 | Viola et al. |
| 5,916,225 | A | 6/1999 | Kugel |
| 5,918,791 | A | 7/1999 | Sorrentino et al. |
| 5,919,198 | A | 7/1999 | Graves, Jr. et al. |
| 5,921,956 | A | 7/1999 | Grinberg et al. |
| 5,922,001 | A | 7/1999 | Yoon |
| 5,922,003 | A | 7/1999 | Anctil et al. |
| 5,924,864 | A | 7/1999 | Loge et al. |
| 5,928,137 | A | 7/1999 | Green |
| 5,928,256 | A | 7/1999 | Riza |
| 5,931,847 | A | 8/1999 | Bittner et al. |
| 5,931,853 | A | 8/1999 | McEwen et al. |
| 5,937,951 | A | 8/1999 | Izuchukwu et al. |
| 5,938,667 | A | 8/1999 | Peyser et al. |
| 5,941,442 | A | 8/1999 | Geiste et al. |
| 5,941,890 | A | 8/1999 | Voegele et al. |
| 5,944,172 | A | 8/1999 | Hannula |
| 5,944,715 | A | 8/1999 | Goble et al. |
| 5,946,978 | A | 9/1999 | Yamashita |
| 5,947,984 | A | 9/1999 | Whipple |
| 5,947,996 | A | 9/1999 | Logeman |
| 5,948,030 | A | 9/1999 | Miller et al. |
| 5,948,429 | A | 9/1999 | Bell et al. |
| 5,951,301 | A | 9/1999 | Younker |
| 5,951,516 | A | 9/1999 | Bunyan |
| 5,951,552 | A | 9/1999 | Long et al. |
| 5,951,574 | A | 9/1999 | Stefanchik et al. |
| 5,951,575 | A | 9/1999 | Bolduc et al. |
| 5,951,581 | A | 9/1999 | Saadat et al. |
| 5,954,259 | A | 9/1999 | Viola et al. |
| 5,954,536 | A | 9/1999 | Fuerst et al. |
| 5,957,831 | A | 9/1999 | Adair |
| 5,964,394 | A | 10/1999 | Robertson |
| 5,964,774 | A | 10/1999 | McKean et al. |
| 5,966,126 | A | 10/1999 | Szabo |
| 5,971,916 | A | 10/1999 | Koren |
| 5,973,221 | A | 10/1999 | Collyer et al. |
| D416,089 | S | 11/1999 | Barton et al. |
| 5,976,122 | A | 11/1999 | Madhani et al. |
| 5,977,746 | A | 11/1999 | Hershberger et al. |
| 5,980,248 | A | 11/1999 | Kusakabe et al. |
| 5,980,569 | A | 11/1999 | Scirica |
| 5,984,949 | A | 11/1999 | Levin |
| 5,988,479 | A | 11/1999 | Palmer |
| 5,990,379 | A | 11/1999 | Gregory |
| 5,993,464 | A | 11/1999 | Knodel |
| 5,993,466 | A | 11/1999 | Yoon |
| 5,997,528 | A | 12/1999 | Bisch et al. |
| 5,997,552 | A | 12/1999 | Person et al. |
| 6,001,108 | A | 12/1999 | Wang et al. |
| 6,003,517 | A | 12/1999 | Sheffield et al. |
| 6,004,319 | A | 12/1999 | Goble et al. |
| 6,004,335 | A | 12/1999 | Vaitekunas et al. |
| 6,007,521 | A | 12/1999 | Bidwell et al. |
| 6,010,054 | A | 1/2000 | Johnson et al. |
| 6,010,513 | A | 1/2000 | Tormala et al. |
| 6,010,520 | A | 1/2000 | Pattison |
| 6,012,494 | A | 1/2000 | Balazs |
| 6,013,076 | A | 1/2000 | Goble et al. |
| 6,013,991 | A | 1/2000 | Philipp |
| 6,015,406 | A | 1/2000 | Goble et al. |
| 6,015,417 | A | 1/2000 | Reynolds, Jr. |
| 6,017,322 | A | 1/2000 | Snoke et al. |
| 6,017,354 | A | 1/2000 | Culp et al. |
| 6,017,356 | A | 1/2000 | Frederick et al. |
| 6,018,227 | A | 1/2000 | Kumar et al. |
| 6,019,745 | A | 2/2000 | Gray |
| 6,019,780 | A | 2/2000 | Lombardo et al. |
| 6,022,352 | A | 2/2000 | Vandewalle |
| 6,023,275 | A | 2/2000 | Horvitz et al. |
| 6,023,641 | A | 2/2000 | Thompson |
| 6,024,708 | A | 2/2000 | Bales et al. |
| 6,024,741 | A | 2/2000 | Williamson, IV et al. |
| 6,024,748 | A | 2/2000 | Manzo et al. |
| 6,024,750 | A | 2/2000 | Mastri et al. |
| 6,024,764 | A | 2/2000 | Schroeppel |
| 6,027,501 | A | 2/2000 | Goble et al. |
| 6,030,384 | A | 2/2000 | Nezhat |
| 6,031,148 | A | 2/2000 | Hayes et al. |
| 6,032,849 | A | 3/2000 | Mastri et al. |
| 6,033,105 | A | 3/2000 | Barker et al. |
| 6,033,378 | A | 3/2000 | Lundquist et al. |
| 6,033,399 | A | 3/2000 | Gines |
| 6,033,427 | A | 3/2000 | Lee |
| 6,036,641 | A | 3/2000 | Taylor et al. |
| 6,036,667 | A | 3/2000 | Manna et al. |
| 6,037,724 | A | 3/2000 | Buss et al. |
| 6,037,927 | A | 3/2000 | Rosenberg |
| 6,039,126 | A | 3/2000 | Hsieh |
| 6,039,733 | A | 3/2000 | Buysse et al. |
| 6,039,734 | A | 3/2000 | Goble |
| 6,042,601 | A | 3/2000 | Smith |
| 6,042,607 | A | 3/2000 | Williamson, IV et al. |
| 6,043,626 | A | 3/2000 | Snyder et al. |
| D422,545 | S | 4/2000 | Palalau et al. |
| 6,045,560 | A | 4/2000 | McKean et al. |
| 6,047,861 | A | 4/2000 | Vidal et al. |
| 6,049,145 | A | 4/2000 | Austin et al. |
| 6,050,172 | A | 4/2000 | Corves et al. |
| 6,050,472 | A | 4/2000 | Shibata |
| 6,050,989 | A | 4/2000 | Fox et al. |
| 6,050,990 | A | 4/2000 | Tankovich et al. |
| 6,050,996 | A | 4/2000 | Schmaltz et al. |
| 6,053,390 | A | 4/2000 | Green et al. |
| 6,053,899 | A | 4/2000 | Slanda et al. |
| 6,053,922 | A | 4/2000 | Krause et al. |
| 6,054,142 | A | 4/2000 | Li et al. |
| 6,055,062 | A | 4/2000 | Dina et al. |
| RE36,720 | E | 5/2000 | Green et al. |
| 6,056,735 | A | 5/2000 | Okada et al. |

(56) References Cited

U.S. PATENT DOCUMENTS

| | | | |
|---|---|---|---|
| 6,056,746 | A | 5/2000 | Goble et al. |
| 6,059,806 | A | 5/2000 | Hoegerle |
| 6,062,360 | A | 5/2000 | Shields |
| 6,063,020 | A | 5/2000 | Jones et al. |
| 6,063,025 | A | 5/2000 | Bridges et al. |
| 6,063,050 | A | 5/2000 | Manna et al. |
| 6,063,095 | A | 5/2000 | Wang et al. |
| 6,063,097 | A | 5/2000 | Oi et al. |
| 6,063,098 | A | 5/2000 | Houser et al. |
| 6,065,679 | A | 5/2000 | Levie et al. |
| 6,065,919 | A | 5/2000 | Peck |
| 6,066,132 | A | 5/2000 | Chen et al. |
| 6,066,144 | A | 5/2000 | Wolf et al. |
| 6,066,151 | A | 5/2000 | Miyawaki et al. |
| 6,068,627 | A | 5/2000 | Orszulak et al. |
| 6,071,233 | A | 6/2000 | Ishikawa et al. |
| 6,072,299 | A | 6/2000 | Kurle et al. |
| 6,074,386 | A | 6/2000 | Goble et al. |
| 6,074,401 | A | 6/2000 | Gardiner et al. |
| 6,075,441 | A | 6/2000 | Maloney |
| 6,077,280 | A | 6/2000 | Fossum |
| 6,077,286 | A | 6/2000 | Cuschieri et al. |
| 6,077,290 | A | 6/2000 | Marini |
| 6,079,606 | A | 6/2000 | Milliman et al. |
| 6,080,181 | A | 6/2000 | Jensen et al. |
| 6,082,577 | A | 7/2000 | Coates et al. |
| 6,083,191 | A | 7/2000 | Rose |
| 6,083,223 | A | 7/2000 | Baker |
| 6,083,234 | A | 7/2000 | Nicholas et al. |
| 6,083,242 | A | 7/2000 | Cook |
| 6,086,544 | A | 7/2000 | Hibner et al. |
| 6,086,600 | A | 7/2000 | Kortenbach |
| 6,090,106 | A | 7/2000 | Goble et al. |
| 6,090,123 | A | 7/2000 | Culp et al. |
| 6,093,186 | A | 7/2000 | Goble |
| 6,094,021 | A | 7/2000 | Noro et al. |
| D429,252 | S | 8/2000 | Haitani et al. |
| 6,099,537 | A | 8/2000 | Sugai et al. |
| 6,099,551 | A | 8/2000 | Gabbay |
| 6,102,271 | A | 8/2000 | Longo et al. |
| 6,102,926 | A | 8/2000 | Tartaglia et al. |
| 6,104,162 | A | 8/2000 | Sainsbury et al. |
| 6,104,304 | A | 8/2000 | Clark et al. |
| 6,106,511 | A | 8/2000 | Jensen |
| 6,109,500 | A | 8/2000 | Alli et al. |
| 6,110,187 | A | 8/2000 | Donlon |
| 6,113,618 | A | 9/2000 | Nic |
| 6,117,148 | A | 9/2000 | Ravo et al. |
| 6,117,158 | A | 9/2000 | Measamer et al. |
| 6,119,913 | A | 9/2000 | Adams et al. |
| 6,120,433 | A | 9/2000 | Mizuno et al. |
| 6,120,462 | A | 9/2000 | Hibner et al. |
| 6,123,241 | A | 9/2000 | Walter et al. |
| 6,123,701 | A | 9/2000 | Nezhat |
| H1904 | H | 10/2000 | Yates et al. |
| RE36,923 | E | 10/2000 | Hiroi et al. |
| 6,126,058 | A | 10/2000 | Adams et al. |
| 6,126,359 | A | 10/2000 | Dittrich et al. |
| 6,126,670 | A | 10/2000 | Walker et al. |
| 6,131,789 | A | 10/2000 | Schulze et al. |
| 6,131,790 | A | 10/2000 | Piraka |
| 6,132,368 | A | 10/2000 | Cooper |
| 6,134,962 | A | 10/2000 | Sugitani |
| 6,139,546 | A | 10/2000 | Koenig et al. |
| 6,142,149 | A | 11/2000 | Steen |
| 6,142,933 | A | 11/2000 | Longo et al. |
| 6,147,135 | A | 11/2000 | Yuan et al. |
| 6,148,979 | A | 11/2000 | Roach et al. |
| 6,149,660 | A | 11/2000 | Laufer et al. |
| 6,151,323 | A | 11/2000 | O'Connell et al. |
| 6,152,935 | A | 11/2000 | Kammerer et al. |
| 6,155,083 | A | 12/2000 | Goeser et al. |
| 6,155,473 | A | 12/2000 | Tompkins et al. |
| 6,156,056 | A | 12/2000 | Kearns et al. |
| 6,157,169 | A | 12/2000 | Lee |
| 6,157,303 | A | 12/2000 | Bodie et al. |
| 6,159,146 | A | 12/2000 | El Gazayerli |
| 6,159,200 | A | 12/2000 | Verdura et al. |
| 6,159,224 | A | 12/2000 | Yoon |
| 6,162,208 | A | 12/2000 | Hipps |
| 6,162,220 | A | 12/2000 | Nezhat |
| 6,162,537 | A | 12/2000 | Martin et al. |
| 6,165,175 | A | 12/2000 | Wampler et al. |
| 6,165,184 | A | 12/2000 | Verdura et al. |
| 6,165,188 | A | 12/2000 | Saadat et al. |
| 6,167,185 | A | 12/2000 | Smiley et al. |
| 6,168,605 | B1 | 1/2001 | Measamer et al. |
| 6,171,305 | B1 | 1/2001 | Sherman |
| 6,171,316 | B1 | 1/2001 | Kovac et al. |
| 6,171,330 | B1 | 1/2001 | Benchetrit |
| 6,173,074 | B1 | 1/2001 | Russo |
| 6,174,308 | B1 | 1/2001 | Goble et al. |
| 6,174,309 | B1 | 1/2001 | Wrublewski et al. |
| 6,174,318 | B1 | 1/2001 | Bates et al. |
| 6,175,290 | B1 | 1/2001 | Forsythe et al. |
| 6,179,195 | B1 | 1/2001 | Adams et al. |
| 6,179,776 | B1 | 1/2001 | Adams et al. |
| 6,181,105 | B1 | 1/2001 | Cutolo et al. |
| 6,182,673 | B1 | 2/2001 | Kindermann et al. |
| 6,185,356 | B1 | 2/2001 | Parker et al. |
| 6,186,142 | B1 | 2/2001 | Schmidt et al. |
| 6,186,957 | B1 | 2/2001 | Milam |
| 6,187,003 | B1 | 2/2001 | Buysse et al. |
| 6,190,386 | B1 | 2/2001 | Rydell |
| 6,193,129 | B1 | 2/2001 | Bittner et al. |
| 6,197,042 | B1 | 3/2001 | Ginn et al. |
| 6,200,311 | B1 | 3/2001 | Danek et al. |
| 6,200,330 | B1 | 3/2001 | Benderev et al. |
| 6,202,914 | B1 | 3/2001 | Geiste et al. |
| 6,206,894 | B1 | 3/2001 | Thompson et al. |
| 6,206,897 | B1 | 3/2001 | Jamiolkowski et al. |
| 6,206,903 | B1 | 3/2001 | Ramans |
| 6,206,904 | B1 | 3/2001 | Ouchi |
| 6,209,414 | B1 | 4/2001 | Uneme |
| 6,210,403 | B1 | 4/2001 | Klicek |
| 6,211,626 | B1 | 4/2001 | Lys et al. |
| 6,213,999 | B1 | 4/2001 | Platt, Jr. et al. |
| 6,214,028 | B1 | 4/2001 | Yoon et al. |
| 6,217,168 | B1 | 4/2001 | Elgee |
| 6,220,368 | B1 | 4/2001 | Ark et al. |
| 6,221,007 | B1 | 4/2001 | Green |
| 6,221,023 | B1 | 4/2001 | Matsuba et al. |
| 6,223,100 | B1 | 4/2001 | Green |
| 6,223,835 | B1 | 5/2001 | Habedank et al. |
| 6,224,617 | B1 | 5/2001 | Saadat et al. |
| 6,228,080 | B1 | 5/2001 | Gines |
| 6,228,081 | B1 | 5/2001 | Goble |
| 6,228,083 | B1 | 5/2001 | Lands et al. |
| 6,228,084 | B1 | 5/2001 | Kirwan, Jr. |
| 6,228,089 | B1 | 5/2001 | Wahrburg |
| 6,228,098 | B1 | 5/2001 | Kayan et al. |
| 6,231,565 | B1 | 5/2001 | Tovey et al. |
| 6,234,178 | B1 | 5/2001 | Goble et al. |
| 6,235,036 | B1 | 5/2001 | Gardner et al. |
| 6,237,604 | B1 | 5/2001 | Burnside et al. |
| 6,238,384 | B1 | 5/2001 | Peer |
| 6,241,139 | B1 | 6/2001 | Milliman et al. |
| 6,241,140 | B1 | 6/2001 | Adams et al. |
| 6,241,723 | B1 | 6/2001 | Heim et al. |
| 6,245,084 | B1 | 6/2001 | Mark et al. |
| 6,248,116 | B1 | 6/2001 | Chevillon et al. |
| 6,248,117 | B1 | 6/2001 | Blatter |
| 6,249,076 | B1 | 6/2001 | Madden et al. |
| 6,249,105 | B1 | 6/2001 | Andrews et al. |
| 6,250,532 | B1 | 6/2001 | Green et al. |
| 6,251,485 | B1 | 6/2001 | Harris et al. |
| D445,745 | S | 7/2001 | Norman |
| 6,254,534 | B1 | 7/2001 | Butler et al. |
| 6,254,619 | B1 | 7/2001 | Garabet et al. |
| 6,254,642 | B1 | 7/2001 | Taylor |
| 6,258,107 | B1 | 7/2001 | Balazs et al. |
| 6,261,246 | B1 | 7/2001 | Pantages et al. |
| 6,261,286 | B1 | 7/2001 | Goble et al. |
| 6,261,679 | B1 | 7/2001 | Chen et al. |

(56) References Cited

U.S. PATENT DOCUMENTS

| | | | |
|---|---|---|---|
| 6,264,086 | B1 | 7/2001 | McGuckin, Jr. |
| 6,264,087 | B1 | 7/2001 | Whitman |
| 6,264,617 | B1 | 7/2001 | Bales et al. |
| 6,269,997 | B1 | 8/2001 | Balazs et al. |
| 6,270,508 | B1 | 8/2001 | Klieman et al. |
| 6,270,916 | B1 | 8/2001 | Sink et al. |
| 6,273,252 | B1 | 8/2001 | Mitchell |
| 6,273,876 | B1 | 8/2001 | Klima et al. |
| 6,273,897 | B1 | 8/2001 | Dalessandro et al. |
| 6,277,114 | B1 | 8/2001 | Bullivant et al. |
| 6,280,407 | B1 | 8/2001 | Manna et al. |
| 6,283,981 | B1 | 9/2001 | Beaupre |
| 6,293,927 | B1 | 9/2001 | McGuckin, Jr. |
| 6,293,942 | B1 | 9/2001 | Goble et al. |
| 6,296,607 | B1 | 10/2001 | Milbocker |
| 6,296,640 | B1 | 10/2001 | Wampler et al. |
| 6,302,311 | B1 | 10/2001 | Adams et al. |
| 6,302,743 | B1 | 10/2001 | Chiu et al. |
| 6,305,891 | B1 | 10/2001 | Burlingame |
| 6,306,134 | B1 | 10/2001 | Goble et al. |
| 6,306,149 | B1 | 10/2001 | Meade |
| 6,306,424 | B1 | 10/2001 | Vyakarnam et al. |
| 6,309,397 | B1 | 10/2001 | Julian et al. |
| 6,309,400 | B2 | 10/2001 | Beaupre |
| 6,309,403 | B1 | 10/2001 | Minor et al. |
| 6,312,435 | B1 | 11/2001 | Wallace et al. |
| 6,315,184 | B1 | 11/2001 | Whitman |
| 6,317,616 | B1 | 11/2001 | Glossop |
| 6,319,510 | B1 | 11/2001 | Yates |
| 6,320,123 | B1 | 11/2001 | Reimers |
| 6,322,494 | B1 | 11/2001 | Bullivant et al. |
| 6,324,339 | B1 | 11/2001 | Hudson et al. |
| 6,325,799 | B1 | 12/2001 | Goble |
| 6,325,805 | B1 | 12/2001 | Ogilvie et al. |
| 6,325,810 | B1 | 12/2001 | Hamilton et al. |
| 6,328,498 | B1 | 12/2001 | Mersch |
| 6,330,965 | B1 | 12/2001 | Milliman et al. |
| 6,331,181 | B1 | 12/2001 | Tierney et al. |
| 6,331,761 | B1 | 12/2001 | Kumar et al. |
| 6,333,029 | B1 | 12/2001 | Vyakarnam et al. |
| 6,334,860 | B1 | 1/2002 | Dorn |
| 6,334,861 | B1 | 1/2002 | Chandler et al. |
| 6,336,926 | B1 | 1/2002 | Goble |
| 6,338,737 | B1 | 1/2002 | Toledano |
| 6,338,738 | B1 | 1/2002 | Bellotti et al. |
| 6,343,731 | B1 | 2/2002 | Adams et al. |
| 6,346,077 | B1 | 2/2002 | Taylor et al. |
| 6,348,061 | B1 | 2/2002 | Whitman |
| 6,349,868 | B1 | 2/2002 | Mattingly et al. |
| D454,951 | S | 3/2002 | Bon |
| 6,352,503 | B1 | 3/2002 | Matsui et al. |
| 6,352,532 | B1 | 3/2002 | Kramer et al. |
| 6,355,699 | B1 | 3/2002 | Vyakarnam et al. |
| 6,356,072 | B1 | 3/2002 | Chass |
| 6,358,224 | B1 | 3/2002 | Tims et al. |
| 6,358,263 | B2 | 3/2002 | Mark et al. |
| 6,358,459 | B1 | 3/2002 | Ziegler et al. |
| 6,361,542 | B1 | 3/2002 | Dimitriu et al. |
| 6,364,828 | B1 | 4/2002 | Yeung et al. |
| 6,364,877 | B1 | 4/2002 | Goble et al. |
| 6,364,888 | B1 | 4/2002 | Niemeyer et al. |
| 6,366,441 | B1 | 4/2002 | Ozawa et al. |
| 6,370,981 | B2 | 4/2002 | Watarai |
| 6,371,114 | B1 | 4/2002 | Schmidt et al. |
| 6,373,152 | B1 | 4/2002 | Wang et al. |
| 6,377,011 | B1 | 4/2002 | Ben-Ur |
| 6,383,201 | B1 | 5/2002 | Dong |
| 6,387,092 | B1 | 5/2002 | Burnside et al. |
| 6,387,113 | B1 | 5/2002 | Hawkins et al. |
| 6,387,114 | B2 | 5/2002 | Adams |
| 6,391,038 | B2 | 5/2002 | Vargas et al. |
| 6,392,854 | B1 | 5/2002 | O'Gorman |
| 6,394,998 | B1 | 5/2002 | Wallace et al. |
| 6,398,779 | B1 | 6/2002 | Buysse et al. |
| 6,398,781 | B1 | 6/2002 | Goble et al. |
| 6,398,797 | B2 | 6/2002 | Bombard et al. |
| 6,402,766 | B2 | 6/2002 | Bowman et al. |
| 6,402,780 | B2 | 6/2002 | Williamson, IV et al. |
| 6,406,440 | B1 | 6/2002 | Stefanchik |
| 6,406,472 | B1 | 6/2002 | Jensen |
| 6,409,724 | B1 | 6/2002 | Penny et al. |
| H2037 | H | 7/2002 | Yates et al. |
| 6,412,639 | B1 | 7/2002 | Hickey |
| 6,413,274 | B1 | 7/2002 | Pedros |
| 6,415,542 | B1 | 7/2002 | Bates et al. |
| 6,416,486 | B1 | 7/2002 | Wampler |
| 6,416,509 | B1 | 7/2002 | Goble et al. |
| 6,419,695 | B1 | 7/2002 | Gabbay |
| 6,423,079 | B1 | 7/2002 | Blake, III |
| 6,424,885 | B1 | 7/2002 | Niemeyer et al. |
| RE37,814 | E | 8/2002 | Allgeyer |
| 6,428,070 | B1 | 8/2002 | Takanashi et al. |
| 6,428,487 | B1 | 8/2002 | Burdorff et al. |
| 6,429,611 | B1 | 8/2002 | Li |
| 6,430,298 | B1 | 8/2002 | Kettl et al. |
| 6,432,065 | B1 | 8/2002 | Burdorff et al. |
| 6,436,097 | B1 | 8/2002 | Nardella |
| 6,436,107 | B1 | 8/2002 | Wang et al. |
| 6,436,110 | B2 | 8/2002 | Bowman et al. |
| 6,436,115 | B1 | 8/2002 | Beaupre |
| 6,436,122 | B1 | 8/2002 | Frank et al. |
| 6,439,439 | B1 | 8/2002 | Rickard et al. |
| 6,439,446 | B1 | 8/2002 | Perry et al. |
| 6,440,146 | B2 | 8/2002 | Nicholas et al. |
| 6,441,577 | B2 | 8/2002 | Blumenkranz et al. |
| D462,758 | S | 9/2002 | Epstein et al. |
| 6,443,973 | B1 | 9/2002 | Whitman |
| 6,445,530 | B1 | 9/2002 | Baker |
| 6,447,518 | B1 | 9/2002 | Krause et al. |
| 6,447,523 | B1 | 9/2002 | Middleman et al. |
| 6,447,799 | B1 | 9/2002 | Ullman |
| 6,447,864 | B2 | 9/2002 | Johnson et al. |
| 6,450,391 | B1 | 9/2002 | Kayan et al. |
| 6,450,989 | B2 | 9/2002 | Dubrul et al. |
| 6,454,656 | B2 | 9/2002 | Brissette et al. |
| 6,454,781 | B1 | 9/2002 | Witt et al. |
| 6,457,338 | B1 | 10/2002 | Frenken |
| 6,457,625 | B1 | 10/2002 | Tormala et al. |
| 6,458,077 | B1 | 10/2002 | Boebel et al. |
| 6,458,142 | B1 | 10/2002 | Faller et al. |
| 6,458,147 | B1 | 10/2002 | Cruise et al. |
| 6,460,627 | B1 | 10/2002 | Below et al. |
| 6,463,824 | B1 | 10/2002 | Prell et al. |
| 6,468,275 | B1 | 10/2002 | Wampler et al. |
| 6,468,286 | B2 | 10/2002 | Mastri et al. |
| 6,471,106 | B1 | 10/2002 | Reining |
| 6,471,659 | B2 | 10/2002 | Eggers et al. |
| 6,478,210 | B2 | 11/2002 | Adams et al. |
| 6,482,063 | B1 | 11/2002 | Frigard |
| 6,482,200 | B2 | 11/2002 | Shippert |
| 6,482,217 | B1 | 11/2002 | Pintor et al. |
| 6,485,490 | B2 | 11/2002 | Wampler et al. |
| 6,485,503 | B2 | 11/2002 | Jacobs et al. |
| 6,485,667 | B1 | 11/2002 | Tan |
| 6,486,286 | B1 | 11/2002 | McGall et al. |
| 6,488,196 | B1 | 12/2002 | Fenton, Jr. |
| 6,488,197 | B1 | 12/2002 | Whitman |
| 6,488,659 | B1 | 12/2002 | Rosenman |
| 6,491,201 | B1 | 12/2002 | Whitman |
| 6,491,690 | B1 | 12/2002 | Goble et al. |
| 6,491,701 | B2 | 12/2002 | Tierney et al. |
| 6,491,702 | B2 | 12/2002 | Heilbrun et al. |
| 6,492,785 | B1 | 12/2002 | Kasten et al. |
| 6,494,882 | B1 | 12/2002 | Lebouitz et al. |
| 6,494,885 | B1 | 12/2002 | Dhindsa |
| 6,494,888 | B1 | 12/2002 | Laufer et al. |
| 6,494,896 | B1 | 12/2002 | D'Alessio et al. |
| 6,498,480 | B1 | 12/2002 | Manara |
| 6,500,176 | B1 | 12/2002 | Truckai et al. |
| 6,500,189 | B1 | 12/2002 | Lang et al. |
| 6,500,194 | B2 | 12/2002 | Benderev et al. |
| D468,749 | S | 1/2003 | Friedman |
| 6,503,139 | B2 | 1/2003 | Coral |
| 6,503,257 | B2 | 1/2003 | Grant et al. |

(56) References Cited

U.S. PATENT DOCUMENTS

| | | | |
|---|---|---|---|
| 6,503,259 | B2 | 1/2003 | Huxel et al. |
| 6,505,768 | B2 | 1/2003 | Whitman |
| 6,506,197 | B1 | 1/2003 | Rollero et al. |
| 6,506,399 | B2 | 1/2003 | Donovan |
| 6,510,854 | B2 | 1/2003 | Goble |
| 6,511,468 | B1 | 1/2003 | Cragg et al. |
| 6,512,360 | B1 | 1/2003 | Goto et al. |
| 6,514,252 | B2 | 2/2003 | Nezhat et al. |
| 6,516,073 | B1 | 2/2003 | Schulz et al. |
| 6,517,528 | B1 | 2/2003 | Pantages et al. |
| 6,517,535 | B2 | 2/2003 | Edwards |
| 6,517,565 | B1 | 2/2003 | Whitman et al. |
| 6,517,566 | B1 | 2/2003 | Hovland et al. |
| 6,520,971 | B1 | 2/2003 | Perry et al. |
| 6,520,972 | B2 | 2/2003 | Peters |
| 6,522,101 | B2 | 2/2003 | Malackowski |
| 6,524,180 | B1 | 2/2003 | Simms et al. |
| 6,525,499 | B2 | 2/2003 | Naganuma |
| D471,206 | S | 3/2003 | Buzzard et al. |
| 6,527,782 | B2 | 3/2003 | Hogg et al. |
| 6,527,785 | B2 | 3/2003 | Sancoff et al. |
| 6,530,942 | B2 | 3/2003 | Fogarty et al. |
| 6,532,958 | B1 | 3/2003 | Buan et al. |
| 6,533,157 | B1 | 3/2003 | Whitman |
| 6,533,723 | B1 | 3/2003 | Lockery et al. |
| 6,533,784 | B2 | 3/2003 | Truckai et al. |
| 6,535,764 | B2 | 3/2003 | Imran et al. |
| 6,539,297 | B2 | 3/2003 | Weiberle et al. |
| D473,239 | S | 4/2003 | Cockerill |
| 6,539,816 | B2 | 4/2003 | Kogiso et al. |
| 6,540,737 | B2 | 4/2003 | Bacher et al. |
| 6,543,456 | B1 | 4/2003 | Freeman |
| 6,545,384 | B1 | 4/2003 | Pelrine et al. |
| 6,547,786 | B1 | 4/2003 | Goble |
| 6,550,546 | B2 | 4/2003 | Thurler et al. |
| 6,551,333 | B2 | 4/2003 | Kuhns et al. |
| 6,554,844 | B2 | 4/2003 | Lee et al. |
| 6,554,861 | B2 | 4/2003 | Knox et al. |
| 6,555,770 | B2 | 4/2003 | Kawase |
| 6,558,378 | B2 | 5/2003 | Sherman et al. |
| 6,558,379 | B1 | 5/2003 | Batchelor et al. |
| 6,558,429 | B2 | 5/2003 | Taylor |
| 6,561,187 | B2 | 5/2003 | Schmidt et al. |
| 6,565,560 | B1 | 5/2003 | Goble et al. |
| 6,566,619 | B2 | 5/2003 | Gillman et al. |
| 6,569,085 | B2 | 5/2003 | Kortenbach et al. |
| 6,569,171 | B2 | 5/2003 | DeGuillebon et al. |
| 6,569,173 | B1 | 5/2003 | Blatter et al. |
| 6,572,629 | B2 | 6/2003 | Kalloo et al. |
| 6,575,969 | B1 | 6/2003 | Rittman, III et al. |
| 6,578,751 | B2 | 6/2003 | Hartwick |
| 6,582,364 | B2 | 6/2003 | Butler et al. |
| 6,582,427 | B1 | 6/2003 | Goble et al. |
| 6,582,441 | B1 | 6/2003 | He et al. |
| 6,583,533 | B2 | 6/2003 | Pelrine et al. |
| 6,585,144 | B2 | 7/2003 | Adams et al. |
| 6,585,664 | B2 | 7/2003 | Burdorff et al. |
| 6,586,898 | B2 | 7/2003 | King et al. |
| 6,587,750 | B2 | 7/2003 | Gerbi et al. |
| 6,588,277 | B2 | 7/2003 | Giordano et al. |
| 6,588,643 | B2 | 7/2003 | Bolduc et al. |
| 6,588,931 | B2 | 7/2003 | Betzner et al. |
| 6,589,118 | B1 | 7/2003 | Soma et al. |
| 6,589,164 | B1 | 7/2003 | Flaherty |
| 6,592,538 | B1 | 7/2003 | Hotchkiss et al. |
| 6,592,572 | B1 | 7/2003 | Suzuta |
| 6,592,597 | B2 | 7/2003 | Grant et al. |
| 6,594,552 | B1 | 7/2003 | Nowlin et al. |
| 6,595,914 | B2 | 7/2003 | Kato |
| 6,596,296 | B1 | 7/2003 | Nelson et al. |
| 6,596,304 | B1 | 7/2003 | Bayon et al. |
| 6,596,432 | B2 | 7/2003 | Kawakami et al. |
| 6,599,295 | B1 | 7/2003 | Tornier et al. |
| 6,599,323 | B2 | 7/2003 | Melican et al. |
| D478,665 | S | 8/2003 | Isaacs et al. |
| D478,986 | S | 8/2003 | Johnston et al. |
| 6,601,749 | B2 | 8/2003 | Sullivan et al. |
| 6,602,252 | B2 | 8/2003 | Mollenauer |
| 6,602,262 | B2 | 8/2003 | Griego et al. |
| 6,603,050 | B2 | 8/2003 | Heaton |
| 6,605,078 | B2 | 8/2003 | Adams |
| 6,605,669 | B2 | 8/2003 | Awokola et al. |
| 6,605,911 | B1 | 8/2003 | Klesing |
| 6,607,475 | B2 | 8/2003 | Doyle et al. |
| 6,611,793 | B1 | 8/2003 | Burnside et al. |
| 6,613,069 | B2 | 9/2003 | Boyd et al. |
| 6,616,686 | B2 | 9/2003 | Coleman et al. |
| 6,619,529 | B2 | 9/2003 | Green et al. |
| 6,620,111 | B2 | 9/2003 | Stephens et al. |
| 6,620,161 | B2 | 9/2003 | Schulze et al. |
| 6,620,166 | B1 | 9/2003 | Wenstrom, Jr. et al. |
| 6,623,482 | B2 | 9/2003 | Pendekanti et al. |
| 6,625,517 | B1 | 9/2003 | Bogdanov et al. |
| 6,626,834 | B2 | 9/2003 | Dunne et al. |
| 6,626,901 | B1 | 9/2003 | Treat et al. |
| 6,626,938 | B1 | 9/2003 | Butaric et al. |
| H2086 | H | 10/2003 | Amsler |
| 6,629,630 | B2 | 10/2003 | Adams |
| 6,629,974 | B2 | 10/2003 | Penny et al. |
| 6,629,988 | B2 | 10/2003 | Weadock |
| 6,635,838 | B1 | 10/2003 | Kornelson |
| 6,636,412 | B2 | 10/2003 | Smith |
| 6,638,108 | B2 | 10/2003 | Tachi |
| 6,638,285 | B2 | 10/2003 | Gabbay |
| 6,638,297 | B1 | 10/2003 | Huitema |
| RE38,335 | E | 11/2003 | Aust et al. |
| 6,641,528 | B2 | 11/2003 | Torii |
| 6,644,532 | B2 | 11/2003 | Green et al. |
| 6,645,201 | B1 | 11/2003 | Utley et al. |
| 6,646,307 | B1 | 11/2003 | Yu et al. |
| 6,648,816 | B2 | 11/2003 | Irion et al. |
| 6,648,901 | B2 | 11/2003 | Fleischman et al. |
| 6,652,595 | B1 | 11/2003 | Nicolo |
| D484,243 | S | 12/2003 | Ryan et al. |
| D484,595 | S | 12/2003 | Ryan et al. |
| D484,596 | S | 12/2003 | Ryan et al. |
| 6,656,177 | B2 | 12/2003 | Truckai et al. |
| 6,656,193 | B2 | 12/2003 | Grant et al. |
| 6,659,940 | B2 | 12/2003 | Adler |
| 6,660,008 | B1 | 12/2003 | Foerster et al. |
| 6,663,623 | B1 | 12/2003 | Oyama et al. |
| 6,663,641 | B1 | 12/2003 | Kovac et al. |
| 6,666,854 | B1 | 12/2003 | Lange |
| 6,666,860 | B1 | 12/2003 | Takahashi |
| 6,666,875 | B1 | 12/2003 | Sakurai et al. |
| 6,667,825 | B2 | 12/2003 | Lu et al. |
| 6,669,073 | B2 | 12/2003 | Milliman et al. |
| 6,670,806 | B2 | 12/2003 | Wendt et al. |
| 6,671,185 | B2 | 12/2003 | Duval |
| D484,977 | S | 1/2004 | Ryan et al. |
| 6,676,660 | B2 | 1/2004 | Wampler et al. |
| 6,677,687 | B2 | 1/2004 | Ho et al. |
| 6,679,269 | B2 | 1/2004 | Swanson |
| 6,679,410 | B2 | 1/2004 | Wursch et al. |
| 6,681,978 | B2 | 1/2004 | Geiste et al. |
| 6,681,979 | B2 | 1/2004 | Whitman |
| 6,682,527 | B2 | 1/2004 | Strul |
| 6,682,528 | B2 | 1/2004 | Frazier et al. |
| 6,682,544 | B2 | 1/2004 | Mastri et al. |
| 6,685,698 | B2 | 2/2004 | Morley et al. |
| 6,685,727 | B2 | 2/2004 | Fisher et al. |
| 6,689,153 | B1 | 2/2004 | Skiba |
| 6,692,507 | B2 | 2/2004 | Pugsley et al. |
| 6,692,692 | B2 | 2/2004 | Stetzel |
| 6,695,198 | B2 | 2/2004 | Adams et al. |
| 6,695,199 | B2 | 2/2004 | Whitman |
| 6,695,774 | B2 | 2/2004 | Hale et al. |
| 6,695,849 | B2 | 2/2004 | Michelson |
| 6,696,814 | B2 | 2/2004 | Henderson et al. |
| 6,697,048 | B2 | 2/2004 | Rosenberg et al. |
| 6,698,643 | B2 | 3/2004 | Whitman |
| 6,699,177 | B1 | 3/2004 | Wang et al. |
| 6,699,214 | B2 | 3/2004 | Gellman |
| 6,699,235 | B2 | 3/2004 | Wallace et al. |

(56) References Cited

U.S. PATENT DOCUMENTS 6,704,210 B1 3/2004 Myers
6,705,503 B1 3/2004 Pedicini et al.
6,709,445 B2 3/2004 Boebel et al.
6,712,773 B1 3/2004 Viola
6,716,215 B1 4/2004 David et al.
6,716,223 B2 4/2004 Leopold et al.
6,716,232 B1 4/2004 Vidal et al.
6,716,233 B1 4/2004 Whitman
6,720,734 B2 4/2004 Norris
6,722,550 B1 4/2004 Ricordi et al.
6,722,552 B2 4/2004 Fenton, Jr.
6,723,087 B2 4/2004 O'Neill et al.
6,723,091 B2 4/2004 Goble et al.
6,723,106 B1 4/2004 Charles et al.
6,723,109 B2 4/2004 Solingen
6,726,651 B1 4/2004 Robinson et al.
6,726,697 B2 4/2004 Nicholas et al.
6,726,705 B2 4/2004 Peterson et al.
6,726,706 B2 4/2004 Dominguez
6,729,119 B2 5/2004 Schnipke et al.
6,731,976 B2 5/2004 Penn et al.
6,736,810 B2 5/2004 Hoey et al.
6,736,825 B2 5/2004 Blatter et al.
6,736,854 B2 5/2004 Vadurro et al.
6,740,030 B2 5/2004 Martone et al.
6,743,230 B2 6/2004 Lutze et al.
6,744,385 B2 6/2004 Kazuya et al.
6,747,121 B2 6/2004 Gogolewski
6,747,300 B2 6/2004 Nadd et al.
6,749,560 B1 6/2004 Konstorum et al.
6,749,600 B1 6/2004 Levy
6,750,622 B2 6/2004 Simizu et al.
6,752,768 B2 6/2004 Burdorff et al.
6,752,816 B2 6/2004 Culp et al.
6,754,959 B1 6/2004 Guiette, III et al.
6,755,195 B1 6/2004 Lemke et al.
6,755,338 B2 6/2004 Hahnen et al.
6,755,825 B2 6/2004 Shoenman et al.
6,755,843 B2 6/2004 Chung et al.
6,756,705 B2 6/2004 Pulford, Jr.
6,758,846 B2 7/2004 Goble et al.
6,761,685 B2 7/2004 Adams et al.
6,762,339 B1 7/2004 Klun et al.
6,763,307 B2 7/2004 Berg et al.
6,764,445 B2 7/2004 Ramans et al.
6,766,957 B2 7/2004 Matsuura et al.
6,767,352 B2 7/2004 Field et al.
6,767,356 B2 7/2004 Kanner et al.
6,769,590 B2 8/2004 Vresh et al.
6,769,594 B2 8/2004 Orban, III
6,770,027 B2 8/2004 Banik et al.
6,770,070 B1 8/2004 Balbierz
6,770,072 B1 8/2004 Truckai et al.
6,770,078 B2 8/2004 Bonutti
6,773,409 B2 8/2004 Truckai et al.
6,773,437 B2 8/2004 Ogilvie et al.
6,773,438 B1 8/2004 Knodel et al.
6,773,458 B1 8/2004 Brauker et al.
6,775,575 B2 8/2004 Bommannan et al.
6,777,838 B2 8/2004 Miekka et al.
6,778,846 B1 8/2004 Martinez et al.
6,780,151 B2 8/2004 Grabover et al.
6,780,180 B1 8/2004 Goble et al.
6,783,524 B2 8/2004 Anderson et al.
6,784,775 B2 8/2004 Mandell et al.
6,786,382 B1 9/2004 Hoffman
6,786,864 B2 9/2004 Matsuura et al.
6,786,896 B1 9/2004 Madhani et al.
6,788,018 B1 9/2004 Blumenkranz
6,790,173 B2 9/2004 Saadat et al.
6,793,652 B1 9/2004 Whitman et al.
6,793,661 B2 9/2004 Hamilton et al.
6,793,663 B2 9/2004 Kneifel et al.
6,793,669 B2 9/2004 Nakamura et al.
6,796,921 B1 9/2004 Buck et al.
6,799,669 B2 10/2004 Fukumura et al.
6,801,009 B2 10/2004 Makaran et al.
6,802,822 B1 10/2004 Dodge
6,802,843 B2 10/2004 Truckai et al.
6,802,844 B2 10/2004 Ferree
6,805,273 B2 10/2004 Bilotti et al.
6,806,808 B1 10/2004 Watters et al.
6,806,867 B1 10/2004 Arruda et al.
6,808,525 B2 10/2004 Latterell et al.
6,810,359 B2 10/2004 Sakaguchi
6,814,154 B2 11/2004 Chou
6,814,741 B2 11/2004 Bowman et al.
6,817,508 B1 11/2004 Racenet et al.
6,817,509 B2 11/2004 Geiste et al.
6,817,974 B2 11/2004 Cooper et al.
6,818,018 B1 11/2004 Sawhney
6,819,269 B2 11/2004 Flick
6,820,791 B2 11/2004 Adams
6,821,273 B2 11/2004 Mollenauer
6,821,282 B2 11/2004 Perry et al.
6,821,284 B2 11/2004 Sturtz et al.
6,827,246 B2 12/2004 Sullivan et al.
6,827,712 B2 12/2004 Tovey et al.
6,827,725 B2 12/2004 Batchelor et al.
6,828,902 B2 12/2004 Casden
6,830,174 B2 12/2004 Hillstead et al.
6,831,629 B2 12/2004 Nishino et al.
6,832,998 B2 12/2004 Goble
6,834,001 B2 12/2004 Myono
6,835,173 B2 12/2004 Couvillon, Jr.
6,835,199 B2 12/2004 McGuckin, Jr. et al.
6,835,336 B2 12/2004 Watt
6,836,611 B2 12/2004 Popovic et al.
6,837,846 B2 1/2005 Jaffe et al.
6,837,883 B2 1/2005 Moll et al.
6,838,493 B2 1/2005 Williams et al.
6,840,423 B2 1/2005 Adams et al.
6,840,938 B1 1/2005 Morley et al.
6,841,967 B2 1/2005 Kim et al.
6,843,403 B2 1/2005 Whitman
6,843,789 B2 1/2005 Goble
6,843,793 B2 1/2005 Brock et al.
6,846,307 B2 1/2005 Whitman et al.
6,846,308 B2 1/2005 Whitman et al.
6,846,309 B2 1/2005 Whitman et al.
6,847,190 B2 1/2005 Schaefer et al.
6,849,071 B2 2/2005 Whitman et al.
6,850,817 B1 2/2005 Green
6,852,122 B2 2/2005 Rush
6,852,330 B2 2/2005 Bowman et al.
6,853,879 B2 2/2005 Sunaoshi
6,858,005 B2 2/2005 Ohline et al.
6,859,882 B2 2/2005 Fung
RE38,708 E 3/2005 Bolanos et al.
D502,994 S 3/2005 Blake, III
6,860,169 B2 3/2005 Shinozaki
6,861,142 B1 3/2005 Wilkie et al.
6,861,954 B2 3/2005 Levin
6,863,668 B2 3/2005 Gillespie et al.
6,863,694 B1 3/2005 Boyce et al.
6,863,924 B2 3/2005 Ranganathan et al.
6,866,178 B2 3/2005 Adams et al.
6,866,668 B2 3/2005 Giannetti et al.
6,866,671 B2 3/2005 Tierney et al.
6,867,248 B1 3/2005 Martin et al.
6,869,430 B2 3/2005 Balbierz et al.
6,869,435 B2 3/2005 Blake, III
6,872,214 B2 3/2005 Sonnenschein et al.
6,874,669 B2 4/2005 Adams et al.
6,876,850 B2 4/2005 Maeshima et al.
6,877,647 B2 4/2005 Green et al.
6,878,106 B1 4/2005 Herrmann
6,882,127 B2 4/2005 Konigbauer
6,883,199 B1 4/2005 Lundell et al.
6,884,392 B2 4/2005 Malkin et al.
6,884,428 B2 4/2005 Binette et al.
6,886,730 B2 5/2005 Fujisawa et al.
6,887,244 B1 5/2005 Walker et al.
6,887,710 B2 5/2005 Call et al.

(56) References Cited

U.S. PATENT DOCUMENTS 6,889,116 B2 5/2005 Jinno
6,893,435 B2 5/2005 Goble
6,894,140 B2 5/2005 Roby
6,895,176 B2 5/2005 Archer et al.
6,899,538 B2 5/2005 Matoba
6,899,593 B1 5/2005 Moeller et al.
6,899,705 B2 5/2005 Niemeyer
6,899,915 B2 5/2005 Yelick et al.
6,905,057 B2 6/2005 Swayze et al.
6,905,497 B2 6/2005 Truckai et al.
6,905,498 B2 6/2005 Hooven
6,908,472 B2 6/2005 Wiener et al.
6,911,033 B2 6/2005 de Guillebon et al.
6,911,916 B1 6/2005 Wang et al.
6,913,579 B2 7/2005 Truckai et al.
6,913,608 B2 7/2005 Liddicoat et al.
6,913,613 B2 7/2005 Schwarz et al.
6,921,397 B2 7/2005 Corcoran et al.
6,921,412 B1 7/2005 Black et al.
6,923,093 B2 8/2005 Ullah
6,923,803 B2 8/2005 Goble
6,923,819 B2 8/2005 Meade et al.
6,925,849 B2 8/2005 Jairam
6,926,716 B2 8/2005 Baker et al.
6,927,315 B1 8/2005 Heinecke et al.
6,928,902 B1 8/2005 Eyssallenne
6,929,641 B2 8/2005 Goble et al.
6,929,644 B2 8/2005 Truckai et al.
6,931,830 B2 8/2005 Liao
6,932,218 B2 8/2005 Kosann et al.
6,932,810 B2 8/2005 Ryan
6,936,042 B2 8/2005 Wallace et al.
6,936,948 B2 8/2005 Bell et al.
D509,297 S 9/2005 Wells
D509,589 S 9/2005 Wells
6,938,706 B2 9/2005 Ng
6,939,358 B2 9/2005 Palacios et al.
6,942,662 B2 9/2005 Goble et al.
6,942,674 B2 9/2005 Belef et al.
6,945,444 B2 9/2005 Gresham et al.
6,945,981 B2 9/2005 Donofrio et al.
6,949,196 B2 9/2005 Schmitz et al.
6,951,562 B2 10/2005 Zwirnmann
6,953,138 B1 10/2005 Dworak et al.
6,953,139 B2 10/2005 Milliman et al.
6,953,461 B2 10/2005 McClurken et al.
6,957,758 B2 10/2005 Aranyi
6,958,035 B2 10/2005 Friedman et al.
6,958,070 B2 10/2005 Witt et al.
D511,525 S 11/2005 Hernandez et al.
6,959,851 B2 11/2005 Heinrich
6,959,852 B2 11/2005 Shelton, IV et al.
6,960,107 B1 11/2005 Schaub et al.
6,960,163 B2 11/2005 Ewers et al.
6,960,220 B2 11/2005 Marino et al.
6,960,894 B2 11/2005 Carusillo et al.
6,962,587 B2 11/2005 Johnson et al.
6,963,792 B1 11/2005 Green
6,964,363 B2 11/2005 Wales et al.
6,966,907 B2 11/2005 Goble
6,966,909 B2 11/2005 Marshall et al.
6,968,908 B2 11/2005 Tokunaga et al.
6,969,385 B2 11/2005 Moreyra
6,969,395 B2 11/2005 Eskuri
6,971,988 B2 12/2005 Orban, III
6,972,199 B2 12/2005 Lebouitz et al.
6,974,435 B2 12/2005 Daw et al.
6,974,462 B2 12/2005 Sater
6,978,921 B2 12/2005 Shelton, IV et al.
6,978,922 B2 12/2005 Bilotti et al.
6,981,628 B2 1/2006 Wales
6,981,941 B2 1/2006 Whitman et al.
6,981,978 B2 1/2006 Gannoe
6,984,203 B2 1/2006 Tartaglia et al.
6,984,231 B2 1/2006 Goble et al.
6,986,451 B1 1/2006 Mastri et al.
6,988,649 B2 1/2006 Shelton, IV et al.
6,988,650 B2 1/2006 Schwemberger et al.
6,989,034 B2 1/2006 Hammer et al.
6,990,731 B2 1/2006 Haytayan
6,990,796 B2 1/2006 Schnipke et al.
6,991,146 B2 1/2006 Sinisi et al.
6,993,200 B2 1/2006 Tastl et al.
6,993,413 B2 1/2006 Sunaoshi
6,994,708 B2 2/2006 Manzo
6,995,729 B2 2/2006 Govari et al.
6,996,433 B2 2/2006 Burbank et al.
6,997,931 B2 2/2006 Sauer et al.
6,997,935 B2 2/2006 Anderson et al.
6,998,736 B2 2/2006 Lee et al.
6,998,816 B2 2/2006 Wieck et al.
6,999,821 B2 2/2006 Jenney et al.
7,000,818 B2 2/2006 Shelton, IV et al.
7,000,819 B2 2/2006 Swayze et al.
7,000,911 B2 2/2006 McCormick et al.
7,001,380 B2 2/2006 Goble
7,001,408 B2 2/2006 Knodel et al.
7,004,174 B2 2/2006 Eggers et al.
7,005,828 B2 2/2006 Karikomi
7,007,176 B2 2/2006 Goodfellow et al.
7,008,433 B2 3/2006 Voellmicke et al.
7,008,435 B2 3/2006 Cummins
7,009,039 B2 3/2006 Yayon et al.
7,011,213 B2 3/2006 Clark et al.
7,011,657 B2 3/2006 Truckai et al.
7,014,640 B2 3/2006 Kemppainen et al.
7,018,357 B2 3/2006 Emmons
7,018,390 B2 3/2006 Turovskiy et al.
7,021,399 B2 4/2006 Driessen
7,021,669 B1 4/2006 Lindermeir et al.
7,022,131 B1 4/2006 Derowe et al.
7,023,159 B2 4/2006 Gorti et al.
7,025,064 B2 4/2006 Wang et al.
7,025,732 B2 4/2006 Thompson et al.
7,025,743 B2 4/2006 Mann et al.
7,025,774 B2 4/2006 Freeman et al.
7,025,775 B2 4/2006 Gadberry et al.
7,028,570 B2 4/2006 Ohta et al.
7,029,435 B2 4/2006 Nakao
7,029,439 B2 4/2006 Roberts et al.
7,030,904 B2 4/2006 Adair et al.
7,032,798 B2 4/2006 Whitman et al.
7,032,799 B2 4/2006 Viola et al.
7,033,356 B2 4/2006 Latterell et al.
7,033,378 B2 4/2006 Smith et al.
7,035,716 B2 4/2006 Harris et al.
7,035,762 B2 4/2006 Menard et al.
7,036,680 B1 5/2006 Flannery
7,037,314 B2 5/2006 Armstrong
7,037,344 B2 5/2006 Kagan et al.
7,038,421 B2 5/2006 Trifilo
7,041,088 B2 5/2006 Nawrocki et al.
7,041,102 B2 5/2006 Truckai et al.
7,041,868 B2 5/2006 Greene et al.
7,043,852 B2 5/2006 Hayashida et al.
7,044,350 B2 5/2006 Kameyama et al.
7,044,352 B2 5/2006 Shelton, IV et al.
7,044,353 B2 5/2006 Mastri et al.
7,046,082 B2 5/2006 Komiya et al.
7,048,165 B2 5/2006 Haramiishi
7,048,687 B1 5/2006 Reuss et al.
7,048,716 B1 5/2006 Kucharczyk et al.
7,048,745 B2 5/2006 Tierney et al.
7,052,454 B2 5/2006 Taylor
7,052,494 B2 5/2006 Goble et al.
7,052,499 B2 5/2006 Steger et al.
7,055,730 B2 6/2006 Ehrenfels et al.
7,055,731 B2 6/2006 Shelton, IV et al.
7,056,123 B2 6/2006 Gregorio et al.
7,056,284 B2 6/2006 Martone et al.
7,056,330 B2 6/2006 Gayton
7,059,331 B2 6/2006 Adams et al.
7,059,508 B2 6/2006 Shelton, IV et al.
7,063,671 B2 6/2006 Couvillon, Jr.

(56) References Cited

U.S. PATENT DOCUMENTS

| | | | |
|---|---|---|---|
| 7,063,712 | B2 | 6/2006 | Vargas et al. |
| 7,064,509 | B1 | 6/2006 | Fu et al. |
| 7,066,879 | B2 | 6/2006 | Fowler et al. |
| 7,066,944 | B2 | 6/2006 | Laufer et al. |
| 7,067,038 | B2 | 6/2006 | Trokhan et al. |
| 7,070,083 | B2 | 7/2006 | Jankowski |
| 7,070,559 | B2 | 7/2006 | Adams et al. |
| 7,070,597 | B2 | 7/2006 | Truckai et al. |
| 7,071,287 | B2 | 7/2006 | Rhine et al. |
| 7,075,412 | B1 | 7/2006 | Reynolds et al. |
| 7,075,770 | B1 | 7/2006 | Smith |
| 7,077,856 | B2 | 7/2006 | Whitman |
| 7,080,769 | B2 | 7/2006 | Vresh et al. |
| 7,081,114 | B2 | 7/2006 | Rashidi |
| 7,081,318 | B2 | 7/2006 | Lee et al. |
| 7,083,073 | B2 | 8/2006 | Yoshie et al. |
| 7,083,075 | B2 | 8/2006 | Swayze et al. |
| 7,083,571 | B2 | 8/2006 | Wang et al. |
| 7,083,615 | B2 | 8/2006 | Peterson et al. |
| 7,083,619 | B2 | 8/2006 | Truckai et al. |
| 7,083,620 | B2 | 8/2006 | Jahns et al. |
| 7,083,626 | B2 | 8/2006 | Hart et al. |
| 7,086,267 | B2 | 8/2006 | Dworak et al. |
| 7,087,049 | B2 | 8/2006 | Nowlin et al. |
| 7,087,054 | B2 | 8/2006 | Truckai et al. |
| 7,087,071 | B2 | 8/2006 | Nicholas et al. |
| 7,090,637 | B2 | 8/2006 | Danitz et al. |
| 7,090,673 | B2 | 8/2006 | Dycus et al. |
| 7,090,683 | B2 | 8/2006 | Brock et al. |
| 7,090,684 | B2 | 8/2006 | McGuckin, Jr. et al. |
| 7,091,191 | B2 | 8/2006 | Laredo et al. |
| 7,091,412 | B2 | 8/2006 | Wang et al. |
| 7,093,492 | B2 | 8/2006 | Treiber et al. |
| 7,094,202 | B2 | 8/2006 | Nobis et al. |
| 7,094,247 | B2 | 8/2006 | Monassevitch et al. |
| 7,094,916 | B2 | 8/2006 | DeLuca et al. |
| 7,096,972 | B2 | 8/2006 | Orozco, Jr. |
| 7,097,089 | B2 | 8/2006 | Marczyk |
| 7,097,644 | B2 | 8/2006 | Long |
| 7,097,650 | B2 | 8/2006 | Weller et al. |
| 7,098,794 | B2 | 8/2006 | Lindsay et al. |
| 7,100,949 | B2 | 9/2006 | Williams et al. |
| 7,101,187 | B1 | 9/2006 | Deconinck et al. |
| 7,101,363 | B2 | 9/2006 | Nishizawa et al. |
| 7,101,371 | B2 | 9/2006 | Dycus et al. |
| 7,101,394 | B2 | 9/2006 | Hamm et al. |
| 7,104,741 | B2 | 9/2006 | Krohn |
| 7,108,695 | B2 | 9/2006 | Witt et al. |
| 7,108,701 | B2 | 9/2006 | Evens et al. |
| 7,108,709 | B2 | 9/2006 | Cummins |
| 7,111,768 | B2 | 9/2006 | Cummins et al. |
| 7,111,769 | B2 | 9/2006 | Wales et al. |
| 7,112,201 | B2 | 9/2006 | Truckai et al. |
| 7,112,214 | B2 | 9/2006 | Peterson et al. |
| RE39,358 | E | 10/2006 | Goble |
| D530,339 | S | 10/2006 | Hernandez et al. |
| 7,114,642 | B2 | 10/2006 | Whitman |
| 7,116,100 | B1 | 10/2006 | Mock et al. |
| 7,118,020 | B2 | 10/2006 | Lee et al. |
| 7,118,528 | B1 | 10/2006 | Piskun |
| 7,118,563 | B2 | 10/2006 | Weckwerth et al. |
| 7,118,582 | B1 | 10/2006 | Wang et al. |
| 7,119,534 | B2 | 10/2006 | Butzmann |
| 7,121,446 | B2 | 10/2006 | Arad et al. |
| 7,121,773 | B2 | 10/2006 | Mikiya et al. |
| 7,122,028 | B2 | 10/2006 | Looper et al. |
| 7,125,403 | B2 | 10/2006 | Julian et al. |
| 7,125,409 | B2 | 10/2006 | Truckai et al. |
| 7,126,303 | B2 | 10/2006 | Farritor et al. |
| 7,126,879 | B2 | 10/2006 | Snyder |
| 7,128,253 | B2 | 10/2006 | Mastri et al. |
| 7,128,254 | B2 | 10/2006 | Shelton, IV et al. |
| 7,128,748 | B2 | 10/2006 | Mooradian et al. |
| 7,131,445 | B2 | 11/2006 | Amoah |
| 7,133,601 | B2 | 11/2006 | Phillips et al. |
| 7,134,364 | B2 | 11/2006 | Kageler et al. |
| 7,134,587 | B2 | 11/2006 | Schwemberger et al. |
| 7,135,027 | B2 | 11/2006 | Delmotte |
| 7,137,980 | B2 | 11/2006 | Buysse et al. |
| 7,137,981 | B2 | 11/2006 | Long |
| 7,139,016 | B2 | 11/2006 | Squilla et al. |
| 7,140,527 | B2 | 11/2006 | Ehrenfels et al. |
| 7,140,528 | B2 | 11/2006 | Shelton, IV |
| 7,141,055 | B2 | 11/2006 | Abrams et al. |
| 7,143,923 | B2 | 12/2006 | Shelton, IV et al. |
| 7,143,924 | B2 | 12/2006 | Scirica et al. |
| 7,143,925 | B2 | 12/2006 | Shelton, IV et al. |
| 7,143,926 | B2 | 12/2006 | Shelton, IV et al. |
| 7,146,191 | B2 | 12/2006 | Kerner et al. |
| 7,147,138 | B2 | 12/2006 | Shelton, IV |
| 7,147,139 | B2 | 12/2006 | Schwemberger et al. |
| 7,147,140 | B2 | 12/2006 | Wukusick et al. |
| 7,147,637 | B2 | 12/2006 | Goble |
| 7,147,648 | B2 | 12/2006 | Lin |
| 7,147,650 | B2 | 12/2006 | Lee |
| 7,150,748 | B2 | 12/2006 | Ebbutt et al. |
| 7,153,300 | B2 | 12/2006 | Goble |
| 7,153,314 | B2 | 12/2006 | Laufer et al. |
| 7,155,316 | B2 | 12/2006 | Sutherland et al. |
| 7,156,846 | B2 | 1/2007 | Dycus et al. |
| 7,156,863 | B2 | 1/2007 | Sonnenschein et al. |
| 7,159,750 | B2 | 1/2007 | Racenet et al. |
| 7,160,296 | B2 | 1/2007 | Pearson et al. |
| 7,160,299 | B2 | 1/2007 | Baily |
| 7,160,311 | B2 | 1/2007 | Blatter et al. |
| 7,161,036 | B2 | 1/2007 | Oikawa et al. |
| 7,161,580 | B2 | 1/2007 | Bailey et al. |
| 7,162,758 | B2 | 1/2007 | Skinner |
| 7,163,563 | B2 | 1/2007 | Schwartz et al. |
| 7,166,117 | B2 | 1/2007 | Hellenkamp |
| 7,166,133 | B2 | 1/2007 | Evans et al. |
| 7,168,604 | B2 | 1/2007 | Milliman et al. |
| 7,169,146 | B2 | 1/2007 | Truckai et al. |
| 7,170,910 | B2 | 1/2007 | Chen et al. |
| 7,171,279 | B2 | 1/2007 | Buckingham et al. |
| 7,172,104 | B2 | 2/2007 | Scirica et al. |
| 7,172,593 | B2 | 2/2007 | Trieu et al. |
| 7,172,615 | B2 | 2/2007 | Morriss et al. |
| 7,174,202 | B2 | 2/2007 | Bladen et al. |
| 7,174,636 | B2 | 2/2007 | Lowe |
| 7,177,533 | B2 | 2/2007 | McFarlin et al. |
| 7,179,223 | B2 | 2/2007 | Motoki et al. |
| 7,179,267 | B2 | 2/2007 | Nolan et al. |
| 7,182,239 | B1 | 2/2007 | Myers |
| 7,182,763 | B2 | 2/2007 | Nardella |
| 7,183,737 | B2 | 2/2007 | Kitagawa |
| 7,187,960 | B2 | 3/2007 | Abreu |
| 7,188,758 | B2 | 3/2007 | Viola et al. |
| 7,189,207 | B2 | 3/2007 | Viola |
| 7,190,147 | B2 | 3/2007 | Gileff et al. |
| 7,193,199 | B2 | 3/2007 | Jang |
| 7,195,627 | B2 | 3/2007 | Amoah et al. |
| 7,196,911 | B2 | 3/2007 | Takano et al. |
| D541,418 | S | 4/2007 | Schechter et al. |
| 7,197,965 | B1 | 4/2007 | Anderson |
| 7,199,537 | B2 | 4/2007 | Okamura et al. |
| 7,199,545 | B2 | 4/2007 | Oleynikov et al. |
| 7,202,576 | B1 | 4/2007 | Dechene et al. |
| 7,202,653 | B2 | 4/2007 | Pai |
| 7,204,404 | B2 | 4/2007 | Nguyen et al. |
| 7,204,835 | B2 | 4/2007 | Latterell et al. |
| 7,205,959 | B2 | 4/2007 | Henriksson |
| 7,206,626 | B2 | 4/2007 | Quaid, III |
| 7,207,233 | B2 | 4/2007 | Wadge |
| 7,207,471 | B2 | 4/2007 | Heinrich et al. |
| 7,207,472 | B2 | 4/2007 | Wukusick et al. |
| 7,207,556 | B2 | 4/2007 | Saitoh et al. |
| 7,208,005 | B2 | 4/2007 | Frecker et al. |
| 7,210,609 | B2 | 5/2007 | Leiboff et al. |
| 7,211,081 | B2 | 5/2007 | Goble |
| 7,211,084 | B2 | 5/2007 | Goble et al. |
| 7,211,092 | B2 | 5/2007 | Hughett |
| 7,211,979 | B2 | 5/2007 | Khatib et al. |
| 7,213,736 | B2 | 5/2007 | Wales et al. |

(56) References Cited

U.S. PATENT DOCUMENTS

| | | | |
|---|---|---|---|
| 7,214,224 | B2 | 5/2007 | Goble |
| 7,215,517 | B2 | 5/2007 | Takamatsu |
| 7,217,285 | B2 | 5/2007 | Vargas et al. |
| 7,220,260 | B2 | 5/2007 | Fleming et al. |
| 7,220,272 | B2 | 5/2007 | Weadock |
| 7,225,959 | B2 | 6/2007 | Patton et al. |
| 7,225,963 | B2 | 6/2007 | Scirica |
| 7,225,964 | B2 | 6/2007 | Mastri et al. |
| 7,226,450 | B2 | 6/2007 | Athanasiou et al. |
| 7,226,467 | B2 | 6/2007 | Lucatero et al. |
| 7,228,505 | B2 | 6/2007 | Shimazu et al. |
| 7,229,408 | B2 | 6/2007 | Douglas et al. |
| 7,234,624 | B2 | 6/2007 | Gresham et al. |
| 7,235,072 | B2 | 6/2007 | Sartor et al. |
| 7,235,089 | B1 | 6/2007 | McGuckin, Jr. |
| 7,235,302 | B2 | 6/2007 | Jing et al. |
| 7,237,708 | B1 | 7/2007 | Guy et al. |
| 7,238,195 | B2 | 7/2007 | Viola |
| 7,238,901 | B2 | 7/2007 | Kim et al. |
| 7,239,657 | B1 | 7/2007 | Gunnarsson |
| 7,241,288 | B2 | 7/2007 | Braun |
| 7,241,289 | B2 | 7/2007 | Braun |
| 7,246,734 | B2 | 7/2007 | Shelton, IV |
| 7,247,161 | B2 | 7/2007 | Johnston et al. |
| 7,249,267 | B2 | 7/2007 | Chapuis |
| 7,252,641 | B2 | 8/2007 | Thompson et al. |
| 7,252,660 | B2 | 8/2007 | Kunz |
| 7,255,012 | B2 | 8/2007 | Hedtke |
| 7,255,696 | B2 | 8/2007 | Goble et al. |
| 7,256,695 | B2 | 8/2007 | Hamel et al. |
| 7,258,262 | B2 | 8/2007 | Mastri et al. |
| 7,258,546 | B2 | 8/2007 | Beier et al. |
| 7,260,431 | B2 | 8/2007 | Libbus et al. |
| 7,265,374 | B2 | 9/2007 | Lee et al. |
| 7,267,677 | B2 | 9/2007 | Johnson et al. |
| 7,267,679 | B2 | 9/2007 | McGuckin, Jr. et al. |
| 7,272,002 | B2 | 9/2007 | Drapeau |
| 7,273,483 | B2 | 9/2007 | Wiener et al. |
| 7,273,488 | B2 | 9/2007 | Nakamura et al. |
| D552,623 | S | 10/2007 | Vong et al. |
| 7,275,674 | B2 | 10/2007 | Racenet et al. |
| 7,276,044 | B2 | 10/2007 | Ferry et al. |
| 7,276,068 | B2 | 10/2007 | Johnson et al. |
| 7,278,562 | B2 | 10/2007 | Mastri et al. |
| 7,278,563 | B1 | 10/2007 | Green |
| 7,278,949 | B2 | 10/2007 | Bader |
| 7,278,994 | B2 | 10/2007 | Goble |
| 7,282,048 | B2 | 10/2007 | Goble et al. |
| 7,283,096 | B2 | 10/2007 | Geisheimer et al. |
| 7,286,850 | B2 | 10/2007 | Frielink et al. |
| 7,287,682 | B1 | 10/2007 | Ezzat et al. |
| 7,289,139 | B2 | 10/2007 | Amling et al. |
| 7,293,685 | B2 | 11/2007 | Ehrenfels et al. |
| 7,295,893 | B2 | 11/2007 | Sunaoshi |
| 7,295,907 | B2 | 11/2007 | Lu et al. |
| 7,296,722 | B2 | 11/2007 | Ivanko |
| 7,296,724 | B2 | 11/2007 | Green et al. |
| 7,297,149 | B2 | 11/2007 | Vitali et al. |
| 7,300,373 | B2 | 11/2007 | Jinno et al. |
| 7,300,431 | B2 | 11/2007 | Dubrovsky |
| 7,300,450 | B2 | 11/2007 | Vleugels et al. |
| 7,303,106 | B2 | 12/2007 | Milliman et al. |
| 7,303,107 | B2 | 12/2007 | Milliman et al. |
| 7,303,108 | B2 | 12/2007 | Shelton, IV |
| 7,303,502 | B2 | 12/2007 | Thompson |
| 7,303,556 | B2 | 12/2007 | Metzger |
| 7,306,597 | B2 | 12/2007 | Manzo |
| 7,308,998 | B2 | 12/2007 | Mastri et al. |
| 7,311,238 | B2 | 12/2007 | Liu |
| 7,311,709 | B2 | 12/2007 | Truckai et al. |
| 7,313,430 | B2 | 12/2007 | Urquhart et al. |
| 7,314,473 | B2 | 1/2008 | Jinno et al. |
| 7,317,955 | B2 | 1/2008 | McGreevy |
| 7,320,704 | B2 | 1/2008 | Lashinski et al. |
| 7,322,859 | B2 | 1/2008 | Evans |
| 7,322,975 | B2 | 1/2008 | Goble et al. |
| 7,322,994 | B2 | 1/2008 | Nicholas et al. |
| 7,324,572 | B2 | 1/2008 | Chang |
| 7,326,203 | B2 | 2/2008 | Papineau et al. |
| 7,326,213 | B2 | 2/2008 | Benderev et al. |
| 7,328,828 | B2 | 2/2008 | Ortiz et al. |
| 7,328,829 | B2 | 2/2008 | Arad et al. |
| 7,330,004 | B2 | 2/2008 | DeJonge et al. |
| 7,331,340 | B2 | 2/2008 | Barney |
| 7,331,343 | B2 | 2/2008 | Schmidt et al. |
| 7,331,403 | B2 | 2/2008 | Berry et al. |
| 7,331,406 | B2 | 2/2008 | Wottreng, Jr. et al. |
| 7,331,969 | B1 | 2/2008 | Inganas et al. |
| 7,334,717 | B2 | 2/2008 | Rethy et al. |
| 7,334,718 | B2 | 2/2008 | McAlister et al. |
| 7,335,199 | B2 | 2/2008 | Goble et al. |
| 7,335,401 | B2 | 2/2008 | Finke et al. |
| 7,336,045 | B2 | 2/2008 | Clermonts |
| 7,336,048 | B2 | 2/2008 | Lohr |
| 7,336,183 | B2 | 2/2008 | Reddy et al. |
| 7,336,184 | B2 | 2/2008 | Smith et al. |
| 7,337,774 | B2 | 3/2008 | Webb |
| 7,338,505 | B2 | 3/2008 | Belson |
| 7,338,513 | B2 | 3/2008 | Lee et al. |
| 7,341,554 | B2 | 3/2008 | Sekine et al. |
| 7,341,555 | B2 | 3/2008 | Ootawara et al. |
| 7,341,591 | B2 | 3/2008 | Grinberg |
| 7,343,920 | B2 | 3/2008 | Toby et al. |
| 7,344,532 | B2 | 3/2008 | Goble et al. |
| 7,344,533 | B2 | 3/2008 | Pearson et al. |
| 7,346,344 | B2 | 3/2008 | Fontaine |
| 7,346,406 | B2 | 3/2008 | Brotto et al. |
| 7,348,763 | B1 | 3/2008 | Reinhart et al. |
| 7,348,875 | B2 | 3/2008 | Hughes et al. |
| RE40,237 | E | 4/2008 | Bilotti et al. |
| 7,351,258 | B2 | 4/2008 | Ricotta et al. |
| 7,354,398 | B2 | 4/2008 | Kanazawa |
| 7,354,440 | B2 | 4/2008 | Truckal et al. |
| 7,354,447 | B2 | 4/2008 | Shelton, IV et al. |
| 7,354,502 | B2 | 4/2008 | Polat et al. |
| 7,357,287 | B2 | 4/2008 | Shelton, IV et al. |
| 7,357,806 | B2 | 4/2008 | Rivera et al. |
| 7,361,168 | B2 | 4/2008 | Makower et al. |
| 7,361,195 | B2 | 4/2008 | Schwartz et al. |
| 7,362,062 | B2 | 4/2008 | Schneider et al. |
| 7,364,060 | B2 | 4/2008 | Milliman |
| 7,364,061 | B2 | 4/2008 | Swayze et al. |
| 7,367,485 | B2 | 5/2008 | Shelton, IV et al. |
| 7,367,973 | B2 | 5/2008 | Manzo et al. |
| 7,368,124 | B2 | 5/2008 | Chun et al. |
| 7,371,210 | B2 | 5/2008 | Brock et al. |
| 7,371,403 | B2 | 5/2008 | McCarthy et al. |
| 7,375,493 | B2 | 5/2008 | Calhoon et al. |
| 7,377,918 | B2 | 5/2008 | Amoah |
| 7,377,928 | B2 | 5/2008 | Zubik et al. |
| 7,378,817 | B2 | 5/2008 | Calhoon et al. |
| RE40,388 | E | 6/2008 | Gines |
| D570,868 | S | 6/2008 | Hosokawa et al. |
| 7,380,695 | B2 | 6/2008 | Doll et al. |
| 7,380,696 | B2 | 6/2008 | Shelton, IV et al. |
| 7,384,403 | B2 | 6/2008 | Sherman |
| 7,384,417 | B2 | 6/2008 | Cucin |
| 7,386,365 | B2 | 6/2008 | Nixon |
| 7,386,730 | B2 | 6/2008 | Uchikubo |
| 7,388,217 | B2 | 6/2008 | Buschbeck et al. |
| 7,388,484 | B2 | 6/2008 | Hsu |
| 7,391,173 | B2 | 6/2008 | Schena |
| 7,394,190 | B2 | 7/2008 | Huang |
| 7,396,356 | B2 | 7/2008 | Mollenauer |
| 7,397,364 | B2 | 7/2008 | Govari |
| 7,398,707 | B2 | 7/2008 | Morley et al. |
| 7,398,907 | B2 | 7/2008 | Racenet et al. |
| 7,398,908 | B2 | 7/2008 | Holsten et al. |
| 7,400,107 | B2 | 7/2008 | Schneider et al. |
| 7,400,752 | B2 | 7/2008 | Zacharias |
| 7,401,000 | B2 | 7/2008 | Nakamura |
| 7,401,721 | B2 | 7/2008 | Holsten et al. |
| 7,404,449 | B2 | 7/2008 | Bermingham et al. |
| 7,404,508 | B2 | 7/2008 | Smith et al. |

(56) References Cited

U.S. PATENT DOCUMENTS

| | | | |
|---|---|---|---|
| 7,404,509 | B2 | 7/2008 | Ortiz et al. |
| 7,404,822 | B2 | 7/2008 | Viart et al. |
| D575,793 | S | 8/2008 | Ording |
| 7,407,074 | B2 | 8/2008 | Ortiz et al. |
| 7,407,075 | B2 | 8/2008 | Holsten et al. |
| 7,407,076 | B2 | 8/2008 | Racenet et al. |
| 7,407,077 | B2 | 8/2008 | Ortiz et al. |
| 7,407,078 | B2 | 8/2008 | Shelton, IV et al. |
| 7,408,310 | B2 | 8/2008 | Hong et al. |
| 7,410,085 | B2 | 8/2008 | Wolf et al. |
| 7,410,086 | B2 | 8/2008 | Ortiz et al. |
| 7,410,483 | B2 | 8/2008 | Danitz et al. |
| 7,413,563 | B2 | 8/2008 | Corcoran et al. |
| 7,416,101 | B2 | 8/2008 | Shelton, IV et al. |
| 7,418,078 | B2 | 8/2008 | Blanz et al. |
| RE40,514 | E | 9/2008 | Mastri et al. |
| 7,419,080 | B2 | 9/2008 | Smith et al. |
| 7,419,081 | B2 | 9/2008 | Ehrenfels et al. |
| 7,419,321 | B2 | 9/2008 | Tereschouk |
| 7,419,495 | B2 | 9/2008 | Menn et al. |
| 7,422,136 | B1 | 9/2008 | Marczyk |
| 7,422,138 | B2 | 9/2008 | Bilotti et al. |
| 7,422,139 | B2 | 9/2008 | Shelton, IV et al. |
| 7,422,582 | B2 | 9/2008 | Malackowski et al. |
| 7,424,965 | B2 | 9/2008 | Racenet et al. |
| 7,427,607 | B2 | 9/2008 | Suzuki |
| D578,644 | S | 10/2008 | Shumer et al. |
| 7,430,772 | B2 | 10/2008 | Van Es |
| 7,430,849 | B1 | 10/2008 | Coutts et al. |
| 7,431,188 | B1 | 10/2008 | Marczyk |
| 7,431,189 | B2 | 10/2008 | Shelton, IV et al. |
| 7,431,230 | B2 | 10/2008 | McPherson et al. |
| 7,431,694 | B2 | 10/2008 | Stefanchik et al. |
| 7,431,730 | B2 | 10/2008 | Viola |
| 7,434,715 | B2 | 10/2008 | Shelton, IV et al. |
| 7,434,717 | B2 | 10/2008 | Shelton, IV et al. |
| 7,435,249 | B2 | 10/2008 | Buysse et al. |
| 7,438,209 | B1 | 10/2008 | Hess et al. |
| 7,438,718 | B2 | 10/2008 | Milliman et al. |
| 7,439,354 | B2 | 10/2008 | Lenges et al. |
| 7,441,684 | B2 | 10/2008 | Shelton, IV et al. |
| 7,441,685 | B1 | 10/2008 | Boudreaux |
| 7,442,201 | B2 | 10/2008 | Pugsley et al. |
| 7,443,547 | B2 | 10/2008 | Moreno et al. |
| D580,942 | S | 11/2008 | Oshiro et al. |
| 7,446,131 | B1 | 11/2008 | Liu et al. |
| 7,448,525 | B2 | 11/2008 | Shelton, IV et al. |
| 7,450,010 | B1 | 11/2008 | Gravelle et al. |
| 7,450,991 | B2 | 11/2008 | Smith et al. |
| 7,451,904 | B2 | 11/2008 | Shelton, IV |
| 7,455,208 | B2 | 11/2008 | Wales et al. |
| 7,455,676 | B2 | 11/2008 | Holsten et al. |
| 7,455,682 | B2 | 11/2008 | Viola |
| 7,455,687 | B2 | 11/2008 | Saunders et al. |
| D582,934 | S | 12/2008 | Byeon |
| 7,461,767 | B2 | 12/2008 | Viola et al. |
| 7,462,187 | B2 | 12/2008 | Johnston et al. |
| 7,464,845 | B2 | 12/2008 | Chou |
| 7,464,846 | B2 | 12/2008 | Shelton, IV et al. |
| 7,464,847 | B2 | 12/2008 | Viola et al. |
| 7,464,848 | B2 | 12/2008 | Green et al. |
| 7,464,849 | B2 | 12/2008 | Shelton, IV et al. |
| 7,467,740 | B2 | 12/2008 | Shelton, IV et al. |
| 7,467,849 | B2 | 12/2008 | Silverbrook et al. |
| 7,472,814 | B2 | 1/2009 | Mastri et al. |
| 7,472,815 | B2 | 1/2009 | Shelton, IV et al. |
| 7,472,816 | B2 | 1/2009 | Holsten et al. |
| 7,473,221 | B2 | 1/2009 | Ewers et al. |
| 7,473,253 | B2 | 1/2009 | Dycus et al. |
| 7,473,263 | B2 | 1/2009 | Johnston et al. |
| 7,476,237 | B2 | 1/2009 | Taniguchi et al. |
| 7,479,147 | B2 | 1/2009 | Honeycutt et al. |
| 7,479,608 | B2 | 1/2009 | Smith |
| 7,481,347 | B2 | 1/2009 | Roy |
| 7,481,348 | B2 | 1/2009 | Marczyk |
| 7,481,349 | B2 | 1/2009 | Holsten et al. |
| 7,481,824 | B2 | 1/2009 | Boudreaux et al. |
| 7,485,124 | B2 | 2/2009 | Kuhns et al. |
| 7,485,133 | B2 | 2/2009 | Cannon et al. |
| 7,485,142 | B2 | 2/2009 | Milo |
| 7,487,899 | B2 | 2/2009 | Shelton, IV et al. |
| 7,489,055 | B2 | 2/2009 | Jeong et al. |
| 7,490,749 | B2 | 2/2009 | Schall et al. |
| 7,491,232 | B2 | 2/2009 | Bolduc et al. |
| 7,492,261 | B2 | 2/2009 | Cambre et al. |
| 7,494,039 | B2 | 2/2009 | Racenet et al. |
| 7,494,460 | B2 | 2/2009 | Haarstad et al. |
| 7,494,499 | B2 | 2/2009 | Nagase et al. |
| 7,494,501 | B2 | 2/2009 | Ahlberg et al. |
| 7,497,137 | B2 | 3/2009 | Tellenbach et al. |
| 7,500,979 | B2 | 3/2009 | Hueil et al. |
| 7,501,198 | B2 | 3/2009 | Barlev et al. |
| 7,503,474 | B2 | 3/2009 | Hillstead et al. |
| 7,506,790 | B2 | 3/2009 | Shelton, IV |
| 7,506,791 | B2 | 3/2009 | Omaits et al. |
| 7,507,202 | B2 | 3/2009 | Schoellhorn |
| 7,510,107 | B2 | 3/2009 | Timm et al. |
| 7,510,534 | B2 | 3/2009 | Burdorff et al. |
| 7,510,566 | B2 | 3/2009 | Jacobs et al. |
| 7,513,407 | B1 | 4/2009 | Chang |
| 7,513,408 | B2 | 4/2009 | Shelton, IV et al. |
| 7,517,356 | B2 | 4/2009 | Heinrich |
| 7,524,320 | B2 | 4/2009 | Tierney et al. |
| 7,527,632 | B2 | 5/2009 | Houghton et al. |
| 7,530,984 | B2 | 5/2009 | Sonnenschein et al. |
| 7,530,985 | B2 | 5/2009 | Takemoto et al. |
| 7,533,790 | B1 | 5/2009 | Knodel et al. |
| 7,533,906 | B2 | 5/2009 | Luettgen et al. |
| 7,534,259 | B2 | 5/2009 | Lashinski et al. |
| 7,540,867 | B2 | 6/2009 | Jinno et al. |
| 7,540,872 | B2 | 6/2009 | Schechter et al. |
| 7,542,807 | B2 | 6/2009 | Bertolero et al. |
| 7,543,730 | B1 | 6/2009 | Marczyk |
| 7,544,197 | B2 | 6/2009 | Kelsch et al. |
| 7,546,939 | B2 | 6/2009 | Adams et al. |
| 7,546,940 | B2 | 6/2009 | Milliman et al. |
| 7,547,287 | B2 | 6/2009 | Boecker et al. |
| 7,547,312 | B2 | 6/2009 | Bauman et al. |
| 7,549,563 | B2 | 6/2009 | Mather et al. |
| 7,549,564 | B2 | 6/2009 | Boudreaux |
| 7,549,998 | B2 | 6/2009 | Braun |
| 7,552,854 | B2 | 6/2009 | Wixey et al. |
| 7,553,173 | B2 | 6/2009 | Kowalick |
| 7,553,275 | B2 | 6/2009 | Padget et al. |
| 7,554,343 | B2 | 6/2009 | Bromfield |
| 7,556,185 | B2 | 7/2009 | Viola |
| 7,556,186 | B2 | 7/2009 | Milliman |
| 7,556,647 | B2 | 7/2009 | Drews et al. |
| 7,559,449 | B2 | 7/2009 | Viola |
| 7,559,450 | B2 | 7/2009 | Wales et al. |
| 7,559,452 | B2 | 7/2009 | Wales et al. |
| 7,559,937 | B2 | 7/2009 | de la Torre et al. |
| 7,561,637 | B2 | 7/2009 | Jonsson et al. |
| 7,562,910 | B2 | 7/2009 | Kertesz et al. |
| 7,563,269 | B2 | 7/2009 | Hashiguchi |
| 7,563,862 | B2 | 7/2009 | Sieg et al. |
| 7,565,993 | B2 | 7/2009 | Milliman et al. |
| 7,566,300 | B2 | 7/2009 | Devierre et al. |
| 7,567,045 | B2 | 7/2009 | Fristedt |
| 7,568,603 | B2 | 8/2009 | Shelton, IV et al. |
| 7,568,604 | B2 | 8/2009 | Ehrenfels et al. |
| 7,568,619 | B2 | 8/2009 | Todd et al. |
| 7,572,285 | B2 | 8/2009 | Frey et al. |
| 7,572,298 | B2 | 8/2009 | Roller et al. |
| 7,575,144 | B2 | 8/2009 | Ortiz et al. |
| 7,578,825 | B2 | 8/2009 | Huebner |
| D600,703 | S | 9/2009 | LaManna et al. |
| D600,712 | S | 9/2009 | LaManna et al. |
| 7,582,086 | B2 | 9/2009 | Privitera et al. |
| 7,583,063 | B2 | 9/2009 | Dooley |
| 7,584,880 | B2 | 9/2009 | Racenet et al. |
| 7,586,289 | B2 | 9/2009 | Andruk et al. |
| 7,588,174 | B2 | 9/2009 | Holsten et al. |
| 7,588,175 | B2 | 9/2009 | Timm et al. |

(56) References Cited

U.S. PATENT DOCUMENTS

| | | | |
|---|---|---|---|
| 7,588,176 | B2 | 9/2009 | Timm et al. |
| 7,588,177 | B2 | 9/2009 | Racenet |
| 7,591,783 | B2 | 9/2009 | Boulais et al. |
| 7,591,818 | B2 | 9/2009 | Bertolero et al. |
| 7,593,766 | B2 | 9/2009 | Faber et al. |
| 7,595,642 | B2 | 9/2009 | Doyle |
| D601,578 | S | 10/2009 | Poulet et al. |
| 7,597,229 | B2 | 10/2009 | Boudreaux et al. |
| 7,597,230 | B2 | 10/2009 | Racenet et al. |
| 7,597,693 | B2 | 10/2009 | Garrison |
| 7,597,699 | B2 | 10/2009 | Rogers |
| 7,598,972 | B2 | 10/2009 | Tomita |
| 7,600,663 | B2 | 10/2009 | Green |
| 7,604,118 | B2 | 10/2009 | Iio et al. |
| 7,604,150 | B2 | 10/2009 | Boudreaux |
| 7,604,151 | B2 | 10/2009 | Hess et al. |
| 7,604,668 | B2 | 10/2009 | Farnsworth et al. |
| 7,605,826 | B2 | 10/2009 | Sauer |
| 7,607,557 | B2 | 10/2009 | Shelton, IV et al. |
| 7,608,091 | B2 | 10/2009 | Goldfarb et al. |
| D604,325 | S | 11/2009 | Ebeling et al. |
| 7,611,038 | B2 | 11/2009 | Racenet et al. |
| 7,611,474 | B2 | 11/2009 | Hibner et al. |
| 7,615,003 | B2 | 11/2009 | Stefanchik et al. |
| 7,615,006 | B2 | 11/2009 | Abe |
| 7,615,067 | B2 | 11/2009 | Lee et al. |
| 7,617,961 | B2 | 11/2009 | Viola |
| 7,618,427 | B2 | 11/2009 | Ortiz et al. |
| D605,201 | S | 12/2009 | Lorenz et al. |
| D606,992 | S | 12/2009 | Liu et al. |
| D607,010 | S | 12/2009 | Kocmick |
| 7,624,902 | B2 | 12/2009 | Marczyk et al. |
| 7,624,903 | B2 | 12/2009 | Green et al. |
| 7,625,370 | B2 | 12/2009 | Hart et al. |
| 7,625,388 | B2 | 12/2009 | Boukhny et al. |
| 7,625,662 | B2 | 12/2009 | Vaisnys et al. |
| 7,630,841 | B2 | 12/2009 | Comisky et al. |
| 7,631,793 | B2 | 12/2009 | Rethy et al. |
| 7,631,794 | B2 | 12/2009 | Rethy et al. |
| 7,635,074 | B2 | 12/2009 | Olson et al. |
| 7,635,922 | B2 | 12/2009 | Becker |
| 7,637,409 | B2 | 12/2009 | Marczyk |
| 7,637,410 | B2 | 12/2009 | Marczyk |
| 7,638,958 | B2 | 12/2009 | Philipp et al. |
| 7,639,598 | B2 | 12/2009 | Sovenyi |
| 7,641,091 | B2 | 1/2010 | Olson et al. |
| 7,641,092 | B2 | 1/2010 | Kruszynski et al. |
| 7,641,093 | B2 | 1/2010 | Doll et al. |
| 7,641,095 | B2 | 1/2010 | Viola |
| 7,641,671 | B2 | 1/2010 | Crainich |
| 7,644,016 | B2 | 1/2010 | Nycz et al. |
| 7,644,484 | B2 | 1/2010 | Vereschagin |
| 7,644,783 | B2 | 1/2010 | Roberts et al. |
| 7,644,848 | B2 | 1/2010 | Swayze et al. |
| 7,645,230 | B2 | 1/2010 | Mikkaichi et al. |
| 7,648,055 | B2 | 1/2010 | Marczyk |
| 7,648,457 | B2 | 1/2010 | Stefanchik et al. |
| 7,648,519 | B2 | 1/2010 | Lee et al. |
| 7,650,185 | B2 | 1/2010 | Maile et al. |
| 7,651,017 | B2 | 1/2010 | Ortiz et al. |
| 7,651,498 | B2 | 1/2010 | Shifrin et al. |
| 7,654,431 | B2 | 2/2010 | Hueil et al. |
| 7,655,003 | B2 | 2/2010 | Lorang et al. |
| 7,655,004 | B2 | 2/2010 | Long |
| 7,655,288 | B2 | 2/2010 | Bauman et al. |
| 7,655,584 | B2 | 2/2010 | Biran et al. |
| 7,656,131 | B2 | 2/2010 | Embrey et al. |
| 7,658,311 | B2 | 2/2010 | Boudreaux |
| 7,658,312 | B2 | 2/2010 | Vidal et al. |
| 7,658,705 | B2 | 2/2010 | Melvin et al. |
| 7,659,219 | B2 | 2/2010 | Biran et al. |
| 7,661,448 | B2 | 2/2010 | Kim et al. |
| 7,662,161 | B2 | 2/2010 | Briganti et al. |
| 7,665,646 | B2 | 2/2010 | Prommersberger |
| 7,665,647 | B2 | 2/2010 | Shelton, IV et al. |
| 7,666,195 | B2 | 2/2010 | Kelleher et al. |
| 7,669,746 | B2 | 3/2010 | Shelton, IV |
| 7,669,747 | B2 | 3/2010 | Weisenburgh, II et al. |
| 7,670,334 | B2 | 3/2010 | Hueil et al. |
| 7,670,337 | B2 | 3/2010 | Young |
| 7,673,780 | B2 | 3/2010 | Shelton, IV et al. |
| 7,673,781 | B2 | 3/2010 | Swayze et al. |
| 7,673,782 | B2 | 3/2010 | Hess et al. |
| 7,673,783 | B2 | 3/2010 | Morgan et al. |
| 7,674,253 | B2 | 3/2010 | Fisher et al. |
| 7,674,255 | B2 | 3/2010 | Braun |
| 7,674,263 | B2 | 3/2010 | Ryan |
| 7,674,270 | B2 | 3/2010 | Layer |
| 7,678,121 | B1 | 3/2010 | Knodel |
| 7,682,307 | B2 | 3/2010 | Danitz et al. |
| 7,682,367 | B2 | 3/2010 | Shah et al. |
| 7,682,686 | B2 | 3/2010 | Curro et al. |
| 7,686,201 | B2 | 3/2010 | Csiky |
| 7,686,804 | B2 | 3/2010 | Johnson et al. |
| 7,686,826 | B2 | 3/2010 | Lee et al. |
| 7,688,028 | B2 | 3/2010 | Phillips et al. |
| 7,690,547 | B2 | 4/2010 | Racenet et al. |
| 7,691,098 | B2 | 4/2010 | Wallace et al. |
| 7,691,103 | B2 | 4/2010 | Fernandez et al. |
| 7,691,106 | B2 | 4/2010 | Schenberger et al. |
| 7,694,864 | B2 | 4/2010 | Okada et al. |
| 7,694,865 | B2 | 4/2010 | Scirica |
| 7,695,485 | B2 | 4/2010 | Whitman et al. |
| 7,695,493 | B2 | 4/2010 | Saadat et al. |
| 7,699,204 | B2 | 4/2010 | Viola |
| 7,699,835 | B2 | 4/2010 | Lee et al. |
| 7,699,844 | B2 | 4/2010 | Utley et al. |
| 7,699,846 | B2 | 4/2010 | Ryan |
| 7,699,856 | B2 | 4/2010 | Van Wyk et al. |
| 7,699,859 | B2 | 4/2010 | Bombard et al. |
| 7,699,860 | B2 | 4/2010 | Huitema et al. |
| 7,699,868 | B2 | 4/2010 | Frank et al. |
| 7,703,653 | B2 | 4/2010 | Shah et al. |
| 7,705,559 | B2 | 4/2010 | Powell et al. |
| 7,706,853 | B2 | 4/2010 | Hacker et al. |
| 7,708,180 | B2 | 5/2010 | Murray et al. |
| 7,708,181 | B2 | 5/2010 | Cole et al. |
| 7,708,182 | B2 | 5/2010 | Viola |
| 7,708,758 | B2 | 5/2010 | Lee et al. |
| 7,708,768 | B2 | 5/2010 | Danek et al. |
| 7,709,136 | B2 | 5/2010 | Touchton et al. |
| 7,712,182 | B2 | 5/2010 | Zeiler et al. |
| 7,713,190 | B2 | 5/2010 | Brock et al. |
| 7,713,542 | B2 | 5/2010 | Xu et al. |
| 7,714,239 | B2 | 5/2010 | Smith |
| 7,714,334 | B2 | 5/2010 | Lin |
| 7,717,312 | B2 | 5/2010 | Beetel |
| 7,717,313 | B2 | 5/2010 | Criscuolo et al. |
| 7,717,846 | B2 | 5/2010 | Zirps et al. |
| 7,717,873 | B2 | 5/2010 | Swick |
| 7,717,915 | B2 | 5/2010 | Miyazawa |
| 7,717,926 | B2 | 5/2010 | Whitfield et al. |
| 7,718,180 | B2 | 5/2010 | Karp |
| 7,718,556 | B2 | 5/2010 | Matsuda et al. |
| 7,721,930 | B2 | 5/2010 | McKenna et al. |
| 7,721,931 | B2 | 5/2010 | Shelton, IV et al. |
| 7,721,932 | B2 | 5/2010 | Cole et al. |
| 7,721,933 | B2 | 5/2010 | Ehrenfels et al. |
| 7,721,934 | B2 | 5/2010 | Shelton, IV et al. |
| 7,721,936 | B2 | 5/2010 | Shalton, IV et al. |
| 7,722,527 | B2 | 5/2010 | Bouchier et al. |
| 7,722,607 | B2 | 5/2010 | Dumbauld et al. |
| 7,722,610 | B2 | 5/2010 | Viola et al. |
| 7,725,214 | B2 | 5/2010 | Diolaiti |
| 7,726,171 | B2 | 6/2010 | Langlotz et al. |
| 7,726,537 | B2 | 6/2010 | Olson et al. |
| 7,726,538 | B2 | 6/2010 | Holsten et al. |
| 7,726,539 | B2 | 6/2010 | Holsten et al. |
| 7,727,954 | B2 | 6/2010 | McKay |
| 7,728,553 | B2 | 6/2010 | Carrier et al. |
| 7,729,742 | B2 | 6/2010 | Govari |
| 7,731,072 | B2 | 6/2010 | Timm et al. |
| 7,731,073 | B2 | 6/2010 | Wixey et al. |
| 7,731,724 | B2 | 6/2010 | Huitema et al. |

(56) References Cited

U.S. PATENT DOCUMENTS

| | | | |
|---|---|---|---|
| 7,735,703 | B2 | 6/2010 | Morgan et al. |
| 7,735,704 | B2 | 6/2010 | Bilotti |
| 7,736,254 | B2 | 6/2010 | Schena |
| 7,736,306 | B2 | 6/2010 | Brustad et al. |
| 7,736,356 | B2 | 6/2010 | Cooper et al. |
| 7,736,374 | B2 | 6/2010 | Vaughan et al. |
| 7,738,971 | B2 | 6/2010 | Swayze et al. |
| 7,740,159 | B2 | 6/2010 | Shelton, IV et al. |
| 7,742,036 | B2 | 6/2010 | Grant et al. |
| 7,743,960 | B2 | 6/2010 | Whitman et al. |
| 7,744,624 | B2 | 6/2010 | Bettuchi |
| 7,744,627 | B2 | 6/2010 | Orban, III et al. |
| 7,744,628 | B2 | 6/2010 | Viola |
| 7,747,146 | B2 | 6/2010 | Milano et al. |
| 7,748,587 | B2 | 7/2010 | Haramiishi et al. |
| 7,748,632 | B2 | 7/2010 | Coleman et al. |
| 7,749,204 | B2 | 7/2010 | Dhanaraj et al. |
| 7,749,240 | B2 | 7/2010 | Takahashi et al. |
| 7,751,870 | B2 | 7/2010 | Whitman |
| 7,753,245 | B2 | 7/2010 | Boudreaux et al. |
| 7,753,246 | B2 | 7/2010 | Scirica |
| 7,753,904 | B2 | 7/2010 | Shelton, IV et al. |
| 7,757,924 | B2 | 7/2010 | Gerbi et al. |
| 7,758,594 | B2 | 7/2010 | Lamson et al. |
| 7,758,612 | B2 | 7/2010 | Shipp |
| 7,758,613 | B2 | 7/2010 | Whitman |
| 7,762,462 | B2 | 7/2010 | Gelbman |
| 7,762,998 | B2 | 7/2010 | Birk et al. |
| D622,286 | S | 8/2010 | Umezawa |
| 7,766,207 | B2 | 8/2010 | Mather et al. |
| 7,766,209 | B2 | 8/2010 | Baxter, III et al. |
| 7,766,210 | B2 | 8/2010 | Shelton, IV et al. |
| 7,766,821 | B2 | 8/2010 | Brunnen et al. |
| 7,766,894 | B2 | 8/2010 | Weitzner et al. |
| 7,766,910 | B2 | 8/2010 | Hixson et al. |
| 7,770,658 | B2 | 8/2010 | Ito et al. |
| 7,770,773 | B2 | 8/2010 | Whitman et al. |
| 7,770,774 | B2 | 8/2010 | Mastri et al. |
| 7,770,775 | B2 | 8/2010 | Shelton, IV et al. |
| 7,770,776 | B2 | 8/2010 | Chen et al. |
| 7,771,396 | B2 | 8/2010 | Stefanchik et al. |
| 7,772,720 | B2 | 8/2010 | McGee et al. |
| 7,772,725 | B2 | 8/2010 | Siman-Tov |
| 7,775,972 | B2 | 8/2010 | Brock et al. |
| 7,776,037 | B2 | 8/2010 | Odom |
| 7,776,060 | B2 | 8/2010 | Mooradian et al. |
| 7,776,065 | B2 | 8/2010 | Griffiths et al. |
| 7,778,004 | B2 | 8/2010 | Nerheim et al. |
| 7,779,614 | B1 | 8/2010 | McGonagle et al. |
| 7,779,737 | B2 | 8/2010 | Newman, Jr. et al. |
| 7,780,054 | B2 | 8/2010 | Wales |
| 7,780,055 | B2 | 8/2010 | Scirica et al. |
| 7,780,309 | B2 | 8/2010 | McMillan et al. |
| 7,780,651 | B2 | 8/2010 | Madhani et al. |
| 7,780,663 | B2 | 8/2010 | Yates et al. |
| 7,780,685 | B2 | 8/2010 | Hunt et al. |
| 7,782,382 | B2 | 8/2010 | Fujimura |
| 7,784,662 | B2 | 8/2010 | Wales et al. |
| 7,784,663 | B2 | 8/2010 | Shelton, IV |
| 7,787,256 | B2 | 8/2010 | Chan et al. |
| 7,789,283 | B2 | 9/2010 | Shah |
| 7,789,875 | B2 | 9/2010 | Brock et al. |
| 7,789,883 | B2 | 9/2010 | Takashino et al. |
| 7,789,889 | B2 | 9/2010 | Zubik et al. |
| 7,793,812 | B2 | 9/2010 | Moore et al. |
| 7,794,475 | B2 | 9/2010 | Hess et al. |
| 7,798,386 | B2 | 9/2010 | Schall et al. |
| 7,799,039 | B2 | 9/2010 | Shelton, IV et al. |
| 7,799,044 | B2 | 9/2010 | Johnston et al. |
| 7,799,965 | B2 | 9/2010 | Patel et al. |
| 7,803,151 | B2 | 9/2010 | Whitman |
| 7,806,871 | B2 | 10/2010 | Li et al. |
| 7,806,891 | B2 | 10/2010 | Nowlin et al. |
| 7,810,690 | B2 | 10/2010 | Bilotti et al. |
| 7,810,691 | B2 | 10/2010 | Boyden et al. |
| 7,810,692 | B2 | 10/2010 | Hall et al. |
| 7,810,693 | B2 | 10/2010 | Broehl et al. |
| 7,811,275 | B2 | 10/2010 | Birk et al. |
| 7,814,816 | B2 | 10/2010 | Alberti et al. |
| 7,815,092 | B2 | 10/2010 | Whitman et al. |
| 7,815,565 | B2 | 10/2010 | Stefanchik et al. |
| 7,815,662 | B2 | 10/2010 | Spivey et al. |
| 7,819,296 | B2 | 10/2010 | Hueil et al. |
| 7,819,297 | B2 | 10/2010 | Doll et al. |
| 7,819,298 | B2 | 10/2010 | Hall et al. |
| 7,819,299 | B2 | 10/2010 | Shelton, IV et al. |
| 7,819,799 | B2 | 10/2010 | Merril et al. |
| 7,819,884 | B2 | 10/2010 | Lee et al. |
| 7,819,885 | B2 | 10/2010 | Cooper |
| 7,819,886 | B2 | 10/2010 | Whitfield et al. |
| 7,819,894 | B2 | 10/2010 | Mitsuishi et al. |
| 7,823,076 | B2 | 10/2010 | Borovsky et al. |
| 7,823,592 | B2 | 11/2010 | Bettuchi et al. |
| 7,823,760 | B2 | 11/2010 | Zemlok et al. |
| 7,824,401 | B2 | 11/2010 | Manzo et al. |
| 7,824,422 | B2 | 11/2010 | Benchetrit |
| 7,824,426 | B2 | 11/2010 | Racenet et al. |
| 7,828,189 | B2 | 11/2010 | Holsten et al. |
| 7,828,794 | B2 | 11/2010 | Sartor |
| 7,828,808 | B2 | 11/2010 | Hinman et al. |
| 7,829,416 | B2 | 11/2010 | Kudou et al. |
| 7,831,292 | B2 | 11/2010 | Quaid et al. |
| 7,832,408 | B2 | 11/2010 | Shelton, IV et al. |
| 7,832,611 | B2 | 11/2010 | Boyden et al. |
| 7,832,612 | B2 | 11/2010 | Baxter, III et al. |
| 7,833,234 | B2 | 11/2010 | Bailly et al. |
| 7,835,823 | B2 | 11/2010 | Sillman et al. |
| 7,836,400 | B2 | 11/2010 | May et al. |
| 7,837,079 | B2 | 11/2010 | Holsten et al. |
| 7,837,080 | B2 | 11/2010 | Schwemberger |
| 7,837,081 | B2 | 11/2010 | Holsten et al. |
| 7,837,425 | B2 | 11/2010 | Saeki et al. |
| 7,837,685 | B2 | 11/2010 | Weinberg et al. |
| 7,837,687 | B2 | 11/2010 | Harp |
| 7,837,694 | B2 | 11/2010 | Tethrake et al. |
| 7,838,789 | B2 | 11/2010 | Stoffers et al. |
| 7,839,109 | B2 | 11/2010 | Carmen, Jr. et al. |
| 7,840,253 | B2 | 11/2010 | Tremblay et al. |
| 7,841,503 | B2 | 11/2010 | Sonnenschein et al. |
| 7,842,025 | B2 | 11/2010 | Coleman et al. |
| 7,842,028 | B2 | 11/2010 | Lee |
| 7,843,158 | B2 | 11/2010 | Prisco |
| 7,845,533 | B2 | 12/2010 | Marczyk et al. |
| 7,845,534 | B2 | 12/2010 | Viola et al. |
| 7,845,535 | B2 | 12/2010 | Scircia |
| 7,845,536 | B2 | 12/2010 | Viola et al. |
| 7,845,537 | B2 | 12/2010 | Shelton, IV et al. |
| 7,845,538 | B2 | 12/2010 | Whitman |
| 7,845,912 | B2 | 12/2010 | Sung et al. |
| 7,846,085 | B2 | 12/2010 | Silverman et al. |
| 7,846,149 | B2 | 12/2010 | Jankowski |
| 7,846,161 | B2 | 12/2010 | Dumbauld et al. |
| 7,848,066 | B2 | 12/2010 | Yanagishima |
| 7,850,623 | B2 | 12/2010 | Griffin et al. |
| 7,850,642 | B2 | 12/2010 | Moll et al. |
| 7,850,982 | B2 | 12/2010 | Stopek et al. |
| 7,853,813 | B2 | 12/2010 | Lee |
| 7,854,735 | B2 | 12/2010 | Houser et al. |
| 7,854,736 | B2 | 12/2010 | Ryan |
| 7,857,183 | B2 | 12/2010 | Shelton, IV |
| 7,857,184 | B2 | 12/2010 | Viola |
| 7,857,185 | B2 | 12/2010 | Swayze et al. |
| 7,857,186 | B2 | 12/2010 | Baxter, III et al. |
| 7,857,813 | B2 | 12/2010 | Schmitz et al. |
| 7,861,906 | B2 | 1/2011 | Doll et al. |
| 7,862,502 | B2 | 1/2011 | Pool et al. |
| 7,862,546 | B2 | 1/2011 | Conlon et al. |
| 7,862,579 | B2 | 1/2011 | Ortiz et al. |
| 7,866,525 | B2 | 1/2011 | Scirica |
| 7,866,527 | B2 | 1/2011 | Hall et al. |
| 7,866,528 | B2 | 1/2011 | Olson et al. |
| 7,870,989 | B2 | 1/2011 | Viola et al. |
| 7,871,418 | B2 | 1/2011 | Thompson et al. |
| 7,871,440 | B2 | 1/2011 | Schwartz et al. |

(56) References Cited

U.S. PATENT DOCUMENTS

| | | | |
|---|---|---|---|
| 7,875,055 | B2 | 1/2011 | Cichocki, Jr. |
| 7,877,869 | B2 | 2/2011 | Mehdizadeh et al. |
| 7,879,063 | B2 | 2/2011 | Khosravi |
| 7,879,070 | B2 | 2/2011 | Ortiz et al. |
| 7,879,367 | B2 | 2/2011 | Heublein et al. |
| 7,883,461 | B2 | 2/2011 | Albrecht et al. |
| 7,883,465 | B2 | 2/2011 | Donofrio et al. |
| 7,883,540 | B2 | 2/2011 | Niwa et al. |
| 7,886,951 | B2 | 2/2011 | Hessler |
| 7,886,952 | B2 | 2/2011 | Scirica et al. |
| 7,887,530 | B2 | 2/2011 | Zemlok et al. |
| 7,887,535 | B2 | 2/2011 | Lands et al. |
| 7,887,536 | B2 | 2/2011 | Johnson et al. |
| 7,887,563 | B2 | 2/2011 | Cummins |
| 7,887,755 | B2 | 2/2011 | Mingerink et al. |
| 7,891,531 | B1 | 2/2011 | Ward |
| 7,891,532 | B2 | 2/2011 | Mastri et al. |
| 7,892,200 | B2 | 2/2011 | Birk et al. |
| 7,892,245 | B2 | 2/2011 | Liddicoat et al. |
| 7,893,586 | B2 | 2/2011 | West et al. |
| 7,896,214 | B2 | 3/2011 | Farascioni |
| 7,896,215 | B2 | 3/2011 | Adams et al. |
| 7,896,671 | B2 | 3/2011 | Kim et al. |
| 7,896,869 | B2 | 3/2011 | DiSilvestro et al. |
| 7,896,877 | B2 | 3/2011 | Hall et al. |
| 7,896,895 | B2 | 3/2011 | Boudreaux et al. |
| 7,896,897 | B2 | 3/2011 | Gresham et al. |
| 7,896,900 | B2 | 3/2011 | Frank et al. |
| 7,898,198 | B2 | 3/2011 | Murphree |
| 7,900,805 | B2 | 3/2011 | Shelton, IV et al. |
| 7,900,806 | B2 | 3/2011 | Chen et al. |
| 7,901,381 | B2 | 3/2011 | Birk et al. |
| 7,905,380 | B2 | 3/2011 | Shelton, IV et al. |
| 7,905,381 | B2 | 3/2011 | Baxter, III et al. |
| 7,905,881 | B2 | 3/2011 | Masuda et al. |
| 7,905,889 | B2 | 3/2011 | Catanese, III et al. |
| 7,905,890 | B2 | 3/2011 | Whitfield et al. |
| 7,905,902 | B2 | 3/2011 | Huitema et al. |
| 7,909,039 | B2 | 3/2011 | Hur |
| 7,909,191 | B2 | 3/2011 | Baker et al. |
| 7,909,220 | B2 | 3/2011 | Viola |
| 7,909,221 | B2 | 3/2011 | Viola et al. |
| 7,909,224 | B2 | 3/2011 | Prommersberger |
| 7,913,891 | B2 | 3/2011 | Doll et al. |
| 7,913,893 | B2 | 3/2011 | Mastri et al. |
| 7,914,521 | B2 | 3/2011 | Wang et al. |
| 7,914,543 | B2 | 3/2011 | Roth et al. |
| 7,914,551 | B2 | 3/2011 | Ortiz et al. |
| 7,918,230 | B2 | 4/2011 | Whitman et al. |
| 7,918,376 | B1 | 4/2011 | Knodel et al. |
| 7,918,377 | B2 | 4/2011 | Measamer et al. |
| 7,918,845 | B2 | 4/2011 | Saadat et al. |
| 7,918,848 | B2 | 4/2011 | Lau et al. |
| 7,918,861 | B2 | 4/2011 | Brock et al. |
| 7,918,867 | B2 | 4/2011 | Dana et al. |
| 7,922,061 | B2 | 4/2011 | Shelton, IV et al. |
| 7,922,063 | B2 | 4/2011 | Zemlok et al. |
| 7,922,743 | B2 | 4/2011 | Heinrich et al. |
| 7,923,144 | B2 | 4/2011 | Kohn et al. |
| 7,926,691 | B2 | 4/2011 | Viola et al. |
| 7,926,692 | B2 | 4/2011 | Racenet et al. |
| 7,927,328 | B2 | 4/2011 | Orszulak et al. |
| 7,928,281 | B2 | 4/2011 | Augustine |
| 7,930,040 | B1 | 4/2011 | Kelsch et al. |
| 7,930,065 | B2 | 4/2011 | Larkin et al. |
| 7,931,660 | B2 | 4/2011 | Aranyi et al. |
| 7,931,695 | B2 | 4/2011 | Ringeisen |
| 7,931,877 | B2 | 4/2011 | Steffens et al. |
| D638,028 | S | 5/2011 | Cook et al. |
| 7,934,630 | B2 | 5/2011 | Shelton, IV et al. |
| 7,934,631 | B2 | 5/2011 | Balbierz et al. |
| 7,934,896 | B2 | 5/2011 | Schnier |
| 7,935,130 | B2 | 5/2011 | Williams |
| 7,935,773 | B2 | 5/2011 | Hadba et al. |
| 7,936,142 | B2 | 5/2011 | Otsuka et al. |
| 7,938,307 | B2 | 5/2011 | Bettuchi |
| 7,939,152 | B2 | 5/2011 | Haskin et al. |
| 7,941,865 | B2 | 5/2011 | Seman, Jr. et al. |
| 7,942,300 | B2 | 5/2011 | Rethy et al. |
| 7,942,303 | B2 | 5/2011 | Shah |
| 7,942,890 | B2 | 5/2011 | D'Agostino et al. |
| 7,944,175 | B2 | 5/2011 | Mori et al. |
| 7,945,792 | B2 | 5/2011 | Cherpantier |
| 7,945,798 | B2 | 5/2011 | Carlson et al. |
| 7,946,453 | B2 | 5/2011 | Voegele et al. |
| 7,947,011 | B2 | 5/2011 | Birk et al. |
| 7,948,381 | B2 | 5/2011 | Lindsay et al. |
| 7,950,560 | B2 | 5/2011 | Zemlok et al. |
| 7,950,561 | B2 | 5/2011 | Aranyi |
| 7,950,562 | B2 | 5/2011 | Beardsley et al. |
| 7,951,071 | B2 | 5/2011 | Whitman et al. |
| 7,951,166 | B2 | 5/2011 | Orban, III et al. |
| 7,952,464 | B2 | 5/2011 | Nikitin et al. |
| 7,954,682 | B2 | 6/2011 | Giordano et al. |
| 7,954,684 | B2 | 6/2011 | Boudreaux |
| 7,954,685 | B2 | 6/2011 | Viola |
| 7,954,686 | B2 | 6/2011 | Baxter, III et al. |
| 7,954,687 | B2 | 6/2011 | Zemlok et al. |
| 7,954,688 | B2 | 6/2011 | Argentine et al. |
| 7,955,253 | B2 | 6/2011 | Ewers et al. |
| 7,955,257 | B2 | 6/2011 | Frasier et al. |
| 7,955,322 | B2 | 6/2011 | Devengenzo et al. |
| 7,955,327 | B2 | 6/2011 | Sartor et al. |
| 7,955,380 | B2 | 6/2011 | Chu et al. |
| 7,959,050 | B2 | 6/2011 | Smith et al. |
| 7,959,051 | B2 | 6/2011 | Smith et al. |
| 7,959,052 | B2 | 6/2011 | Sonnenschein et al. |
| 7,963,432 | B2 | 6/2011 | Knodel et al. |
| 7,963,433 | B2 | 6/2011 | Whitman et al. |
| 7,963,913 | B2 | 6/2011 | Devengenzo et al. |
| 7,963,963 | B2 | 6/2011 | Francischelli et al. |
| 7,963,964 | B2 | 6/2011 | Santilli et al. |
| 7,964,206 | B2 | 6/2011 | Suokas et al. |
| 7,966,236 | B2 | 6/2011 | Noriega et al. |
| 7,966,269 | B2 | 6/2011 | Bauer et al. |
| 7,966,799 | B2 | 6/2011 | Morgan et al. |
| 7,967,178 | B2 | 6/2011 | Scirica et al. |
| 7,967,179 | B2 | 6/2011 | Olson et al. |
| 7,967,180 | B2 | 6/2011 | Scirica |
| 7,967,181 | B2 | 6/2011 | Viola et al. |
| 7,967,791 | B2 | 6/2011 | Franer et al. |
| 7,967,839 | B2 | 6/2011 | Flock et al. |
| 7,972,298 | B2 | 7/2011 | Wallace et al. |
| 7,972,315 | B2 | 7/2011 | Birk et al. |
| 7,976,213 | B2 | 7/2011 | Bertolotti et al. |
| 7,976,508 | B2 | 7/2011 | Hoag |
| 7,976,563 | B2 | 7/2011 | Summerer |
| 7,979,137 | B2 | 7/2011 | Tracey et al. |
| 7,980,443 | B2 | 7/2011 | Scheib et al. |
| 7,981,025 | B2 | 7/2011 | Pool et al. |
| 7,981,102 | B2 | 7/2011 | Patel et al. |
| 7,981,132 | B2 | 7/2011 | Dubrul et al. |
| 7,987,405 | B2 | 7/2011 | Turner et al. |
| 7,988,015 | B2 | 8/2011 | Mason, II et al. |
| 7,988,026 | B2 | 8/2011 | Knodel et al. |
| 7,988,027 | B2 | 8/2011 | Olson et al. |
| 7,988,028 | B2 | 8/2011 | Farascioni et al. |
| 7,988,779 | B2 | 8/2011 | Disalvo et al. |
| 7,992,757 | B2 | 8/2011 | Wheeler et al. |
| 7,993,360 | B2 | 8/2011 | Hacker et al. |
| 7,994,670 | B2 | 8/2011 | Ji |
| 7,996,064 | B2 | 8/2011 | Simon et al. |
| 7,997,054 | B2 | 8/2011 | Bertsch et al. |
| 7,997,468 | B2 | 8/2011 | Farascioni |
| 7,997,469 | B2 | 8/2011 | Olson et al. |
| 8,002,696 | B2 | 8/2011 | Suzuki |
| 8,002,784 | B2 | 8/2011 | Jinno et al. |
| 8,002,785 | B2 | 8/2011 | Weiss et al. |
| 8,002,795 | B2 | 8/2011 | Beetel |
| 8,006,365 | B2 | 8/2011 | Levin et al. |
| 8,006,885 | B2 | 8/2011 | Marczyk |
| 8,006,889 | B2 | 8/2011 | Adams et al. |
| 8,007,370 | B2 | 8/2011 | Hirsch et al. |
| 8,007,465 | B2 | 8/2011 | Birk et al. |

(56) References Cited

U.S. PATENT DOCUMENTS

| | | | |
|---|---|---|---|
| 8,007,479 | B2 | 8/2011 | Birk et al. |
| 8,007,511 | B2 | 8/2011 | Brock et al. |
| 8,007,513 | B2 | 8/2011 | Nalagatla et al. |
| 8,008,598 | B2 | 8/2011 | Whitman et al. |
| 8,010,180 | B2 | 8/2011 | Quaid et al. |
| 8,011,550 | B2 | 9/2011 | Aranyi et al. |
| 8,011,551 | B2 | 9/2011 | Marczyk et al. |
| 8,011,553 | B2 | 9/2011 | Mastri et al. |
| 8,011,555 | B2 | 9/2011 | Tarinelli et al. |
| 8,012,170 | B2 | 9/2011 | Whitman et al. |
| 8,016,176 | B2 | 9/2011 | Kasvikis et al. |
| 8,016,177 | B2 | 9/2011 | Bettuchi et al. |
| 8,016,178 | B2 | 9/2011 | Olson et al. |
| 8,016,849 | B2 | 9/2011 | Wenchell |
| 8,016,855 | B2 | 9/2011 | Whitman et al. |
| 8,016,858 | B2 | 9/2011 | Whitman |
| 8,016,881 | B2 | 9/2011 | Furst |
| 8,020,741 | B2 | 9/2011 | Cole et al. |
| 8,020,742 | B2 | 9/2011 | Marczyk |
| 8,020,743 | B2 | 9/2011 | Shelton, IV |
| 8,021,375 | B2 | 9/2011 | Aldrich et al. |
| 8,025,199 | B2 | 9/2011 | Whitman et al. |
| 8,025,896 | B2 | 9/2011 | Malaviya et al. |
| 8,028,835 | B2 | 10/2011 | Yasuda et al. |
| 8,028,882 | B2 | 10/2011 | Viola |
| 8,028,883 | B2 | 10/2011 | Stopek |
| 8,028,884 | B2 | 10/2011 | Sniffin et al. |
| 8,028,885 | B2 | 10/2011 | Smith et al. |
| 8,029,510 | B2 | 10/2011 | Hoegerle |
| 8,031,069 | B2 | 10/2011 | Cohn et al. |
| 8,033,438 | B2 | 10/2011 | Scirica |
| 8,033,439 | B2 | 10/2011 | Racenet et al. |
| 8,033,440 | B2 | 10/2011 | Wenchell et al. |
| 8,033,442 | B2 | 10/2011 | Racenet et al. |
| 8,034,077 | B2 | 10/2011 | Smith et al. |
| 8,034,337 | B2 | 10/2011 | Simard |
| 8,034,363 | B2 | 10/2011 | Li et al. |
| 8,035,487 | B2 | 10/2011 | Malackowski |
| 8,037,591 | B2 | 10/2011 | Spivey et al. |
| 8,038,044 | B2 | 10/2011 | Viola |
| 8,038,045 | B2 | 10/2011 | Bettuchi et al. |
| 8,038,046 | B2 | 10/2011 | Smith et al. |
| 8,038,686 | B2 | 10/2011 | Huitema et al. |
| 8,043,207 | B2 | 10/2011 | Adams |
| 8,043,328 | B2 | 10/2011 | Hahnen et al. |
| 8,044,536 | B2 | 10/2011 | Nguyen et al. |
| 8,044,604 | B2 | 10/2011 | Hagino et al. |
| 8,047,236 | B2 | 11/2011 | Perry |
| 8,048,503 | B2 | 11/2011 | Farnsworth et al. |
| 8,052,024 | B2 | 11/2011 | Viola et al. |
| 8,052,636 | B2 | 11/2011 | Moll et al. |
| 8,052,697 | B2 | 11/2011 | Phillips |
| 8,056,787 | B2 | 11/2011 | Boudreaux et al. |
| 8,056,788 | B2 | 11/2011 | Mastri et al. |
| 8,056,789 | B1 | 11/2011 | White et al. |
| 8,057,508 | B2 | 11/2011 | Shelton, IV |
| 8,058,771 | B2 | 11/2011 | Giordano et al. |
| 8,060,250 | B2 | 11/2011 | Reiland et al. |
| 8,061,014 | B2 | 11/2011 | Smith et al. |
| 8,061,576 | B2 | 11/2011 | Cappola |
| 8,062,236 | B2 | 11/2011 | Soltz |
| 8,062,306 | B2 | 11/2011 | Nobis et al. |
| 8,062,330 | B2 | 11/2011 | Prommersberger et al. |
| 8,063,619 | B2 | 11/2011 | Zhu et al. |
| 8,066,158 | B2 | 11/2011 | Vogel et al. |
| 8,066,166 | B2 | 11/2011 | Demmy et al. |
| 8,066,167 | B2 | 11/2011 | Measamer et al. |
| 8,066,168 | B2 | 11/2011 | Vidal et al. |
| 8,066,720 | B2 | 11/2011 | Knodel et al. |
| D650,074 | S | 12/2011 | Hunt et al. |
| D650,789 | S | 12/2011 | Arnold |
| 8,070,033 | B2 | 12/2011 | Milliman et al. |
| 8,070,034 | B1 | 12/2011 | Knodel |
| 8,070,035 | B2 | 12/2011 | Holsten et al. |
| 8,070,743 | B2 | 12/2011 | Kagan et al. |
| 8,074,858 | B2 | 12/2011 | Marczyk |
| 8,074,859 | B2 | 12/2011 | Kostrzewski |
| 8,074,861 | B2 | 12/2011 | Ehrenfels et al. |
| 8,075,476 | B2 | 12/2011 | Vargas |
| 8,075,571 | B2 | 12/2011 | Vitali et al. |
| 8,079,950 | B2 | 12/2011 | Stern et al. |
| 8,079,989 | B2 | 12/2011 | Birk et al. |
| 8,080,004 | B2 | 12/2011 | Downey et al. |
| 8,083,118 | B2 | 12/2011 | Milliman et al. |
| 8,083,119 | B2 | 12/2011 | Prommersberger |
| 8,083,120 | B2 | 12/2011 | Shelton, IV et al. |
| 8,084,001 | B2 | 12/2011 | Burns et al. |
| 8,084,969 | B2 | 12/2011 | David et al. |
| 8,085,013 | B2 | 12/2011 | Wei et al. |
| D652,048 | S | 1/2012 | Joseph |
| 8,087,562 | B1 | 1/2012 | Manoux et al. |
| 8,087,563 | B2 | 1/2012 | Milliman et al. |
| 8,089,509 | B2 | 1/2012 | Chatenever et al. |
| 8,091,753 | B2 | 1/2012 | Viola |
| 8,091,756 | B2 | 1/2012 | Viola |
| 8,092,443 | B2 | 1/2012 | Bischoff |
| 8,092,493 | B2 | 1/2012 | Marczyk |
| 8,092,932 | B2 | 1/2012 | Phillips et al. |
| 8,093,572 | B2 | 1/2012 | Kuduvalli |
| 8,096,458 | B2 | 1/2012 | Hessler |
| 8,096,459 | B2 | 1/2012 | Ortiz et al. |
| 8,097,017 | B2 | 1/2012 | Viola |
| 8,100,310 | B2 | 1/2012 | Zemlok |
| 8,100,824 | B2 | 1/2012 | Hegeman et al. |
| 8,100,872 | B2 | 1/2012 | Patel |
| 8,102,138 | B2 | 1/2012 | Sekine et al. |
| 8,102,278 | B2 | 1/2012 | Deck et al. |
| 8,105,320 | B2 | 1/2012 | Manzo |
| 8,105,350 | B2 | 1/2012 | Lee et al. |
| 8,107,925 | B2 | 1/2012 | Natsuno et al. |
| 8,108,033 | B2 | 1/2012 | Drew et al. |
| 8,108,072 | B2 | 1/2012 | Zhao et al. |
| 8,109,426 | B2 | 2/2012 | Milliman et al. |
| 8,110,208 | B1 | 2/2012 | Hen |
| 8,113,405 | B2 | 2/2012 | Milliman |
| 8,113,407 | B2 | 2/2012 | Holsten et al. |
| 8,113,408 | B2 | 2/2012 | Wenchell et al. |
| 8,113,410 | B2 | 2/2012 | Hall et al. |
| 8,114,017 | B2 | 2/2012 | Bacher |
| 8,114,100 | B2 | 2/2012 | Smith et al. |
| 8,114,345 | B2 | 2/2012 | Dlugos, Jr. et al. |
| 8,118,206 | B2 | 2/2012 | Zand et al. |
| 8,118,207 | B2 | 2/2012 | Racenet et al. |
| 8,120,301 | B2 | 2/2012 | Goldberg et al. |
| 8,122,128 | B2 | 2/2012 | Burke, II et al. |
| 8,123,103 | B2 | 2/2012 | Milliman |
| 8,123,523 | B2 | 2/2012 | Carron et al. |
| 8,123,766 | B2 | 2/2012 | Bauman et al. |
| 8,123,767 | B2 | 2/2012 | Bauman et al. |
| 8,125,168 | B2 | 2/2012 | Johnson et al. |
| 8,127,975 | B2 | 3/2012 | Olson et al. |
| 8,127,976 | B2 | 3/2012 | Scirica et al. |
| 8,128,624 | B2 | 3/2012 | Couture et al. |
| 8,128,642 | B2 | 3/2012 | Heeps et al. |
| 8,128,643 | B2 | 3/2012 | Aranyi et al. |
| 8,128,645 | B2 | 3/2012 | Sonnenschein et al. |
| 8,128,662 | B2 | 3/2012 | Altarac et al. |
| 8,132,703 | B2 | 3/2012 | Milliman et al. |
| 8,132,705 | B2 | 3/2012 | Viola et al. |
| 8,132,706 | B2 | 3/2012 | Marczyk et al. |
| 8,133,500 | B2 | 3/2012 | Ringeisen et al. |
| 8,134,306 | B2 | 3/2012 | Drader et al. |
| 8,136,711 | B2 | 3/2012 | Beardsley et al. |
| 8,136,712 | B2 | 3/2012 | Zingman |
| 8,136,713 | B2 | 3/2012 | Hathaway et al. |
| 8,137,339 | B2 | 3/2012 | Jinno et al. |
| 8,140,417 | B2 | 3/2012 | Shibata |
| 8,141,762 | B2 | 3/2012 | Bedi et al. |
| 8,141,763 | B2 | 3/2012 | Milliman |
| 8,142,200 | B2 | 3/2012 | Crunkilton et al. |
| 8,142,425 | B2 | 3/2012 | Eggers |
| 8,142,461 | B2 | 3/2012 | Houser et al. |
| 8,142,515 | B2 | 3/2012 | Therin et al. |
| 8,143,520 | B2 | 3/2012 | Cutler |

(56) References Cited

U.S. PATENT DOCUMENTS

| | | | |
|---|---|---|---|
| 8,146,790 | B2 | 4/2012 | Milliman |
| 8,147,421 | B2 | 4/2012 | Farquhar et al. |
| 8,147,456 | B2 | 4/2012 | Fisher et al. |
| 8,147,485 | B2 | 4/2012 | Wham et al. |
| 8,152,041 | B2 | 4/2012 | Kostrzewski |
| 8,152,756 | B2 | 4/2012 | Webster et al. |
| 8,154,239 | B2 | 4/2012 | Katsuki et al. |
| 8,157,145 | B2 | 4/2012 | Shelton, IV et al. |
| 8,157,148 | B2 | 4/2012 | Scirica |
| 8,157,150 | B2 | 4/2012 | Viola et al. |
| 8,157,151 | B2 | 4/2012 | Ingmanson et al. |
| 8,157,152 | B2 | 4/2012 | Holsten et al. |
| 8,157,153 | B2 | 4/2012 | Shelton, IV et al. |
| 8,157,793 | B2 | 4/2012 | Omori et al. |
| 8,157,834 | B2 | 4/2012 | Conlon |
| 8,161,977 | B2 | 4/2012 | Shelton, IV et al. |
| 8,162,138 | B2 | 4/2012 | Bettenhausen et al. |
| 8,162,197 | B2 | 4/2012 | Mastri et al. |
| 8,162,668 | B2 | 4/2012 | Toly |
| 8,162,933 | B2 | 4/2012 | Francischelli et al. |
| 8,162,965 | B2 | 4/2012 | Reschke et al. |
| 8,167,185 | B2 | 5/2012 | Shelton, IV et al. |
| 8,167,622 | B2 | 5/2012 | Zhou |
| 8,167,895 | B2 | 5/2012 | D'Agostino et al. |
| 8,167,898 | B1 | 5/2012 | Schaller et al. |
| 8,170,241 | B2 | 5/2012 | Roe et al. |
| 8,172,004 | B2 | 5/2012 | Ho |
| 8,172,120 | B2 | 5/2012 | Boyden et al. |
| 8,172,122 | B2 | 5/2012 | Kasvikis et al. |
| 8,172,124 | B2 | 5/2012 | Shelton, IV et al. |
| 8,177,776 | B2 | 5/2012 | Humayun et al. |
| 8,177,797 | B2 | 5/2012 | Shimoji et al. |
| 8,179,705 | B2 | 5/2012 | Chapuis |
| 8,180,458 | B2 | 5/2012 | Kane et al. |
| 8,181,839 | B2 | 5/2012 | Beetel |
| 8,181,840 | B2 | 5/2012 | Milliman |
| 8,182,422 | B2 | 5/2012 | Bayer et al. |
| 8,182,444 | B2 | 5/2012 | Uber, III et al. |
| 8,183,807 | B2 | 5/2012 | Tsai et al. |
| 8,186,555 | B2 | 5/2012 | Shelton, IV et al. |
| 8,186,556 | B2 | 5/2012 | Viola |
| 8,186,558 | B2 | 5/2012 | Sapienza |
| 8,186,560 | B2 | 5/2012 | Hess et al. |
| 8,190,238 | B2 | 5/2012 | Moll et al. |
| D661,314 | S | 6/2012 | Marchetti |
| D661,315 | S | 6/2012 | Marchetti et al. |
| 8,191,752 | B2 | 6/2012 | Scirica |
| 8,192,350 | B2 | 6/2012 | Ortiz et al. |
| 8,192,460 | B2 | 6/2012 | Orban, III et al. |
| 8,192,651 | B2 | 6/2012 | Young et al. |
| 8,193,129 | B2 | 6/2012 | Tagawa et al. |
| 8,196,795 | B2 | 6/2012 | Moore et al. |
| 8,196,796 | B2 | 6/2012 | Shelton, IV et al. |
| 8,197,501 | B2 | 6/2012 | Shadeck et al. |
| 8,197,502 | B2 | 6/2012 | Smith et al. |
| 8,197,837 | B2 | 6/2012 | Jamiolkowski et al. |
| 8,201,720 | B2 | 6/2012 | Hessler |
| 8,201,721 | B2 | 6/2012 | Zemlok et al. |
| 8,202,549 | B2 | 6/2012 | Stucky et al. |
| 8,205,779 | B2 | 6/2012 | Ma et al. |
| 8,205,780 | B2 | 6/2012 | Sorrentino et al. |
| 8,205,781 | B2 | 6/2012 | Baxter, III et al. |
| 8,207,863 | B2 | 6/2012 | Neubauer et al. |
| 8,210,411 | B2 | 7/2012 | Yates et al. |
| 8,210,413 | B2 | 7/2012 | Whitman et al. |
| 8,210,414 | B2 | 7/2012 | Bettuchi et al. |
| 8,210,415 | B2 | 7/2012 | Ward |
| 8,210,416 | B2 | 7/2012 | Milliman et al. |
| 8,210,721 | B2 | 7/2012 | Chen et al. |
| 8,211,125 | B2 | 7/2012 | Spivey |
| 8,214,019 | B2 | 7/2012 | Govari et al. |
| 8,215,531 | B2 | 7/2012 | Shelton, IV et al. |
| 8,215,532 | B2 | 7/2012 | Marczyk |
| 8,215,533 | B2 | 7/2012 | Viola et al. |
| 8,220,468 | B2 | 7/2012 | Cooper et al. |
| 8,220,688 | B2 | 7/2012 | Laurent et al. |
| 8,220,690 | B2 | 7/2012 | Hess et al. |
| 8,221,402 | B2 | 7/2012 | Francischelli et al. |
| 8,221,424 | B2 | 7/2012 | Cha |
| 8,221,433 | B2 | 7/2012 | Lozier et al. |
| 8,225,799 | B2 | 7/2012 | Bettuchi |
| 8,225,979 | B2 | 7/2012 | Farascioni et al. |
| 8,226,553 | B2 | 7/2012 | Shelton, IV et al. |
| 8,226,635 | B2 | 7/2012 | Petrie et al. |
| 8,226,675 | B2 | 7/2012 | Houser et al. |
| 8,226,715 | B2 | 7/2012 | Hwang et al. |
| 8,227,946 | B2 | 7/2012 | Kim |
| 8,228,020 | B2 | 7/2012 | Shin et al. |
| 8,228,048 | B2 | 7/2012 | Spencer |
| 8,229,549 | B2 | 7/2012 | Whitman et al. |
| 8,230,235 | B2 | 7/2012 | Goodman et al. |
| 8,231,040 | B2 | 7/2012 | Zemlok et al. |
| 8,231,042 | B2 | 7/2012 | Hessler et al. |
| 8,231,043 | B2 | 7/2012 | Tarinelli et al. |
| 8,235,272 | B2 | 8/2012 | Nicholas et al. |
| 8,235,274 | B2 | 8/2012 | Cappola |
| 8,236,010 | B2 | 8/2012 | Ortiz et al. |
| 8,236,011 | B2 | 8/2012 | Harris et al. |
| 8,236,020 | B2 | 8/2012 | Smith et al. |
| 8,237,388 | B2 | 8/2012 | Jinno et al. |
| 8,240,536 | B2 | 8/2012 | Marczyk |
| 8,240,537 | B2 | 8/2012 | Marczyk |
| 8,241,271 | B2 | 8/2012 | Millman et al. |
| 8,241,284 | B2 | 8/2012 | Dycus et al. |
| 8,241,308 | B2 | 8/2012 | Kortenbach et al. |
| 8,241,322 | B2 | 8/2012 | Whitman et al. |
| 8,245,594 | B2 | 8/2012 | Rogers et al. |
| 8,245,898 | B2 | 8/2012 | Smith et al. |
| 8,245,899 | B2 | 8/2012 | Swensgard et al. |
| 8,245,900 | B2 | 8/2012 | Scirica |
| 8,245,901 | B2 | 8/2012 | Stopek |
| 8,246,608 | B2 | 8/2012 | Omori et al. |
| 8,246,637 | B2 | 8/2012 | Viola et al. |
| 8,251,921 | B2 | 8/2012 | Briggs et al. |
| 8,252,009 | B2 | 8/2012 | Weller et al. |
| D667,450 | S | 9/2012 | Eby et al. |
| 8,256,654 | B2 | 9/2012 | Bettuchi et al. |
| 8,256,655 | B2 | 9/2012 | Sniffin et al. |
| 8,256,656 | B2 | 9/2012 | Milliman et al. |
| 8,257,251 | B2 | 9/2012 | Shelton, IV et al. |
| 8,257,356 | B2 | 9/2012 | Bleich et al. |
| 8,257,386 | B2 | 9/2012 | Lee et al. |
| 8,257,391 | B2 | 9/2012 | Orban, III et al. |
| 8,257,634 | B2 | 9/2012 | Scirica |
| 8,258,745 | B2 | 9/2012 | Smith et al. |
| 8,261,958 | B1 | 9/2012 | Knodel |
| 8,262,560 | B2 | 9/2012 | Whitman |
| 8,262,655 | B2 | 9/2012 | Ghabrial et al. |
| 8,266,232 | B2 | 9/2012 | Piper et al. |
| 8,267,300 | B2 | 9/2012 | Boudreaux |
| 8,267,849 | B2 | 9/2012 | Wazer et al. |
| 8,267,924 | B2 | 9/2012 | Zemlok et al. |
| 8,267,946 | B2 | 9/2012 | Whitfield et al. |
| 8,267,951 | B2 | 9/2012 | Whayne et al. |
| 8,268,344 | B2 | 9/2012 | Ma et al. |
| 8,269,121 | B2 | 9/2012 | Smith |
| 8,272,553 | B2 | 9/2012 | Mastri et al. |
| 8,272,554 | B2 | 9/2012 | Whitman et al. |
| 8,272,918 | B2 | 9/2012 | Lam |
| 8,273,404 | B2 | 9/2012 | Dave et al. |
| 8,276,594 | B2 | 10/2012 | Shah |
| 8,276,801 | B2 | 10/2012 | Zemlok et al. |
| 8,276,802 | B2 | 10/2012 | Kostrzewski |
| 8,277,473 | B2 | 10/2012 | Sunaoshi et al. |
| 8,281,446 | B2 | 10/2012 | Moskovich |
| 8,281,973 | B2 | 10/2012 | Wenchell et al. |
| 8,281,974 | B2 | 10/2012 | Hessler et al. |
| 8,282,654 | B2 | 10/2012 | Ferrari et al. |
| 8,285,367 | B2 | 10/2012 | Hyde et al. |
| 8,286,723 | B2 | 10/2012 | Puzio et al. |
| 8,286,845 | B2 | 10/2012 | Perry et al. |
| 8,286,846 | B2 | 10/2012 | Smith et al. |
| 8,286,847 | B2 | 10/2012 | Taylor |
| 8,287,487 | B2 | 10/2012 | Estes |

(56) References Cited

U.S. PATENT DOCUMENTS 8,287,522 B2 10/2012 Moses et al.
8,287,561 B2 10/2012 Nunez et al.
8,288,984 B2 10/2012 Yang
8,289,403 B2 10/2012 Dobashi et al.
8,290,883 B2 10/2012 Takeuchi et al.
8,292,147 B2 10/2012 Viola
8,292,148 B2 10/2012 Viola
8,292,150 B2 10/2012 Bryant
8,292,151 B2 10/2012 Viola
8,292,152 B2 10/2012 Milliman et al.
8,292,155 B2 10/2012 Shelton, IV et al.
8,292,157 B2 10/2012 Smith et al.
8,292,158 B2 10/2012 Sapienza
8,292,801 B2 10/2012 Dejima et al.
8,292,888 B2 10/2012 Whitman
8,292,906 B2 10/2012 Taylor et al.
8,294,399 B2 10/2012 Suzuki et al.
8,298,161 B2 10/2012 Vargas
8,298,189 B2 10/2012 Fisher et al.
8,298,233 B2 10/2012 Mueller
8,298,677 B2 10/2012 Wiesner et al.
8,302,323 B2 11/2012 Fortier et al.
8,303,621 B2 11/2012 Miyamoto et al.
8,308,040 B2 11/2012 Huang et al.
8,308,041 B2 11/2012 Kostrzewski
8,308,042 B2 11/2012 Aranyi
8,308,043 B2 11/2012 Bindra et al.
8,308,046 B2 11/2012 Prommersberger
8,308,659 B2 11/2012 Scheibe et al.
8,308,725 B2 11/2012 Bell et al.
8,310,188 B2 11/2012 Nakai
8,313,444 B2 11/2012 Thompson et al.
8,313,496 B2 11/2012 Sauer et al.
8,313,499 B2 11/2012 Magnusson et al.
8,313,509 B2 11/2012 Kostrzewski
8,317,070 B2 11/2012 Hueil et al.
8,317,071 B1 11/2012 Knodel
8,317,074 B2 11/2012 Ortiz et al.
8,317,437 B2 11/2012 Merkley et al.
8,317,744 B2 11/2012 Kirschenman
8,317,790 B2 11/2012 Bell et al.
8,319,002 B2 11/2012 Daniels et al.
D672,784 S 12/2012 Clanton et al.
8,322,455 B2 12/2012 Shelton, IV et al.
8,322,589 B2 12/2012 Boudreaux
8,322,590 B2 12/2012 Patel et al.
8,322,901 B2 12/2012 Michelotti
8,323,271 B2 12/2012 Humayun et al.
8,323,789 B2 12/2012 Rozhin et al.
8,324,585 B2 12/2012 McBroom et al.
8,327,514 B2 12/2012 Kim
8,328,061 B2 12/2012 Kasvikis
8,328,062 B2 12/2012 Viola
8,328,063 B2 12/2012 Milliman et al.
8,328,064 B2 12/2012 Racenet et al.
8,328,065 B2 12/2012 Shah
8,328,802 B2 12/2012 Deville et al.
8,328,823 B2 12/2012 Aranyi et al.
8,333,313 B2 12/2012 Boudreaux et al.
8,333,691 B2 12/2012 Schaaf
8,333,764 B2 12/2012 Francischelli et al.
8,333,779 B2 12/2012 Smith et al.
8,334,468 B2 12/2012 Palmer et al.
8,336,753 B2 12/2012 Olson et al.
8,336,754 B2 12/2012 Cappola et al.
8,342,377 B2 1/2013 Milliman et al.
8,342,378 B2 1/2013 Marczyk et al.
8,342,379 B2 1/2013 Whitman et al.
8,342,380 B2 1/2013 Viola
8,343,150 B2 1/2013 Artale
8,347,978 B2 1/2013 Forster et al.
8,348,118 B2 1/2013 Segura
8,348,123 B2 1/2013 Scirica et al.
8,348,124 B2 1/2013 Scirica
8,348,125 B2 1/2013 Viola et al.
8,348,126 B2 1/2013 Olson et al.
8,348,127 B2 1/2013 Marczyk
8,348,129 B2 1/2013 Bedi et al.
8,348,130 B2 1/2013 Shah et al.
8,348,131 B2 1/2013 Omaits et al.
8,348,837 B2 1/2013 Wenchell
8,348,948 B2 1/2013 Bahney
8,348,959 B2 1/2013 Wolford et al.
8,348,972 B2 1/2013 Soltz et al.
8,349,987 B2 1/2013 Kapiamba et al.
8,352,004 B2 1/2013 Mannheimer et al.
8,353,437 B2 1/2013 Boudreaux
8,353,438 B2 1/2013 Baxter, III et al.
8,353,439 B2 1/2013 Baxter, III et al.
8,356,740 B1 1/2013 Knodel
8,357,144 B2 1/2013 Whitman et al.
8,357,158 B2 1/2013 McKenna et al.
8,357,161 B2 1/2013 Mueller
8,359,174 B2 1/2013 Nakashima et al.
8,360,296 B2 1/2013 Zingman
8,360,297 B2 1/2013 Shelton, IV et al.
8,360,298 B2 1/2013 Farascioni et al.
8,360,299 B2 1/2013 Zemlok et al.
8,361,501 B2 1/2013 DiTizio et al.
D676,866 S 2/2013 Chaudhri
8,365,972 B2 2/2013 Aranyi et al.
8,365,973 B1 2/2013 White et al.
8,365,975 B1 2/2013 Manoux et al.
8,365,976 B2 2/2013 Hess et al.
8,366,559 B2 2/2013 Papenfuss et al.
8,366,719 B2 2/2013 Markey et al.
8,366,787 B2 2/2013 Brown et al.
8,368,327 B2 2/2013 Benning et al.
8,369,056 B2 2/2013 Senriuchi et al.
8,371,393 B2 2/2013 Higuchi et al.
8,371,491 B2 2/2013 Huitema et al.
8,371,492 B2 2/2013 Aranyi et al.
8,371,493 B2 2/2013 Aranyi et al.
8,371,494 B2 2/2013 Racenet et al.
8,372,094 B2 2/2013 Bettuchi et al.
8,374,723 B2 2/2013 Zhao et al.
8,376,865 B2 2/2013 Forster et al.
8,377,029 B2 2/2013 Nagao et al.
8,377,044 B2 2/2013 Coe et al.
8,377,059 B2 2/2013 Deville et al.
8,381,828 B2 2/2013 Whitman et al.
8,381,834 B2 2/2013 Barhitte et al.
8,382,773 B2 2/2013 Whitfield et al.
8,382,790 B2 2/2013 Uenohara et al.
D677,273 S 3/2013 Randall et al.
8,387,848 B2 3/2013 Johnson et al.
8,388,633 B2 3/2013 Rousseau et al.
8,389,588 B2 3/2013 Ringeisen et al.
8,393,513 B2 3/2013 Jankowski
8,393,514 B2 3/2013 Shelton, IV et al.
8,393,516 B2 3/2013 Kostrzewski
8,395,342 B2 3/2013 Prisco
8,397,832 B2 3/2013 Blickle et al.
8,397,971 B2 3/2013 Yates et al.
8,397,972 B2 3/2013 Kostrzewski
8,397,973 B1 3/2013 Hausen
8,398,633 B2 3/2013 Mueller
8,398,669 B2 3/2013 Kim
8,398,673 B2 3/2013 Hinchliffe et al.
8,398,674 B2 3/2013 Prestel
8,400,108 B2 3/2013 Powell et al.
8,400,851 B2 3/2013 Byun
8,403,138 B2 3/2013 Weisshaupt et al.
8,403,195 B2 3/2013 Beardsley et al.
8,403,196 B2 3/2013 Beardsley et al.
8,403,198 B2 3/2013 Sorrentino et al.
8,403,832 B2 3/2013 Cunningham et al.
8,403,926 B2 3/2013 Nobis et al.
8,403,945 B2 3/2013 Whitfield et al.
8,403,946 B2 3/2013 Whitfield et al.
8,403,950 B2 3/2013 Palmer et al.
D679,726 S 4/2013 Kobayashi
D680,646 S 4/2013 Hunt et al.
8,408,439 B2 4/2013 Huang et al.

(56) References Cited

U.S. PATENT DOCUMENTS

| | | | |
|---|---|---|---|
| 8,408,442 | B2 | 4/2013 | Racenet et al. |
| 8,409,079 | B2 | 4/2013 | Okamoto et al. |
| 8,409,174 | B2 | 4/2013 | Omori |
| 8,409,175 | B2 | 4/2013 | Lee et al. |
| 8,409,211 | B2 | 4/2013 | Baroud |
| 8,409,222 | B2 | 4/2013 | Whitfield et al. |
| 8,409,223 | B2 | 4/2013 | Sorrentino et al. |
| 8,409,234 | B2 | 4/2013 | Stahler et al. |
| 8,411,500 | B2 | 4/2013 | Gapihan et al. |
| 8,413,661 | B2 | 4/2013 | Rousseau et al. |
| 8,413,870 | B2 | 4/2013 | Pastorelli et al. |
| 8,413,871 | B2 | 4/2013 | Racenet et al. |
| 8,413,872 | B2 | 4/2013 | Patel |
| 8,414,469 | B2 | 4/2013 | Diolaiti |
| 8,414,577 | B2 | 4/2013 | Boudreaux et al. |
| 8,414,598 | B2 | 4/2013 | Brock et al. |
| 8,418,073 | B2 | 4/2013 | Mohr et al. |
| 8,418,906 | B2 | 4/2013 | Farascioni et al. |
| 8,418,907 | B2 | 4/2013 | Johnson et al. |
| 8,418,908 | B1 | 4/2013 | Beardsley |
| 8,418,909 | B2 | 4/2013 | Kostrzewski |
| 8,419,635 | B2 | 4/2013 | Shelton, IV et al. |
| 8,419,717 | B2 | 4/2013 | Diolaiti et al. |
| 8,419,747 | B2 | 4/2013 | Hinman et al. |
| 8,419,754 | B2 | 4/2013 | Laby et al. |
| 8,419,755 | B2 | 4/2013 | Deem et al. |
| 8,423,182 | B2 | 4/2013 | Robinson et al. |
| 8,424,737 | B2 | 4/2013 | Scirica |
| 8,424,739 | B2 | 4/2013 | Racenet et al. |
| 8,424,740 | B2 | 4/2013 | Shelton, IV et al. |
| 8,424,741 | B2 | 4/2013 | McGuckin, Jr. et al. |
| 8,424,742 | B2 | 4/2013 | Bettuchi |
| 8,425,600 | B2 | 4/2013 | Maxwell |
| 8,427,430 | B2 | 4/2013 | Lee et al. |
| 8,430,292 | B2 | 4/2013 | Patel et al. |
| 8,430,892 | B2 | 4/2013 | Bindra et al. |
| 8,430,898 | B2 | 4/2013 | Wiener et al. |
| D681,674 | S | 5/2013 | Koehn et al. |
| 8,435,257 | B2 | 5/2013 | Smith et al. |
| 8,439,246 | B1 | 5/2013 | Knodel |
| 8,439,830 | B2 | 5/2013 | McKinley et al. |
| 8,444,036 | B2 | 5/2013 | Shelton, IV |
| 8,444,037 | B2 | 5/2013 | Nicholas et al. |
| 8,444,549 | B2 | 5/2013 | Viola et al. |
| 8,449,536 | B2 | 5/2013 | Selig |
| 8,449,560 | B2 | 5/2013 | Roth et al. |
| 8,453,904 | B2 | 6/2013 | Eskaros et al. |
| 8,453,906 | B2 | 6/2013 | Huang et al. |
| 8,453,907 | B2 | 6/2013 | Laurent et al. |
| 8,453,908 | B2 | 6/2013 | Bedi et al. |
| 8,453,912 | B2 | 6/2013 | Mastri et al. |
| 8,453,914 | B2 | 6/2013 | Laurent et al. |
| 8,454,495 | B2 | 6/2013 | Kawano et al. |
| 8,454,551 | B2 | 6/2013 | Allen et al. |
| 8,454,628 | B2 | 6/2013 | Smith et al. |
| 8,454,640 | B2 | 6/2013 | Johnston et al. |
| 8,457,757 | B2 | 6/2013 | Cauller et al. |
| 8,459,520 | B2 | 6/2013 | Giordano et al. |
| 8,459,521 | B2 | 6/2013 | Zemlok et al. |
| 8,459,524 | B2 | 6/2013 | Pribanic et al. |
| 8,459,525 | B2 | 6/2013 | Yates et al. |
| 8,460,207 | B2 | 6/2013 | Burdorff et al. |
| 8,464,922 | B2 | 6/2013 | Marczyk |
| 8,464,923 | B2 | 6/2013 | Shelton, IV |
| 8,464,924 | B2 | 6/2013 | Gresham et al. |
| 8,464,925 | B2 | 6/2013 | Hull et al. |
| 8,465,475 | B2 | 6/2013 | Isbell, Jr. |
| 8,465,502 | B2 | 6/2013 | Zergiebel |
| 8,465,515 | B2 | 6/2013 | Drew et al. |
| 8,469,254 | B2 | 6/2013 | Czernik et al. |
| 8,469,946 | B2 | 6/2013 | Sugita |
| 8,469,973 | B2 | 6/2013 | Meade et al. |
| 8,470,355 | B2 | 6/2013 | Skalla et al. |
| D686,240 | S | 7/2013 | Lin |
| D686,244 | S | 7/2013 | Moriya et al. |
| 8,474,677 | B2 | 7/2013 | Woodard, Jr. et al. |
| 8,475,453 | B2 | 7/2013 | Marczyk et al. |
| 8,475,454 | B1 | 7/2013 | Alshemari |
| 8,475,474 | B2 | 7/2013 | Bombard et al. |
| 8,479,968 | B2 | 7/2013 | Hodgkinson et al. |
| 8,479,969 | B2 | 7/2013 | Shelton, IV |
| 8,480,703 | B2 | 7/2013 | Nicholas et al. |
| 8,483,509 | B2 | 7/2013 | Matsuzaka |
| 8,485,412 | B2 | 7/2013 | Shelton, IV et al. |
| 8,485,413 | B2 | 7/2013 | Scheib et al. |
| 8,485,970 | B2 | 7/2013 | Widenhouse et al. |
| 8,486,047 | B2 | 7/2013 | Stopek |
| 8,487,199 | B2 | 7/2013 | Palmer et al. |
| 8,487,487 | B2 | 7/2013 | Dietz et al. |
| 8,490,851 | B2 | 7/2013 | Blier et al. |
| 8,490,852 | B2 | 7/2013 | Viola |
| 8,490,853 | B2 | 7/2013 | Criscuolo et al. |
| 8,491,581 | B2 | 7/2013 | Deville et al. |
| 8,491,603 | B2 | 7/2013 | Yeung et al. |
| 8,491,624 | B2 | 7/2013 | Kerr et al. |
| 8,496,153 | B2 | 7/2013 | Demmy et al. |
| 8,496,154 | B2 | 7/2013 | Marczyk et al. |
| 8,496,156 | B2 | 7/2013 | Sniffin et al. |
| 8,496,683 | B2 | 7/2013 | Prommersberger et al. |
| 8,498,691 | B2 | 7/2013 | Moll et al. |
| 8,499,673 | B2 | 8/2013 | Keller |
| 8,499,966 | B2 | 8/2013 | Palmer et al. |
| 8,499,992 | B2 | 8/2013 | Whitman et al. |
| 8,499,993 | B2 | 8/2013 | Shelton, IV et al. |
| 8,499,994 | B2 | 8/2013 | D'Arcangelo |
| 8,500,721 | B2 | 8/2013 | Jinno |
| 8,500,762 | B2 | 8/2013 | Sholev et al. |
| 8,502,091 | B2 | 8/2013 | Palmer et al. |
| 8,505,649 | B2 | 8/2013 | Scrimshaw et al. |
| 8,505,799 | B2 | 8/2013 | Viola et al. |
| 8,505,801 | B2 | 8/2013 | Ehrenfels et al. |
| 8,505,802 | B2 | 8/2013 | Viola et al. |
| 8,506,555 | B2 | 8/2013 | Ruiz Morales |
| 8,506,557 | B2 | 8/2013 | Zemlok et al. |
| 8,506,580 | B2 | 8/2013 | Zergiebel et al. |
| 8,506,581 | B2 | 8/2013 | Wingardner, III et al. |
| 8,511,308 | B2 | 8/2013 | Hecox et al. |
| 8,512,359 | B2 | 8/2013 | Whitman et al. |
| 8,512,402 | B2 | 8/2013 | Marczyk et al. |
| 8,517,239 | B2 | 8/2013 | Scheib et al. |
| 8,517,241 | B2 | 8/2013 | Nicholas et al. |
| 8,517,243 | B2 | 8/2013 | Giordano et al. |
| 8,517,244 | B2 | 8/2013 | Shelton, IV et al. |
| 8,517,938 | B2 | 8/2013 | Eisenhardt et al. |
| 8,518,024 | B2 | 8/2013 | Williams et al. |
| 8,521,273 | B2 | 8/2013 | Kliman |
| 8,523,042 | B2 | 9/2013 | Masiakos et al. |
| 8,523,043 | B2 | 9/2013 | Ullrich et al. |
| 8,523,787 | B2 | 9/2013 | Ludwin et al. |
| 8,523,881 | B2 | 9/2013 | Cabiri et al. |
| 8,523,882 | B2 | 9/2013 | Huitema et al. |
| 8,523,900 | B2 | 9/2013 | Jinno et al. |
| 8,529,588 | B2 | 9/2013 | Ahlberg et al. |
| 8,529,599 | B2 | 9/2013 | Holsten |
| 8,529,600 | B2 | 9/2013 | Woodard, Jr. et al. |
| 8,529,819 | B2 | 9/2013 | Ostapoff et al. |
| 8,531,153 | B2 | 9/2013 | Baarman et al. |
| 8,532,747 | B2 | 9/2013 | Nock et al. |
| 8,534,527 | B2 | 9/2013 | Brendel et al. |
| 8,534,528 | B2 | 9/2013 | Shelton, IV |
| 8,535,304 | B2 | 9/2013 | Sklar et al. |
| 8,535,340 | B2 | 9/2013 | Allen |
| 8,539,866 | B2 | 9/2013 | Nayak et al. |
| 8,540,128 | B2 | 9/2013 | Shelton, IV et al. |
| 8,540,129 | B2 | 9/2013 | Baxter, III et al. |
| 8,540,130 | B2 | 9/2013 | Moore et al. |
| 8,540,131 | B2 | 9/2013 | Swayze |
| 8,540,133 | B2 | 9/2013 | Bedi et al. |
| 8,540,646 | B2 | 9/2013 | Mendez-Coll |
| 8,540,733 | B2 | 9/2013 | Whitman et al. |
| 8,540,735 | B2 | 9/2013 | Mitelberg et al. |
| D690,614 | S | 10/2013 | Mascadri et al. |
| 8,550,984 | B2 | 10/2013 | Takemoto |
| 8,551,076 | B2 | 10/2013 | Duval et al. |

(56) References Cited

U.S. PATENT DOCUMENTS

| | | | |
|---|---|---|---|
| 8,555,660 | B2 | 10/2013 | Takenaka et al. |
| 8,556,151 | B2 | 10/2013 | Viola |
| 8,556,918 | B2 | 10/2013 | Bauman et al. |
| 8,556,935 | B1 | 10/2013 | Knodel et al. |
| 8,560,147 | B2 | 10/2013 | Taylor et al. |
| 8,561,617 | B2 | 10/2013 | Lindh et al. |
| 8,561,870 | B2 | 10/2013 | Baxter, III et al. |
| 8,561,871 | B2 | 10/2013 | Rajappa et al. |
| 8,561,873 | B2 | 10/2013 | Ingmanson et al. |
| 8,562,592 | B2 | 10/2013 | Conlon et al. |
| 8,562,598 | B2 | 10/2013 | Falkenstein et al. |
| 8,567,656 | B2 | 10/2013 | Shelton, IV et al. |
| 8,568,416 | B2 | 10/2013 | Schmitz et al. |
| 8,568,425 | B2 | 10/2013 | Ross et al. |
| D692,916 | S | 11/2013 | Granchi et al. |
| 8,573,459 | B2 | 11/2013 | Smith et al. |
| 8,573,461 | B2 | 11/2013 | Shelton, IV et al. |
| 8,573,462 | B2 | 11/2013 | Smith et al. |
| 8,573,465 | B2 | 11/2013 | Shelton, IV |
| 8,574,199 | B2 | 11/2013 | von Bulow et al. |
| 8,574,263 | B2 | 11/2013 | Mueller |
| 8,575,880 | B2 | 11/2013 | Grantz |
| 8,575,895 | B2 | 11/2013 | Garrastacho et al. |
| 8,579,176 | B2 | 11/2013 | Smith et al. |
| 8,579,178 | B2 | 11/2013 | Holsten et al. |
| 8,579,897 | B2 | 11/2013 | Vakharia et al. |
| 8,579,937 | B2 | 11/2013 | Gresham |
| 8,584,919 | B2 | 11/2013 | Hueil et al. |
| 8,584,920 | B2 | 11/2013 | Hodgkinson |
| 8,584,921 | B2 | 11/2013 | Scirica |
| 8,585,583 | B2 | 11/2013 | Sakaguchi et al. |
| 8,585,598 | B2 | 11/2013 | Razzaque et al. |
| 8,585,721 | B2 | 11/2013 | Kirsch |
| 8,590,760 | B2 | 11/2013 | Cummins et al. |
| 8,590,762 | B2 | 11/2013 | Hess et al. |
| 8,590,764 | B2 | 11/2013 | Hartwick et al. |
| 8,591,400 | B2 | 11/2013 | Sugiyama |
| D695,310 | S | 12/2013 | Jang et al. |
| 8,596,515 | B2 | 12/2013 | Okoniewski |
| 8,597,745 | B2 | 12/2013 | Farnsworth et al. |
| 8,599,450 | B2 | 12/2013 | Kubo et al. |
| 8,602,125 | B2 | 12/2013 | King |
| 8,602,287 | B2 | 12/2013 | Yates et al. |
| 8,602,288 | B2 | 12/2013 | Shelton, IV et al. |
| 8,603,077 | B2 | 12/2013 | Cooper et al. |
| 8,603,089 | B2 | 12/2013 | Viola |
| 8,603,110 | B2 | 12/2013 | Maruyama et al. |
| 8,603,135 | B2 | 12/2013 | Mueller |
| 8,608,043 | B2 | 12/2013 | Scirica |
| 8,608,044 | B2 | 12/2013 | Hueil et al. |
| 8,608,045 | B2 | 12/2013 | Smith et al. |
| 8,608,046 | B2 | 12/2013 | Laurent et al. |
| 8,608,745 | B2 | 12/2013 | Guzman et al. |
| 8,613,383 | B2 | 12/2013 | Beckman et al. |
| 8,613,384 | B2 | 12/2013 | Pastorelli et al. |
| 8,616,427 | B2 | 12/2013 | Viola |
| 8,616,431 | B2 | 12/2013 | Timm et al. |
| 8,617,155 | B2 | 12/2013 | Johnson et al. |
| 8,620,473 | B2 | 12/2013 | Diolaiti et al. |
| 8,622,274 | B2 | 1/2014 | Yates et al. |
| 8,622,275 | B2 | 1/2014 | Baxter, III et al. |
| 8,627,993 | B2 | 1/2014 | Smith et al. |
| 8,627,994 | B2 | 1/2014 | Zemlok et al. |
| 8,627,995 | B2 | 1/2014 | Smith et al. |
| 8,628,467 | B2 | 1/2014 | Whitman et al. |
| 8,628,518 | B2 | 1/2014 | Blumenkranz et al. |
| 8,628,544 | B2 | 1/2014 | Farascioni |
| 8,628,545 | B2 | 1/2014 | Cabrera et al. |
| 8,631,987 | B2 | 1/2014 | Shelton, IV et al. |
| 8,631,992 | B1 | 1/2014 | Hausen et al. |
| 8,631,993 | B2 | 1/2014 | Kostrzewski |
| 8,632,462 | B2 | 1/2014 | Yoo et al. |
| 8,632,525 | B2 | 1/2014 | Kerr et al. |
| 8,632,535 | B2 | 1/2014 | Shelton, IV et al. |
| 8,632,539 | B2 | 1/2014 | Twomey et al. |
| 8,632,563 | B2 | 1/2014 | Nagase et al. |
| 8,636,187 | B2 | 1/2014 | Hueil et al. |
| 8,636,190 | B2 | 1/2014 | Zemlok et al. |
| 8,636,191 | B2 | 1/2014 | Meagher |
| 8,636,193 | B2 | 1/2014 | Whitman et al. |
| 8,636,736 | B2 | 1/2014 | Yates et al. |
| 8,636,766 | B2 | 1/2014 | Milliman et al. |
| 8,639,936 | B2 | 1/2014 | Hu et al. |
| 8,640,788 | B2 | 2/2014 | Dachs et al. |
| 8,646,674 | B2 | 2/2014 | Schulte et al. |
| 8,647,258 | B2 | 2/2014 | Aranyi et al. |
| 8,652,120 | B2 | 2/2014 | Giordano et al. |
| 8,652,151 | B2 | 2/2014 | Lehman et al. |
| 8,652,155 | B2 | 2/2014 | Houser et al. |
| 8,656,929 | B2 | 2/2014 | Miller et al. |
| 8,657,174 | B2 | 2/2014 | Yates et al. |
| 8,657,175 | B2 | 2/2014 | Sonnenschein et al. |
| 8,657,176 | B2 | 2/2014 | Shelton, IV et al. |
| 8,657,177 | B2 | 2/2014 | Scirica et al. |
| 8,657,178 | B2 | 2/2014 | Hueil et al. |
| 8,657,482 | B2 | 2/2014 | Malackowski et al. |
| 8,657,808 | B2 | 2/2014 | McPherson et al. |
| 8,657,814 | B2 | 2/2014 | Werneth et al. |
| 8,657,821 | B2 | 2/2014 | Palermo |
| D701,238 | S | 3/2014 | Lai et al. |
| 8,662,370 | B2 | 3/2014 | Takei |
| 8,663,106 | B2 | 3/2014 | Stivoric et al. |
| 8,663,192 | B2 | 3/2014 | Hester et al. |
| 8,663,245 | B2 | 3/2014 | Francischelli et al. |
| 8,663,262 | B2 | 3/2014 | Smith et al. |
| 8,663,270 | B2 | 3/2014 | Donnigan et al. |
| 8,664,792 | B2 | 3/2014 | Rebsdorf |
| 8,668,129 | B2 | 3/2014 | Olson |
| 8,668,130 | B2 | 3/2014 | Hess et al. |
| 8,672,206 | B2 | 3/2014 | Aranyi et al. |
| 8,672,207 | B2 | 3/2014 | Shelton, IV et al. |
| 8,672,208 | B2 | 3/2014 | Hess et al. |
| 8,672,209 | B2 | 3/2014 | Crainich |
| 8,672,922 | B2 | 3/2014 | Loh et al. |
| 8,672,935 | B2 | 3/2014 | Okada et al. |
| 8,672,951 | B2 | 3/2014 | Smith et al. |
| 8,673,210 | B2 | 3/2014 | Deshays |
| 8,675,820 | B2 | 3/2014 | Baic et al. |
| 8,678,263 | B2 | 3/2014 | Viola |
| 8,678,994 | B2 | 3/2014 | Sonnenschein et al. |
| 8,679,093 | B2 | 3/2014 | Farra |
| 8,679,098 | B2 | 3/2014 | Hart |
| 8,679,114 | B2 | 3/2014 | Chapman et al. |
| 8,679,137 | B2 | 3/2014 | Bauman et al. |
| 8,679,154 | B2 | 3/2014 | Smith et al. |
| 8,679,156 | B2 | 3/2014 | Smith et al. |
| 8,679,454 | B2 | 3/2014 | Guire et al. |
| 8,684,248 | B2 | 4/2014 | Milliman |
| 8,684,249 | B2 | 4/2014 | Racenet et al. |
| 8,684,250 | B2 | 4/2014 | Bettuchi et al. |
| 8,684,253 | B2 | 4/2014 | Giordano et al. |
| 8,684,962 | B2 | 4/2014 | Kirschenman et al. |
| 8,685,004 | B2 | 4/2014 | Zemlock et al. |
| 8,685,020 | B2 | 4/2014 | Weizman et al. |
| 8,690,893 | B2 | 4/2014 | Deitch et al. |
| 8,695,866 | B2 | 4/2014 | Leimbach et al. |
| 8,696,665 | B2 | 4/2014 | Hunt et al. |
| 8,701,958 | B2 | 4/2014 | Shelton, IV et al. |
| 8,701,959 | B2 | 4/2014 | Shah |
| 8,706,316 | B1 | 4/2014 | Hoevenaar |
| 8,708,210 | B2 | 4/2014 | Zemlok et al. |
| 8,708,211 | B2 | 4/2014 | Zemlok et al. |
| 8,708,212 | B2 | 4/2014 | Williams |
| 8,708,213 | B2 | 4/2014 | Shelton, IV et al. |
| 8,709,012 | B2 | 4/2014 | Muller |
| 8,712,549 | B2 | 4/2014 | Zdeblick et al. |
| 8,714,352 | B2 | 5/2014 | Farascioni et al. |
| 8,714,429 | B2 | 5/2014 | Demmy |
| 8,714,430 | B2 | 5/2014 | Natarajan et al. |
| 8,715,256 | B2 | 5/2014 | Greener |
| 8,715,302 | B2 | 5/2014 | Ibrahim et al. |
| 8,720,766 | B2 | 5/2014 | Hess et al. |
| 8,721,630 | B2 | 5/2014 | Ortiz et al. |
| 8,721,666 | B2 | 5/2014 | Schroeder et al. |

(56) References Cited

U.S. PATENT DOCUMENTS

| | | | |
|---|---|---|---|
| 8,727,197 | B2 | 5/2014 | Hess et al. |
| 8,727,199 | B2 | 5/2014 | Wenchell |
| 8,727,200 | B2 | 5/2014 | Roy |
| 8,727,961 | B2 | 5/2014 | Ziv |
| 8,728,099 | B2 | 5/2014 | Cohn et al. |
| 8,728,119 | B2 | 5/2014 | Cummins |
| 8,733,470 | B2 | 5/2014 | Matthias et al. |
| 8,733,611 | B2 | 5/2014 | Milliman |
| 8,733,612 | B2 | 5/2014 | Ma |
| 8,733,613 | B2 | 5/2014 | Huitema et al. |
| 8,733,614 | B2 | 5/2014 | Ross et al. |
| 8,734,336 | B2 | 5/2014 | Bonadio et al. |
| 8,734,359 | B2 | 5/2014 | Ibanez et al. |
| 8,734,431 | B2 | 5/2014 | Shimada et al. |
| 8,734,478 | B2 | 5/2014 | Widenhouse et al. |
| 8,734,831 | B2 | 5/2014 | Kim et al. |
| 8,739,033 | B2 | 5/2014 | Rosenberg |
| 8,739,417 | B2 | 6/2014 | Tokunaga et al. |
| 8,740,034 | B2 | 6/2014 | Morgan et al. |
| 8,740,037 | B2 | 6/2014 | Shelton, IV et al. |
| 8,740,038 | B2 | 6/2014 | Shelton, IV et al. |
| 8,740,987 | B2 | 6/2014 | Geremakis et al. |
| 8,746,529 | B2 | 6/2014 | Shelton, IV et al. |
| 8,746,530 | B2 | 6/2014 | Giordano et al. |
| 8,746,533 | B2 | 6/2014 | Whitman et al. |
| 8,746,535 | B2 | 6/2014 | Shelton, IV et al. |
| 8,747,238 | B2 | 6/2014 | Shelton, IV et al. |
| 8,747,441 | B2 | 6/2014 | Konieczynski et al. |
| 8,752,264 | B2 | 6/2014 | Ackley et al. |
| 8,752,699 | B2 | 6/2014 | Morgan et al. |
| 8,752,747 | B2 | 6/2014 | Shelton, IV et al. |
| 8,752,748 | B2 | 6/2014 | Whitman et al. |
| 8,752,749 | B2 | 6/2014 | Moore et al. |
| 8,753,664 | B2 | 6/2014 | Dao et al. |
| 8,757,287 | B2 | 6/2014 | Mak et al. |
| 8,757,465 | B2 | 6/2014 | Woodard, Jr. et al. |
| 8,758,235 | B2 | 6/2014 | Jaworek |
| 8,758,366 | B2 | 6/2014 | McLean et al. |
| 8,758,391 | B2 | 6/2014 | Swayze et al. |
| 8,758,438 | B2 | 6/2014 | Boyce et al. |
| 8,763,875 | B2 | 7/2014 | Morgan et al. |
| 8,763,876 | B2 | 7/2014 | Kostrzewski |
| 8,763,877 | B2 | 7/2014 | Schall et al. |
| 8,763,879 | B2 | 7/2014 | Shelton, IV et al. |
| 8,764,732 | B2 | 7/2014 | Hartwell |
| 8,765,942 | B2 | 7/2014 | Feraud et al. |
| 8,770,458 | B2 | 7/2014 | Scirica |
| 8,770,459 | B2 | 7/2014 | Racenet et al. |
| 8,770,460 | B2 | 7/2014 | Belzer |
| 8,771,169 | B2 | 7/2014 | Whitman et al. |
| 8,771,260 | B2 | 7/2014 | Conlon et al. |
| 8,777,004 | B2 | 7/2014 | Shelton, IV et al. |
| 8,777,082 | B2 | 7/2014 | Scirica |
| 8,777,083 | B2 | 7/2014 | Racenet et al. |
| 8,777,898 | B2 | 7/2014 | Suon et al. |
| 8,783,541 | B2 | 7/2014 | Shelton, IV et al. |
| 8,783,542 | B2 | 7/2014 | Riestenberg et al. |
| 8,783,543 | B2 | 7/2014 | Shelton, IV et al. |
| 8,784,304 | B2 | 7/2014 | Mikkaichi et al. |
| 8,784,404 | B2 | 7/2014 | Doyle et al. |
| 8,784,415 | B2 | 7/2014 | Malackowski et al. |
| 8,789,737 | B2 | 7/2014 | Hodgkinson et al. |
| 8,789,739 | B2 | 7/2014 | Swensgard |
| 8,789,740 | B2 | 7/2014 | Baxter, III et al. |
| 8,789,741 | B2 | 7/2014 | Baxter, III et al. |
| 8,790,658 | B2 | 7/2014 | Cigarini et al. |
| 8,790,684 | B2 | 7/2014 | Dave et al. |
| D711,905 | S | 8/2014 | Morrison et al. |
| 8,794,098 | B2 | 8/2014 | Long |
| 8,794,496 | B2 | 8/2014 | Scirica |
| 8,794,497 | B2 | 8/2014 | Zingman |
| 8,795,159 | B2 | 8/2014 | Moriyama |
| 8,795,276 | B2 | 8/2014 | Dietz et al. |
| 8,795,308 | B2 | 8/2014 | Valin |
| 8,795,324 | B2 | 8/2014 | Kawai et al. |
| 8,796,995 | B2 | 8/2014 | Cunanan et al. |
| 8,800,681 | B2 | 8/2014 | Rousson et al. |
| 8,800,837 | B2 | 8/2014 | Zemlok |
| 8,800,838 | B2 | 8/2014 | Shelton, IV |
| 8,800,839 | B2 | 8/2014 | Beetel |
| 8,800,840 | B2 | 8/2014 | Jankowski |
| 8,800,841 | B2 | 8/2014 | Ellerhorst et al. |
| 8,801,710 | B2 | 8/2014 | Ullrich et al. |
| 8,801,734 | B2 | 8/2014 | Shelton, IV et al. |
| 8,801,735 | B2 | 8/2014 | Shelton, IV et al. |
| 8,801,752 | B2 | 8/2014 | Fortier et al. |
| 8,801,801 | B2 | 8/2014 | Datta et al. |
| 8,806,973 | B2 | 8/2014 | Ross et al. |
| 8,807,414 | B2 | 8/2014 | Ross et al. |
| 8,808,161 | B2 | 8/2014 | Gregg et al. |
| 8,808,164 | B2 | 8/2014 | Hoffman et al. |
| 8,808,274 | B2 | 8/2014 | Hartwell |
| 8,808,294 | B2 | 8/2014 | Fox et al. |
| 8,808,308 | B2 | 8/2014 | Boukhny et al. |
| 8,808,311 | B2 | 8/2014 | Heinrich et al. |
| 8,808,325 | B2 | 8/2014 | Hess et al. |
| 8,810,197 | B2 | 8/2014 | Juergens |
| 8,811,017 | B2 | 8/2014 | Fujii et al. |
| 8,813,866 | B2 | 8/2014 | Suzuki |
| 8,814,024 | B2 | 8/2014 | Woodard, Jr. et al. |
| 8,814,025 | B2 | 8/2014 | Miller et al. |
| 8,814,836 | B2 | 8/2014 | Ignon et al. |
| 8,815,594 | B2 | 8/2014 | Harris et al. |
| 8,818,523 | B2 | 8/2014 | Olson et al. |
| 8,820,603 | B2 | 9/2014 | Shelton, IV et al. |
| 8,820,605 | B2 | 9/2014 | Shelton, IV |
| 8,820,606 | B2 | 9/2014 | Hodgkinson |
| 8,820,607 | B2 | 9/2014 | Marczyk |
| 8,820,608 | B2 | 9/2014 | Miyamoto |
| 8,821,514 | B2 | 9/2014 | Aranyi |
| 8,822,934 | B2 | 9/2014 | Sayeh et al. |
| 8,825,164 | B2 | 9/2014 | Tweden et al. |
| 8,827,133 | B2 | 9/2014 | Shelton, IV et al. |
| 8,827,134 | B2 | 9/2014 | Viola et al. |
| 8,827,903 | B2 | 9/2014 | Shelton, IV et al. |
| 8,828,046 | B2 | 9/2014 | Stefanchik et al. |
| 8,831,779 | B2 | 9/2014 | Ortmaier et al. |
| 8,833,219 | B2 | 9/2014 | Pierce |
| 8,833,630 | B2 | 9/2014 | Milliman |
| 8,833,632 | B2 | 9/2014 | Swensgard |
| 8,834,353 | B2 | 9/2014 | Dejima et al. |
| 8,834,465 | B2 | 9/2014 | Ramstein et al. |
| 8,834,498 | B2 | 9/2014 | Byrum et al. |
| 8,834,518 | B2 | 9/2014 | Faller et al. |
| 8,840,003 | B2 | 9/2014 | Morgan et al. |
| 8,840,004 | B2 | 9/2014 | Holsten et al. |
| 8,840,603 | B2 | 9/2014 | Shelton, IV et al. |
| 8,840,609 | B2 | 9/2014 | Stuebe |
| 8,840,876 | B2 | 9/2014 | Eemeta et al. |
| 8,844,789 | B2 | 9/2014 | Shelton, IV et al. |
| 8,844,790 | B2 | 9/2014 | Demmy et al. |
| 8,845,622 | B2 | 9/2014 | Paik et al. |
| 8,851,215 | B2 | 10/2014 | Goto |
| 8,851,354 | B2 | 10/2014 | Swensgard et al. |
| 8,851,355 | B2 | 10/2014 | Aranyi et al. |
| 8,852,174 | B2 | 10/2014 | Burbank |
| 8,852,185 | B2 | 10/2014 | Twomey |
| 8,852,199 | B2 | 10/2014 | Deslauriers et al. |
| 8,852,218 | B2 | 10/2014 | Hughett, Sr. et al. |
| 8,852,473 | B1 | 10/2014 | Tan |
| 8,855,822 | B2 | 10/2014 | Bartol et al. |
| 8,857,692 | B2 | 10/2014 | Shima et al. |
| 8,857,693 | B2 | 10/2014 | Schuckmann et al. |
| 8,857,694 | B2 | 10/2014 | Shelton, IV et al. |
| 8,858,538 | B2 | 10/2014 | Belson et al. |
| 8,858,547 | B2 | 10/2014 | Brogna |
| 8,858,571 | B2 | 10/2014 | Shelton, IV et al. |
| 8,858,590 | B2 | 10/2014 | Shelton, IV et al. |
| 8,864,007 | B2 | 10/2014 | Widenhouse et al. |
| 8,864,009 | B2 | 10/2014 | Shelton, IV et al. |
| 8,864,010 | B2 | 10/2014 | Williams |
| 8,864,750 | B2 | 10/2014 | Ross et al. |
| 8,869,912 | B2 | 10/2014 | Roßkamp et al. |
| 8,869,913 | B2 | 10/2014 | Matthias et al. |

(56) References Cited

U.S. PATENT DOCUMENTS

| | | | |
|---|---|---|---|
| 8,870,049 | B2 | 10/2014 | Amid et al. |
| 8,870,050 | B2 | 10/2014 | Hodgkinson |
| 8,870,867 | B2 | 10/2014 | Walberg et al. |
| 8,870,912 | B2 | 10/2014 | Brisson et al. |
| 8,871,829 | B2 | 10/2014 | Gerold et al. |
| D716,820 | S | 11/2014 | Wood |
| 8,875,971 | B2 | 11/2014 | Hall et al. |
| 8,875,972 | B2 | 11/2014 | Weisenburgh, II et al. |
| 8,876,698 | B2 | 11/2014 | Sakamoto et al. |
| 8,876,857 | B2 | 11/2014 | Burbank |
| 8,876,858 | B2 | 11/2014 | Braun |
| 8,882,660 | B2 | 11/2014 | Phee et al. |
| 8,882,792 | B2 | 11/2014 | Dietz et al. |
| 8,884,560 | B2 | 11/2014 | Ito |
| 8,887,979 | B2 | 11/2014 | Mastri et al. |
| 8,888,688 | B2 | 11/2014 | Julian et al. |
| 8,888,695 | B2 | 11/2014 | Piskun et al. |
| 8,888,792 | B2 | 11/2014 | Harris et al. |
| 8,888,809 | B2 | 11/2014 | Davison et al. |
| 8,893,946 | B2 | 11/2014 | Boudreaux et al. |
| 8,893,949 | B2 | 11/2014 | Shelton, IV et al. |
| 8,893,950 | B2 | 11/2014 | Marczyk |
| 8,894,634 | B2 | 11/2014 | Devengenzo et al. |
| 8,894,647 | B2 | 11/2014 | Beardsley et al. |
| 8,894,654 | B2 | 11/2014 | Anderson |
| 8,899,460 | B2 | 12/2014 | Wojcicki |
| 8,899,461 | B2 | 12/2014 | Farascioni |
| 8,899,462 | B2 | 12/2014 | Kostrzewski et al. |
| 8,899,463 | B2 | 12/2014 | Schall et al. |
| 8,899,464 | B2 | 12/2014 | Hueil et al. |
| 8,899,465 | B2 | 12/2014 | Shelton, IV et al. |
| 8,899,466 | B2 | 12/2014 | Baxter, III et al. |
| 8,900,267 | B2 | 12/2014 | Woolfson et al. |
| 8,905,287 | B2 | 12/2014 | Racenet et al. |
| 8,905,977 | B2 | 12/2014 | Shelton et al. |
| 8,910,846 | B2 | 12/2014 | Viola |
| 8,910,847 | B2 | 12/2014 | Nalagatla et al. |
| 8,911,426 | B2 | 12/2014 | Coppeta et al. |
| 8,911,448 | B2 | 12/2014 | Stein |
| 8,911,460 | B2 | 12/2014 | Neurohr et al. |
| 8,911,471 | B2 | 12/2014 | Spivey et al. |
| 8,912,746 | B2 | 12/2014 | Reid et al. |
| 8,915,842 | B2 | 12/2014 | Weisenburgh, II et al. |
| 8,920,368 | B2 | 12/2014 | Sandhu et al. |
| 8,920,433 | B2 | 12/2014 | Barrier et al. |
| 8,920,435 | B2 | 12/2014 | Smith et al. |
| 8,920,438 | B2 | 12/2014 | Aranyi et al. |
| 8,920,443 | B2 | 12/2014 | Hiles et al. |
| 8,920,444 | B2 | 12/2014 | Hiles et al. |
| 8,922,163 | B2 | 12/2014 | Macdonald |
| 8,925,782 | B2 | 1/2015 | Shelton, IV |
| 8,925,783 | B2 | 1/2015 | Zemlok et al. |
| 8,925,788 | B2 | 1/2015 | Hess et al. |
| 8,926,506 | B2 | 1/2015 | Widenhouse et al. |
| 8,926,598 | B2 | 1/2015 | Mollere et al. |
| 8,931,576 | B2 | 1/2015 | Iwata |
| 8,931,679 | B2 | 1/2015 | Kostrzewski |
| 8,931,680 | B2 | 1/2015 | Milliman |
| 8,931,682 | B2 | 1/2015 | Timm et al. |
| 8,931,692 | B2 | 1/2015 | Sancak |
| 8,936,614 | B2 | 1/2015 | Allen, IV |
| 8,937,408 | B2 | 1/2015 | Ganem et al. |
| 8,939,343 | B2 | 1/2015 | Milliman et al. |
| 8,939,344 | B2 | 1/2015 | Olson et al. |
| 8,939,898 | B2 | 1/2015 | Omoto |
| 8,944,069 | B2 | 2/2015 | Miller et al. |
| 8,945,095 | B2 | 2/2015 | Blumenkranz et al. |
| 8,945,098 | B2 | 2/2015 | Seibold et al. |
| 8,945,163 | B2 | 2/2015 | Voegele et al. |
| 8,955,732 | B2 | 2/2015 | Zemlok et al. |
| 8,956,342 | B1 | 2/2015 | Russo et al. |
| 8,956,390 | B2 | 2/2015 | Shah et al. |
| 8,958,860 | B2 | 2/2015 | Banerjee et al. |
| 8,960,519 | B2 | 2/2015 | Whitman et al. |
| 8,960,520 | B2 | 2/2015 | McCuen |
| 8,960,521 | B2 | 2/2015 | Kostrzewski |
| 8,961,191 | B2 | 2/2015 | Hanshew |
| 8,961,504 | B2 | 2/2015 | Hoarau et al. |
| 8,961,542 | B2 | 2/2015 | Whitfield et al. |
| 8,963,714 | B2 | 2/2015 | Medhal et al. |
| D725,674 | S | 3/2015 | Jung et al. |
| 8,967,443 | B2 | 3/2015 | McCuen |
| 8,967,444 | B2 | 3/2015 | Beetel |
| 8,967,446 | B2 | 3/2015 | Beardsley et al. |
| 8,967,448 | B2 | 3/2015 | Carter et al. |
| 8,968,276 | B2 | 3/2015 | Zemlok et al. |
| 8,968,308 | B2 | 3/2015 | Horner et al. |
| 8,968,312 | B2 | 3/2015 | Marczyk et al. |
| 8,968,337 | B2 | 3/2015 | Whitfield et al. |
| 8,968,340 | B2 | 3/2015 | Chowaniec et al. |
| 8,968,355 | B2 | 3/2015 | Malkowski et al. |
| 8,968,358 | B2 | 3/2015 | Reschke |
| 8,970,507 | B2 | 3/2015 | Holbein et al. |
| 8,973,803 | B2 | 3/2015 | Hall et al. |
| 8,973,804 | B2 | 3/2015 | Hess et al. |
| 8,973,805 | B2 | 3/2015 | Scirica et al. |
| 8,974,440 | B2 | 3/2015 | Farritor et al. |
| 8,974,542 | B2 | 3/2015 | Fujimoto et al. |
| 8,974,932 | B2 | 3/2015 | McGahan et al. |
| 8,978,954 | B2 | 3/2015 | Shelton, IV et al. |
| 8,978,955 | B2 | 3/2015 | Aronhalt et al. |
| 8,978,956 | B2 | 3/2015 | Schall et al. |
| 8,979,843 | B2 | 3/2015 | Timm et al. |
| 8,979,890 | B2 | 3/2015 | Boudreaux |
| 8,982,195 | B2 | 3/2015 | Claus et al. |
| 8,984,711 | B2 | 3/2015 | Ota et al. |
| 8,985,240 | B2 | 3/2015 | Winnard |
| 8,985,429 | B2 | 3/2015 | Balek et al. |
| 8,986,302 | B2 | 3/2015 | Aldridge et al. |
| 8,989,903 | B2 | 3/2015 | Weir et al. |
| 8,991,676 | B2 | 3/2015 | Hess et al. |
| 8,991,677 | B2 | 3/2015 | Moore et al. |
| 8,991,678 | B2 | 3/2015 | Wellman et al. |
| 8,992,042 | B2 | 3/2015 | Eichenholz |
| 8,992,422 | B2 | 3/2015 | Spivey et al. |
| 8,992,565 | B2 | 3/2015 | Brisson et al. |
| 8,996,165 | B2 | 3/2015 | Wang et al. |
| 8,998,058 | B2 | 4/2015 | Moore et al. |
| 8,998,059 | B2 | 4/2015 | Smith et al. |
| 8,998,060 | B2 | 4/2015 | Bruewer et al. |
| 8,998,061 | B2 | 4/2015 | Williams et al. |
| 8,998,939 | B2 | 4/2015 | Price et al. |
| 9,000,720 | B2 | 4/2015 | Stulen et al. |
| 9,002,518 | B2 | 4/2015 | Manzo et al. |
| 9,004,339 | B1 | 4/2015 | Park |
| 9,004,799 | B1 | 4/2015 | Tibbits |
| 9,005,230 | B2 | 4/2015 | Yates et al. |
| 9,005,238 | B2 | 4/2015 | DeSantis et al. |
| 9,005,243 | B2 | 4/2015 | Stopek et al. |
| 9,010,606 | B2 | 4/2015 | Aranyi et al. |
| 9,010,608 | B2 | 4/2015 | Casasanta, Jr. et al. |
| 9,010,609 | B2 | 4/2015 | Carter et al. |
| 9,010,611 | B2 | 4/2015 | Ross et al. |
| 9,011,437 | B2 | 4/2015 | Woodruff et al. |
| 9,011,439 | B2 | 4/2015 | Shalaby et al. |
| 9,011,471 | B2 | 4/2015 | Timm et al. |
| 9,014,856 | B2 | 4/2015 | Manzo et al. |
| 9,016,539 | B2 | 4/2015 | Kostrzewski et al. |
| 9,016,540 | B2 | 4/2015 | Whitman et al. |
| 9,016,541 | B2 | 4/2015 | Viola et al. |
| 9,016,542 | B2 | 4/2015 | Shelton, IV et al. |
| 9,016,545 | B2 | 4/2015 | Aranyi et al. |
| 9,017,331 | B2 | 4/2015 | Fox |
| 9,017,355 | B2 | 4/2015 | Smith et al. |
| 9,017,369 | B2 | 4/2015 | Renger et al. |
| 9,017,371 | B2 | 4/2015 | Whitman et al. |
| 9,017,849 | B2 | 4/2015 | Stulen et al. |
| 9,017,851 | B2 | 4/2015 | Felder et al. |
| D729,274 | S | 5/2015 | Clement et al. |
| D730,393 | S | 5/2015 | Bray et al. |
| 9,021,684 | B2 | 5/2015 | Lenker et al. |
| 9,023,014 | B2 | 5/2015 | Chowaniec et al. |
| 9,023,069 | B2 | 5/2015 | Kasvikis et al. |
| 9,023,071 | B2 | 5/2015 | Miller et al. |

(56) References Cited

U.S. PATENT DOCUMENTS

| | | | |
|---|---|---|---|
| 9,026,347 | B2 | 5/2015 | Gadh et al. |
| 9,027,817 | B2 | 5/2015 | Milliman et al. |
| 9,028,468 | B2 | 5/2015 | Scarfogliero et al. |
| 9,028,494 | B2 | 5/2015 | Shelton, IV et al. |
| 9,028,495 | B2 | 5/2015 | Mueller et al. |
| 9,028,510 | B2 | 5/2015 | Miyamoto et al. |
| 9,028,511 | B2 | 5/2015 | Weller et al. |
| 9,028,519 | B2 | 5/2015 | Yates et al. |
| 9,028,529 | B2 | 5/2015 | Fox et al. |
| 9,030,166 | B2 | 5/2015 | Kano |
| 9,030,169 | B2 | 5/2015 | Christensen et al. |
| 9,033,203 | B2 | 5/2015 | Woodard, Jr. et al. |
| 9,033,204 | B2 | 5/2015 | Shelton, IV et al. |
| 9,034,505 | B2 | 5/2015 | Detry et al. |
| 9,038,881 | B1 | 5/2015 | Schaller et al. |
| 9,039,690 | B2 | 5/2015 | Kersten et al. |
| 9,039,694 | B2 | 5/2015 | Ross et al. |
| 9,039,720 | B2 | 5/2015 | Madan |
| 9,039,736 | B2 | 5/2015 | Scirica et al. |
| 9,040,062 | B2 | 5/2015 | Maeda et al. |
| 9,043,027 | B2 | 5/2015 | Durant et al. |
| 9,044,227 | B2 | 6/2015 | Shelton, IV et al. |
| 9,044,228 | B2 | 6/2015 | Woodard, Jr. et al. |
| 9,044,229 | B2 | 6/2015 | Scheib et al. |
| 9,044,230 | B2 | 6/2015 | Morgan et al. |
| 9,044,238 | B2 | 6/2015 | Orszulak |
| 9,044,241 | B2 | 6/2015 | Barner et al. |
| 9,044,261 | B2 | 6/2015 | Houser |
| 9,044,281 | B2 | 6/2015 | Pool et al. |
| 9,050,083 | B2 | 6/2015 | Yates et al. |
| 9,050,084 | B2 | 6/2015 | Schmid et al. |
| 9,050,089 | B2 | 6/2015 | Orszulak |
| 9,050,100 | B2 | 6/2015 | Yates et al. |
| 9,050,120 | B2 | 6/2015 | Swarup et al. |
| 9,050,123 | B2 | 6/2015 | Krause et al. |
| 9,050,176 | B2 | 6/2015 | Datta et al. |
| 9,050,192 | B2 | 6/2015 | Mansmann |
| 9,055,941 | B2 | 6/2015 | Schmid et al. |
| 9,055,942 | B2 | 6/2015 | Balbierz et al. |
| 9,055,943 | B2 | 6/2015 | Zemlok et al. |
| 9,055,944 | B2 | 6/2015 | Hodgkinson et al. |
| 9,055,961 | B2 | 6/2015 | Manzo et al. |
| 9,060,770 | B2 | 6/2015 | Shelton, IV et al. |
| 9,060,776 | B2 | 6/2015 | Yates et al. |
| 9,060,794 | B2 | 6/2015 | Kang et al. |
| 9,060,894 | B2 | 6/2015 | Wubbeling |
| 9,061,392 | B2 | 6/2015 | Forgues et al. |
| 9,070,068 | B2 | 6/2015 | Coveley et al. |
| D733,727 | S | 7/2015 | Cojuangco et al. |
| 9,072,515 | B2 | 7/2015 | Hall et al. |
| 9,072,523 | B2 | 7/2015 | Houser et al. |
| 9,072,535 | B2 | 7/2015 | Shelton, IV et al. |
| 9,072,536 | B2 | 7/2015 | Shelton, IV et al. |
| 9,078,653 | B2 | 7/2015 | Leimbach et al. |
| 9,078,654 | B2 | 7/2015 | Whitman et al. |
| 9,084,586 | B2 | 7/2015 | Hafner et al. |
| 9,084,601 | B2 | 7/2015 | Moore et al. |
| 9,084,602 | B2 | 7/2015 | Gleiman |
| 9,086,875 | B2 | 7/2015 | Harrat et al. |
| 9,089,317 | B2 | 7/2015 | Burdorff et al. |
| 9,089,326 | B2 | 7/2015 | Krumanaker et al. |
| 9,089,330 | B2 | 7/2015 | Widenhouse et al. |
| 9,089,338 | B2 | 7/2015 | Smith et al. |
| 9,089,352 | B2 | 7/2015 | Jeong |
| 9,089,360 | B2 | 7/2015 | Messerly et al. |
| 9,091,588 | B2 | 7/2015 | Lefler |
| D736,792 | S | 8/2015 | Brinda et al. |
| 9,095,339 | B2 | 8/2015 | Moore et al. |
| 9,095,346 | B2 | 8/2015 | Houser et al. |
| 9,095,362 | B2 | 8/2015 | Dachs, II et al. |
| 9,095,367 | B2 | 8/2015 | Olson et al. |
| 9,095,642 | B2 | 8/2015 | Harder et al. |
| 9,096,033 | B2 | 8/2015 | Holop et al. |
| 9,098,153 | B2 | 8/2015 | Shen et al. |
| 9,099,863 | B2 | 8/2015 | Smith et al. |
| 9,099,877 | B2 | 8/2015 | Banos et al. |
| 9,099,922 | B2 | 8/2015 | Toosky et al. |
| 9,101,358 | B2 | 8/2015 | Kerr et al. |
| 9,101,359 | B2 | 8/2015 | Smith et al. |
| 9,101,385 | B2 | 8/2015 | Shelton, IV et al. |
| 9,101,475 | B2 | 8/2015 | Wei et al. |
| 9,101,621 | B2 | 8/2015 | Zeldis |
| 9,107,663 | B2 | 8/2015 | Swensgard |
| 9,107,667 | B2 | 8/2015 | Hodgkinson |
| 9,107,690 | B2 | 8/2015 | Bales, Jr. et al. |
| 9,110,587 | B2 | 8/2015 | Kim et al. |
| 9,113,862 | B2 | 8/2015 | Morgan et al. |
| 9,113,864 | B2 | 8/2015 | Morgan et al. |
| 9,113,865 | B2 | 8/2015 | Shelton, IV et al. |
| 9,113,866 | B2 | 8/2015 | Felder et al. |
| 9,113,868 | B2 | 8/2015 | Felder et al. |
| 9,113,873 | B2 | 8/2015 | Marczyk et al. |
| 9,113,874 | B2 | 8/2015 | Shelton, IV et al. |
| 9,113,875 | B2 | 8/2015 | Viola et al. |
| 9,113,876 | B2 | 8/2015 | Zemlok et al. |
| 9,113,877 | B1 | 8/2015 | Whitman et al. |
| 9,113,879 | B2 | 8/2015 | Felder et al. |
| 9,113,880 | B2 | 8/2015 | Zemlok et al. |
| 9,113,881 | B2 | 8/2015 | Scirica |
| 9,113,883 | B2 | 8/2015 | Aronhalt et al. |
| 9,113,884 | B2 | 8/2015 | Shelton, IV et al. |
| 9,113,887 | B2 | 8/2015 | Behnke, II et al. |
| 9,119,615 | B2 | 9/2015 | Felder et al. |
| 9,119,657 | B2 | 9/2015 | Shelton, IV et al. |
| 9,119,898 | B2 | 9/2015 | Bayon et al. |
| 9,119,957 | B2 | 9/2015 | Gantz et al. |
| 9,123,286 | B2 | 9/2015 | Park |
| 9,124,097 | B2 | 9/2015 | Cruz |
| 9,125,651 | B2 | 9/2015 | Mandakolathur Vasudevan et al. |
| 9,125,654 | B2 | 9/2015 | Aronhalt et al. |
| 9,125,662 | B2 | 9/2015 | Shelton, IV |
| 9,126,317 | B2 | 9/2015 | Lawton et al. |
| 9,131,835 | B2 | 9/2015 | Widenhouse et al. |
| 9,131,940 | B2 | 9/2015 | Huitema et al. |
| 9,131,950 | B2 | 9/2015 | Matthew |
| 9,131,957 | B2 | 9/2015 | Skarbnik et al. |
| 9,138,225 | B2 | 9/2015 | Huang et al. |
| 9,138,226 | B2 | 9/2015 | Racenet et al. |
| 9,144,455 | B2 | 9/2015 | Kennedy et al. |
| D740,414 | S | 10/2015 | Katsura |
| D741,882 | S | 10/2015 | Shmilov et al. |
| 9,149,274 | B2 | 10/2015 | Spivey et al. |
| 9,149,324 | B2 | 10/2015 | Huang et al. |
| 9,149,325 | B2 | 10/2015 | Worrell et al. |
| 9,153,994 | B2 | 10/2015 | Wood et al. |
| 9,154,189 | B2 | 10/2015 | Von Novak et al. |
| 9,161,753 | B2 | 10/2015 | Prior |
| 9,161,769 | B2 | 10/2015 | Stoddard et al. |
| 9,161,803 | B2 | 10/2015 | Yates et al. |
| 9,161,807 | B2 | 10/2015 | Garrison |
| 9,161,855 | B2 | 10/2015 | Rousseau et al. |
| 9,164,271 | B2 | 10/2015 | Ebata et al. |
| 9,167,960 | B2 | 10/2015 | Yamaguchi et al. |
| 9,168,038 | B2 | 10/2015 | Shelton, IV et al. |
| 9,168,039 | B1 | 10/2015 | Knodel |
| 9,168,042 | B2 | 10/2015 | Milliman |
| 9,168,054 | B2 | 10/2015 | Turner et al. |
| 9,168,144 | B2 | 10/2015 | Rivin et al. |
| 9,171,244 | B2 | 10/2015 | Endou et al. |
| 9,179,832 | B2 | 11/2015 | Diolaiti |
| 9,179,911 | B2 | 11/2015 | Morgan et al. |
| 9,179,912 | B2 | 11/2015 | Yates et al. |
| 9,180,223 | B2 | 11/2015 | Yu et al. |
| 9,182,244 | B2 | 11/2015 | Luke et al. |
| 9,186,046 | B2 | 11/2015 | Ramamurthy et al. |
| 9,186,137 | B2 | 11/2015 | Farascioni et al. |
| 9,186,140 | B2 | 11/2015 | Hiles et al. |
| 9,186,142 | B2 | 11/2015 | Fanelli et al. |
| 9,186,143 | B2 | 11/2015 | Timm et al. |
| 9,186,148 | B2 | 11/2015 | Felder et al. |
| 9,186,221 | B2 | 11/2015 | Burbank |
| 9,192,376 | B2 | 11/2015 | Almodovar |
| 9,192,380 | B2 | 11/2015 | (Tarinelli) Racenet et al. |
| 9,192,384 | B2 | 11/2015 | Bettuchi |

(56) References Cited

U.S. PATENT DOCUMENTS

| | | | |
|---|---|---|---|
| 9,192,430 | B2 | 11/2015 | Rachlin et al. |
| 9,192,434 | B2 | 11/2015 | Twomey et al. |
| 9,193,045 | B2 | 11/2015 | Saur et al. |
| 9,197,079 | B2 | 11/2015 | Yip et al. |
| D744,528 | S | 12/2015 | Agrawal |
| D746,459 | S | 12/2015 | Kaercher et al. |
| 9,198,642 | B2 | 12/2015 | Storz |
| 9,198,644 | B2 | 12/2015 | Balek et al. |
| 9,198,661 | B2 | 12/2015 | Swensgard |
| 9,198,662 | B2 | 12/2015 | Barton et al. |
| 9,198,683 | B2 | 12/2015 | Friedman et al. |
| 9,204,830 | B2 | 12/2015 | Zand et al. |
| 9,204,877 | B2 | 12/2015 | Whitman et al. |
| 9,204,878 | B2 | 12/2015 | Hall et al. |
| 9,204,879 | B2 | 12/2015 | Shelton, IV |
| 9,204,880 | B2 | 12/2015 | Baxter, III et al. |
| 9,204,881 | B2 | 12/2015 | Penna |
| 9,204,923 | B2 | 12/2015 | Manzo et al. |
| 9,204,924 | B2 | 12/2015 | Marczyk et al. |
| 9,211,120 | B2 | 12/2015 | Scheib et al. |
| 9,211,121 | B2 | 12/2015 | Hall et al. |
| 9,211,122 | B2 | 12/2015 | Hagerty et al. |
| 9,216,013 | B2 | 12/2015 | Scirica et al. |
| 9,216,019 | B2 | 12/2015 | Schmid et al. |
| 9,216,020 | B2 | 12/2015 | Zhang et al. |
| 9,216,030 | B2 | 12/2015 | Fan et al. |
| 9,216,062 | B2 | 12/2015 | Duque et al. |
| 9,220,500 | B2 | 12/2015 | Swayze et al. |
| 9,220,501 | B2 | 12/2015 | Baxter, III et al. |
| 9,220,502 | B2 | 12/2015 | Zemlok et al. |
| 9,220,504 | B2 | 12/2015 | Viola et al. |
| 9,220,508 | B2 | 12/2015 | Dannaher |
| 9,220,559 | B2 | 12/2015 | Worrell et al. |
| 9,220,570 | B2 | 12/2015 | Kim et al. |
| D746,854 | S | 1/2016 | Shardlow et al. |
| 9,226,686 | B2 | 1/2016 | Blair |
| 9,226,750 | B2 | 1/2016 | Weir et al. |
| 9,226,751 | B2 | 1/2016 | Shelton, IV et al. |
| 9,226,754 | B2 | 1/2016 | D'Agostino et al. |
| 9,226,760 | B2 | 1/2016 | Shelton, IV |
| 9,226,761 | B2 | 1/2016 | Burbank |
| 9,226,767 | B2 | 1/2016 | Stulen et al. |
| 9,226,799 | B2 | 1/2016 | Lightcap et al. |
| 9,232,941 | B2 | 1/2016 | Mandakolathur Vasudevan et al. |
| 9,232,945 | B2 | 1/2016 | Zingman |
| 9,232,979 | B2 | 1/2016 | Parihar et al. |
| 9,233,610 | B2 | 1/2016 | Kim et al. |
| 9,237,891 | B2 | 1/2016 | Shelton, IV |
| 9,237,892 | B2 | 1/2016 | Hodgkinson |
| 9,237,895 | B2 | 1/2016 | McCarthy et al. |
| 9,237,900 | B2 | 1/2016 | Boudreaux et al. |
| 9,237,921 | B2 | 1/2016 | Messerly et al. |
| 9,239,064 | B2 | 1/2016 | Helbig et al. |
| 9,240,740 | B2 | 1/2016 | Zeng et al. |
| 9,241,711 | B2 | 1/2016 | Ivanko |
| 9,241,712 | B2 | 1/2016 | Zemlok et al. |
| 9,241,714 | B2 | 1/2016 | Timm et al. |
| 9,241,716 | B2 | 1/2016 | Whitman |
| 9,241,731 | B2 | 1/2016 | Boudreaux et al. |
| 9,241,758 | B2 | 1/2016 | Franer et al. |
| 9,244,524 | B2 | 1/2016 | Inoue et al. |
| D748,668 | S | 2/2016 | Kim et al. |
| D749,128 | S | 2/2016 | Perez et al. |
| D749,623 | S | 2/2016 | Gray et al. |
| D750,122 | S | 2/2016 | Shardlow et al. |
| D750,129 | S | 2/2016 | Kwon |
| 9,254,131 | B2 | 2/2016 | Soltz et al. |
| 9,254,170 | B2 | 2/2016 | Parihar et al. |
| 9,259,265 | B2 | 2/2016 | Harris et al. |
| 9,259,268 | B2 | 2/2016 | Behnke, II et al. |
| 9,259,274 | B2 | 2/2016 | Prisco |
| 9,259,275 | B2 | 2/2016 | Burbank |
| 9,261,172 | B2 | 2/2016 | Solomon et al. |
| 9,265,500 | B2 | 2/2016 | Sorrentino et al. |
| 9,265,510 | B2 | 2/2016 | Dietzel et al. |
| 9,265,516 | B2 | 2/2016 | Casey et al. |
| 9,265,585 | B2 | 2/2016 | Wingardner et al. |
| 9,271,718 | B2 | 3/2016 | Milad et al. |
| 9,271,727 | B2 | 3/2016 | McGuckin, Jr. et al. |
| 9,271,753 | B2 | 3/2016 | Butler et al. |
| 9,271,799 | B2 | 3/2016 | Shelton, IV et al. |
| 9,272,406 | B2 | 3/2016 | Aronhalt et al. |
| 9,274,095 | B2 | 3/2016 | Humayun et al. |
| 9,277,919 | B2 | 3/2016 | Timmer et al. |
| 9,277,922 | B2 | 3/2016 | Carter et al. |
| 9,277,969 | B2 | 3/2016 | Brannan et al. |
| 9,282,962 | B2 | 3/2016 | Schmid et al. |
| 9,282,963 | B2 | 3/2016 | Bryant |
| 9,282,966 | B2 | 3/2016 | Shelton, IV et al. |
| 9,282,974 | B2 | 3/2016 | Shelton, IV |
| 9,283,028 | B2 | 3/2016 | Johnson |
| 9,283,045 | B2 | 3/2016 | Rhee et al. |
| 9,283,054 | B2 | 3/2016 | Morgan et al. |
| 9,283,334 | B2 | 3/2016 | Mantell et al. |
| 9,289,206 | B2 | 3/2016 | Hess et al. |
| 9,289,207 | B2 | 3/2016 | Shelton, IV |
| 9,289,210 | B2 | 3/2016 | Baxter, III et al. |
| 9,289,211 | B2 | 3/2016 | Williams et al. |
| 9,289,212 | B2 | 3/2016 | Shelton, IV et al. |
| 9,289,225 | B2 | 3/2016 | Shelton, IV et al. |
| 9,289,256 | B2 | 3/2016 | Shelton, IV et al. |
| 9,293,757 | B2 | 3/2016 | Toussaint et al. |
| 9,295,464 | B2 | 3/2016 | Shelton, IV et al. |
| 9,295,465 | B2 | 3/2016 | Farascioni |
| 9,295,466 | B2 | 3/2016 | Hodgkinson et al. |
| 9,295,467 | B2 | 3/2016 | Scirica |
| 9,295,468 | B2 | 3/2016 | Heinrich et al. |
| 9,295,514 | B2 | 3/2016 | Shelton, IV et al. |
| 9,295,522 | B2 | 3/2016 | Kostrzewski |
| 9,295,565 | B2 | 3/2016 | McLean |
| 9,295,784 | B2 | 3/2016 | Eggert et al. |
| D753,167 | S | 4/2016 | Yu et al. |
| 9,301,691 | B2 | 4/2016 | Hufnagel et al. |
| 9,301,752 | B2 | 4/2016 | Mandakolathur Vasudevan et al. |
| 9,301,753 | B2 | 4/2016 | Aldridge et al. |
| 9,301,755 | B2 | 4/2016 | Shelton, IV et al. |
| 9,301,759 | B2 | 4/2016 | Spivey et al. |
| 9,301,811 | B2 | 4/2016 | Goldberg et al. |
| 9,307,965 | B2 | 4/2016 | Ming et al. |
| 9,307,986 | B2 | 4/2016 | Hall et al. |
| 9,307,987 | B2 | 4/2016 | Swensgard et al. |
| 9,307,988 | B2 | 4/2016 | Shelton, IV |
| 9,307,989 | B2 | 4/2016 | Shelton, IV et al. |
| 9,307,994 | B2 | 4/2016 | Gresham et al. |
| 9,308,009 | B2 | 4/2016 | Madan et al. |
| 9,308,011 | B2 | 4/2016 | Chao et al. |
| 9,308,646 | B2 | 4/2016 | Lim et al. |
| 9,313,915 | B2 | 4/2016 | Niu et al. |
| 9,314,246 | B2 | 4/2016 | Shelton, IV et al. |
| 9,314,247 | B2 | 4/2016 | Shelton, IV et al. |
| 9,314,261 | B2 | 4/2016 | Bales, Jr. et al. |
| 9,314,291 | B2 | 4/2016 | Schall et al. |
| 9,314,339 | B2 | 4/2016 | Mansmann |
| 9,314,908 | B2 | 4/2016 | Tanimoto et al. |
| 9,320,518 | B2 | 4/2016 | Henderson et al. |
| 9,320,520 | B2 | 4/2016 | Shelton, IV et al. |
| 9,320,521 | B2 | 4/2016 | Shelton, IV et al. |
| 9,320,523 | B2 | 4/2016 | Shelton, IV et al. |
| 9,325,516 | B2 | 4/2016 | Pera et al. |
| D755,196 | S | 5/2016 | Meyers et al. |
| D756,373 | S | 5/2016 | Raskin et al. |
| D756,377 | S | 5/2016 | Connolly et al. |
| D757,028 | S | 5/2016 | Goldenberg et al. |
| 9,326,767 | B2 | 5/2016 | Koch, Jr. et al. |
| 9,326,768 | B2 | 5/2016 | Shelton, IV |
| 9,326,769 | B2 | 5/2016 | Shelton, IV et al. |
| 9,326,770 | B2 | 5/2016 | Shelton, IV et al. |
| 9,326,771 | B2 | 5/2016 | Baxter, III et al. |
| 9,326,773 | B2 | 5/2016 | Casasanta, Jr. et al. |
| 9,326,788 | B2 | 5/2016 | Batross et al. |
| 9,326,812 | B2 | 5/2016 | Waaler et al. |
| 9,326,824 | B2 | 5/2016 | Inoue et al. |
| 9,327,061 | B2 | 5/2016 | Govil et al. |
| 9,331,721 | B2 | 5/2016 | Martinez Nuevo et al. |

(56) References Cited

U.S. PATENT DOCUMENTS 9,332,890 B2 5/2016 Ozawa
9,332,974 B2 5/2016 Henderson et al.
9,332,984 B2 5/2016 Weaner et al.
9,332,987 B2 5/2016 Leimbach et al.
9,333,040 B2 5/2016 Shellenberger et al.
9,333,082 B2 5/2016 Wei et al.
9,337,668 B2 5/2016 Yip
9,339,226 B2 5/2016 van der Walt et al.
9,339,342 B2 5/2016 Prisco et al.
9,345,477 B2 5/2016 Anim et al.
9,345,479 B2 5/2016 (Tarinelli) Racenet et al.
9,345,480 B2 5/2016 Hessler et al.
9,345,481 B2 5/2016 Hall et al.
9,345,503 B2 5/2016 Ishida et al.
9,351,726 B2 5/2016 Leimbach et al.
9,351,727 B2 5/2016 Leimbach et al.
9,351,728 B2 5/2016 Sniffin et al.
9,351,730 B2 5/2016 Schmid et al.
9,351,731 B2 5/2016 Carter et al.
9,351,732 B2 5/2016 Hodgkinson
9,352,071 B2 5/2016 Landgrebe et al.
D758,433 S 6/2016 Lee et al.
D759,063 S 6/2016 Chen
9,358,003 B2 6/2016 Hall et al.
9,358,004 B2 6/2016 Sniffin et al.
9,358,005 B2 6/2016 Shelton, IV et al.
9,358,015 B2 6/2016 Sorrentino et al.
9,358,031 B2 6/2016 Manzo
9,358,065 B2 6/2016 Ladtkow et al.
9,364,217 B2 6/2016 Kostrzewski et al.
9,364,219 B2 6/2016 Olson et al.
9,364,220 B2 6/2016 Williams
9,364,223 B2 6/2016 Scirica
9,364,226 B2 6/2016 Zemlok et al.
9,364,228 B2 6/2016 Straehnz et al.
9,364,229 B2 6/2016 D'Agostino et al.
9,364,230 B2 6/2016 Shelton, IV et al.
9,364,231 B2 6/2016 Wenchell
9,364,233 B2 6/2016 Alexander, III et al.
9,364,279 B2 6/2016 Houser et al.
9,368,991 B2 6/2016 Qahouq
9,370,341 B2 6/2016 Ceniccola et al.
9,370,358 B2 6/2016 Shelton, IV et al.
9,370,361 B2 6/2016 Viola et al.
9,370,362 B2 6/2016 Petty et al.
9,370,364 B2 6/2016 Smith et al.
9,370,400 B2 6/2016 Parihar
9,375,206 B2 6/2016 Vidal et al.
9,375,218 B2 6/2016 Wheeler et al.
9,375,230 B2 6/2016 Ross et al.
9,375,232 B2 6/2016 Hunt et al.
9,375,255 B2 6/2016 Houser et al.
D761,309 S 7/2016 Lee et al.
9,381,058 B2 7/2016 Houser et al.
9,383,881 B2 7/2016 Day et al.
9,385,640 B2 7/2016 Sun et al.
9,386,983 B2 7/2016 Swensgard et al.
9,386,984 B2 7/2016 Aronhalt et al.
9,386,985 B2 7/2016 Koch, Jr. et al.
9,386,988 B2 7/2016 Baxter, III et al.
9,387,003 B2 7/2016 Kaercher et al.
9,392,885 B2 7/2016 Vogler et al.
9,393,015 B2 7/2016 Laurent et al.
9,393,017 B2 7/2016 Flanagan et al.
9,393,018 B2 7/2016 Wang et al.
9,393,354 B2 7/2016 Freedman et al.
9,396,369 B1 7/2016 Whitehurst et al.
9,396,669 B2 7/2016 Karkanias et al.
9,398,905 B2 7/2016 Martin
9,398,911 B2 7/2016 Auld
D763,277 S 8/2016 Ahmed et al.
D764,498 S 8/2016 Capela et al.
9,402,604 B2 8/2016 Williams et al.
9,402,625 B2 8/2016 Coleman et al.
9,402,626 B2 8/2016 Ortiz et al.
9,402,627 B2 8/2016 Stevenson et al.
9,402,629 B2 8/2016 Ehrenfels et al.
9,402,679 B2 8/2016 Ginnebaugh et al.
9,402,682 B2 8/2016 Worrell et al.
9,402,688 B2 8/2016 Min et al.
9,408,604 B2 8/2016 Shelton, IV et al.
9,408,605 B1 8/2016 Knodel et al.
9,408,606 B2 8/2016 Shelton, IV
9,408,622 B2 8/2016 Stulen et al.
9,408,668 B2 8/2016 Durant et al.
9,411,370 B2 8/2016 Benni et al.
9,413,128 B2 8/2016 Tien et al.
9,414,838 B2 8/2016 Shelton, IV et al.
9,414,849 B2 8/2016 Nagashimada
9,414,880 B2 8/2016 Monson et al.
9,420,967 B2 8/2016 Zand et al.
9,421,003 B2 8/2016 Williams et al.
9,421,014 B2 8/2016 Ingmanson et al.
9,421,030 B2 8/2016 Cole et al.
9,421,060 B2 8/2016 Monson et al.
9,421,062 B2 8/2016 Houser et al.
9,421,682 B2 8/2016 McClaskey et al.
9,427,223 B2 8/2016 Park et al.
9,427,231 B2 8/2016 Racenet et al.
9,429,204 B2 8/2016 Stefan et al.
D767,624 S 9/2016 Lee et al.
9,433,411 B2 9/2016 Racenet et al.
9,433,414 B2 9/2016 Chen et al.
9,433,418 B2 9/2016 Whitman et al.
9,433,419 B2 9/2016 Gonzalez et al.
9,433,420 B2 9/2016 Hodgkinson
9,439,649 B2 9/2016 Shelton, IV et al.
9,439,650 B2 9/2016 McGuckin, Jr. et al.
9,439,651 B2 9/2016 Smith et al.
9,439,668 B2 9/2016 Timm et al.
9,445,808 B2 9/2016 Woodard, Jr. et al.
9,445,813 B2 9/2016 Shelton, IV et al.
9,445,816 B2 9/2016 Swayze et al.
9,445,817 B2 9/2016 Bettuchi
9,446,226 B2 9/2016 Zilberman
9,451,938 B2 9/2016 Overes et al.
9,451,958 B2 9/2016 Shelton, IV et al.
9,452,020 B2 9/2016 Griffiths et al.
D768,152 S 10/2016 Gutierrez et al.
D768,156 S 10/2016 Frincke
D768,167 S 10/2016 Jones et al.
D769,315 S 10/2016 Scotti
D769,930 S 10/2016 Agrawal
9,461,340 B2 10/2016 Li et al.
9,463,012 B2 10/2016 Bonutti et al.
9,463,040 B2 10/2016 Jeong et al.
9,463,260 B2 10/2016 Stopek
9,468,438 B2 10/2016 Baber et al.
9,468,447 B2 10/2016 Aman et al.
9,470,297 B2 10/2016 Aranyi et al.
9,471,969 B2 10/2016 Zeng et al.
9,474,506 B2 10/2016 Magnin et al.
9,474,513 B2 10/2016 Ishida et al.
9,474,523 B2 10/2016 Meade et al.
9,474,528 B2 10/2016 Marczyk
9,474,540 B2 10/2016 Stokes et al.
9,474,581 B2 10/2016 Niemeyer
9,475,180 B2 10/2016 Eshleman et al.
9,477,649 B1 10/2016 Davidson et al.
D770,476 S 11/2016 Jitkoff et al.
D770,515 S 11/2016 Cho et al.
D771,116 S 11/2016 Dellinger et al.
D772,905 S 11/2016 Ingenlath
9,480,476 B2 11/2016 Aldridge et al.
9,480,492 B2 11/2016 Aranyi et al.
9,483,095 B2 11/2016 Tran et al.
9,486,186 B2 11/2016 Fiebig et al.
9,486,213 B2 11/2016 Altman et al.
9,486,214 B2 11/2016 Shelton, IV
9,486,215 B2 11/2016 Olson et al.
9,486,302 B2 11/2016 Boey et al.
9,488,197 B2 11/2016 Wi
9,492,146 B2 11/2016 Kostrzewski et al.
9,492,167 B2 11/2016 Shelton, IV et al.

(56) References Cited

U.S. PATENT DOCUMENTS

| | | | |
|---|---|---|---|
| 9,492,170 | B2 | 11/2016 | Bear et al. |
| 9,492,172 | B2 | 11/2016 | Weisshaupt et al. |
| 9,492,189 | B2 | 11/2016 | Williams et al. |
| 9,492,192 | B2 | 11/2016 | To et al. |
| 9,492,237 | B2 | 11/2016 | Kang et al. |
| 9,498,213 | B2 | 11/2016 | Marczyk et al. |
| 9,498,219 | B2 | 11/2016 | Moore et al. |
| 9,498,231 | B2 | 11/2016 | Haider et al. |
| 9,504,455 | B2 | 11/2016 | Whitman et al. |
| 9,504,483 | B2 | 11/2016 | Houser et al. |
| 9,504,520 | B2 | 11/2016 | Worrell et al. |
| 9,504,521 | B2 | 11/2016 | Deutmeyer et al. |
| 9,504,528 | B2 | 11/2016 | Ivinson et al. |
| 9,507,399 | B2 | 11/2016 | Chien |
| D774,547 | S | 12/2016 | Capela et al. |
| D775,336 | S | 12/2016 | Shelton, IV et al. |
| 9,510,827 | B2 | 12/2016 | Kostrzewski |
| 9,510,828 | B2 | 12/2016 | Yates et al. |
| 9,510,830 | B2 | 12/2016 | Shelton, IV et al. |
| 9,510,846 | B2 | 12/2016 | Sholev et al. |
| 9,510,895 | B2 | 12/2016 | Houser et al. |
| 9,510,925 | B2 | 12/2016 | Hotter et al. |
| 9,515,366 | B2 | 12/2016 | Herbsommer et al. |
| 9,517,063 | B2 | 12/2016 | Swayze et al. |
| 9,517,065 | B2 | 12/2016 | Simms et al. |
| 9,517,068 | B2 | 12/2016 | Shelton, IV et al. |
| 9,517,326 | B2 | 12/2016 | Hinman et al. |
| 9,519,341 | B2 | 12/2016 | Hasegawa et al. |
| 9,521,996 | B2 | 12/2016 | Armstrong |
| 9,522,003 | B2 | 12/2016 | Weir et al. |
| 9,522,005 | B2 | 12/2016 | Williams et al. |
| 9,522,014 | B2 | 12/2016 | Nishizawa et al. |
| 9,522,029 | B2 | 12/2016 | Yates et al. |
| 9,526,481 | B2 | 12/2016 | Storz et al. |
| 9,526,499 | B2 | 12/2016 | Kostrzewski et al. |
| 9,526,563 | B2 | 12/2016 | Twomey |
| 9,526,564 | B2 | 12/2016 | Rusin |
| 9,526,921 | B2 | 12/2016 | Kimball et al. |
| D776,683 | S | 1/2017 | Gobinski et al. |
| D777,773 | S | 1/2017 | Shi |
| 9,532,783 | B2 | 1/2017 | Swayze et al. |
| 9,539,060 | B2 | 1/2017 | Lightcap et al. |
| 9,539,726 | B2 | 1/2017 | Simaan et al. |
| 9,545,253 | B2 | 1/2017 | Worrell et al. |
| 9,545,258 | B2 | 1/2017 | Smith et al. |
| 9,549,732 | B2 | 1/2017 | Yates et al. |
| 9,549,733 | B2 | 1/2017 | Knodel |
| 9,549,735 | B2 | 1/2017 | Shelton, IV et al. |
| 9,549,750 | B2 | 1/2017 | Shelton, IV et al. |
| 9,554,794 | B2 | 1/2017 | Baber et al. |
| 9,554,796 | B2 | 1/2017 | Kostrzewski |
| 9,554,803 | B2 | 1/2017 | Smith et al. |
| 9,554,812 | B2 | 1/2017 | Inkpen et al. |
| 9,554,854 | B2 | 1/2017 | Yates et al. |
| 9,559,624 | B2 | 1/2017 | Philipp |
| 9,561,013 | B2 | 2/2017 | Tsuchiya |
| 9,561,029 | B2 | 2/2017 | Scheib et al. |
| 9,561,030 | B2 | 2/2017 | Zhang et al. |
| 9,561,031 | B2 | 2/2017 | Heinrich et al. |
| 9,561,032 | B2 | 2/2017 | Shelton, IV et al. |
| 9,561,038 | B2 | 2/2017 | Shelton, IV et al. |
| 9,561,045 | B2 | 2/2017 | Hinman et al. |
| 9,561,072 | B2 | 2/2017 | Ko |
| 9,561,082 | B2 | 2/2017 | Yen et al. |
| 9,566,061 | B2 | 2/2017 | Aronhalt et al. |
| 9,566,062 | B2 | 2/2017 | Boudreaux |
| 9,566,064 | B2 | 2/2017 | Williams et al. |
| 9,566,065 | B2 | 2/2017 | Knodel |
| 9,566,067 | B2 | 2/2017 | Milliman et al. |
| 9,566,124 | B2 | 2/2017 | Prisco et al. |
| 9,572,552 | B1 | 2/2017 | Bodor et al. |
| 9,572,574 | B2 | 2/2017 | Shelton, IV et al. |
| 9,572,576 | B2 | 2/2017 | Hodgkinson et al. |
| 9,572,577 | B2 | 2/2017 | Lloyd et al. |
| 9,572,592 | B2 | 2/2017 | Price et al. |
| 9,574,644 | B2 | 2/2017 | Parihar |
| 9,579,039 | B2 | 2/2017 | Jansen et al. |
| 9,579,088 | B2 | 2/2017 | Farritor et al. |
| 9,579,143 | B2 | 2/2017 | Ullrich et al. |
| 9,579,158 | B2 | 2/2017 | Brianza et al. |
| D780,803 | S | 3/2017 | Gill et al. |
| D781,879 | S | 3/2017 | Butcher et al. |
| D782,530 | S | 3/2017 | Paek et al. |
| 9,585,550 | B2 | 3/2017 | Abel et al. |
| 9,585,657 | B2 | 3/2017 | Shelton, IV et al. |
| 9,585,658 | B2 | 3/2017 | Shelton, IV |
| 9,585,659 | B2 | 3/2017 | Viola et al. |
| 9,585,660 | B2 | 3/2017 | Laurent et al. |
| 9,585,662 | B2 | 3/2017 | Shelton, IV et al. |
| 9,585,663 | B2 | 3/2017 | Shelton, IV et al. |
| 9,585,672 | B2 | 3/2017 | Bastia |
| 9,590,433 | B2 | 3/2017 | Li |
| 9,592,050 | B2 | 3/2017 | Schmid et al. |
| 9,592,052 | B2 | 3/2017 | Shelton, IV |
| 9,592,053 | B2 | 3/2017 | Shelton, IV et al. |
| 9,592,054 | B2 | 3/2017 | Schmid et al. |
| 9,597,073 | B2 | 3/2017 | Sorrentino et al. |
| 9,597,075 | B2 | 3/2017 | Shelton, IV et al. |
| 9,597,078 | B2 | 3/2017 | Scirica et al. |
| 9,597,080 | B2 | 3/2017 | Milliman et al. |
| 9,597,104 | B2 | 3/2017 | Nicholas et al. |
| 9,597,143 | B2 | 3/2017 | Madan et al. |
| 9,603,595 | B2 | 3/2017 | Shelton, IV et al. |
| 9,603,598 | B2 | 3/2017 | Shelton, IV et al. |
| 9,603,599 | B2 | 3/2017 | Miller et al. |
| 9,603,991 | B2 | 3/2017 | Shelton, IV et al. |
| D783,658 | S | 4/2017 | Hurst et al. |
| 9,610,068 | B2 | 4/2017 | Kappel et al. |
| 9,610,079 | B2 | 4/2017 | Kamei et al. |
| 9,610,080 | B2 | 4/2017 | Whitfield et al. |
| 9,610,412 | B2 | 4/2017 | Zemlok et al. |
| 9,614,258 | B2 | 4/2017 | Takahashi et al. |
| 9,615,826 | B2 | 4/2017 | Shelton, IV et al. |
| 9,622,745 | B2 | 4/2017 | Ingmanson et al. |
| 9,622,746 | B2 | 4/2017 | Simms et al. |
| 9,629,623 | B2 | 4/2017 | Lytle, IV et al. |
| 9,629,626 | B2 | 4/2017 | Soltz et al. |
| 9,629,627 | B2 | 4/2017 | Kostrzewski et al. |
| 9,629,628 | B2 | 4/2017 | Aranyi |
| 9,629,629 | B2 | 4/2017 | Leimbach et al. |
| 9,629,631 | B2 | 4/2017 | Nicholas et al. |
| 9,629,632 | B2 | 4/2017 | Linder et al. |
| 9,629,652 | B2 | 4/2017 | Mumaw et al. |
| 9,629,814 | B2 | 4/2017 | Widenhouse et al. |
| D785,794 | S | 5/2017 | Magno, Jr. |
| D786,280 | S | 5/2017 | Ma |
| D786,896 | S | 5/2017 | Kim et al. |
| D787,547 | S | 5/2017 | Basargin et al. |
| D788,123 | S | 5/2017 | Shan et al. |
| D788,140 | S | 5/2017 | Hemsley et al. |
| 9,636,091 | B2 | 5/2017 | Beardsley et al. |
| 9,636,111 | B2 | 5/2017 | Wenchell |
| 9,636,112 | B2 | 5/2017 | Penna et al. |
| 9,636,113 | B2 | 5/2017 | Wenchell |
| 9,636,850 | B2 | 5/2017 | Stopek et al. |
| 9,641,122 | B2 | 5/2017 | Romanowich et al. |
| 9,642,620 | B2 | 5/2017 | Baxter, III et al. |
| 9,642,642 | B2 | 5/2017 | Lim |
| 9,649,096 | B2 | 5/2017 | Sholev |
| 9,649,110 | B2 | 5/2017 | Parihar et al. |
| 9,649,111 | B2 | 5/2017 | Shelton, IV et al. |
| 9,649,190 | B2 | 5/2017 | Mathies |
| 9,651,032 | B2 | 5/2017 | Weaver et al. |
| 9,655,613 | B2 | 5/2017 | Schaller |
| 9,655,614 | B2 | 5/2017 | Swensgard et al. |
| 9,655,615 | B2 | 5/2017 | Knodel et al. |
| 9,655,616 | B2 | 5/2017 | Aranyi |
| 9,655,624 | B2 | 5/2017 | Shelton, IV et al. |
| 9,661,991 | B2 | 5/2017 | Glossop |
| 9,662,108 | B2 | 5/2017 | Williams |
| 9,662,110 | B2 | 5/2017 | Huang et al. |
| 9,662,111 | B2 | 5/2017 | Holsten et al. |
| 9,662,116 | B2 | 5/2017 | Smith et al. |
| 9,662,130 | B2 | 5/2017 | Bartels et al. |

(56) References Cited

U.S. PATENT DOCUMENTS

| | | | |
|---|---|---|---|
| 9,662,131 | B2 | 5/2017 | Omori et al. |
| D788,792 | S | 6/2017 | Alessandri et al. |
| D789,384 | S | 6/2017 | Lin et al. |
| D790,570 | S | 6/2017 | Butcher et al. |
| 9,668,728 | B2 | 6/2017 | Williams et al. |
| 9,668,729 | B2 | 6/2017 | Williams et al. |
| 9,668,732 | B2 | 6/2017 | Patel et al. |
| 9,668,733 | B2 | 6/2017 | Williams |
| 9,668,734 | B2 | 6/2017 | Kostrzewski et al. |
| 9,668,735 | B2 | 6/2017 | Beetel |
| 9,675,344 | B2 | 6/2017 | Combrowski et al. |
| 9,675,348 | B2 | 6/2017 | Smith et al. |
| 9,675,351 | B2 | 6/2017 | Hodgkinson et al. |
| 9,675,354 | B2 | 6/2017 | Weir et al. |
| 9,675,355 | B2 | 6/2017 | Shelton, IV et al. |
| 9,675,368 | B2 | 6/2017 | Guo et al. |
| 9,675,372 | B2 | 6/2017 | Laurent et al. |
| 9,675,375 | B2 | 6/2017 | Houser et al. |
| 9,675,405 | B2 | 6/2017 | Trees et al. |
| 9,675,819 | B2 | 6/2017 | Dunbar et al. |
| 9,681,870 | B2 | 6/2017 | Baxter, III et al. |
| 9,681,873 | B2 | 6/2017 | Smith et al. |
| 9,681,884 | B2 | 6/2017 | Clem et al. |
| 9,687,230 | B2 | 6/2017 | Leimbach et al. |
| 9,687,231 | B2 | 6/2017 | Baxter, III et al. |
| 9,687,232 | B2 | 6/2017 | Shelton, IV et al. |
| 9,687,233 | B2 | 6/2017 | Fernandez et al. |
| 9,687,236 | B2 | 6/2017 | Leimbach et al. |
| 9,687,237 | B2 | 6/2017 | Schmid et al. |
| 9,687,253 | B2 | 6/2017 | Detry et al. |
| 9,689,466 | B2 | 6/2017 | Kanai et al. |
| 9,690,362 | B2 | 6/2017 | Leimbach et al. |
| 9,693,772 | B2 | 7/2017 | Ingmanson et al. |
| 9,693,774 | B2 | 7/2017 | Gettinger et al. |
| 9,693,775 | B2 | 7/2017 | Agarwal et al. |
| 9,693,777 | B2 | 7/2017 | Schellin et al. |
| 9,700,309 | B2 | 7/2017 | Jaworek et al. |
| 9,700,310 | B2 | 7/2017 | Morgan et al. |
| 9,700,312 | B2 | 7/2017 | Kostrzewski et al. |
| 9,700,314 | B2 | 7/2017 | Marczyk |
| 9,700,315 | B2 | 7/2017 | Chen et al. |
| 9,700,317 | B2 | 7/2017 | Aronhalt et al. |
| 9,700,318 | B2 | 7/2017 | Scirica et al. |
| 9,700,319 | B2 | 7/2017 | Motooka et al. |
| 9,700,320 | B2 | 7/2017 | Dinardo et al. |
| 9,700,321 | B2 | 7/2017 | Shelton, IV et al. |
| 9,700,334 | B2 | 7/2017 | Hinman et al. |
| 9,700,381 | B2 | 7/2017 | Amat Girbau |
| 9,702,823 | B2 | 7/2017 | Maher et al. |
| 9,706,674 | B2 | 7/2017 | Collins et al. |
| 9,706,981 | B2 | 7/2017 | Nicholas et al. |
| 9,706,991 | B2 | 7/2017 | Hess et al. |
| 9,706,993 | B2 | 7/2017 | Hessler et al. |
| 9,707,003 | B2 | 7/2017 | Hoell, Jr. et al. |
| 9,707,005 | B2 | 7/2017 | Strobl et al. |
| 9,707,026 | B2 | 7/2017 | Malackowski et al. |
| 9,707,033 | B2 | 7/2017 | Parihar et al. |
| 9,707,043 | B2 | 7/2017 | Bozung |
| 9,707,684 | B2 | 7/2017 | Ruiz Morales et al. |
| 9,713,466 | B2 | 7/2017 | Kostrzewski |
| 9,713,468 | B2 | 7/2017 | Harris et al. |
| 9,713,470 | B2 | 7/2017 | Scirica et al. |
| 9,713,474 | B2 | 7/2017 | Lorenz |
| D795,919 | S | 8/2017 | Bischoff et al. |
| 9,717,497 | B2 | 8/2017 | Zerkle et al. |
| 9,717,498 | B2 | 8/2017 | Aranyi et al. |
| 9,718,190 | B2 | 8/2017 | Larkin et al. |
| 9,722,236 | B2 | 8/2017 | Sathrum |
| 9,724,091 | B2 | 8/2017 | Shelton, IV et al. |
| 9,724,092 | B2 | 8/2017 | Baxter, III et al. |
| 9,724,094 | B2 | 8/2017 | Baber et al. |
| 9,724,095 | B2 | 8/2017 | Gupta et al. |
| 9,724,096 | B2 | 8/2017 | Thompson et al. |
| 9,724,098 | B2 | 8/2017 | Baxter, III et al. |
| 9,724,118 | B2 | 8/2017 | Schulte et al. |
| 9,724,163 | B2 | 8/2017 | Orban |
| 9,730,692 | B2 | 8/2017 | Shelton, IV et al. |
| 9,730,695 | B2 | 8/2017 | Leimbach et al. |
| 9,730,697 | B2 | 8/2017 | Morgan et al. |
| 9,730,717 | B2 | 8/2017 | Katsuki et al. |
| 9,730,757 | B2 | 8/2017 | Brudniok |
| 9,731,410 | B2 | 8/2017 | Hirabayashi et al. |
| 9,733,663 | B2 | 8/2017 | Leimbach et al. |
| 9,737,297 | B2 | 8/2017 | Racenet et al. |
| 9,737,298 | B2 | 8/2017 | Isbell, Jr. |
| 9,737,299 | B2 | 8/2017 | Yan |
| 9,737,301 | B2 | 8/2017 | Baber et al. |
| 9,737,302 | B2 | 8/2017 | Shelton, IV et al. |
| 9,737,303 | B2 | 8/2017 | Shelton, IV et al. |
| 9,737,323 | B2 | 8/2017 | Thapliyal et al. |
| 9,737,365 | B2 | 8/2017 | Hegeman et al. |
| 9,743,927 | B2 | 8/2017 | Whitman |
| 9,743,928 | B2 | 8/2017 | Shelton, IV et al. |
| 9,743,929 | B2 | 8/2017 | Leimbach et al. |
| D798,319 | S | 9/2017 | Bergstrand et al. |
| 9,750,498 | B2 | 9/2017 | Timm et al. |
| 9,750,499 | B2 | 9/2017 | Leimbach et al. |
| 9,750,501 | B2 | 9/2017 | Shelton, IV et al. |
| 9,750,502 | B2 | 9/2017 | Scirica et al. |
| 9,750,503 | B2 | 9/2017 | Milliman |
| 9,750,639 | B2 | 9/2017 | Barnes et al. |
| 9,751,176 | B2 | 9/2017 | McRoberts et al. |
| 9,757,123 | B2 | 9/2017 | Giordano et al. |
| 9,757,124 | B2 | 9/2017 | Schellin et al. |
| 9,757,126 | B2 | 9/2017 | Cappola |
| 9,757,128 | B2 | 9/2017 | Baber et al. |
| 9,757,129 | B2 | 9/2017 | Williams |
| 9,757,130 | B2 | 9/2017 | Shelton, IV |
| 9,763,662 | B2 | 9/2017 | Shelton, IV et al. |
| 9,763,668 | B2 | 9/2017 | Whitfield et al. |
| 9,770,245 | B2 | 9/2017 | Swayze et al. |
| 9,770,274 | B2 | 9/2017 | Pool et al. |
| D798,886 | S | 10/2017 | Prophete et al. |
| D800,742 | S | 10/2017 | Rhodes |
| D800,744 | S | 10/2017 | Jitkoff et al. |
| D800,766 | S | 10/2017 | Park et al. |
| D800,904 | S | 10/2017 | Leimbach et al. |
| 9,775,608 | B2 | 10/2017 | Aronhalt et al. |
| 9,775,609 | B2 | 10/2017 | Shelton, IV et al. |
| 9,775,610 | B2 | 10/2017 | Nicholas et al. |
| 9,775,611 | B2 | 10/2017 | Kostrzewski |
| 9,775,613 | B2 | 10/2017 | Shelton, IV et al. |
| 9,775,614 | B2 | 10/2017 | Shelton, IV et al. |
| 9,775,618 | B2 | 10/2017 | Bettuchi et al. |
| 9,775,635 | B2 | 10/2017 | Take |
| 9,775,678 | B2 | 10/2017 | Lohmeier |
| 9,782,169 | B2 | 10/2017 | Kimsey et al. |
| 9,782,170 | B2 | 10/2017 | Zemlok et al. |
| 9,782,180 | B2 | 10/2017 | Smith et al. |
| 9,782,187 | B2 | 10/2017 | Zergiebel et al. |
| 9,782,193 | B2 | 10/2017 | Thistle |
| 9,782,214 | B2 | 10/2017 | Houser et al. |
| 9,788,834 | B2 | 10/2017 | Schmid et al. |
| 9,788,835 | B2 | 10/2017 | Morgan et al. |
| 9,788,836 | B2 | 10/2017 | Overmyer et al. |
| 9,788,847 | B2 | 10/2017 | Jinno |
| 9,788,851 | B2 | 10/2017 | Dannaher et al. |
| 9,788,902 | B2 | 10/2017 | Inoue et al. |
| 9,795,379 | B2 | 10/2017 | Leimbach et al. |
| 9,795,380 | B2 | 10/2017 | Shelton, IV et al. |
| 9,795,381 | B2 | 10/2017 | Shelton, IV |
| 9,795,382 | B2 | 10/2017 | Shelton, IV |
| 9,795,383 | B2 | 10/2017 | Aldridge et al. |
| 9,795,384 | B2 | 10/2017 | Weaner et al. |
| 9,797,486 | B2 | 10/2017 | Zergiebel et al. |
| 9,801,626 | B2 | 10/2017 | Parihar et al. |
| 9,801,627 | B2 | 10/2017 | Harris et al. |
| 9,801,628 | B2 | 10/2017 | Harris et al. |
| 9,801,634 | B2 | 10/2017 | Shelton, IV et al. |
| 9,801,679 | B2 | 10/2017 | Trees et al. |
| 9,802,033 | B2 | 10/2017 | Hibner et al. |
| 9,804,618 | B2 | 10/2017 | Leimbach et al. |
| D803,234 | S | 11/2017 | Day et al. |
| D803,235 | S | 11/2017 | Markson et al. |

(56) References Cited

U.S. PATENT DOCUMENTS

D803,850 S 11/2017 Chang et al.
9,808,244 B2 11/2017 Leimbach et al.
9,808,246 B2 11/2017 Shelton, IV et al.
9,808,247 B2 11/2017 Shelton, IV et al.
9,808,248 B2 11/2017 Hoffman
9,808,249 B2 11/2017 Shelton, IV
9,814,460 B2 11/2017 Kimsey et al.
9,814,462 B2 11/2017 Woodard, Jr. et al.
9,814,463 B2 11/2017 Williams et al.
9,814,530 B2 11/2017 Weir et al.
9,814,561 B2 11/2017 Forsell
9,815,118 B1 11/2017 Schmitt et al.
9,820,445 B2 11/2017 Simpson et al.
9,820,737 B2 11/2017 Beardsley et al.
9,820,738 B2 11/2017 Lytle, IV et al.
9,820,741 B2 11/2017 Kostrzewski
9,820,768 B2 11/2017 Gee et al.
9,825,455 B2 11/2017 Sandhu et al.
9,826,976 B2 11/2017 Parihar et al.
9,826,977 B2 11/2017 Leimbach et al.
9,826,978 B2 11/2017 Shelton, IV et al.
9,829,698 B2 11/2017 Haraguchi et al.
D806,108 S 12/2017 Day
9,833,235 B2 12/2017 Penna et al.
9,833,236 B2 12/2017 Shelton, IV et al.
9,833,238 B2 12/2017 Baxter, III et al.
9,833,239 B2 12/2017 Yates et al.
9,833,241 B2 12/2017 Huitema et al.
9,833,242 B2 12/2017 Baxter, III et al.
9,839,420 B2 12/2017 Shelton, IV et al.
9,839,421 B2 12/2017 Zerkle et al.
9,839,422 B2 12/2017 Schellin et al.
9,839,423 B2 12/2017 Vendely et al.
9,839,427 B2 12/2017 Swayze et al.
9,839,428 B2 12/2017 Baxter, III et al.
9,839,429 B2 12/2017 Weisenburgh, II et al.
9,839,480 B2 12/2017 Pribanic et al.
9,839,481 B2 12/2017 Blumenkranz et al.
9,844,313 B2 12/2017 DiCarlo et al.
9,844,368 B2 12/2017 Boudreaux et al.
9,844,369 B2 12/2017 Huitema et al.
9,844,371 B2 12/2017 Scirica et al.
9,844,372 B2 12/2017 Shelton, IV et al.
9,844,373 B2 12/2017 Swayze et al.
9,844,374 B2 12/2017 Lytle, IV et al.
9,844,375 B2 12/2017 Overmyer et al.
9,844,376 B2 12/2017 Baxter, III et al.
9,844,379 B2 12/2017 Shelton, IV et al.
9,848,871 B2 12/2017 Harris et al.
9,848,873 B2 12/2017 Shelton, IV
9,848,875 B2 12/2017 Aronhalt et al.
9,848,877 B2 12/2017 Shelton, IV et al.
9,850,499 B2 12/2017 Baylink et al.
9,850,994 B2 12/2017 Schena
D808,989 S 1/2018 Ayvazian et al.
9,855,039 B2 1/2018 Racenet et al.
9,855,040 B2 1/2018 Kostrzewski
9,855,662 B2 1/2018 Ruiz Morales et al.
9,861,261 B2 1/2018 Shahinian
9,861,359 B2 1/2018 Shelton, IV et al.
9,861,361 B2 1/2018 Aronhalt et al.
9,861,362 B2 1/2018 Whitman et al.
9,861,366 B2 1/2018 Aranyi
9,861,382 B2 1/2018 Smith et al.
9,861,446 B2 1/2018 Lang
9,867,612 B2 1/2018 Parihar et al.
9,867,613 B2 1/2018 Marczyk et al.
9,867,615 B2 1/2018 Fanelli et al.
9,867,617 B2 1/2018 Ma
9,867,618 B2 1/2018 Hall et al.
9,867,620 B2 1/2018 Fischvogt et al.
9,868,198 B2 1/2018 Nicholas et al.
9,872,682 B2 1/2018 Hess et al.
9,872,683 B2 1/2018 Hopkins et al.
9,872,684 B2 1/2018 Hall et al.
9,872,722 B2 1/2018 Lech
9,877,718 B2 1/2018 Weir et al.
9,877,721 B2 1/2018 Schellin et al.
9,877,722 B2 1/2018 Schellin et al.
9,877,723 B2 1/2018 Hall et al.
9,877,776 B2 1/2018 Boudreaux
D810,099 S 2/2018 Riedel
9,883,843 B2 2/2018 Garlow
9,883,860 B2 2/2018 Leimbach et al.
9,883,861 B2 2/2018 Shelton, IV et al.
9,884,456 B2 2/2018 Schellin et al.
9,888,914 B2 2/2018 Martin et al.
9,888,919 B2 2/2018 Leimbach et al.
9,888,921 B2 2/2018 Williams et al.
9,888,924 B2 2/2018 Ebersole et al.
9,889,230 B2 2/2018 Bennett et al.
9,895,147 B2 2/2018 Shelton, IV
9,895,148 B2 2/2018 Shelton, IV et al.
9,895,813 B2 2/2018 Blumenkranz et al.
9,901,339 B2 2/2018 Farascioni
9,901,341 B2 2/2018 Kostrzewski
9,901,342 B2 2/2018 Shelton, IV et al.
9,901,344 B2 2/2018 Moore et al.
9,901,345 B2 2/2018 Moore et al.
9,901,346 B2 2/2018 Moore et al.
9,901,358 B2 2/2018 Faller et al.
9,901,406 B2 2/2018 State et al.
9,901,412 B2 2/2018 Lathrop et al.
D813,899 S 3/2018 Erant et al.
9,907,456 B2 3/2018 Miyoshi
9,907,552 B2 3/2018 Measamer et al.
9,907,553 B2 3/2018 Cole et al.
9,907,600 B2 3/2018 Stulen et al.
9,907,620 B2 3/2018 Shelton, IV et al.
9,913,641 B2 3/2018 Takemoto et al.
9,913,642 B2 3/2018 Leimbach et al.
9,913,644 B2 3/2018 McCuen
9,913,646 B2 3/2018 Shelton, IV
9,913,647 B2 3/2018 Weisenburgh, II et al.
9,913,648 B2 3/2018 Shelton, IV et al.
9,913,694 B2 3/2018 Brisson
9,913,733 B2 3/2018 Piron et al.
9,918,704 B2 3/2018 Shelton, IV et al.
9,918,714 B2 3/2018 Gibbons, Jr.
9,918,715 B2 3/2018 Menn
9,918,716 B2 3/2018 Baxter, III et al.
9,918,717 B2 3/2018 Czernik
9,918,730 B2 3/2018 Trees et al.
9,924,941 B2 3/2018 Burbank
9,924,942 B2 3/2018 Swayze et al.
9,924,943 B2 3/2018 Mohan Pinjala et al.
9,924,944 B2 3/2018 Shelton, IV et al.
9,924,945 B2 3/2018 Zheng et al.
9,924,946 B2 3/2018 Vendely et al.
9,924,947 B2 3/2018 Shelton, IV et al.
9,924,961 B2 3/2018 Shelton, IV et al.
9,931,106 B2 4/2018 Au et al.
9,931,116 B2 4/2018 Racenet et al.
9,931,117 B2 4/2018 Hathaway et al.
9,931,118 B2 4/2018 Shelton, IV et al.
9,931,120 B2 4/2018 Chen et al.
9,936,949 B2 4/2018 Measamer et al.
9,936,950 B2 4/2018 Shelton, IV et al.
9,936,951 B2 4/2018 Hufnagel et al.
9,936,952 B2 4/2018 Demmy
9,936,954 B2 4/2018 Shelton, IV et al.
9,937,626 B2 4/2018 Rockrohr
9,943,309 B2 4/2018 Shelton, IV et al.
9,943,310 B2 4/2018 Harris et al.
9,943,312 B2 4/2018 Posada et al.
9,949,754 B2 4/2018 Newhauser et al.
9,953,193 B2 4/2018 Butler et al.
D819,072 S 5/2018 Clediere
9,955,954 B2 5/2018 Destoumieux et al.
9,955,965 B2 5/2018 Chen et al.
9,955,966 B2 5/2018 Zergiebel
9,956,677 B2 5/2018 Baskar et al.
9,962,129 B2 5/2018 Jerebko et al.
9,962,157 B2 5/2018 Sapre

(56) References Cited

U.S. PATENT DOCUMENTS 9,962,158 B2 5/2018 Hall et al.
9,962,159 B2 5/2018 Heinrich et al.
9,962,161 B2 5/2018 Scheib et al.
9,968,354 B2 5/2018 Shelton, IV et al.
9,968,355 B2 5/2018 Shelton, IV et al.
9,968,356 B2 5/2018 Shelton, IV et al.
9,968,397 B2 5/2018 Taylor et al.
9,974,529 B2 5/2018 Shelton, IV et al.
9,974,538 B2 5/2018 Baxter, III et al.
9,974,539 B2 5/2018 Yates et al.
9,974,541 B2 5/2018 Calderoni
9,974,542 B2 5/2018 Hodgkinson
9,980,713 B2 5/2018 Aronhalt et al.
9,980,724 B2 5/2018 Farascioni et al.
9,980,729 B2 5/2018 Moore et al.
9,980,740 B2 5/2018 Krause et al.
9,980,769 B2 5/2018 Trees et al.
D819,680 S 6/2018 Nguyen
D819,682 S 6/2018 Howard et al.
D819,684 S 6/2018 Dart
D820,307 S 6/2018 Jian et al.
D820,867 S 6/2018 Dickens et al.
9,987,000 B2 6/2018 Shelton, IV et al.
9,987,003 B2 6/2018 Timm et al.
9,987,005 B2 6/2018 Viola et al.
9,987,006 B2 6/2018 Morgan et al.
9,987,008 B2 6/2018 Scirica et al.
9,987,095 B2 6/2018 Chowaniec et al.
9,987,097 B2 6/2018 van der Weide et al.
9,987,099 B2 6/2018 Chen et al.
9,993,248 B2 6/2018 Shelton, IV et al.
9,993,258 B2 6/2018 Shelton, IV et al.
9,993,284 B2 6/2018 Boudreaux
9,999,408 B2 6/2018 Boudreaux et al.
9,999,423 B2 6/2018 Schuckmann et al.
9,999,426 B2 6/2018 Moore et al.
9,999,431 B2 6/2018 Shelton, IV et al.
9,999,472 B2 6/2018 Weir et al.
9,999,759 B2 6/2018 Matonick et al.
10,004,497 B2 6/2018 Overmyer et al.
10,004,498 B2 6/2018 Morgan et al.
10,004,500 B2 6/2018 Shelton, IV et al.
10,004,501 B2 6/2018 Shelton, IV et al.
10,004,505 B2 6/2018 Moore et al.
10,004,506 B2 6/2018 Shelton, IV et al.
10,004,552 B1 6/2018 Kleyman et al.
D822,206 S 7/2018 Shelton, IV et al.
D823,858 S 7/2018 Li et al.
10,010,322 B2 7/2018 Shelton, IV et al.
10,010,324 B2 7/2018 Huitema et al.
10,010,395 B2 7/2018 Puckett et al.
10,013,049 B2 7/2018 Leimbach et al.
10,016,199 B2 7/2018 Baber et al.
10,016,656 B2 7/2018 Devor et al.
10,022,120 B2 7/2018 Martin et al.
10,022,123 B2 7/2018 Williams et al.
10,022,125 B2 7/2018 (Prommersberger) Stopek et al.
10,024,407 B2 7/2018 Aranyi et al.
10,028,742 B2 7/2018 Shelton, IV et al.
10,028,743 B2 7/2018 Shelton, IV et al.
10,028,744 B2 7/2018 Shelton, IV et al.
10,028,761 B2 7/2018 Leimbach et al.
10,029,108 B2 7/2018 Powers et al.
10,029,125 B2 7/2018 Shapiro et al.
10,034,344 B2 7/2018 Yoshida
10,034,668 B2 7/2018 Ebner
D826,405 S 8/2018 Shelton, IV et al.
10,039,440 B2 8/2018 Fenech et al.
10,039,529 B2 8/2018 Kerr et al.
10,039,532 B2 8/2018 Srinivas et al.
10,039,545 B2 8/2018 Sadowski et al.
10,041,822 B2 8/2018 Zemlok
10,045,769 B2 8/2018 Aronhalt et al.
10,045,776 B2 8/2018 Shelton, IV et al.
10,045,778 B2 8/2018 Yates et al.
10,045,779 B2 8/2018 Savage et al.
10,045,781 B2 8/2018 Cropper et al.
10,045,782 B2 8/2018 Murthy Aravalli
10,045,869 B2 8/2018 Forsell
10,046,904 B2 8/2018 Evans et al.
10,052,044 B2 8/2018 Shelton, IV et al.
10,052,099 B2 8/2018 Morgan et al.
10,052,100 B2 8/2018 Morgan et al.
10,052,102 B2 8/2018 Baxter, III et al.
10,052,104 B2 8/2018 Shelton, IV et al.
10,052,164 B2 8/2018 Overmyer
10,058,317 B2 8/2018 Fan et al.
10,058,327 B2 8/2018 Weisenburgh, II et al.
10,058,373 B2 8/2018 Takashino et al.
10,058,395 B2 8/2018 Devengenzo et al.
10,058,963 B2 8/2018 Shelton, IV et al.
10,064,620 B2 9/2018 Gettinger et al.
10,064,621 B2 9/2018 Kerr et al.
10,064,622 B2 9/2018 Murthy Aravalli
10,064,624 B2 9/2018 Shelton, IV et al.
10,064,639 B2 9/2018 Ishida et al.
10,064,642 B2 9/2018 Marczyk et al.
10,064,649 B2 9/2018 Golebieski et al.
10,064,688 B2 9/2018 Shelton, IV et al.
10,070,861 B2 9/2018 Spivey et al.
10,070,863 B2 9/2018 Swayze et al.
10,071,452 B2 9/2018 Shelton, IV et al.
10,076,325 B2 9/2018 Huang et al.
10,076,326 B2 9/2018 Yates et al.
10,076,340 B2 9/2018 Belagali et al.
10,080,552 B2 9/2018 Nicholas et al.
D830,550 S 10/2018 Miller et al.
D831,209 S 10/2018 Huitema et al.
D831,676 S 10/2018 Park et al.
D832,301 S 10/2018 Smith
10,085,624 B2 10/2018 Isoda et al.
10,085,643 B2 10/2018 Bandic et al.
10,085,728 B2 10/2018 Jogasaki et al.
10,085,746 B2 10/2018 Fischvogt
10,085,748 B2 10/2018 Morgan et al.
10,085,749 B2 10/2018 Cappola et al.
10,085,750 B2 10/2018 Zergiebel et al.
10,085,751 B2 10/2018 Overmyer et al.
10,085,754 B2 10/2018 Sniffin et al.
10,085,806 B2 10/2018 Hagn et al.
10,092,290 B2 10/2018 Yigit et al.
10,092,292 B2 10/2018 Boudreaux et al.
10,098,635 B2 10/2018 Burbank
10,098,636 B2 10/2018 Shelton, IV et al.
10,098,640 B2 10/2018 Bertolero et al.
10,098,642 B2 10/2018 Baxter, III et al.
10,099,303 B2 10/2018 Yoshida et al.
10,101,861 B2 10/2018 Kiyoto
10,105,126 B2 10/2018 Sauer
10,105,128 B2 10/2018 Cooper et al.
10,105,136 B2 10/2018 Yates et al.
10,105,139 B2 10/2018 Yates et al.
10,105,140 B2 10/2018 Malinouskas et al.
10,105,142 B2 10/2018 Baxter, III et al.
10,105,149 B2 10/2018 Haider et al.
10,106,932 B2 10/2018 Anderson et al.
10,111,657 B2 10/2018 McCuen
10,111,658 B2 10/2018 Chowaniec et al.
10,111,660 B2 10/2018 Hemmann
10,111,665 B2 10/2018 Aranyi et al.
10,111,679 B2 10/2018 Baber et al.
10,111,698 B2 10/2018 Scheib et al.
10,111,702 B2 10/2018 Kostrzewski
D833,608 S 11/2018 Miller et al.
10,117,649 B2 11/2018 Baxter, III et al.
10,117,650 B2 11/2018 Nicholas et al.
10,117,652 B2 11/2018 Schmid et al.
10,117,653 B2 11/2018 Leimbach et al.
10,117,654 B2 11/2018 Ingmanson et al.
10,123,798 B2 11/2018 Baxter, III et al.
10,123,845 B2 11/2018 Yeung
10,124,493 B2 11/2018 Rothfuss et al.
10,130,352 B2 11/2018 Widenhouse et al.
10,130,359 B2 11/2018 Hess et al.

(56) References Cited

U.S. PATENT DOCUMENTS 10,130,360 B2 11/2018 Olson et al.
10,130,361 B2 11/2018 Yates et al.
10,130,363 B2 11/2018 Huitema et al.
10,130,366 B2 11/2018 Shelton, IV et al.
10,130,367 B2 11/2018 Cappola et al.
10,130,382 B2 11/2018 Gladstone
10,130,738 B2 11/2018 Shelton, IV et al.
10,130,830 B2 11/2018 Miret Carceller et al.
10,133,248 B2 11/2018 Fitzsimmons et al.
10,135,242 B2 11/2018 Baber et al.
10,136,879 B2 11/2018 Ross et al.
10,136,887 B2 11/2018 Shelton, IV et al.
10,136,889 B2 11/2018 Shelton, IV et al.
10,136,890 B2 11/2018 Shelton, IV et al.
10,136,891 B2 11/2018 Shelton, IV et al.
10,136,949 B2 11/2018 Felder et al.
D835,659 S 12/2018 Anzures et al.
D836,124 S 12/2018 Fan
10,143,474 B2 12/2018 Bucciaglia et al.
10,146,423 B1 12/2018 Reed et al.
10,149,679 B2 12/2018 Shelton, IV et al.
10,149,680 B2 12/2018 Parihar et al.
10,149,682 B2 12/2018 Shelton, IV et al.
10,149,683 B2 12/2018 Smith et al.
10,149,712 B2 12/2018 Manwaring et al.
10,152,789 B2 12/2018 Carnes et al.
10,154,841 B2 12/2018 Weaner et al.
10,159,481 B2 12/2018 Whitman et al.
10,159,482 B2 12/2018 Swayze et al.
10,159,483 B2 12/2018 Beckman et al.
10,159,506 B2 12/2018 Boudreaux et al.
10,161,816 B2 12/2018 Jackson et al.
10,163,065 B1 12/2018 Koski et al.
10,163,589 B2 12/2018 Zergiebel et al.
10,164,466 B2 12/2018 Calderoni
D837,244 S 1/2019 Kuo et al.
D837,245 S 1/2019 Kuo et al.
10,166,023 B2 1/2019 Vendely et al.
10,166,025 B2 1/2019 Leimbach et al.
10,166,026 B2 1/2019 Shelton, IV et al.
10,172,611 B2 1/2019 Shelton, IV et al.
10,172,615 B2 1/2019 Marczyk et al.
10,172,616 B2 1/2019 Murray et al.
10,172,617 B2 1/2019 Shelton, IV et al.
10,172,618 B2 1/2019 Shelton, IV et al.
10,172,619 B2 1/2019 Harris et al.
10,172,620 B2 1/2019 Harris et al.
10,172,636 B2 1/2019 Stulen et al.
10,172,669 B2 1/2019 Felder et al.
10,175,127 B2 1/2019 Collins et al.
10,178,992 B2 1/2019 Wise et al.
10,180,463 B2 1/2019 Beckman et al.
10,182,813 B2 1/2019 Leimbach et al.
10,182,815 B2 1/2019 Williams et al.
10,182,816 B2 1/2019 Shelton, IV et al.
10,182,818 B2 1/2019 Hensel et al.
10,182,819 B2 1/2019 Shelton, IV
10,182,868 B2 1/2019 Meier et al.
10,188,385 B2 1/2019 Kerr et al.
10,188,389 B2 1/2019 Vendely et al.
10,188,393 B2 1/2019 Smith et al.
10,188,394 B2 1/2019 Shelton, IV et al.
10,190,888 B2 1/2019 Hryb et al.
D839,900 S 2/2019 Gan
D841,667 S 2/2019 Coren
10,194,801 B2 2/2019 Elhawary et al.
10,194,904 B2 2/2019 Viola et al.
10,194,907 B2 2/2019 Marczyk et al.
10,194,908 B2 2/2019 Duque et al.
10,194,910 B2 2/2019 Shelton, IV et al.
10,194,911 B2 2/2019 Miller et al.
10,194,912 B2 2/2019 Scheib et al.
10,194,913 B2 2/2019 Nalagatla et al.
10,194,976 B2 2/2019 Boudreaux
10,194,981 B2 2/2019 Balbas et al.
10,194,992 B2 2/2019 Robinson
10,201,348 B2 2/2019 Scheib et al.
10,201,349 B2 2/2019 Leimbach et al.
10,201,363 B2 2/2019 Shelton, IV
10,201,364 B2 2/2019 Leimbach et al.
10,201,365 B2 2/2019 Boudreaux et al.
10,201,381 B2 2/2019 Zergiebel et al.
10,206,605 B2 2/2019 Shelton, IV et al.
10,206,676 B2 2/2019 Shelton, IV
10,206,677 B2 2/2019 Harris et al.
10,206,678 B2 2/2019 Shelton, IV et al.
10,206,748 B2 2/2019 Burbank
10,210,244 B1 2/2019 Branavan et al.
10,211,586 B2 2/2019 Adams et al.
10,213,198 B2 2/2019 Aronhalt et al.
10,213,201 B2 2/2019 Shelton, IV et al.
10,213,202 B2 2/2019 Flanagan et al.
10,213,203 B2 2/2019 Swayze et al.
10,213,204 B2 2/2019 Aranyi et al.
10,213,262 B2 2/2019 Shelton, IV et al.
D842,328 S 3/2019 Jian et al.
10,219,811 B2 3/2019 Haider et al.
10,219,832 B2 3/2019 Bagwell et al.
10,220,522 B2 3/2019 Rockrohr
10,226,239 B2 3/2019 Nicholas et al.
10,226,249 B2 3/2019 Jaworek et al.
10,226,250 B2 3/2019 Beckman et al.
10,226,251 B2 3/2019 Scheib et al.
10,226,274 B2 3/2019 Worrell et al.
10,231,634 B2 3/2019 Zand et al.
10,231,653 B2 3/2019 Bohm et al.
10,231,734 B2 3/2019 Thompson et al.
10,231,794 B2 3/2019 Shelton, IV et al.
10,238,385 B2 3/2019 Yates et al.
10,238,386 B2 3/2019 Overmyer et al.
10,238,387 B2 3/2019 Yates et al.
10,238,389 B2 3/2019 Yates et al.
10,238,390 B2 3/2019 Harris et al.
10,238,391 B2 3/2019 Leimbach et al.
D844,666 S 4/2019 Espeleta et al.
D844,667 S 4/2019 Espeleta et al.
D845,342 S 4/2019 Espeleta et al.
D847,199 S 4/2019 Whitmore
10,244,991 B2 4/2019 Shademan et al.
10,245,027 B2 4/2019 Shelton, IV et al.
10,245,028 B2 4/2019 Shelton, IV et al.
10,245,029 B2 4/2019 Hunter et al.
10,245,030 B2 4/2019 Hunter et al.
10,245,032 B2 4/2019 Shelton, IV
10,245,033 B2 4/2019 Overmyer et al.
10,245,034 B2 4/2019 Shelton, IV et al.
10,245,035 B2 4/2019 Swayze et al.
10,245,038 B2 4/2019 Hopkins et al.
10,245,058 B2 4/2019 Omori et al.
10,251,645 B2 4/2019 Kostrzewski
10,251,648 B2 4/2019 Harris et al.
10,251,649 B2 4/2019 Schellin et al.
10,251,725 B2 4/2019 Valentine et al.
10,258,322 B2 4/2019 Fanton et al.
10,258,330 B2 4/2019 Shelton, IV et al.
10,258,331 B2 4/2019 Shelton, IV et al.
10,258,332 B2 4/2019 Schmid et al.
10,258,333 B2 4/2019 Shelton, IV et al.
10,258,336 B2 4/2019 Baxter, III et al.
10,258,363 B2 4/2019 Worrell et al.
10,258,418 B2 4/2019 Shelton, IV et al.
10,264,797 B2 4/2019 Zhang et al.
10,265,065 B2 4/2019 Shelton, IV et al.
10,265,067 B2 4/2019 Yates et al.
10,265,068 B2 4/2019 Harris et al.
10,265,072 B2 4/2019 Shelton, IV et al.
10,265,073 B2 4/2019 Scheib et al.
10,265,074 B2 4/2019 Shelton, IV et al.
10,265,090 B2 4/2019 Ingmanson et al.
10,271,840 B2 4/2019 Sapre
10,271,844 B2 4/2019 Valentine et al.
10,271,845 B2 4/2019 Shelton, IV
10,271,846 B2 4/2019 Shelton, IV et al.
10,271,847 B2 4/2019 Racenet et al.

(56) References Cited

U.S. PATENT DOCUMENTS

| | | | |
|---|---|---|---|
| 10,271,849 | B2 | 4/2019 | Vendely et al. |
| 10,271,851 | B2 | 4/2019 | Shelton, IV et al. |
| D847,989 | S | 5/2019 | Shelton, IV et al. |
| D848,473 | S | 5/2019 | Zhu et al. |
| D849,046 | S | 5/2019 | Kuo et al. |
| 10,278,696 | B2 | 5/2019 | Gurumurthy et al. |
| 10,278,697 | B2 | 5/2019 | Shelton, IV et al. |
| 10,278,702 | B2 | 5/2019 | Shelton, IV et al. |
| 10,278,703 | B2 | 5/2019 | Nativ et al. |
| 10,278,707 | B2 | 5/2019 | Thompson et al. |
| 10,278,722 | B2 | 5/2019 | Shelton, IV et al. |
| 10,278,780 | B2 | 5/2019 | Shelton, IV |
| 10,285,694 | B2 | 5/2019 | Viola et al. |
| 10,285,695 | B2 | 5/2019 | Jaworek et al. |
| 10,285,696 | B2 | 5/2019 | Marczyk |
| 10,285,699 | B2 | 5/2019 | Vendely et al. |
| 10,285,700 | B2 | 5/2019 | Scheib |
| 10,285,705 | B2 | 5/2019 | Shelton, IV et al. |
| 10,285,724 | B2 | 5/2019 | Faller et al. |
| 10,285,750 | B2 | 5/2019 | Coulson et al. |
| 10,292,701 | B2 | 5/2019 | Scheib et al. |
| 10,292,704 | B2 | 5/2019 | Harris et al. |
| 10,292,707 | B2 | 5/2019 | Shelton, IV et al. |
| 10,293,100 | B2 | 5/2019 | Shelton, IV et al. |
| 10,293,553 | B2 | 5/2019 | Racenet et al. |
| 10,299,787 | B2 | 5/2019 | Shelton, IV |
| 10,299,788 | B2 | 5/2019 | Heinrich et al. |
| 10,299,789 | B2 | 5/2019 | Marczyk et al. |
| 10,299,790 | B2 | 5/2019 | Beardsley |
| 10,299,792 | B2 | 5/2019 | Huitema et al. |
| 10,299,817 | B2 | 5/2019 | Shelton, IV et al. |
| 10,299,818 | B2 | 5/2019 | Riva |
| 10,299,878 | B2 | 5/2019 | Shelton, IV et al. |
| 10,303,851 | B2 | 5/2019 | Nguyen et al. |
| D850,617 | S | 6/2019 | Shelton, IV et al. |
| D851,676 | S | 6/2019 | Foss et al. |
| D851,762 | S | 6/2019 | Shelton, IV et al. |
| 10,307,159 | B2 | 6/2019 | Harris et al. |
| 10,307,160 | B2 | 6/2019 | Vendely et al. |
| 10,307,161 | B2 | 6/2019 | Jankowski |
| 10,307,163 | B2 | 6/2019 | Moore et al. |
| 10,307,170 | B2 | 6/2019 | Parfett et al. |
| 10,307,202 | B2 | 6/2019 | Smith et al. |
| 10,314,559 | B2 | 6/2019 | Razzaque et al. |
| 10,314,577 | B2 | 6/2019 | Laurent et al. |
| 10,314,578 | B2 | 6/2019 | Leimbach et al. |
| 10,314,579 | B2 | 6/2019 | Chowaniec et al. |
| 10,314,580 | B2 | 6/2019 | Scheib et al. |
| 10,314,582 | B2 | 6/2019 | Shelton, IV et al. |
| 10,314,584 | B2 | 6/2019 | Scirica et al. |
| 10,314,587 | B2 | 6/2019 | Harris et al. |
| 10,314,588 | B2 | 6/2019 | Turner et al. |
| 10,314,589 | B2 | 6/2019 | Shelton, IV et al. |
| 10,314,590 | B2 | 6/2019 | Shelton, IV et al. |
| 10,315,566 | B2 | 6/2019 | Choi et al. |
| 10,321,907 | B2 | 6/2019 | Shelton, IV et al. |
| 10,321,909 | B2 | 6/2019 | Shelton, IV et al. |
| 10,321,927 | B2 | 6/2019 | Hinman |
| 10,327,743 | B2 | 6/2019 | St. Goar et al. |
| 10,327,764 | B2 | 6/2019 | Harris et al. |
| 10,327,765 | B2 | 6/2019 | Timm et al. |
| 10,327,767 | B2 | 6/2019 | Shelton, IV et al. |
| 10,327,769 | B2 | 6/2019 | Overmyer et al. |
| 10,327,776 | B2 | 6/2019 | Harris et al. |
| 10,327,777 | B2 | 6/2019 | Harris et al. |
| D854,032 | S | 7/2019 | Jones et al. |
| D854,151 | S | 7/2019 | Shelton, IV et al. |
| 10,335,144 | B2 | 7/2019 | Shelton, IV et al. |
| 10,335,145 | B2 | 7/2019 | Harris et al. |
| 10,335,147 | B2 | 7/2019 | Rector et al. |
| 10,335,148 | B2 | 7/2019 | Shelton, IV et al. |
| 10,335,149 | B2 | 7/2019 | Baxter, III et al. |
| 10,335,150 | B2 | 7/2019 | Shelton, IV |
| 10,335,151 | B2 | 7/2019 | Shelton, IV et al. |
| 10,337,148 | B2 | 7/2019 | Rouse et al. |
| 10,342,533 | B2 | 7/2019 | Shelton, IV et al. |
| 10,342,535 | B2 | 7/2019 | Scheib et al. |
| 10,342,541 | B2 | 7/2019 | Shelton, IV et al. |
| 10,342,543 | B2 | 7/2019 | Shelton, IV et al. |
| 10,342,623 | B2 | 7/2019 | Huelman et al. |
| 10,349,937 | B2 | 7/2019 | Williams |
| 10,349,939 | B2 | 7/2019 | Shelton, IV et al. |
| 10,349,941 | B2 | 7/2019 | Marczyk et al. |
| 10,349,963 | B2 | 7/2019 | Fiksen et al. |
| 10,350,016 | B2 | 7/2019 | Burbank et al. |
| 10,357,246 | B2 | 7/2019 | Shelton, IV et al. |
| 10,357,247 | B2 | 7/2019 | Shelton, IV et al. |
| 10,357,248 | B2 | 7/2019 | Dalessandro et al. |
| 10,357,252 | B2 | 7/2019 | Harris et al. |
| 10,363,031 | B2 | 7/2019 | Alexander, III et al. |
| 10,363,033 | B2 | 7/2019 | Timm et al. |
| 10,363,036 | B2 | 7/2019 | Yates et al. |
| 10,363,037 | B2 | 7/2019 | Aronhalt et al. |
| D855,634 | S | 8/2019 | Kim |
| D856,359 | S | 8/2019 | Huang et al. |
| 10,368,838 | B2 | 8/2019 | Williams et al. |
| 10,368,861 | B2 | 8/2019 | Baxter, III et al. |
| 10,368,863 | B2 | 8/2019 | Timm et al. |
| 10,368,864 | B2 | 8/2019 | Harris et al. |
| 10,368,865 | B2 | 8/2019 | Harris et al. |
| 10,368,866 | B2 | 8/2019 | Wang et al. |
| 10,368,867 | B2 | 8/2019 | Harris et al. |
| 10,368,892 | B2 | 8/2019 | Stulen et al. |
| 10,374,544 | B2 | 8/2019 | Yokoyama et al. |
| 10,376,263 | B2 | 8/2019 | Morgan et al. |
| 10,383,626 | B2 | 8/2019 | Soltz |
| 10,383,628 | B2 | 8/2019 | Kang et al. |
| 10,383,629 | B2 | 8/2019 | Ross et al. |
| 10,383,630 | B2 | 8/2019 | Shelton, IV et al. |
| 10,383,631 | B2 | 8/2019 | Collings et al. |
| 10,383,633 | B2 | 8/2019 | Shelton, IV et al. |
| 10,383,634 | B2 | 8/2019 | Shelton, IV et al. |
| 10,390,823 | B2 | 8/2019 | Shelton, IV et al. |
| 10,390,825 | B2 | 8/2019 | Shelton, IV et al. |
| 10,390,828 | B2 | 8/2019 | Vendely et al. |
| 10,390,829 | B2 | 8/2019 | Eckert et al. |
| 10,390,830 | B2 | 8/2019 | Schulz |
| 10,390,841 | B2 | 8/2019 | Shelton, IV et al. |
| 10,390,897 | B2 | 8/2019 | Kostrzewski |
| D859,466 | S | 9/2019 | Okada et al. |
| D860,219 | S | 9/2019 | Rasmussen et al. |
| D861,035 | S | 9/2019 | Park et al. |
| 10,398,433 | B2 | 9/2019 | Boudreaux et al. |
| 10,398,434 | B2 | 9/2019 | Shelton, IV et al. |
| 10,398,436 | B2 | 9/2019 | Shelton, IV et al. |
| 10,398,460 | B2 | 9/2019 | Overmyer |
| 10,404,136 | B2 | 9/2019 | Oktavec et al. |
| 10,405,854 | B2 | 9/2019 | Schmid et al. |
| 10,405,857 | B2 | 9/2019 | Shelton, IV et al. |
| 10,405,859 | B2 | 9/2019 | Harris et al. |
| 10,405,863 | B2 | 9/2019 | Wise et al. |
| 10,405,914 | B2 | 9/2019 | Manwaring et al. |
| 10,405,932 | B2 | 9/2019 | Overmyer |
| 10,405,937 | B2 | 9/2019 | Black et al. |
| 10,413,155 | B2 | 9/2019 | Inoue |
| 10,413,291 | B2 | 9/2019 | Worthington et al. |
| 10,413,293 | B2 | 9/2019 | Shelton, IV et al. |
| 10,413,294 | B2 | 9/2019 | Shelton, IV et al. |
| 10,413,297 | B2 | 9/2019 | Harris et al. |
| 10,413,370 | B2 | 9/2019 | Yates et al. |
| 10,413,373 | B2 | 9/2019 | Yates et al. |
| 10,420,548 | B2 | 9/2019 | Whitman et al. |
| 10,420,549 | B2 | 9/2019 | Yates et al. |
| 10,420,550 | B2 | 9/2019 | Shelton, IV |
| 10,420,551 | B2 | 9/2019 | Calderoni |
| 10,420,552 | B2 | 9/2019 | Shelton, IV et al. |
| 10,420,553 | B2 | 9/2019 | Shelton, IV et al. |
| 10,420,554 | B2 | 9/2019 | Collings et al. |
| 10,420,555 | B2 | 9/2019 | Shelton, IV et al. |
| 10,420,558 | B2 | 9/2019 | Nalagatla et al. |
| 10,420,559 | B2 | 9/2019 | Marczyk et al. |
| 10,420,560 | B2 | 9/2019 | Shelton, IV et al. |
| 10,420,561 | B2 | 9/2019 | Shelton, IV et al. |
| 10,420,577 | B2 | 9/2019 | Chowaniec et al. |

(56) References Cited

U.S. PATENT DOCUMENTS

| | | | |
|---|---|---|---|
| D861,707 | S | 10/2019 | Yang |
| D862,518 | S | 10/2019 | Niven et al. |
| D863,343 | S | 10/2019 | Mazlish et al. |
| D864,388 | S | 10/2019 | Barber |
| D865,174 | S | 10/2019 | Auld et al. |
| D865,175 | S | 10/2019 | Widenhouse et al. |
| 10,426,463 | B2 | 10/2019 | Shelton, IV et al. |
| 10,426,466 | B2 | 10/2019 | Contini et al. |
| 10,426,467 | B2 | 10/2019 | Miller et al. |
| 10,426,468 | B2 | 10/2019 | Contini et al. |
| 10,426,469 | B2 | 10/2019 | Shelton, IV et al. |
| 10,426,471 | B2 | 10/2019 | Shelton, IV et al. |
| 10,426,476 | B2 | 10/2019 | Harris et al. |
| 10,426,477 | B2 | 10/2019 | Harris et al. |
| 10,426,478 | B2 | 10/2019 | Shelton, IV et al. |
| 10,426,481 | B2 | 10/2019 | Aronhalt et al. |
| 10,426,555 | B2 | 10/2019 | Crowley et al. |
| 10,433,837 | B2 | 10/2019 | Worthington et al. |
| 10,433,839 | B2 | 10/2019 | Scheib et al. |
| 10,433,840 | B2 | 10/2019 | Shelton, IV et al. |
| 10,433,842 | B2 | 10/2019 | Amariglio et al. |
| 10,433,844 | B2 | 10/2019 | Shelton, IV et al. |
| 10,433,845 | B2 | 10/2019 | Baxter, III et al. |
| 10,433,846 | B2 | 10/2019 | Vendely et al. |
| 10,433,849 | B2 | 10/2019 | Shelton, IV et al. |
| 10,433,918 | B2 | 10/2019 | Shelton, IV et al. |
| 10,441,279 | B2 | 10/2019 | Shelton, IV et al. |
| 10,441,280 | B2 | 10/2019 | Timm et al. |
| 10,441,281 | B2 | 10/2019 | Shelton, IV et al. |
| 10,441,285 | B2 | 10/2019 | Shelton, IV et al. |
| 10,441,286 | B2 | 10/2019 | Shelton, IV et al. |
| 10,441,345 | B2 | 10/2019 | Aldridge et al. |
| 10,441,369 | B2 | 10/2019 | Shelton, IV et al. |
| 10,448,948 | B2 | 10/2019 | Shelton, IV et al. |
| 10,448,950 | B2 | 10/2019 | Shelton, IV et al. |
| 10,448,952 | B2 | 10/2019 | Shelton, IV et al. |
| 10,456,122 | B2 | 10/2019 | Koltz et al. |
| 10,456,132 | B2 | 10/2019 | Gettinger et al. |
| 10,456,133 | B2 | 10/2019 | Yates et al. |
| 10,456,137 | B2 | 10/2019 | Vendely et al. |
| 10,456,140 | B2 | 10/2019 | Shelton, IV et al. |
| D865,796 | S | 11/2019 | Xu et al. |
| 10,463,367 | B2 | 11/2019 | Kostrzewski et al. |
| 10,463,369 | B2 | 11/2019 | Shelton, IV et al. |
| 10,463,370 | B2 | 11/2019 | Yates et al. |
| 10,463,371 | B2 | 11/2019 | Kostrzewski |
| 10,463,372 | B2 | 11/2019 | Shelton, IV et al. |
| 10,463,373 | B2 | 11/2019 | Mozdzierz et al. |
| 10,463,382 | B2 | 11/2019 | Ingmanson et al. |
| 10,463,383 | B2 | 11/2019 | Shelton, IV et al. |
| 10,463,384 | B2 | 11/2019 | Shelton, IV et al. |
| 10,470,762 | B2 | 11/2019 | Leimbach et al. |
| 10,470,763 | B2 | 11/2019 | Yates et al. |
| 10,470,764 | B2 | 11/2019 | Baxter, III et al. |
| 10,470,767 | B2 | 11/2019 | Gleiman et al. |
| 10,470,768 | B2 | 11/2019 | Harris et al. |
| 10,470,769 | B2 | 11/2019 | Shelton, IV et al. |
| 10,471,282 | B2 | 11/2019 | Kirk et al. |
| 10,471,576 | B2 | 11/2019 | Totsu |
| 10,471,607 | B2 | 11/2019 | Butt et al. |
| 10,478,181 | B2 | 11/2019 | Shelton, IV et al. |
| 10,478,182 | B2 | 11/2019 | Taylor |
| 10,478,185 | B2 | 11/2019 | Nicholas |
| 10,478,187 | B2 | 11/2019 | Shelton, IV et al. |
| 10,478,188 | B2 | 11/2019 | Harris et al. |
| 10,478,189 | B2 | 11/2019 | Bear et al. |
| 10,478,190 | B2 | 11/2019 | Miller et al. |
| 10,478,207 | B2 | 11/2019 | Lathrop |
| 10,482,292 | B2 | 11/2019 | Clouser et al. |
| 10,485,536 | B2 | 11/2019 | Ming et al. |
| 10,485,537 | B2 | 11/2019 | Yates et al. |
| 10,485,539 | B2 | 11/2019 | Shelton, IV et al. |
| 10,485,541 | B2 | 11/2019 | Shelton, IV et al. |
| 10,485,542 | B2 | 11/2019 | Shelton, IV et al. |
| 10,485,543 | B2 | 11/2019 | Shelton, IV et al. |
| 10,485,546 | B2 | 11/2019 | Shelton, IV et al. |
| 10,485,547 | B2 | 11/2019 | Shelton, IV et al. |
| D869,655 | S | 12/2019 | Shelton, IV et al. |
| D870,742 | S | 12/2019 | Cornell |
| 10,492,783 | B2 | 12/2019 | Shelton, IV et al. |
| 10,492,785 | B2 | 12/2019 | Overmyer et al. |
| 10,492,787 | B2 | 12/2019 | Smith et al. |
| 10,492,814 | B2 | 12/2019 | Snow et al. |
| 10,492,847 | B2 | 12/2019 | Godara et al. |
| 10,492,851 | B2 | 12/2019 | Hughett, Sr. et al. |
| 10,498,269 | B2 | 12/2019 | Zemlok et al. |
| 10,499,890 | B2 | 12/2019 | Shelton, IV et al. |
| 10,499,914 | B2 | 12/2019 | Huang et al. |
| 10,499,917 | B2 | 12/2019 | Scheib et al. |
| 10,499,918 | B2 | 12/2019 | Schellin et al. |
| 10,500,000 | B2 | 12/2019 | Swayze et al. |
| 10,500,004 | B2 | 12/2019 | Hanuschik et al. |
| 10,500,309 | B2 | 12/2019 | Shah et al. |
| 10,507,034 | B2 | 12/2019 | Timm |
| 10,508,720 | B2 | 12/2019 | Nicholas |
| 10,512,461 | B2 | 12/2019 | Gupta et al. |
| 10,512,462 | B2 | 12/2019 | Felder et al. |
| 10,512,464 | B2 | 12/2019 | Park et al. |
| 10,517,590 | B2 | 12/2019 | Giordano et al. |
| 10,517,592 | B2 | 12/2019 | Shelton, IV et al. |
| 10,517,594 | B2 | 12/2019 | Shelton, IV et al. |
| 10,517,595 | B2 | 12/2019 | Hunter et al. |
| 10,517,596 | B2 | 12/2019 | Hunter et al. |
| 10,517,599 | B2 | 12/2019 | Baxter, III et al. |
| 10,517,682 | B2 | 12/2019 | Giordano et al. |
| 10,524,784 | B2 | 1/2020 | Kostrzewski |
| 10,524,787 | B2 | 1/2020 | Shelton, IV et al. |
| 10,524,788 | B2 | 1/2020 | Vendely et al. |
| 10,524,789 | B2 | 1/2020 | Swayze et al. |
| 10,524,790 | B2 | 1/2020 | Shelton, IV et al. |
| 10,524,795 | B2 | 1/2020 | Nalagatla et al. |
| 10,524,870 | B2 | 1/2020 | Saraliev et al. |
| 10,531,874 | B2 | 1/2020 | Morgan et al. |
| 10,531,887 | B2 | 1/2020 | Shelton, IV et al. |
| 10,537,323 | B2 | 1/2020 | Racenet et al. |
| 10,537,324 | B2 | 1/2020 | Shelton, IV et al. |
| 10,537,325 | B2 | 1/2020 | Bakos et al. |
| 10,537,351 | B2 | 1/2020 | Shelton, IV et al. |
| 10,537,381 | B2 | 1/2020 | Joseph et al. |
| 10,542,908 | B2 | 1/2020 | Mei et al. |
| 10,542,974 | B2 | 1/2020 | Yates et al. |
| 10,542,976 | B2 | 1/2020 | Calderoni et al. |
| 10,542,978 | B2 | 1/2020 | Chowaniec et al. |
| 10,542,979 | B2 | 1/2020 | Shelton, IV et al. |
| 10,542,982 | B2 | 1/2020 | Beckman et al. |
| 10,542,985 | B2 | 1/2020 | Zhan et al. |
| 10,542,988 | B2 | 1/2020 | Schellin et al. |
| 10,542,991 | B2 | 1/2020 | Shelton, IV et al. |
| D876,478 | S | 2/2020 | Sakata et al. |
| 10,548,504 | B2 | 2/2020 | Shelton, IV et al. |
| 10,548,593 | B2 | 2/2020 | Shelton, IV et al. |
| 10,548,600 | B2 | 2/2020 | Shelton, IV et al. |
| 10,548,673 | B2 | 2/2020 | Harris et al. |
| 10,561,412 | B2 | 2/2020 | Bookbinder et al. |
| 10,561,418 | B2 | 2/2020 | Richard et al. |
| 10,561,419 | B2 | 2/2020 | Beardsley |
| 10,561,420 | B2 | 2/2020 | Harris et al. |
| 10,561,422 | B2 | 2/2020 | Schellin et al. |
| 10,561,432 | B2 | 2/2020 | Estrella et al. |
| 10,561,474 | B2 | 2/2020 | Adams et al. |
| 10,562,160 | B2 | 2/2020 | Iwata et al. |
| 10,568,493 | B2 | 2/2020 | Blase et al. |
| 10,568,621 | B2 | 2/2020 | Shelton, IV et al. |
| 10,568,624 | B2 | 2/2020 | Shelton, IV et al. |
| 10,568,625 | B2 | 2/2020 | Harris et al. |
| 10,568,626 | B2 | 2/2020 | Shelton, IV et al. |
| 10,568,629 | B2 | 2/2020 | Shelton, IV et al. |
| 10,568,632 | B2 | 2/2020 | Miller et al. |
| 10,568,652 | B2 | 2/2020 | Hess et al. |
| 10,569,071 | B2 | 2/2020 | Harris et al. |
| D879,808 | S | 3/2020 | Harris et al. |
| D879,809 | S | 3/2020 | Harris et al. |
| 10,575,868 | B2 | 3/2020 | Hall et al. |
| 10,580,320 | B2 | 3/2020 | Kamiguchi et al. |

(56) References Cited

U.S. PATENT DOCUMENTS 10,582,928 B2 3/2020 Hunter et al.
10,588,231 B2 3/2020 Sgroi, Jr. et al.
10,588,623 B2 3/2020 Schmid et al.
10,588,625 B2 3/2020 Weaner et al.
10,588,626 B2 3/2020 Overmyer et al.
10,588,629 B2 3/2020 Malinouskas et al.
10,588,630 B2 3/2020 Shelton, IV et al.
10,588,631 B2 3/2020 Shelton, IV et al.
10,588,632 B2 3/2020 Shelton, IV et al.
10,588,633 B2 3/2020 Shelton, IV et al.
10,589,410 B2 3/2020 Aho
10,595,835 B2 3/2020 Kerr et al.
10,595,862 B2 3/2020 Shelton, IV et al.
10,595,882 B2 3/2020 Parfett et al.
10,595,887 B2 3/2020 Shelton, IV et al.
10,595,929 B2 3/2020 Boudreaux et al.
10,603,036 B2 3/2020 Hunter et al.
10,603,039 B2 3/2020 Vendely et al.
10,603,041 B2 3/2020 Miller et al.
10,603,117 B2 3/2020 Schings et al.
10,603,128 B2 3/2020 Zergiebel et al.
D882,783 S 4/2020 Shelton, IV et al.
10,610,224 B2 4/2020 Shelton, IV et al.
10,610,225 B2 4/2020 Reed et al.
10,610,236 B2 4/2020 Baril
10,610,313 B2 4/2020 Bailey et al.
10,610,346 B2 4/2020 Schwartz
10,614,184 B2 4/2020 Solki
10,617,411 B2 4/2020 Williams
10,617,412 B2 4/2020 Shelton, IV et al.
10,617,413 B2 4/2020 Shelton, IV et al.
10,617,414 B2 4/2020 Shelton, IV et al.
10,617,416 B2 4/2020 Leimbach et al.
10,617,417 B2 4/2020 Baxter, III et al.
10,617,418 B2 4/2020 Barton et al.
10,617,420 B2 4/2020 Shelton, IV et al.
10,617,438 B2 4/2020 O'Keefe et al.
10,624,616 B2 4/2020 Mukherjee et al.
10,624,630 B2 4/2020 Deville et al.
10,624,633 B2 4/2020 Shelton, IV et al.
10,624,634 B2 4/2020 Shelton, IV et al.
10,624,635 B2 4/2020 Harris et al.
10,624,709 B2 4/2020 Remm
10,624,861 B2 4/2020 Widenhouse et al.
10,625,062 B2 4/2020 Matlock et al.
10,631,857 B2 4/2020 Kostrzewski
10,631,858 B2 4/2020 Burbank
10,631,859 B2 4/2020 Shelton, IV et al.
10,631,860 B2 4/2020 Bakos et al.
10,636,104 B2 4/2020 Mazar et al.
10,639,018 B2 5/2020 Shelton, IV et al.
10,639,034 B2 5/2020 Harris et al.
10,639,035 B2 5/2020 Shelton, IV et al.
10,639,036 B2 5/2020 Yates et al.
10,639,037 B2 5/2020 Shelton, IV et al.
10,639,038 B2 5/2020 Scott et al.
10,639,089 B2 5/2020 Manwaring et al.
10,639,115 B2 5/2020 Shelton, IV et al.
10,642,633 B1 5/2020 Chopra et al.
10,645,905 B2 5/2020 Gandola et al.
10,646,220 B2 5/2020 Shelton, IV et al.
10,646,292 B2 5/2020 Solomon et al.
10,653,413 B2 5/2020 Worthington et al.
10,653,417 B2 5/2020 Shelton, IV et al.
10,653,435 B2 5/2020 Shelton, IV et al.
10,653,477 B2 5/2020 Nagtegaal
10,660,640 B2 5/2020 Yates et al.
10,667,408 B2 5/2020 Sgroi, Jr. et al.
D888,953 S 6/2020 Baxter, III et al.
10,667,808 B2 6/2020 Baxter, III et al.
10,667,809 B2 6/2020 Bakos et al.
10,667,810 B2 6/2020 Shelton, IV et al.
10,667,811 B2 6/2020 Harris et al.
10,667,818 B2 6/2020 McLain et al.
10,674,895 B2 6/2020 Yeung et al.
10,675,021 B2 6/2020 Harris et al.
10,675,024 B2 6/2020 Shelton, IV et al.
10,675,025 B2 6/2020 Swayze et al.
10,675,026 B2 6/2020 Harris et al.
10,675,028 B2 6/2020 Shelton, IV et al.
10,675,035 B2 6/2020 Zingman
10,675,080 B2 6/2020 Woloszko et al.
10,675,102 B2 6/2020 Forgione et al.
10,677,035 B2 6/2020 Balan et al.
10,682,134 B2 6/2020 Shelton, IV et al.
10,682,136 B2 6/2020 Harris et al.
10,682,137 B2 6/2020 Stokes et al.
10,682,138 B2 6/2020 Shelton, IV et al.
10,682,141 B2 6/2020 Moore et al.
10,682,142 B2 6/2020 Shelton, IV et al.
10,687,806 B2 6/2020 Shelton, IV et al.
10,687,809 B2 6/2020 Shelton, IV et al.
10,687,810 B2 6/2020 Shelton, IV et al.
10,687,812 B2 6/2020 Shelton, IV et al.
10,687,813 B2 6/2020 Shelton, IV et al.
10,687,817 B2 6/2020 Shelton, IV et al.
10,687,819 B2 6/2020 Stokes et al.
10,687,904 B2 6/2020 Harris et al.
10,695,053 B2 6/2020 Hess et al.
10,695,055 B2 6/2020 Shelton, IV et al.
10,695,057 B2 6/2020 Shelton, IV et al.
10,695,058 B2 6/2020 Lytle, IV et al.
10,695,062 B2 6/2020 Leimbach et al.
10,695,063 B2 6/2020 Morgan et al.
10,695,074 B2 6/2020 Carusillo
10,695,081 B2 6/2020 Shelton, IV et al.
10,695,119 B2 6/2020 Smith
10,695,123 B2 6/2020 Allen, IV
10,695,187 B2 6/2020 Moskowitz et al.
D890,784 S 7/2020 Shelton, IV et al.
D890,805 S 7/2020 Echeverri et al.
10,702,266 B2 7/2020 Parihar et al.
10,702,267 B2 7/2020 Hess et al.
10,702,270 B2 7/2020 Shelton, IV et al.
10,702,271 B2 7/2020 Aranyi et al.
10,705,660 B2 7/2020 Xiao
10,709,446 B2 7/2020 Harris et al.
10,709,468 B2 7/2020 Shelton, IV et al.
10,709,469 B2 7/2020 Shelton, IV et al.
10,709,495 B2 7/2020 Broderick et al.
10,709,496 B2 7/2020 Moua et al.
10,716,563 B2 7/2020 Shelton, IV et al.
10,716,565 B2 7/2020 Shelton, IV et al.
10,716,568 B2 7/2020 Hall et al.
10,716,614 B2 7/2020 Yates et al.
10,717,179 B2 7/2020 Koenig et al.
10,722,232 B2 7/2020 Yates et al.
10,722,233 B2 7/2020 Wellman
10,722,292 B2 7/2020 Arya et al.
10,722,293 B2 7/2020 Arya et al.
10,722,317 B2 7/2020 Ward et al.
D893,717 S 8/2020 Messerly et al.
10,729,432 B2 8/2020 Shelton, IV et al.
10,729,434 B2 8/2020 Harris et al.
10,729,435 B2 8/2020 Richard
10,729,436 B2 8/2020 Shelton, IV et al.
10,729,443 B2 8/2020 Cabrera et al.
10,729,458 B2 8/2020 Stoddard et al.
10,729,501 B2 8/2020 Leimbach et al.
10,729,509 B2 8/2020 Shelton, IV et al.
10,736,616 B2 8/2020 Scheib et al.
10,736,628 B2 8/2020 Yates et al.
10,736,629 B2 8/2020 Shelton, IV et al.
10,736,630 B2 8/2020 Huang et al.
10,736,633 B2 8/2020 Vendely et al.
10,736,634 B2 8/2020 Shelton, IV et al.
10,736,636 B2 8/2020 Baxter, III et al.
10,736,644 B2 8/2020 Windolf et al.
10,736,702 B2 8/2020 Harris et al.
10,737,398 B2 8/2020 Remirez et al.
10,743,849 B2 8/2020 Shelton, IV et al.
10,743,850 B2 8/2020 Hibner et al.
10,743,851 B2 8/2020 Swayze et al.
10,743,868 B2 8/2020 Shelton, IV et al.

(56) References Cited

U.S. PATENT DOCUMENTS

| | | | |
|---|---|---|---|
| 10,743,870 | B2 | 8/2020 | Hall et al. |
| 10,743,872 | B2 | 8/2020 | Leimbach et al. |
| 10,743,873 | B2 | 8/2020 | Overmyer et al. |
| 10,743,874 | B2 | 8/2020 | Shelton, IV et al. |
| 10,743,875 | B2 | 8/2020 | Shelton, IV et al. |
| 10,743,877 | B2 | 8/2020 | Shelton, IV et al. |
| 10,743,930 | B2 | 8/2020 | Nagtegaal |
| 10,751,048 | B2 | 8/2020 | Whitman et al. |
| 10,751,051 | B2 | 8/2020 | Weir et al. |
| 10,751,053 | B2 | 8/2020 | Harris et al. |
| 10,751,076 | B2 | 8/2020 | Laurent et al. |
| 10,751,104 | B2 | 8/2020 | Mistry et al. |
| 10,751,138 | B2 | 8/2020 | Giordano et al. |
| 10,758,226 | B2 | 9/2020 | Weir et al. |
| 10,758,229 | B2 | 9/2020 | Shelton, IV et al. |
| 10,758,230 | B2 | 9/2020 | Shelton, IV et al. |
| 10,758,232 | B2 | 9/2020 | Shelton, IV et al. |
| 10,758,233 | B2 | 9/2020 | Scheib et al. |
| 10,758,259 | B2 | 9/2020 | Demmy et al. |
| 10,765,425 | B2 | 9/2020 | Yates et al. |
| 10,765,427 | B2 | 9/2020 | Shelton, IV et al. |
| 10,765,429 | B2 | 9/2020 | Leimbach et al. |
| 10,765,430 | B2 | 9/2020 | Wixey |
| 10,765,432 | B2 | 9/2020 | Moore et al. |
| 10,765,442 | B2 | 9/2020 | Strobl |
| 10,772,625 | B2 | 9/2020 | Shelton, IV et al. |
| 10,772,628 | B2 | 9/2020 | Chen et al. |
| 10,772,629 | B2 | 9/2020 | Shelton, IV et al. |
| 10,772,630 | B2 | 9/2020 | Wixey |
| 10,772,631 | B2 | 9/2020 | Zergiebel et al. |
| 10,772,632 | B2 | 9/2020 | Kostrzewski |
| 10,772,651 | B2 | 9/2020 | Shelton, IV et al. |
| 10,779,818 | B2 | 9/2020 | Zemlok et al. |
| 10,779,820 | B2 | 9/2020 | Harris et al. |
| 10,779,821 | B2 | 9/2020 | Harris et al. |
| 10,779,822 | B2 | 9/2020 | Yates et al. |
| 10,779,823 | B2 | 9/2020 | Shelton, IV et al. |
| 10,779,824 | B2 | 9/2020 | Shelton, IV et al. |
| 10,779,825 | B2 | 9/2020 | Shelton, IV et al. |
| 10,779,826 | B2 | 9/2020 | Shelton, IV et al. |
| 10,779,903 | B2 | 9/2020 | Wise et al. |
| 10,780,539 | B2 | 9/2020 | Shelton, IV et al. |
| 10,786,248 | B2 | 9/2020 | Rousseau et al. |
| 10,786,253 | B2 | 9/2020 | Shelton, IV et al. |
| 10,786,255 | B2 | 9/2020 | Hodgkinson et al. |
| D898,767 | S | 10/2020 | Shah et al. |
| D899,455 | S | 10/2020 | Rondoni et al. |
| 10,792,038 | B2 | 10/2020 | Becerra et al. |
| 10,796,471 | B2 | 10/2020 | Leimbach et al. |
| 10,799,240 | B2 | 10/2020 | Shelton, IV et al. |
| 10,799,306 | B2 | 10/2020 | Robinson et al. |
| 10,806,448 | B2 | 10/2020 | Shelton, IV et al. |
| 10,806,449 | B2 | 10/2020 | Shelton, IV et al. |
| 10,806,450 | B2 | 10/2020 | Yates et al. |
| 10,806,451 | B2 | 10/2020 | Harris et al. |
| 10,806,453 | B2 | 10/2020 | Chen et al. |
| 10,806,479 | B2 | 10/2020 | Shelton, IV et al. |
| 10,813,638 | B2 | 10/2020 | Shelton, IV et al. |
| 10,813,639 | B2 | 10/2020 | Shelton, IV et al. |
| 10,813,640 | B2 | 10/2020 | Adams et al. |
| 10,813,641 | B2 | 10/2020 | Setser et al. |
| 10,813,683 | B2 | 10/2020 | Baxter, III et al. |
| 10,813,705 | B2 | 10/2020 | Hares et al. |
| 10,813,710 | B2 | 10/2020 | Grubbs |
| 10,820,939 | B2 | 11/2020 | Sartor |
| 10,828,028 | B2 | 11/2020 | Harris et al. |
| 10,828,030 | B2 | 11/2020 | Weir et al. |
| 10,828,032 | B2 | 11/2020 | Leimbach et al. |
| 10,828,033 | B2 | 11/2020 | Shelton, IV et al. |
| 10,828,089 | B2 | 11/2020 | Clark et al. |
| 10,835,216 | B2 | 11/2020 | Stevenson et al. |
| 10,835,245 | B2 | 11/2020 | Swayze et al. |
| 10,835,246 | B2 | 11/2020 | Shelton, IV et al. |
| 10,835,247 | B2 | 11/2020 | Shelton, IV et al. |
| 10,835,249 | B2 | 11/2020 | Schellin et al. |
| 10,835,251 | B2 | 11/2020 | Shelton, IV et al. |
| 10,835,330 | B2 | 11/2020 | Shelton, IV et al. |
| 10,842,357 | B2 | 11/2020 | Moskowitz et al. |
| 10,842,473 | B2 | 11/2020 | Scheib et al. |
| 10,842,488 | B2 | 11/2020 | Swayze et al. |
| 10,842,489 | B2 | 11/2020 | Shelton, IV |
| 10,842,490 | B2 | 11/2020 | DiNardo et al. |
| 10,842,491 | B2 | 11/2020 | Shelton, IV et al. |
| 10,842,492 | B2 | 11/2020 | Shelton, IV et al. |
| 10,842,523 | B2 | 11/2020 | Shelton, IV et al. |
| D904,612 | S | 12/2020 | Wynn et al. |
| D904,613 | S | 12/2020 | Wynn et al. |
| D906,355 | S | 12/2020 | Messerly et al. |
| 10,849,621 | B2 | 12/2020 | Whitfield et al. |
| 10,849,623 | B2 | 12/2020 | Dunki-Jacobs et al. |
| 10,849,697 | B2 | 12/2020 | Yates et al. |
| 10,856,866 | B2 | 12/2020 | Shelton, IV et al. |
| 10,856,867 | B2 | 12/2020 | Shelton, IV et al. |
| 10,856,868 | B2 | 12/2020 | Shelton, IV et al. |
| 10,856,869 | B2 | 12/2020 | Shelton, IV et al. |
| 10,856,870 | B2 | 12/2020 | Harris et al. |
| 10,863,981 | B2 | 12/2020 | Overmyer et al. |
| 10,863,984 | B2 | 12/2020 | Shelton, IV et al. |
| 10,863,986 | B2 | 12/2020 | Yates et al. |
| 10,869,663 | B2 | 12/2020 | Shelton, IV et al. |
| 10,869,664 | B2 | 12/2020 | Shelton, IV |
| 10,869,665 | B2 | 12/2020 | Shelton, IV et al. |
| 10,869,666 | B2 | 12/2020 | Shelton, IV et al. |
| 10,869,669 | B2 | 12/2020 | Shelton, IV et al. |
| 10,874,290 | B2 | 12/2020 | Walen et al. |
| 10,874,391 | B2 | 12/2020 | Shelton, IV et al. |
| 10,874,392 | B2 | 12/2020 | Scirica et al. |
| 10,874,393 | B2 | 12/2020 | Satti, III et al. |
| 10,874,396 | B2 | 12/2020 | Moore et al. |
| 10,874,399 | B2 | 12/2020 | Zhang |
| 10,874,474 | B2 | 12/2020 | Wu et al. |
| 10,879,275 | B2 | 12/2020 | Li et al. |
| D907,647 | S | 1/2021 | Siebel et al. |
| D907,648 | S | 1/2021 | Siebel et al. |
| D908,216 | S | 1/2021 | Messerly et al. |
| 10,881,339 | B2 | 1/2021 | Peyser et al. |
| 10,881,395 | B2 | 1/2021 | Merchant et al. |
| 10,881,396 | B2 | 1/2021 | Shelton, IV et al. |
| 10,881,398 | B2 | 1/2021 | Whitman et al. |
| 10,881,399 | B2 | 1/2021 | Shelton, IV et al. |
| 10,881,401 | B2 | 1/2021 | Baber et al. |
| 10,881,446 | B2 | 1/2021 | Strobl |
| 10,888,318 | B2 | 1/2021 | Parihar et al. |
| 10,888,321 | B2 | 1/2021 | Shelton, IV et al. |
| 10,888,322 | B2 | 1/2021 | Morgan et al. |
| 10,888,323 | B2 | 1/2021 | Chen et al. |
| 10,888,325 | B2 | 1/2021 | Harris et al. |
| 10,888,328 | B2 | 1/2021 | Shelton, IV et al. |
| 10,888,329 | B2 | 1/2021 | Moore et al. |
| 10,888,330 | B2 | 1/2021 | Moore et al. |
| 10,888,369 | B2 | 1/2021 | Messerly et al. |
| 10,892,899 | B2 | 1/2021 | Shelton, IV et al. |
| 10,893,853 | B2 | 1/2021 | Shelton, IV et al. |
| 10,893,863 | B2 | 1/2021 | Shelton, IV et al. |
| 10,893,864 | B2 | 1/2021 | Harris et al. |
| 10,893,867 | B2 | 1/2021 | Leimbach et al. |
| 10,898,183 | B2 | 1/2021 | Shelton, IV et al. |
| 10,898,184 | B2 | 1/2021 | Yates et al. |
| 10,898,185 | B2 | 1/2021 | Overmyer et al. |
| 10,898,186 | B2 | 1/2021 | Bakos et al. |
| 10,898,190 | B2 | 1/2021 | Yates et al. |
| 10,898,193 | B2 | 1/2021 | Shelton, IV et al. |
| 10,898,194 | B2 | 1/2021 | Moore et al. |
| 10,898,195 | B2 | 1/2021 | Moore et al. |
| 10,903,685 | B2 | 1/2021 | Yates et al. |
| D910,847 | S | 2/2021 | Shelton, IV et al. |
| 10,905,415 | B2 | 2/2021 | DiNardo et al. |
| 10,905,418 | B2 | 2/2021 | Shelton, IV et al. |
| 10,905,420 | B2 | 2/2021 | Jasemian et al. |
| 10,905,422 | B2 | 2/2021 | Bakos et al. |
| 10,905,423 | B2 | 2/2021 | Baber et al. |
| 10,905,426 | B2 | 2/2021 | Moore et al. |
| 10,905,427 | B2 | 2/2021 | Moore et al. |
| 10,911,515 | B2 | 2/2021 | Biasi et al. |

(56) References Cited

U.S. PATENT DOCUMENTS

| | | | |
|---|---|---|---|
| 10,912,559 | B2 | 2/2021 | Harris et al. |
| 10,912,562 | B2 | 2/2021 | Dunki-Jacobs et al. |
| 10,912,575 | B2 | 2/2021 | Shelton, IV et al. |
| 10,918,364 | B2 | 2/2021 | Applegate et al. |
| 10,918,380 | B2 | 2/2021 | Morgan et al. |
| 10,918,385 | B2 | 2/2021 | Overmyer et al. |
| 10,918,386 | B2 | 2/2021 | Shelton, IV et al. |
| 10,919,156 | B2 | 2/2021 | Roberts et al. |
| 10,925,600 | B2 | 2/2021 | McCuen |
| 10,925,605 | B2 | 2/2021 | Moore et al. |
| D914,878 | S | 3/2021 | Shelton, IV et al. |
| 10,932,772 | B2 | 3/2021 | Shelton, IV et al. |
| 10,932,774 | B2 | 3/2021 | Shelton, IV |
| 10,932,775 | B2 | 3/2021 | Shelton, IV et al. |
| 10,932,778 | B2 | 3/2021 | Smith et al. |
| 10,932,779 | B2 | 3/2021 | Vendely et al. |
| 10,932,784 | B2 | 3/2021 | Mozdzierz et al. |
| 10,932,804 | B2 | 3/2021 | Scheib et al. |
| 10,932,806 | B2 | 3/2021 | Shelton, IV et al. |
| 10,932,872 | B2 | 3/2021 | Shelton, IV et al. |
| 10,944,728 | B2 | 3/2021 | Wiener et al. |
| 10,945,727 | B2 | 3/2021 | Shelton, IV et al. |
| 10,945,728 | B2 | 3/2021 | Morgan et al. |
| 10,945,729 | B2 | 3/2021 | Shelton, IV et al. |
| 10,945,731 | B2 | 3/2021 | Baxter, III et al. |
| 10,952,708 | B2 | 3/2021 | Scheib et al. |
| 10,952,726 | B2 | 3/2021 | Chowaniec |
| 10,952,727 | B2 | 3/2021 | Giordano et al. |
| 10,952,728 | B2 | 3/2021 | Shelton, IV et al. |
| 10,952,759 | B2 | 3/2021 | Messerly et al. |
| 10,952,767 | B2 | 3/2021 | Kostrzewski et al. |
| 10,959,722 | B2 | 3/2021 | Morgan et al. |
| 10,959,725 | B2 | 3/2021 | Kerr et al. |
| 10,959,726 | B2 | 3/2021 | Williams et al. |
| 10,959,727 | B2 | 3/2021 | Hunter et al. |
| 10,959,731 | B2 | 3/2021 | Casasanta, Jr. et al. |
| 10,959,744 | B2 | 3/2021 | Shelton, IV et al. |
| 10,959,797 | B2 | 3/2021 | Licht et al. |
| D917,500 | S | 4/2021 | Siebel et al. |
| 10,966,627 | B2 | 4/2021 | Shelton, IV et al. |
| 10,966,717 | B2 | 4/2021 | Shah et al. |
| 10,966,718 | B2 | 4/2021 | Shelton, IV et al. |
| 10,966,791 | B2 | 4/2021 | Harris et al. |
| 10,973,515 | B2 | 4/2021 | Harris et al. |
| 10,973,516 | B2 | 4/2021 | Shelton, IV et al. |
| 10,973,517 | B2 | 4/2021 | Wixey |
| 10,973,519 | B2 | 4/2021 | Weir et al. |
| 10,973,520 | B2 | 4/2021 | Shelton, IV et al. |
| 10,980,534 | B2 | 4/2021 | Yates et al. |
| 10,980,535 | B2 | 4/2021 | Yates et al. |
| 10,980,536 | B2 | 4/2021 | Weaner et al. |
| 10,980,537 | B2 | 4/2021 | Shelton, IV et al. |
| 10,980,538 | B2 | 4/2021 | Nalagatla et al. |
| 10,980,539 | B2 | 4/2021 | Harris et al. |
| 10,980,560 | B2 | 4/2021 | Shelton, IV et al. |
| 10,983,646 | B2 | 4/2021 | Yoon et al. |
| 10,987,102 | B2 | 4/2021 | Gonzalez et al. |
| 10,987,178 | B2 | 4/2021 | Shelton, IV et al. |
| 10,993,713 | B2 | 5/2021 | Shelton, IV et al. |
| 10,993,715 | B2 | 5/2021 | Shelton, IV et al. |
| 10,993,716 | B2 | 5/2021 | Shelton, IV et al. |
| 10,993,717 | B2 | 5/2021 | Shelton, IV et al. |
| 11,000,274 | B2 | 5/2021 | Shelton, IV et al. |
| 11,000,275 | B2 | 5/2021 | Shelton, IV et al. |
| 11,000,277 | B2 | 5/2021 | Giordano et al. |
| 11,000,278 | B2 | 5/2021 | Shelton, IV et al. |
| 11,000,279 | B2 | 5/2021 | Shelton, IV et al. |
| 11,005,291 | B2 | 5/2021 | Calderoni |
| 11,006,951 | B2 | 5/2021 | Giordano et al. |
| 11,006,955 | B2 | 5/2021 | Shelton, IV et al. |
| 11,007,004 | B2 | 5/2021 | Shelton, IV et al. |
| 11,007,022 | B2 | 5/2021 | Shelton, IV et al. |
| 11,013,511 | B2 | 5/2021 | Huang et al. |
| 11,013,552 | B2 | 5/2021 | Widenhouse et al. |
| 11,013,563 | B2 | 5/2021 | Shelton, IV et al. |
| 11,020,016 | B2 | 6/2021 | Wallace et al. |
| 11,020,112 | B2 | 6/2021 | Shelton, IV et al. |
| 11,020,113 | B2 | 6/2021 | Shelton, IV et al. |
| 11,020,114 | B2 | 6/2021 | Shelton, IV et al. |
| 11,020,115 | B2 | 6/2021 | Scheib et al. |
| 11,020,172 | B2 | 6/2021 | Garrison |
| 11,026,678 | B2 | 6/2021 | Overmyer et al. |
| 11,026,680 | B2 | 6/2021 | Shelton, IV et al. |
| 11,026,684 | B2 | 6/2021 | Shelton, IV et al. |
| 11,026,686 | B2 | 6/2021 | Aranyi |
| 11,026,687 | B2 | 6/2021 | Shelton, IV et al. |
| 11,026,712 | B2 | 6/2021 | Shelton, IV et al. |
| 11,026,713 | B2 | 6/2021 | Stokes et al. |
| 11,026,751 | B2 | 6/2021 | Shelton, IV et al. |
| 11,033,267 | B2 | 6/2021 | Shelton, IV et al. |
| 11,039,834 | B2 | 6/2021 | Harris et al. |
| 11,039,836 | B2 | 6/2021 | Shelton, IV et al. |
| 11,039,837 | B2 | 6/2021 | Shelton, IV et al. |
| 11,039,849 | B2 | 6/2021 | Bucciaglia et al. |
| 11,045,189 | B2 | 6/2021 | Yates et al. |
| 11,045,191 | B2 | 6/2021 | Shelton, IV et al. |
| 11,045,192 | B2 | 6/2021 | Harris et al. |
| 11,045,196 | B2 | 6/2021 | Olson et al. |
| 11,045,197 | B2 | 6/2021 | Shelton, IV et al. |
| 11,045,199 | B2 | 6/2021 | Mozdzierz et al. |
| 11,045,270 | B2 | 6/2021 | Shelton, IV et al. |
| D925,563 | S | 7/2021 | Melvin et al. |
| 11,051,807 | B2 | 7/2021 | Shelton, IV et al. |
| 11,051,810 | B2 | 7/2021 | Harris et al. |
| 11,051,811 | B2 | 7/2021 | Shelton, IV et al. |
| 11,051,813 | B2 | 7/2021 | Shelton, IV et al. |
| 11,051,836 | B2 | 7/2021 | Shelton, IV et al. |
| 11,051,840 | B2 | 7/2021 | Shelton, IV et al. |
| 11,051,873 | B2 | 7/2021 | Wiener et al. |
| 11,058,418 | B2 | 7/2021 | Shelton, IV et al. |
| 11,058,420 | B2 | 7/2021 | Shelton, IV et al. |
| 11,058,422 | B2 | 7/2021 | Harris et al. |
| 11,058,423 | B2 | 7/2021 | Shelton, IV et al. |
| 11,058,424 | B2 | 7/2021 | Shelton, IV et al. |
| 11,058,425 | B2 | 7/2021 | Widenhouse et al. |
| 11,058,426 | B2 | 7/2021 | Nalagatla et al. |
| 11,058,498 | B2 | 7/2021 | Shelton, IV et al. |
| 11,064,997 | B2 | 7/2021 | Shelton, IV et al. |
| 11,064,998 | B2 | 7/2021 | Shelton, IV |
| 11,065,000 | B2 | 7/2021 | Shankarsetty et al. |
| 11,065,048 | B2 | 7/2021 | Messerly et al. |
| 11,069,012 | B2 | 7/2021 | Shelton, IV et al. |
| 11,071,542 | B2 | 7/2021 | Chen et al. |
| 11,071,543 | B2 | 7/2021 | Shelton, IV et al. |
| 11,071,545 | B2 | 7/2021 | Baber et al. |
| 11,071,554 | B2 | 7/2021 | Parfett et al. |
| 11,071,560 | B2 | 7/2021 | Deck et al. |
| 11,076,853 | B2 | 8/2021 | Parfett et al. |
| 11,076,854 | B2 | 8/2021 | Baber et al. |
| 11,076,921 | B2 | 8/2021 | Shelton, IV et al. |
| 11,076,929 | B2 | 8/2021 | Shelton, IV et al. |
| 11,083,452 | B2 | 8/2021 | Schmid et al. |
| 11,083,453 | B2 | 8/2021 | Shelton, IV et al. |
| 11,083,454 | B2 | 8/2021 | Harris et al. |
| 11,083,455 | B2 | 8/2021 | Shelton, IV et al. |
| 11,083,456 | B2 | 8/2021 | Shelton, IV et al. |
| 11,083,457 | B2 | 8/2021 | Shelton, IV et al. |
| 11,083,458 | B2 | 8/2021 | Harris et al. |
| 11,090,045 | B2 | 8/2021 | Shelton, IV |
| 11,090,046 | B2 | 8/2021 | Shelton, IV et al. |
| 11,090,047 | B2 | 8/2021 | Shelton, IV et al. |
| 11,090,048 | B2 | 8/2021 | Fanelli et al. |
| 11,090,049 | B2 | 8/2021 | Bakos et al. |
| 11,090,075 | B2 | 8/2021 | Hunter et al. |
| 11,096,687 | B2 | 8/2021 | Flanagan et al. |
| 11,096,688 | B2 | 8/2021 | Shelton, IV et al. |
| 11,096,689 | B2 | 8/2021 | Overmyer et al. |
| 11,100,631 | B2 | 8/2021 | Yates et al. |
| 11,103,241 | B2 | 8/2021 | Yates et al. |
| 11,103,248 | B2 | 8/2021 | Shelton, IV et al. |
| 11,103,268 | B2 | 8/2021 | Shelton, IV et al. |
| 11,103,269 | B2 | 8/2021 | Shelton, IV et al. |
| 11,103,301 | B2 | 8/2021 | Messerly et al. |
| 11,109,858 | B2 | 9/2021 | Shelton, IV et al. |

(56) References Cited

U.S. PATENT DOCUMENTS

| | | | |
|---|---|---|---|
| 11,109,859 | B2 | 9/2021 | Overmyer et al. |
| 11,109,860 | B2 | 9/2021 | Shelton, IV et al. |
| 11,109,866 | B2 | 9/2021 | Shelton, IV et al. |
| 11,109,878 | B2 | 9/2021 | Shelton, IV et al. |
| 11,109,925 | B2 | 9/2021 | Cooper et al. |
| 11,116,485 | B2 | 9/2021 | Scheib et al. |
| 11,116,502 | B2 | 9/2021 | Shelton, IV et al. |
| 11,116,594 | B2 | 9/2021 | Beardsley |
| 11,123,069 | B2 | 9/2021 | Baxter, III et al. |
| 11,123,070 | B2 | 9/2021 | Shelton, IV et al. |
| 11,129,611 | B2 | 9/2021 | Shelton, IV et al. |
| 11,129,613 | B2 | 9/2021 | Harris et al. |
| 11,129,615 | B2 | 9/2021 | Scheib et al. |
| 11,129,616 | B2 | 9/2021 | Shelton, IV et al. |
| 11,129,634 | B2 | 9/2021 | Scheib et al. |
| 11,129,636 | B2 | 9/2021 | Shelton, IV et al. |
| 11,129,666 | B2 | 9/2021 | Messerly et al. |
| 11,129,680 | B2 | 9/2021 | Shelton, IV et al. |
| 11,132,462 | B2 | 9/2021 | Shelton, IV et al. |
| 11,133,106 | B2 | 9/2021 | Shelton, IV et al. |
| 11,134,938 | B2 | 10/2021 | Timm et al. |
| 11,134,940 | B2 | 10/2021 | Shelton, IV et al. |
| 11,134,942 | B2 | 10/2021 | Harris et al. |
| 11,134,943 | B2 | 10/2021 | Giordano et al. |
| 11,134,944 | B2 | 10/2021 | Wise et al. |
| 11,134,947 | B2 | 10/2021 | Shelton, IV et al. |
| 11,135,352 | B2 | 10/2021 | Shelton, IV et al. |
| 11,141,152 | B2 | 10/2021 | Ingmanson et al. |
| 11,141,153 | B2 | 10/2021 | Shelton, IV et al. |
| 11,141,154 | B2 | 10/2021 | Shelton, IV et al. |
| 11,141,155 | B2 | 10/2021 | Shelton, IV |
| 11,141,156 | B2 | 10/2021 | Shelton, IV |
| 11,141,159 | B2 | 10/2021 | Scheib et al. |
| 11,141,160 | B2 | 10/2021 | Shelton, IV et al. |
| 11,147,547 | B2 | 10/2021 | Shelton, IV et al. |
| 11,147,549 | B2 | 10/2021 | Timm et al. |
| 11,147,551 | B2 | 10/2021 | Shelton, IV |
| 11,147,553 | B2 | 10/2021 | Shelton, IV |
| 11,147,554 | B2 | 10/2021 | Aronhalt et al. |
| 11,154,296 | B2 | 10/2021 | Aronhalt et al. |
| 11,154,297 | B2 | 10/2021 | Swayze et al. |
| 11,154,298 | B2 | 10/2021 | Timm et al. |
| 11,154,299 | B2 | 10/2021 | Shelton, IV et al. |
| 11,154,300 | B2 | 10/2021 | Nalagatla et al. |
| 11,154,301 | B2 | 10/2021 | Beckman et al. |
| D936,684 | S | 11/2021 | Luo et al. |
| 11,160,551 | B2 | 11/2021 | Shelton, IV et al. |
| 11,160,553 | B2 | 11/2021 | Simms et al. |
| 11,160,601 | B2 | 11/2021 | Worrell et al. |
| 11,166,716 | B2 | 11/2021 | Shelton, IV et al. |
| 11,166,717 | B2 | 11/2021 | Shelton, IV et al. |
| 11,166,720 | B2 | 11/2021 | Giordano et al. |
| 11,166,772 | B2 | 11/2021 | Shelton, IV et al. |
| 11,166,773 | B2 | 11/2021 | Ragosta et al. |
| 11,172,580 | B2 | 11/2021 | Gaertner |
| 11,172,927 | B2 | 11/2021 | Shelton, IV |
| 11,172,929 | B2 | 11/2021 | Shelton, IV |
| 11,179,150 | B2 | 11/2021 | Yates et al. |
| 11,179,151 | B2 | 11/2021 | Shelton, IV et al. |
| 11,179,152 | B2 | 11/2021 | Morgan et al. |
| 11,179,153 | B2 | 11/2021 | Shelton, IV |
| 11,179,155 | B2 | 11/2021 | Shelton, IV et al. |
| 11,179,208 | B2 | 11/2021 | Yates et al. |
| 11,185,325 | B2 | 11/2021 | Shelton, IV et al. |
| 11,185,330 | B2 | 11/2021 | Huitema et al. |
| 11,191,539 | B2 | 12/2021 | Overmyer et al. |
| 11,191,540 | B2 | 12/2021 | Aronhalt et al. |
| 11,191,543 | B2 | 12/2021 | Overmyer et al. |
| 11,191,545 | B2 | 12/2021 | Vendely et al. |
| 11,197,668 | B2 | 12/2021 | Shelton, IV et al. |
| 11,197,670 | B2 | 12/2021 | Shelton, IV et al. |
| 11,197,671 | B2 | 12/2021 | Shelton, IV et al. |
| 11,197,672 | B2 | 12/2021 | Dunki-Jacobs et al. |
| 11,202,570 | B2 | 12/2021 | Shelton, IV et al. |
| 11,202,631 | B2 | 12/2021 | Shelton, IV et al. |
| 11,202,633 | B2 | 12/2021 | Harris et al. |
| 11,207,064 | B2 | 12/2021 | Shelton, IV et al. |
| 11,207,065 | B2 | 12/2021 | Harris et al. |
| 11,207,067 | B2 | 12/2021 | Shelton, IV et al. |
| 11,207,089 | B2 | 12/2021 | Kostrzewski et al. |
| 11,207,090 | B2 | 12/2021 | Shelton, IV et al. |
| 11,207,146 | B2 | 12/2021 | Shelton, IV et al. |
| 11,213,293 | B2 | 1/2022 | Worthington et al. |
| 11,213,294 | B2 | 1/2022 | Shelton, IV et al. |
| 11,213,302 | B2 | 1/2022 | Parfett et al. |
| 11,213,359 | B2 | 1/2022 | Shelton, IV et al. |
| 11,219,453 | B2 | 1/2022 | Shelton, IV et al. |
| 11,219,455 | B2 | 1/2022 | Shelton, IV et al. |
| 11,224,423 | B2 | 1/2022 | Shelton, IV et al. |
| 11,224,426 | B2 | 1/2022 | Shelton, IV et al. |
| 11,224,427 | B2 | 1/2022 | Shelton, IV et al. |
| 11,224,428 | B2 | 1/2022 | Scott et al. |
| 11,224,454 | B2 | 1/2022 | Shelton, IV et al. |
| 11,224,497 | B2 | 1/2022 | Shelton, IV et al. |
| 11,229,436 | B2 | 1/2022 | Shelton, IV et al. |
| 11,229,437 | B2 | 1/2022 | Shelton, IV et al. |
| 11,234,698 | B2 | 2/2022 | Shelton, IV et al. |
| 11,234,700 | B2 | 2/2022 | Ragosta et al. |
| 11,241,229 | B2 | 2/2022 | Shelton, IV et al. |
| 11,241,230 | B2 | 2/2022 | Shelton, IV et al. |
| 11,241,235 | B2 | 2/2022 | Shelton, IV et al. |
| 11,246,590 | B2 | 2/2022 | Swayze et al. |
| 11,246,592 | B2 | 2/2022 | Shelton, IV et al. |
| 11,246,616 | B2 | 2/2022 | Shelton, IV et al. |
| 11,246,618 | B2 | 2/2022 | Hall et al. |
| 11,246,678 | B2 | 2/2022 | Shelton, IV et al. |
| 11,253,254 | B2 | 2/2022 | Kimball et al. |
| 11,253,256 | B2 | 2/2022 | Harris et al. |
| D946,025 | S | 3/2022 | Vogler-Ivashchanka et al. |
| D946,617 | S | 3/2022 | Ahmed |
| 11,259,799 | B2 | 3/2022 | Overmyer et al. |
| 11,259,803 | B2 | 3/2022 | Shelton, IV et al. |
| 11,259,805 | B2 | 3/2022 | Shelton, IV et al. |
| 11,259,806 | B2 | 3/2022 | Shelton, IV et al. |
| 11,259,807 | B2 | 3/2022 | Shelton, IV et al. |
| 11,266,405 | B2 | 3/2022 | Shelton, IV et al. |
| 11,266,406 | B2 | 3/2022 | Leimbach et al. |
| 11,266,409 | B2 | 3/2022 | Huitema et al. |
| 11,266,410 | B2 | 3/2022 | Shelton, IV et al. |
| 11,266,468 | B2 | 3/2022 | Shelton, IV et al. |
| 11,272,927 | B2 | 3/2022 | Swayze et al. |
| 11,272,928 | B2 | 3/2022 | Shelton, IV |
| 11,272,931 | B2 | 3/2022 | Boudreaux et al. |
| 11,272,938 | B2 | 3/2022 | Shelton, IV et al. |
| 11,278,279 | B2 | 3/2022 | Morgan et al. |
| 11,278,280 | B2 | 3/2022 | Shelton, IV et al. |
| 11,278,284 | B2 | 3/2022 | Shelton, IV et al. |
| 11,278,288 | B2 | 3/2022 | Rector et al. |
| 11,284,890 | B2 | 3/2022 | Nalagatla et al. |
| 11,284,891 | B2 | 3/2022 | Shelton, IV et al. |
| 11,284,898 | B2 | 3/2022 | Baxter, III et al. |
| 11,284,953 | B2 | 3/2022 | Shelton, IV et al. |
| 11,291,440 | B2 | 4/2022 | Harris et al. |
| 11,291,441 | B2 | 4/2022 | Giordano et al. |
| 11,291,442 | B2 | 4/2022 | Wixey et al. |
| 11,291,443 | B2 | 4/2022 | Viola et al. |
| 11,291,444 | B2 | 4/2022 | Boudreaux et al. |
| 11,291,445 | B2 | 4/2022 | Shelton, IV et al. |
| 11,291,447 | B2 | 4/2022 | Shelton, IV et al. |
| 11,291,449 | B2 | 4/2022 | Swensgard et al. |
| 11,291,451 | B2 | 4/2022 | Shelton, IV |
| 11,291,465 | B2 | 4/2022 | Parihar et al. |
| 11,291,510 | B2 | 4/2022 | Shelton, IV et al. |
| 11,298,125 | B2 | 4/2022 | Ming et al. |
| 11,298,127 | B2 | 4/2022 | Shelton, IV |
| 11,298,128 | B2 | 4/2022 | Messerly et al. |
| 11,298,129 | B2 | 4/2022 | Bakos et al. |
| 11,298,130 | B2 | 4/2022 | Bakos et al. |
| 11,298,132 | B2 | 4/2022 | Shelton, IV et al. |
| 11,298,134 | B2 | 4/2022 | Huitema et al. |
| 11,304,695 | B2 | 4/2022 | Shelton, IV et al. |
| 11,304,696 | B2 | 4/2022 | Shelton, IV et al. |
| 11,304,697 | B2 | 4/2022 | Fanelli et al. |
| 11,304,699 | B2 | 4/2022 | Shelton, IV et al. |

(56) References Cited

U.S. PATENT DOCUMENTS

| | | | |
|---|---|---|---|
| 11,304,704 | B2 | 4/2022 | Thomas et al. |
| 11,311,290 | B2 | 4/2022 | Shelton, IV et al. |
| 11,311,292 | B2 | 4/2022 | Shelton, IV et al. |
| 11,311,294 | B2 | 4/2022 | Swayze et al. |
| 11,311,295 | B2 | 4/2022 | Wingardner et al. |
| 11,311,342 | B2 | 4/2022 | Parihar et al. |
| D950,728 | S | 5/2022 | Bakos et al. |
| D952,144 | S | 5/2022 | Boudreaux |
| 11,317,910 | B2 | 5/2022 | Miller et al. |
| 11,317,912 | B2 | 5/2022 | Jenkins et al. |
| 11,317,913 | B2 | 5/2022 | Shelton, IV et al. |
| 11,317,915 | B2 | 5/2022 | Boudreaux et al. |
| 11,317,917 | B2 | 5/2022 | Shelton, IV et al. |
| 11,317,919 | B2 | 5/2022 | Shelton, IV et al. |
| 11,317,978 | B2 | 5/2022 | Cameron et al. |
| 11,324,501 | B2 | 5/2022 | Shelton, IV et al. |
| 11,324,503 | B2 | 5/2022 | Shelton, IV et al. |
| 11,324,506 | B2 | 5/2022 | Beckman et al. |
| 11,324,557 | B2 | 5/2022 | Shelton, IV et al. |
| 11,331,100 | B2 | 5/2022 | Boudreaux et al. |
| 11,331,101 | B2 | 5/2022 | Harris et al. |
| 11,337,691 | B2 | 5/2022 | Widenhouse et al. |
| 11,337,693 | B2 | 5/2022 | Hess et al. |
| 11,337,698 | B2 | 5/2022 | Baxter, III et al. |
| 11,344,299 | B2 | 5/2022 | Yates et al. |
| 11,344,303 | B2 | 5/2022 | Shelton, IV et al. |
| D954,736 | S | 6/2022 | Teague et al. |
| 11,350,843 | B2 | 6/2022 | Shelton, IV et al. |
| 11,350,916 | B2 | 6/2022 | Shelton, IV et al. |
| 11,350,928 | B2 | 6/2022 | Shelton, IV et al. |
| 11,350,929 | B2 | 6/2022 | Giordano et al. |
| 11,350,932 | B2 | 6/2022 | Shelton, IV et al. |
| 11,350,934 | B2 | 6/2022 | Bakos et al. |
| 11,350,935 | B2 | 6/2022 | Shelton, IV et al. |
| 11,350,938 | B2 | 6/2022 | Shelton, IV et al. |
| 11,357,503 | B2 | 6/2022 | Bakos et al. |
| 11,361,176 | B2 | 6/2022 | Shelton, IV et al. |
| 11,364,027 | B2 | 6/2022 | Harris et al. |
| 11,364,046 | B2 | 6/2022 | Shelton, IV et al. |
| 11,369,366 | B2 | 6/2022 | Scheib et al. |
| 11,369,368 | B2 | 6/2022 | Shelton, IV et al. |
| 11,369,376 | B2 | 6/2022 | Simms et al. |
| 11,369,377 | B2 | 6/2022 | Boudreaux et al. |
| 11,373,755 | B2 | 6/2022 | Shelton, IV et al. |
| 11,376,001 | B2 | 7/2022 | Shelton, IV et al. |
| 11,376,002 | B2 | 7/2022 | Shelton, IV et al. |
| 11,376,082 | B2 | 7/2022 | Shelton, IV et al. |
| 11,376,098 | B2 | 7/2022 | Shelton, IV et al. |
| 11,382,625 | B2 | 7/2022 | Huitema et al. |
| 11,382,626 | B2 | 7/2022 | Shelton, IV et al. |
| 11,382,627 | B2 | 7/2022 | Huitema et al. |
| 11,382,628 | B2 | 7/2022 | Baxter, III et al. |
| 11,382,638 | B2 | 7/2022 | Harris et al. |
| 11,382,697 | B2 | 7/2022 | Shelton, IV et al. |
| 11,382,704 | B2 | 7/2022 | Overmyer et al. |
| 11,389,160 | B2 | 7/2022 | Shelton, IV et al. |
| 11,389,161 | B2 | 7/2022 | Shelton, IV et al. |
| 11,389,162 | B2 | 7/2022 | Baber et al. |
| 11,389,164 | B2 | 7/2022 | Yates et al. |
| 11,395,651 | B2 | 7/2022 | Shelton, IV et al. |
| 11,395,652 | B2 | 7/2022 | Parihar et al. |
| 11,399,828 | B2 | 8/2022 | Swayze et al. |
| 11,399,829 | B2 | 8/2022 | Leimbach et al. |
| 11,399,831 | B2 | 8/2022 | Overmyer et al. |
| 11,399,837 | B2 | 8/2022 | Shelton, IV et al. |
| 11,406,377 | B2 | 8/2022 | Schmid et al. |
| 11,406,378 | B2 | 8/2022 | Baxter, III et al. |
| 11,406,380 | B2 | 8/2022 | Yates et al. |
| 11,406,381 | B2 | 8/2022 | Parihar et al. |
| 11,406,382 | B2 | 8/2022 | Shelton, IV et al. |
| 11,406,386 | B2 | 8/2022 | Baber et al. |
| 11,406,390 | B2 | 8/2022 | Shelton, IV et al. |
| 11,406,442 | B2 | 8/2022 | Davison et al. |
| 11,410,259 | B2 | 8/2022 | Harris et al. |
| 11,413,041 | B2 | 8/2022 | Viola et al. |
| 11,413,042 | B2 | 8/2022 | Shelton, IV et al. |
| 11,413,102 | B2 | 8/2022 | Shelton, IV et al. |
| 11,419,606 | B2 | 8/2022 | Overmyer et al. |
| 11,419,630 | B2 | 8/2022 | Yates et al. |
| 11,424,027 | B2 | 8/2022 | Shelton, IV |
| 11,426,160 | B2 | 8/2022 | Shelton, IV et al. |
| 11,426,167 | B2 | 8/2022 | Shelton, IV et al. |
| 11,426,251 | B2 | 8/2022 | Kimball et al. |
| D962,980 | S | 9/2022 | Frenkler et al. |
| D964,564 | S | 9/2022 | Boudreaux |
| 11,432,816 | B2 | 9/2022 | Leimbach et al. |
| 11,432,819 | B2 | 9/2022 | Rector et al. |
| 11,432,885 | B2 | 9/2022 | Shelton, IV et al. |
| 11,439,391 | B2 | 9/2022 | Bruns et al. |
| 11,439,470 | B2 | 9/2022 | Spivey et al. |
| 11,446,029 | B2 | 9/2022 | Shelton, IV et al. |
| 11,446,034 | B2 | 9/2022 | Shelton, IV et al. |
| 11,452,526 | B2 | 9/2022 | Ross et al. |
| 11,452,528 | B2 | 9/2022 | Leimbach et al. |
| D966,512 | S | 10/2022 | Shelton, IV et al. |
| D967,421 | S | 10/2022 | Shelton, IV et al. |
| 11,457,918 | B2 | 10/2022 | Shelton, IV et al. |
| 11,464,511 | B2 | 10/2022 | Timm et al. |
| 11,464,512 | B2 | 10/2022 | Shelton, IV et al. |
| 11,464,513 | B2 | 10/2022 | Shelton, IV et al. |
| 11,464,514 | B2 | 10/2022 | Yates et al. |
| 11,464,601 | B2 | 10/2022 | Shelton, IV et al. |
| 11,471,155 | B2 | 10/2022 | Shelton, IV et al. |
| 11,471,156 | B2 | 10/2022 | Shelton, IV et al. |
| 11,471,157 | B2 | 10/2022 | Baxter, III et al. |
| 11,478,241 | B2 | 10/2022 | Shelton, IV et al. |
| 11,478,242 | B2 | 10/2022 | Shelton, IV et al. |
| 11,478,244 | B2 | 10/2022 | DiNardo et al. |
| D969,849 | S | 11/2022 | Stipech et al. |
| D971,232 | S | 11/2022 | Siebel et al. |
| 11,484,307 | B2 | 11/2022 | Hall et al. |
| 11,484,309 | B2 | 11/2022 | Harris et al. |
| 11,484,310 | B2 | 11/2022 | Shelton, IV et al. |
| 11,484,311 | B2 | 11/2022 | Shelton, IV et al. |
| 11,484,312 | B2 | 11/2022 | Shelton, IV et al. |
| 11,490,889 | B2 | 11/2022 | Overmyer et al. |
| 11,497,488 | B2 | 11/2022 | Leimbach et al. |
| 11,497,489 | B2 | 11/2022 | Baxter, III et al. |
| 11,497,492 | B2 | 11/2022 | Shelton, IV |
| 11,497,499 | B2 | 11/2022 | Shelton, IV et al. |
| 11,504,116 | B2 | 11/2022 | Schmid et al. |
| 11,504,119 | B2 | 11/2022 | Shelton, IV et al. |
| 11,504,122 | B2 | 11/2022 | Shelton, IV et al. |
| 11,504,192 | B2 | 11/2022 | Shelton, IV et al. |
| 11,510,671 | B2 | 11/2022 | Shelton, IV et al. |
| 11,510,673 | B1 | 11/2022 | Chen et al. |
| 11,510,741 | B2 | 11/2022 | Shelton, IV et al. |
| 11,517,304 | B2 | 12/2022 | Yates et al. |
| 11,517,306 | B2 | 12/2022 | Miller et al. |
| 11,517,309 | B2 | 12/2022 | Bakos et al. |
| 11,517,311 | B2 | 12/2022 | Lytle, IV et al. |
| 11,517,315 | B2 | 12/2022 | Huitema et al. |
| 11,517,325 | B2 | 12/2022 | Shelton, IV et al. |
| 11,517,390 | B2 | 12/2022 | Baxter, III |
| 11,523,821 | B2 | 12/2022 | Harris et al. |
| 11,523,822 | B2 | 12/2022 | Shelton, IV et al. |
| 11,523,823 | B2 | 12/2022 | Hunter et al. |
| 11,523,824 | B2 | 12/2022 | Williams |
| 11,523,859 | B2 | 12/2022 | Shelton, IV et al. |
| 11,529,137 | B2 | 12/2022 | Shelton, IV et al. |
| 11,529,138 | B2 | 12/2022 | Jaworek et al. |
| 11,529,139 | B2 | 12/2022 | Shelton, IV et al. |
| 11,529,140 | B2 | 12/2022 | Shelton, IV et al. |
| 11,529,142 | B2 | 12/2022 | Leimbach et al. |
| 11,534,162 | B2 | 12/2022 | Shelton, IV |
| 11,534,259 | B2 | 12/2022 | Leimbach et al. |
| D974,560 | S | 1/2023 | Shelton, IV et al. |
| D975,278 | S | 1/2023 | Shelton, IV et al. |
| D975,850 | S | 1/2023 | Shelton, IV et al. |
| D975,851 | S | 1/2023 | Shelton, IV et al. |
| D976,401 | S | 1/2023 | Shelton, IV et al. |
| 11,540,824 | B2 | 1/2023 | Shelton, IV et al. |
| 11,540,829 | B2 | 1/2023 | Shelton, IV et al. |
| 11,547,403 | B2 | 1/2023 | Shelton, IV et al. |

(56) References Cited

U.S. PATENT DOCUMENTS

| | | | |
|---|---|---|---|
| 11,547,404 | B2 | 1/2023 | Shelton, IV et al. |
| 11,553,911 | B2 | 1/2023 | Shelton, IV et al. |
| 11,553,916 | B2 | 1/2023 | Vendely et al. |
| 11,553,919 | B2 | 1/2023 | Shelton, IV et al. |
| 11,553,971 | B2 | 1/2023 | Shelton, IV et al. |
| 11,559,302 | B2 | 1/2023 | Timm et al. |
| 11,559,303 | B2 | 1/2023 | Shelton, IV et al. |
| 11,559,304 | B2 | 1/2023 | Boudreaux et al. |
| 11,559,307 | B2 | 1/2023 | Shelton, IV et al. |
| 11,559,308 | B2 | 1/2023 | Yates et al. |
| 11,559,496 | B2 | 1/2023 | Widenhouse et al. |
| 11,564,679 | B2 | 1/2023 | Parihar et al. |
| 11,564,682 | B2 | 1/2023 | Timm et al. |
| 11,564,686 | B2 | 1/2023 | Yates et al. |
| 11,564,688 | B2 | 1/2023 | Swayze et al. |
| 11,564,703 | B2 | 1/2023 | Shelton, IV et al. |
| 11,564,756 | B2 | 1/2023 | Shelton, IV et al. |
| 11,571,207 | B2 | 2/2023 | Shelton, IV et al. |
| 11,571,210 | B2 | 2/2023 | Shelton, IV et al. |
| 11,571,212 | B2 | 2/2023 | Yates et al. |
| 11,571,215 | B2 | 2/2023 | Shelton, IV et al. |
| 11,571,231 | B2 | 2/2023 | Hess et al. |
| 11,576,668 | B2 | 2/2023 | Shelton, IV et al. |
| 11,576,672 | B2 | 2/2023 | Shelton, IV et al. |
| 11,576,673 | B2 | 2/2023 | Shelton, IV |
| 11,576,677 | B2 | 2/2023 | Shelton, IV et al. |
| 11,583,274 | B2 | 2/2023 | Widenhouse et al. |
| 11,583,277 | B2 | 2/2023 | Shelton, IV et al. |
| 11,583,278 | B2 | 2/2023 | Shelton, IV et al. |
| 11,583,279 | B2 | 2/2023 | Smith et al. |
| 11,589,863 | B2 | 2/2023 | Weir et al. |
| 11,589,865 | B2 | 2/2023 | Shelton, IV et al. |
| 11,589,888 | B2 | 2/2023 | Shelton, IV et al. |
| D980,425 | S | 3/2023 | Baxter, III |
| 11,596,406 | B2 | 3/2023 | Huitema et al. |
| 11,602,340 | B2 | 3/2023 | Schmid et al. |
| 11,602,346 | B2 | 3/2023 | Shelton, IV |
| 11,602,366 | B2 | 3/2023 | Shelton, IV et al. |
| 11,607,219 | B2 | 3/2023 | Shelton, IV et al. |
| 11,607,239 | B2 | 3/2023 | Swensgard et al. |
| 11,607,278 | B2 | 3/2023 | Shelton, IV et al. |
| 11,612,393 | B2 | 3/2023 | Morgan et al. |
| 11,612,394 | B2 | 3/2023 | Morgan et al. |
| 11,612,395 | B2 | 3/2023 | Yates et al. |
| 11,617,575 | B2 | 4/2023 | Yates et al. |
| 11,617,576 | B2 | 4/2023 | Yates et al. |
| 11,617,577 | B2 | 4/2023 | Huang |
| 11,622,763 | B2 | 4/2023 | Parihar et al. |
| 11,622,766 | B2 | 4/2023 | Shelton, IV |
| 11,622,785 | B2 | 4/2023 | Hess et al. |
| 11,627,959 | B2 | 4/2023 | Shelton, IV et al. |
| 11,627,960 | B2 | 4/2023 | Shelton, IV et al. |
| 11,628,006 | B2 | 4/2023 | Henderson et al. |
| 11,633,183 | B2 | 4/2023 | Parihar et al. |
| 11,633,185 | B2 | 4/2023 | Wilson et al. |
| D985,009 | S | 5/2023 | Barrett et al. |
| D985,617 | S | 5/2023 | Bahatyrevich et al. |
| 11,638,581 | B2 | 5/2023 | Parihar et al. |
| 11,638,582 | B2 | 5/2023 | Bakos et al. |
| 11,638,583 | B2 | 5/2023 | Yates et al. |
| 11,638,587 | B2 | 5/2023 | Shelton, IV et al. |
| 11,642,125 | B2 | 5/2023 | Harris et al. |
| 11,642,128 | B2 | 5/2023 | Shelton, IV et al. |
| 11,648,005 | B2 | 5/2023 | Yates et al. |
| 11,648,006 | B2 | 5/2023 | Timm et al. |
| 11,648,008 | B2 | 5/2023 | Shelton, IV et al. |
| 11,648,009 | B2 | 5/2023 | Jenkins |
| 11,648,022 | B2 | 5/2023 | Shelton, IV |
| 11,648,024 | B2 | 5/2023 | Shelton, IV et al. |
| 11,653,914 | B2 | 5/2023 | Shelton, IV et al. |
| 11,653,915 | B2 | 5/2023 | Shelton, IV et al. |
| 11,653,917 | B2 | 5/2023 | Scott et al. |
| 11,653,918 | B2 | 5/2023 | Swayze et al. |
| 11,653,920 | B2 | 5/2023 | Shelton, IV et al. |
| 11,659,023 | B2 | 5/2023 | Shelton, IV et al. |
| 11,660,090 | B2 | 5/2023 | Bakos et al. |
| 11,660,110 | B2 | 5/2023 | Shelton, IV et al. |
| 11,660,163 | B2 | 5/2023 | Shelton, IV et al. |
| 11,666,327 | B2 | 6/2023 | Whitman et al. |
| 11,666,332 | B2 | 6/2023 | Giordano et al. |
| 11,672,531 | B2 | 6/2023 | Timm et al. |
| 11,672,532 | B2 | 6/2023 | Shelton, IV et al. |
| 11,672,536 | B2 | 6/2023 | Shelton, IV et al. |
| 11,672,605 | B2 | 6/2023 | Messerly et al. |
| 11,678,877 | B2 | 6/2023 | Shelton, IV et al. |
| 11,678,880 | B2 | 6/2023 | Shelton, IV et al. |
| 11,678,881 | B2 | 6/2023 | Yates et al. |
| 11,678,882 | B2 | 6/2023 | Shelton, IV et al. |
| 11,684,360 | B2 | 6/2023 | Shelton, IV et al. |
| 11,684,361 | B2 | 6/2023 | Yates et al. |
| 11,684,365 | B2 | 6/2023 | Shelton, IV et al. |
| 11,684,369 | B2 | 6/2023 | Shelton, IV et al. |
| 11,684,434 | B2 | 6/2023 | Shelton, IV |
| 11,690,615 | B2 | 7/2023 | Parihar et al. |
| 11,690,623 | B2 | 7/2023 | Shelton, IV et al. |
| 11,696,757 | B2 | 7/2023 | Shelton, IV et al. |
| 11,696,759 | B2 | 7/2023 | Shelton, IV et al. |
| 11,696,761 | B2 | 7/2023 | Shelton, IV |
| 11,696,778 | B2 | 7/2023 | Shelton, IV et al. |
| 11,701,110 | B2 | 7/2023 | Yates et al. |
| 11,701,111 | B2 | 7/2023 | Shelton, IV et al. |
| 11,701,113 | B2 | 7/2023 | Shelton, IV et al. |
| 11,701,114 | B2 | 7/2023 | Shelton, IV et al. |
| 11,701,115 | B2 | 7/2023 | Harris et al. |
| 11,701,118 | B2 | 7/2023 | Viola et al. |
| 11,707,273 | B2 | 7/2023 | Kerr et al. |
| 11,712,244 | B2 | 8/2023 | Vendely et al. |
| 11,712,303 | B2 | 8/2023 | Shelton, IV et al. |
| 11,717,285 | B2 | 8/2023 | Yates et al. |
| 11,717,289 | B2 | 8/2023 | Leimbach |
| 11,717,291 | B2 | 8/2023 | Morgan et al. |
| 11,717,294 | B2 | 8/2023 | Huitema et al. |
| 11,717,297 | B2 | 8/2023 | Baber et al. |
| 11,723,657 | B2 | 8/2023 | Shelton, IV et al. |
| 11,723,658 | B2 | 8/2023 | Bakos et al. |
| 11,723,662 | B2 | 8/2023 | Leimbach et al. |
| 11,730,471 | B2 | 8/2023 | Worthington et al. |
| 11,730,473 | B2 | 8/2023 | Creamer et al. |
| 11,730,474 | B2 | 8/2023 | Shelton, IV |
| 11,730,477 | B2 | 8/2023 | Smith et al. |
| 11,737,749 | B2 | 8/2023 | Shelton, IV et al. |
| 11,737,751 | B2 | 8/2023 | Shelton, IV et al. |
| 11,737,754 | B2 | 8/2023 | Shelton, IV et al. |
| 11,744,581 | B2 | 9/2023 | Shelton, IV et al. |
| 11,744,583 | B2 | 9/2023 | Shelton, IV et al. |
| 11,744,588 | B2 | 9/2023 | Beckman et al. |
| 11,744,593 | B2 | 9/2023 | Shelton, IV et al. |
| 11,744,603 | B2 | 9/2023 | Shelton, IV et al. |
| 11,744,604 | B2 | 9/2023 | Shelton, IV et al. |
| 11,749,877 | B2 | 9/2023 | Shelton, IV et al. |
| 11,751,867 | B2 | 9/2023 | Shelton, IV et al. |
| 11,751,869 | B2 | 9/2023 | Shelton, IV et al. |
| 11,751,872 | B2 | 9/2023 | Zeiner et al. |
| 11,751,937 | B2 | 9/2023 | Harlev et al. |
| 11,759,202 | B2 | 9/2023 | Morgan et al. |
| 11,759,208 | B2 | 9/2023 | Harris et al. |
| 11,759,224 | B2 | 9/2023 | Shelton, IV et al. |
| 11,766,257 | B2 | 9/2023 | Shelton, IV et al. |
| 11,766,258 | B2 | 9/2023 | Shelton, IV et al. |
| 11,766,259 | B2 | 9/2023 | Shelton, IV et al. |
| 11,766,260 | B2 | 9/2023 | Harris et al. |
| 11,771,419 | B2 | 10/2023 | Shelton, IV et al. |
| 11,771,425 | B2 | 10/2023 | Swayze et al. |
| 11,771,426 | B2 | 10/2023 | Giordano et al. |
| 11,771,454 | B2 | 10/2023 | Swensgard et al. |
| 11,779,336 | B2 | 10/2023 | Shelton, IV et al. |
| 11,779,420 | B2 | 10/2023 | Shelton, IV et al. |
| 11,786,245 | B2 | 10/2023 | Shelton, IV |
| 11,793,509 | B2 | 10/2023 | Baxter, III et al. |
| 11,793,512 | B2 | 10/2023 | Shelton, IV |
| 11,793,513 | B2 | 10/2023 | Harris et al. |
| 11,793,518 | B2 | 10/2023 | Shelton, IV et al. |
| 11,793,522 | B2 | 10/2023 | Vendely et al. |
| 11,793,537 | B2 | 10/2023 | Shelton, IV et al. |

(56) References Cited

U.S. PATENT DOCUMENTS

| | | | |
|---|---|---|---|
| 11,801,047 | B2 | 10/2023 | Yates et al. |
| 11,801,051 | B2 | 10/2023 | Shelton, IV et al. |
| 11,801,098 | B2 | 10/2023 | Stokes et al. |
| 11,806,011 | B2 | 11/2023 | Bakos et al. |
| 11,806,013 | B2 | 11/2023 | Shelton, IV et al. |
| 11,812,954 | B2 | 11/2023 | Yates et al. |
| 11,812,960 | B2 | 11/2023 | Shelton, IV et al. |
| 11,812,961 | B2 | 11/2023 | Giordano et al. |
| 11,812,964 | B2 | 11/2023 | Shelton, IV et al. |
| 11,812,965 | B2 | 11/2023 | Baxter, III et al. |
| 11,819,231 | B2 | 11/2023 | Shelton, IV et al. |
| 11,826,012 | B2 | 11/2023 | Adams et al. |
| 11,826,042 | B2 | 11/2023 | Adams et al. |
| 11,826,047 | B2 | 11/2023 | Huang et al. |
| 11,826,048 | B2 * | 11/2023 | Shelton, IV ....... A61B 18/1445 |
| 11,826,132 | B2 | 11/2023 | Shelton, IV et al. |
| 11,839,352 | B2 | 12/2023 | Shelton, IV et al. |
| 11,839,375 | B2 | 12/2023 | Swayze et al. |
| 11,844,518 | B2 | 12/2023 | Leimbach et al. |
| 11,844,521 | B2 | 12/2023 | Giordano et al. |
| 11,849,941 | B2 | 12/2023 | Hess et al. |
| 11,849,947 | B2 | 12/2023 | Giordano et al. |
| 11,849,952 | B2 | 12/2023 | Shelton, IV |
| 11,850,310 | B2 | 12/2023 | Shelton, IV et al. |
| 11,853,835 | B2 | 12/2023 | Shelton, IV |
| 11,857,152 | B2 | 1/2024 | Shelton, IV et al. |
| 11,857,181 | B2 | 1/2024 | Timm et al. |
| 11,857,187 | B2 | 1/2024 | Baxter, III et al. |
| 11,857,189 | B2 | 1/2024 | Shelton, IV et al. |
| 2001/0000531 | A1 | 4/2001 | Casscells et al. |
| 2001/0025183 | A1 | 9/2001 | Shahidi |
| 2001/0025184 | A1 | 9/2001 | Messerly |
| 2001/0030219 | A1 | 10/2001 | Green et al. |
| 2001/0034530 | A1 | 10/2001 | Malackowski et al. |
| 2001/0045442 | A1 | 11/2001 | Whitman |
| 2002/0014510 | A1 | 2/2002 | Richter et al. |
| 2002/0022810 | A1 | 2/2002 | Urich |
| 2002/0022836 | A1 | 2/2002 | Goble et al. |
| 2002/0022861 | A1 | 2/2002 | Jacobs et al. |
| 2002/0023126 | A1 | 2/2002 | Flavin |
| 2002/0029032 | A1 | 3/2002 | Arkin |
| 2002/0029036 | A1 | 3/2002 | Goble et al. |
| 2002/0042620 | A1 | 4/2002 | Julian et al. |
| 2002/0045905 | A1 | 4/2002 | Gerbi et al. |
| 2002/0054158 | A1 | 5/2002 | Asami |
| 2002/0065535 | A1 | 5/2002 | Kneifel et al. |
| 2002/0066764 | A1 | 6/2002 | Perry et al. |
| 2002/0077660 | A1 | 6/2002 | Kayan et al. |
| 2002/0082612 | A1 | 6/2002 | Moll et al. |
| 2002/0087048 | A1 | 7/2002 | Brock et al. |
| 2002/0087148 | A1 | 7/2002 | Brock et al. |
| 2002/0091374 | A1 | 7/2002 | Cooper |
| 2002/0095175 | A1 | 7/2002 | Brock et al. |
| 2002/0099374 | A1 | 7/2002 | Pendekanti et al. |
| 2002/0103494 | A1 | 8/2002 | Pacey |
| 2002/0111621 | A1 | 8/2002 | Wallace et al. |
| 2002/0111624 | A1 | 8/2002 | Witt et al. |
| 2002/0116063 | A1 | 8/2002 | Giannetti et al. |
| 2002/0117533 | A1 | 8/2002 | Milliman et al. |
| 2002/0117534 | A1 | 8/2002 | Green et al. |
| 2002/0127265 | A1 | 9/2002 | Bowman et al. |
| 2002/0128633 | A1 | 9/2002 | Brock et al. |
| 2002/0133236 | A1 | 9/2002 | Rousseau |
| 2002/0134811 | A1 | 9/2002 | Napier et al. |
| 2002/0135474 | A1 | 9/2002 | Sylliassen |
| 2002/0138086 | A1 | 9/2002 | Sixto et al. |
| 2002/0143340 | A1 | 10/2002 | Kaneko |
| 2002/0151770 | A1 | 10/2002 | Noll et al. |
| 2002/0156497 | A1 | 10/2002 | Nagase et al. |
| 2002/0158593 | A1 | 10/2002 | Henderson et al. |
| 2002/0161277 | A1 | 10/2002 | Boone et al. |
| 2002/0165559 | A1 | 11/2002 | Grant et al. |
| 2002/0165562 | A1 | 11/2002 | Grant et al. |
| 2002/0177848 | A1 | 11/2002 | Truckai et al. |
| 2002/0185514 | A1 | 12/2002 | Adams et al. |
| 2002/0188170 | A1 | 12/2002 | Santamore et al. |
| 2002/0188287 | A1 | 12/2002 | Zvuloni et al. |
| 2003/0004610 | A1 | 1/2003 | Niemeyer et al. |
| 2003/0009193 | A1 | 1/2003 | Corsaro |
| 2003/0011245 | A1 | 1/2003 | Fiebig |
| 2003/0012805 | A1 | 1/2003 | Chen et al. |
| 2003/0018323 | A1 | 1/2003 | Wallace et al. |
| 2003/0028236 | A1 | 2/2003 | Gillick et al. |
| 2003/0040670 | A1 | 2/2003 | Govari |
| 2003/0045835 | A1 | 3/2003 | Anderson et al. |
| 2003/0045900 | A1 | 3/2003 | Hahnen et al. |
| 2003/0047230 | A1 | 3/2003 | Kim |
| 2003/0047582 | A1 | 3/2003 | Sonnenschein et al. |
| 2003/0050628 | A1 | 3/2003 | Whitman et al. |
| 2003/0050654 | A1 | 3/2003 | Whitman et al. |
| 2003/0066858 | A1 | 4/2003 | Holgersson |
| 2003/0078647 | A1 | 4/2003 | Vallana et al. |
| 2003/0083648 | A1 | 5/2003 | Wang et al. |
| 2003/0084983 | A1 | 5/2003 | Rangachari et al. |
| 2003/0093103 | A1 | 5/2003 | Malackowski et al. |
| 2003/0093160 | A1 | 5/2003 | Maksimovic et al. |
| 2003/0094356 | A1 | 5/2003 | Waldron |
| 2003/0096158 | A1 | 5/2003 | Takano et al. |
| 2003/0105475 | A1 | 6/2003 | Sancoff et al. |
| 2003/0114851 | A1 | 6/2003 | Truckai et al. |
| 2003/0121586 | A1 | 7/2003 | Mitra et al. |
| 2003/0129382 | A1 | 7/2003 | Treat |
| 2003/0135204 | A1 | 7/2003 | Lee et al. |
| 2003/0135388 | A1 | 7/2003 | Martucci et al. |
| 2003/0139741 | A1 | 7/2003 | Goble et al. |
| 2003/0144660 | A1 | 7/2003 | Mollenauer |
| 2003/0149406 | A1 | 8/2003 | Martineau et al. |
| 2003/0153908 | A1 | 8/2003 | Goble et al. |
| 2003/0153968 | A1 | 8/2003 | Geis et al. |
| 2003/0158463 | A1 | 8/2003 | Julian et al. |
| 2003/0163029 | A1 | 8/2003 | Sonnenschein et al. |
| 2003/0163085 | A1 | 8/2003 | Tanner et al. |
| 2003/0164172 | A1 | 9/2003 | Chumas et al. |
| 2003/0181800 | A1 | 9/2003 | Bonutti |
| 2003/0181900 | A1 | 9/2003 | Long |
| 2003/0190584 | A1 | 10/2003 | Heasley |
| 2003/0195387 | A1 | 10/2003 | Kortenbach et al. |
| 2003/0205029 | A1 | 11/2003 | Chapolini et al. |
| 2003/0212005 | A1 | 11/2003 | Petito et al. |
| 2003/0216619 | A1 | 11/2003 | Scirica et al. |
| 2003/0216732 | A1 | 11/2003 | Truckai et al. |
| 2003/0220541 | A1 | 11/2003 | Salisbury et al. |
| 2003/0236505 | A1 | 12/2003 | Bonadio et al. |
| 2004/0006335 | A1 | 1/2004 | Garrison |
| 2004/0006340 | A1 | 1/2004 | Latterell et al. |
| 2004/0007608 | A1 | 1/2004 | Ehrenfels et al. |
| 2004/0024457 | A1 | 2/2004 | Boyce et al. |
| 2004/0028502 | A1 | 2/2004 | Cummins |
| 2004/0030333 | A1 | 2/2004 | Goble |
| 2004/0034287 | A1 | 2/2004 | Hickle |
| 2004/0034357 | A1 | 2/2004 | Beane et al. |
| 2004/0044295 | A1 | 3/2004 | Reinert et al. |
| 2004/0044364 | A1 | 3/2004 | DeVries et al. |
| 2004/0049121 | A1 | 3/2004 | Yaron |
| 2004/0049172 | A1 | 3/2004 | Root et al. |
| 2004/0059362 | A1 | 3/2004 | Knodel et al. |
| 2004/0068161 | A1 | 4/2004 | Couvillon |
| 2004/0068224 | A1 | 4/2004 | Couvillon et al. |
| 2004/0068307 | A1 | 4/2004 | Goble |
| 2004/0070369 | A1 | 4/2004 | Sakakibara |
| 2004/0073222 | A1 | 4/2004 | Koseki |
| 2004/0078037 | A1 | 4/2004 | Batchelor et al. |
| 2004/0082952 | A1 | 4/2004 | Dycus et al. |
| 2004/0085180 | A1 | 5/2004 | Juang |
| 2004/0092967 | A1 | 5/2004 | Sancoff et al. |
| 2004/0092992 | A1 | 5/2004 | Adams et al. |
| 2004/0093020 | A1 | 5/2004 | Sinton |
| 2004/0093024 | A1 | 5/2004 | Lousararian et al. |
| 2004/0093029 | A1 | 5/2004 | Zubik et al. |
| 2004/0098040 | A1 | 5/2004 | Taniguchi et al. |
| 2004/0101822 | A1 | 5/2004 | Wiesner et al. |
| 2004/0102783 | A1 | 5/2004 | Sutterlin et al. |
| 2004/0108357 | A1 | 6/2004 | Milliman et al. |
| 2004/0110439 | A1 | 6/2004 | Chaikof et al. |

(56) References Cited

U.S. PATENT DOCUMENTS

2004/0115022 A1 6/2004 Albertson et al.
2004/0116952 A1 6/2004 Sakurai et al.
2004/0119185 A1 6/2004 Chen
2004/0122419 A1 6/2004 Neuberger
2004/0122423 A1 6/2004 Dycus et al.
2004/0133095 A1 7/2004 Dunki-Jacobs et al.
2004/0133189 A1 7/2004 Sakurai
2004/0143297 A1 7/2004 Ramsey
2004/0147909 A1 7/2004 Johnston et al.
2004/0153100 A1 8/2004 Ahlberg et al.
2004/0158261 A1 8/2004 Vu
2004/0164123 A1 8/2004 Racenet et al.
2004/0166169 A1 8/2004 Malaviya et al.
2004/0167572 A1 8/2004 Roth et al.
2004/0181219 A1 9/2004 Goble et al.
2004/0193189 A1 9/2004 Kortenbach et al.
2004/0197367 A1 10/2004 Rezania et al.
2004/0199181 A1 10/2004 Knodel et al.
2004/0204735 A1 10/2004 Shiroff et al.
2004/0218451 A1 11/2004 Said et al.
2004/0222268 A1 11/2004 Bilotti et al.
2004/0225186 A1 11/2004 Horne et al.
2004/0230230 A1 11/2004 Lindstrom et al.
2004/0231870 A1 11/2004 McCormick et al.
2004/0232194 A1 11/2004 Pedicini et al.
2004/0232197 A1 11/2004 Shelton, IV et al.
2004/0232201 A1 11/2004 Wenchell et al.
2004/0236352 A1 11/2004 Wang et al.
2004/0239582 A1 12/2004 Seymour
2004/0243147 A1 12/2004 Lipow
2004/0243151 A1 12/2004 Demmy et al.
2004/0243163 A1 12/2004 Casiano et al.
2004/0247415 A1 12/2004 Mangone
2004/0249366 A1 12/2004 Kunz
2004/0254455 A1 12/2004 Iddan
2004/0254566 A1 12/2004 Plicchi et al.
2004/0254590 A1 12/2004 Hoffman et al.
2004/0254680 A1 12/2004 Sunaoshi
2004/0260315 A1 12/2004 Dell et al.
2004/0267310 A1 12/2004 Racenet et al.
2004/0267362 A1 12/2004 Hwang et al.
2005/0010158 A1 1/2005 Brugger et al.
2005/0010213 A1 1/2005 Stad et al.
2005/0021078 A1 1/2005 Vleugels et al.
2005/0023325 A1 2/2005 Gresham et al.
2005/0032511 A1 2/2005 Malone et al.
2005/0033136 A1 2/2005 Govari et al.
2005/0033352 A1 2/2005 Zepf et al.
2005/0044489 A1 2/2005 Yamagami et al.
2005/0051163 A1 3/2005 Deem et al.
2005/0054946 A1 3/2005 Krzyzanowski
2005/0057225 A1 3/2005 Marquet
2005/0058890 A1 3/2005 Brazell et al.
2005/0059997 A1 3/2005 Bauman et al.
2005/0067548 A1 3/2005 Inoue
2005/0070925 A1 3/2005 Shelton et al.
2005/0070929 A1 3/2005 Dalessandro et al.
2005/0074593 A1 4/2005 Day et al.
2005/0075561 A1 4/2005 Golden
2005/0079088 A1 4/2005 Wirth et al.
2005/0080342 A1 4/2005 Gilreath et al.
2005/0085693 A1 4/2005 Belson et al.
2005/0085838 A1 4/2005 Thompson et al.
2005/0090709 A1 4/2005 Okada et al.
2005/0090817 A1 4/2005 Phan
2005/0096683 A1 5/2005 Ellins et al.
2005/0108643 A1 5/2005 Schybergson et al.
2005/0116673 A1 6/2005 Carl et al.
2005/0118048 A1 6/2005 Traxinger
2005/0119524 A1 6/2005 Sekine et al.
2005/0120836 A1 6/2005 Anderson
2005/0121390 A1 6/2005 Wallace et al.
2005/0124855 A1 6/2005 Jaffe et al.
2005/0125028 A1 6/2005 Looper et al.
2005/0125897 A1 6/2005 Wyslucha et al.
2005/0129730 A1 6/2005 Pang et al.
2005/0129735 A1 6/2005 Cook et al.
2005/0130682 A1 6/2005 Takara et al.
2005/0131173 A1 6/2005 McDaniel et al.
2005/0131211 A1 6/2005 Bayley et al.
2005/0131390 A1 6/2005 Heinrich et al.
2005/0131436 A1 6/2005 Johnston et al.
2005/0131457 A1 6/2005 Douglas et al.
2005/0137454 A1 6/2005 Saadat et al.
2005/0137455 A1 6/2005 Ewers et al.
2005/0139635 A1 6/2005 Wukusick et al.
2005/0139636 A1 6/2005 Schwemberger et al.
2005/0143759 A1 6/2005 Kelly
2005/0143769 A1 6/2005 White et al.
2005/0145671 A1 7/2005 Viola
2005/0145672 A1 7/2005 Schwemberger et al.
2005/0150928 A1 7/2005 Kameyama et al.
2005/0154258 A1 7/2005 Tartaglia et al.
2005/0154406 A1 7/2005 Bombard et al.
2005/0159778 A1 7/2005 Heinrich et al.
2005/0165419 A1 7/2005 Sauer et al.
2005/0169974 A1 8/2005 Tenerz et al.
2005/0171522 A1 8/2005 Christopherson
2005/0177176 A1 8/2005 Gerbi et al.
2005/0177181 A1 8/2005 Kagan et al.
2005/0177249 A1 8/2005 Kladakis et al.
2005/0178813 A1 8/2005 Swayze et al.
2005/0182298 A1 8/2005 Ikeda et al.
2005/0182443 A1 8/2005 Jonn et al.
2005/0184121 A1 8/2005 Heinrich
2005/0186240 A1 8/2005 Ringeisen et al.
2005/0187545 A1 8/2005 Hooven et al.
2005/0191936 A1 9/2005 Marine et al.
2005/0197859 A1 9/2005 Wilson et al.
2005/0203550 A1 9/2005 Laufer et al.
2005/0209614 A1 9/2005 Fenter et al.
2005/0216055 A1 9/2005 Scirica et al.
2005/0222587 A1 10/2005 Jinno et al.
2005/0222611 A1 10/2005 Weitkamp
2005/0222616 A1 10/2005 Rethy et al.
2005/0222665 A1 10/2005 Aranyi
2005/0228224 A1 10/2005 Okada et al.
2005/0228446 A1 10/2005 Mooradian et al.
2005/0230453 A1 10/2005 Viola
2005/0240178 A1 10/2005 Morley et al.
2005/0242950 A1 11/2005 Lindsay et al.
2005/0245965 A1 11/2005 Orban, III et al.
2005/0246881 A1 11/2005 Kelly et al.
2005/0251063 A1 11/2005 Basude
2005/0251110 A1 11/2005 Nixon
2005/0256452 A1 11/2005 DeMarchi et al.
2005/0256546 A1 11/2005 Vaisnys et al.
2005/0258963 A1 11/2005 Rodriguez et al.
2005/0261676 A1 11/2005 Hall et al.
2005/0263563 A1 12/2005 Racenet et al.
2005/0267455 A1 12/2005 Eggers et al.
2005/0267464 A1 12/2005 Truckai et al.
2005/0267529 A1 12/2005 Crockett et al.
2005/0274034 A1 12/2005 Hayashida et al.
2005/0283188 A1 12/2005 Loshakove et al.
2005/0283226 A1 12/2005 Haverkost
2006/0000867 A1 1/2006 Shelton et al.
2006/0008504 A1 1/2006 Kerr et al.
2006/0008787 A1 1/2006 Hayman et al.
2006/0011698 A1 1/2006 Okada et al.
2006/0015009 A1 1/2006 Jaffe et al.
2006/0016853 A1 1/2006 Racenet
2006/0019056 A1 1/2006 Turner et al.
2006/0020167 A1 1/2006 Sitzmann
2006/0020258 A1 1/2006 Strauss et al.
2006/0020272 A1 1/2006 Gildenberg
2006/0020336 A1 1/2006 Liddicoat
2006/0025812 A1 2/2006 Shelton
2006/0041188 A1 2/2006 Dirusso et al.
2006/0047275 A1 3/2006 Goble
2006/0049229 A1 3/2006 Milliman et al.
2006/0052824 A1 3/2006 Ransick et al.
2006/0052825 A1 3/2006 Ransick et al.
2006/0053951 A1 3/2006 Revelis et al.

(56) References Cited

U.S. PATENT DOCUMENTS

2006/0064086 A1 3/2006 Odom
2006/0079735 A1 4/2006 Martone et al.
2006/0079874 A1 4/2006 Faller et al.
2006/0079879 A1 4/2006 Faller et al.
2006/0086032 A1 4/2006 Valencic et al.
2006/0087746 A1 4/2006 Lipow
2006/0089535 A1 4/2006 Raz et al.
2006/0089628 A1 4/2006 Whitman
2006/0097026 A1 5/2006 Shelton
2006/0097699 A1 5/2006 Kamenoff
2006/0100643 A1 5/2006 Laufer et al.
2006/0100649 A1 5/2006 Hart
2006/0106369 A1 5/2006 Desai et al.
2006/0111711 A1 5/2006 Goble
2006/0111723 A1 5/2006 Chapolini et al.
2006/0111738 A1 5/2006 Wenchell
2006/0116634 A1 6/2006 Shachar
2006/0142656 A1 6/2006 Malackowski et al.
2006/0142772 A1 6/2006 Ralph et al.
2006/0144898 A1 7/2006 Bilotti et al.
2006/0154546 A1 7/2006 Murphy et al.
2006/0161050 A1 7/2006 Butler et al.
2006/0161185 A1 7/2006 Saadat et al.
2006/0167471 A1 7/2006 Phillips
2006/0173290 A1 8/2006 Lavallee et al.
2006/0173470 A1 8/2006 Oray et al.
2006/0176031 A1 8/2006 Forman et al.
2006/0176242 A1 8/2006 Jaramaz et al.
2006/0178556 A1 8/2006 Hasser et al.
2006/0180633 A1 8/2006 Emmons
2006/0180634 A1 8/2006 Shelton et al.
2006/0185682 A1 8/2006 Marczyk
2006/0189440 A1 8/2006 Gravagne
2006/0199999 A1 9/2006 Ikeda et al.
2006/0201989 A1 9/2006 Ojeda
2006/0206100 A1 9/2006 Eskridge et al.
2006/0217729 A1 9/2006 Eskridge et al.
2006/0226196 A1 10/2006 Hueil et al.
2006/0226957 A1 10/2006 Miller et al.
2006/0229493 A1 10/2006 Weiser et al.
2006/0235368 A1 10/2006 Oz
2006/0241666 A1 10/2006 Briggs et al.
2006/0241691 A1 10/2006 Wilk
2006/0243469 A1 11/2006 Webster
2006/0244460 A1 11/2006 Weaver
2006/0247584 A1 11/2006 Sheetz et al.
2006/0252981 A1 11/2006 Matsuda et al.
2006/0252990 A1 11/2006 Kubach
2006/0252993 A1 11/2006 Freed et al.
2006/0258904 A1 11/2006 Stefanchik et al.
2006/0259073 A1 11/2006 Miyamoto et al.
2006/0261763 A1 11/2006 Iott et al.
2006/0263444 A1 11/2006 Ming et al.
2006/0264831 A1 11/2006 Skwarek et al.
2006/0264929 A1 11/2006 Goble et al.
2006/0271042 A1 11/2006 Latterell et al.
2006/0271102 A1 11/2006 Bosshard et al.
2006/0282064 A1 12/2006 Shimizu et al.
2006/0284730 A1 12/2006 Schmid et al.
2006/0287576 A1 12/2006 Tsuji et al.
2006/0289600 A1 12/2006 Wales et al.
2006/0289602 A1 12/2006 Wales et al.
2006/0291981 A1 12/2006 Viola et al.
2007/0005045 A1 1/2007 Mintz et al.
2007/0009570 A1 1/2007 Kim et al.
2007/0010702 A1 1/2007 Wang et al.
2007/0010838 A1 1/2007 Shelton et al.
2007/0016235 A1 1/2007 Tanaka et al.
2007/0016272 A1 1/2007 Thompson et al.
2007/0018958 A1 1/2007 Tavakoli et al.
2007/0026039 A1 2/2007 Drumheller et al.
2007/0026040 A1 2/2007 Crawley et al.
2007/0027459 A1 2/2007 Horvath et al.
2007/0027468 A1 2/2007 Wales et al.
2007/0027551 A1 2/2007 Farnsworth et al.
2007/0034668 A1 2/2007 Holsten et al.
2007/0034669 A1 2/2007 de la Torre et al.
2007/0043338 A1 2/2007 Moll et al.
2007/0043384 A1 2/2007 Ortiz et al.
2007/0043387 A1 2/2007 Vargas et al.
2007/0049951 A1 3/2007 Menn
2007/0049966 A1 3/2007 Bonadio et al.
2007/0051375 A1 3/2007 Milliman
2007/0055228 A1 3/2007 Berg et al.
2007/0055305 A1 3/2007 Schnyder et al.
2007/0069851 A1 3/2007 Sung et al.
2007/0073341 A1 3/2007 Smith et al.
2007/0073389 A1 3/2007 Bolduc et al.
2007/0078328 A1 4/2007 Ozaki et al.
2007/0078484 A1 4/2007 Talarico et al.
2007/0084897 A1 4/2007 Shelton et al.
2007/0088376 A1 4/2007 Zacharias
2007/0090788 A1 4/2007 Hansford et al.
2007/0093869 A1 4/2007 Bloom et al.
2007/0102472 A1 5/2007 Shelton
2007/0102476 A1 5/2007 Shelton et al.
2007/0103437 A1 5/2007 Rosenberg
2007/0106113 A1 5/2007 Ravo
2007/0106317 A1 5/2007 Shelton et al.
2007/0118115 A1 5/2007 Artale et al.
2007/0134251 A1 6/2007 Ashkenazi et al.
2007/0135686 A1 6/2007 Pruitt et al.
2007/0135803 A1 6/2007 Belson
2007/0152612 A1 7/2007 Chen et al.
2007/0152829 A1 7/2007 Lindsay et al.
2007/0155010 A1 7/2007 Farnsworth et al.
2007/0162056 A1 7/2007 Gerbi et al.
2007/0170225 A1 7/2007 Shelton et al.
2007/0173687 A1 7/2007 Shima et al.
2007/0173813 A1 7/2007 Odom
2007/0173872 A1 7/2007 Neuenfeldt
2007/0175950 A1 8/2007 Shelton et al.
2007/0175951 A1 8/2007 Shelton et al.
2007/0175955 A1 8/2007 Shelton et al.
2007/0179476 A1 8/2007 Shelton et al.
2007/0179477 A1 8/2007 Danger
2007/0185545 A1 8/2007 Duke
2007/0187857 A1 8/2007 Riley et al.
2007/0190110 A1 8/2007 Pameijer et al.
2007/0191868 A1 8/2007 Theroux et al.
2007/0191915 A1 8/2007 Strother et al.
2007/0194079 A1 8/2007 Hueil et al.
2007/0194081 A1 8/2007 Hueil et al.
2007/0194082 A1 8/2007 Morgan et al.
2007/0197954 A1 8/2007 Keenan
2007/0198039 A1 8/2007 Jones et al.
2007/0203510 A1 8/2007 Bettuchi
2007/0207010 A1 9/2007 Caspi
2007/0207186 A1 9/2007 Scanlon et al.
2007/0208359 A1 9/2007 Hoffman
2007/0208375 A1 9/2007 Nishizawa et al.
2007/0213750 A1 9/2007 Weadock
2007/0221701 A1 9/2007 Ortiz et al.
2007/0225562 A1 9/2007 Spivey et al.
2007/0233163 A1 10/2007 Bombard et al.
2007/0243227 A1 10/2007 Gertner
2007/0244471 A1 10/2007 Malackowski
2007/0244496 A1 10/2007 Hellenkamp
2007/0246505 A1 10/2007 Pace-Floridia et al.
2007/0250093 A1 10/2007 Makower et al.
2007/0260132 A1 11/2007 Sterling
2007/0260242 A1 11/2007 Dycus et al.
2007/0262592 A1 11/2007 Hwang et al.
2007/0270660 A1 11/2007 Caylor et al.
2007/0270790 A1 11/2007 Smith et al.
2007/0275035 A1 11/2007 Herman et al.
2007/0276409 A1 11/2007 Ortiz et al.
2007/0279011 A1 12/2007 Jones et al.
2007/0286892 A1 12/2007 Herzberg et al.
2007/0290027 A1 12/2007 Maatta et al.
2007/0296286 A1 12/2007 Avenell
2008/0000941 A1 1/2008 Sonnenschein et al.
2008/0003196 A1 1/2008 Jonn et al.
2008/0007237 A1 1/2008 Nagashima et al.

(56) References Cited

U.S. PATENT DOCUMENTS

| | | | |
|---|---|---|---|
| 2008/0015598 | A1 | 1/2008 | Prommersberger |
| 2008/0021486 | A1 | 1/2008 | Oyola et al. |
| 2008/0029570 | A1 | 2/2008 | Shelton et al. |
| 2008/0029573 | A1 | 2/2008 | Shelton et al. |
| 2008/0029574 | A1 | 2/2008 | Shelton et al. |
| 2008/0029575 | A1 | 2/2008 | Shelton et al. |
| 2008/0029576 | A1 | 2/2008 | Shelton et al. |
| 2008/0030170 | A1 | 2/2008 | Dacquay et al. |
| 2008/0039746 | A1 | 2/2008 | Hissong et al. |
| 2008/0042861 | A1 | 2/2008 | Dacquay et al. |
| 2008/0044622 | A1 | 2/2008 | Noda et al. |
| 2008/0046000 | A1 | 2/2008 | Lee et al. |
| 2008/0051833 | A1 | 2/2008 | Gramuglia et al. |
| 2008/0064920 | A1 | 3/2008 | Bakos et al. |
| 2008/0064921 | A1 | 3/2008 | Larkin et al. |
| 2008/0065153 | A1 | 3/2008 | Allard et al. |
| 2008/0069736 | A1 | 3/2008 | Mingerink et al. |
| 2008/0071328 | A1 | 3/2008 | Haubrich et al. |
| 2008/0077158 | A1 | 3/2008 | Haider et al. |
| 2008/0078802 | A1 | 4/2008 | Hess et al. |
| 2008/0081948 | A1 | 4/2008 | Weisenburgh et al. |
| 2008/0082114 | A1 | 4/2008 | McKenna et al. |
| 2008/0082125 | A1 | 4/2008 | Murray et al. |
| 2008/0082126 | A1 | 4/2008 | Murray et al. |
| 2008/0083807 | A1 | 4/2008 | Beardsley et al. |
| 2008/0083811 | A1 | 4/2008 | Marczyk |
| 2008/0085296 | A1 | 4/2008 | Powell et al. |
| 2008/0086078 | A1 | 4/2008 | Powell et al. |
| 2008/0091072 | A1 | 4/2008 | Omori et al. |
| 2008/0094228 | A1 | 4/2008 | Welch et al. |
| 2008/0108443 | A1 | 5/2008 | Jinno et al. |
| 2008/0114250 | A1 | 5/2008 | Urbano et al. |
| 2008/0125634 | A1 | 5/2008 | Ryan et al. |
| 2008/0125749 | A1 | 5/2008 | Olson |
| 2008/0126984 | A1 | 5/2008 | Fleishman et al. |
| 2008/0128469 | A1 | 6/2008 | Dalessandro et al. |
| 2008/0129253 | A1 | 6/2008 | Shiue et al. |
| 2008/0132894 | A1 | 6/2008 | Coilard-Lavirotte et al. |
| 2008/0135600 | A1 | 6/2008 | Hiranuma et al. |
| 2008/0140088 | A1 | 6/2008 | Orban, III |
| 2008/0140115 | A1 | 6/2008 | Stopek |
| 2008/0140159 | A1 | 6/2008 | Bornhoft et al. |
| 2008/0149682 | A1 | 6/2008 | Uhm |
| 2008/0154299 | A1 | 6/2008 | Livneh |
| 2008/0154335 | A1 | 6/2008 | Thrope et al. |
| 2008/0169328 | A1 | 7/2008 | Shelton |
| 2008/0169330 | A1 | 7/2008 | Shelton et al. |
| 2008/0169332 | A1 | 7/2008 | Shelton et al. |
| 2008/0169333 | A1 | 7/2008 | Shelton et al. |
| 2008/0172087 | A1 | 7/2008 | Fuchs et al. |
| 2008/0177392 | A1 | 7/2008 | Williams et al. |
| 2008/0190989 | A1 | 8/2008 | Crews et al. |
| 2008/0196253 | A1 | 8/2008 | Ezra et al. |
| 2008/0196419 | A1 | 8/2008 | Dube |
| 2008/0197167 | A1 | 8/2008 | Viola et al. |
| 2008/0200755 | A1 | 8/2008 | Bakos |
| 2008/0200762 | A1 | 8/2008 | Stokes et al. |
| 2008/0200835 | A1 | 8/2008 | Monson et al. |
| 2008/0200911 | A1 | 8/2008 | Long |
| 2008/0200933 | A1 | 8/2008 | Bakos et al. |
| 2008/0200934 | A1 | 8/2008 | Fox |
| 2008/0206186 | A1 | 8/2008 | Butler et al. |
| 2008/0208058 | A1 | 8/2008 | Sabata et al. |
| 2008/0214967 | A1 | 9/2008 | Aranyi et al. |
| 2008/0216704 | A1 | 9/2008 | Eisenbeis et al. |
| 2008/0217376 | A1 | 9/2008 | Clauson et al. |
| 2008/0234709 | A1 | 9/2008 | Houser |
| 2008/0234866 | A1 | 9/2008 | Kishi et al. |
| 2008/0237296 | A1 | 10/2008 | Boudreaux et al. |
| 2008/0242939 | A1 | 10/2008 | Johnston |
| 2008/0243088 | A1 | 10/2008 | Evans |
| 2008/0243143 | A1 | 10/2008 | Kuhns et al. |
| 2008/0249536 | A1 | 10/2008 | Stahler et al. |
| 2008/0249608 | A1 | 10/2008 | Dave |
| 2008/0255413 | A1 | 10/2008 | Zemlok et al. |
| 2008/0255420 | A1 | 10/2008 | Lee et al. |
| 2008/0255421 | A1 | 10/2008 | Hegeman et al. |
| 2008/0255663 | A1 | 10/2008 | Akpek et al. |
| 2008/0262654 | A1 | 10/2008 | Omori et al. |
| 2008/0269596 | A1 | 10/2008 | Revie et al. |
| 2008/0281171 | A1 | 11/2008 | Fennell et al. |
| 2008/0281332 | A1 | 11/2008 | Taylor |
| 2008/0287944 | A1 | 11/2008 | Pearson et al. |
| 2008/0293910 | A1 | 11/2008 | Kapiamba et al. |
| 2008/0294179 | A1 | 11/2008 | Balbierz et al. |
| 2008/0296343 | A1 | 12/2008 | Schall et al. |
| 2008/0296346 | A1 | 12/2008 | Shelton, IV et al. |
| 2008/0296347 | A1 | 12/2008 | Shelton, IV et al. |
| 2008/0297287 | A1 | 12/2008 | Shachar et al. |
| 2008/0298784 | A1 | 12/2008 | Kastner |
| 2008/0300579 | A1 | 12/2008 | Broehl et al. |
| 2008/0308504 | A1 | 12/2008 | Hallan et al. |
| 2008/0308602 | A1 | 12/2008 | Timm et al. |
| 2008/0308603 | A1 | 12/2008 | Shelton et al. |
| 2008/0308607 | A1 | 12/2008 | Timm et al. |
| 2008/0308608 | A1 | 12/2008 | Prommersberger |
| 2008/0308807 | A1 | 12/2008 | Yamazaki et al. |
| 2008/0312686 | A1 | 12/2008 | Ellingwood |
| 2008/0312687 | A1 | 12/2008 | Blier |
| 2008/0315829 | A1 | 12/2008 | Jones et al. |
| 2009/0001121 | A1 | 1/2009 | Hess et al. |
| 2009/0001130 | A1 | 1/2009 | Hess et al. |
| 2009/0004455 | A1 | 1/2009 | Gravagna et al. |
| 2009/0005809 | A1 | 1/2009 | Hess et al. |
| 2009/0007014 | A1 | 1/2009 | Coomer et al. |
| 2009/0012534 | A1 | 1/2009 | Madhani et al. |
| 2009/0015195 | A1 | 1/2009 | Loth-Krausser |
| 2009/0020958 | A1 | 1/2009 | Soul |
| 2009/0030437 | A1 | 1/2009 | Houser et al. |
| 2009/0043253 | A1 | 2/2009 | Podaima |
| 2009/0048583 | A1 | 2/2009 | Williams et al. |
| 2009/0048589 | A1 | 2/2009 | Takashino et al. |
| 2009/0053288 | A1 | 2/2009 | Eskridge, Jr. et al. |
| 2009/0057369 | A1 | 3/2009 | Smith et al. |
| 2009/0069806 | A1 | 3/2009 | De La Mora Levy et al. |
| 2009/0076506 | A1 | 3/2009 | Baker |
| 2009/0076510 | A1 | 3/2009 | Bell et al. |
| 2009/0078736 | A1 | 3/2009 | Van Lue |
| 2009/0078739 | A1 | 3/2009 | Viola |
| 2009/0081313 | A1 | 3/2009 | Aghion et al. |
| 2009/0088659 | A1 | 4/2009 | Graham et al. |
| 2009/0090763 | A1 | 4/2009 | Zemlok et al. |
| 2009/0090764 | A1 | 4/2009 | Viola |
| 2009/0099579 | A1 | 4/2009 | Nentwick et al. |
| 2009/0099876 | A1 | 4/2009 | Whitman |
| 2009/0110533 | A1 | 4/2009 | Jinno |
| 2009/0112234 | A1 | 4/2009 | Crainich et al. |
| 2009/0114701 | A1 | 5/2009 | Zemlok et al. |
| 2009/0118762 | A1 | 5/2009 | Crainch et al. |
| 2009/0119011 | A1 | 5/2009 | Kondo et al. |
| 2009/0120994 | A1 | 5/2009 | Murray et al. |
| 2009/0131819 | A1 | 5/2009 | Ritchie et al. |
| 2009/0132400 | A1 | 5/2009 | Conway |
| 2009/0135280 | A1 | 5/2009 | Johnston et al. |
| 2009/0138003 | A1 | 5/2009 | Deville et al. |
| 2009/0143797 | A1 | 6/2009 | Smith et al. |
| 2009/0143855 | A1 | 6/2009 | Weber et al. |
| 2009/0149871 | A9 | 6/2009 | Kagan et al. |
| 2009/0167548 | A1 | 7/2009 | Sugahara |
| 2009/0171147 | A1 | 7/2009 | Lee et al. |
| 2009/0177218 | A1 | 7/2009 | Young et al. |
| 2009/0177226 | A1 | 7/2009 | Reinprecht et al. |
| 2009/0181290 | A1 | 7/2009 | Baldwin et al. |
| 2009/0188964 | A1 | 7/2009 | Orlov |
| 2009/0192534 | A1 | 7/2009 | Ortiz et al. |
| 2009/0196903 | A1 | 8/2009 | Kliman |
| 2009/0198272 | A1 | 8/2009 | Kerver et al. |
| 2009/0204108 | A1 | 8/2009 | Steffen |
| 2009/0204109 | A1 | 8/2009 | Grove et al. |
| 2009/0204126 | A1 | 8/2009 | Le |
| 2009/0204925 | A1 | 8/2009 | Bhat et al. |
| 2009/0206125 | A1 | 8/2009 | Huitema et al. |
| 2009/0206126 | A1 | 8/2009 | Huitema et al. |
| 2009/0206131 | A1 | 8/2009 | Weisenburgh, II et al. |

(56) References Cited

U.S. PATENT DOCUMENTS

| | | | |
|---|---|---|---|
| 2009/0206133 | A1 | 8/2009 | Morgan et al. |
| 2009/0206137 | A1 | 8/2009 | Hall et al. |
| 2009/0206139 | A1 | 8/2009 | Hall et al. |
| 2009/0206141 | A1 | 8/2009 | Huitema et al. |
| 2009/0206142 | A1 | 8/2009 | Huitema et al. |
| 2009/0206143 | A1 | 8/2009 | Huitema et al. |
| 2009/0218384 | A1 | 9/2009 | Aranyi |
| 2009/0221993 | A1 | 9/2009 | Sohi et al. |
| 2009/0227834 | A1 | 9/2009 | Nakamoto et al. |
| 2009/0234273 | A1 | 9/2009 | Intoccia et al. |
| 2009/0236401 | A1 | 9/2009 | Cole et al. |
| 2009/0242610 | A1 | 10/2009 | Shelton, IV et al. |
| 2009/0246873 | A1 | 10/2009 | Yamamoto et al. |
| 2009/0247368 | A1 | 10/2009 | Chiang |
| 2009/0247901 | A1 | 10/2009 | Zimmer |
| 2009/0248100 | A1 | 10/2009 | Vaisnys et al. |
| 2009/0253959 | A1 | 10/2009 | Yoshie et al. |
| 2009/0255974 | A1 | 10/2009 | Viola |
| 2009/0255977 | A1 | 10/2009 | Zemlok |
| 2009/0261141 | A1 | 10/2009 | Stratton et al. |
| 2009/0262078 | A1 | 10/2009 | Pizzi |
| 2009/0264940 | A1 | 10/2009 | Beale et al. |
| 2009/0270853 | A1 | 10/2009 | Yachi et al. |
| 2009/0270895 | A1 | 10/2009 | Churchill et al. |
| 2009/0273353 | A1 | 11/2009 | Kroh et al. |
| 2009/0277288 | A1 | 11/2009 | Doepker et al. |
| 2009/0278406 | A1 | 11/2009 | Hoffman |
| 2009/0287300 | A1 | 11/2009 | Dave et al. |
| 2009/0290016 | A1 | 11/2009 | Suda |
| 2009/0292283 | A1 | 11/2009 | Odom |
| 2009/0306639 | A1 | 12/2009 | Nevo et al. |
| 2009/0308907 | A1 | 12/2009 | Nalagatla et al. |
| 2009/0318557 | A1 | 12/2009 | Stockel |
| 2009/0318936 | A1 | 12/2009 | Harris et al. |
| 2009/0325859 | A1 | 12/2009 | Ameer et al. |
| 2010/0002013 | A1 | 1/2010 | Kagaya |
| 2010/0005035 | A1 | 1/2010 | Carpenter et al. |
| 2010/0012703 | A1 | 1/2010 | Calabrese et al. |
| 2010/0015104 | A1 | 1/2010 | Fraser et al. |
| 2010/0016853 | A1 | 1/2010 | Burbank |
| 2010/0016888 | A1 | 1/2010 | Calabrese et al. |
| 2010/0017715 | A1 | 1/2010 | Balassanian |
| 2010/0023024 | A1 | 1/2010 | Zeiner et al. |
| 2010/0030233 | A1 | 2/2010 | Whitman et al. |
| 2010/0030239 | A1 | 2/2010 | Viola et al. |
| 2010/0032179 | A1 | 2/2010 | Hanspers et al. |
| 2010/0032470 | A1 | 2/2010 | Hess et al. |
| 2010/0036370 | A1 | 2/2010 | Mirel et al. |
| 2010/0036441 | A1 | 2/2010 | Procter |
| 2010/0051668 | A1 | 3/2010 | Milliman et al. |
| 2010/0057118 | A1 | 3/2010 | Dietz et al. |
| 2010/0065604 | A1 | 3/2010 | Weng |
| 2010/0069833 | A1 | 3/2010 | Wenderow et al. |
| 2010/0069942 | A1 | 3/2010 | Shelton, IV |
| 2010/0076433 | A1 | 3/2010 | Taylor et al. |
| 2010/0076483 | A1 | 3/2010 | Imuta |
| 2010/0076489 | A1 | 3/2010 | Stopek et al. |
| 2010/0081883 | A1 | 4/2010 | Murray et al. |
| 2010/0094312 | A1 | 4/2010 | Ruiz Morales et al. |
| 2010/0094340 | A1 | 4/2010 | Stopek et al. |
| 2010/0094400 | A1 | 4/2010 | Bolduc et al. |
| 2010/0100123 | A1 | 4/2010 | Bennett |
| 2010/0100124 | A1 | 4/2010 | Calabrese et al. |
| 2010/0106167 | A1 | 4/2010 | Boulnois et al. |
| 2010/0116519 | A1 | 5/2010 | Gareis |
| 2010/0122339 | A1 | 5/2010 | Boccacci |
| 2010/0125786 | A1 | 5/2010 | Ozawa et al. |
| 2010/0133317 | A1 | 6/2010 | Shelton, IV et al. |
| 2010/0137990 | A1 | 6/2010 | Apatsidis et al. |
| 2010/0138659 | A1 | 6/2010 | Carmichael et al. |
| 2010/0145146 | A1 | 6/2010 | Melder |
| 2010/0147921 | A1 | 6/2010 | Olson |
| 2010/0147922 | A1 | 6/2010 | Olson |
| 2010/0159435 | A1 | 6/2010 | Mueller et al. |
| 2010/0168741 | A1 | 7/2010 | Sanai et al. |
| 2010/0179022 | A1 | 7/2010 | Shirokoshi |
| 2010/0180711 | A1 | 7/2010 | Kilibarda et al. |
| 2010/0181364 | A1 | 7/2010 | Shelton, IV et al. |
| 2010/0187285 | A1 | 7/2010 | Harris et al. |
| 2010/0191255 | A1 | 7/2010 | Crainich et al. |
| 2010/0191262 | A1 | 7/2010 | Harris et al. |
| 2010/0191292 | A1 | 7/2010 | DeMeo et al. |
| 2010/0193566 | A1 | 8/2010 | Scheib et al. |
| 2010/0194541 | A1 | 8/2010 | Stevenson et al. |
| 2010/0198159 | A1 | 8/2010 | Voss et al. |
| 2010/0200257 | A1 | 8/2010 | Scrimshaw et al. |
| 2010/0204717 | A1 | 8/2010 | Knodel |
| 2010/0204721 | A1 | 8/2010 | Young et al. |
| 2010/0217281 | A1 | 8/2010 | Matsuoka et al. |
| 2010/0218019 | A1 | 8/2010 | Eckhard |
| 2010/0222901 | A1 | 9/2010 | Swayze et al. |
| 2010/0228250 | A1 | 9/2010 | Brogna |
| 2010/0234687 | A1 | 9/2010 | Azarbarzin et al. |
| 2010/0241115 | A1 | 9/2010 | Benamou et al. |
| 2010/0241137 | A1 | 9/2010 | Doyle et al. |
| 2010/0243707 | A1 | 9/2010 | Olson et al. |
| 2010/0245102 | A1 | 9/2010 | Yokoi |
| 2010/0249497 | A1 | 9/2010 | Peine et al. |
| 2010/0249947 | A1 | 9/2010 | Lesh et al. |
| 2010/0256675 | A1 | 10/2010 | Romans |
| 2010/0258327 | A1 | 10/2010 | Esenwein et al. |
| 2010/0267525 | A1 | 10/2010 | Tanner |
| 2010/0267662 | A1 | 10/2010 | Fielder et al. |
| 2010/0274160 | A1 | 10/2010 | Yachi et al. |
| 2010/0291184 | A1 | 11/2010 | Clark et al. |
| 2010/0292540 | A1 | 11/2010 | Hess et al. |
| 2010/0298636 | A1 | 11/2010 | Castro et al. |
| 2010/0298642 | A1 | 11/2010 | Trusty et al. |
| 2010/0301097 | A1 | 12/2010 | Scirica et al. |
| 2010/0310623 | A1 | 12/2010 | Laurencin et al. |
| 2010/0312261 | A1 | 12/2010 | Suzuki et al. |
| 2010/0318085 | A1 | 12/2010 | Austin et al. |
| 2010/0325568 | A1 | 12/2010 | Pedersen et al. |
| 2010/0327041 | A1 | 12/2010 | Milliman et al. |
| 2010/0331856 | A1 | 12/2010 | Carlson et al. |
| 2011/0006101 | A1 | 1/2011 | Hall et al. |
| 2011/0009694 | A1 | 1/2011 | Schultz et al. |
| 2011/0009863 | A1 | 1/2011 | Marczyk et al. |
| 2011/0011916 | A1 | 1/2011 | Levine |
| 2011/0016960 | A1 | 1/2011 | Debrailly |
| 2011/0021871 | A1 | 1/2011 | Berkelaar |
| 2011/0022032 | A1 | 1/2011 | Zemlok et al. |
| 2011/0024477 | A1 | 2/2011 | Hall |
| 2011/0024478 | A1 | 2/2011 | Shelton, IV |
| 2011/0025311 | A1 | 2/2011 | Chauvin et al. |
| 2011/0028991 | A1 | 2/2011 | Ikeda et al. |
| 2011/0029003 | A1 | 2/2011 | Lavigne et al. |
| 2011/0029270 | A1 | 2/2011 | Mueglitz |
| 2011/0036891 | A1 | 2/2011 | Zemlok et al. |
| 2011/0046667 | A1 | 2/2011 | Culligan et al. |
| 2011/0049213 | A1 | 3/2011 | Schneider et al. |
| 2011/0052660 | A1 | 3/2011 | Yang et al. |
| 2011/0056717 | A1 | 3/2011 | Herisse |
| 2011/0060363 | A1 | 3/2011 | Hess et al. |
| 2011/0066156 | A1 | 3/2011 | McGahan et al. |
| 2011/0066243 | A1 | 3/2011 | Rivin et al. |
| 2011/0071473 | A1 | 3/2011 | Rogers et al. |
| 2011/0082538 | A1 | 4/2011 | Dahlgren et al. |
| 2011/0087276 | A1 | 4/2011 | Bedi et al. |
| 2011/0088921 | A1 | 4/2011 | Forgues et al. |
| 2011/0091515 | A1 | 4/2011 | Zilberman et al. |
| 2011/0095064 | A1 | 4/2011 | Taylor et al. |
| 2011/0095067 | A1 | 4/2011 | Ohdaira |
| 2011/0101069 | A1 | 5/2011 | Bombard et al. |
| 2011/0101794 | A1 | 5/2011 | Schroeder et al. |
| 2011/0112513 | A1 | 5/2011 | Hester et al. |
| 2011/0112517 | A1 | 5/2011 | Peine et al. |
| 2011/0112530 | A1 | 5/2011 | Keller |
| 2011/0114697 | A1 | 5/2011 | Baxter, III et al. |
| 2011/0118708 | A1 | 5/2011 | Burbank et al. |
| 2011/0118754 | A1 | 5/2011 | Dachs, II et al. |
| 2011/0125149 | A1 | 5/2011 | El-Galley et al. |
| 2011/0125176 | A1 | 5/2011 | Yates et al. |
| 2011/0127945 | A1 | 6/2011 | Yoneda |

(56) References Cited

U.S. PATENT DOCUMENTS

2011/0129706 A1 6/2011 Takahashi et al.
2011/0144764 A1 6/2011 Bagga et al.
2011/0147433 A1 6/2011 Shelton, IV et al.
2011/0160725 A1 6/2011 Kabaya et al.
2011/0163146 A1 7/2011 Ortiz et al.
2011/0172495 A1 7/2011 Armstrong
2011/0174861 A1 7/2011 Shelton, IV et al.
2011/0189957 A1 8/2011 Hocke
2011/0192882 A1 8/2011 Hess et al.
2011/0198381 A1 8/2011 McCardle et al.
2011/0199225 A1 8/2011 Touchberry et al.
2011/0218400 A1 9/2011 Ma et al.
2011/0218550 A1 9/2011 Ma
2011/0220381 A1 9/2011 Friese et al.
2011/0224543 A1 9/2011 Johnson et al.
2011/0225105 A1 9/2011 Scholer et al.
2011/0230713 A1 9/2011 Kleemann et al.
2011/0235168 A1 9/2011 Sander
2011/0238044 A1 9/2011 Main et al.
2011/0241597 A1 10/2011 Zhu et al.
2011/0251606 A1 10/2011 Kerr
2011/0256266 A1 10/2011 Orme et al.
2011/0271186 A1 11/2011 Owens
2011/0275901 A1 11/2011 Shelton, IV
2011/0276083 A1 11/2011 Shelton, IV et al.
2011/0278035 A1 11/2011 Chen
2011/0278343 A1 11/2011 Knodel et al.
2011/0279268 A1 11/2011 Konishi et al.
2011/0285507 A1 11/2011 Nelson
2011/0290856 A1 12/2011 Shelton, IV et al.
2011/0290858 A1 12/2011 Whitman et al.
2011/0292258 A1 12/2011 Adler et al.
2011/0293690 A1 12/2011 Griffin et al.
2011/0295295 A1 12/2011 Shelton, IV et al.
2011/0295299 A1 12/2011 Braithwaite et al.
2011/0313894 A1 12/2011 Dye et al.
2011/0315413 A1 12/2011 Fisher et al.
2012/0004636 A1 1/2012 Lo
2012/0007442 A1 1/2012 Rhodes et al.
2012/0008880 A1 1/2012 Toth
2012/0010615 A1 1/2012 Cummings et al.
2012/0016239 A1 1/2012 Barthe et al.
2012/0016413 A1 1/2012 Timm et al.
2012/0016467 A1 1/2012 Chen et al.
2012/0018487 A1 1/2012 Bettuchi et al.
2012/0022583 A1 1/2012 Sugalski et al.
2012/0029272 A1 2/2012 Shelton, IV et al.
2012/0029550 A1 2/2012 Forsell
2012/0033360 A1 2/2012 Hsu
2012/0043100 A1 2/2012 Isobe et al.
2012/0059286 A1 3/2012 Hastings et al.
2012/0064483 A1 3/2012 Lint et al.
2012/0074200 A1 3/2012 Schmid et al.
2012/0078243 A1 3/2012 Worrell et al.
2012/0078244 A1 3/2012 Worrell et al.
2012/0080336 A1 4/2012 Shelton, IV et al.
2012/0080344 A1 4/2012 Shelton, IV
2012/0080478 A1 4/2012 Morgan et al.
2012/0080489 A1 4/2012 Shelton, IV et al.
2012/0080491 A1 4/2012 Shelton, IV et al.
2012/0080498 A1 4/2012 Shelton, IV et al.
2012/0083836 A1 4/2012 Shelton, IV et al.
2012/0086276 A1 4/2012 Sawyers
2012/0095458 A1 4/2012 Cybulski et al.
2012/0101488 A1 4/2012 Aldridge et al.
2012/0109186 A1 5/2012 Parrott et al.
2012/0116261 A1 5/2012 Mumaw et al.
2012/0116262 A1 5/2012 Houser et al.
2012/0116263 A1 5/2012 Houser et al.
2012/0116265 A1 5/2012 Houser et al.
2012/0116266 A1 5/2012 Houser et al.
2012/0116381 A1 5/2012 Houser et al.
2012/0118595 A1 5/2012 Pellenc
2012/0123463 A1 5/2012 Jacobs
2012/0125792 A1 5/2012 Cassivi
2012/0130217 A1 5/2012 Kauphusman et al.
2012/0132286 A1 5/2012 Lim et al.
2012/0132663 A1 5/2012 Kasvikis et al.
2012/0143173 A1 6/2012 Steege et al.
2012/0143175 A1 6/2012 Hermann et al.
2012/0171539 A1 7/2012 Rejman et al.
2012/0175142 A1 7/2012 Van Der Linde et al.
2012/0175398 A1 7/2012 Sandborn et al.
2012/0190964 A1 7/2012 Hyde et al.
2012/0197239 A1 8/2012 Smith et al.
2012/0197272 A1 8/2012 Oray et al.
2012/0203213 A1 8/2012 Kimball et al.
2012/0211542 A1 8/2012 Racenet
2012/0220990 A1 8/2012 Mckenzie et al.
2012/0233298 A1 9/2012 Verbandt et al.
2012/0234895 A1 9/2012 O'Connor et al.
2012/0234897 A1 9/2012 Shelton, IV et al.
2012/0239068 A1 9/2012 Morris et al.
2012/0241494 A1 9/2012 Marczyk
2012/0241503 A1 9/2012 Baxter, III et al.
2012/0248169 A1 10/2012 Widenhouse et al.
2012/0251861 A1 10/2012 Liang et al.
2012/0253328 A1 10/2012 Cunningham et al.
2012/0256494 A1 10/2012 Kesler et al.
2012/0271327 A1 10/2012 West et al.
2012/0273547 A1 11/2012 Hodgkinson et al.
2012/0283707 A1 11/2012 Giordano et al.
2012/0286019 A1 11/2012 Hueil et al.
2012/0289811 A1 11/2012 Viola et al.
2012/0289979 A1 11/2012 Eskaros et al.
2012/0292367 A1 11/2012 Morgan et al.
2012/0296316 A1 11/2012 Imuta
2012/0296342 A1 11/2012 Haglund Wendelschafer
2012/0298722 A1 11/2012 Hess et al.
2012/0301498 A1 11/2012 Altreuter et al.
2012/0310254 A1 12/2012 Manzo et al.
2012/0312861 A1 12/2012 Gurumurthy et al.
2012/0316424 A1 12/2012 Stopek
2012/0330285 A1 12/2012 Hartoumbekis et al.
2012/0330329 A1 12/2012 Harris et al.
2013/0006227 A1 1/2013 Takashino
2013/0008937 A1 1/2013 Viola
2013/0012983 A1 1/2013 Kleyman
2013/0018400 A1 1/2013 Milton et al.
2013/0020375 A1 1/2013 Shelton, IV et al.
2013/0020376 A1 1/2013 Shelton, IV et al.
2013/0023861 A1 1/2013 Shelton, IV et al.
2013/0023910 A1 1/2013 Solomon et al.
2013/0023915 A1 1/2013 Mueller
2013/0026208 A1 1/2013 Shelton, IV et al.
2013/0026210 A1 1/2013 Shelton, IV et al.
2013/0030462 A1 1/2013 Keating et al.
2013/0041292 A1 2/2013 Cunningham
2013/0056522 A1 3/2013 Swensgard
2013/0057162 A1 3/2013 Pollischansky
2013/0068816 A1 3/2013 Mandakolathur Vasudevan et al.
2013/0069088 A1 3/2013 Speck et al.
2013/0075447 A1 3/2013 Weisenburgh, II et al.
2013/0087597 A1 4/2013 Shelton, IV et al.
2013/0090534 A1 4/2013 Burns et al.
2013/0096568 A1 4/2013 Justis
2013/0098968 A1 4/2013 Aranyi et al.
2013/0098970 A1 4/2013 Racenet et al.
2013/0105548 A1 5/2013 Hodgkinson et al.
2013/0106352 A1 5/2013 Nagamine
2013/0112729 A1 5/2013 Beardsley et al.
2013/0116669 A1 5/2013 Shelton, IV et al.
2013/0123816 A1 5/2013 Hodgkinson et al.
2013/0126202 A1 5/2013 Oomori et al.
2013/0131476 A1 5/2013 Siu et al.
2013/0131651 A1 5/2013 Strobl et al.
2013/0136969 A1 5/2013 Yasui et al.
2013/0153639 A1 6/2013 Hodgkinson et al.
2013/0153641 A1 6/2013 Shelton, IV et al.
2013/0158390 A1 6/2013 Tan et al.
2013/0162198 A1 6/2013 Yokota et al.
2013/0165908 A1 6/2013 Purdy et al.
2013/0169217 A1 7/2013 Watanabe et al.
2013/0172713 A1 7/2013 Kirschenman

(56) References Cited

U.S. PATENT DOCUMENTS

2013/0172878 A1 7/2013 Smith
2013/0175315 A1 7/2013 Milliman
2013/0175317 A1 7/2013 Yates et al.
2013/0183769 A1 7/2013 Tajima
2013/0186936 A1 7/2013 Shelton, IV
2013/0211244 A1 8/2013 Nathaniel
2013/0214025 A1 8/2013 Zemlok et al.
2013/0215449 A1 8/2013 Yamasaki
2013/0231681 A1 9/2013 Robinson et al.
2013/0233906 A1 9/2013 Hess et al.
2013/0238021 A1 9/2013 Gross et al.
2013/0248578 A1 9/2013 Arteaga Gonzalez
2013/0253480 A1 9/2013 Kimball et al.
2013/0253499 A1 9/2013 Kimball et al.
2013/0256368 A1 10/2013 Timm et al.
2013/0256373 A1 10/2013 Schmid et al.
2013/0256380 A1 10/2013 Schmid et al.
2013/0267950 A1 10/2013 Rosa et al.
2013/0267978 A1 10/2013 Trissel
2013/0270322 A1 10/2013 Scheib et al.
2013/0277410 A1 10/2013 Fernandez et al.
2013/0284792 A1 10/2013 Ma
2013/0289565 A1 10/2013 Hassler, Jr.
2013/0293353 A1 11/2013 McPherson et al.
2013/0303845 A1 11/2013 Skula et al.
2013/0304084 A1 11/2013 Beira et al.
2013/0306704 A1 11/2013 Balbierz et al.
2013/0310849 A1 11/2013 Malkowski
2013/0327552 A1 12/2013 Lovelass et al.
2013/0331826 A1 12/2013 Steege
2013/0333910 A1 12/2013 Tanimoto et al.
2013/0334280 A1 12/2013 Krehel et al.
2013/0334283 A1 12/2013 Swayze et al.
2013/0334285 A1 12/2013 Swayze et al.
2013/0341374 A1 12/2013 Shelton, IV et al.
2014/0001231 A1 1/2014 Shelton, IV et al.
2014/0001234 A1 1/2014 Shelton, IV et al.
2014/0002322 A1 1/2014 Kanome et al.
2014/0005550 A1 1/2014 Lu et al.
2014/0005640 A1 1/2014 Shelton, IV et al.
2014/0005678 A1 1/2014 Shelton, IV et al.
2014/0005702 A1 1/2014 Timm et al.
2014/0005718 A1 1/2014 Shelton, IV et al.
2014/0008289 A1 1/2014 Williams et al.
2014/0014704 A1 1/2014 Onukuri et al.
2014/0014705 A1 1/2014 Baxter, III
2014/0014707 A1 1/2014 Onukuri et al.
2014/0018832 A1 1/2014 Shelton, IV
2014/0022283 A1 1/2014 Chan et al.
2014/0039549 A1 2/2014 Belsky et al.
2014/0041191 A1 2/2014 Knodel
2014/0048580 A1 2/2014 Merchant et al.
2014/0069240 A1 3/2014 Dauvin et al.
2014/0078715 A1 3/2014 Pickard et al.
2014/0081176 A1 3/2014 Hassan
2014/0088614 A1 3/2014 Blumenkranz
2014/0088639 A1 3/2014 Bartels et al.
2014/0094681 A1 4/2014 Valentine et al.
2014/0100554 A1 4/2014 Williams
2014/0100558 A1 4/2014 Schmitz et al.
2014/0107697 A1 4/2014 Patani et al.
2014/0110453 A1 4/2014 Wingardner et al.
2014/0115229 A1 4/2014 Kothamasu et al.
2014/0131418 A1 5/2014 Kostrzewski
2014/0131419 A1 5/2014 Bettuchi
2014/0135832 A1 5/2014 Park et al.
2014/0148803 A1 5/2014 Taylor
2014/0151433 A1 6/2014 Shelton, IV et al.
2014/0155916 A1 6/2014 Hodgkinson et al.
2014/0158747 A1 6/2014 Measamer et al.
2014/0166718 A1 6/2014 Swayze et al.
2014/0166723 A1 6/2014 Beardsley et al.
2014/0166724 A1 6/2014 Schellin et al.
2014/0166725 A1 6/2014 Schellin et al.
2014/0166726 A1 6/2014 Schellin et al.
2014/0175147 A1 6/2014 Manoux et al.
2014/0175150 A1 6/2014 Shelton, IV et al.
2014/0175152 A1 6/2014 Hess et al.
2014/0181710 A1 6/2014 Baalu et al.
2014/0183244 A1 7/2014 Duque et al.
2014/0188091 A1 7/2014 Vidal et al.
2014/0188101 A1 7/2014 Bales, Jr. et al.
2014/0188159 A1 7/2014 Steege
2014/0194874 A1 7/2014 Dietz et al.
2014/0207124 A1 7/2014 Aldridge et al.
2014/0209658 A1 7/2014 Skalla et al.
2014/0215242 A1 7/2014 Jung
2014/0224857 A1 8/2014 Schmid
2014/0228632 A1 8/2014 Sholev et al.
2014/0228867 A1 8/2014 Thomas et al.
2014/0239047 A1 8/2014 Hodgkinson et al.
2014/0243865 A1 8/2014 Swayze et al.
2014/0246475 A1 9/2014 Hall et al.
2014/0248167 A1 9/2014 Sugimoto et al.
2014/0249557 A1 9/2014 Koch, Jr. et al.
2014/0249573 A1 9/2014 Arav
2014/0262408 A1 9/2014 Woodard
2014/0263535 A1 9/2014 Rajani et al.
2014/0263541 A1 9/2014 Leimbach et al.
2014/0263552 A1 9/2014 Hall et al.
2014/0263558 A1 9/2014 Hausen et al.
2014/0276720 A1 9/2014 Parihar et al.
2014/0276730 A1 9/2014 Boudreaux et al.
2014/0276776 A1 9/2014 Parihar et al.
2014/0284371 A1 9/2014 Morgan et al.
2014/0287703 A1 9/2014 Herbsommer et al.
2014/0288460 A1 9/2014 Ouyang et al.
2014/0291379 A1 10/2014 Schellin et al.
2014/0291383 A1 10/2014 Spivey et al.
2014/0299648 A1 10/2014 Shelton, IV et al.
2014/0303645 A1 10/2014 Morgan et al.
2014/0303660 A1 10/2014 Boyden et al.
2014/0330161 A1 11/2014 Swayze et al.
2014/0330298 A1 11/2014 Arshonsky et al.
2014/0330579 A1 11/2014 Cashman et al.
2014/0358163 A1 12/2014 Farin et al.
2014/0367445 A1 12/2014 Ingmanson et al.
2014/0371764 A1 12/2014 Oyola et al.
2014/0373003 A1 12/2014 Grez et al.
2014/0374130 A1 12/2014 Nakamura et al.
2014/0378950 A1 12/2014 Chiu
2014/0379000 A1 12/2014 Romo et al.
2015/0001272 A1 1/2015 Sniffin et al.
2015/0002089 A1 1/2015 Rejman et al.
2015/0022012 A1 1/2015 Kim et al.
2015/0025549 A1 1/2015 Kilroy et al.
2015/0025571 A1 1/2015 Suzuki et al.
2015/0034697 A1 2/2015 Mastri et al.
2015/0039010 A1 2/2015 Beardsley et al.
2015/0053737 A1 2/2015 Leimbach et al.
2015/0053743 A1 2/2015 Yates et al.
2015/0053746 A1 2/2015 Shelton, IV et al.
2015/0053748 A1 2/2015 Yates et al.
2015/0060516 A1 3/2015 Collings et al.
2015/0060519 A1 3/2015 Shelton, IV et al.
2015/0060520 A1 3/2015 Shelton, IV et al.
2015/0060521 A1 3/2015 Weisenburgh, II et al.
2015/0066000 A1 3/2015 An et al.
2015/0067582 A1 3/2015 Donnelly et al.
2015/0076208 A1 3/2015 Shelton, IV
2015/0076209 A1 3/2015 Shelton, IV et al.
2015/0076210 A1 3/2015 Shelton, IV et al.
2015/0076211 A1 3/2015 Irka et al.
2015/0080883 A1 3/2015 Haverkost et al.
2015/0082624 A1 3/2015 Craig et al.
2015/0083781 A1 3/2015 Giordano et al.
2015/0087952 A1 3/2015 Albert et al.
2015/0088127 A1 3/2015 Craig et al.
2015/0088547 A1 3/2015 Balram et al.
2015/0090760 A1 4/2015 Giordano et al.
2015/0090762 A1 4/2015 Giordano et al.
2015/0127021 A1 5/2015 Harris et al.
2015/0133957 A1 5/2015 Kostrzewski
2015/0134077 A1 5/2015 Shelton, IV et al.

(56) References Cited

U.S. PATENT DOCUMENTS

| | | | | |
|---|---|---|---|---|
| 2015/0142047 | A1* | 5/2015 | Burbank | A61B 50/10 606/205 |
| 2015/0150620 | A1 | 6/2015 | Miyamoto et al. | |
| 2015/0173749 | A1 | 6/2015 | Shelton, IV et al. | |
| 2015/0173756 | A1 | 6/2015 | Baxter, III et al. | |
| 2015/0173789 | A1 | 6/2015 | Baxter, III et al. | |
| 2015/0196295 | A1 | 7/2015 | Shelton, IV et al. | |
| 2015/0196299 | A1 | 7/2015 | Swayze et al. | |
| 2015/0201918 | A1 | 7/2015 | Kumar et al. | |
| 2015/0201932 | A1 | 7/2015 | Swayze et al. | |
| 2015/0201936 | A1 | 7/2015 | Swayze et al. | |
| 2015/0201937 | A1 | 7/2015 | Swayze et al. | |
| 2015/0201938 | A1 | 7/2015 | Swayze et al. | |
| 2015/0201939 | A1 | 7/2015 | Swayze et al. | |
| 2015/0201940 | A1 | 7/2015 | Swayze et al. | |
| 2015/0201941 | A1 | 7/2015 | Swayze et al. | |
| 2015/0202013 | A1 | 7/2015 | Teichtmann et al. | |
| 2015/0209045 | A1 | 7/2015 | Hodgkinson et al. | |
| 2015/0216605 | A1 | 8/2015 | Baldwin | |
| 2015/0222212 | A1 | 8/2015 | Iwata | |
| 2015/0223868 | A1 | 8/2015 | Brandt et al. | |
| 2015/0230697 | A1 | 8/2015 | Phee et al. | |
| 2015/0230794 | A1 | 8/2015 | Wellman et al. | |
| 2015/0230861 | A1 | 8/2015 | Woloszko et al. | |
| 2015/0231409 | A1 | 8/2015 | Racenet et al. | |
| 2015/0238118 | A1 | 8/2015 | Legassey et al. | |
| 2015/0272557 | A1 | 10/2015 | Overmyer et al. | |
| 2015/0272571 | A1 | 10/2015 | Leimbach et al. | |
| 2015/0272580 | A1 | 10/2015 | Leimbach et al. | |
| 2015/0272582 | A1 | 10/2015 | Leimbach et al. | |
| 2015/0272606 | A1 | 10/2015 | Nobis | |
| 2015/0297200 | A1 | 10/2015 | Fitzsimmons et al. | |
| 2015/0297222 | A1 | 10/2015 | Huitema et al. | |
| 2015/0297223 | A1 | 10/2015 | Huitema et al. | |
| 2015/0297225 | A1 | 10/2015 | Huitema et al. | |
| 2015/0297824 | A1 | 10/2015 | Cabiri et al. | |
| 2015/0303417 | A1 | 10/2015 | Koeder et al. | |
| 2015/0305743 | A1 | 10/2015 | Casasanta et al. | |
| 2015/0313594 | A1 | 11/2015 | Shelton, IV et al. | |
| 2015/0324317 | A1 | 11/2015 | Collins et al. | |
| 2015/0352699 | A1 | 12/2015 | Sakai et al. | |
| 2015/0366585 | A1 | 12/2015 | Lemay et al. | |
| 2015/0367497 | A1 | 12/2015 | Ito et al. | |
| 2015/0372265 | A1 | 12/2015 | Morisaku et al. | |
| 2015/0374372 | A1 | 12/2015 | Zergiebel et al. | |
| 2015/0374378 | A1 | 12/2015 | Giordano et al. | |
| 2016/0000437 | A1 | 1/2016 | Giordano et al. | |
| 2016/0000452 | A1 | 1/2016 | Yates et al. | |
| 2016/0029998 | A1 | 2/2016 | Brister et al. | |
| 2016/0030042 | A1 | 2/2016 | Heinrich et al. | |
| 2016/0030043 | A1 | 2/2016 | Fanelli et al. | |
| 2016/0030076 | A1 | 2/2016 | Faller et al. | |
| 2016/0034167 | A1 | 2/2016 | Wilson et al. | |
| 2016/0047423 | A1 | 2/2016 | Bodtker | |
| 2016/0051316 | A1 | 2/2016 | Boudreaux | |
| 2016/0066913 | A1 | 3/2016 | Swayze et al. | |
| 2016/0069449 | A1 | 3/2016 | Kanai et al. | |
| 2016/0074035 | A1 | 3/2016 | Whitman et al. | |
| 2016/0074040 | A1 | 3/2016 | Widenhouse et al. | |
| 2016/0081678 | A1 | 3/2016 | Kappel et al. | |
| 2016/0082161 | A1 | 3/2016 | Zilberman et al. | |
| 2016/0089175 | A1 | 3/2016 | Hibner et al. | |
| 2016/0099601 | A1 | 4/2016 | Leabman et al. | |
| 2016/0100838 | A1 | 4/2016 | Beaupré et al. | |
| 2016/0118201 | A1 | 4/2016 | Nicholas et al. | |
| 2016/0132026 | A1 | 5/2016 | Wingardner et al. | |
| 2016/0135835 | A1 | 5/2016 | Onuma | |
| 2016/0135895 | A1 | 5/2016 | Faasse et al. | |
| 2016/0139666 | A1 | 5/2016 | Rubin et al. | |
| 2016/0166256 | A1* | 6/2016 | Baxter, III | A61B 17/115 227/176.1 |
| 2016/0174969 | A1 | 6/2016 | Kerr et al. | |
| 2016/0174983 | A1 | 6/2016 | Shelton, IV et al. | |
| 2016/0175021 | A1 | 6/2016 | Hassler, Jr. | |
| 2016/0183939 | A1 | 6/2016 | Shelton, IV et al. | |
| 2016/0183944 | A1 | 6/2016 | Swensgard et al. | |
| 2016/0192927 | A1 | 7/2016 | Kostrzewski | |
| 2016/0192960 | A1 | 7/2016 | Bueno et al. | |
| 2016/0199063 | A1 | 7/2016 | Mandakolathur Vasudevan et al. | |
| 2016/0199956 | A1 | 7/2016 | Shelton, IV et al. | |
| 2016/0220150 | A1 | 8/2016 | Sharonov | |
| 2016/0235494 | A1 | 8/2016 | Shelton, IV et al. | |
| 2016/0242783 | A1 | 8/2016 | Shelton, IV et al. | |
| 2016/0242855 | A1 | 8/2016 | Fichtinger et al. | |
| 2016/0249910 | A1 | 9/2016 | Shelton, IV et al. | |
| 2016/0249922 | A1 | 9/2016 | Morgan et al. | |
| 2016/0249929 | A1 | 9/2016 | Cappola et al. | |
| 2016/0256159 | A1 | 9/2016 | Pinjala et al. | |
| 2016/0256184 | A1 | 9/2016 | Shelton, IV et al. | |
| 2016/0256221 | A1 | 9/2016 | Smith | |
| 2016/0256229 | A1 | 9/2016 | Morgan et al. | |
| 2016/0262745 | A1 | 9/2016 | Morgan et al. | |
| 2016/0262921 | A1 | 9/2016 | Balbierz et al. | |
| 2016/0270781 | A1 | 9/2016 | Scirica | |
| 2016/0287265 | A1 | 10/2016 | Macdonald et al. | |
| 2016/0287279 | A1 | 10/2016 | Bovay et al. | |
| 2016/0302820 | A1 | 10/2016 | Hibner et al. | |
| 2016/0310143 | A1 | 10/2016 | Bettuchi | |
| 2016/0314716 | A1 | 10/2016 | Grubbs | |
| 2016/0314717 | A1 | 10/2016 | Grubbs | |
| 2016/0345972 | A1 | 12/2016 | Beardsley et al. | |
| 2016/0367122 | A1 | 12/2016 | Ichimura et al. | |
| 2016/0374669 | A1 | 12/2016 | Overmyer et al. | |
| 2016/0374716 | A1 | 12/2016 | Kessler | |
| 2017/0000549 | A1 | 1/2017 | Gilbert et al. | |
| 2017/0007234 | A1 | 1/2017 | Chin et al. | |
| 2017/0007244 | A1 | 1/2017 | Shelton, IV et al. | |
| 2017/0007245 | A1 | 1/2017 | Shelton, IV et al. | |
| 2017/0007347 | A1 | 1/2017 | Jaworek et al. | |
| 2017/0020616 | A1 | 1/2017 | Vale et al. | |
| 2017/0035419 | A1 | 2/2017 | Decker et al. | |
| 2017/0055819 | A1 | 3/2017 | Hansen et al. | |
| 2017/0055980 | A1 | 3/2017 | Vendely et al. | |
| 2017/0056008 | A1 | 3/2017 | Shelton, IV et al. | |
| 2017/0056016 | A1 | 3/2017 | Barton et al. | |
| 2017/0056018 | A1 | 3/2017 | Zeiner et al. | |
| 2017/0066054 | A1 | 3/2017 | Birky | |
| 2017/0066147 | A1 | 3/2017 | Ball et al. | |
| 2017/0079642 | A1 | 3/2017 | Overmyer et al. | |
| 2017/0086829 | A1 | 3/2017 | Vendely et al. | |
| 2017/0086830 | A1 | 3/2017 | Yates et al. | |
| 2017/0086930 | A1 | 3/2017 | Thompson et al. | |
| 2017/0086932 | A1 | 3/2017 | Auld et al. | |
| 2017/0095252 | A1 | 4/2017 | Smith et al. | |
| 2017/0095922 | A1 | 4/2017 | Licht et al. | |
| 2017/0105727 | A1 | 4/2017 | Scheib et al. | |
| 2017/0105733 | A1 | 4/2017 | Scheib et al. | |
| 2017/0105786 | A1 | 4/2017 | Scheib et al. | |
| 2017/0106302 | A1 | 4/2017 | Cummings et al. | |
| 2017/0135711 | A1 | 5/2017 | Overmyer et al. | |
| 2017/0135717 | A1 | 5/2017 | Boudreaux et al. | |
| 2017/0135747 | A1 | 5/2017 | Broderick et al. | |
| 2017/0143336 | A1 | 5/2017 | Shah et al. | |
| 2017/0168187 | A1 | 6/2017 | Calderoni et al. | |
| 2017/0172382 | A1 | 6/2017 | Nir et al. | |
| 2017/0172549 | A1 | 6/2017 | Smaby et al. | |
| 2017/0172662 | A1 | 6/2017 | Panescu et al. | |
| 2017/0181803 | A1 | 6/2017 | Mayer-Ullmann et al. | |
| 2017/0182195 | A1 | 6/2017 | Wagner | |
| 2017/0182211 | A1 | 6/2017 | Raxworthy et al. | |
| 2017/0196558 | A1 | 7/2017 | Morgan et al. | |
| 2017/0196649 | A1 | 7/2017 | Yates et al. | |
| 2017/0202605 | A1 | 7/2017 | Shelton, IV et al. | |
| 2017/0202607 | A1 | 7/2017 | Shelton, IV et al. | |
| 2017/0202770 | A1 | 7/2017 | Friedrich et al. | |
| 2017/0224332 | A1 | 8/2017 | Hunter et al. | |
| 2017/0224428 | A1 | 8/2017 | Kopp | |
| 2017/0231628 | A1 | 8/2017 | Shelton, IV et al. | |
| 2017/0231629 | A1 | 8/2017 | Stopek et al. | |
| 2017/0238962 | A1 | 8/2017 | Hansen et al. | |
| 2017/0238991 | A1 | 8/2017 | Worrell et al. | |
| 2017/0242455 | A1 | 8/2017 | Dickens | |
| 2017/0245880 | A1 | 8/2017 | Honda et al. | |
| 2017/0245949 | A1 | 8/2017 | Randle | |

(56) References Cited

U.S. PATENT DOCUMENTS

2017/0249431 A1 8/2017 Shelton, IV et al.
2017/0252060 A1 9/2017 Ellingson et al.
2017/0255799 A1 9/2017 Zhao et al.
2017/0258471 A1 9/2017 DiNardo et al.
2017/0262110 A1 9/2017 Polishchuk et al.
2017/0265774 A1 9/2017 Johnson et al.
2017/0281186 A1 10/2017 Shelton, IV et al.
2017/0296173 A1 10/2017 Shelton, IV et al.
2017/0303984 A1 10/2017 Malackowski
2017/0308665 A1 10/2017 Heck et al.
2017/0312042 A1 11/2017 Giordano et al.
2017/0319047 A1 11/2017 Poulsen et al.
2017/0319201 A1 11/2017 Morgan et al.
2017/0333034 A1 11/2017 Morgan et al.
2017/0333035 A1 11/2017 Morgan et al.
2017/0340325 A1 11/2017 Baril et al.
2017/0348010 A1 12/2017 Chiang
2017/0348042 A1 12/2017 Drochner et al.
2017/0348043 A1 12/2017 Wang et al.
2017/0354413 A1 12/2017 Chen et al.
2017/0358052 A1 12/2017 Yuan
2017/0360441 A1 12/2017 Sgroi
2018/0008265 A1 1/2018 Hatanaka et al.
2018/0036024 A1 2/2018 Allen, IV
2018/0036025 A1 2/2018 Drochner et al.
2018/0042610 A1 2/2018 Sgroi, Jr.
2018/0042689 A1 2/2018 Mozdzierz et al.
2018/0049738 A1 2/2018 Meloul et al.
2018/0049794 A1 2/2018 Swayze et al.
2018/0051780 A1 2/2018 Shelton, IV et al.
2018/0055501 A1 3/2018 Zemlok et al.
2018/0067004 A1 3/2018 Sgroi, Jr.
2018/0085117 A1 3/2018 Shelton, IV et al.
2018/0085120 A1 3/2018 Viola
2018/0092710 A1 4/2018 Bosisio et al.
2018/0114591 A1 4/2018 Pribanic et al.
2018/0116658 A1 5/2018 Aronhalt, IV et al.
2018/0125481 A1 5/2018 Yates et al.
2018/0125487 A1 5/2018 Beardsley
2018/0125488 A1 5/2018 Morgan et al.
2018/0125594 A1 5/2018 Beardsley
2018/0132849 A1 5/2018 Miller et al.
2018/0132850 A1 5/2018 Leimbach et al.
2018/0132926 A1 5/2018 Asher et al.
2018/0132952 A1 5/2018 Spivey et al.
2018/0133521 A1 5/2018 Frushour et al.
2018/0140299 A1 5/2018 Weaner et al.
2018/0146960 A1 5/2018 Shelton, IV et al.
2018/0153542 A1 6/2018 Shelton, IV et al.
2018/0153634 A1 6/2018 Zemlok et al.
2018/0161034 A1 6/2018 Scheib et al.
2018/0168572 A1 6/2018 Burbank
2018/0168574 A1 6/2018 Robinson et al.
2018/0168575 A1 6/2018 Simms et al.
2018/0168577 A1 6/2018 Aronhalt et al.
2018/0168579 A1 6/2018 Aronhalt et al.
2018/0168598 A1 6/2018 Shelton, IV et al.
2018/0168608 A1 6/2018 Shelton, IV et al.
2018/0168609 A1 6/2018 Fanelli et al.
2018/0168615 A1 6/2018 Shelton, IV et al.
2018/0168618 A1 6/2018 Scott et al.
2018/0168619 A1 6/2018 Scott et al.
2018/0168623 A1 6/2018 Simms et al.
2018/0168625 A1 6/2018 Posada et al.
2018/0168633 A1 6/2018 Shelton, IV et al.
2018/0168647 A1 6/2018 Shelton, IV et al.
2018/0168648 A1 6/2018 Shelton, IV et al.
2018/0168650 A1 6/2018 Shelton, IV et al.
2018/0168754 A1 6/2018 Overmyer
2018/0168756 A1 6/2018 Liao et al.
2018/0206904 A1 7/2018 Felder et al.
2018/0228490 A1 8/2018 Richard et al.
2018/0231111 A1 8/2018 Mika et al.
2018/0231475 A1 8/2018 Brown et al.
2018/0235609 A1 8/2018 Harris et al.
2018/0235617 A1 8/2018 Shelton, IV et al.
2018/0235618 A1 8/2018 Kostrzewski
2018/0235626 A1 8/2018 Shelton, IV et al.
2018/0236181 A1 8/2018 Marlin et al.
2018/0242970 A1 8/2018 Mozdzierz
2018/0247711 A1 8/2018 Terry
2018/0250002 A1 9/2018 Eschbach
2018/0271526 A1 9/2018 Zammataro
2018/0271553 A1 9/2018 Worrell
2018/0271604 A1 9/2018 Grout et al.
2018/0273597 A1 9/2018 Stimson
2018/0279994 A1 10/2018 Schaer et al.
2018/0280026 A1 10/2018 Zhang et al.
2018/0280073 A1 10/2018 Sanai et al.
2018/0289371 A1 10/2018 Wang et al.
2018/0296216 A1 10/2018 Shelton, IV et al.
2018/0296290 A1 10/2018 Namiki et al.
2018/0310995 A1 11/2018 Gliner et al.
2018/0317905 A1 11/2018 Olson et al.
2018/0317915 A1 11/2018 Mcdonald, II
2018/0325514 A1 11/2018 Harris et al.
2018/0333169 A1 11/2018 Leimbach et al.
2018/0360456 A1 12/2018 Shelton, IV et al.
2018/0368066 A1 12/2018 Howell et al.
2018/0368844 A1 12/2018 Bakos et al.
2018/0372806 A1 12/2018 Laughery et al.
2018/0375165 A1 12/2018 Shelton, IV et al.
2019/0000459 A1 1/2019 Shelton, IV et al.
2019/0000461 A1 1/2019 Shelton, IV et al.
2019/0000481 A1 1/2019 Harris et al.
2019/0000533 A1 1/2019 Messerly et al.
2019/0000535 A1 1/2019 Messerly et al.
2019/0000536 A1 1/2019 Yates et al.
2019/0006047 A1 1/2019 Gorek et al.
2019/0008515 A1 1/2019 Beardsley et al.
2019/0015102 A1 1/2019 Baber et al.
2019/0015165 A1 1/2019 Giordano et al.
2019/0017311 A1 1/2019 McGettrick et al.
2019/0021733 A1 1/2019 Burbank
2019/0029682 A1 1/2019 Huitema et al.
2019/0038281 A1 2/2019 Shelton, IV et al.
2019/0038283 A1 2/2019 Shelton, IV et al.
2019/0038285 A1 2/2019 Mozdzierz
2019/0059888 A1 2/2019 Shelton, IV et al.
2019/0059890 A1 2/2019 Shelton, IV et al.
2019/0059891 A1 2/2019 Shelton, IV et al.
2019/0059984 A1 2/2019 Otrembiak et al.
2019/0059986 A1 2/2019 Shelton, IV et al.
2019/0076143 A1 3/2019 Smith
2019/0090871 A1 3/2019 Shelton, IV et al.
2019/0091183 A1 3/2019 Tomat et al.
2019/0104919 A1 4/2019 Shelton, IV et al.
2019/0105035 A1 4/2019 Shelton, IV et al.
2019/0105036 A1 4/2019 Morgan et al.
2019/0105037 A1 4/2019 Morgan et al.
2019/0105039 A1 4/2019 Morgan et al.
2019/0105044 A1 4/2019 Shelton, IV et al.
2019/0110779 A1 4/2019 Gardner et al.
2019/0110791 A1 4/2019 Shelton, IV et al.
2019/0117220 A1 4/2019 Nativ et al.
2019/0117224 A1 4/2019 Setser et al.
2019/0117287 A1 4/2019 Nativ et al.
2019/0122840 A1 4/2019 Zergiebel et al.
2019/0125320 A1 5/2019 Shelton, IV et al.
2019/0125336 A1 5/2019 Deck et al.
2019/0125342 A1 5/2019 Beardsley et al.
2019/0125344 A1 5/2019 DiNardo et al.
2019/0125361 A1 5/2019 Shelton, IV et al.
2019/0125432 A1 5/2019 Shelton, IV et al.
2019/0125476 A1 5/2019 Shelton, IV et al.
2019/0133422 A1 5/2019 Nakamura
2019/0133577 A1 5/2019 Weadock et al.
2019/0137349 A1 5/2019 Collins et al.
2019/0138770 A1 5/2019 Compaijen et al.
2019/0142423 A1 5/2019 Satti, III et al.
2019/0142506 A1 5/2019 Miyajima et al.
2019/0150925 A1 5/2019 Marczyk et al.
2019/0151029 A1 5/2019 Robinson
2019/0175847 A1 6/2019 Pocreva, III et al.

(56) References Cited

U.S. PATENT DOCUMENTS

| | | | |
|---|---|---|---|
| 2019/0183502 | A1 | 6/2019 | Shelton, IV et al. |
| 2019/0192147 | A1 | 6/2019 | Shelton, IV et al. |
| 2019/0192148 | A1 | 6/2019 | Shelton, IV et al. |
| 2019/0192151 | A1 | 6/2019 | Shelton, IV et al. |
| 2019/0192155 | A1 | 6/2019 | Shelton, IV et al. |
| 2019/0200844 | A1 | 7/2019 | Shelton, IV et al. |
| 2019/0200905 | A1 | 7/2019 | Shelton, IV et al. |
| 2019/0200906 | A1 | 7/2019 | Shelton, IV et al. |
| 2019/0200977 | A1 | 7/2019 | Shelton, IV et al. |
| 2019/0200981 | A1 | 7/2019 | Harris et al. |
| 2019/0200986 | A1 | 7/2019 | Shelton, IV et al. |
| 2019/0200987 | A1 | 7/2019 | Shelton, IV et al. |
| 2019/0200989 | A1 | 7/2019 | Burbank et al. |
| 2019/0200997 | A1 | 7/2019 | Shelton, IV et al. |
| 2019/0200998 | A1 | 7/2019 | Shelton, IV et al. |
| 2019/0201020 | A1 | 7/2019 | Shelton, IV et al. |
| 2019/0201024 | A1 | 7/2019 | Shelton, IV et al. |
| 2019/0201027 | A1 | 7/2019 | Shelton, IV et al. |
| 2019/0201029 | A1 | 7/2019 | Shelton, IV et al. |
| 2019/0201030 | A1 | 7/2019 | Shelton, IV et al. |
| 2019/0201034 | A1 | 7/2019 | Shelton, IV et al. |
| 2019/0201045 | A1 | 7/2019 | Yates et al. |
| 2019/0201079 | A1 | 7/2019 | Shelton, IV et al. |
| 2019/0201112 | A1 | 7/2019 | Wiener et al. |
| 2019/0201113 | A1 | 7/2019 | Shelton, IV et al. |
| 2019/0201115 | A1 | 7/2019 | Shelton, IV et al. |
| 2019/0201118 | A1 | 7/2019 | Shelton, IV et al. |
| 2019/0201139 | A1 | 7/2019 | Shelton, IV et al. |
| 2019/0201140 | A1 | 7/2019 | Yates et al. |
| 2019/0201142 | A1 | 7/2019 | Shelton, IV et al. |
| 2019/0201146 | A1 | 7/2019 | Shelton, IV et al. |
| 2019/0201158 | A1 | 7/2019 | Shelton, IV et al. |
| 2019/0201594 | A1 | 7/2019 | Shelton, IV et al. |
| 2019/0205567 | A1 | 7/2019 | Shelton, IV et al. |
| 2019/0206555 | A1 | 7/2019 | Morgan et al. |
| 2019/0206561 | A1 | 7/2019 | Shelton, IV et al. |
| 2019/0206564 | A1 | 7/2019 | Shelton, IV et al. |
| 2019/0206569 | A1 | 7/2019 | Shelton, IV et al. |
| 2019/0209248 | A1 | 7/2019 | Giordano et al. |
| 2019/0209249 | A1 | 7/2019 | Giordano et al. |
| 2019/0209250 | A1 | 7/2019 | Giordano et al. |
| 2019/0239873 | A1 | 8/2019 | Laurent et al. |
| 2019/0247048 | A1 | 8/2019 | Gasparovich et al. |
| 2019/0261982 | A1 | 8/2019 | Holsten |
| 2019/0261983 | A1 | 8/2019 | Granger et al. |
| 2019/0261984 | A1 | 8/2019 | Nelson et al. |
| 2019/0261987 | A1 | 8/2019 | Viola et al. |
| 2019/0262153 | A1 | 8/2019 | Tassoni et al. |
| 2019/0269400 | A1 | 9/2019 | Mandakolathur Vasudevan et al. |
| 2019/0269402 | A1 | 9/2019 | Murray et al. |
| 2019/0269428 | A1 | 9/2019 | Allen et al. |
| 2019/0274685 | A1 | 9/2019 | Olson et al. |
| 2019/0274716 | A1 | 9/2019 | Nott et al. |
| 2019/0282233 | A1 | 9/2019 | Burbank et al. |
| 2019/0290264 | A1 | 9/2019 | Morgan et al. |
| 2019/0290266 | A1 | 9/2019 | Scheib et al. |
| 2019/0290297 | A1 | 9/2019 | Haider et al. |
| 2019/0298353 | A1 | 10/2019 | Shelton, IV et al. |
| 2019/0298361 | A1 | 10/2019 | Shelton, IV et al. |
| 2019/0298362 | A1 | 10/2019 | Shelton, IV et al. |
| 2019/0298381 | A1 | 10/2019 | Kreidler et al. |
| 2019/0307452 | A1 | 10/2019 | Shelton, IV et al. |
| 2019/0307453 | A1 | 10/2019 | Shelton, IV et al. |
| 2019/0307454 | A1 | 10/2019 | Shelton, IV et al. |
| 2019/0307456 | A1 | 10/2019 | Shelton, IV et al. |
| 2019/0314015 | A1 | 10/2019 | Shelton, IV et al. |
| 2019/0321062 | A1 | 10/2019 | Williams |
| 2019/0328387 | A1 | 10/2019 | Overmyer et al. |
| 2019/0339224 | A1 | 11/2019 | Bhavaraju et al. |
| 2019/0388091 | A1 | 12/2019 | Eschbach et al. |
| 2020/0008802 | A1 | 1/2020 | Aronhalt et al. |
| 2020/0008809 | A1 | 1/2020 | Shelton, IV et al. |
| 2020/0008827 | A1 | 1/2020 | Dearden et al. |
| 2020/0015817 | A1 | 1/2020 | Harris et al. |
| 2020/0015836 | A1 | 1/2020 | Nicholas et al. |
| 2020/0015915 | A1 | 1/2020 | Swayze et al. |
| 2020/0030020 | A1 | 1/2020 | Wang et al. |
| 2020/0037939 | A1 | 2/2020 | Castagna et al. |
| 2020/0038016 | A1 | 2/2020 | Shelton, IV et al. |
| 2020/0038018 | A1 | 2/2020 | Shelton, IV et al. |
| 2020/0038021 | A1 | 2/2020 | Contini et al. |
| 2020/0046355 | A1 | 2/2020 | Harris et al. |
| 2020/0046356 | A1 | 2/2020 | Baxter, III et al. |
| 2020/0054320 | A1 | 2/2020 | Harris et al. |
| 2020/0054321 | A1 | 2/2020 | Harris et al. |
| 2020/0054329 | A1 | 2/2020 | Shelton, IV et al. |
| 2020/0054332 | A1 | 2/2020 | Shelton, IV et al. |
| 2020/0054334 | A1 | 2/2020 | Shelton, IV et al. |
| 2020/0054355 | A1 | 2/2020 | Laurent et al. |
| 2020/0060523 | A1 | 2/2020 | Matsuda et al. |
| 2020/0060713 | A1 | 2/2020 | Leimbach et al. |
| 2020/0061385 | A1 | 2/2020 | Schwarz et al. |
| 2020/0085435 | A1 | 3/2020 | Shelton, IV et al. |
| 2020/0093484 | A1 | 3/2020 | Shelton, IV et al. |
| 2020/0093506 | A1 | 3/2020 | Leimbach et al. |
| 2020/0093550 | A1 | 3/2020 | Spivey et al. |
| 2020/0107829 | A1 | 4/2020 | Shelton, IV et al. |
| 2020/0113563 | A1 | 4/2020 | Gupta et al. |
| 2020/0114505 | A1 | 4/2020 | Kikuchi |
| 2020/0121377 | A1 | 4/2020 | Kitamura |
| 2020/0138507 | A1 | 5/2020 | Davison et al. |
| 2020/0138534 | A1 | 5/2020 | Garcia Kilroy et al. |
| 2020/0146166 | A1 | 5/2020 | Sgroi, Jr. |
| 2020/0146741 | A1 | 5/2020 | Long et al. |
| 2020/0187943 | A1 | 6/2020 | Shelton, IV et al. |
| 2020/0197027 | A1 | 6/2020 | Hershberger et al. |
| 2020/0205810 | A1 | 7/2020 | Posey et al. |
| 2020/0205811 | A1 | 7/2020 | Posey et al. |
| 2020/0205823 | A1 | 7/2020 | Vendely et al. |
| 2020/0214706 | A1 | 7/2020 | Vendely et al. |
| 2020/0214731 | A1 | 7/2020 | Shelton, IV et al. |
| 2020/0229814 | A1 | 7/2020 | Amariglio et al. |
| 2020/0237371 | A1 | 7/2020 | Huitema et al. |
| 2020/0268377 | A1 | 8/2020 | Schmid et al. |
| 2020/0268381 | A1 | 8/2020 | Roberts et al. |
| 2020/0275927 | A1 | 9/2020 | Shelton, IV et al. |
| 2020/0280219 | A1 | 9/2020 | Laughery et al. |
| 2020/0289112 | A1 | 9/2020 | Whitfield et al. |
| 2020/0289119 | A1 | 9/2020 | Viola et al. |
| 2020/0305863 | A1 | 10/2020 | Yates et al. |
| 2020/0305864 | A1 | 10/2020 | Yates et al. |
| 2020/0305872 | A1 | 10/2020 | Weidner et al. |
| 2020/0315623 | A1 | 10/2020 | Eisinger et al. |
| 2020/0323526 | A1 | 10/2020 | Huang et al. |
| 2020/0330181 | A1 | 10/2020 | Junger et al. |
| 2020/0337706 | A1 | 10/2020 | Truckai et al. |
| 2020/0345346 | A1 | 11/2020 | Shelton, IV et al. |
| 2020/0345349 | A1 | 11/2020 | Kimball et al. |
| 2020/0345352 | A1 | 11/2020 | Shelton, IV et al. |
| 2020/0345353 | A1 | 11/2020 | Leimbach et al. |
| 2020/0345356 | A1 | 11/2020 | Leimbach et al. |
| 2020/0345357 | A1 | 11/2020 | Leimbach et al. |
| 2020/0345359 | A1 | 11/2020 | Baxter, III et al. |
| 2020/0345363 | A1 | 11/2020 | Shelton, IV et al. |
| 2020/0345435 | A1 | 11/2020 | Traina |
| 2020/0352562 | A1 | 11/2020 | Timm et al. |
| 2020/0352569 | A1 | 11/2020 | Viola et al. |
| 2020/0367886 | A1 | 11/2020 | Shelton, IV et al. |
| 2020/0375585 | A1 | 12/2020 | Swayze et al. |
| 2020/0375597 | A1 | 12/2020 | Shelton, IV et al. |
| 2020/0390444 | A1 | 12/2020 | Harris et al. |
| 2020/0397430 | A1 | 12/2020 | Patel et al. |
| 2020/0397439 | A1 | 12/2020 | Eisinger |
| 2020/0405292 | A1 | 12/2020 | Shelton, IV et al. |
| 2020/0405302 | A1 | 12/2020 | Shelton, IV et al. |
| 2020/0405304 | A1 | 12/2020 | Mozdzierz et al. |
| 2020/0405306 | A1 | 12/2020 | Shelton, IV et al. |
| 2020/0405307 | A1 | 12/2020 | Shelton, IV et al. |
| 2020/0405308 | A1 | 12/2020 | Shelton, IV |
| 2020/0405375 | A1 | 12/2020 | Shelton, IV et al. |
| 2020/0405403 | A1 | 12/2020 | Shelton, IV et al. |
| 2021/0000466 | A1 | 1/2021 | Leimbach et al. |
| 2021/0000467 | A1 | 1/2021 | Shelton, IV et al. |
| 2021/0007742 | A1 | 1/2021 | Rector et al. |

(56) References Cited

U.S. PATENT DOCUMENTS

| | | | |
|---|---|---|---|
| 2021/0007826 | A1 | 1/2021 | Shafer et al. |
| 2021/0015480 | A1 | 1/2021 | Shelton, IV et al. |
| 2021/0045742 | A1 | 2/2021 | Shelton, IV et al. |
| 2021/0059661 | A1 | 3/2021 | Schmid et al. |
| 2021/0059662 | A1 | 3/2021 | Shelton, IV |
| 2021/0059664 | A1 | 3/2021 | Hensel et al. |
| 2021/0059670 | A1 | 3/2021 | Overmyer et al. |
| 2021/0059673 | A1 | 3/2021 | Shelton, IV et al. |
| 2021/0068829 | A1 | 3/2021 | Miller et al. |
| 2021/0068835 | A1 | 3/2021 | Shelton, IV et al. |
| 2021/0077099 | A1 | 3/2021 | Shelton, IV et al. |
| 2021/0077109 | A1 | 3/2021 | Harris et al. |
| 2021/0084700 | A1 | 3/2021 | Daniels |
| 2021/0085313 | A1 | 3/2021 | Morgan et al. |
| 2021/0085315 | A1 | 3/2021 | Aronhalt et al. |
| 2021/0085316 | A1 | 3/2021 | Harris et al. |
| 2021/0085320 | A1 | 3/2021 | Leimbach et al. |
| 2021/0085321 | A1 | 3/2021 | Shelton, IV et al. |
| 2021/0085325 | A1 | 3/2021 | Shelton, IV et al. |
| 2021/0093321 | A1 | 4/2021 | Auld et al. |
| 2021/0093323 | A1 | 4/2021 | Scirica et al. |
| 2021/0100541 | A1 | 4/2021 | Shelton, IV et al. |
| 2021/0100982 | A1 | 4/2021 | Laby et al. |
| 2021/0107031 | A1 | 4/2021 | Bales, Jr. et al. |
| 2021/0128153 | A1 | 5/2021 | Sgroi |
| 2021/0137522 | A1 | 5/2021 | Shelton, IV et al. |
| 2021/0145441 | A1 | 5/2021 | Weir et al. |
| 2021/0153866 | A1 | 5/2021 | Knapp et al. |
| 2021/0177401 | A1 | 6/2021 | Abramek et al. |
| 2021/0177411 | A1 | 6/2021 | Williams |
| 2021/0177528 | A1 | 6/2021 | Cappelleri et al. |
| 2021/0186492 | A1 | 6/2021 | Shelton, IV et al. |
| 2021/0186497 | A1 | 6/2021 | Shelton, IV et al. |
| 2021/0186499 | A1 | 6/2021 | Shelton, IV et al. |
| 2021/0186501 | A1 | 6/2021 | Shelton, IV et al. |
| 2021/0196265 | A1 | 7/2021 | Shelton, IV et al. |
| 2021/0196269 | A1 | 7/2021 | Shelton, IV et al. |
| 2021/0196270 | A1 | 7/2021 | Shelton, IV et al. |
| 2021/0196425 | A1 | 7/2021 | Shelton, IV et al. |
| 2021/0204941 | A1 | 7/2021 | Dewaele et al. |
| 2021/0204951 | A1 | 7/2021 | Sgroi et al. |
| 2021/0212671 | A1 | 7/2021 | Ramadan et al. |
| 2021/0212776 | A1 | 7/2021 | Schmitt et al. |
| 2021/0225140 | A1 | 7/2021 | Adachi et al. |
| 2021/0228209 | A1 | 7/2021 | Shelton, IV et al. |
| 2021/0244407 | A1 | 8/2021 | Shelton, IV et al. |
| 2021/0244411 | A1 | 8/2021 | Smith et al. |
| 2021/0251720 | A1 | 8/2021 | Jhaveri et al. |
| 2021/0259681 | A1 | 8/2021 | Shelton, IV et al. |
| 2021/0259687 | A1 | 8/2021 | Gonzalez et al. |
| 2021/0259790 | A1 | 8/2021 | Kaiser |
| 2021/0259986 | A1 | 8/2021 | Widenhouse et al. |
| 2021/0267589 | A1 | 9/2021 | Swayze et al. |
| 2021/0267594 | A1 | 9/2021 | Morgan et al. |
| 2021/0267595 | A1 | 9/2021 | Posada et al. |
| 2021/0267596 | A1 | 9/2021 | Fanelli et al. |
| 2021/0275172 | A1 | 9/2021 | Harris et al. |
| 2021/0275173 | A1 | 9/2021 | Shelton, IV et al. |
| 2021/0275175 | A1 | 9/2021 | Vadali et al. |
| 2021/0282767 | A1 | 9/2021 | Shelton, IV et al. |
| 2021/0282776 | A1 | 9/2021 | Overmyer et al. |
| 2021/0290226 | A1 | 9/2021 | Mandakolathur Vasudevan et al. |
| 2021/0290232 | A1 | 9/2021 | Harris et al. |
| 2021/0290233 | A1 | 9/2021 | Shelton, IV et al. |
| 2021/0290236 | A1 | 9/2021 | Moore et al. |
| 2021/0290322 | A1 | 9/2021 | Traina |
| 2021/0298745 | A1 | 9/2021 | Leimbach et al. |
| 2021/0298746 | A1 | 9/2021 | Leimbach et al. |
| 2021/0307657 | A1 | 10/2021 | Halac et al. |
| 2021/0307695 | A1 | 10/2021 | Halac et al. |
| 2021/0307744 | A1 | 10/2021 | Walcott et al. |
| 2021/0307748 | A1 | 10/2021 | Harris et al. |
| 2021/0313975 | A1 | 10/2021 | Shan et al. |
| 2021/0315573 | A1 | 10/2021 | Shelton, IV et al. |
| 2021/0315574 | A1 | 10/2021 | Shelton, IV et al. |
| 2021/0315576 | A1 | 10/2021 | Shelton, IV et al. |
| 2021/0315577 | A1 | 10/2021 | Shelton, IV et al. |
| 2021/0322009 | A1 | 10/2021 | Huang et al. |
| 2021/0330321 | A1 | 10/2021 | Leimbach et al. |
| 2021/0338233 | A1 | 11/2021 | Shelton, IV et al. |
| 2021/0338234 | A1 | 11/2021 | Shelton, IV et al. |
| 2021/0338260 | A1 | 11/2021 | Le Rolland et al. |
| 2021/0346082 | A1 | 11/2021 | Adams et al. |
| 2021/0353284 | A1 | 11/2021 | Yang et al. |
| 2021/0369271 | A1 | 12/2021 | Schings et al. |
| 2021/0378669 | A1 | 12/2021 | Shelton, IV et al. |
| 2021/0393366 | A1 | 12/2021 | Shelton, IV et al. |
| 2021/0401487 | A1 | 12/2021 | Apostolopoulos et al. |
| 2021/0401513 | A1 | 12/2021 | Apostolopoulos et al. |
| 2022/0000479 | A1 | 1/2022 | Shelton, IV et al. |
| 2022/0015760 | A1 | 1/2022 | Beardsley et al. |
| 2022/0031315 | A1 | 2/2022 | Bakos et al. |
| 2022/0031319 | A1 | 2/2022 | Witte et al. |
| 2022/0031320 | A1 | 2/2022 | Hall et al. |
| 2022/0031322 | A1 | 2/2022 | Parks |
| 2022/0031323 | A1 | 2/2022 | Witte |
| 2022/0031324 | A1 | 2/2022 | Hall et al. |
| 2022/0031345 | A1 | 2/2022 | Witte |
| 2022/0031346 | A1 | 2/2022 | Parks |
| 2022/0031350 | A1 | 2/2022 | Witte |
| 2022/0031351 | A1 | 2/2022 | Moubarak et al. |
| 2022/0049593 | A1 | 2/2022 | Groover et al. |
| 2022/0054125 | A1 | 2/2022 | Ji et al. |
| 2022/0054130 | A1 | 2/2022 | Overmyer et al. |
| 2022/0061642 | A1 | 3/2022 | Park et al. |
| 2022/0061836 | A1 | 3/2022 | Parihar et al. |
| 2022/0061842 | A1 | 3/2022 | Shelton, IV et al. |
| 2022/0061843 | A1 | 3/2022 | Vendely et al. |
| 2022/0061845 | A1 | 3/2022 | Shelton, IV et al. |
| 2022/0061862 | A1 | 3/2022 | Shelton, IV et al. |
| 2022/0071631 | A1 | 3/2022 | Harris et al. |
| 2022/0071632 | A1 | 3/2022 | Patel et al. |
| 2022/0071635 | A1 | 3/2022 | Shelton, IV et al. |
| 2022/0079580 | A1 | 3/2022 | Vendely et al. |
| 2022/0079586 | A1 | 3/2022 | Shelton, IV et al. |
| 2022/0079588 | A1 | 3/2022 | Harris et al. |
| 2022/0079589 | A1 | 3/2022 | Harris et al. |
| 2022/0079595 | A1 | 3/2022 | Huitema et al. |
| 2022/0079596 | A1 | 3/2022 | Huitema et al. |
| 2022/0104695 | A1 | 4/2022 | Russell |
| 2022/0104814 | A1 | 4/2022 | Shelton, IV et al. |
| 2022/0104816 | A1 | 4/2022 | Fernandes et al. |
| 2022/0104820 | A1 | 4/2022 | Shelton, IV et al. |
| 2022/0110673 | A1 | 4/2022 | Boronyak et al. |
| 2022/0117602 | A1 | 4/2022 | Wise et al. |
| 2022/0125472 | A1 | 4/2022 | Beckman et al. |
| 2022/0133299 | A1 | 5/2022 | Baxter, III |
| 2022/0133300 | A1 | 5/2022 | Leimbach et al. |
| 2022/0133302 | A1 | 5/2022 | Zerkle et al. |
| 2022/0133303 | A1 | 5/2022 | Huang |
| 2022/0133310 | A1 | 5/2022 | Ross |
| 2022/0133312 | A1 | 5/2022 | Huang |
| 2022/0133318 | A1 | 5/2022 | Hudson et al. |
| 2022/0142643 | A1 | 5/2022 | Shelton, IV et al. |
| 2022/0151611 | A1 | 5/2022 | Shelton, IV et al. |
| 2022/0151614 | A1 | 5/2022 | Vendely et al. |
| 2022/0151616 | A1 | 5/2022 | Shelton, IV et al. |
| 2022/0160355 | A1 | 5/2022 | Harris et al. |
| 2022/0160358 | A1 | 5/2022 | Wixey |
| 2022/0167970 | A1 | 6/2022 | Aronhalt et al. |
| 2022/0167972 | A1 | 6/2022 | Shelton, IV et al. |
| 2022/0167973 | A1 | 6/2022 | Shelton, IV et al. |
| 2022/0167977 | A1 | 6/2022 | Shelton, IV et al. |
| 2022/0167979 | A1 | 6/2022 | Yates et al. |
| 2022/0167981 | A1 | 6/2022 | Shelton, IV et al. |
| 2022/0167982 | A1 | 6/2022 | Shelton, IV et al. |
| 2022/0167995 | A1 | 6/2022 | Parfett et al. |
| 2022/0168038 | A1 | 6/2022 | Shelton, IV et al. |
| 2022/0175370 | A1 | 6/2022 | Shelton, IV et al. |
| 2022/0175372 | A1 | 6/2022 | Shelton, IV et al. |
| 2022/0175375 | A1 | 6/2022 | Harris et al. |
| 2022/0175378 | A1 | 6/2022 | Leimbach et al. |
| 2022/0175381 | A1 | 6/2022 | Scheib et al. |
| 2022/0183685 | A1 | 6/2022 | Shelton, IV et al. |

(56) References Cited

U.S. PATENT DOCUMENTS

| | | | |
|---|---|---|---|
| 2022/0183687 | A1 | 6/2022 | Wixey et al. |
| 2022/0202487 | A1 | 6/2022 | Shelton, IV et al. |
| 2022/0211367 | A1 | 7/2022 | Schmid et al. |
| 2022/0218332 | A1 | 7/2022 | Shelton, IV et al. |
| 2022/0218338 | A1 | 7/2022 | Shelton, IV et al. |
| 2022/0218344 | A1 | 7/2022 | Leimbach et al. |
| 2022/0218345 | A1 | 7/2022 | Shelton, IV et al. |
| 2022/0218346 | A1 | 7/2022 | Shelton, IV et al. |
| 2022/0218348 | A1 | 7/2022 | Swensgard et al. |
| 2022/0218349 | A1 | 7/2022 | Shelton, IV et al. |
| 2022/0218350 | A1 | 7/2022 | Shelton, IV et al. |
| 2022/0218351 | A1 | 7/2022 | Shelton, IV et al. |
| 2022/0218376 | A1 | 7/2022 | Shelton, IV et al. |
| 2022/0218381 | A1 | 7/2022 | Leimbach et al. |
| 2022/0218382 | A1 | 7/2022 | Leimbach et al. |
| 2022/0225993 | A1 | 7/2022 | Huitema et al. |
| 2022/0225994 | A1 | 7/2022 | Setser et al. |
| 2022/0226013 | A1 | 7/2022 | Hall et al. |
| 2022/0233186 | A1 | 7/2022 | Timm et al. |
| 2022/0233188 | A1 | 7/2022 | Timm et al. |
| 2022/0233194 | A1 | 7/2022 | Baxter, III et al. |
| 2022/0233195 | A1 | 7/2022 | Shelton, IV et al. |
| 2022/0233257 | A1 | 7/2022 | Shelton, IV et al. |
| 2022/0240928 | A1 | 8/2022 | Timm et al. |
| 2022/0240929 | A1 | 8/2022 | Timm et al. |
| 2022/0240930 | A1 | 8/2022 | Yates et al. |
| 2022/0240936 | A1 | 8/2022 | Huitema et al. |
| 2022/0240937 | A1 | 8/2022 | Shelton, IV et al. |
| 2022/0265272 | A1 | 8/2022 | Li et al. |
| 2022/0273293 | A1 | 9/2022 | Shelton, IV et al. |
| 2022/0273294 | A1 | 9/2022 | Creamer et al. |
| 2022/0273300 | A1 | 9/2022 | Shelton, IV et al. |
| 2022/0273303 | A1 | 9/2022 | Creamer et al. |
| 2022/0273304 | A1 | 9/2022 | Shelton, IV et al. |
| 2022/0273306 | A1 | 9/2022 | Shelton, IV et al. |
| 2022/0273307 | A1 | 9/2022 | Shelton, IV et al. |
| 2022/0273308 | A1 | 9/2022 | Shelton, IV et al. |
| 2022/0287711 | A1 | 9/2022 | Ming et al. |
| 2022/0296230 | A1 | 9/2022 | Adams et al. |
| 2022/0304679 | A1 | 9/2022 | Bakos et al. |
| 2022/0304680 | A1 | 9/2022 | Shelton, IV et al. |
| 2022/0304681 | A1 | 9/2022 | Shelton, IV et al. |
| 2022/0304682 | A1 | 9/2022 | Shelton, IV et al. |
| 2022/0304683 | A1 | 9/2022 | Shelton, IV et al. |
| 2022/0304684 | A1 | 9/2022 | Bakos et al. |
| 2022/0304685 | A1 | 9/2022 | Bakos et al. |
| 2022/0304686 | A1 | 9/2022 | Shelton, IV et al. |
| 2022/0304687 | A1 | 9/2022 | Shelton, IV et al. |
| 2022/0304688 | A1 | 9/2022 | Shelton, IV et al. |
| 2022/0304689 | A1 | 9/2022 | Shelton, IV |
| 2022/0304690 | A1 | 9/2022 | Baxter, III et al. |
| 2022/0304715 | A1 | 9/2022 | Shelton, IV |
| 2022/0313253 | A1 | 10/2022 | Shelton, IV et al. |
| 2022/0313263 | A1 | 10/2022 | Huitema et al. |
| 2022/0313619 | A1 | 10/2022 | Schmid et al. |
| 2022/0323067 | A1 | 10/2022 | Overmyer et al. |
| 2022/0323070 | A1 | 10/2022 | Ross et al. |
| 2022/0330940 | A1 | 10/2022 | Shelton, IV et al. |
| 2022/0338870 | A1 | 10/2022 | Swayze et al. |
| 2022/0346774 | A1 | 11/2022 | Hess et al. |
| 2022/0346775 | A1 | 11/2022 | Hess et al. |
| 2022/0346776 | A1 | 11/2022 | Aronhalt et al. |
| 2022/0346781 | A1 | 11/2022 | Shelton, IV et al. |
| 2022/0346783 | A1 | 11/2022 | Shelton, IV et al. |
| 2022/0346785 | A1 | 11/2022 | Aronhalt et al. |
| 2022/0354492 | A1 | 11/2022 | Baril |
| 2022/0354493 | A1 | 11/2022 | Shelton, IV et al. |
| 2022/0354495 | A1 | 11/2022 | Baxter, III et al. |
| 2022/0361879 | A1 | 11/2022 | Baxter, III et al. |
| 2022/0370069 | A1 | 11/2022 | Simms et al. |
| 2022/0378418 | A1 | 12/2022 | Huang et al. |
| 2022/0378424 | A1 | 12/2022 | Huang et al. |
| 2022/0378425 | A1 | 12/2022 | Huang et al. |
| 2022/0378426 | A1 | 12/2022 | Huang et al. |
| 2022/0378428 | A1 | 12/2022 | Shelton, IV et al. |
| 2022/0378435 | A1 | 12/2022 | Dholakia et al. |
| 2022/0387031 | A1 | 12/2022 | Yates et al. |
| 2022/0387032 | A1 | 12/2022 | Huitema et al. |
| 2022/0387033 | A1 | 12/2022 | Huitema et al. |
| 2022/0387034 | A1 | 12/2022 | Huitema et al. |
| 2022/0387035 | A1 | 12/2022 | Huitema et al. |
| 2022/0387036 | A1 | 12/2022 | Huitema et al. |
| 2022/0387037 | A1 | 12/2022 | Huitema et al. |
| 2022/0387038 | A1 | 12/2022 | Huitema et al. |
| 2022/0387125 | A1 | 12/2022 | Leimbach et al. |
| 2023/0016171 | A1 | 1/2023 | Yates et al. |
| 2023/0018950 | A1 | 1/2023 | Shelton, IV et al. |
| 2023/0055711 | A1 | 2/2023 | Chen et al. |
| 2023/0088531 | A1 | 3/2023 | Hall et al. |
| 2023/0094712 | A1 | 3/2023 | Shelton, IV et al. |
| 2023/0120983 | A1 | 4/2023 | Stokes et al. |
| 2023/0121131 | A1 | 4/2023 | Swayze et al. |
| 2023/0121658 | A1 | 4/2023 | Stokes et al. |
| 2023/0133811 | A1 | 5/2023 | Huang |
| 2023/0134883 | A1 | 5/2023 | Leimbach |
| 2023/0135070 | A1 | 5/2023 | Shelton, IV et al. |
| 2023/0135282 | A1 | 5/2023 | Schings et al. |
| 2023/0135811 | A1 | 5/2023 | Guest |
| 2023/0138314 | A1 | 5/2023 | Jenkins |
| 2023/0138743 | A1 | 5/2023 | Ross et al. |
| 2023/0165582 | A1 | 6/2023 | Harris et al. |
| 2023/0165584 | A1 | 6/2023 | Leimbach et al. |
| 2023/0172607 | A1 | 6/2023 | DiNardo et al. |
| 2023/0200831 | A1 | 6/2023 | Swensgard et al. |
| 2023/0210525 | A1 | 7/2023 | Shelton, IV et al. |
| 2023/0218296 | A1 | 7/2023 | Yates et al. |
| 2023/0240677 | A1 | 8/2023 | Ming et al. |
| 2023/0240678 | A1 | 8/2023 | Overmyer et al. |
| 2023/0255631 | A1 | 8/2023 | Vendely et al. |
| 2023/0270438 | A1 | 8/2023 | Jaworek et al. |
| 2023/0277175 | A1 | 9/2023 | Shelton, IV et al. |
| 2023/0285021 | A1 | 9/2023 | Shelton, IV |
| 2023/0309992 | A1 | 10/2023 | Leimbach et al. |
| 2023/0320729 | A1 | 10/2023 | Yates et al. |
| 2023/0355238 | A1 | 11/2023 | Shelton, IV |
| 2023/0355345 | A1 | 11/2023 | Shelton, IV et al. |
| 2023/0371947 | A1 | 11/2023 | Shelton, IV et al. |
| 2023/0380833 | A1 | 11/2023 | Shelton, IV et al. |
| 2023/0389921 | A1 | 12/2023 | Swayze et al. |
| 2023/0389950 | A1 | 12/2023 | Shelton, IV et al. |
| 2023/0390003 | A1 | 12/2023 | Shelton, IV |

FOREIGN PATENT DOCUMENTS

| | | | |
|---|---|---|---|
| AU | 2012268848 | A1 | 1/2013 |
| AU | 2011218702 | B2 | 6/2013 |
| AU | 2012200178 | B2 | 7/2013 |
| BR | 112013007744 | A2 | 6/2016 |
| BR | 112013027777 | A2 | 1/2017 |
| CA | 1015829 | A | 8/1977 |
| CA | 1125615 | A | 6/1982 |
| CA | 2520413 | A1 | 3/2007 |
| CA | 2725181 | A1 | 11/2007 |
| CA | 2851239 | A1 | 11/2007 |
| CA | 2550059 | C | 8/2008 |
| CA | 2664874 | A1 | 11/2009 |
| CA | 2813230 | A1 | 4/2012 |
| CA | 2940510 | A1 | 8/2015 |
| CA | 2698728 | C | 8/2016 |
| CN | 1163558 | A | 10/1997 |
| CN | 2488482 | Y | 5/2002 |
| CN | 1634601 | A | 7/2005 |
| CN | 2716900 | Y | 8/2005 |
| CN | 2738962 | Y | 11/2005 |
| CN | 1777406 | A | 5/2006 |
| CN | 2785249 | Y | 5/2006 |
| CN | 2796654 | Y | 7/2006 |
| CN | 2868212 | Y | 2/2007 |
| CN | 200942099 | Y | 9/2007 |
| CN | 200984209 | Y | 12/2007 |
| CN | 200991269 | Y | 12/2007 |
| CN | 201001747 | Y | 1/2008 |
| CN | 101143105 | A | 3/2008 |
| CN | 201029899 | Y | 3/2008 |

(56) References Cited

FOREIGN PATENT DOCUMENTS

| | | | |
|---|---|---|---|
| CN | 101188900 | A | 5/2008 |
| CN | 101203085 | A | 6/2008 |
| CN | 101273908 | A | 10/2008 |
| CN | 101378791 | A | 3/2009 |
| CN | 101401736 | A | 4/2009 |
| CN | 101507635 | A | 8/2009 |
| CN | 101522120 | A | 9/2009 |
| CN | 101669833 | A | 3/2010 |
| CN | 101716090 | A | 6/2010 |
| CN | 101721236 | A | 6/2010 |
| CN | 101756727 | A | 6/2010 |
| CN | 101828940 | A | 9/2010 |
| CN | 101856250 | A | 10/2010 |
| CN | 101873834 | A | 10/2010 |
| CN | 201719298 | U | 1/2011 |
| CN | 102038532 | A | 5/2011 |
| CN | 201879759 | U | 6/2011 |
| CN | 201949071 | U | 8/2011 |
| CN | 102217961 | A | 10/2011 |
| CN | 102217963 | A | 10/2011 |
| CN | 102243850 | A | 11/2011 |
| CN | 102247182 | A | 11/2011 |
| CN | 102247183 | A | 11/2011 |
| CN | 101779977 | B | 12/2011 |
| CN | 102309352 | A | 1/2012 |
| CN | 101912284 | B | 7/2012 |
| CN | 102125450 | B | 7/2012 |
| CN | 202313537 | U | 7/2012 |
| CN | 202397539 | U | 8/2012 |
| CN | 202426586 | U | 9/2012 |
| CN | 102743201 | A | 10/2012 |
| CN | 202489990 | U | 10/2012 |
| CN | 102228387 | B | 11/2012 |
| CN | 102835977 | A | 12/2012 |
| CN | 202568350 | U | 12/2012 |
| CN | 103037781 | A | 4/2013 |
| CN | 103083053 | A | 5/2013 |
| CN | 103391037 | A | 11/2013 |
| CN | 203328751 | U | 12/2013 |
| CN | 103505264 | A | 1/2014 |
| CN | 103584893 | A | 2/2014 |
| CN | 103635150 | A | 3/2014 |
| CN | 103690212 | A | 4/2014 |
| CN | 103764046 | A | 4/2014 |
| CN | 203564285 | U | 4/2014 |
| CN | 203564287 | U | 4/2014 |
| CN | 203597997 | U | 5/2014 |
| CN | 103829981 | A | 6/2014 |
| CN | 103829983 | A | 6/2014 |
| CN | 103860221 | A | 6/2014 |
| CN | 103908313 | A | 7/2014 |
| CN | 203693685 | U | 7/2014 |
| CN | 203736251 | U | 7/2014 |
| CN | 103981635 | A | 8/2014 |
| CN | 104027145 | A | 9/2014 |
| CN | 203815517 | U | 9/2014 |
| CN | 102783741 | B | 10/2014 |
| CN | 102973300 | B | 10/2014 |
| CN | 104321021 | A | 1/2015 |
| CN | 204092074 | U | 1/2015 |
| CN | 104337556 | A | 2/2015 |
| CN | 204158440 | U | 2/2015 |
| CN | 204158441 | U | 2/2015 |
| CN | 102469995 | B | 3/2015 |
| CN | 104422849 | A | 3/2015 |
| CN | 104586463 | A | 5/2015 |
| CN | 204520822 | U | 8/2015 |
| CN | 204636451 | U | 9/2015 |
| CN | 103860225 | B | 3/2016 |
| CN | 103750872 | B | 5/2016 |
| CN | 105682566 | A | 6/2016 |
| CN | 105919642 | A | 9/2016 |
| CN | 103648410 | B | 10/2016 |
| CN | 105997173 | A | 10/2016 |
| CN | 106344091 | A | 1/2017 |
| CN | 104921730 | B | 9/2017 |
| CN | 104349800 | B | 11/2017 |
| CN | 107635483 | A | 1/2018 |
| CN | 208625784 | U | 3/2019 |
| DE | 273689 | C | 5/1914 |
| DE | 1775926 | A | 1/1972 |
| DE | 3036217 | A1 | 4/1982 |
| DE | 3210466 | A1 | 9/1983 |
| DE | 3709067 | A1 | 9/1988 |
| DE | 19534043 | A1 | 3/1997 |
| DE | 19851291 | A1 | 1/2000 |
| DE | 19924311 | A1 | 11/2000 |
| DE | 20016423 | U1 | 2/2001 |
| DE | 20112837 | U1 | 10/2001 |
| DE | 20121753 | U1 | 4/2003 |
| DE | 202004012389 | U1 | 9/2004 |
| DE | 10314072 | A1 | 10/2004 |
| DE | 102004014011 | A1 | 10/2005 |
| DE | 102004041871 | A1 | 3/2006 |
| DE | 102004063606 | A1 | 7/2006 |
| DE | 202007003114 | U1 | 6/2007 |
| DE | 102010013150 | A1 | 9/2011 |
| DE | 102012213322 | A1 | 1/2014 |
| DE | 102013101158 | A1 | 8/2014 |
| EM | 002220467-0008 | | 4/2013 |
| EP | 0000756 | A1 | 2/1979 |
| EP | 0122046 | A1 | 10/1984 |
| EP | 0129442 | B1 | 11/1987 |
| EP | 0251444 | A1 | 1/1988 |
| EP | 0255631 | A1 | 2/1988 |
| EP | 0169044 | B1 | 6/1991 |
| EP | 0541950 | A1 | 5/1993 |
| EP | 0548998 | A1 | 6/1993 |
| EP | 0594148 | A1 | 4/1994 |
| EP | 0646357 | A1 | 4/1995 |
| EP | 0505036 | B1 | 5/1995 |
| EP | 0669104 | A1 | 8/1995 |
| EP | 0516544 | B1 | 3/1996 |
| EP | 0705571 | A1 | 4/1996 |
| EP | 0528478 | B1 | 5/1996 |
| EP | 0770355 | A1 | 5/1997 |
| EP | 0625335 | B1 | 11/1997 |
| EP | 0879742 | A1 | 11/1998 |
| EP | 0650701 | B1 | 3/1999 |
| EP | 0923907 | A1 | 6/1999 |
| EP | 0484677 | B2 | 7/2000 |
| EP | 1034747 | A1 | 9/2000 |
| EP | 1034748 | A1 | 9/2000 |
| EP | 0726632 | B1 | 10/2000 |
| EP | 1053719 | A1 | 11/2000 |
| EP | 1055399 | A1 | 11/2000 |
| EP | 1055400 | A1 | 11/2000 |
| EP | 1064882 | A1 | 1/2001 |
| EP | 1080694 | A1 | 3/2001 |
| EP | 1090592 | A1 | 4/2001 |
| EP | 1095627 | A1 | 5/2001 |
| EP | 0806914 | B1 | 9/2001 |
| EP | 1157666 | A1 | 11/2001 |
| EP | 1234587 | A1 | 8/2002 |
| EP | 1284120 | A1 | 2/2003 |
| EP | 0717967 | B1 | 5/2003 |
| EP | 0869742 | B1 | 5/2003 |
| EP | 1374788 | A1 | 1/2004 |
| EP | 1407719 | A2 | 4/2004 |
| EP | 0996378 | B1 | 6/2004 |
| EP | 1558161 | A1 | 8/2005 |
| EP | 0880338 | B1 | 10/2005 |
| EP | 1158917 | B1 | 11/2005 |
| EP | 1344498 | B1 | 11/2005 |
| EP | 1330989 | B1 | 12/2005 |
| EP | 1632191 | A2 | 3/2006 |
| EP | 1082944 | B1 | 5/2006 |
| EP | 1253866 | B1 | 7/2006 |
| EP | 1723914 | A1 | 11/2006 |
| EP | 1285633 | B1 | 12/2006 |
| EP | 1011494 | B1 | 1/2007 |
| EP | 1767163 | A1 | 3/2007 |
| EP | 1837041 | A1 | 9/2007 |
| EP | 0922435 | B1 | 10/2007 |

(56) References Cited

FOREIGN PATENT DOCUMENTS

| | | | |
|---|---|---|---|
| EP | 1599146 | B1 | 10/2007 |
| EP | 1330201 | B1 | 6/2008 |
| EP | 2039302 | A2 | 3/2009 |
| EP | 1719461 | B1 | 6/2009 |
| EP | 2116196 | A2 | 11/2009 |
| EP | 2153793 | A2 | 2/2010 |
| EP | 1769754 | B1 | 6/2010 |
| EP | 1627605 | B1 | 12/2010 |
| EP | 2316345 | A1 | 5/2011 |
| EP | 1962711 | B1 | 2/2012 |
| EP | 2486862 | A2 | 8/2012 |
| EP | 2486868 | A2 | 8/2012 |
| EP | 2510891 | A1 | 10/2012 |
| EP | 2517638 | A1 | 10/2012 |
| EP | 2529671 | A2 | 12/2012 |
| EP | 2606812 | A1 | 6/2013 |
| EP | 2649948 | A1 | 10/2013 |
| EP | 2649949 | A1 | 10/2013 |
| EP | 2668910 | A2 | 12/2013 |
| EP | 2687164 | A2 | 1/2014 |
| EP | 2713902 | A1 | 4/2014 |
| EP | 2743042 | A2 | 6/2014 |
| EP | 2764827 | A2 | 8/2014 |
| EP | 2777524 | A2 | 9/2014 |
| EP | 2789299 | A1 | 10/2014 |
| EP | 2842500 | A1 | 3/2015 |
| EP | 2853220 | A1 | 4/2015 |
| EP | 2878274 | A1 | 6/2015 |
| EP | 2298220 | B1 | 6/2016 |
| EP | 3031404 | A1 | 6/2016 |
| EP | 3047806 | A1 | 7/2016 |
| EP | 3078334 | A1 | 10/2016 |
| EP | 2364651 | B1 | 11/2016 |
| EP | 2747235 | B1 | 11/2016 |
| EP | 3095399 | A2 | 11/2016 |
| EP | 3120781 | A2 | 1/2017 |
| EP | 3135225 | A2 | 3/2017 |
| EP | 2789299 | B1 | 5/2017 |
| EP | 3225190 | A2 | 10/2017 |
| EP | 3235445 | A1 | 10/2017 |
| EP | 3326548 | A1 | 5/2018 |
| EP | 3363378 | A1 | 8/2018 |
| EP | 3409216 | A1 | 12/2018 |
| EP | 3476301 | A1 | 5/2019 |
| EP | 3476334 | A1 | 5/2019 |
| EP | 3275378 | B1 | 7/2019 |
| EP | 3505095 | A1 | 7/2019 |
| EP | 3791810 | A1 | 3/2021 |
| ES | 1070456 | U | 9/2009 |
| FR | 459743 | A | 11/1913 |
| FR | 999646 | A | 2/1952 |
| FR | 1112936 | A | 3/1956 |
| FR | 2598905 | A1 | 11/1987 |
| FR | 2689749 | B1 | 7/1994 |
| FR | 2765794 | A1 | 1/1999 |
| FR | 2815842 | A1 | 5/2002 |
| GB | 939929 | A | 10/1963 |
| GB | 1210522 | A | 10/1970 |
| GB | 1217159 | A | 12/1970 |
| GB | 1339394 | A | 12/1973 |
| GB | 2024012 | A | 1/1980 |
| GB | 2109241 | A | 6/1983 |
| GB | 2090534 | B | 6/1984 |
| GB | 2272159 | A | 5/1994 |
| GB | 2336214 | A | 10/1999 |
| GB | 2509523 | A | 7/2014 |
| GR | 930100110 | A | 11/1993 |
| JP | S4711908 | Y1 | 5/1972 |
| JP | S5033988 | U | 4/1975 |
| JP | S5367286 | A | 6/1978 |
| JP | S56112235 | A | 9/1981 |
| JP | S60113007 | A | 6/1985 |
| JP | S62170011 | U | 10/1987 |
| JP | S6333137 | A | 2/1988 |
| JP | S63270040 | A | 11/1988 |
| JP | S63318824 | A | 12/1988 |
| JP | H0129503 | B2 | 6/1989 |
| JP | H02106189 | A | 4/1990 |
| JP | H0378514 | U | 8/1991 |
| JP | H0385009 | U | 8/1991 |
| JP | H0489041 | A | 3/1992 |
| JP | H04215747 | A | 8/1992 |
| JP | H04131860 | U | 12/1992 |
| JP | H0584252 | A | 4/1993 |
| JP | H05123325 | A | 5/1993 |
| JP | H05226945 | A | 9/1993 |
| JP | H0630945 | A | 2/1994 |
| JP | H0636757 | A | 2/1994 |
| JP | H06237937 | A | 8/1994 |
| JP | H06304176 | A | 11/1994 |
| JP | H06327684 | A | 11/1994 |
| JP | H079622 | U | 2/1995 |
| JP | H07124166 | A | 5/1995 |
| JP | H07163573 | A | 6/1995 |
| JP | H07255735 | A | 10/1995 |
| JP | H07285089 | A | 10/1995 |
| JP | H0833642 | A | 2/1996 |
| JP | H08164141 | A | 6/1996 |
| JP | H08182684 | A | 7/1996 |
| JP | H08507708 | A | 8/1996 |
| JP | H08229050 | A | 9/1996 |
| JP | H08289895 | A | 11/1996 |
| JP | H0950795 | A | 2/1997 |
| JP | H09-323068 | A | 12/1997 |
| JP | H10118090 | A | 5/1998 |
| JP | H10-200699 | A | 7/1998 |
| JP | H10296660 | A | 11/1998 |
| JP | 2000014632 | A | 1/2000 |
| JP | 2000033071 | A | 2/2000 |
| JP | 2000112002 | A | 4/2000 |
| JP | 2000166932 | A | 6/2000 |
| JP | 2000171730 | A | 6/2000 |
| JP | 2000210299 | A | 8/2000 |
| JP | 2000271141 | A | 10/2000 |
| JP | 2000287987 | A | 10/2000 |
| JP | 2000325303 | A | 11/2000 |
| JP | 2001-69758 | A | 3/2001 |
| JP | 2001087272 | A | 4/2001 |
| JP | 2001208655 | A | 8/2001 |
| JP | 2001514541 | A | 9/2001 |
| JP | 2001276091 | A | 10/2001 |
| JP | 2002051974 | A | 2/2002 |
| JP | 2002054903 | A | 2/2002 |
| JP | 2002085415 | A | 3/2002 |
| JP | 2002143078 | A | 5/2002 |
| JP | 2002153481 | A | 5/2002 |
| JP | 2002528161 | A | 9/2002 |
| JP | 2002314298 | A | 10/2002 |
| JP | 2003135473 | A | 5/2003 |
| JP | 2003521301 | A | 7/2003 |
| JP | 3442423 | B2 | 9/2003 |
| JP | 2003300416 | A | 10/2003 |
| JP | 2004147701 | A | 5/2004 |
| JP | 2004162035 | A | 6/2004 |
| JP | 2004229976 | A | 8/2004 |
| JP | 2005013573 | A | 1/2005 |
| JP | 2005080702 | A | 3/2005 |
| JP | 2005131163 | A | 5/2005 |
| JP | 2005131164 | A | 5/2005 |
| JP | 2005131173 | A | 5/2005 |
| JP | 2005131211 | A | 5/2005 |
| JP | 2005131212 | A | 5/2005 |
| JP | 2005137423 | A | 6/2005 |
| JP | 2005187954 | A | 7/2005 |
| JP | 2005211455 | A | 8/2005 |
| JP | 2005328882 | A | 12/2005 |
| JP | 2005335432 | A | 12/2005 |
| JP | 2005342267 | A | 12/2005 |
| JP | 3791856 | B2 | 6/2006 |
| JP | 2006187649 | A | 7/2006 |
| JP | 2006218228 | A | 8/2006 |
| JP | 2006281405 | A | 10/2006 |
| JP | 2006291180 | A | 10/2006 |
| JP | 2006346445 | A | 12/2006 |

(56) References Cited

FOREIGN PATENT DOCUMENTS

| | | | |
|---|---|---|---|
| JP | 2007-97252 | A | 4/2007 |
| JP | 2007289715 | A | 11/2007 |
| JP | 2007304057 | A | 11/2007 |
| JP | 2007306710 | A | 11/2007 |
| JP | D1322057 | | 2/2008 |
| JP | 2008154804 | A | 7/2008 |
| JP | 2008220032 | A | 9/2008 |
| JP | 2009507526 | A | 2/2009 |
| JP | 2009189838 | A | 8/2009 |
| JP | 2009189846 | A | 8/2009 |
| JP | 2009207260 | A | 9/2009 |
| JP | 2009226028 | A | 10/2009 |
| JP | 2009538684 | A | 11/2009 |
| JP | 2009539420 | A | 11/2009 |
| JP | D1383743 | | 2/2010 |
| JP | 2010065594 | A | 3/2010 |
| JP | 2010069307 | A | 4/2010 |
| JP | 2010069310 | A | 4/2010 |
| JP | 2010098844 | A | 4/2010 |
| JP | 2010214128 | A | 9/2010 |
| JP | 2011072574 | A | 4/2011 |
| JP | 4722849 | B2 | 7/2011 |
| JP | 4728996 | B2 | 7/2011 |
| JP | 2011524199 | A | 9/2011 |
| JP | 2011200665 | A | 10/2011 |
| JP | D1432094 | | 12/2011 |
| JP | 1433631 | S | 2/2012 |
| JP | 2012115542 | A | 6/2012 |
| JP | 2012143283 | A | 8/2012 |
| JP | 5154710 | B1 | 2/2013 |
| JP | 2013042921 | A | 3/2013 |
| JP | 2013099551 | A | 5/2013 |
| JP | 2013126430 | A | 6/2013 |
| JP | D1481426 | | 9/2013 |
| JP | 2013541982 | A | 11/2013 |
| JP | 2013541983 | A | 11/2013 |
| JP | 2013541997 | A | 11/2013 |
| JP | 2014018667 | A | 2/2014 |
| JP | D1492363 | | 2/2014 |
| JP | 2014121599 | A | 7/2014 |
| JP | 2014171879 | A | 9/2014 |
| JP | 1517663 | S | 2/2015 |
| JP | 2015512725 | A | 4/2015 |
| JP | 2015513956 | A | 5/2015 |
| JP | 2015513958 | A | 5/2015 |
| JP | 2015514471 | A | 5/2015 |
| JP | 2015516838 | A | 6/2015 |
| JP | 2015521524 | A | 7/2015 |
| JP | 2015521525 | A | 7/2015 |
| JP | 2016007800 | A | 1/2016 |
| JP | 2016508792 | A | 3/2016 |
| JP | 2016512057 | A | 4/2016 |
| JP | 2016518914 | A | 6/2016 |
| JP | 2016530949 | A | 10/2016 |
| JP | 2017513563 | A | 6/2017 |
| JP | 1601498 | S | 4/2018 |
| JP | 2019513530 | A | 5/2019 |
| JP | 2020501797 | A | 1/2020 |
| JP | D1677030 | S | 1/2021 |
| JP | D1696539 | S | 10/2021 |
| KR | 20100110134 | A | 10/2010 |
| KR | 20110003229 | A | 1/2011 |
| KR | 300631507 | | 3/2012 |
| KR | 300747646 | | 6/2014 |
| KR | 20180053811 | A | 5/2018 |
| RU | 1814161 | C | 5/1993 |
| RU | 2008830 | C1 | 3/1994 |
| RU | 2052979 | C1 | 1/1996 |
| RU | 2066128 | C1 | 9/1996 |
| RU | 2069981 | C1 | 12/1996 |
| RU | 2098025 | C1 | 12/1997 |
| RU | 2104671 | C1 | 2/1998 |
| RU | 2110965 | C1 | 5/1998 |
| RU | 2141279 | C1 | 11/1999 |
| RU | 2144791 | C1 | 1/2000 |
| RU | 2161450 | C1 | 1/2001 |
| RU | 2181566 | C2 | 4/2002 |
| RU | 2187249 | C2 | 8/2002 |
| RU | 32984 | U1 | 10/2003 |
| RU | 2225170 | C2 | 3/2004 |
| RU | 42750 | U1 | 12/2004 |
| RU | 61114 | U1 | 2/2007 |
| RU | 61122 | U1 | 2/2007 |
| RU | 2430692 | C2 | 10/2011 |
| SU | 189517 | A | 1/1967 |
| SU | 297156 | A | 5/1971 |
| SU | 328636 | A | 9/1972 |
| SU | 511939 | A1 | 4/1976 |
| SU | 674747 | A1 | 7/1979 |
| SU | 728848 | A1 | 4/1980 |
| SU | 1009439 | A | 4/1983 |
| SU | 1042742 | A1 | 9/1983 |
| SU | 1271497 | A1 | 11/1986 |
| SU | 1333319 | A2 | 8/1987 |
| SU | 1377052 | A1 | 2/1988 |
| SU | 1377053 | A1 | 2/1988 |
| SU | 1443874 | A1 | 12/1988 |
| SU | 1509051 | A1 | 9/1989 |
| SU | 1561964 | A1 | 5/1990 |
| SU | 1708312 | A1 | 1/1992 |
| SU | 1722476 | A1 | 3/1992 |
| SU | 1752361 | A1 | 8/1992 |
| SU | 1814161 | A1 | 5/1993 |
| WO | WO-9308754 | A1 | 5/1993 |
| WO | WO-9315648 | A1 | 8/1993 |
| WO | WO-9420030 | A1 | 9/1994 |
| WO | WO-9517855 | A1 | 7/1995 |
| WO | WO-9520360 | A1 | 8/1995 |
| WO | WO-9623448 | A1 | 8/1996 |
| WO | WO-9635464 | A1 | 11/1996 |
| WO | WO-9639086 | A1 | 12/1996 |
| WO | WO-9639088 | A1 | 12/1996 |
| WO | WO-9724073 | A1 | 7/1997 |
| WO | WO-9734533 | A1 | 9/1997 |
| WO | WO-9827870 | A1 | 7/1998 |
| WO | WO-9903407 | A1 | 1/1999 |
| WO | WO-9903409 | A1 | 1/1999 |
| WO | WO-9948430 | A1 | 9/1999 |
| WO | WO-0024322 | A1 | 5/2000 |
| WO | WO-0024330 | A1 | 5/2000 |
| WO | WO-0036690 | A2 | 6/2000 |
| WO | WO-0053112 | A2 | 9/2000 |
| WO | WO-0024448 | A2 | 10/2000 |
| WO | WO-0057796 | A1 | 10/2000 |
| WO | WO-0105702 | A1 | 1/2001 |
| WO | WO-0154594 | A1 | 8/2001 |
| WO | WO-0158371 | A1 | 8/2001 |
| WO | WO-0162164 | A2 | 8/2001 |
| WO | WO-0162169 | A2 | 8/2001 |
| WO | WO-0191646 | A1 | 12/2001 |
| WO | WO-0219932 | A1 | 3/2002 |
| WO | WO-0226143 | A1 | 4/2002 |
| WO | WO-0236028 | A1 | 5/2002 |
| WO | WO-02065933 | A2 | 8/2002 |
| WO | WO-03055402 | A1 | 7/2003 |
| WO | WO-03094747 | A1 | 11/2003 |
| WO | WO-03079909 | A3 | 3/2004 |
| WO | WO-2004019803 | A1 | 3/2004 |
| WO | WO-2004032783 | A1 | 4/2004 |
| WO | WO-2004047626 | A1 | 6/2004 |
| WO | WO-2004047653 | A2 | 6/2004 |
| WO | WO-2004056277 | A1 | 7/2004 |
| WO | WO-2004078050 | A2 | 9/2004 |
| WO | WO-2004078051 | A2 | 9/2004 |
| WO | WO-2004096015 | A2 | 11/2004 |
| WO | WO-2006044581 | A2 | 4/2006 |
| WO | WO-2006051252 | A1 | 5/2006 |
| WO | WO-2006059067 | A1 | 6/2006 |
| WO | WO-2006073581 | A2 | 7/2006 |
| WO | WO-2006085389 | A1 | 8/2006 |
| WO | WO-2007015971 | A2 | 2/2007 |
| WO | WO-2007074430 | A1 | 7/2007 |
| WO | WO-2007129121 | A1 | 11/2007 |
| WO | WO-2007137304 | A2 | 11/2007 |

(56) References Cited

FOREIGN PATENT DOCUMENTS

| | | |
|---|---|---|
| WO | WO-2007142625 A2 | 12/2007 |
| WO | WO-2008021969 A2 | 2/2008 |
| WO | WO-2008061566 A1 | 5/2008 |
| WO | WO-2008089404 A2 | 7/2008 |
| WO | WO-2009005969 A2 | 1/2009 |
| WO | WO-2009046490 A1 | 4/2009 |
| WO | WO-2009067649 A2 | 5/2009 |
| WO | WO-2009091497 A2 | 7/2009 |
| WO | WO-2010126129 A1 | 11/2010 |
| WO | WO-2010134913 A1 | 11/2010 |
| WO | WO-2011008672 A2 | 1/2011 |
| WO | WO-2011044343 A2 | 4/2011 |
| WO | WO-2012006306 A2 | 1/2012 |
| WO | WO-2012013577 A1 | 2/2012 |
| WO | WO-2012044606 A2 | 4/2012 |
| WO | WO-2012061725 A1 | 5/2012 |
| WO | WO-2012072133 A1 | 6/2012 |
| WO | WO-2012166503 A1 | 12/2012 |
| WO | WO-2013087092 A1 | 6/2013 |
| WO | WO-2013151888 A1 | 10/2013 |
| WO | WO-2014004209 A2 | 1/2014 |
| WO | WO-2014113438 A1 | 7/2014 |
| WO | WO-2014175894 A1 | 10/2014 |
| WO | WO-2015032797 A1 | 3/2015 |
| WO | WO-2015076780 A1 | 5/2015 |
| WO | WO-2015137040 A1 | 9/2015 |
| WO | WO-2015138760 A1 | 9/2015 |
| WO | WO-2015187107 A1 | 12/2015 |
| WO | WO-2016100682 A1 | 6/2016 |
| WO | WO-2016107448 A1 | 7/2016 |
| WO | WO-2017138905 A1 | 8/2017 |
| WO | WO-2018011664 A1 | 1/2018 |
| WO | WO-2019036490 A1 | 2/2019 |
| WO | WO-2019130087 A1 | 7/2019 |
| WO | WO-2019130089 A1 | 7/2019 |
| WO | WO-2019208902 A1 | 10/2019 |
| WO | WO-2021189234 A1 | 9/2021 |
| WO | WO-2022249091 A1 | 12/2022 |
| WO | WO-2022249094 A1 | 12/2022 |

OTHER PUBLICATIONS

ASTM procedure D2240-05, "Standard Test Method for Rubber Property-Durometer Hardness," (Published Apr. 2010).

Van Meer et al., "A Disposable Plastic Compact Wrist for Smart Minimally Invasive Surgical Tools," LAAS/CNRS (Aug. 2005).

Breedveld et al., "A New, Easily Miniaturized Sterrable Endoscope," IEEE Engineering in Medicine and Biology Magazine (Nov./Dec. 2005).

Disclosed Anonymously, "Motor-Driven Surgical Stapler Improvements," Research Disclosure Database No. 526041, Published: Feb. 2008.

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

D. Tuite, Ed., "Get The Lowdown on Ultracapacitors," Nov. 15, 2007; [online] URL: http://electronicdesign.com/Articles/Print.cfm?ArticleID=17465, accessed Jan. 15, 2008 (5 pages).

Datasheet for Panasonic TK Relays Ultra Low Profile 2 A Polarized Relay, Copyright Matsushita Electric Works, Ltd. (Known of at least as early as Aug. 17, 2010), 5 pages.

Schellhammer et al., "Poly-Lactic-Acid for Coating of Endovascular Stents: Preliminary Results in Canine Experimental Av-Fistulae," Mat.-wiss. u. Werkstofftech., 32, pp. 193-199 (2001).

Miyata et al., "Biomolecule-Sensitive Hydrogels," Advanced Drug Delivery Reviews, 54 (2002) pp. 79-98.

Jeong et al., "Thermosensitive Sol-Gel Reversible Hydrogels," Advanced Drug Delivery Reviews, 54 (2002) pp. 37-51.

Covidien Brochure, "Endo GIA™ Ultra Universal Stapler," (2010), 2 pages.

Qiu et al., "Environment-Sensitive Hydrogels for Drug Delivery," Advanced Drug Delivery Reviews, 53 (2001) pp. 321-339.

Hoffman, "Hydrogels for Biomedical Applications," Advanced Drug Delivery Reviews, 43 (2002) pp. 3-12.

Hoffman, "Hydrogels for Biomedical Applications," Advanced Drug Delivery Reviews, 54 (2002) pp. 3-12.

Peppas, "Physiologically Responsive Hydrogels," Journal of Bioactive and Compatible Polymers, vol. 6 (Jul. 1991) pp. 241-246.

Peppas, Editor "Hydrogels in Medicine and Pharmacy," vol. I, Fundamentals, CRC Press, 1986.

Young, "Microcellular foams via phase separation," Journal of Vacuum Science & Technology A 4(3), (May/Jun. 1986).

Ebara, "Carbohydrate-Derived Hydrogels and Microgels," Engineered Carbohydrate-Based Materials for Biomedical Applications: Polymers, Surfaes, Dendrimers, Nanoparticles, and Hydrogels, Edited by Ravin Narain, 2011, pp. 337-345.

http://ninpgan.net/publications/51-100/89.pdf; 2004, Ning Pan, On Uniqueness of Fibrous Materials, Design & Nature II. Eds: Colins, M. and Brebbia, C. WIT Press, Boston, 493-504.

Solorio et al., "Gelatin Microspheres Crosslinked with Genipin for Local Delivery of Growth Factors," J. Tissue Eng. Regen. Med. (2010), 4(7): pp. 514-523.

Covidien iDrive™ Ultra in Service Reference Card, "iDrive™ Ultra Powered Stapling Device," (4 pages).

Covidien iDrive™ Ultra Powered Stapling System ibrochure, "The Power of iDrive™ Ultra Powered Stapling System and Tri-Staple™ Technology," (23 pages).

Covidien "iDrive™ Ultra Powered Stapling System, A Guide for Surgeons," (6 pages).

Covidien "iDrive™ Ultra Powered Stapling System, Cleaning and Sterilization Guide," (2 pages).

Covidien Brochure "iDrive™ Ultra Powered Stapling System," (6 pages).

Covidien Brochure, "Endo GIA™ Reloads with Tri-Staple™ Technology," (2010), 1 page.

Covidien Brochure, "Endo GIA™ Reloads with Tri-Staple™ Technology and Endo GIA™ Ultra Universal Staplers," (2010), 2 pages.

Covidien Brochure, "Endo GIA™ Curved Tip Reload with Tri-Staple™ Technology," (2012), 2 pages.

Covidien Brochure, "Endo GIA™ Reloads with Tri-Staple™ Technology," (2010), 2 pages.

Pitt et al., "Attachment of Hyaluronan to Metallic Surfaces," J. Biomed. Mater. Res. 68A: pp. 95-106, 2004.

Indian Standard: Automotive Vehicles—Brakes and Braking Systems (IS 11852-1:2001), Mar. 1, 2001.

Patrick J. Sweeney: "RFID for Dummies", Mar. 11, 2010, pp. 365-365, XP055150775, ISBN: 978-1-11-805447-5, Retrieved from the Internet: URL: books.google.de/books?isbn=1118054474 [retrieved on Nov. 4, 2014]—book not attached.

Allegro MicroSystems, LLC, Automotive Full Bridge MOSFET Driver, A3941-DS, Rev. 5, 21 pages, http://www.allegromicro.com/~/media/Files/Datasheets/A3941-Datasheet.ashx?la=en.

Data Sheet of LM4F230H5QR, 2007.

Seils et al., Covidien Summary: Clinical Study "UCONN Biodynamics: Final Report on Results," (2 pages).

Byrne et al., "Molecular Imprinting Within Hydrogels," Advanced Drug Delivery Reviews, 54 (2002) pp. 149-161.

Fast, Versatile Blackfin Processors Handle Advanced RFID Reader Applications; Analog Dialogue: vol. 40—Sep. 2006; http://www.analog.com/library/analogDialogue/archives/40-09/rfid.pdf; Wayback Machine to Feb. 15, 2012.

Chen et al., "Elastomeric Biomaterials for Tissue Engineering," Progress in Polymer Science 38 (2013), pp. 584-671.

Matsuda, "Thermodynamics of Formation of Porous Polymeric Membrane from Solutions," Polymer Journal, vol. 23, No. 5, pp. 435-444 (1991).

Covidien Brochure, "Endo GIA™ Black Reload with Tri-Staple™ Technology," (2012), 2 pages.

Biomedical Coatings, Fort Wayne Metals, Research Products Corporation, obtained online at www.fwmetals.com on Jun. 21, 2010 (1 page).

(56) References Cited

OTHER PUBLICATIONS

The Sodem Aseptic Battery Transfer Kit, Sodem Systems, 2000, 3 pages.
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20., pp. 1744-1748.
Serial Communication Protocol; Michael Lemmon Feb. 1, 2009; http://www3.nd.edu/~lemmon/courses/ee224/web-manual/web-manual/lab12/node2.html; Wayback Machine to Apr. 29, 2012.
Lyon et al. "The Relationship Between Current Load and Temperature for Quasi-Steady State and Transient Conditions," SPIE—International Society for Optical Engineering. Proceedings, vol. 4020, (pp. 62-70), Mar. 30, 2000.
Anonymous: "Sense & Control Application Note Current Sensing Using Linear Hall Sensors," Feb. 3, 2009, pp. 1-18. Retrieved from the Internet: URL: http://www.infineon.com/dgdl/Current_Sensing_Rev.1.1.pdf?fileId=db3a304332d040720132d939503e5f17 [retrieved on Oct. 18, 2016].
Mouser Electronics, "LM317M 3—Terminal Adjustable Regulator with Overcurrent/Overtemperature Self Protection", Mar. 31, 2014 (Mar. 31, 2014), XP0555246104, Retrieved from the Internet: URL: http://www.mouser.com/ds/2/405/lm317m-440423.pdf, pp. 1-8.
Mouser Electronics, "LM317 3—Terminal Adjustable Regulator with Overcurrent/Overtemperature Self Protection", Sep. 30, 2016 (Sep. 30, 2016), XP0555246104, Retrieved from the Internet: URL: http://www.mouser.com/ds/2/405/lm317m-440423.pdf, pp. 1-9.
Cuper et al., "The Use of Near-Infrared Light for Safe and Effective Visualization of Subsurface Blood Vessels to Facilitate Blood Withdrawal in Children," Medical Engineering & Physics, vol. 35, No. 4, pp. 433-440 (2013).
Yan et al., Comparison of the effects of Mg—6Zn and Ti—3Al—2.5V alloys on TGF-β/TNF-α/VEGF/b-FGF in the healing of the intestinal track in vivo, Biomed. Mater. 9 (2014), 11 pages.
Pellicer et al. "On the biodegradability, mechanical behavior, and cytocompatibility of amorphous Mg72Zn23Ca5 and crystalline Mg70Zn23Ca5Pd2 alloys as temporary implant materials," J Biomed Mater Res Part A, 2013:101A:502-517.
Anonymous, Analog Devices Wiki, Chapter 11: The Current Mirror, Aug. 20, 2017, 22 pages. https://wiki.analog.com/university/courses/electronics/text/chapter-11?rev=1503222341.
Yan et al., "Comparison of the effects of Mg—6Zn and titanium on intestinal tract in vivo," J Mater Sci: Mater Med (2013), 11 pages.
Brar et al., "Investigation of the mechanical and degradation properties of Mg—Sr and Mg—Zn—Sr alloys for use as potential biodegradable implant materials," J. Mech. Behavior of Biomed. Mater. 7 (2012) pp. 87-95.
Texas Instruments: "Current Recirculation and Decay Modes," Application Report SLVA321—Mar. 2009; Retrieved from the Internet: URL:http://www.ti.com/lit/an/slva321/slva321 [retrieved on Apr. 25, 2017], 7 pages.
Qiu Li Loh et al.: "Three-Dimensional Scaffolds for Tissue Engineering Applications: Role of Porosity and Pore Size", Tissue Engineering Part B—Reviews, vol. 19, No. 6, Dec. 1, 2013, pp. 485-502.
Gao et al., "Mechanical Signature Enhancement of Response Vibrations in the Time Lag Domain," Fifth International Congress on Sound and Vibration, Dec. 15-18, 1997, pp. 1-8.
Trendafilova et al., "Vibration-based Methods for Structural and Machinery Fault Diagnosis Based on Nonlinear Dynamics Tools," In: Fault Diagnosis in Robotic and Industrial Systems, IConcept Press LTD, 2012, pp. 1-29.
Youtube.com; video by Fibran (retrieved from URL https://www.youtube.com/watch?v=vN2Qjt51gFQ); (Year: 2018).
Foot and Ankle: Core Knowledge in Orthopaedics; by DiGiovanni MD, Elsevier; (p. 27, left column, heading "Materials for Soft Orthoses", 7th bullet point); (Year: 2007).
Lee, Youbok, "Antenna Circuit Design for RFID Applications," 2003, pp. 1-50, DS00710C, Microchip Technology Inc., Available: http://ww1.microchip.com/downloads/en/AppNotes/00710c.pdf.
Kawamura, Atsuo, et al. "Wireless Transmission of Power and Information Through One High-Frequency Resonant AC Link Inverter for Robot Manipulator Applications," Journal, May/Jun. 1996, pp. 503-508, vol. 32, No. 3, IEEE Transactions on Industry Applications.
Honda HS1332AT and ATD Model Info, powerequipment.honda.com [online], published on or before Mar. 22, 2016, [retrieved on May 31, 2019], retrieved from the Internet [URL: https://powerequipment.honda.com/snowblowers/models/hss1332at-hss1332atd] {Year: 2016).
Slow Safety Sign, shutterstock.com [online], published on or before May 9, 2017, [retrieved on May 31, 2019], retrieved from the https://www.shutterstock.com/image-victor/slow-safety-sign-twodimensional-turtle-symbolizing- . . . see PDF in file for full URL] (Year: 2017).
Warning Sign Beveled Buttons, by Peter, flarestock.com [online], published on or before Jan. 1, 2017, [retrieved on Jun. 4, 2019], retrieved from the Internet [URL: https://www.flarestock.com/stock-images/warning-sign-beveled-buttons/70257] (Year: 2017).
Arrow Sign Icon Next Button, by Blan-k, shutterstock.com [online], published on or before Aug. 6, 2014, [retrieved on Jun. 4, 2019], retrieved from the Internet [URL:https://www.shutterstock.com/de/image-vector/arrow-sign-icon-next-button-navigation-207700303?irgwc=1&utm . . . see PDF in file for full URL] (Year: 2014).
Elite Icons, by smart/icons, iconfinder.com [online], published on Aug. 18, 2016, [retrieved on Jun. 4, 2019], retrieved from the Internet [URL: https://www.iconfinder.com/iconsets/elite] (Year: 2016).
Tutorial overview of inductively coupled RFID Systems, UPM, May 2003, pp. 1-7, UPM Rafsec, <http://cdn.mobiusconsulting.com/papers/rfidsystems.pdf>.
Schroeter, John, "Demystifying UHF Gen 2 RFID, HF RFID," Online Article, Jun. 2, 2008, pp. 1-3, <https://www.edn.com/design/industrial-control/4019123/Demystifying-UHF-Gen-2-RFID-HF-RFID>.
Adeeb, et al., "An Inductive Link-Based Wireless Power Transfer System for Biomedical Applications," Research Article, Nov. 14, 2011, pp. 1-12, vol. 2012, Article ID 879294, Hindawi Publishing Corporation.
Pushing Pixels (GIF), published on dribble.com, 2013.
Sodium stearate C18H35NaO2, Chemspider Search and Share Chemistry, Royal Society of Chemistry, pp. 1-3, 2015, http://www.chemspider.com/Chemical-Structure.12639.html, accessed May 23, 2016.
NF Monographs: Sodium Stearate, U.S. Pharmacopeia, http://www.pharmacopeia.cn/v29240/usp29nf24s0_m77360.html, accessed May 23, 2016.
Fischer, Martin H, "Colloid-Chemical Studies on Soaps", The Chemical Engineer, pp. 184-193, Aug. 1919.
V.K. Ahluwalia and Madhuri Goyal, A Textbook of Organic Chemistry, Section 19.11.3, p. 356, 2000.
A.V. Kasture and S.G. Wadodkar, Pharmaceutical Chemistry-II: Second Year Diploma in Pharmacy, Nirali Prakashan, p. 339, 2007.
Forum discussion regarding "Speed is Faster", published on Oct. 1, 2014 and retrieved on Nov. 8, 2019 from URL https://english.stackexchange.com/questions/199018/how-is-that-correct-speed-is-faster-or-prices-are-cheaper (Year: 2014).
"Understanding the Requirements of ISO/IEC 14443 for Type B Proximity Contactless Identification Cards," retrieved from https://www.digchip.com/application-notes/22/15746.php on Mar. 2, 2020, pp. 1-28 (Nov. 2005).
Jauchem, J.R., "Effects of low-level radio-frequency (3 kHz to 300 GHZ) enery on human cardiovascular, reproductive, immune, and other systems: A review of the recent literatured," Int. J. Hyg. Environ. Health 211 (2008) 1-29.
Sandvik, "Welding Handbook," https://www.meting.rs/wp-content/uploads/2018/05/welding-handbook.pdf, retrieved on Jun. 22, 2020. pp. 5-6.
Ludois, Daniel C., "Capacitive Power Transfer for Rotor Field Current in Synchronous Machines," IEEE Transactions on Power Electronics, Institute of Electrical and Electronics Engineers, USA, vol. 27, No. 11, Nov. 1, 2012, pp. 4638-4645.
Rotary Systems: Sealed Slip Ring Categories, Rotary Systems, May 22, 2017, retrieved from the internet: http://web.archive.org/we/

(56) References Cited

OTHER PUBLICATIONS

20170522174710/http:/rotarysystems.com: 80/slip-rings/sealed/, retrieved on Aug. 12, 2020, pp. 1-2.
IEEE Std 802.3-2012 (Revision of IEEE Std 802.3-2008, published Dec. 28, 2012.
"ATM-MPLS Network Interworking Version 2.0, af-aic-0178.001" ATM Standard, The ATM Forum Technical Committee, published Aug. 2003.
Yang et al.; "4D printing reconfigurable, deployable and mechanically tunable metamaterials," Material Horizions, vol. 6, pp. 1244-1250 (2019).
"Council Directive 93/42/EEC of Jun. 14, 1993 Concerning Medical Devices," Official Journal of the European Communities, L&C. Ligislation and Competition, S, No. L 169, Jun. 14, 1993, pp. 1-43.
Arjo Loeve et al., Scopes Too Flexible . . . and Too Stiff, 2010, IEEE Pulse, Nov./Dec. 2010 (Year: 2010), 16 pages.
Molina, "Low Level Reader Protocol (LLRP)," Oct. 13, 2010, pp. 1-198.
Makerbot, 10 Advantages of 3D Printing, 2020 (retrieved via the wayback machine), Makerbot.com (Year: 2020).
U.S. Appl. No. 62/798,651, filed Jan. 30, 2019.
U.S. Appl. No. 62/840,602, filed Apr. 30, 2019.

* cited by examiner

SURGICAL INSTRUMENT HAVING ARTICULATION LOCK ACTUATED BY CLOSURE TUBE DISPLACEMENT

CROSS-REFERENCE TO RELATED APPLICATIONS

This application is a continuation application claiming priority under 35 U.S.C. § 120 to U.S. patent application Ser. No. 16/868,218, entitled METHOD FOR ARTICULATING A SURGICAL INSTRUMENT, filed May 6, 2020, which issued on May 9, 2023 as U.S. Pat. No. 11,642,128, which is a divisional application claiming priority under 35 U.S.C. § 121 to U.S. patent application Ser. No. 15/635,663, entitled METHOD FOR ARTICULATING A SURGICAL INSTRUMENT, filed Jun. 28, 2017, which issued on Sep. 8, 2020 as U.S. Pat. No. 10,765,427, the entire disclosures of which are hereby incorporated by reference herein.

BACKGROUND

The present invention relates to surgical instruments and, in various arrangements, to surgical stapling and cutting instruments and staple cartridges for use therewith that are designed to staple and cut tissue.

BRIEF DESCRIPTION OF THE DRAWINGS

Various features of the embodiments described herein, together with advantages thereof, may be understood in accordance with the following description taken in conjunction with the accompanying drawings as follows:

FIG. 97A is a cross-sectional view of the end effector of FIG. 95 illustrated in an articulated configuration;

FIG. 97B is a cross-sectional view of the end effector of FIG. 95 illustrated in an articulated configuration;

FIG. 98 is a partial perspective view of an end effector in accordance with at least one embodiment;

FIG. 99 is a partial perspective view of the end effector of FIG. 98 illustrated with some components removed;

FIG. 100 is a partial plan view of the end effector of FIG. 98 illustrated with some components removed;

FIG. 101 is a partial elevational view of the end effector of FIG. 98 illustrated with some components removed;

FIG. 102 is a cross-sectional view of the end effector of FIG. 98 illustrated in an unarticulated configuration;

FIG. 102A is a cross-sectional view of the end effector of FIG. 98 illustrated in an articulated configuration;

FIG. 102B is a cross-sectional view of the end effector of FIG. 98 illustrated in an articulated configuration;

FIG. 103 is a partial cross-sectional view of an end effector comprising an articulation system including an articulation lock in accordance with at least one embodiment;

FIG. 104 is a partial exploded view of the end effector of FIG. 103;

FIG. 105 is a cross-sectional end view of the end effector of FIG. 103;

Figure 103:
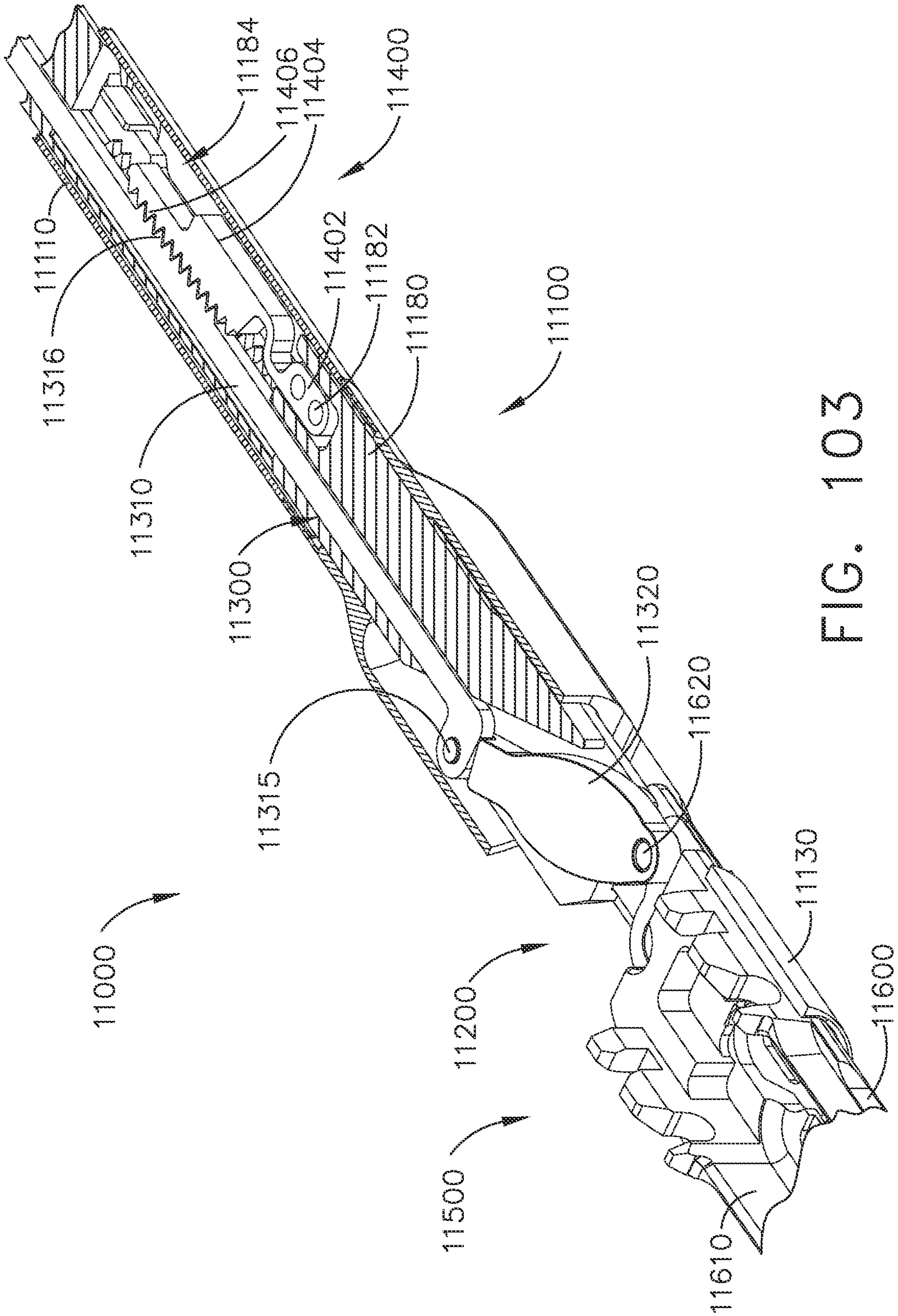
Figure 106:
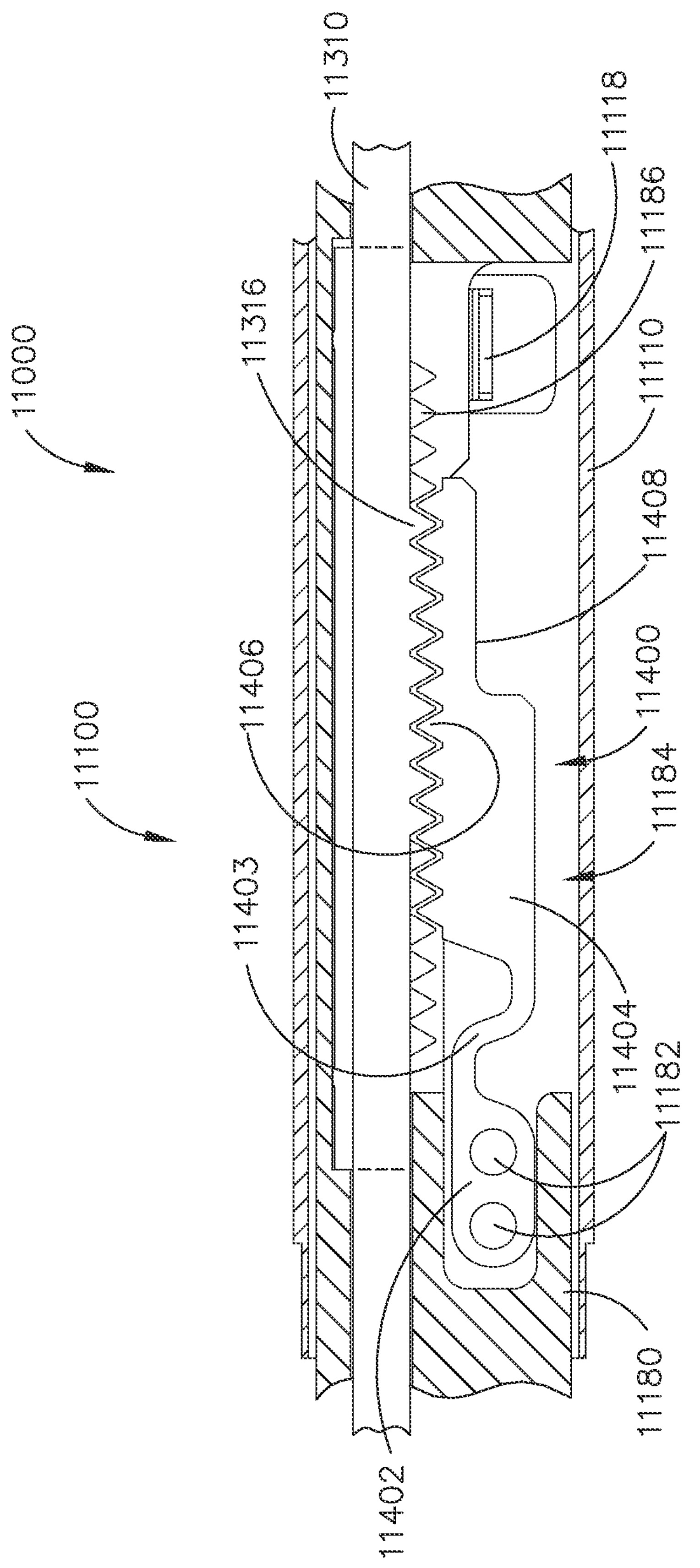
Figure 107:
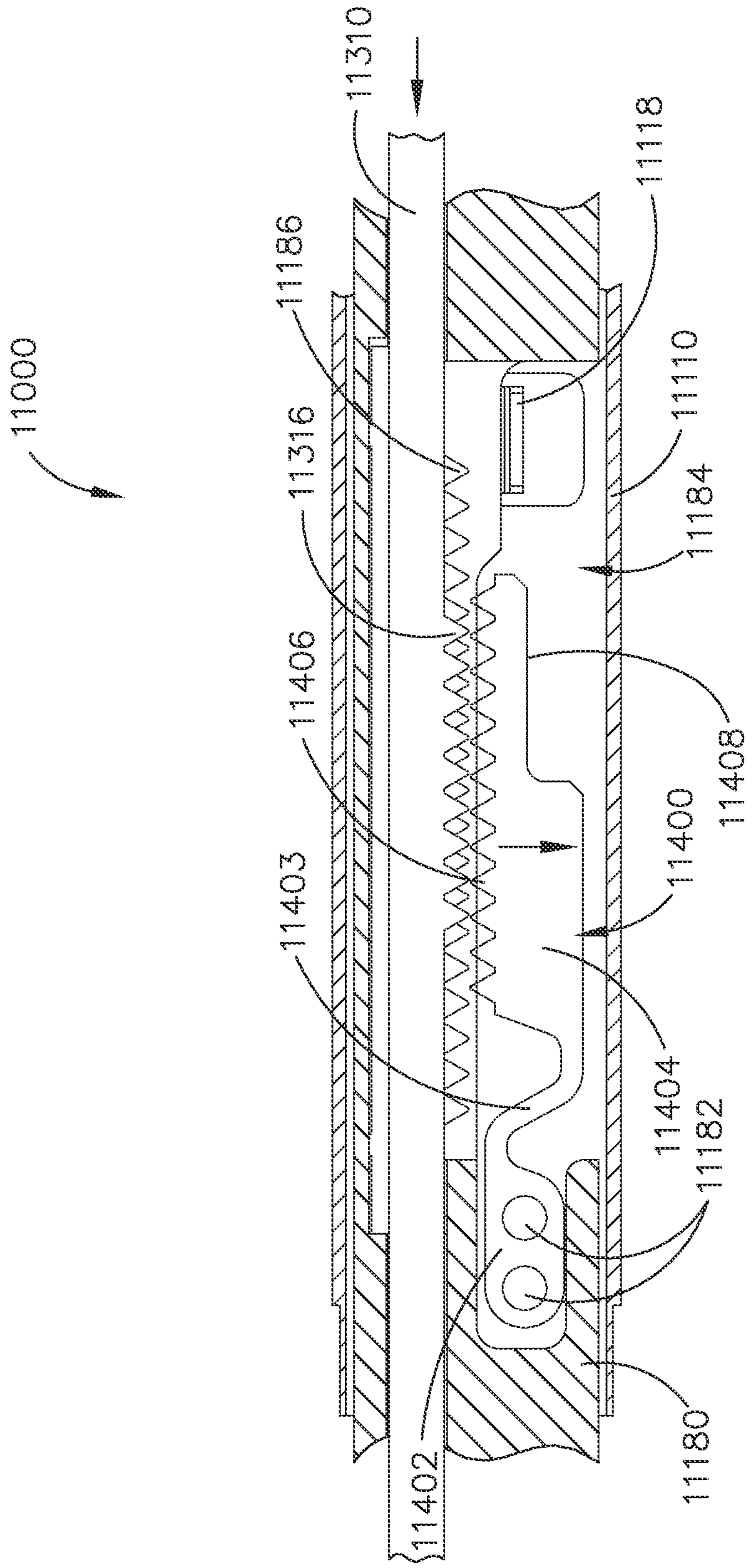
Figure 108:
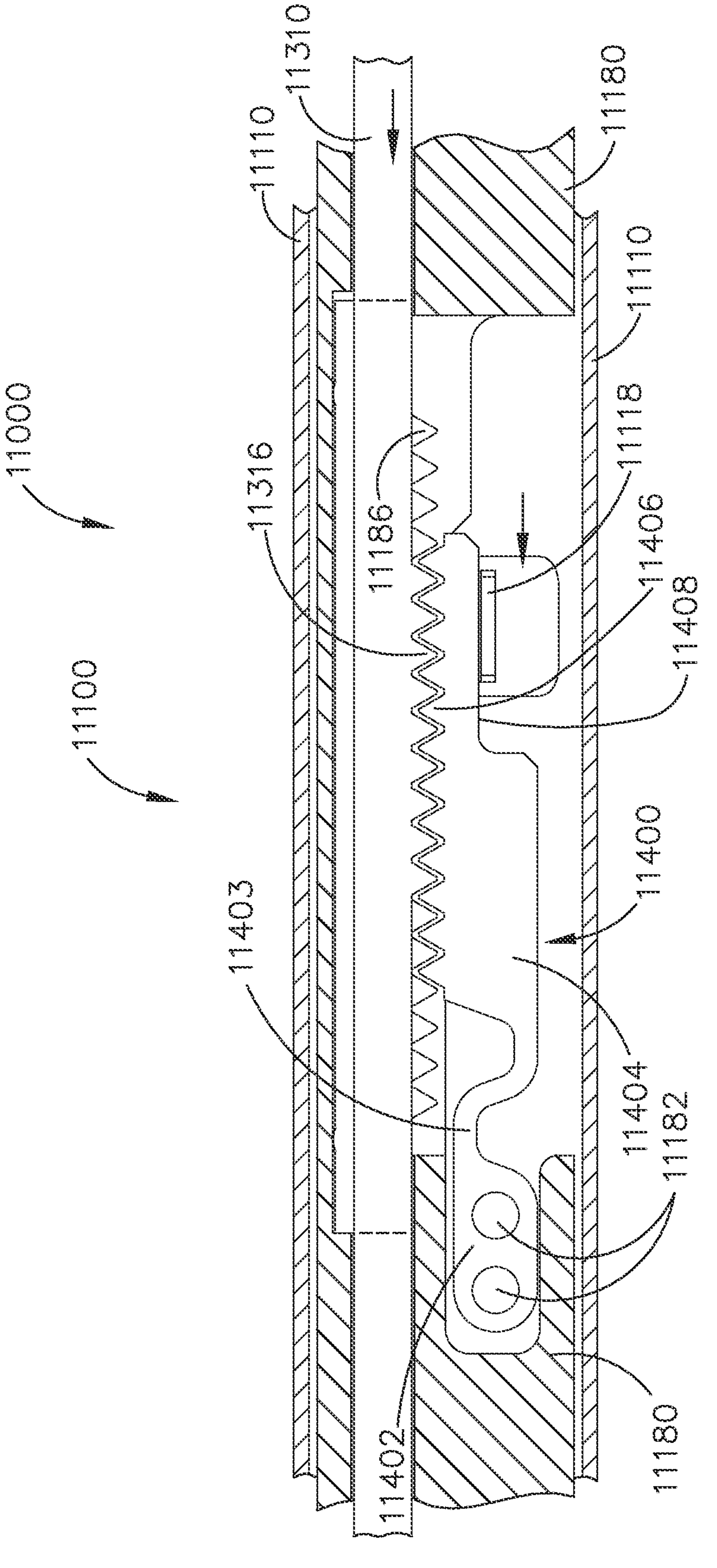
Figure 109:
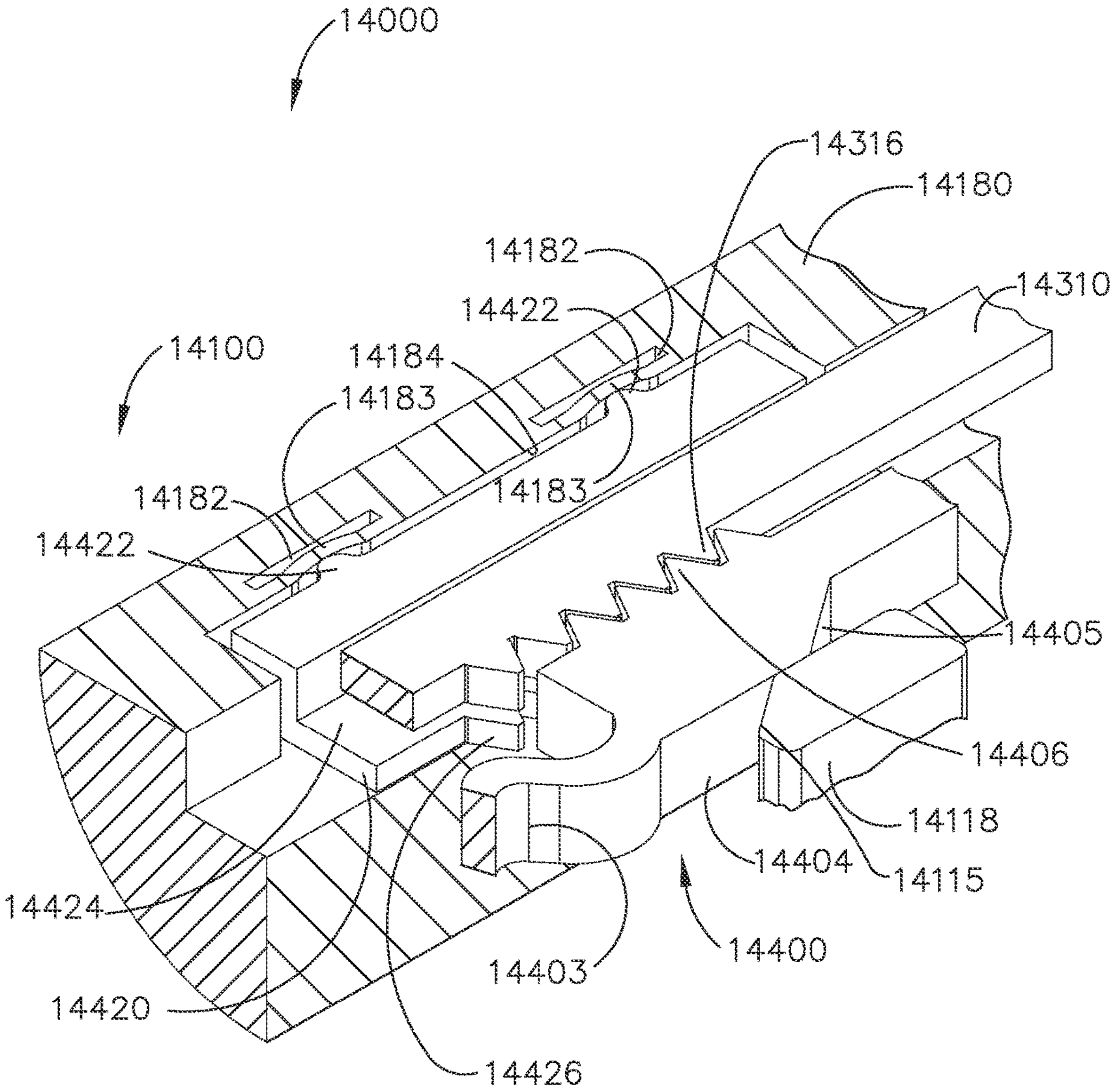
Figure 110:
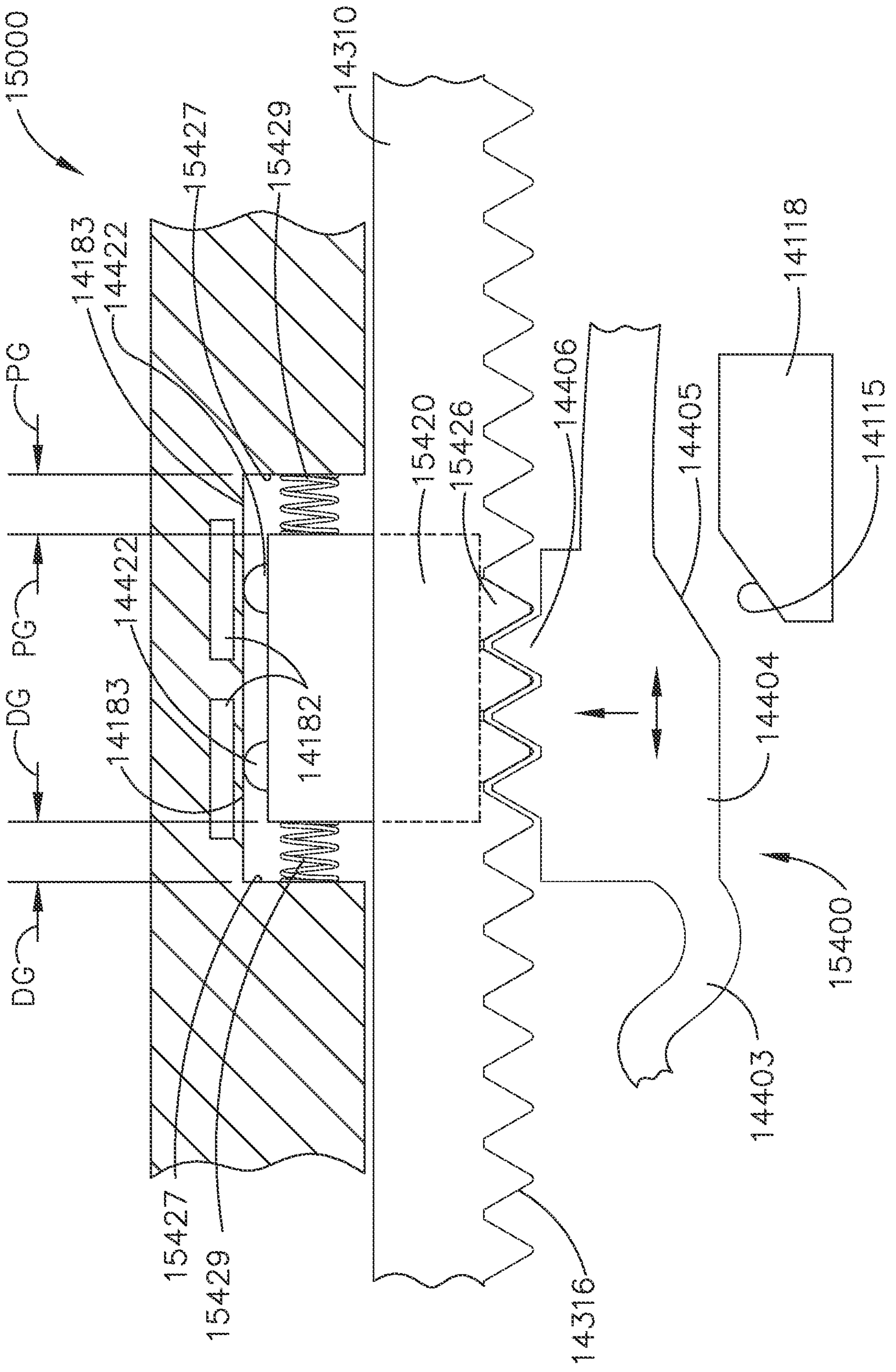
Figure 111:
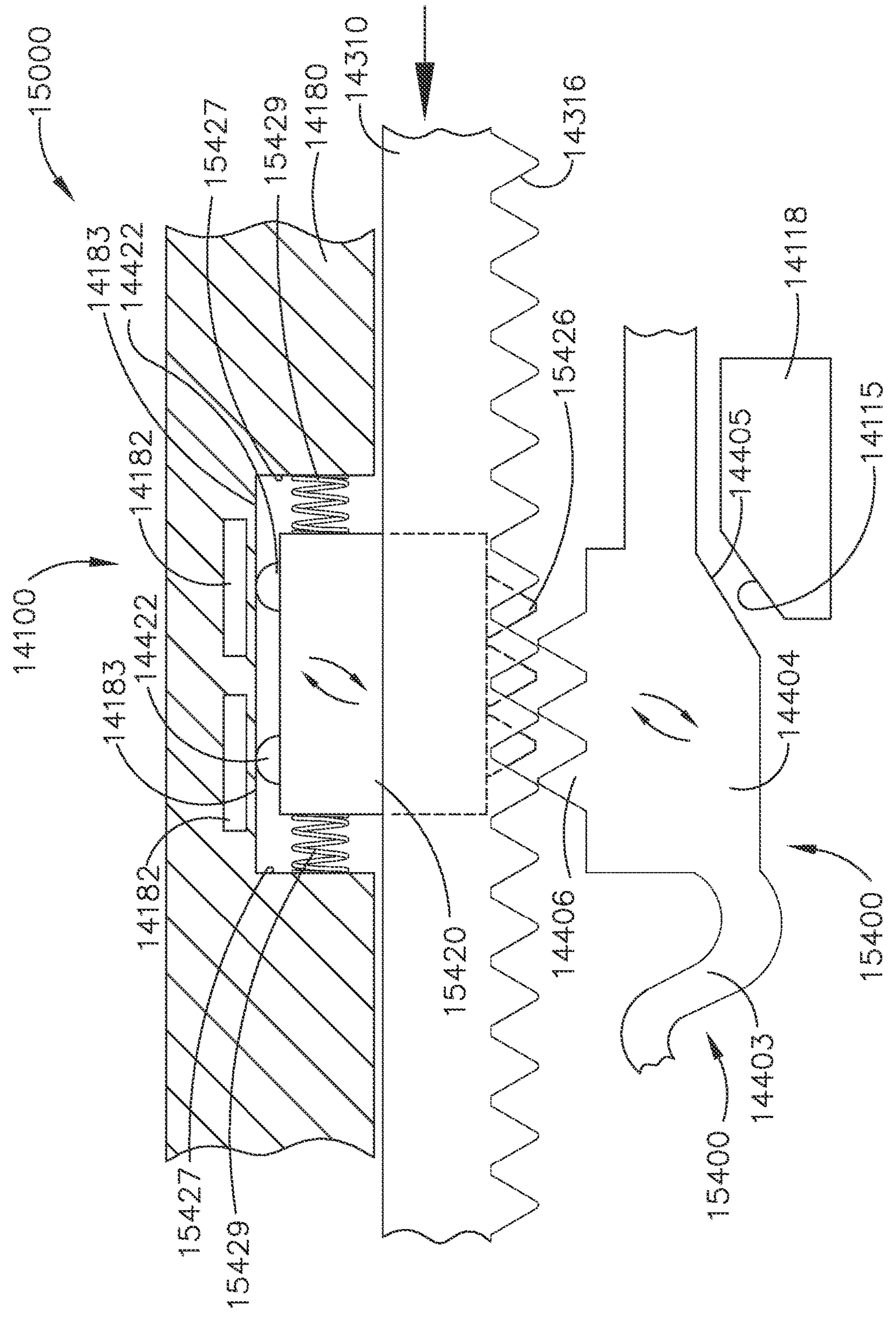
Figure 112:
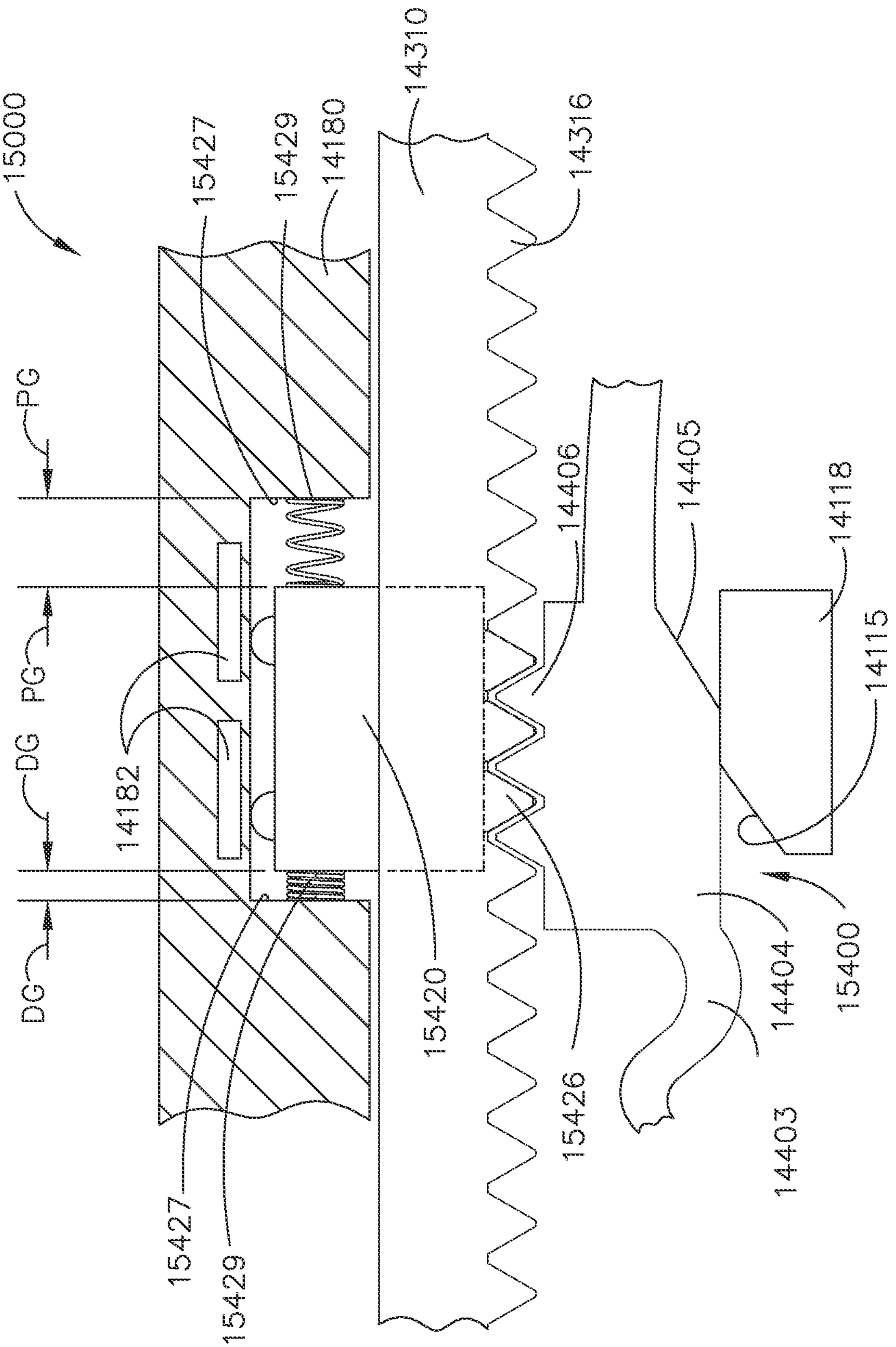
Figure 113:
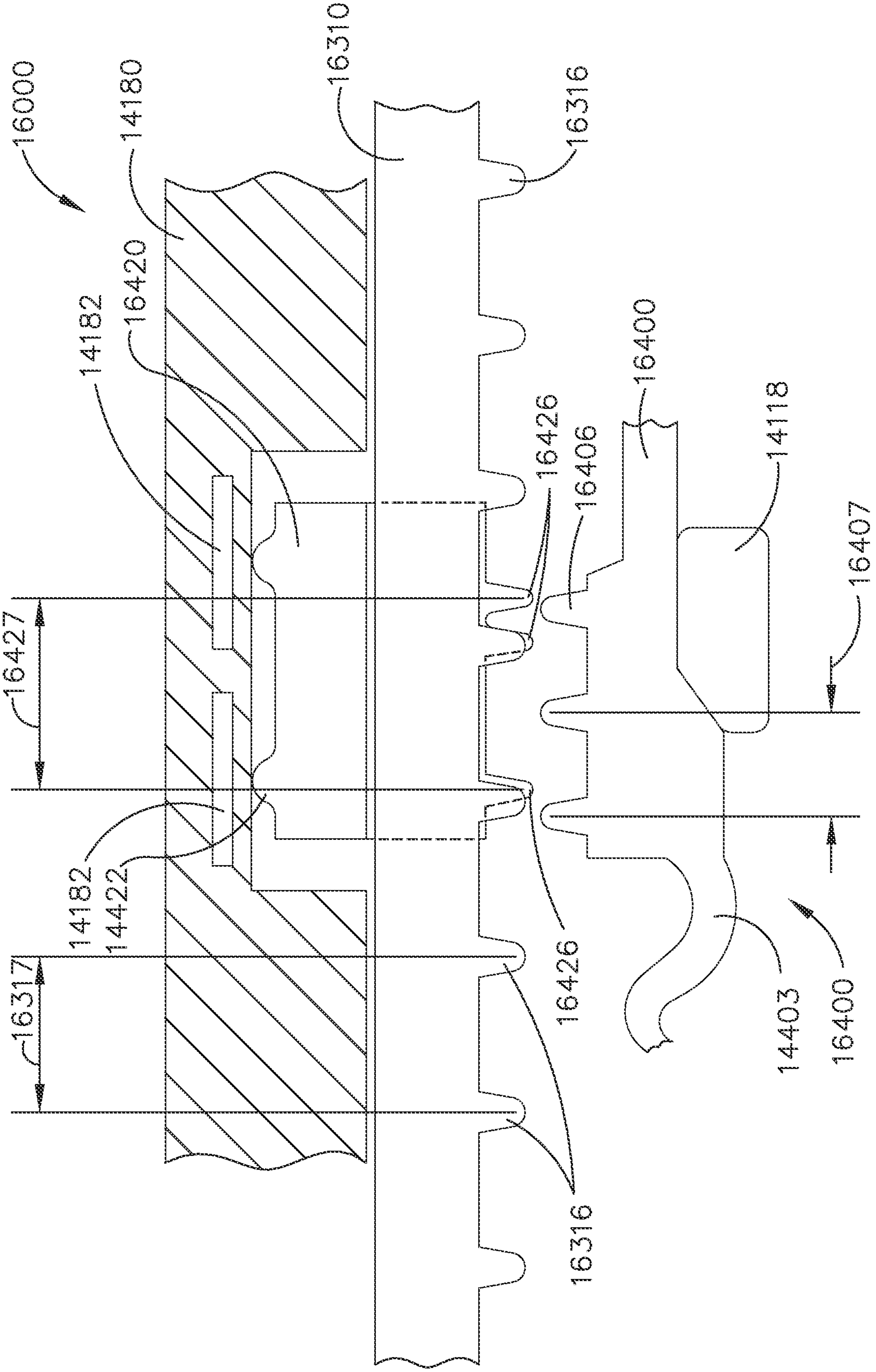
Figure 114:
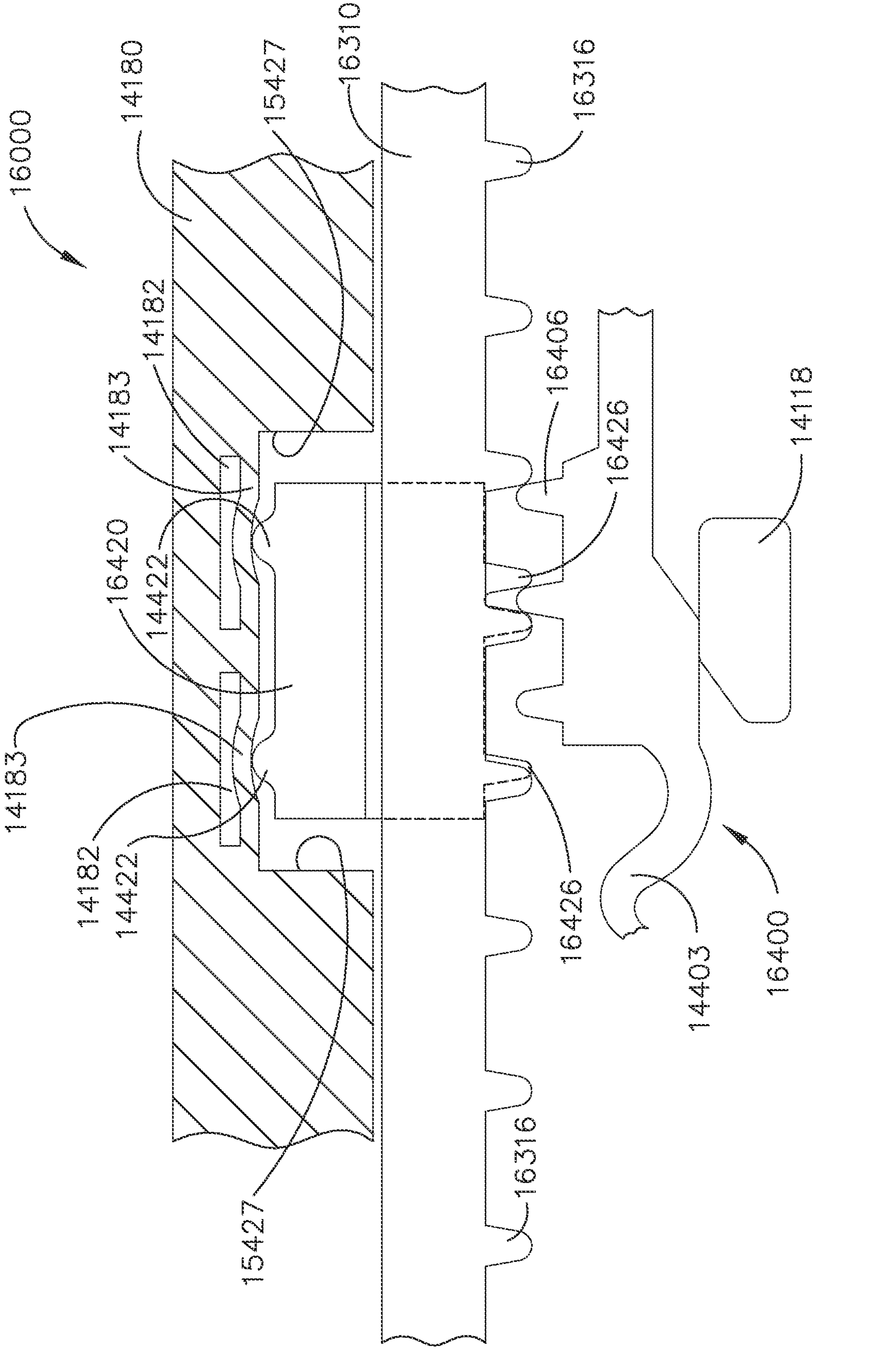
Figure 115:
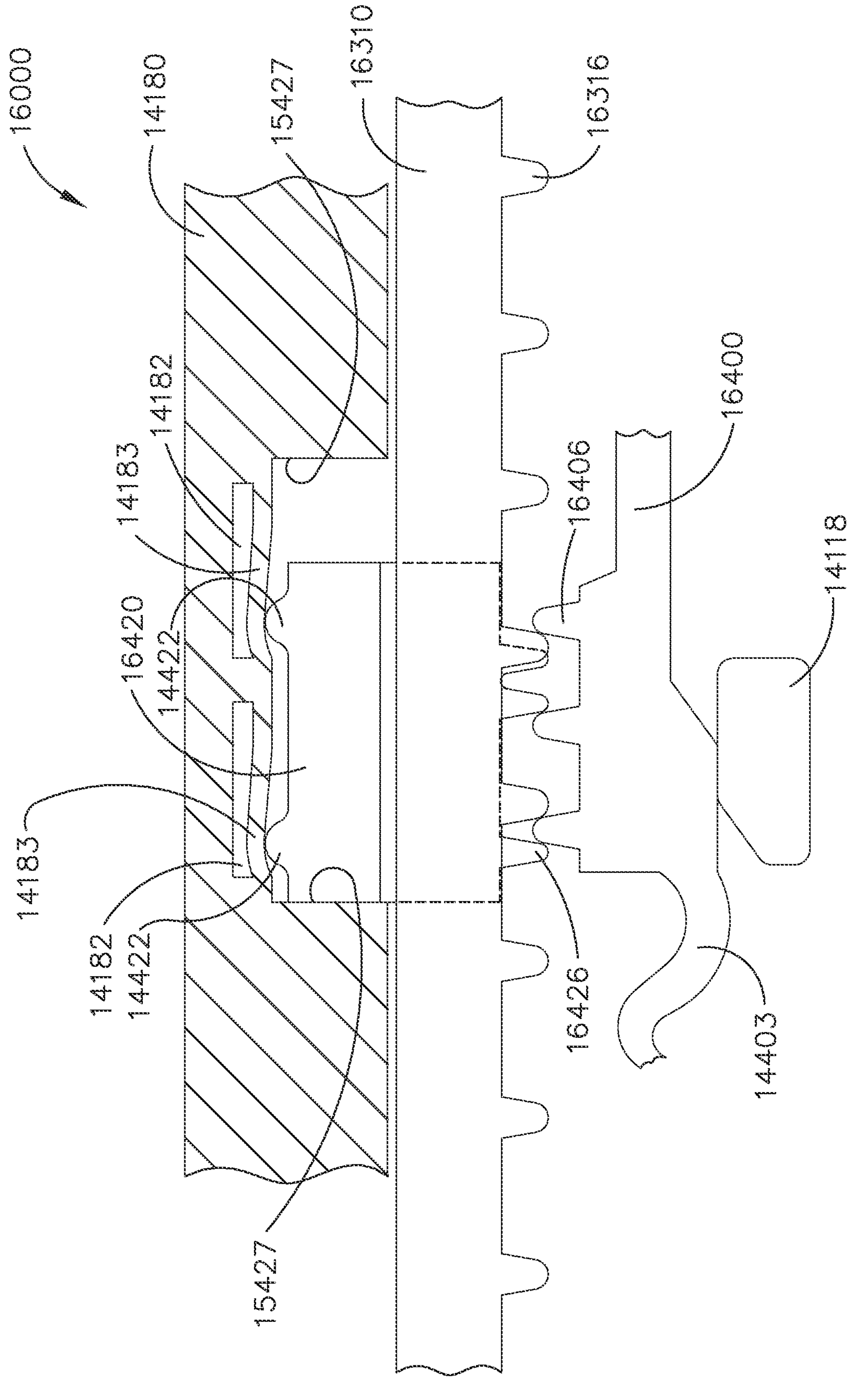
Figure 116A:
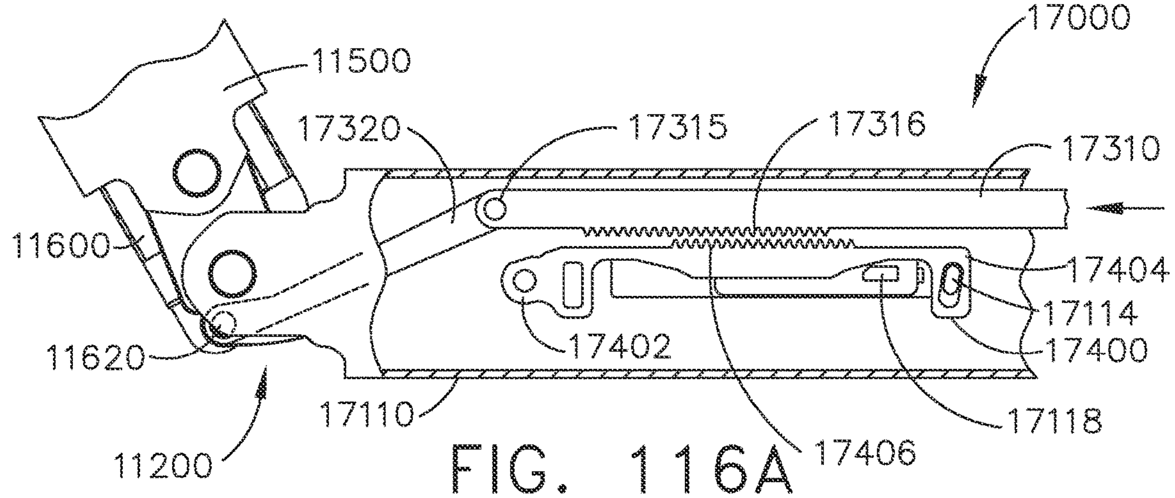
Figure 116:
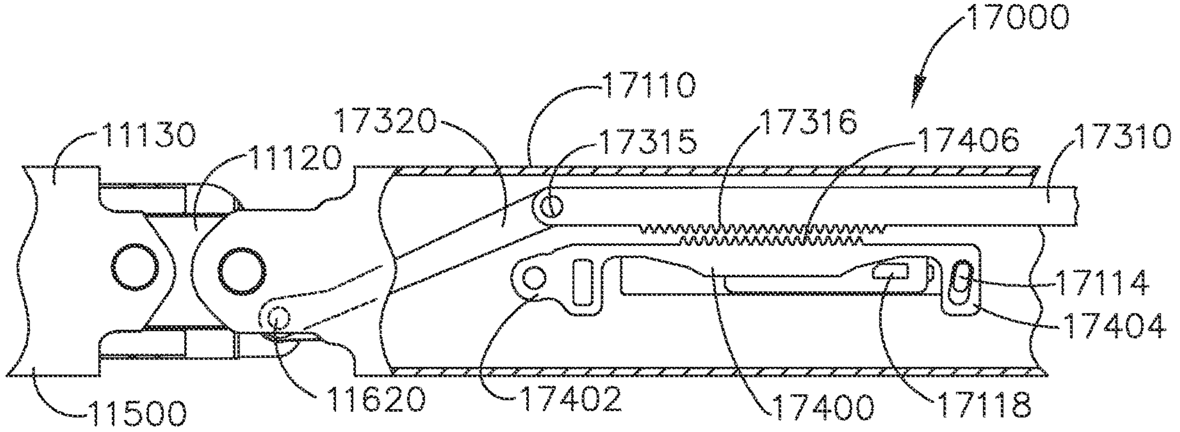
Figure 116B:
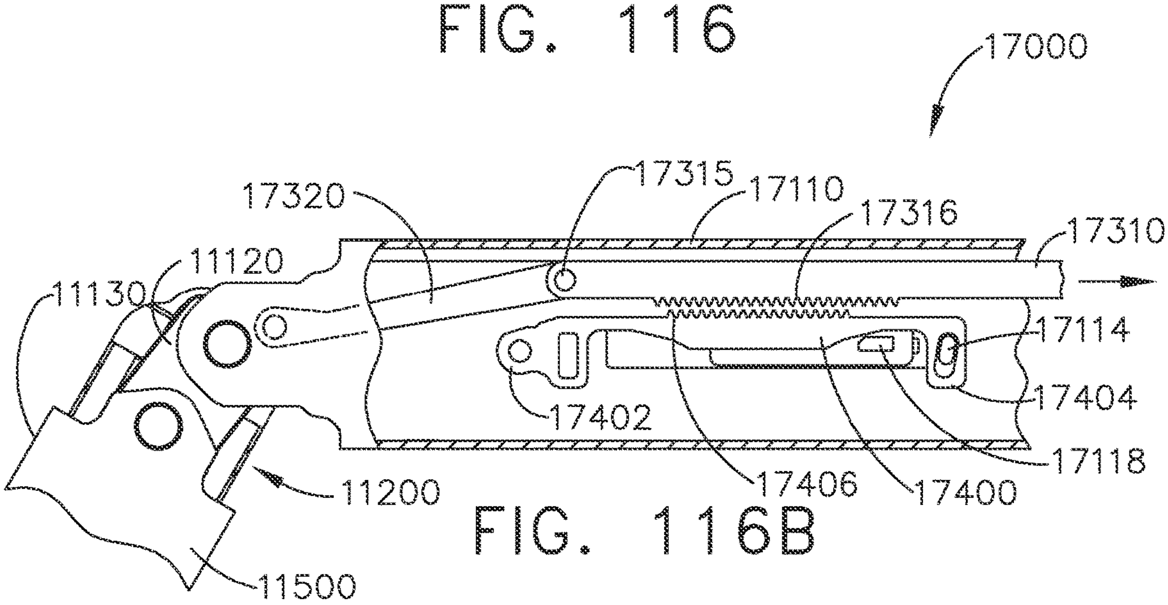
Figure 117:
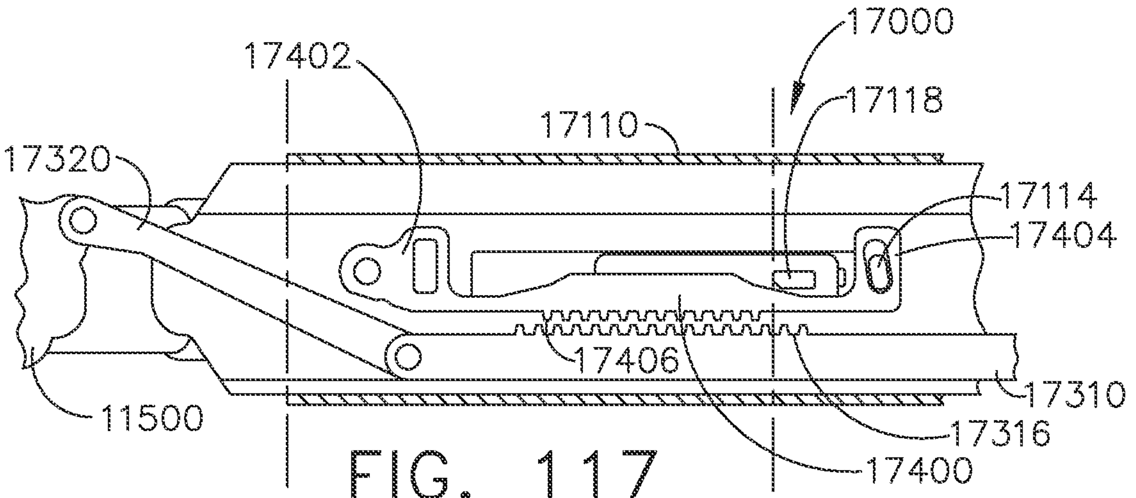
Figure 118:
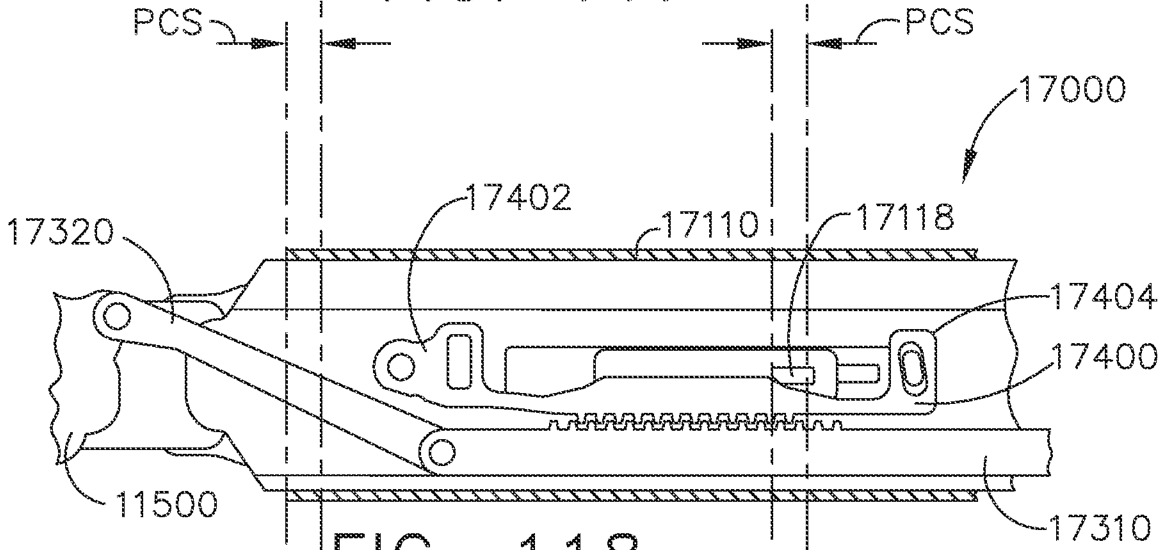
Figure 119:
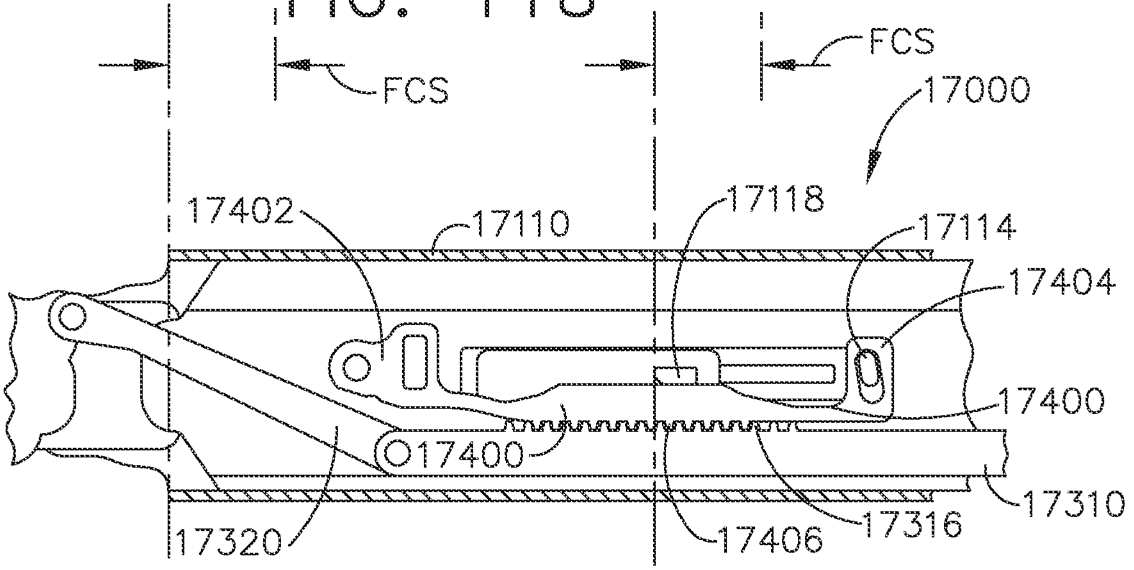
Figure 120:
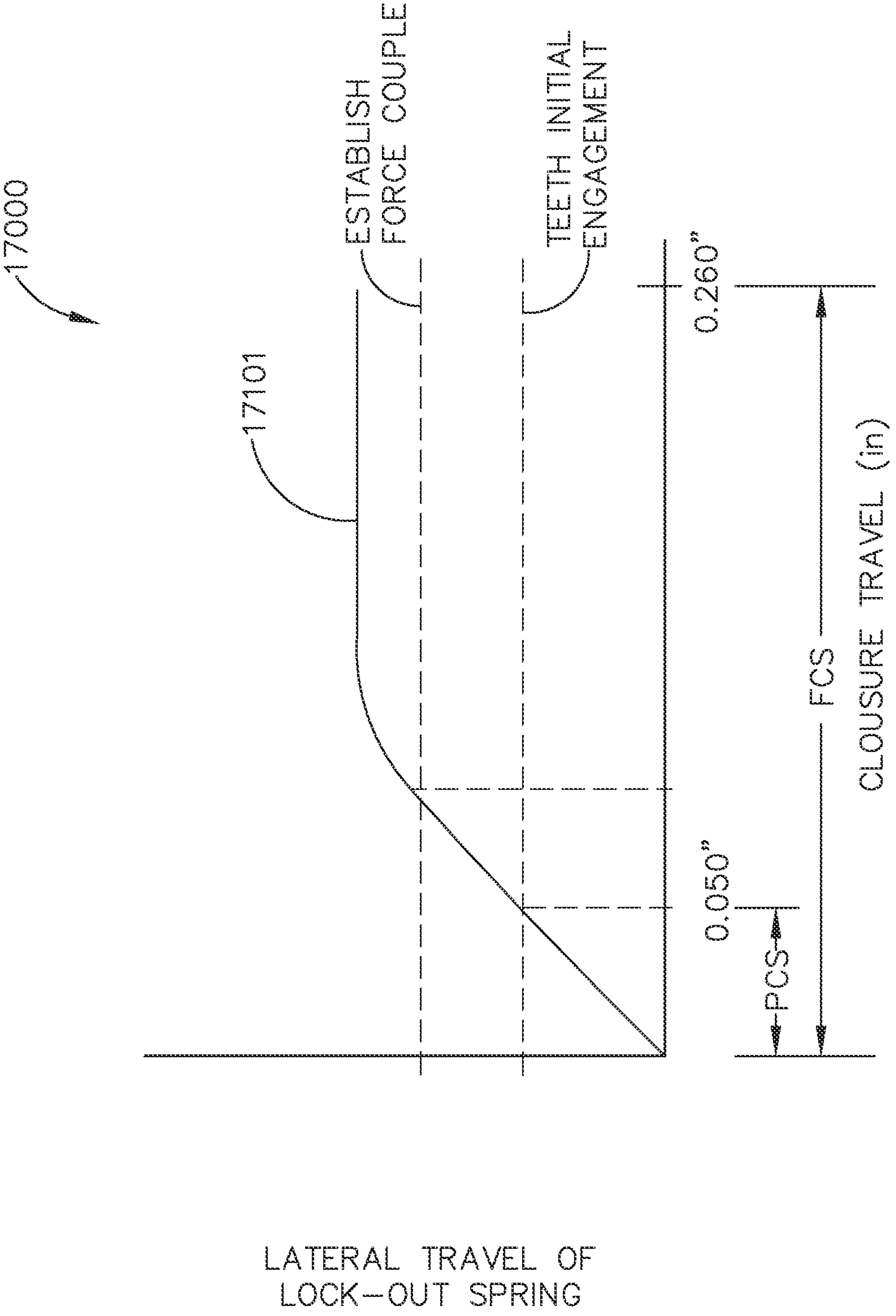
Figure 121:
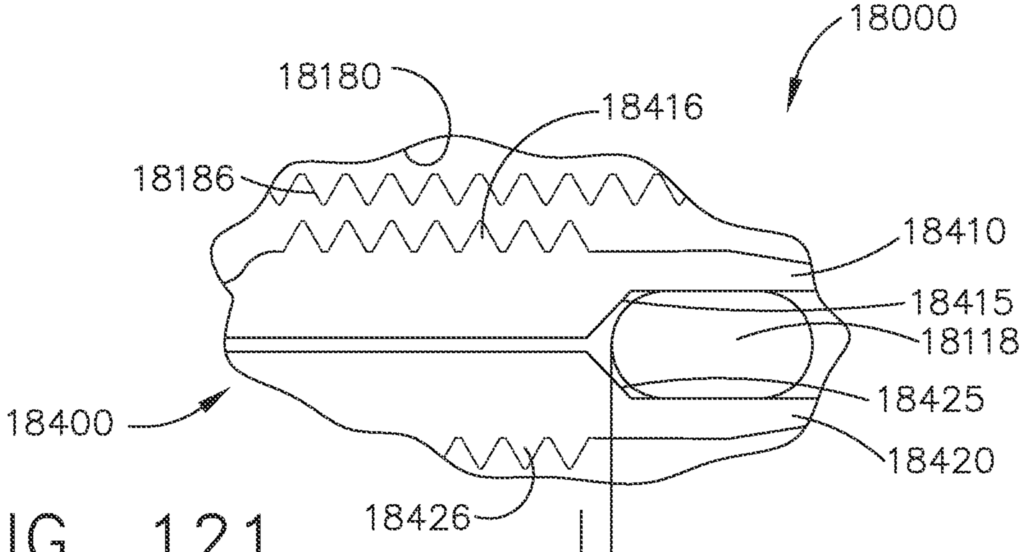
Figure 122:
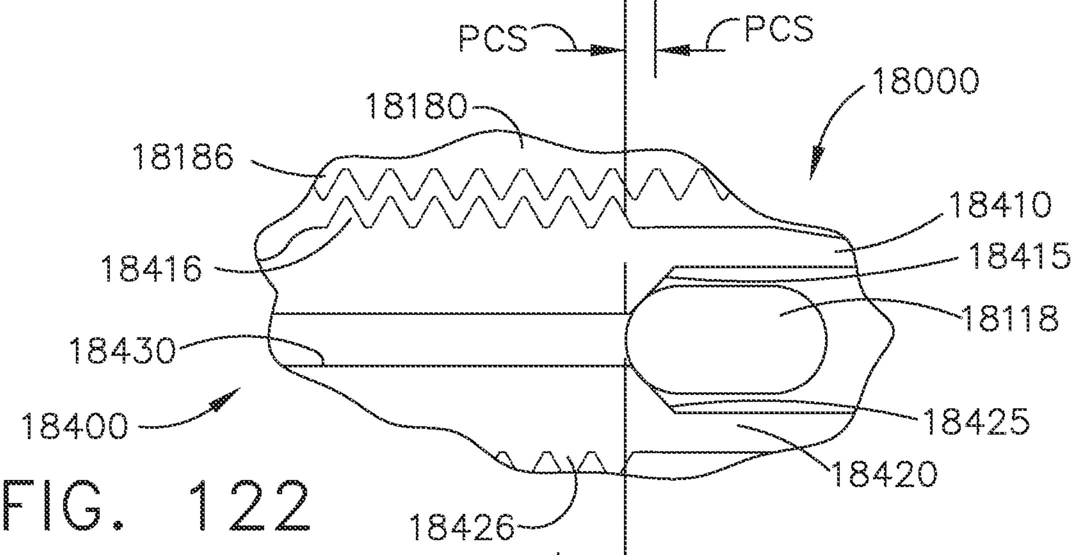
Figure 123:
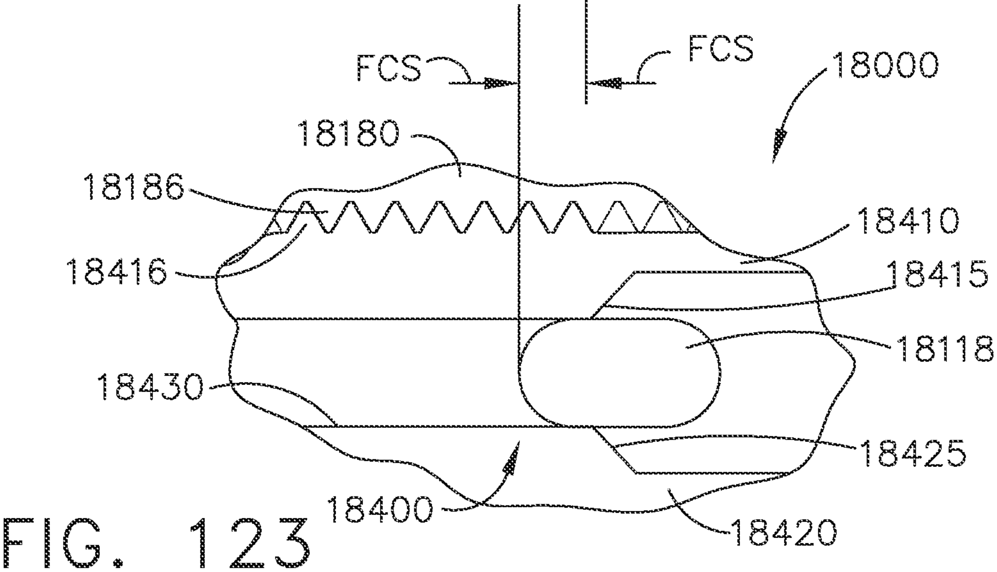
Figure 124:
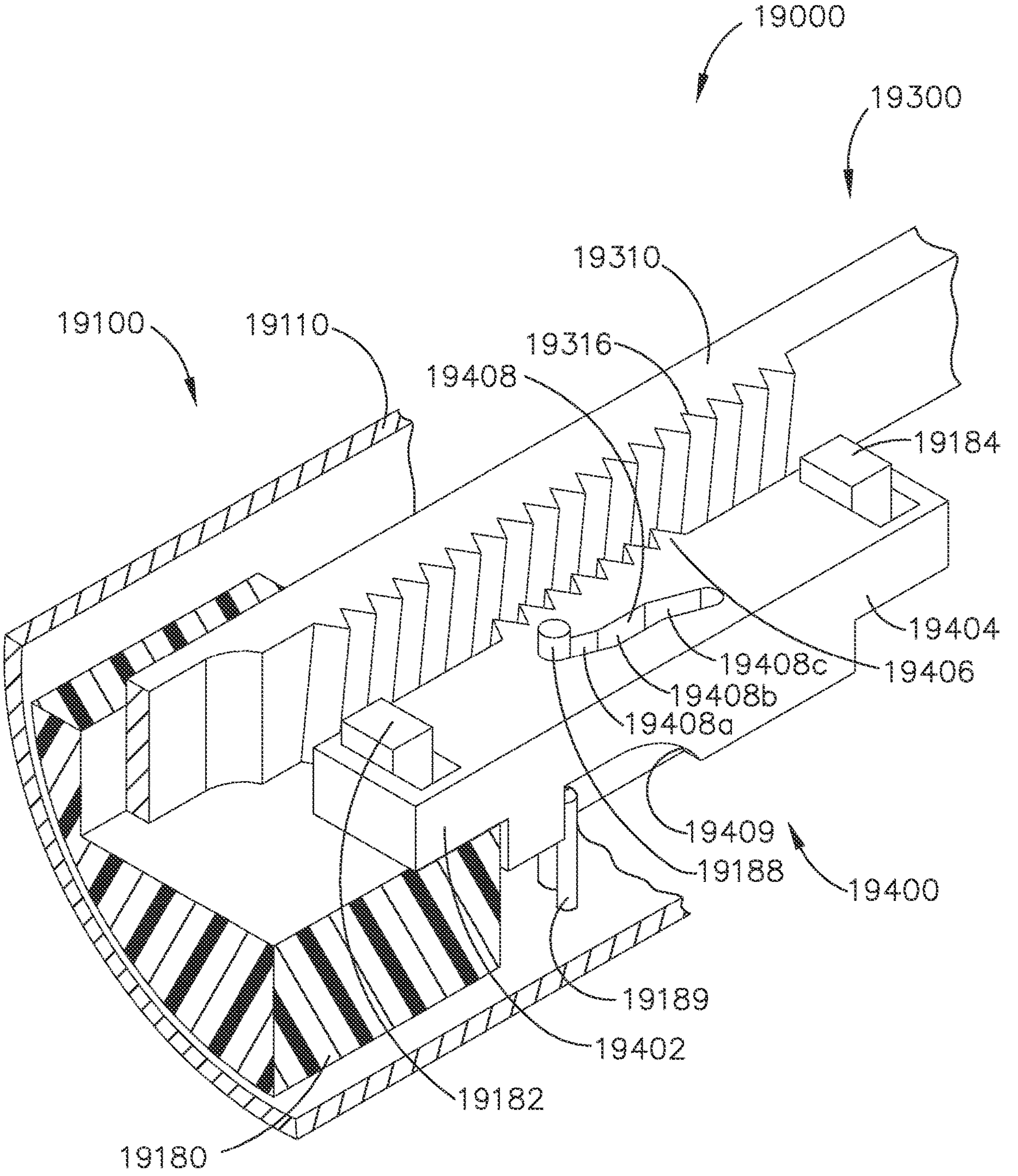
Figure 125:
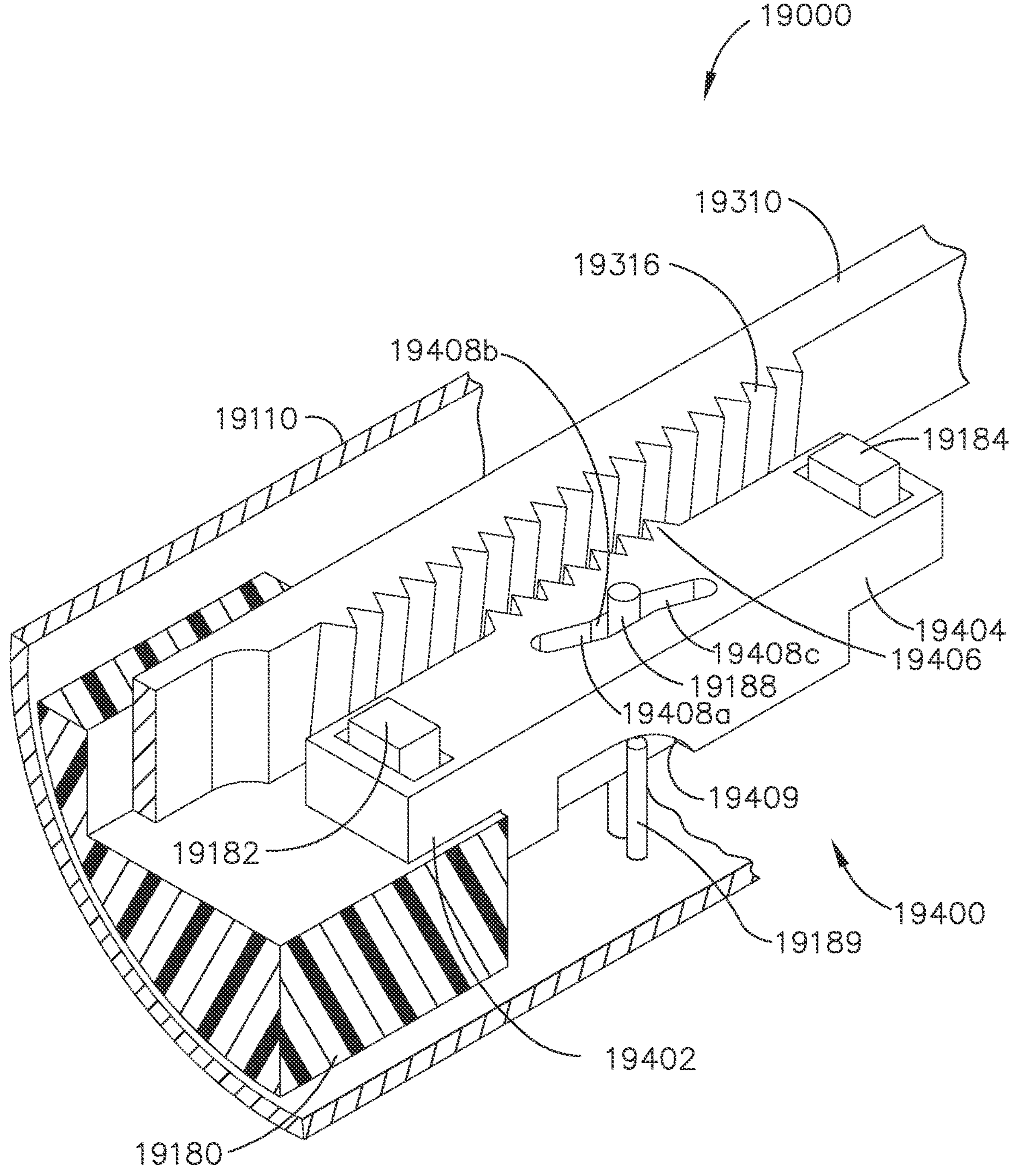
Figure 126:
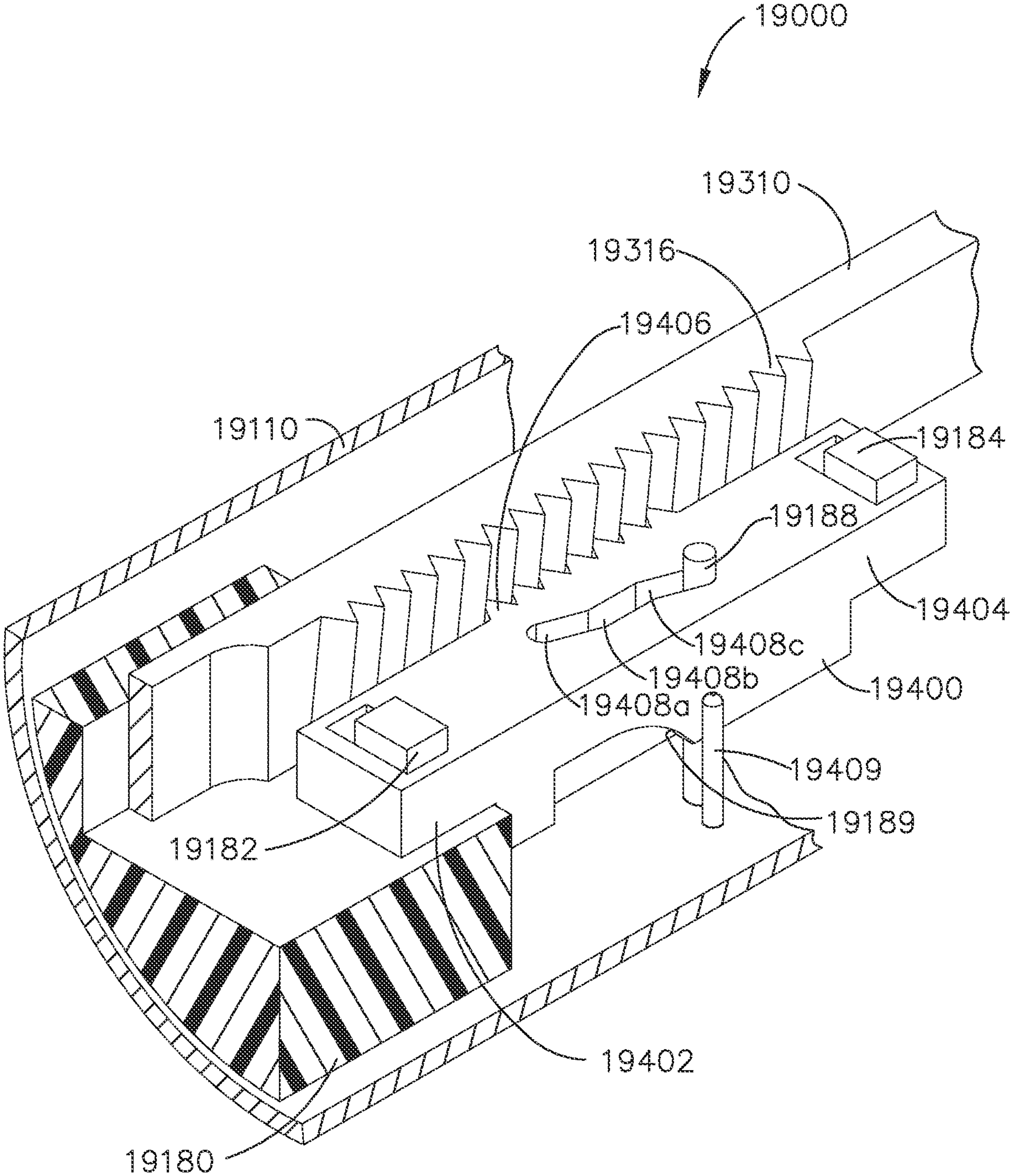
Figure 127:
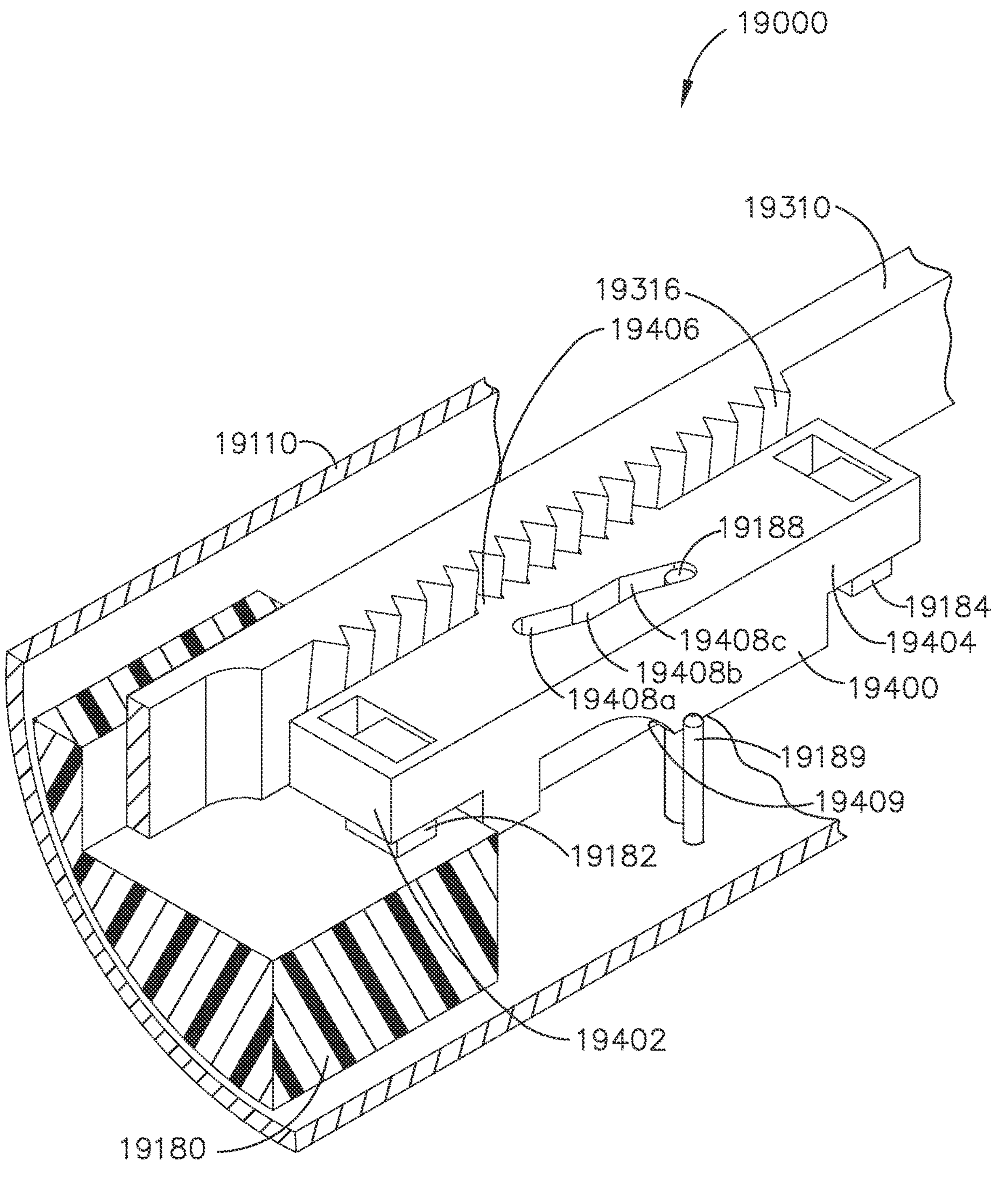
Figure 128:
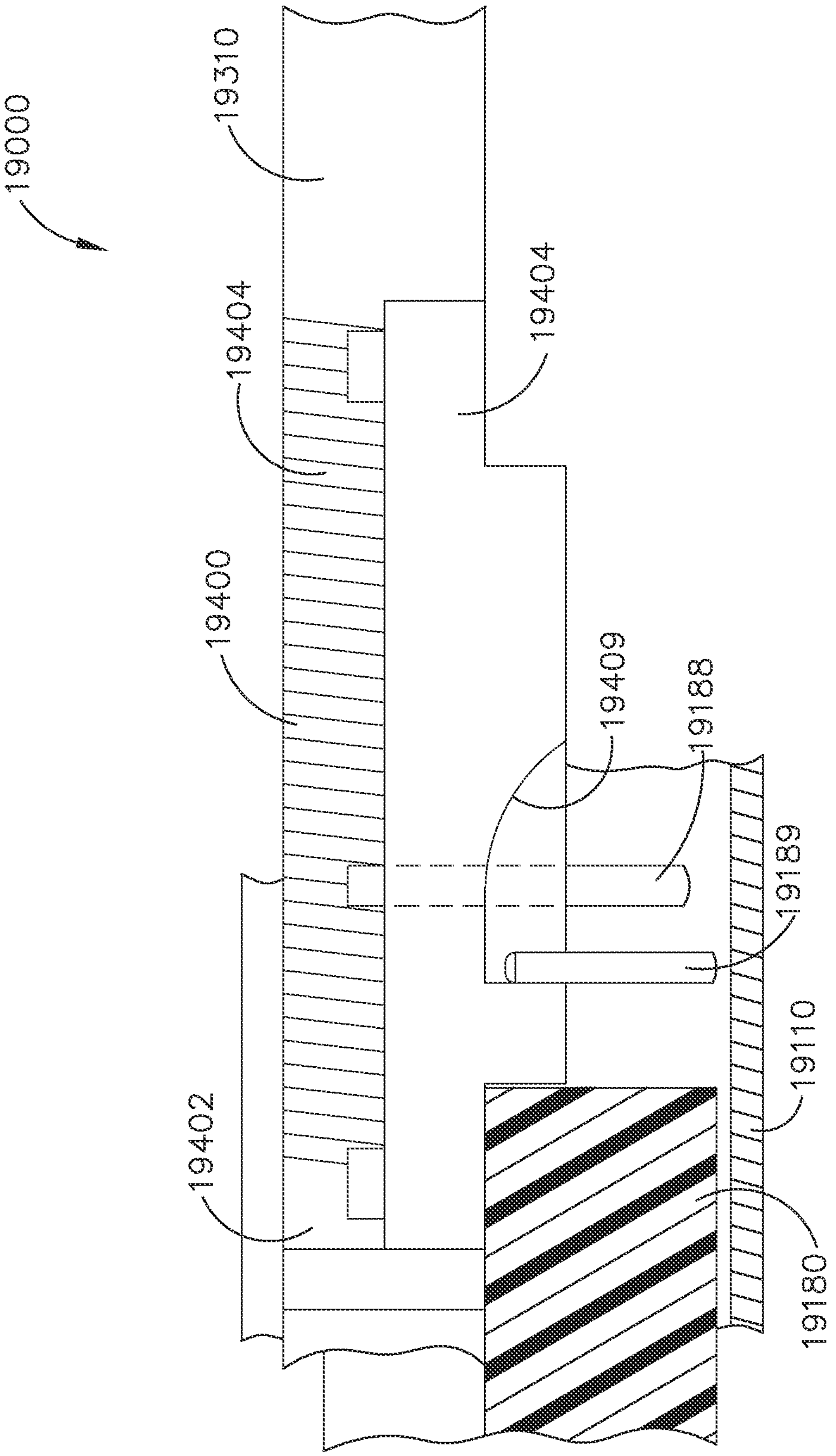
Figure 129:
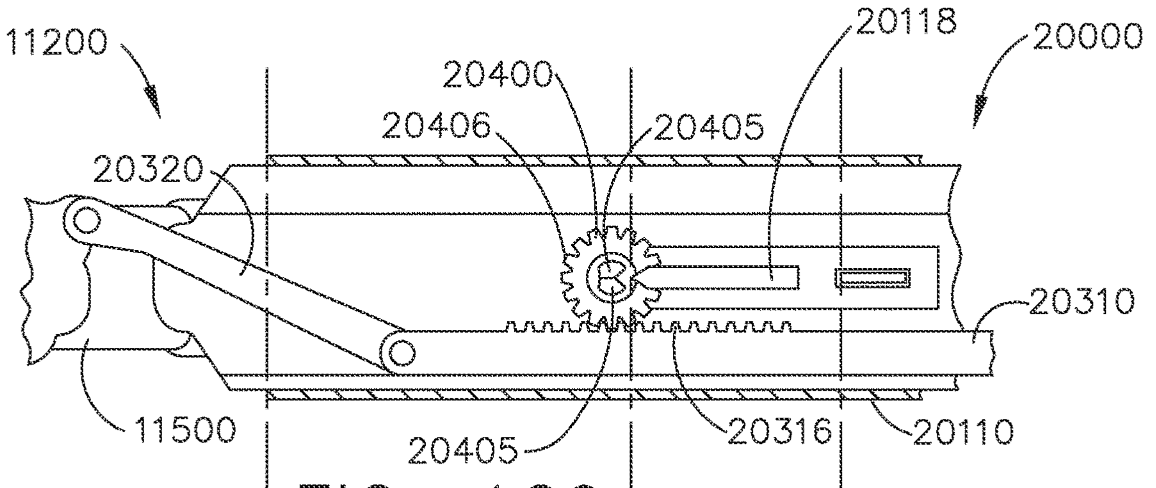
Figure 130:
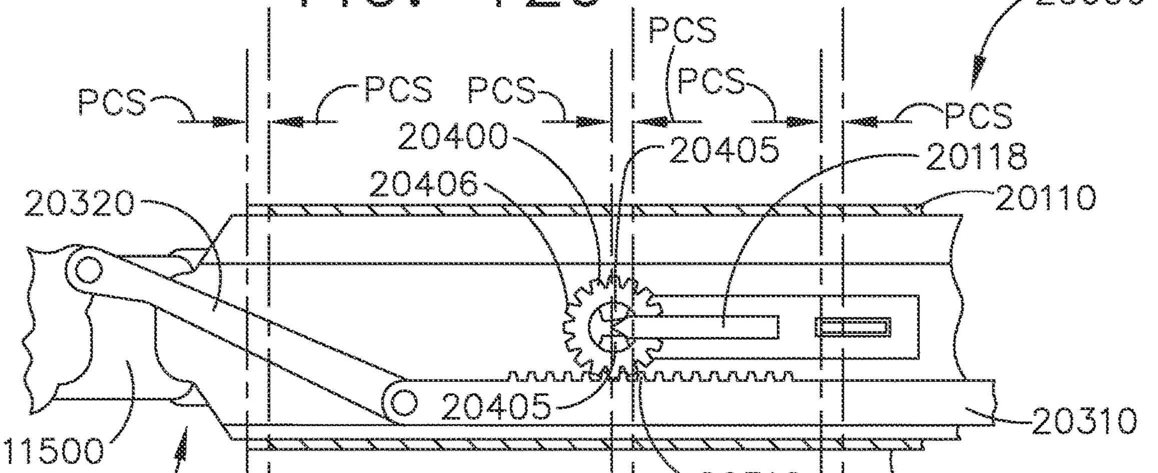
Figure 131:
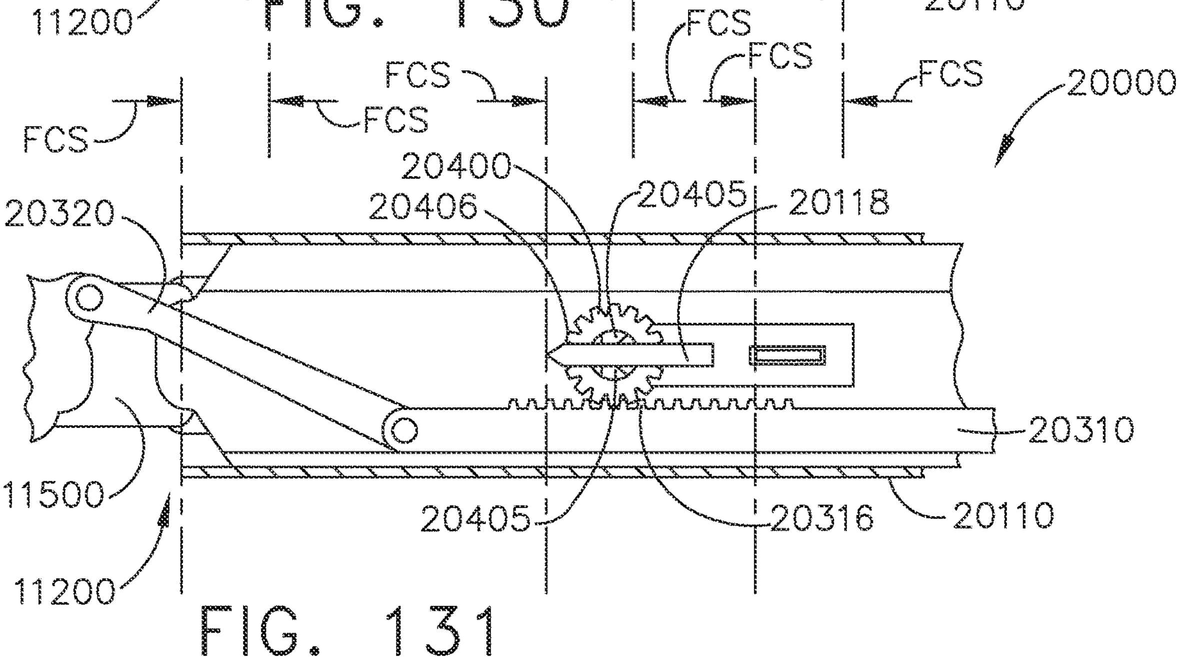
Figure 132:
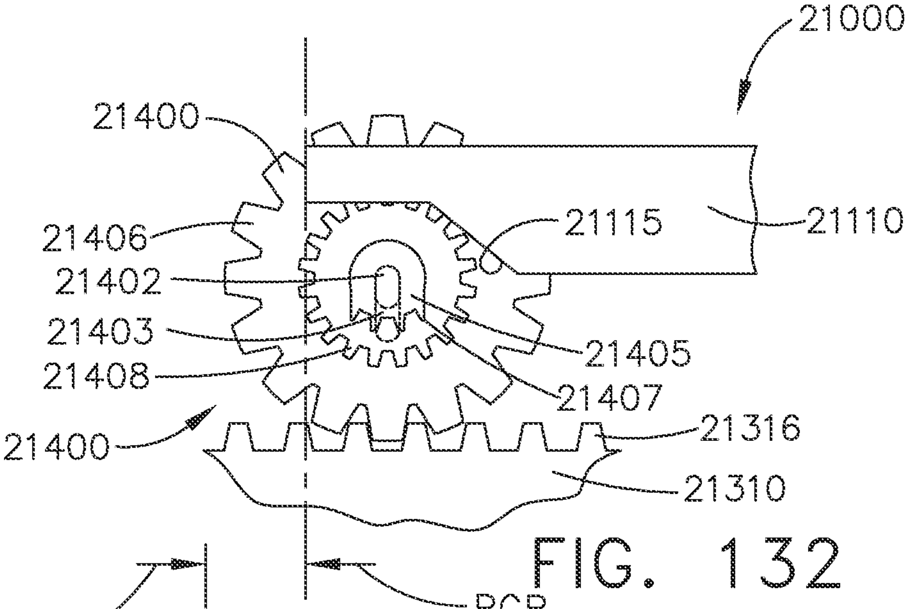
Figure 133:
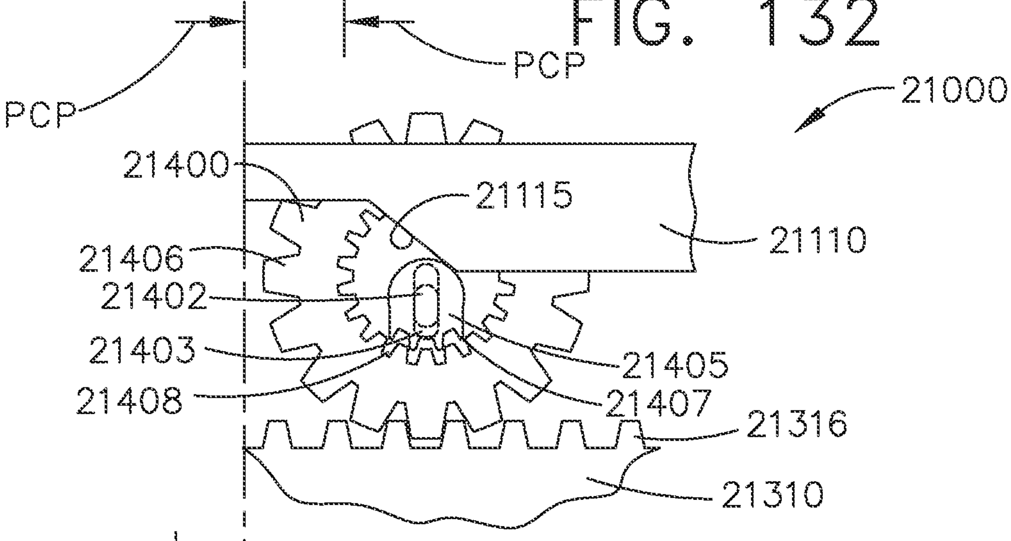
Figure 134:
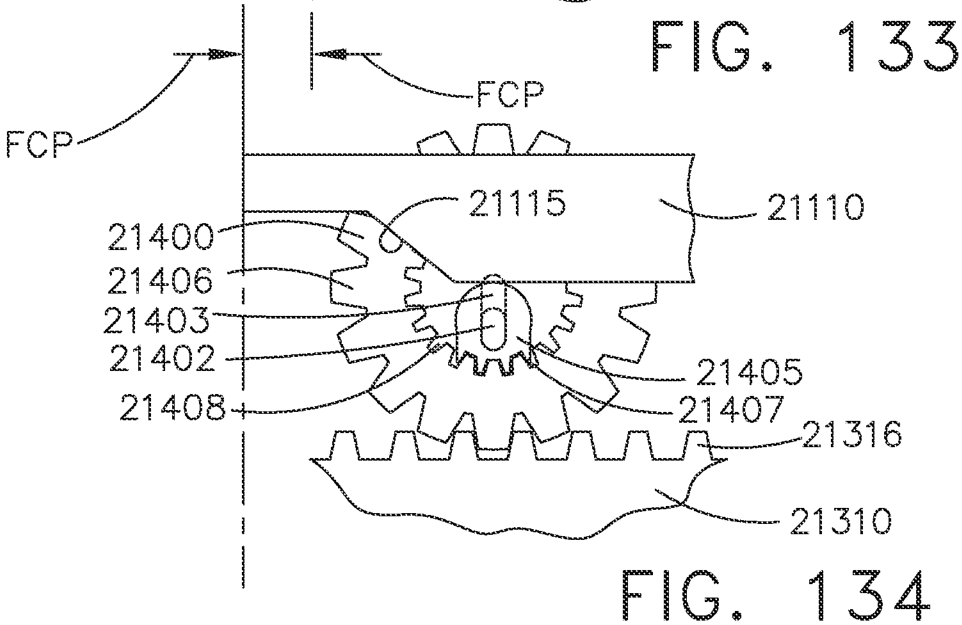
Figure 135:
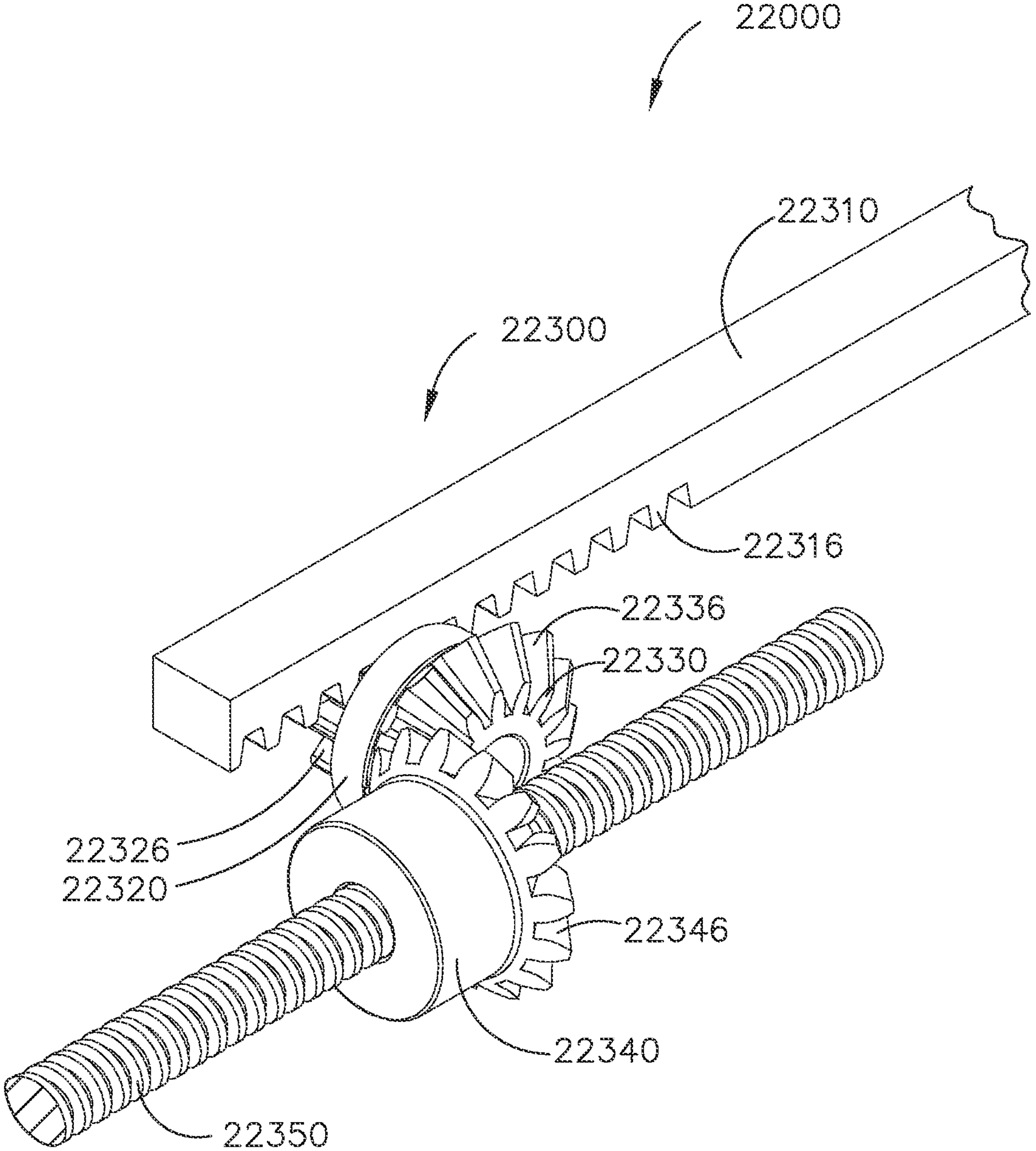
Figure 136:
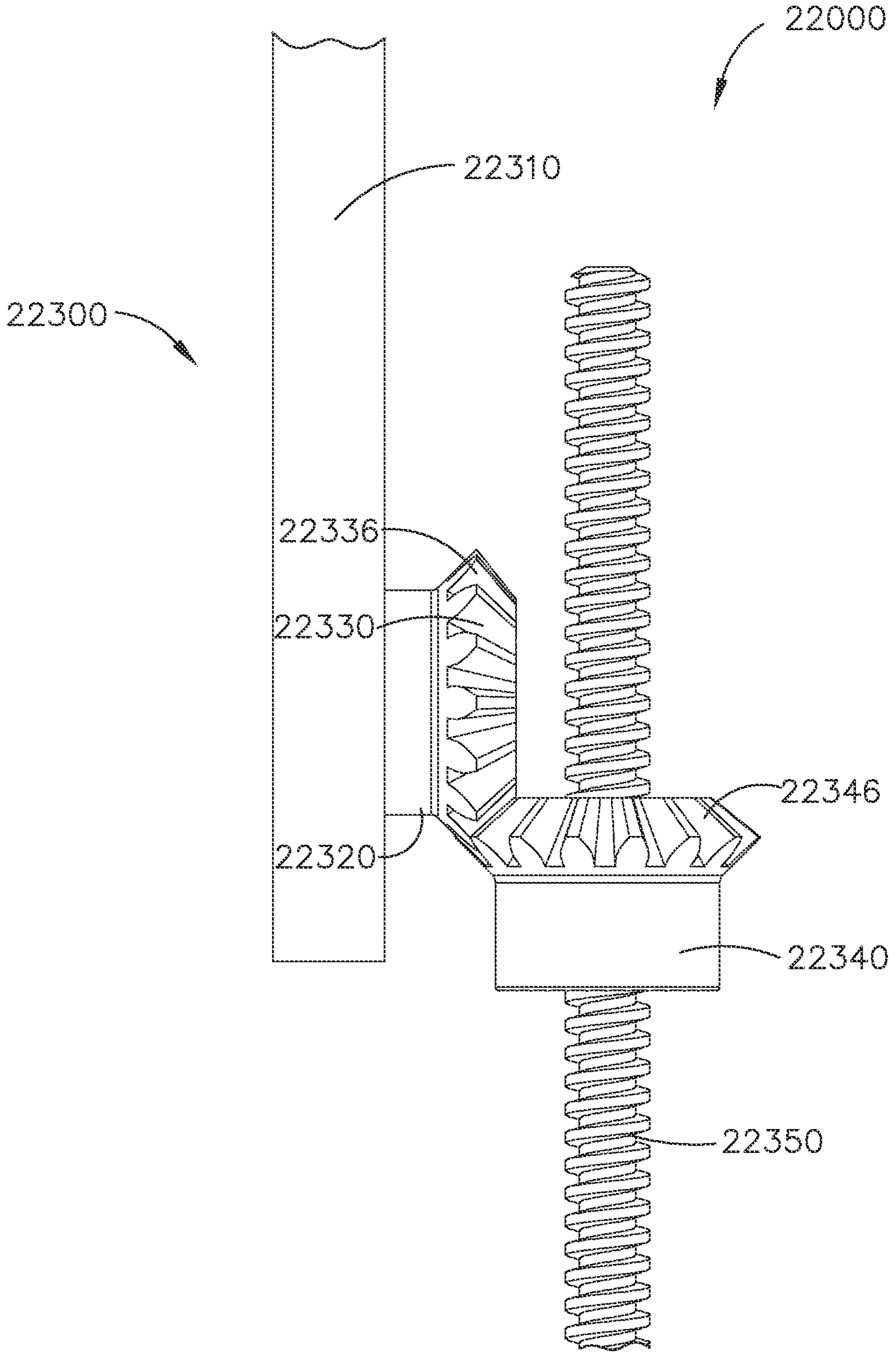
Figure 137:
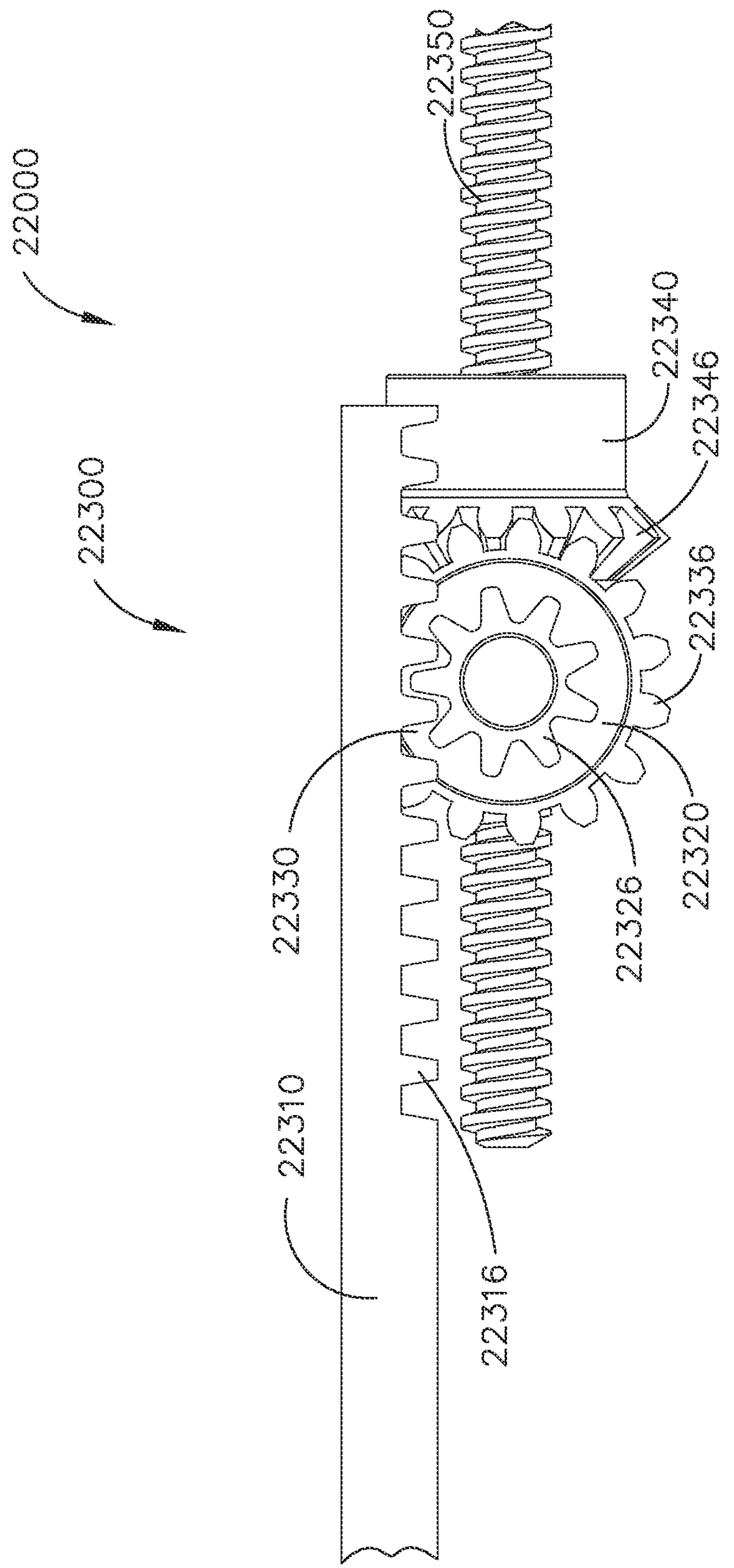
Figure 138:
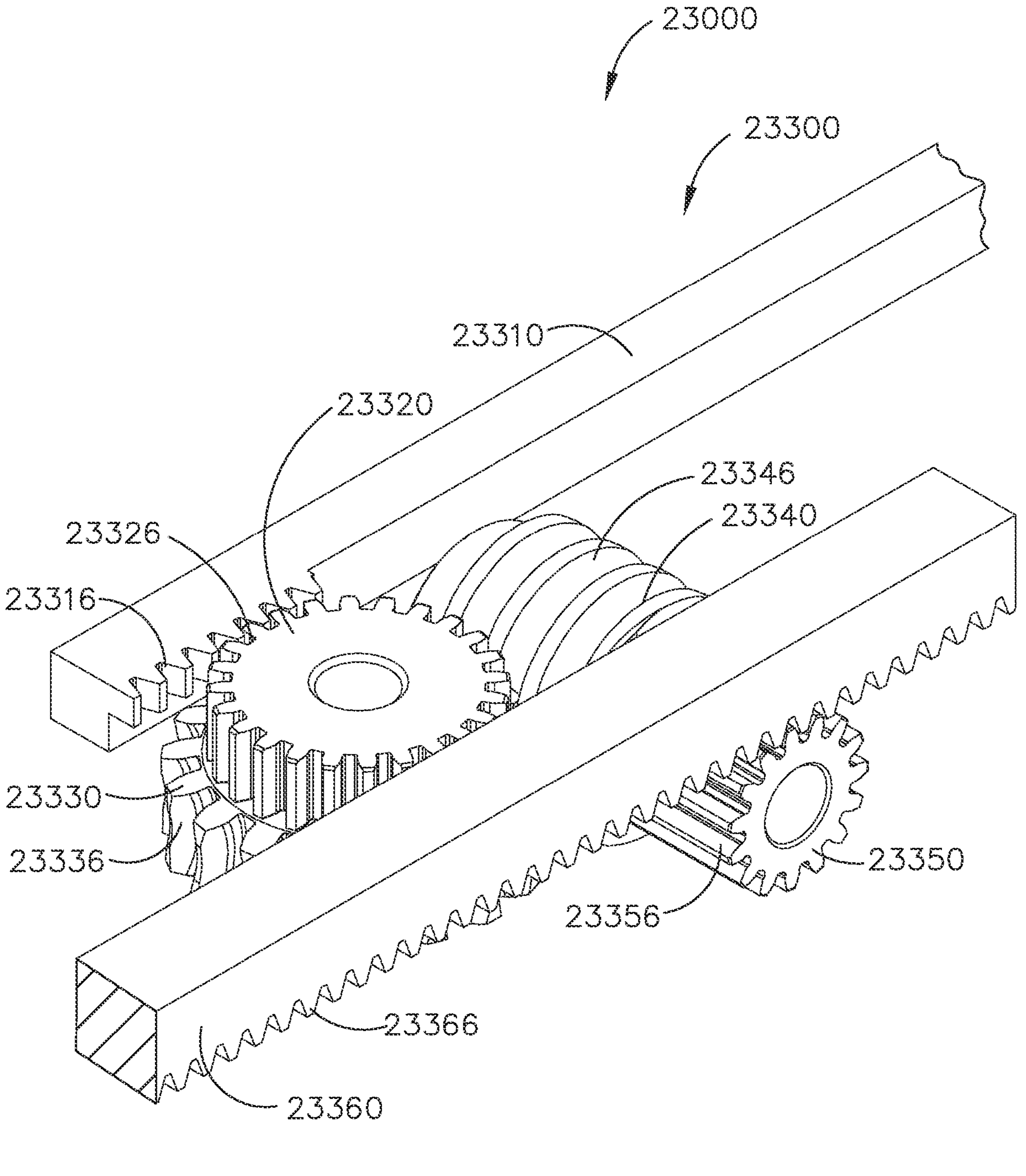
Figure 139:
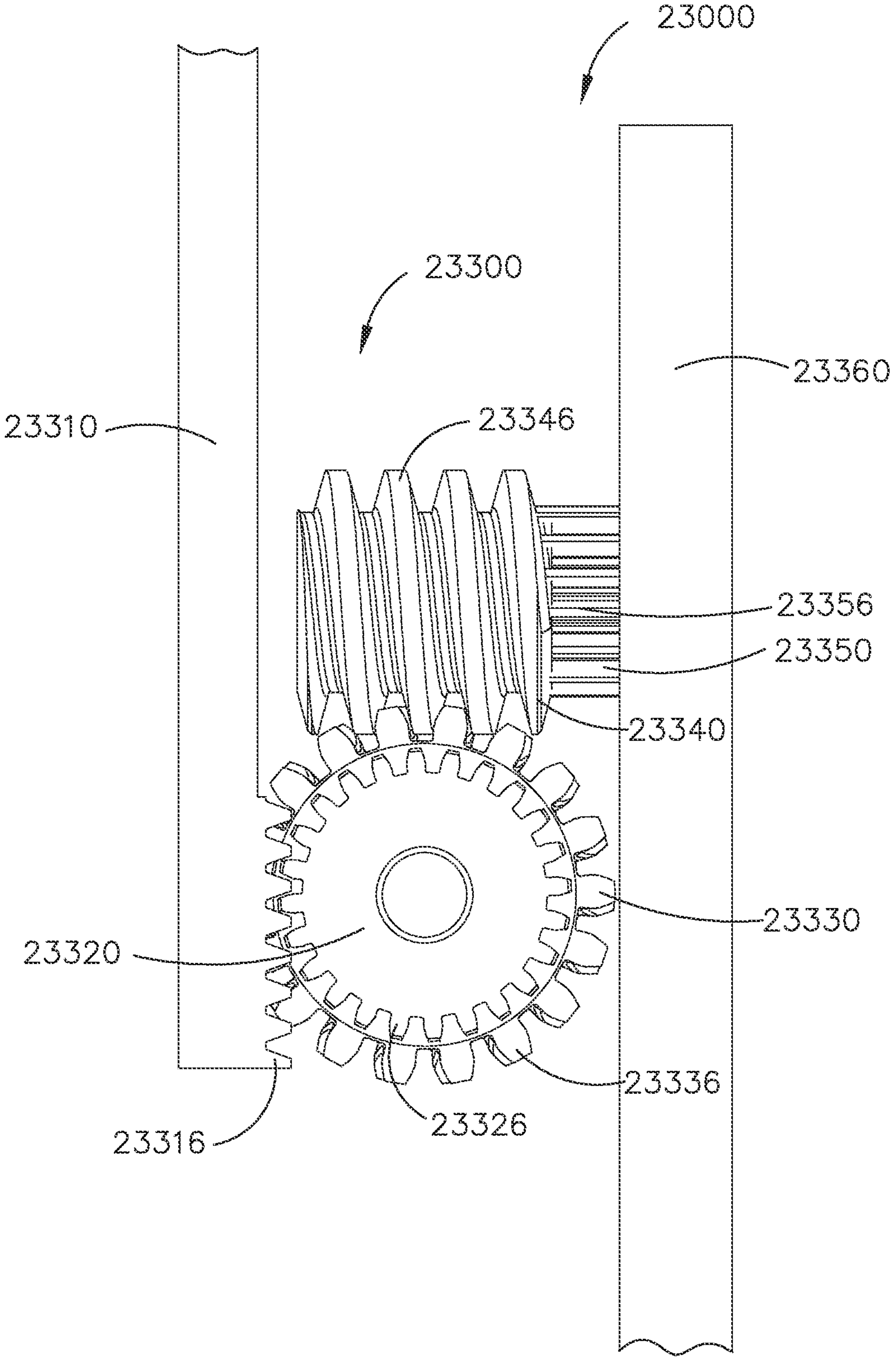
Figure 140:
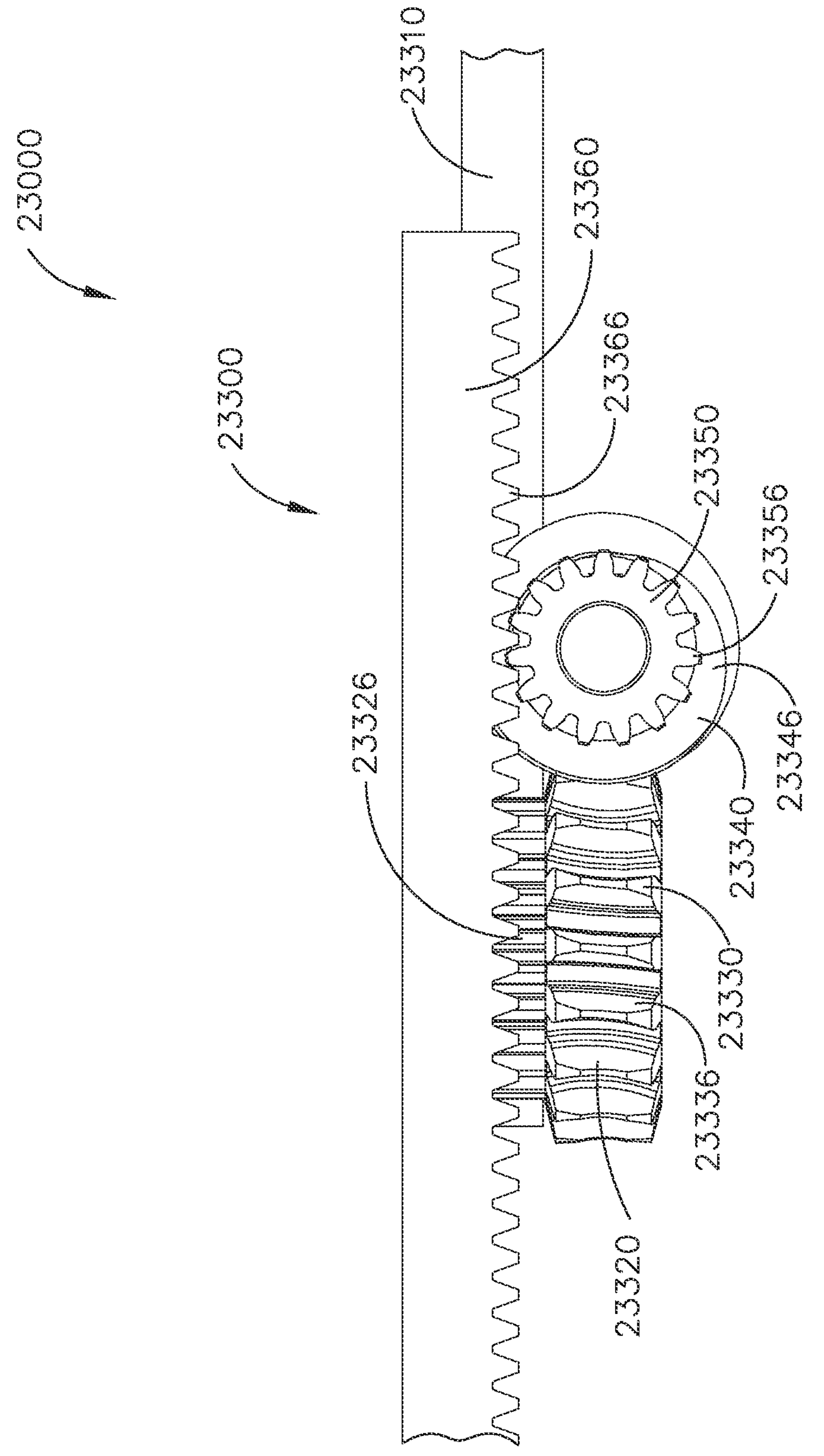
Figure 141:
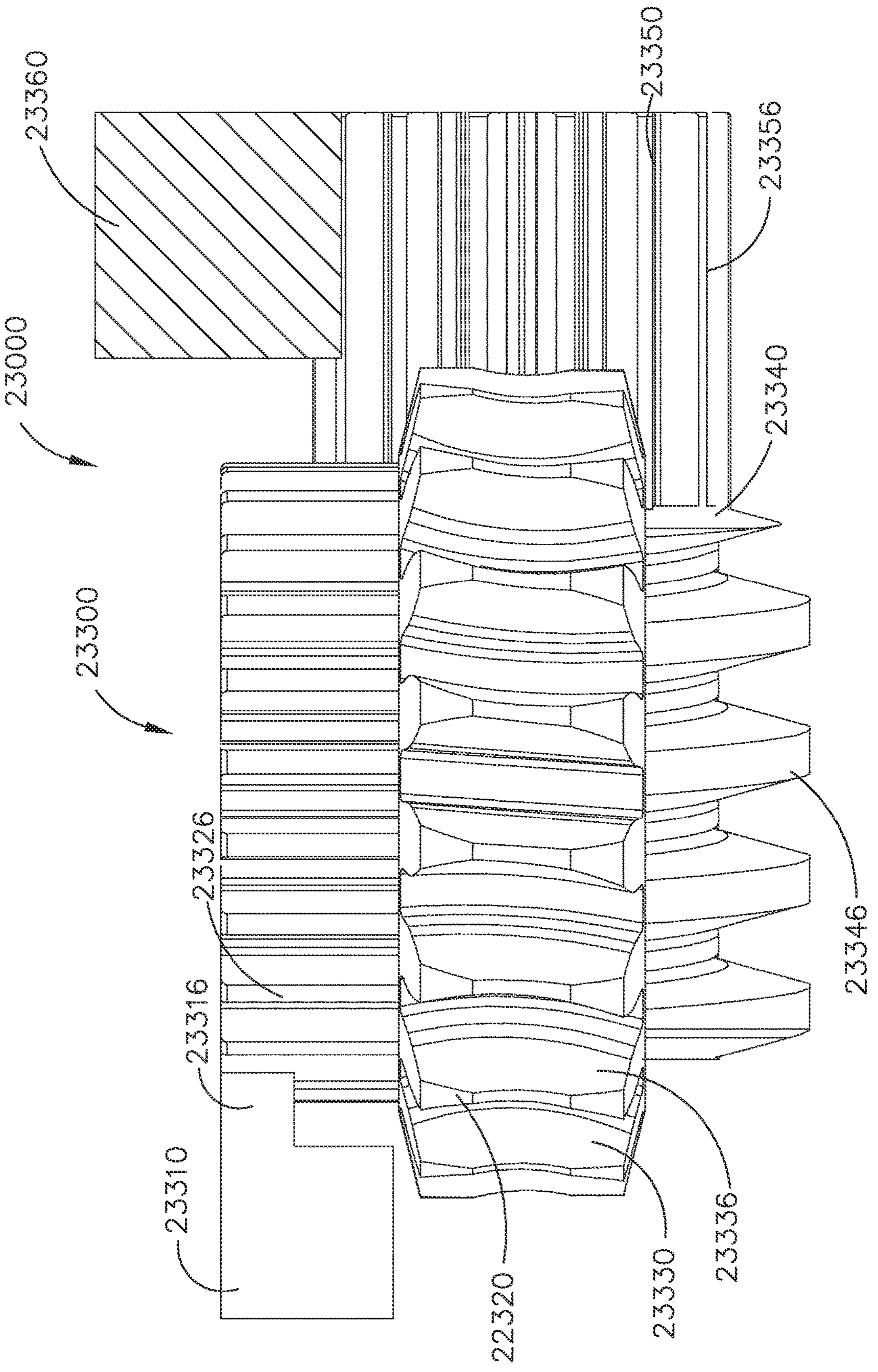
Figure 142:
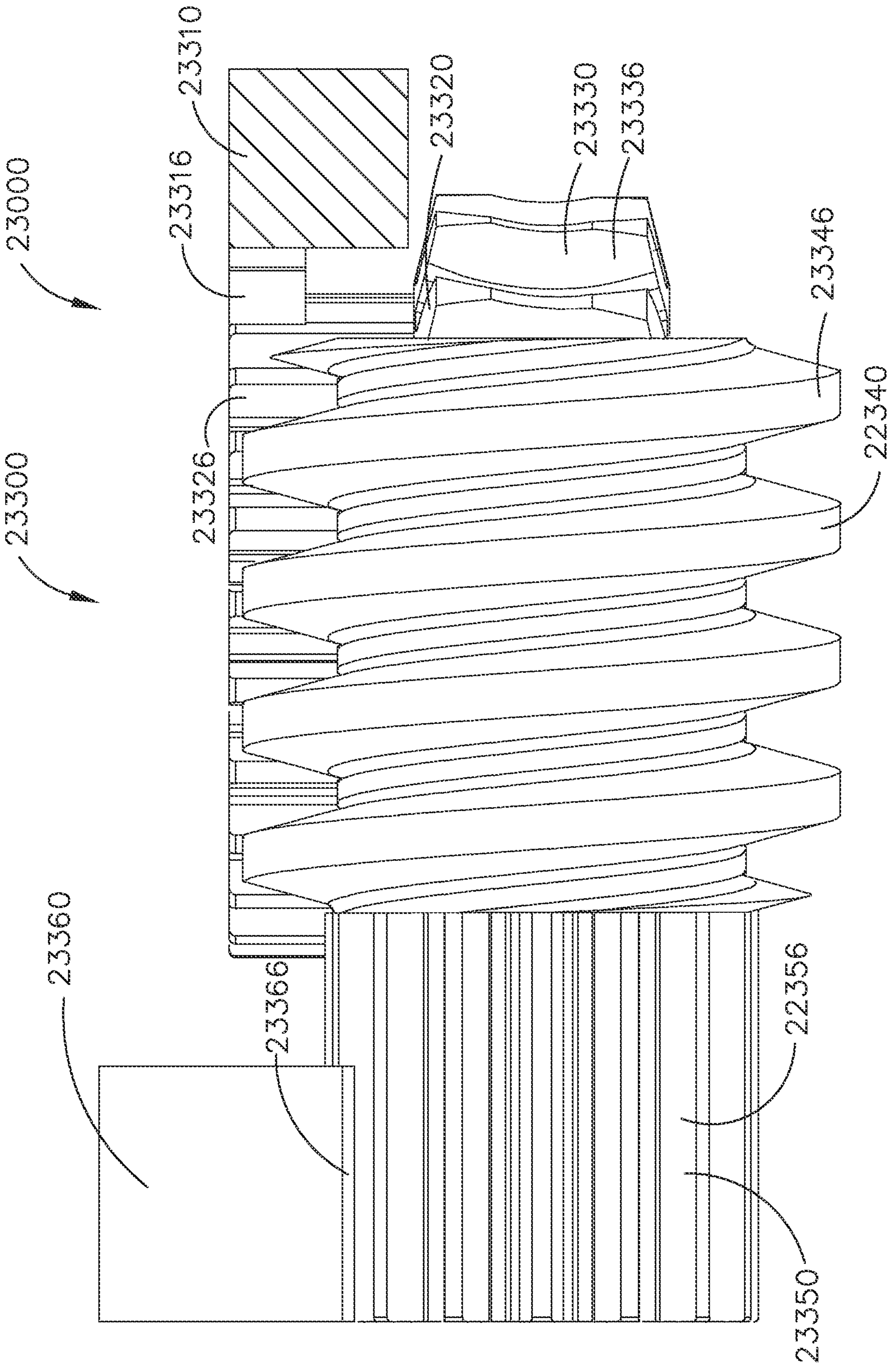
Figure 143:
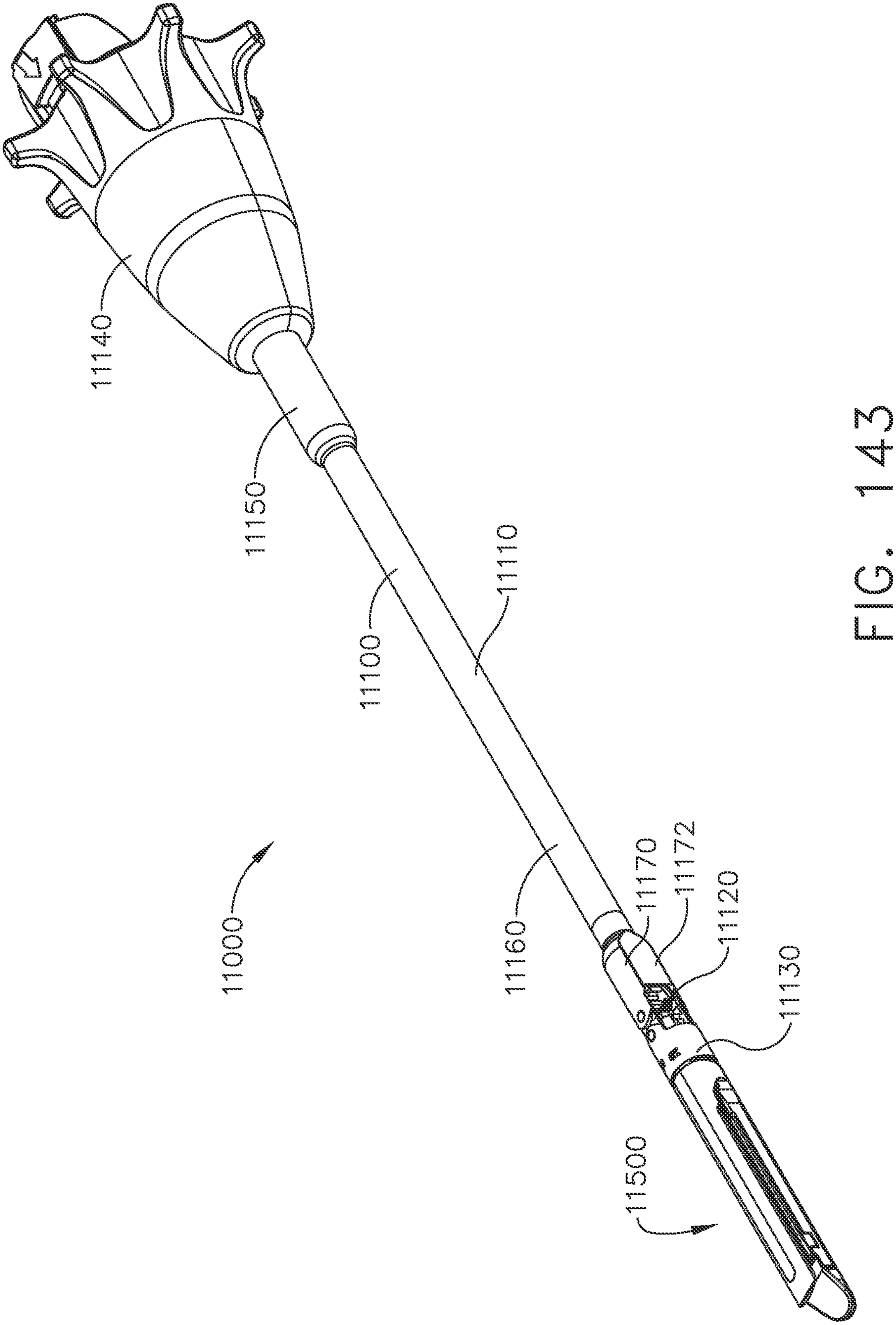
Figure 144:
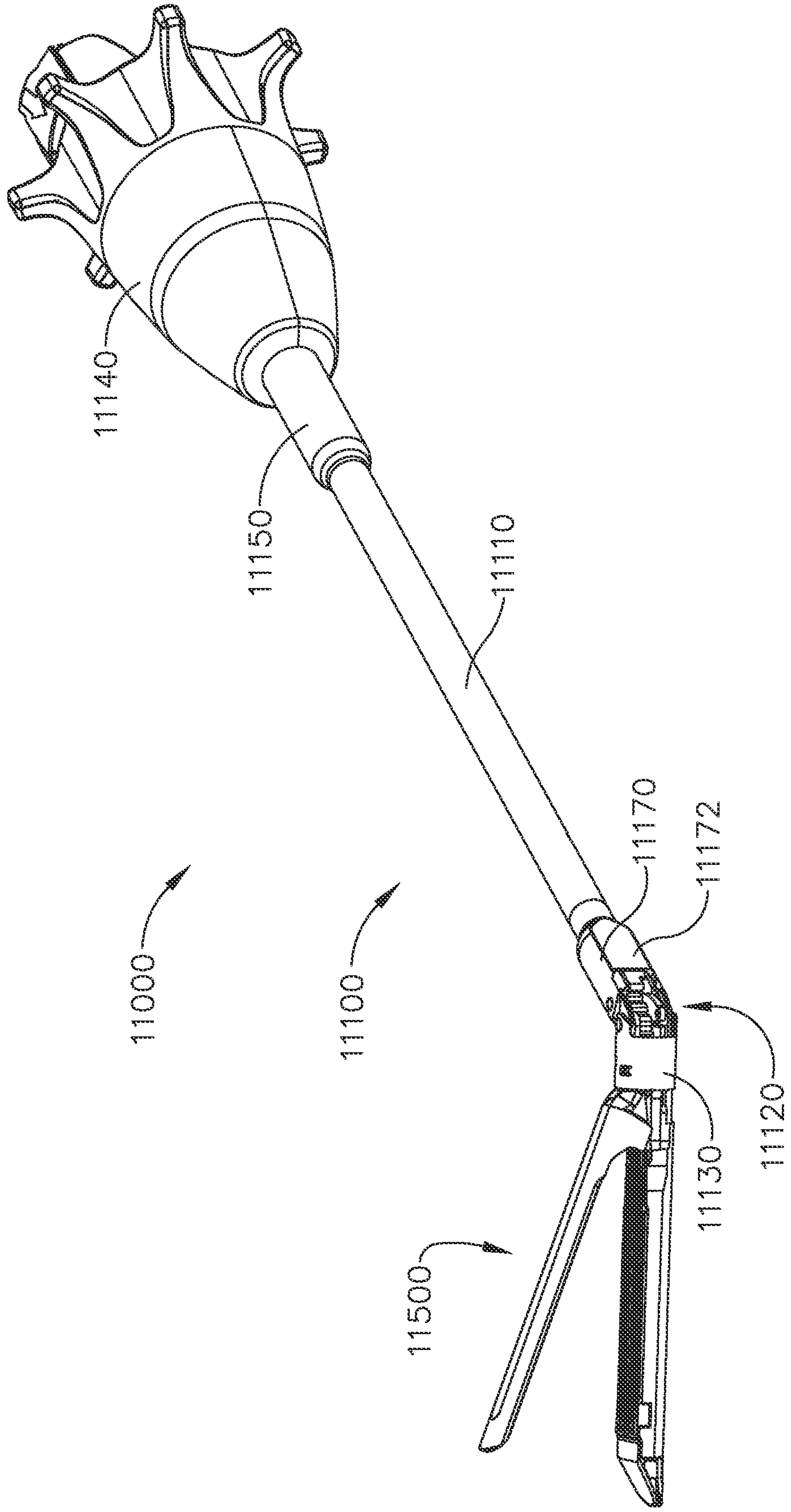
Figure 145:
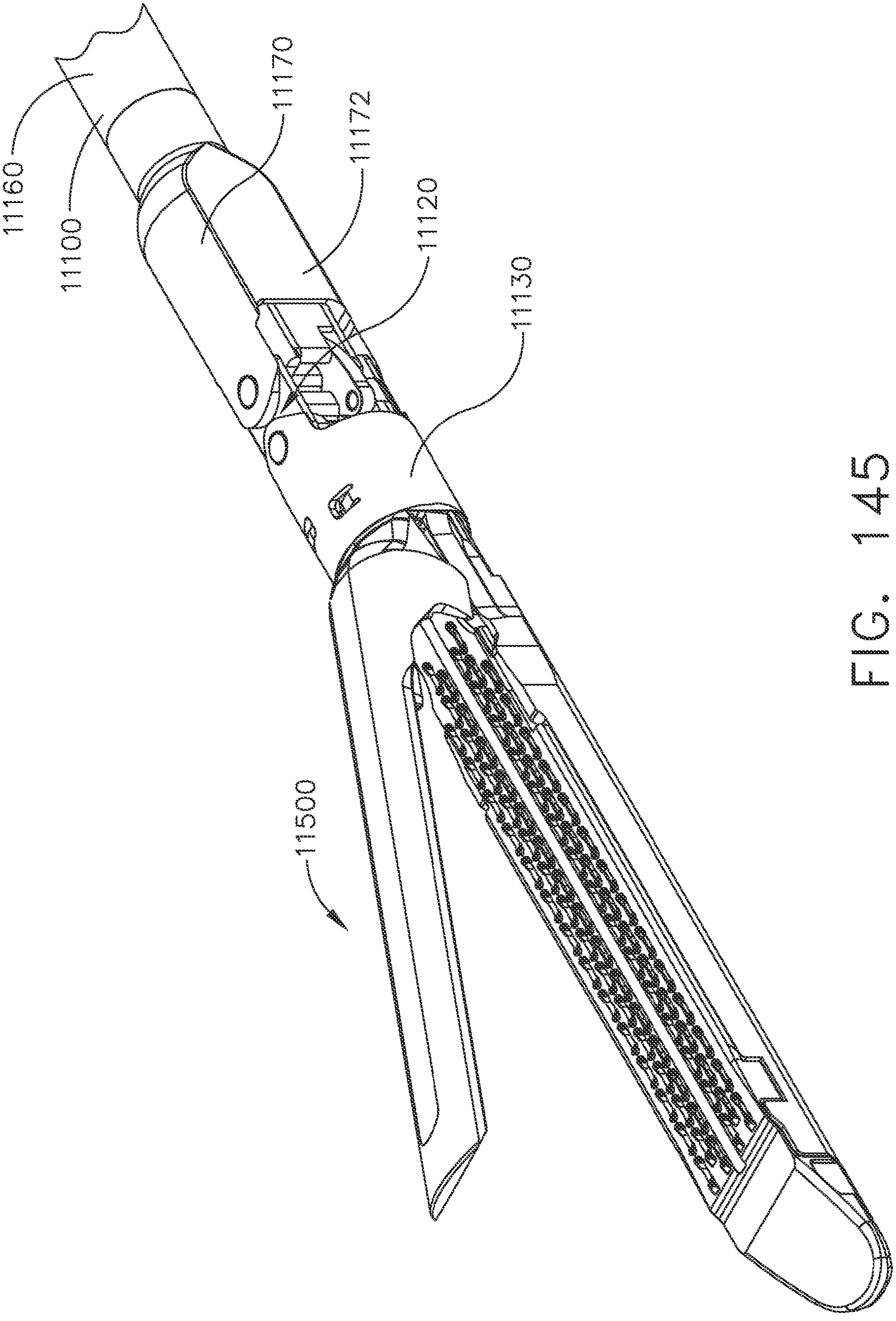
Figure 146:
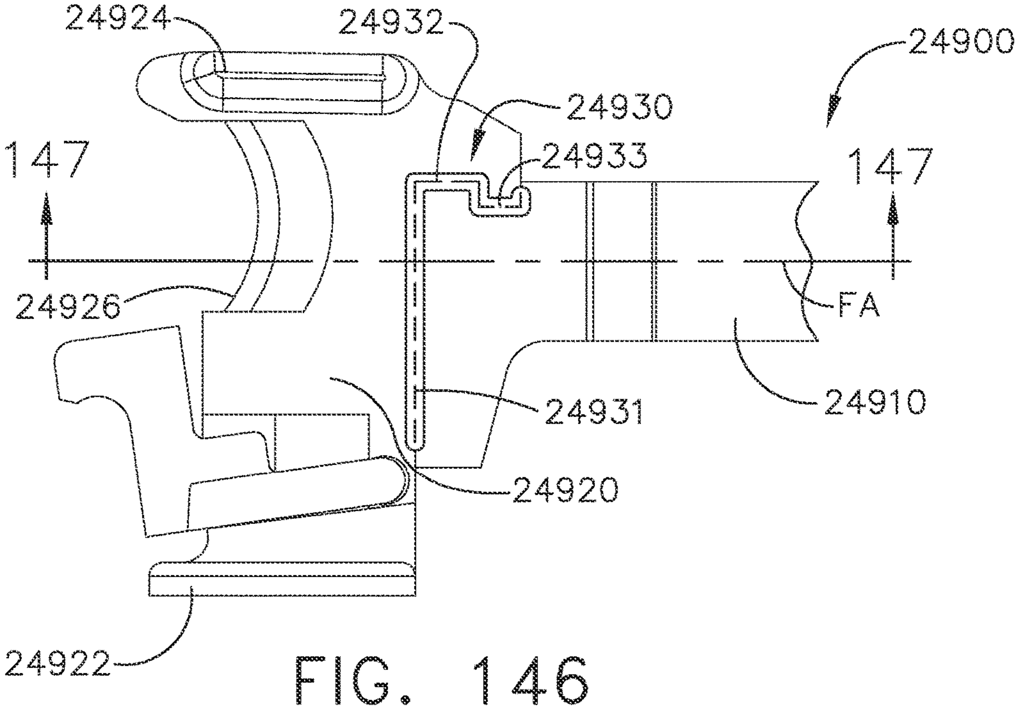
Figure 147:
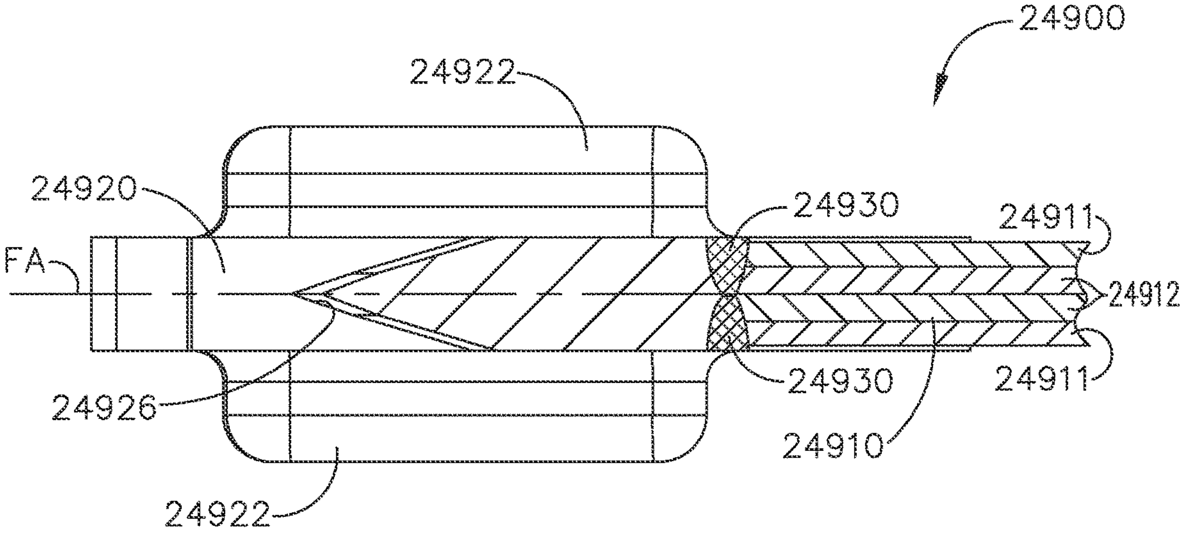
Figures 148, 149:
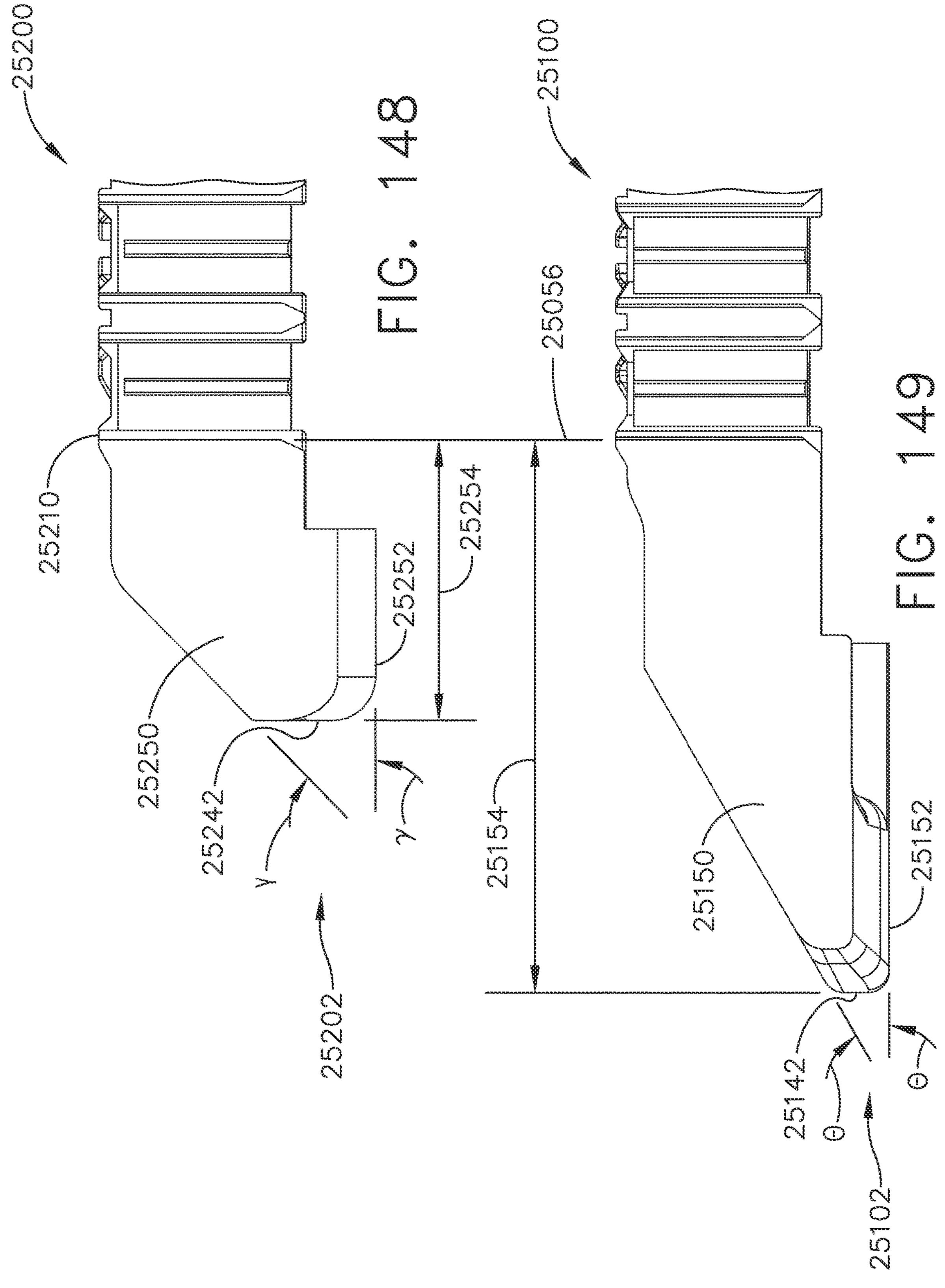
Figure 150:
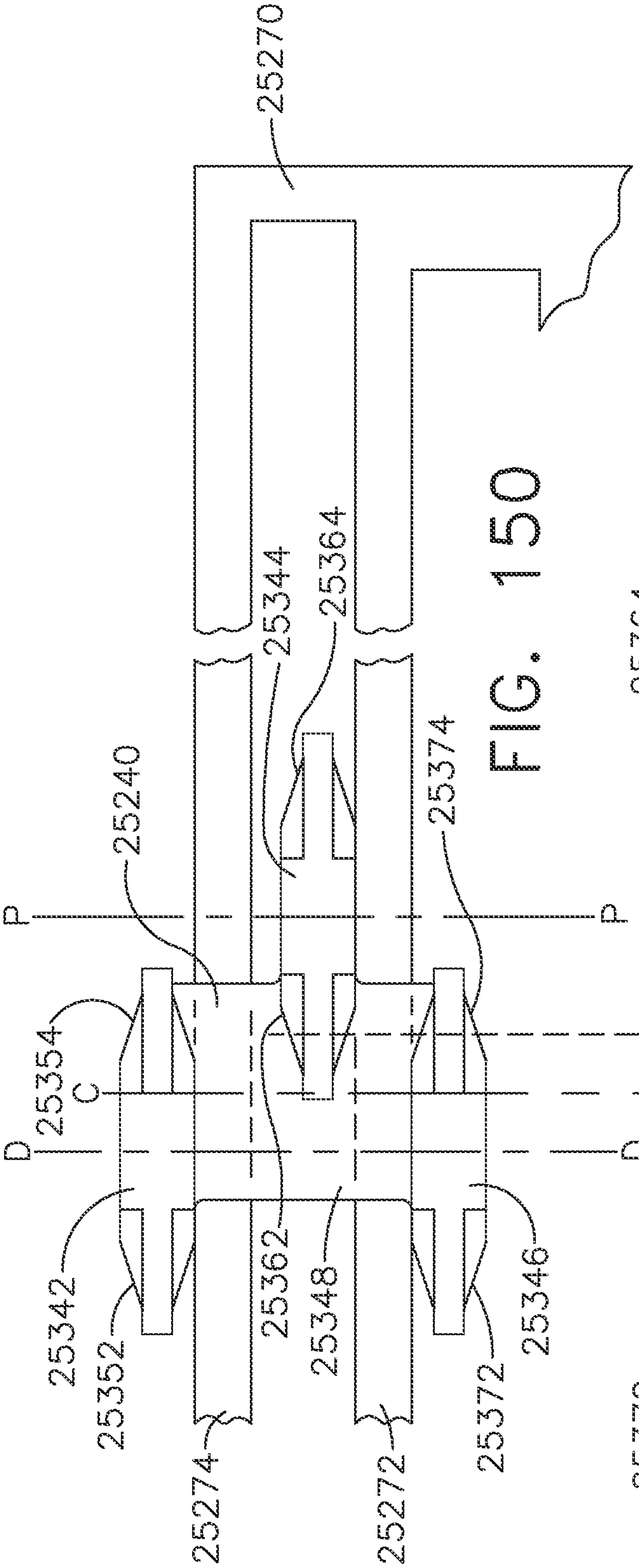
Figure 151:
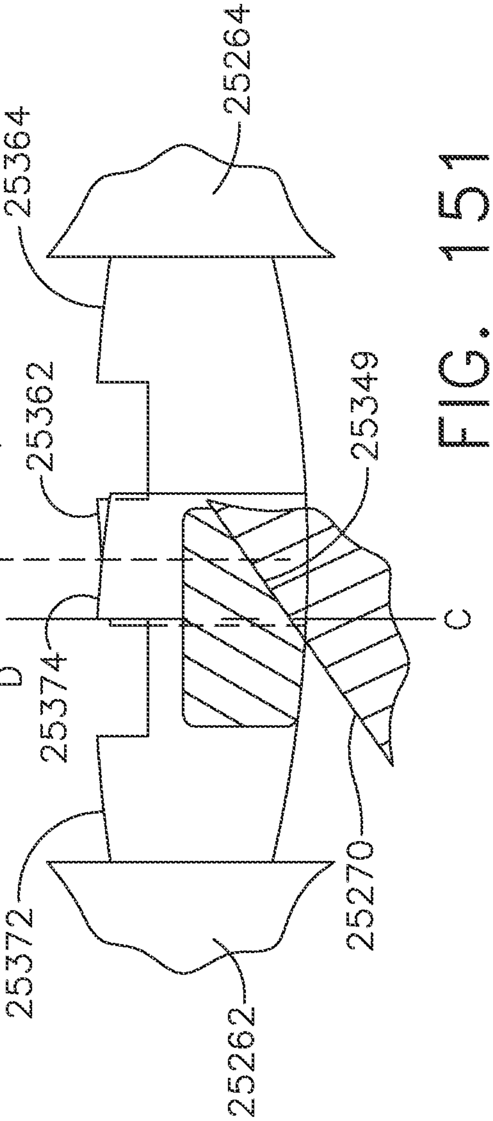
Figure 152:
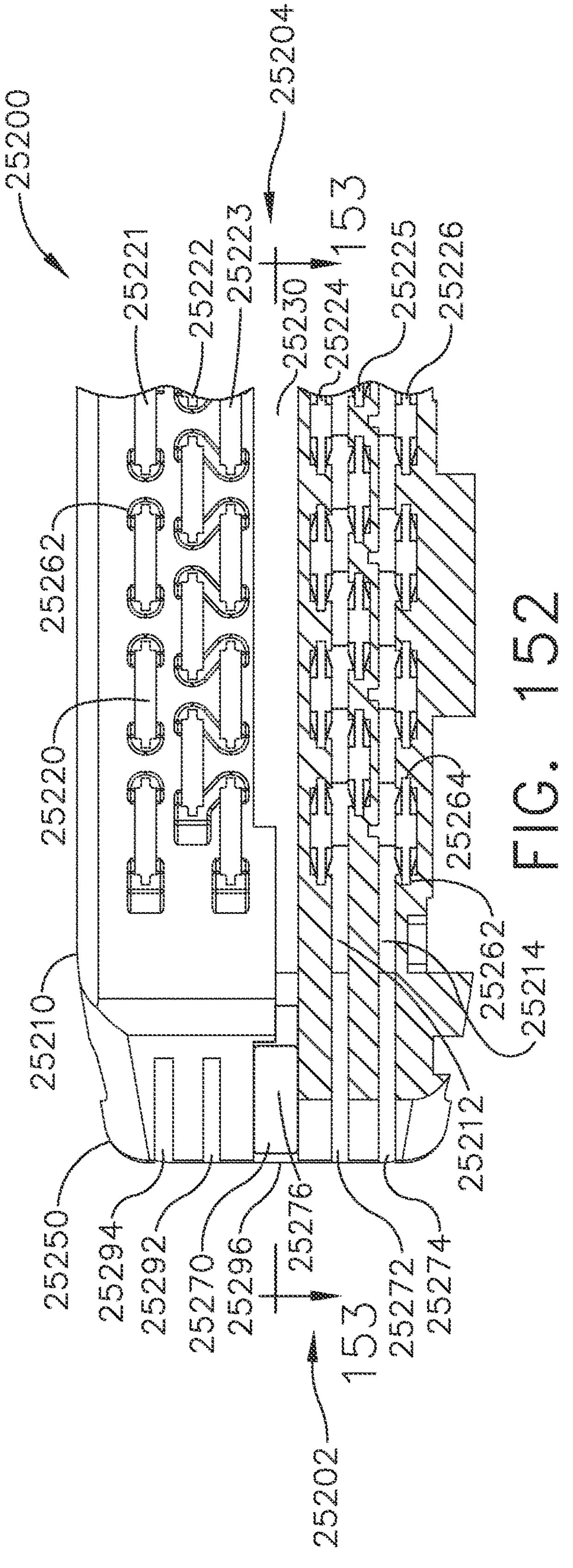
Figure 153:
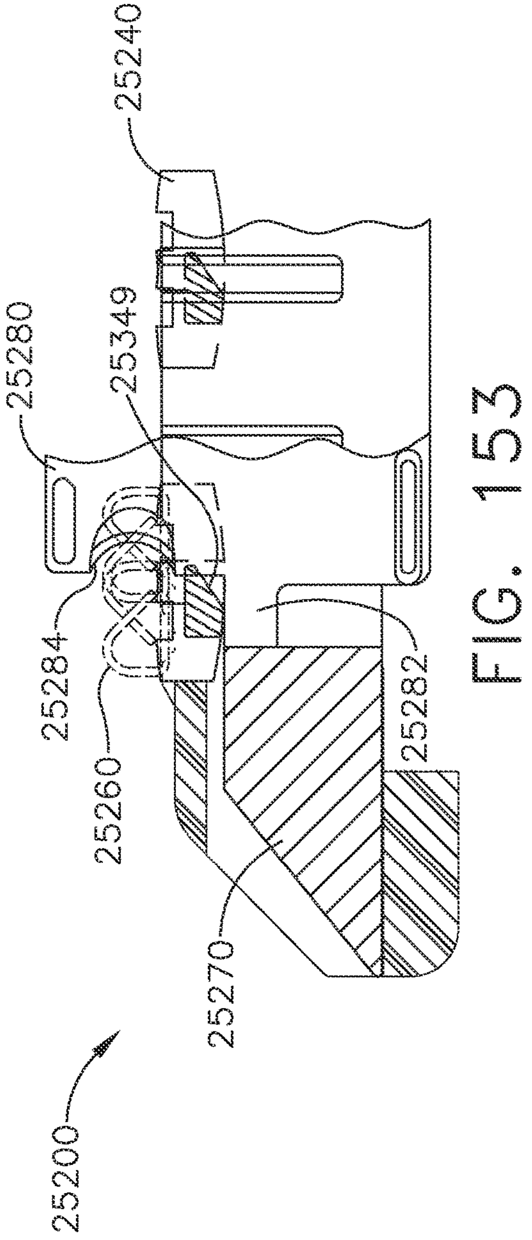
Figure 154:
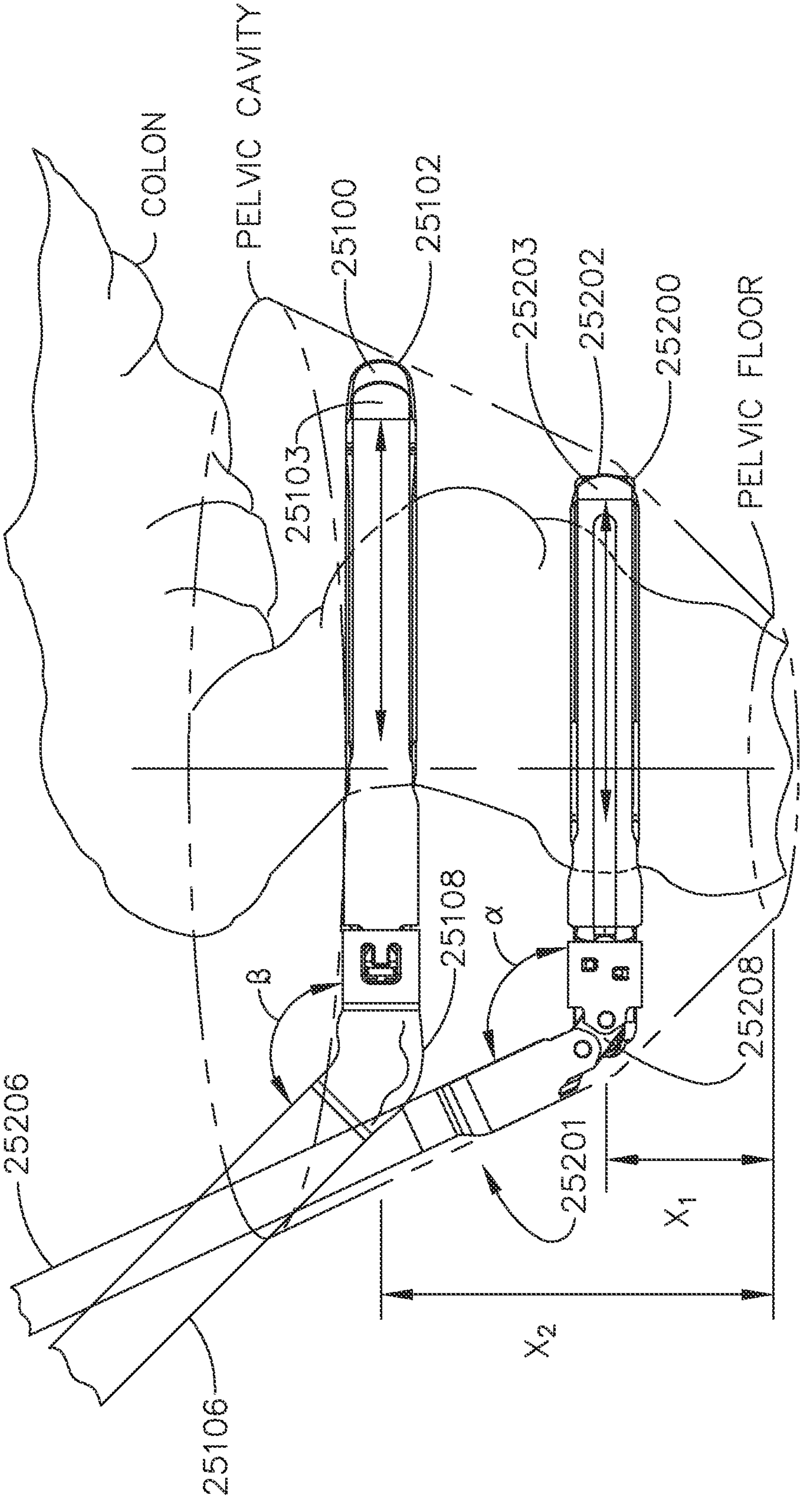
Figure 155:
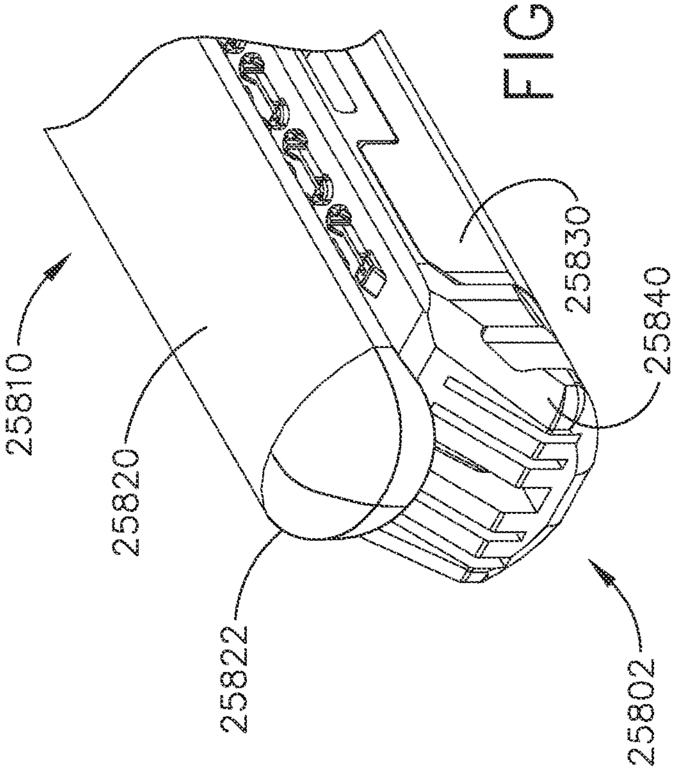
Figure 156:
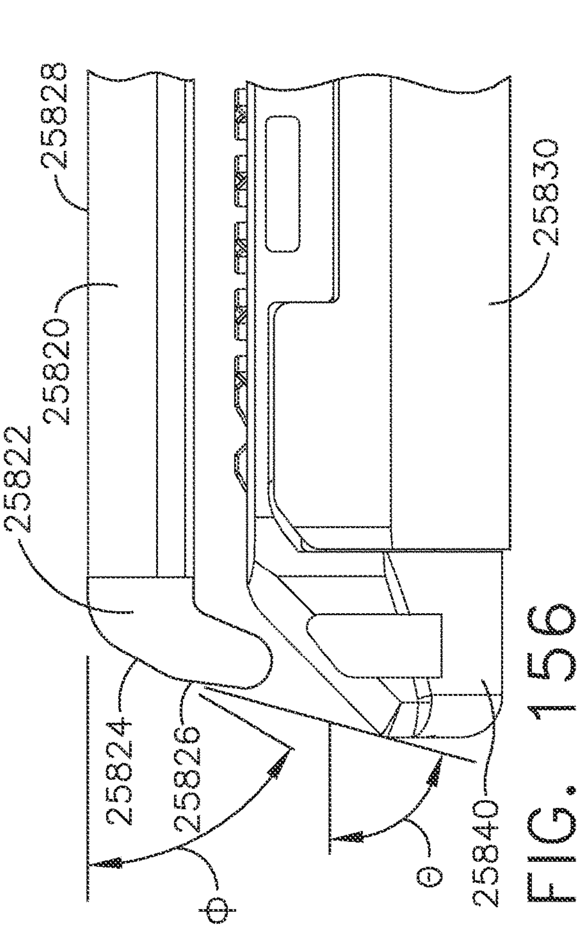
Figure 157:
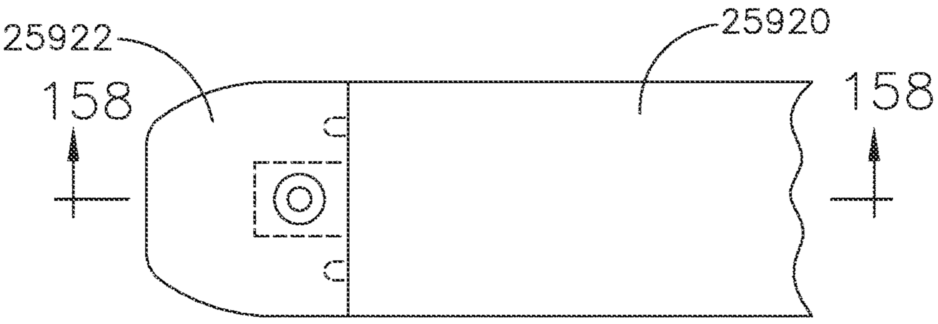
Figure 158:
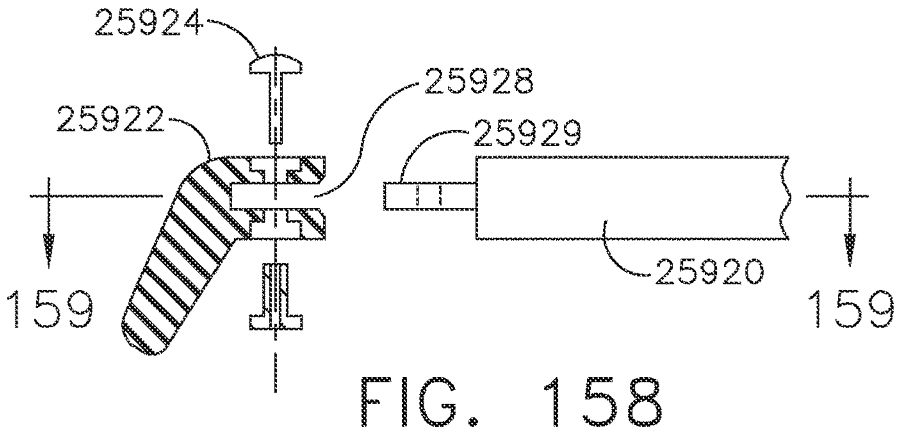
Figure 159:
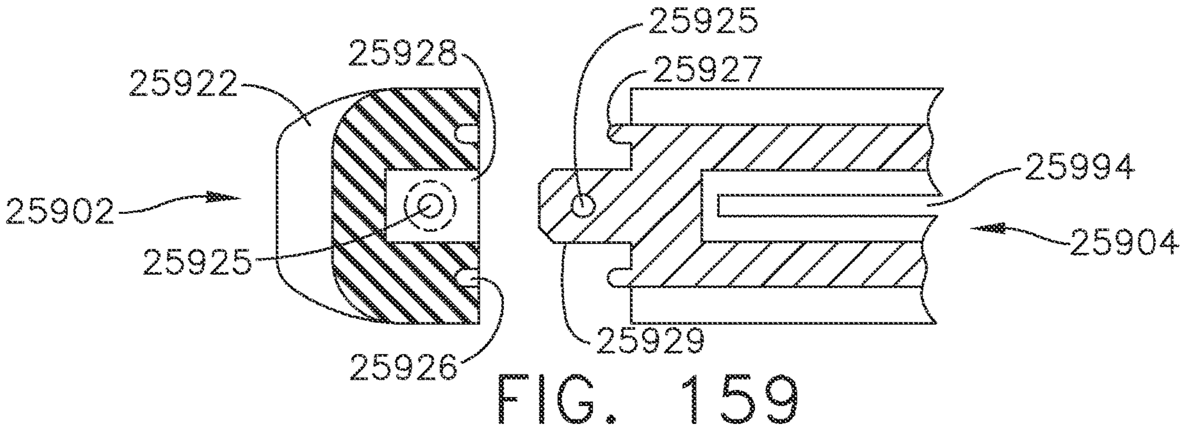
Figure 160:
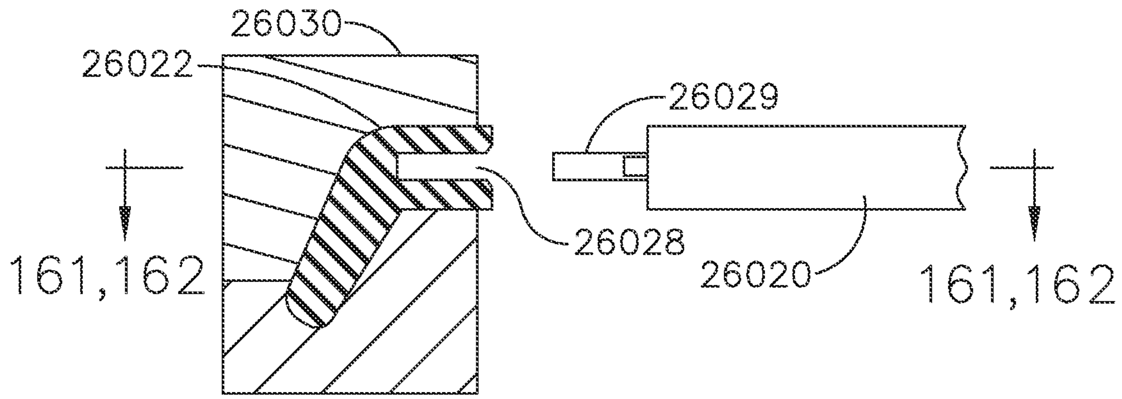
Figure 161:
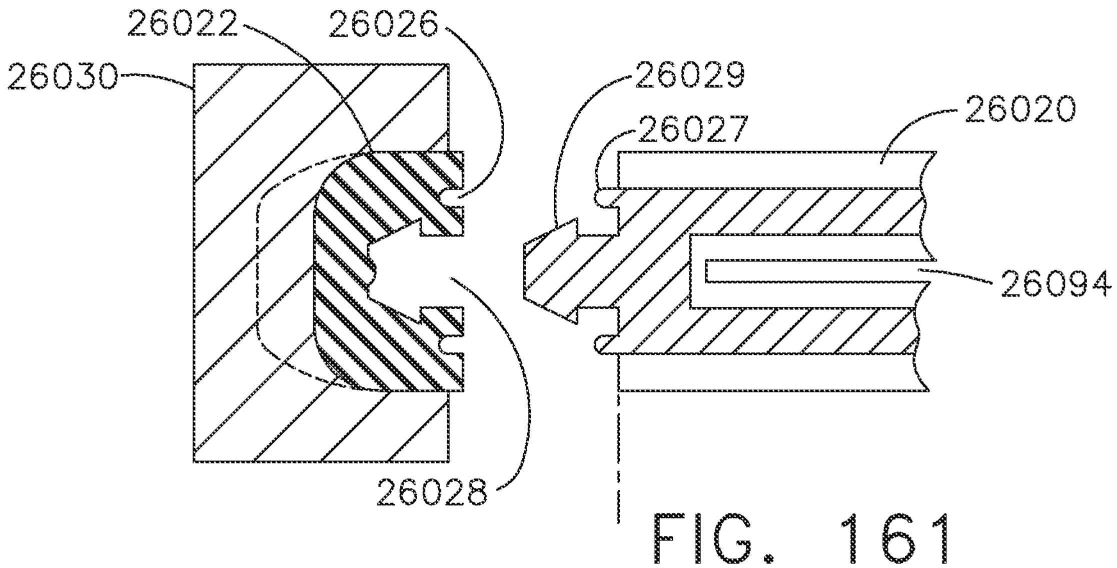
Figure 162:
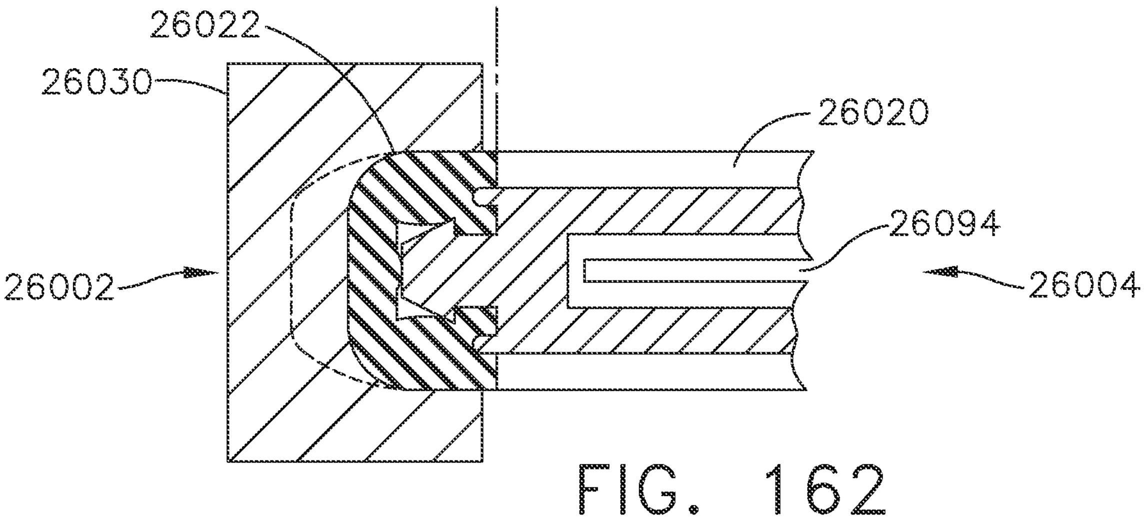
Figure 164:
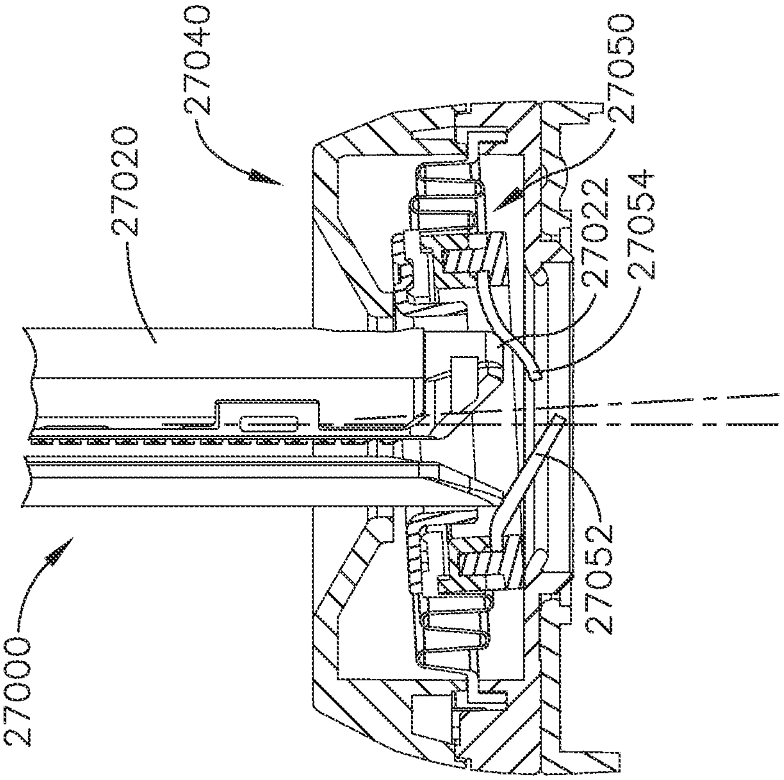
Figure 163:
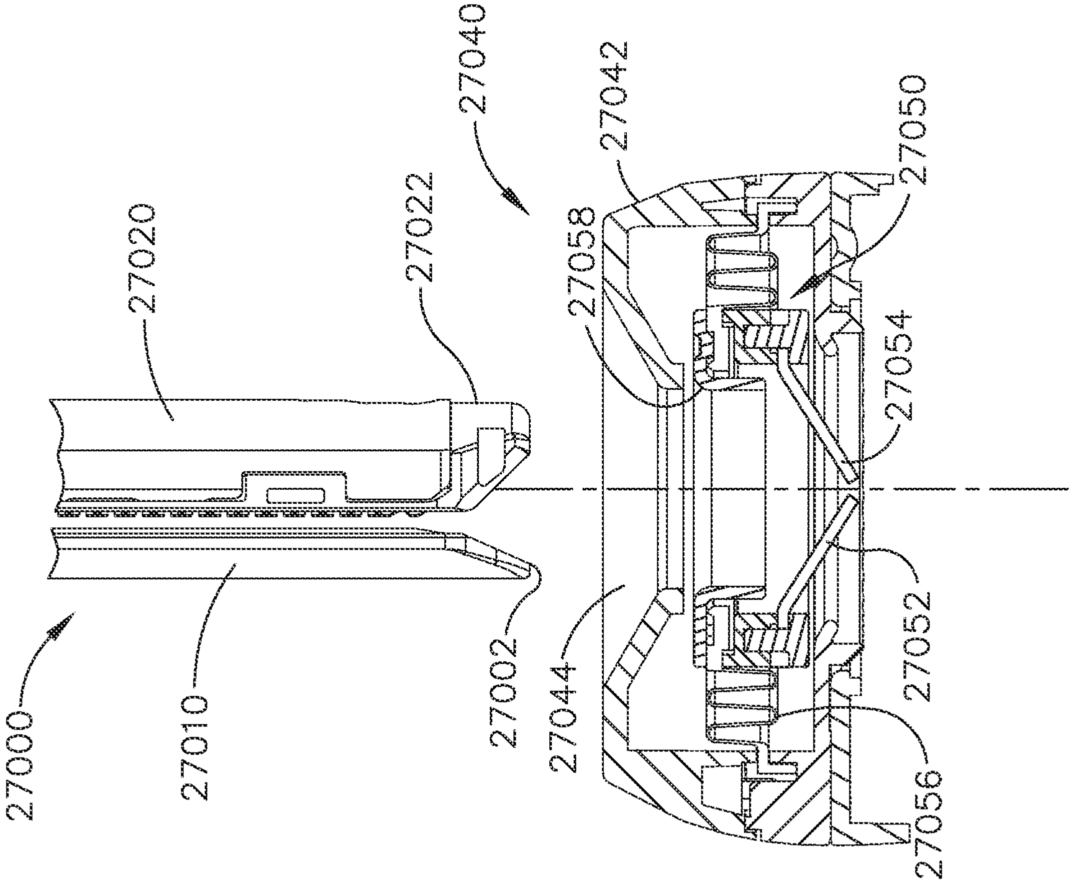
Figure 166:
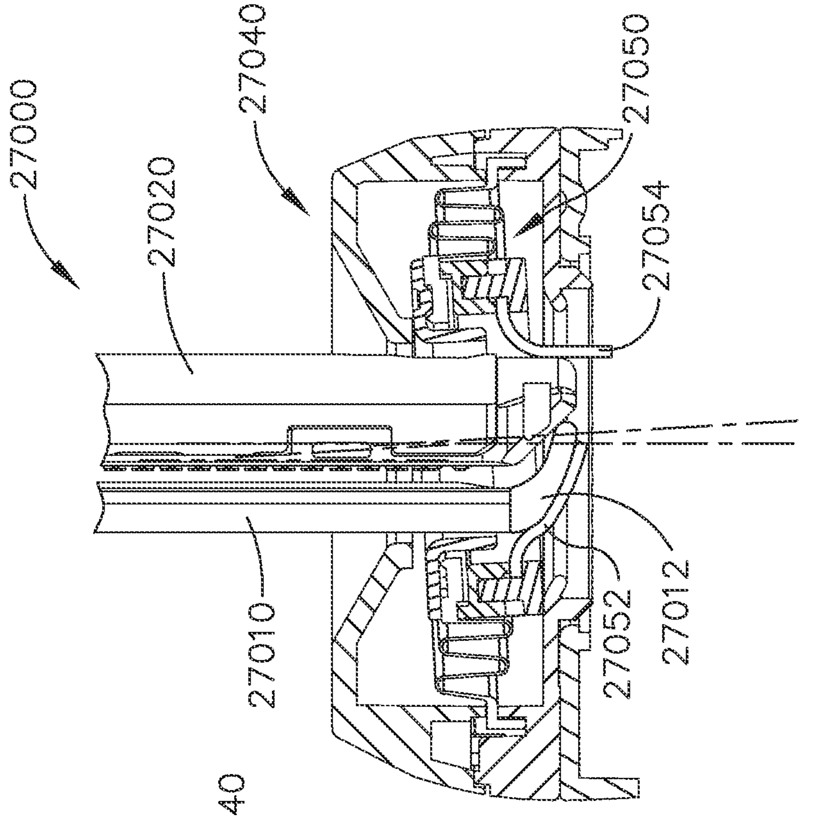
Figure 165:
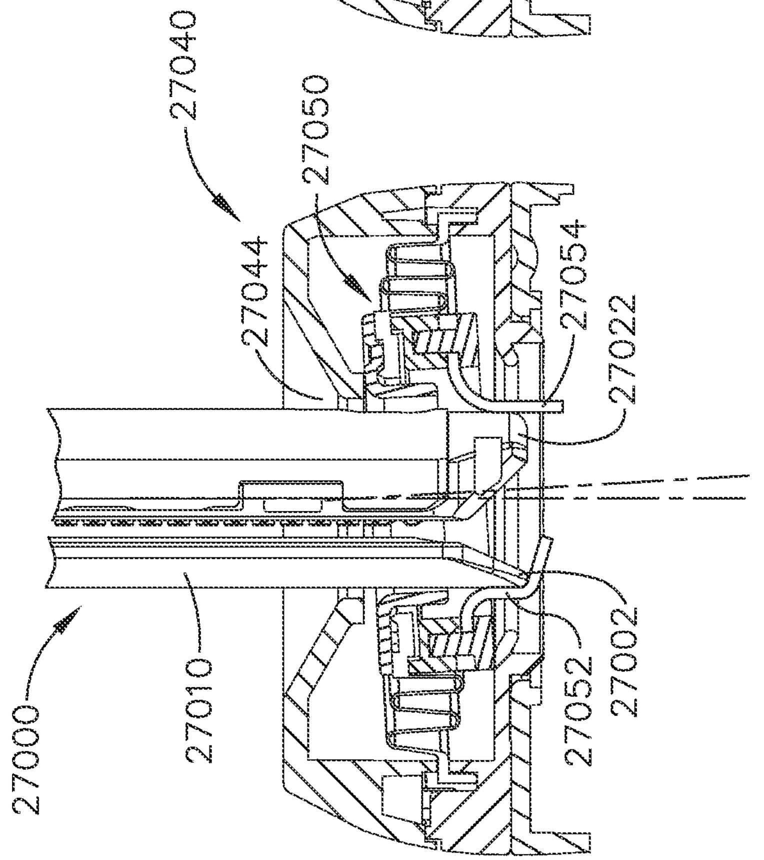
Figure 168:
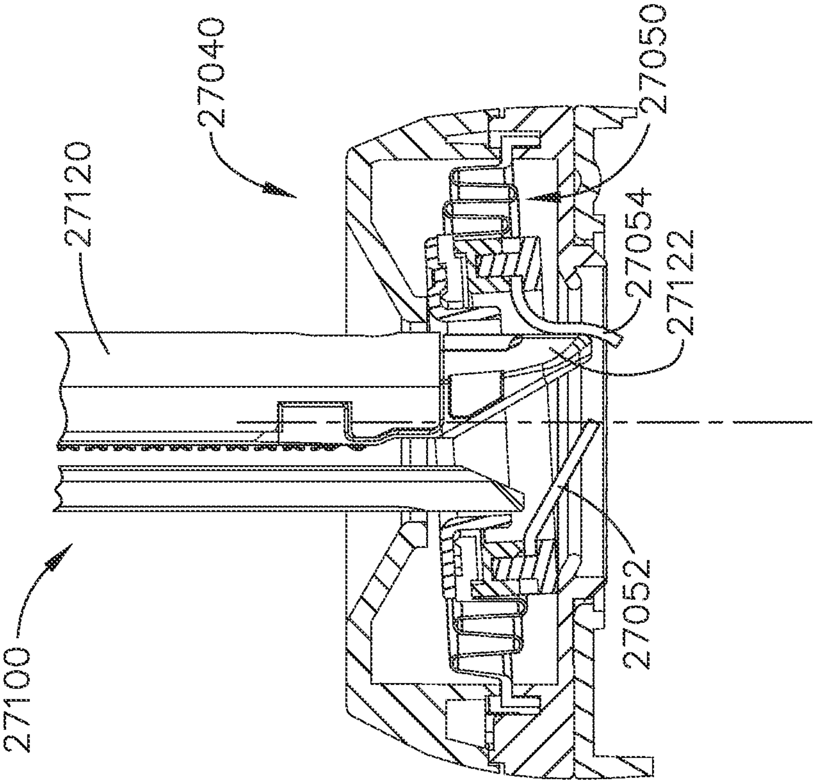
Figure 167:
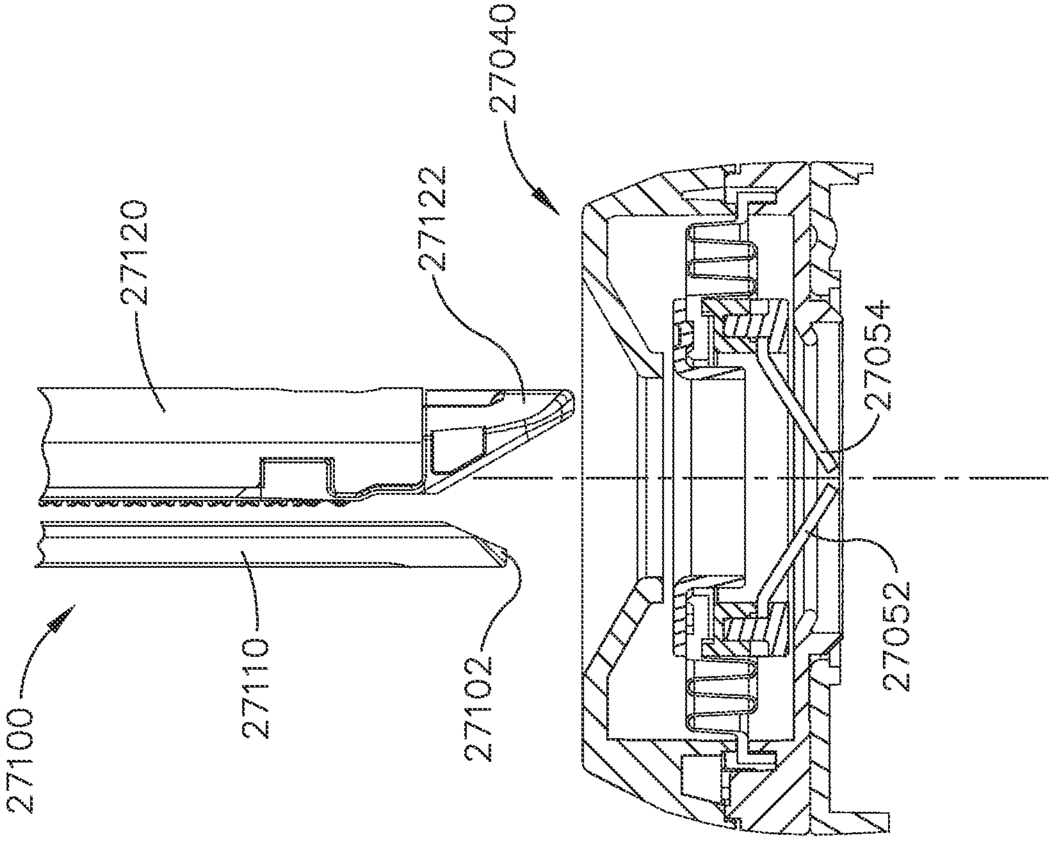
Figure 169:
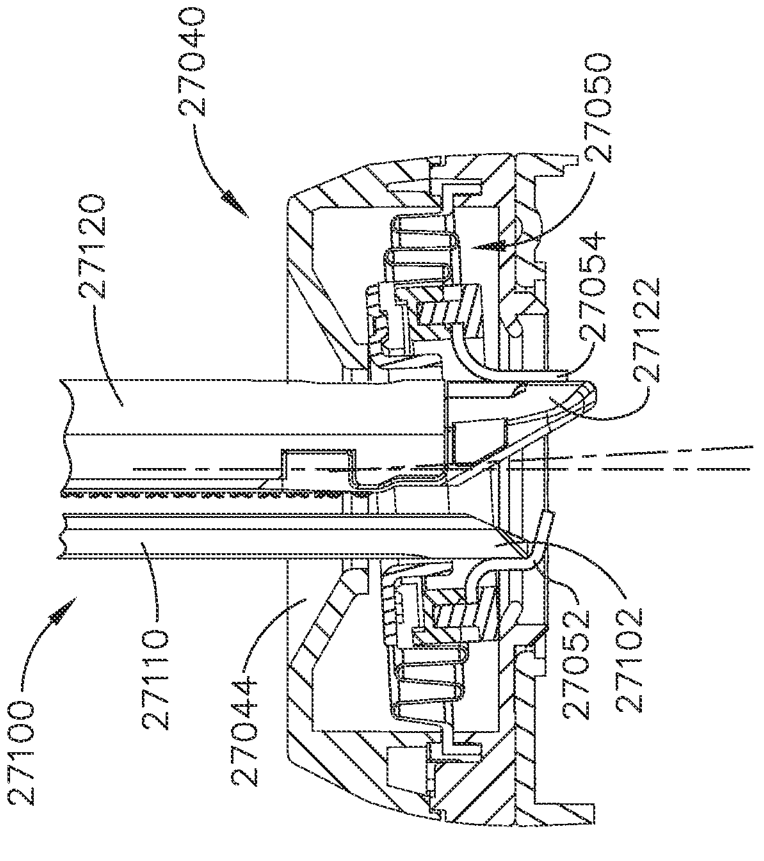

FIG. 106 is a partial cross-sectional view of the end effector of FIG. 103 illustrating the articulation lock in an engaged condition;

FIG. 107 is a partial cross-sectional view of the end effector of FIG. 103 illustrating the articulation lock in an unlocked condition;

FIG. 108 is a partial cross-sectional view of the end effector of FIG. 103 illustrating the articulation lock in a locked condition;

FIG. 109 is a partial cross-sectional view of an end effector including a slidable lock plate in accordance with at least one embodiment;

FIG. 110 is a partial cross-sectional view of another end effector including a slidable lock plate in accordance with at least one embodiment;

FIG. 111 is a partial cross-sectional view of the end effector of FIG. 110 illustrating self-adjustability of the lock plate;

FIG. 112 is a partial cross-sectional view of the end effector of FIG. 110 in a locked condition;

FIG. 113 is a partial cross-sectional view of an end effector including another slidable lock plate in accordance with at least one embodiment;

FIG. 114 is a partial cross-sectional view of the end effector of FIG. 113 illustrated in a locked condition;

FIG. 115 is a partial cross-sectional view of the end effector of FIG. 113 illustrated in another locked condition;

FIG. 116 is a partial cross-sectional view of an end effector comprising an articulation system and an articulation lock in accordance with at least one embodiment illustrated with some components removed;

FIG. 116A is a partial cross-sectional view of the end effector of FIG. 116 articulated in a first direction;

FIG. 116B is a partial cross-sectional view of the end effector of FIG. 116 articulated in a second direction;

FIG. 117 is a partial cross-sectional view of the end effector of FIG. 116 in an unlocked condition;

FIG. 118 is a partial cross-sectional view of the end effector of FIG. 116 in a partially-locked condition;

FIG. 119 is a partial cross-sectional view of the end effector of FIG. 116 in a locked condition;

FIG. 120 is a chart illustrating the gradual locking of the end effector of FIG. 116;

FIG. 121 is a partial cross-sectional view of an end effector comprising an articulation system and an articulation lock in accordance with at least one embodiment illustrated with some components removed;

FIG. 122 is a partial cross-sectional view of the end effector of FIG. 121 illustrated in a partially-locked condition;

FIG. 123 is a partial cross-sectional view of the end effector of FIG. 121 in a locked condition;

FIG. 124 is a partial cross-sectional view of an end effector comprising an articulation system and an articulation lock in accordance with at least one embodiment illustrated with some components removed;

FIG. 125 is a partial cross-sectional view of the end effector of FIG. 124 illustrating the articulation lock being moved toward the articulation system;

FIG. 126 is a partial cross-sectional view of the end effector of FIG. 124 illustrating the articulation lock engaged with the articulation system;

FIG. 127 is a partial cross-sectional view of the end effector of FIG. 124 illustrating the articulation lock in a locked condition;

FIG. 128 is another partial cross-sectional view of the end effector of FIG. 124 illustrating the articulation lock in its locked condition;

FIG. 129 is a partial cross-sectional view of an end effector comprising an articulation system and an articulation lock in accordance with at least one embodiment illustrated with some components removed;

FIG. 130 is a partial cross-sectional view of the end effector of FIG. 129 illustrating the articulation lock engaged with the articulation system;

FIG. 131 is a partial cross-sectional view of the end effector of FIG. 129 illustrating the articulation lock in a locked condition;

FIG. 132 is a partial cross-sectional view of an end effector comprising an articulation system and an articulation lock in accordance with at least one embodiment illustrated with some components removed;

FIG. 133 is a partial cross-sectional view of the end effector of FIG. 132 illustrating the articulation lock being moved toward the articulation system;

FIG. 134 is a partial cross-sectional view of the end effector of FIG. 132 illustrating the articulation lock in a locked condition;

FIG. 135 is a partial perspective view of an end effector articulation drive system in accordance with at least one embodiment;

FIG. 136 is a plan view of the end effector articulation drive system of FIG. 135;

FIG. 137 is an elevational view of the end effector articulation drive system of FIG. 135;

FIG. 138 is a partial perspective view of an end effector articulation drive system in accordance with at least one embodiment;

FIG. 139 is a plan view of the end effector articulation drive system of FIG. 138;

FIG. 140 is an elevational view of the end effector articulation drive system of FIG. 138;

FIG. 141 is a detail view of the end effector articulation drive system of FIG. 138;

FIG. 142 is another detail view of the end effector articulation drive system of FIG. 138;

FIG. 143 is a perspective view of a surgical instrument in accordance with at least one embodiment comprising a shaft and an end effector;

FIG. 144 is a perspective view of the surgical instrument in FIG. 143 illustrating the end effector articulated relative to the shaft;

FIG. 145 is a perspective view of the end effector of FIG. 143 in an open configuration;

FIG. 146 is a partial elevational view of a firing member in accordance with at least one embodiment;

FIG. 147 is a partial cross-sectional plan view of the firing member of FIG. 146;

FIG. 148 is a partial cross-sectional view of a distal end of a staple cartridge with a shortened nose in accordance with at least one embodiment;

FIG. 149 is a partial cross-sectional view of a distal end of a staple cartridge with an elongate nose in accordance with at least one embodiment;

FIG. 150 is a top view of various internal components of the staple cartridge of FIG. 148 illustrating a triple staple driver spanning across three longitudinal rows of staple cavities positioned on top of a portion of a wedge sled;

FIG. 151 is a cross-sectional view of the triple staple driver of FIG. 150 illustrating the centerline of the triple staple driver with respect to the sled;

FIG. 152 is a partial plan view of the staple cartridge of FIG. 148 illustrating one side of the staple cartridge deck in cross-section and showing the position of the sled of FIG. 151 within recesses defined in the shortened nose of the cartridge after the completion of a firing stroke;

FIG. 153 is a partial cross-sectional view of the staple cartridge of FIG. 148 taken along line 153-153 in FIG. 152 illustrating the position of the sled after the completion of a firing stroke;

FIG. 154 is a diagram comparing the accessibility of end effectors comprising the staple cartridges in FIGS. 148 and 149 during a surgical procedure in a pelvic cavity;

FIG. 155 is a partial perspective view of an end effector comprising the staple cartridge of FIG. 148 and a shortened opposing anvil with a protective tip in accordance with at least one embodiment;

FIG. 156 is a partial elevational view of the end effector of FIG. 155;

FIG. 157 is a partial plan view of one embodiment of the anvil depicted in FIG. 155 with a protective tip in an assembled configuration;

FIG. 158 is a partial cross-sectional view of the anvil depicted in FIG. 157 taken along line 158-158 in FIG. 157 and illustrated in a partially disassembled configuration showing exemplary attachment means for removably affixing the protective tip to the anvil;

FIG. 159 is a partial cross-sectional view of the anvil depicted in FIG. 158 taken along line 159-159 in FIG. 158 and illustrated in a partially disassembled configuration showing the geometry of an attachment feature on the anvil for connection to corresponding geometry on the protective tip;

FIG. 160 is a partial cross-sectional view of an additional embodiment of the anvil depicted in FIG. 155 in a partially disassembled configuration, illustrating a protective tip positioned within a temporary holder;

FIG. 161 is a cross-sectional view of the anvil depicted in FIG. 160 taken along line 161-161 in FIG. 160 in a partially disassembled configuration, showing the geometry of a tip attachment feature on the anvil;

FIG. 162 is a cross-sectional view of the anvil depicted in FIG. 160 taken along line 162-162 in FIG. 160 in an assembled configuration with the temporary holder still attached;

FIG. 163 is a cross-sectional view of a trocar seal system prior to the insertion of an end effector there through;

FIG. 164 is a cross-sectional view of the trocar seal system of FIG. 163 illustrating the end effector depicted in FIG. 163 being inserted there through;

FIG. 165 is a cross-sectional view of the trocar seal system of FIG. 163 illustrating the insertion of the end effector depicted in FIG. 163 there through;

FIG. 166 is a cross-sectional view of the trocar seal system of FIG. 163 illustrating an end effector comprising the shortened staple cartridge of FIG. 148 and a shortened anvil with a protective tip being inserted there through;

FIG. 167 is a cross-sectional view of a trocar seal system of FIG. 163 prior to an end effector comprising the elongate cartridge of FIG. 149 and a shortened anvil with a sharp tip being inserted there through;

FIG. 168 is a cross-sectional view of the trocar seal system of FIG. 163 illustrating the end effector depicted in FIG. 167 being inserted there through; and FIG. 169 is a cross-sectional view of the trocar seal system of FIG. 163 illustrating the end effector depicted in FIG. 167 being inserted there through.

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Applicant of the present application owns the following U.S. patent applications that were filed on Jun. 28, 2017 and which are each herein incorporated by reference in their respective entireties:

- U.S. patent application Ser. No. 15/635,693, entitled SURGICAL INSTRUMENT COMPRISING AN OFFSET ARTICULATION JOINT, now U.S. Patent Application Publication No. 2019/0000466;
- U.S. patent application Ser. No. 15/635,729, entitled SURGICAL INSTRUMENT COMPRISING AN ARTICULATION SYSTEM RATIO, now U.S. Patent Application Publication No. 2019/0000467;
- U.S. patent application Ser. No. 15/635,785, entitled SURGICAL INSTRUMENT COMPRISING AN ARTICULATION SYSTEM RATIO, now U.S. Patent Application Publication No. 2019/0000469;
- U.S. patent application Ser. No. 15/635,808, entitled SURGICAL INSTRUMENT COMPRISING FIRING MEMBER SUPPORTS, now U.S. Patent Application Publication No. 2019/0000471;
- U.S. patent application Ser. No. 15/635,837, entitled SURGICAL INSTRUMENT COMPRISING AN ARTICULATION SYSTEM LOCKABLE TO A FRAME, now U.S. Patent Application Publication No. 2019/0000472;
- U.S. patent application Ser. No. 15/635,941, entitled SURGICAL INSTRUMENT COMPRISING AN ARTICULATION SYSTEM LOCKABLE BY A CLOSURE SYSTEM, now U.S. Patent Application Publication No. 2019/0000473;
- U.S. patent application Ser. No. 15/636,029, entitled SURGICAL INSTRUMENT COMPRISING A SHAFT INCLUDING A HOUSING ARRANGEMENT, now U.S. Patent Application Publication No. 2019/0000477;
- U.S. patent application Ser. No. 15/635,958, entitled SURGICAL INSTRUMENT COMPRISING SELECTIVELY ACTUATABLE ROTATABLE COUPLERS, now U.S. Patent Application Publication No. 2019/0000474;
- U.S. patent application Ser. No. 15/635,981, entitled SURGICAL STAPLING INSTRUMENTS COMPRISING SHORTENED STAPLE CARTRIDGE NOSES, now U.S. Patent Application Publication No. 2019/0000475;
- U.S. patent application Ser. No. 15/636,009, entitled SURGICAL INSTRUMENT COMPRISING A SHAFT INCLUDING A CLOSURE TUBE PROFILE, now U.S. Patent Application Publication No. 2019/0000476;
- U.S. patent application Ser. No. 15/635,530, entitled SURGICAL INSTRUMENTS WITH ARTICULATABLE END EFFECTOR WITH AXIALLY SHORT- ENED ARTICULATION JOINT CONFIGURATIONS, now U.S. Patent Application Publication No. 2019/0000457;

U.S. patent application Ser. No. 15/635,549, entitled SURGICAL INSTRUMENTS WITH OPEN AND CLOSABLE JAWS AND AXIALLY MOVABLE FIRING MEMBER THAT IS INITIALLY PARKED IN CLOSE PROXIMITY TO THE JAWS PRIOR TO FIRING, now U.S. Pat. No. 10,588,633;

U.S. patent application Ser. No. 15/635,559, entitled SURGICAL INSTRUMENTS WITH JAWS CONSTRAINED TO PIVOT ABOUT AN AXIS UPON CONTACT WITH A CLOSURE MEMBER THAT IS PARKED IN CLOSE PROXIMITY TO THE PIVOT AXIS, now U.S. Patent Application Publication No. 2019/0000459;

U.S. patent application Ser. No. 15/635,578, entitled SURGICAL END EFFECTORS WITH IMPROVED JAW APERTURE ARRANGEMENTS, now U.S. Patent Application Publication No. 2019/0000460;

U.S. patent application Ser. No. 15/635,594, entitled SURGICAL CUTTING AND FASTENING DEVICES WITH PIVOTABLE ANVIL WITH A TISSUE LOCATING ARRANGEMENT IN CLOSE PROXIMITY TO AN ANVIL PIVOT, now U.S. Patent Application Publication No. 2019/0000461;

U.S. patent application Ser. No. 15/635,612, entitled JAW RETAINER ARRANGEMENT FOR RETAINING A PIVOTABLE SURGICAL INSTRUMENT JAW IN PIVOTABLE RETAINING ENGAGEMENT WITH A SECOND SURGICAL INSTRUMENT JAW, now U.S. Patent Application Publication No. 2019/0000462;

U.S. patent application Ser. No. 15/635,621, entitled SURGICAL INSTRUMENT WITH POSITIVE JAW OPENING FEATURES, now U.S. Patent Application Publication No. 2019/0000463;

U.S. patent application Ser. No. 15/635,631, entitled SURGICAL INSTRUMENT WITH AXIALLY MOVABLE CLOSURE MEMBER, now U.S. Patent Application Publication No. 2019/0000464;

U.S. patent application Ser. No. 15/635,521, entitled SURGICAL INSTRUMENT LOCKOUT ARRANGEMENT, now U.S. Patent Application Publication No. 2019/0000456;

U.S. Design patent application Ser. No. 29/609,087, entitled STAPLE FORMING ANVIL, now U.S. Design Pat. No. D851,762;

U.S. Design patent application Ser. No. 29/609,083, entitled SURGICAL INSTRUMENT SHAFT, now U.S. Design Pat. No. D854,151; and U.S. Design patent application Ser. No. 29/609,093, entitled SURGICAL FASTENER CARTRIDGE, now U.S. Design Pat. No. D869,655.

Applicant of the present application owns the following U.S. patent applications that were filed on Jun. 27, 2017 and which are each herein incorporated by reference in their respective entireties:

U.S. patent application Ser. No. 15/634,024, entitled SURGICAL ANVIL MANUFACTURING METHODS, now U.S. Patent Application Publication No. 2018/0368839;

U.S. patent application Ser. No. 15/634,035, entitled SURGICAL ANVIL ARRANGEMENTS, now U.S. Patent Application Publication No. 2018/0368840;

U.S. patent application Ser. No. 15/634,046, entitled SURGICAL ANVIL ARRANGEMENTS, now U.S. Patent Application Publication No. 2018/0368841;

U.S. patent application Ser. No. 15/634,054, entitled SURGICAL ANVIL ARRANGEMENTS, now U.S. Patent Application Publication No. 2018/0368842;

U.S. patent application Ser. No. 15/634,068, entitled SURGICAL FIRING MEMBER ARRANGEMENTS, now U.S. Patent Application Publication No. 2018/0368843;

U.S. patent application Ser. No. 15/634,076, entitled STAPLE FORMING POCKET ARRANGEMENTS, now U.S. Patent Application Publication No. 2018/0368844;

U.S. patent application Ser. No. 15/634,090 entitled STAPLE FORMING POCKET ARRANGEMENTS, now U.S. Patent Application Publication No. 2018/0368845;

U.S. patent application Ser. No. 15/634,099, entitled SURGICAL END EFFECTORS AND ANVILS, now U.S. Patent Application Publication No. 2018/0368846; and U.S. patent application Ser. No. 15/634,117, entitled ARTICULATION SYSTEMS FOR SURGICAL INSTRUMENTS, now U.S. Pat. No. 10,631,859.

Applicant of the present application owns the following U.S. patent applications that were filed on Dec. 21, 2016 and which are each herein incorporated by reference in their respective entireties:

U.S. patent application Ser. No. 15/386,185, entitled SURGICAL STAPLING INSTRUMENTS AND REPLACEABLE TOOL ASSEMBLIES THEREOF, now U.S. Patent Application Publication No. 2018/0168642;

U.S. patent application Ser. No. 15/386,230, entitled ARTICULATABLE SURGICAL STAPLING INSTRUMENTS, now U.S. Patent Application Publication No. 2018/0168649;

U.S. patent application Ser. No. 15/386,221, entitled LOCKOUT ARRANGEMENTS FOR SURGICAL END EFFECTORS, now U.S. Patent Application Publication No. 2018/0168646;

U.S. patent application Ser. No. 15/386,209, entitled SURGICAL END EFFECTORS AND FIRING MEMBERS THEREOF, now U.S. Pat. No. 10,588,632;

U.S. patent application Ser. No. 15/386,198, entitled LOCKOUT ARRANGEMENTS FOR SURGICAL END EFFECTORS AND REPLACEABLE TOOL ASSEMBLIES, now U.S. Pat. No. 10,610,224;

U.S. patent application Ser. No. 15/386,240, entitled SURGICAL END EFFECTORS AND ADAPTABLE FIRING MEMBERS THEREFOR, now U.S. Patent Application Publication No. 2018/0168651;

U.S. patent application Ser. No. 15/385,939, entitled STAPLE CARTRIDGES AND ARRANGEMENTS OF STAPLES AND STAPLE CAVITIES THEREIN, now U.S.

Patent Application Publication No. 2018/0168629;

U.S. patent application Ser. No. 15/385,941, entitled SURGICAL TOOL ASSEMBLIES WITH CLUTCHING ARRANGEMENTS FOR SHIFTING BETWEEN CLOSURE SYSTEMS WITH CLOSURE STROKE REDUCTION FEATURES AND ARTICULATION AND FIRING SYSTEMS, now U.S. Patent Application Publication No. 2018/0168630;

U.S. patent application Ser. No. 15/385,943, entitled SURGICAL STAPLING INSTRUMENTS AND STAPLE-FORMING ANVILS, now U.S. Patent Application Publication No. 2018/0168631;

U.S. patent application Ser. No. 15/385,950, entitled SURGICAL TOOL ASSEMBLIES WITH CLOSURE STROKE REDUCTION FEATURES, now U.S. Pat. No. 10,588,630;

U.S. patent application Ser. No. 15/385,945, entitled STAPLE CARTRIDGES AND ARRANGEMENTS OF STAPLES AND STAPLE CAVITIES THEREIN, now U.S.

Patent Application Publication No. 2018/0168632;

U.S. patent application Ser. No. 15/385,946, entitled SURGICAL STAPLING INSTRUMENTS AND STAPLE-FORMING ANVILS, now U.S. Patent Application Publication No. 2018/0168633;

U.S. patent application Ser. No. 15/385,951, entitled SURGICAL INSTRUMENTS WITH JAW OPENING FEATURES FOR INCREASING A JAW OPENING DISTANCE, now U.S. Pat. No. 10,568,626;

U.S. patent application Ser. No. 15/385,953, entitled METHODS OF STAPLING TISSUE, now U.S. Patent Application Publication No. 2018/0168637;

U.S. patent application Ser. No. 15/385,954, entitled FIRING MEMBERS WITH NON-PARALLEL JAW ENGAGEMENT FEATURES FOR SURGICAL END EFFECTORS, now U.S. Pat. No. 10,624,635;

U.S. patent application Ser. No. 15/385,955, entitled SURGICAL END EFFECTORS WITH EXPANDABLE TISSUE STOP ARRANGEMENTS, now U.S. Patent Application Publication No. 2018/0168639;

U.S. patent application Ser. No. 15/385,948, entitled SURGICAL STAPLING INSTRUMENTS AND STAPLE-FORMING ANVILS, now U.S. Patent Application Publication No. 2018/0168584;

U.S. patent application Ser. No. 15/385,956, entitled SURGICAL INSTRUMENTS WITH POSITIVE JAW OPENING FEATURES, now U.S. Pat. No. 10,588,631;

U.S. patent application Ser. No. 15/385,958, entitled SURGICAL INSTRUMENTS WITH LOCKOUT ARRANGEMENTS FOR PREVENTING FIRING SYSTEM ACTUATION UNLESS AN UNSPENT STAPLE CARTRIDGE IS PRESENT, now U.S. Patent Application Publication No. 2018/0168641;

U.S. patent application Ser. No. 15/385,947, entitled STAPLE CARTRIDGES AND ARRANGEMENTS OF STAPLES AND STAPLE CAVITIES THEREIN, now U.S. Pat. No. 10,568,625;

U.S. patent application Ser. No. 15/385,896, entitled METHOD FOR RESETTING A FUSE OF A SURGICAL INSTRUMENT SHAFT, now U.S. Patent Application Publication No. 2018/0168597;

U.S. patent application Ser. No. 15/385,898, entitled STAPLE FORMING POCKET ARRANGEMENT TO ACCOMMODATE DIFFERENT TYPES OF STAPLES, now U.S. Pat. No. 10,537,325;

U.S. patent application Ser. No. 15/385,899, entitled SURGICAL INSTRUMENT COMPRISING IMPROVED JAW CONTROL, now U.S. Patent Application Publication No. 2018/0168600;

U.S. patent application Ser. No. 15/385,901, entitled STAPLE CARTRIDGE AND STAPLE CARTRIDGE CHANNEL COMPRISING WINDOWS DEFINED THEREIN, now U.S. Patent Application Publication No. 2018/0168602;

U.S. patent application Ser. No. 15/385,902, entitled SURGICAL INSTRUMENT COMPRISING A CUTTING MEMBER, now U.S. Patent Application Publication No. 2018/0168603;

U.S. patent application Ser. No. 15/385,904, entitled STAPLE FIRING MEMBER COMPRISING A MISSING CARTRIDGE AND/OR SPENT CARTRIDGE LOCKOUT, now U.S. Patent Application Publication No. 2018/0168605;

U.S. patent application Ser. No. 15/385,905, entitled FIRING ASSEMBLY COMPRISING A LOCKOUT, now U.S. Patent Application Publication No. 2018/0168606;

U.S. patent application Ser. No. 15/385,907, entitled SURGICAL INSTRUMENT SYSTEM COMPRISING AN END EFFECTOR LOCKOUT AND A FIRING ASSEMBLY LOCKOUT, now U.S. Patent Application Publication No. 2018/0168608;

U.S. patent application Ser. No. 15/385,908, entitled FIRING ASSEMBLY COMPRISING A FUSE, now U.S. Patent Application Publication No. 2018/0168609;

U.S. patent application Ser. No. 15/385,909, entitled FIRING ASSEMBLY COMPRISING A MULTIPLE FAILED-STATE FUSE, now U.S. Patent Application Publication No. 2018/0168610;

U.S. patent application Ser. No. 15/385,920, entitled STAPLE FORMING POCKET ARRANGEMENTS, now U.S. Pat. No. 10,499,914;

U.S. patent application Ser. No. 15/385,913, entitled ANVIL ARRANGEMENTS FOR SURGICAL STAPLE/FASTENERS, now U.S. Patent Application Publication No. 2018/0168614;

U.S. patent application Ser. No. 15/385,914, entitled METHOD OF DEFORMING STAPLES FROM TWO DIFFERENT TYPES OF STAPLE CARTRIDGES WITH THE SAME SURGICAL STAPLING INSTRUMENT, now U.S. Patent Application Publication No. 2018/0168615;

U.S. patent application Ser. No. 15/385,893, entitled BILATERALLY ASYMMETRIC STAPLE FORMING POCKET PAIRS, now U.S. Patent Application Publication No. 2018/0168594;

U.S. patent application Ser. No. 15/385,929, entitled CLOSURE MEMBERS WITH CAM SURFACE ARRANGEMENTS FOR SURGICAL INSTRUMENTS WITH SEPARATE AND DISTINCT CLOSURE AND FIRING SYSTEMS, now U.S. Patent Application Publication No. 2018/0168626;

U.S. patent application Ser. No. 15/385,911, entitled SURGICAL STAPLE/FASTENERS WITH INDEPENDENTLY ACTUATABLE CLOSING AND FIRING SYSTEMS, now U.S. Pat. No. 10,448,950;

U.S. patent application Ser. No. 15/385,927, entitled SURGICAL STAPLING INSTRUMENTS WITH SMART STAPLE CARTRIDGES, now U.S. Patent Application Publication No. 2018/0168625;

U.S. patent application Ser. No. 15/385,917, entitled STAPLE CARTRIDGE COMPRISING STAPLES WITH DIFFERENT CLAMPING BREADTHS, now U.S. Patent Application Publication No. 2018/0168617;

U.S. patent application Ser. No. 15/385,900, entitled STAPLE FORMING POCKET ARRANGEMENTS COMPRISING PRIMARY SIDEWALLS AND POCKET SIDEWALLS, now U.S. Patent Application Publication No. 2018/0168601;

U.S. patent application Ser. No. 15/385,931, entitled NO-CARTRIDGE AND SPENT CARTRIDGE LOCKOUT ARRANGEMENTS FOR SURGICAL STAPLE/FASTENERS, now U.S. Patent Application Publication No. 2018/0168627;

U.S. patent application Ser. No. 15/385,915, entitled FIRING MEMBER PIN ANGLE, now U.S. Patent Application Publication No. 2018/0168616;

U.S. patent application Ser. No. 15/385,897, entitled STAPLE FORMING POCKET ARRANGEMENTS COMPRISING ZONED FORMING SURFACE GROOVES, now U.S. Patent Application Publication No. 2018/0168598;

U.S. patent application Ser. No. 15/385,922, entitled SURGICAL INSTRUMENT WITH MULTIPLE FAILURE RESPONSE MODES, now U.S. Pat. No. 10,426,471;

U.S. patent application Ser. No. 15/385,924, entitled SURGICAL INSTRUMENT WITH PRIMARY AND SAFETY PROCESSORS, now U.S. Patent Application Publication No. 2018/0168624;

U.S. patent application Ser. No. 15/385,912, entitled SURGICAL INSTRUMENTS WITH JAWS THAT ARE PIVOTABLE ABOUT A FIXED AXIS AND INCLUDE SEPARATE AND DISTINCT CLOSURE AND FIRING SYSTEMS, now U.S. Pat. No. 10,568,624;

U.S. patent application Ser. No. 15/385,910, entitled ANVIL HAVING A KNIFE SLOT WIDTH, now U.S. Pat. No. 10,485,543;

U.S. patent application Ser. No. 15/385,906, entitled FIRING MEMBER PIN CONFIGURATIONS, now U.S. Patent Application Publication No. 2018/0168607;

U.S. patent application Ser. No. 15/386,188, entitled STEPPED STAPLE CARTRIDGE WITH ASYMMETRICAL STAPLES, now U.S. Pat. No. 10,537,324;

U.S. patent application Ser. No. 15/386,192, entitled STEPPED STAPLE CARTRIDGE WITH TISSUE RETENTION AND GAP SETTING FEATURES, now U.S. Patent Application Publication No. 2018/0168643;

U.S. patent application Ser. No. 15/386,206, entitled STAPLE CARTRIDGE WITH DEFORMABLE DRIVER RETENTION FEATURES, now U.S. Patent Application Publication No. 2018/0168586;

U.S. patent application Ser. No. 15/386,226, entitled DURABILITY FEATURES FOR END EFFECTORS AND FIRING ASSEMBLIES OF SURGICAL STAPLING INSTRUMENTS, now U.S. Patent Application Publication No. 2018/0168648;

U.S. patent application Ser. No. 15/386,222, entitled SURGICAL STAPLING INSTRUMENTS HAVING END EFFECTORS WITH POSITIVE OPENING FEATURES, now U.S. Patent Application Publication No. 2018/0168647;

U.S. patent application Ser. No. 15/386,236, entitled CONNECTION PORTIONS FOR DEPOSABLE LOADING UNITS FOR SURGICAL STAPLING INSTRUMENTS, now U.S. Patent Application Publication No. 2018/0168650;

U.S. patent application Ser. No. 15/385,887, entitled METHOD FOR ATTACHING A SHAFT ASSEMBLY TO A SURGICAL INSTRUMENT AND, ALTERNATIVELY, TO A SURGICAL ROBOT, now U.S. Patent Application Publication No. 2018/0168589;

U.S. patent application Ser. No. 15/385,889, entitled SHAFT ASSEMBLY COMPRISING A MANUALLY-OPERABLE RETRACTION SYSTEM FOR USE WITH A MOTORIZED SURGICAL INSTRUMENT SYSTEM, now U.S. Patent Application Publication No. 2018/0168590;

U.S. patent application Ser. No. 15/385,890, entitled SHAFT ASSEMBLY COMPRISING SEPARATELY ACTUATABLE AND RETRACTABLE SYSTEMS, now U.S. Patent Application Publication No. 2018/0168591;

U.S. patent application Ser. No. 15/385,891, entitled SHAFT ASSEMBLY COMPRISING A CLUTCH CONFIGURED TO ADAPT THE OUTPUT OF A ROTARY FIRING MEMBER TO TWO DIFFERENT SYSTEMS, now U.S. Patent Application Publication No. 2018/0168592;

U.S. patent application Ser. No. 15/385,892, entitled SURGICAL SYSTEM COMPRISING A FIRING MEMBER ROTATABLE INTO AN ARTICULATION STATE TO ARTICULATE AN END EFFECTOR OF THE SURGICAL SYSTEM, now U.S. Patent Application Publication No. 2018/0168593;

U.S. patent application Ser. No. 15/385,894, entitled SHAFT ASSEMBLY COMPRISING A LOCKOUT, now U.S. Pat. No. 10,492,785;

U.S. patent application Ser. No. 15/385,895, entitled SHAFT ASSEMBLY COMPRISING FIRST AND SECOND ARTICULATION LOCKOUTS, now U.S. Pat. No. 10,542,982;

U.S. patent application Ser. No. 15/385,916, entitled SURGICAL STAPLING SYSTEMS, now U.S. Patent Application Publication No. 2018/0168575;

U.S. patent application Ser. No. 15/385,918, entitled SURGICAL STAPLING SYSTEMS, now U.S. Patent Application Publication No. 2018/0168618;

U.S. patent application Ser. No. 15/385,919, entitled SURGICAL STAPLING SYSTEMS, now U.S. Patent Application Publication No. 2018/0168619;

U.S. patent application Ser. No. 15/385,921, entitled SURGICAL STAPLE/FASTENER CARTRIDGE WITH MOVABLE CAMMING MEMBER CONFIGURED TO DISENGAGE FIRING MEMBER LOCKOUT FEATURES, now U.S. Patent Application Publication No. 2018/0168621;

U.S. patent application Ser. No. 15/385,923, entitled SURGICAL STAPLING SYSTEMS, now U.S. Patent Application Publication No. 2018/0168623;

U.S. patent application Ser. No. 15/385,925, entitled JAW ACTUATED LOCK ARRANGEMENTS FOR PREVENTING ADVANCEMENT OF A FIRING MEMBER IN A SURGICAL END EFFECTOR UNLESS AN UNFIRED CARTRIDGE IS INSTALLED IN THE END EFFECTOR, now U.S. Pat. No. 10,517,595;

U.S. patent application Ser. No. 15/385,926, entitled AXIALLY MOVABLE CLOSURE SYSTEM ARRANGEMENTS FOR APPLYING CLOSURE MOTIONS TO JAWS OF SURGICAL INSTRUMENTS, now U.S. Patent Application Publication No. 2018/0168577;

U.S. patent application Ser. No. 15/385,928, entitled PROTECTIVE COVER ARRANGEMENTS FOR A JOINT INTERFACE BETWEEN A MOVABLE JAW AND ACTUATOR SHAFT OF A SURGICAL INSTRUMENT, now U.S. Patent Application Publication No. 2018/0168578;

- U.S. patent application Ser. No. 15/385,930, entitled SURGICAL END EFFECTOR WITH TWO SEPARATE COOPERATING OPENING FEATURES FOR OPENING AND CLOSING END EFFECTOR JAWS, now U.S. Patent Application Publication No. 2018/0168579;
- U.S. patent application Ser. No. 15/385,932, entitled ARTICULATABLE SURGICAL END EFFECTOR WITH ASYMMETRIC SHAFT ARRANGEMENT, now U.S. Patent Application Publication No. 2018/0168628;
- U.S. patent application Ser. No. 15/385,933, entitled ARTICULATABLE SURGICAL INSTRUMENT WITH INDEPENDENT PIVOTABLE LINKAGE DISTAL OF AN ARTICULATION LOCK, now U.S. Pat. No. 10,603,036;
- U.S. patent application Ser. No. 15/385,934, entitled ARTICULATION LOCK ARRANGEMENTS FOR LOCKING AN END EFFECTOR IN AN ARTICULATED POSITION IN RESPONSE TO ACTUATION OF A JAW CLOSURE SYSTEM, now U.S. Pat. No. 10,582,928;
- U.S. patent application Ser. No. 15/385,935, entitled LATERALLY ACTUATABLE ARTICULATION LOCK ARRANGEMENTS FOR LOCKING AN END EFFECTOR OF A SURGICAL INSTRUMENT IN AN ARTICULATED CONFIGURATION, now U.S. Pat. No. 10,524,789; and
- U.S. patent application Ser. No. 15/385,936, entitled ARTICULATABLE SURGICAL INSTRUMENTS WITH ARTICULATION STROKE AMPLIFICATION FEATURES, now U.S. Pat. No. 10,517,596.

Applicant of the present application owns the following U.S. patent applications that were filed on Jun. 24, 2016 and which are each herein incorporated by reference in their respective entireties:

- U.S. patent application Ser. No. 15/191,775, entitled STAPLE CARTRIDGE COMPRISING WIRE STAPLES AND STAMPED STAPLES, now U.S. Patent Application Publication No. 2017/0367695;
- U.S. patent application Ser. No. 15/191,807, entitled STAPLING SYSTEM FOR USE WITH WIRE STAPLES AND STAMPED STAPLES, now U.S. Patent Application Publication No. 2017/0367696;
- U.S. patent application Ser. No. 15/191,834, entitled STAMPED STAPLES AND STAPLE CARTRIDGES USING THE SAME, now U.S. Pat. No. 10,542,979;
- U.S. patent application Ser. No. 15/191,788, entitled STAPLE CARTRIDGE COMPRISING OVERDRIVEN STAPLES, now U.S. Patent Application Publication No. 2017/0367698; and
- U.S. patent application Ser. No. 15/191,818, entitled STAPLE CARTRIDGE COMPRISING OFFSET LONGITUDINAL STAPLE ROWS, now U.S. Patent Application Publication No. 2017/0367697.

Applicant of the present application owns the following U.S. patent applications that were filed on Jun. 24, 2016 and which are each herein incorporated by reference in their respective entireties:

- U.S. Design patent application Ser. No. 29/569,218, entitled SURGICAL FASTENER, now U.S. Design Pat. No. D826,405;
- U.S. Design patent application Ser. No. 29/569,227, entitled SURGICAL FASTENER, now U.S. Design Pat. No. D822,206;
- U.S. Design patent application Ser. No. 29/569,259, entitled SURGICAL FASTENER CARTRIDGE, now U.S. Design Pat. No. D847,989; and
- U.S. Design patent application Ser. No. 29/569,264, entitled SURGICAL FASTENER CARTRIDGE, now U.S. Design Pat. No. D850,617.

Applicant of the present application owns the following patent applications that were filed on Apr. 1, 2016 and which are each herein incorporated by reference in their respective entirety:

- U.S. patent application Ser. No. 15/089,325, entitled METHOD FOR OPERATING A SURGICAL STAPLING SYSTEM, now U.S. Patent Application Publication No. 2017/0281171;
- U.S. patent application Ser. No. 15/089,321, entitled MODULAR SURGICAL STAPLING SYSTEM COMPRISING A DISPLAY, now U.S. Pat. No. 10,271,851;
- U.S. patent application Ser. No. 15/089,326, entitled SURGICAL STAPLING SYSTEM COMPRISING A DISPLAY INCLUDING A RE-ORIENTABLE DISPLAY FIELD, now U.S. Pat. No. 10,433,849;
- U.S. patent application Ser. No. 15/089,263, entitled SURGICAL INSTRUMENT HANDLE ASSEMBLY WITH RECONFIGURABLE GRIP PORTION, now U.S. Pat. No. 10,307,159;
- U.S. patent application Ser. No. 15/089,262, entitled ROTARY POWERED SURGICAL INSTRUMENT WITH MANUALLY ACTUATABLE BAILOUT SYSTEM, now U.S. Pat. No. 10,357,246;
- U.S. patent application Ser. No. 15/089,277, entitled SURGICAL CUTTING AND STAPLING END EFFECTOR WITH ANVIL CONCENTRIC DRIVE MEMBER, now U.S. Pat. No. 10,531,874;
- U.S. patent application Ser. No. 15/089,296, entitled INTERCHANGEABLE SURGICAL TOOL ASSEMBLY WITH A SURGICAL END EFFECTOR THAT IS SELECTIVELY ROTATABLE ABOUT A SHAFT AXIS, now U.S. Pat. No. 10,413,293;
- U.S. patent application Ser. No. 15/089,258, entitled SURGICAL STAPLING SYSTEM COMPRISING A SHIFTABLE TRANSMISSION, now U.S. Pat. No. 10,342,543;
- U.S. patent application Ser. No. 15/089,278, entitled SURGICAL STAPLING SYSTEM CONFIGURED TO PROVIDE SELECTIVE CUTTING OF TISSUE, now U.S. Pat. No. 10,420,552;
- U.S. patent application Ser. No. 15/089,284, entitled SURGICAL STAPLING SYSTEM COMPRISING A CONTOURABLE SHAFT, now U.S. Patent Application Publication No. 2017/0281186;
- U.S. patent application Ser. No. 15/089,295, entitled SURGICAL STAPLING SYSTEM COMPRISING A TISSUE COMPRESSION LOCKOUT, now U.S. Patent Application Publication No. 2017/0281187;
- U.S. patent application Ser. No. 15/089,300, entitled SURGICAL STAPLING SYSTEM COMPRISING AN UNCLAMPING LOCKOUT, now U.S. Pat. No. 10,456,140;
- U.S. patent application Ser. No. 15/089,196, entitled SURGICAL STAPLING SYSTEM COMPRISING A JAW CLOSURE LOCKOUT, now U.S. Pat. No. 10,568,632;
- U.S. patent application Ser. No. 15/089,203, entitled SURGICAL STAPLING SYSTEM COMPRISING A JAW ATTACHMENT LOCKOUT, now U.S. Pat. No. 10,542,991;

U.S. patent application Ser. No. 15/089,210, entitled SURGICAL STAPLING SYSTEM COMPRISING A SPENT CARTRIDGE LOCKOUT, now U.S. Pat. No. 10,478,190;

U.S. patent application Ser. No. 15/089,324, entitled SURGICAL INSTRUMENT COMPRISING A SHIFTING MECHANISM, now U.S. Pat. No. 10,314,582;

U.S. patent application Ser. No. 15/089,335, entitled SURGICAL STAPLING INSTRUMENT COMPRISING MULTIPLE LOCKOUTS, now U.S. Pat. No. 10,485,542;

U.S. patent application Ser. No. 15/089,339, entitled SURGICAL STAPLING INSTRUMENT, now U.S. Patent Application Publication No. 2017/0281173;

U.S. patent application Ser. No. 15/089,253, entitled SURGICAL STAPLING SYSTEM CONFIGURED TO APPLY ANNULAR ROWS OF STAPLES HAVING DIFFERENT HEIGHTS, now U.S. Pat. No. 10,413,297;

U.S. patent application Ser. No. 15/089,304, entitled SURGICAL STAPLING SYSTEM COMPRISING A GROOVED FORMING POCKET, now U.S. Pat. No. 10,285,705;

U.S. patent application Ser. No. 15/089,331, entitled ANVIL MODIFICATION MEMBERS FOR SURGICAL STAPLE/FASTENERS, now U.S. Pat. No. 10,376,263;

U.S. patent application Ser. No. 15/089,336, entitled STAPLE CARTRIDGES WITH ATRAUMATIC FEATURES, now U.S. Patent Application Publication No. 2017/0281164;

U.S. patent application Ser. No. 15/089,312, entitled CIRCULAR STAPLING SYSTEM COMPRISING AN INCISABLE TISSUE SUPPORT, now U.S. Patent Application Publication No. 2017/0281189;

U.S. patent application Ser. No. 15/089,309, entitled CIRCULAR STAPLING SYSTEM COMPRISING ROTARY FIRING SYSTEM, now U.S. Patent Application Publication No. 2017/0281169; and U.S. patent application Ser. No. 15/089,349, entitled CIRCULAR STAPLING SYSTEM COMPRISING LOAD CONTROL, now U.S. Patent Application Publication No. 2017/0281174.

Applicant of the present application also owns the U.S. patent applications identified below which were filed on Dec. 31, 2015 which are each herein incorporated by reference in their respective entirety:

U.S. patent application Ser. No. 14/984,488, entitled MECHANISMS FOR COMPENSATING FOR BATTERY PACK FAILURE IN POWERED SURGICAL INSTRUMENTS, now U.S. Pat. No. 10,292,704;

U.S. patent application Ser. No. 14/984,525, entitled MECHANISMS FOR COMPENSATING FOR DRIVETRAIN FAILURE IN POWERED SURGICAL INSTRUMENTS, now U.S. Pat. No. 10,368,865; and U.S. patent application Ser. No. 14/984,552, entitled SURGICAL INSTRUMENTS WITH SEPARABLE MOTORS AND MOTOR CONTROL CIRCUITS, now U.S. Pat. No. 10,265,068.

Applicant of the present application also owns the U.S. patent applications identified below which were filed on Feb. 9, 2016 which are each herein incorporated by reference in their respective entirety:

U.S. patent application Ser. No. 15/019,220, entitled SURGICAL INSTRUMENT WITH ARTICULATING AND AXIALLY TRANSLATABLE END EFFECTOR, now U.S. Pat. No. 10,245,029;

U.S. patent application Ser. No. 15/019,228, entitled SURGICAL INSTRUMENTS WITH MULTIPLE LINK ARTICULATION ARRANGEMENTS, now U.S. Pat. No. 10,433,837;

U.S. patent application Ser. No. 15/019,196, entitled SURGICAL INSTRUMENT ARTICULATION MECHANISM WITH SLOTTED SECONDARY CONSTRAINT, now U.S. Pat. No. 10,413,291;

U.S. patent application Ser. No. 15/019,206, entitled SURGICAL INSTRUMENTS WITH AN END EFFECTOR THAT IS HIGHLY ARTICULATABLE RELATIVE TO AN ELONGATE SHAFT ASSEMBLY, now U.S. Patent Application Publication No. 2017/0224331;

U.S. patent application Ser. No. 15/019,215, entitled SURGICAL INSTRUMENTS WITH NON-SYMMETRICAL ARTICULATION ARRANGEMENTS, now U.S. Patent Application Publication No. 2017/0224332;

U.S. patent application Ser. No. 15/019,227, entitled ARTICULATABLE SURGICAL INSTRUMENTS WITH SINGLE ARTICULATION LINK ARRANGEMENTS, now U.S. Patent Application Publication No. 2017/0224334;

U.S. patent application Ser. No. 15/019,235, entitled SURGICAL INSTRUMENTS WITH TENSIONING ARRANGEMENTS FOR CABLE DRIVEN ARTICULATION SYSTEMS, now U.S. Pat. No. 10,245,030;

U.S. patent application Ser. No. 15/019,230, entitled ARTICULATABLE SURGICAL INSTRUMENTS WITH OFF-AXIS FIRING BEAM ARRANGEMENTS, now U.S. Pat. No. 10,588,625; and U.S. patent application Ser. No. 15/019,245, entitled SURGICAL INSTRUMENTS WITH CLOSURE STROKE REDUCTION ARRANGEMENTS, now U.S. Pat. No. 10,470,764.

Applicant of the present application also owns the U.S. patent applications identified below which were filed on Feb. 12, 2016 which are each herein incorporated by reference in their respective entirety:

U.S. patent application Ser. No. 15/043,254, entitled MECHANISMS FOR COMPENSATING FOR DRIVETRAIN FAILURE IN POWERED SURGICAL INSTRUMENTS, now U.S. Pat. No. 10,258,331;

U.S. patent application Ser. No. 15/043,259, entitled MECHANISMS FOR COMPENSATING FOR DRIVETRAIN FAILURE IN POWERED SURGICAL INSTRUMENTS, now U.S. Pat. No. 10,448,948;

U.S. patent application Ser. No. 15/043,275, entitled MECHANISMS FOR COMPENSATING FOR DRIVETRAIN FAILURE IN POWERED SURGICAL INSTRUMENTS, now U.S. Patent Application Publication No. 2017/0231627; and U.S. patent application Ser. No. 15/043,289, entitled MECHANISMS FOR COMPENSATING FOR DRIVETRAIN FAILURE IN POWERED SURGICAL INSTRUMENTS, now U.S. Patent Application Publication No. 2017/0231628.

Applicant of the present application owns the following patent applications that were filed on Jun. 18, 2015 and which are each herein incorporated by reference in their respective entirety:

U.S. patent application Ser. No. 14/742,925, entitled SURGICAL END EFFECTORS WITH POSITIVE JAW OPENING ARRANGEMENTS, now U.S. Pat. No. 10,182,818;

- U.S. patent application Ser. No. 14/742,941, entitled SURGICAL END EFFECTORS WITH DUAL CAM ACTUATED JAW CLOSING FEATURES, now U.S. Pat. No. 10,052,102;
- U.S. patent application Ser. No. 14/742,914, entitled MOVABLE FIRING BEAM SUPPORT ARRANGEMENTS FOR ARTICULATABLE SURGICAL INSTRUMENTS, now U.S. Pat. No. 10,405,863;
- U.S. patent application Ser. No. 14/742,900, entitled ARTICULATABLE SURGICAL INSTRUMENTS WITH COMPOSITE FIRING BEAM STRUCTURES WITH CENTER FIRING SUPPORT MEMBER FOR ARTICULATION SUPPORT, now U.S. Pat. No. 10,335,149;
- U.S. patent application Ser. No. 14/742,885, entitled DUAL ARTICULATION DRIVE SYSTEM ARRANGEMENTS FOR ARTICULATABLE SURGICAL INSTRUMENTS, now U.S. Pat. No. 10,368, 861; and
- U.S. patent application Ser. No. 14/742,876, entitled PUSH/PULL ARTICULATION DRIVE SYSTEMS FOR ARTICULATABLE SURGICAL INSTRUMENTS, now U.S. Pat. No. 10,178,992.

Applicant of the present application owns the following patent applications that were filed on Mar. 6, 2015 and which are each herein incorporated by reference in their respective entirety:

- U.S. patent application Ser. No. 14/640,746, entitled POWERED SURGICAL INSTRUMENT, now U.S. Pat. No. 9,808,246;
- U.S. patent application Ser. No. 14/640,795, entitled MULTIPLE LEVEL THRESHOLDS TO MODIFY OPERATION OF POWERED SURGICAL INSTRUMENTS, now U.S. Pat. No. 10,441,279;
- U.S. patent application Ser. No. 14/640,832, entitled ADAPTIVE TISSUE COMPRESSION TECHNIQUES TO ADJUST CLOSURE RATES FOR MULTIPLE TISSUE TYPES, now U.S. Patent Application Publication No. 2016/0256154;
- U.S. patent application Ser. No. 14/640,935, entitled OVERLAID MULTI SENSOR RADIO FREQUENCY (RF) ELECTRODE SYSTEM TO MEASURE TISSUE COMPRESSION, now U.S. Pat. No. 10,548,504;
- U.S. patent application Ser. No. 14/640,831, entitled MONITORING SPEED CONTROL AND PRECISION INCREMENTING OF MOTOR FOR POWERED SURGICAL INSTRUMENTS, now U.S. Pat. No. 9,895,148;
- U.S. patent application Ser. No. 14/640,859, entitled TIME DEPENDENT EVALUATION OF SENSOR DATA TO DETERMINE STABILITY, CREEP, AND VISCOELASTIC ELEMENTS OF MEASURES, now U.S. Pat. No. 10,052,044;
- U.S. patent application Ser. No. 14/640,817, entitled INTERACTIVE FEEDBACK SYSTEM FOR POWERED SURGICAL INSTRUMENTS, now U.S. Pat. No. 9,924,961;
- U.S. patent application Ser. No. 14/640,844, entitled CONTROL TECHNIQUES AND SUB-PROCESSOR CONTAINED WITHIN MODULAR SHAFT WITH SELECT CONTROL PROCESSING FROM HANDLE, now U.S. Pat. No. 10,045,776;
- U.S. patent application Ser. No. 14/640,837, entitled SMART SENSORS WITH LOCAL SIGNAL PROCESSING, now U.S. Pat. No. 9,993,248;
- U.S. patent application Ser. No. 14/640,765, entitled SYSTEM FOR DETECTING THE MIS-INSERTION OF A STAPLE CARTRIDGE INTO A SURGICAL STAPLE/FASTENER, now U.S. Pat. No. 10,617,412;
- U.S. patent application Ser. No. 14/640,799, entitled SIGNAL AND POWER COMMUNICATION SYSTEM POSITIONED ON A ROTATABLE SHAFT, now U.S. Pat. No. 9,901,342; and
- U.S. patent application Ser. No. 14/640,780, entitled SURGICAL INSTRUMENT COMPRISING A LOCKABLE BATTERY HOUSING, now U.S. Pat. No. 10,245,033.

Applicant of the present application owns the following patent applications that were filed on Feb. 27, 2015, and which are each herein incorporated by reference in their respective entirety:

- U.S. patent application Ser. No. 14/633,576, entitled SURGICAL INSTRUMENT SYSTEM COMPRISING AN INSPECTION STATION, now U.S. Pat. No. 10,045,779;
- U.S. patent application Ser. No. 14/633,546, entitled SURGICAL APPARATUS CONFIGURED TO ASSESS WHETHER A PERFORMANCE PARAMETER OF THE SURGICAL APPARATUS IS WITHIN AN ACCEPTABLE PERFORMANCE BAND, now U.S. Pat. No. 10,180,463;
- U.S. patent application Ser. No. 14/633,560, entitled SURGICAL CHARGING SYSTEM THAT CHARGES AND/OR CONDITIONS ONE OR MORE BATTERIES, now U.S. Patent Application Publication No. 2016/0249910;
- U.S. patent application Ser. No. 14/633,566, entitled CHARGING SYSTEM THAT ENABLES EMERGENCY RESOLUTIONS FOR CHARGING A BATTERY, now U.S. Pat. No. 10,182,816;
- U.S. patent application Ser. No. 14/633,555, entitled SYSTEM FOR MONITORING WHETHER A SURGICAL INSTRUMENT NEEDS TO BE SERVICED, now U.S. Pat. No. 10,321,907;
- U.S. patent application Ser. No. 14/633,542, entitled REINFORCED BATTERY FOR A SURGICAL INSTRUMENT, now U.S. Pat. No. 9,931,118;
- U.S. patent application Ser. No. 14/633,548, entitled POWER ADAPTER FOR A SURGICAL INSTRUMENT, now U.S. Pat. No. 10,245,028;
- U.S. patent application Ser. No. 14/633,526, entitled ADAPTABLE SURGICAL INSTRUMENT HANDLE, now U.S. Pat. No. 9,993,258;
- U.S. patent application Ser. No. 14/633,541, entitled MODULAR STAPLING ASSEMBLY, now U.S. Pat. No. 10,226,250; and
- U.S. patent application Ser. No. 14/633,562, entitled SURGICAL APPARATUS CONFIGURED TO TRACK AN END-OF-LIFE PARAMETER, now U.S. Pat. No. 10,159,483.

Applicant of the present application owns the following patent applications that were filed on Dec. 18, 2014 and which are each herein incorporated by reference in their respective entirety:

- U.S. patent application Ser. No. 14/574,478, entitled SURGICAL INSTRUMENT SYSTEMS COMPRISING AN ARTICULATABLE END EFFECTOR AND MEANS FOR ADJUSTING THE FIRING STROKE OF A FIRING MEMBER, now U.S. Pat. No. 9,844, 374;
- U.S. patent application Ser. No. 14/574,483, entitled SURGICAL INSTRUMENT ASSEMBLY COMPRISING LOCKABLE SYSTEMS, now U.S. Pat. No. 10,188,385;

U.S. patent application Ser. No. 14/575,139, entitled DRIVE ARRANGEMENTS FOR ARTICULATABLE SURGICAL INSTRUMENTS, now U.S. Pat. No. 9,844,375;

U.S. patent application Ser. No. 14/575,148, entitled LOCKING ARRANGEMENTS FOR DETACHABLE SHAFT ASSEMBLIES WITH ARTICULATABLE SURGICAL END EFFECTORS, now U.S. Pat. No. 10,085,748;

U.S. patent application Ser. No. 14/575,130, entitled SURGICAL INSTRUMENT WITH AN ANVIL THAT IS SELECTIVELY MOVABLE ABOUT A DISCRETE NON-MOVABLE AXIS RELATIVE TO A STAPLE CARTRIDGE, now U.S. Pat. No. 10,245,027;

U.S. patent application Ser. No. 14/575,143, entitled SURGICAL INSTRUMENTS WITH IMPROVED CLOSURE ARRANGEMENTS, now U.S. Pat. No. 10,004,501;

U.S. patent application Ser. No. 14/575,117, entitled SURGICAL INSTRUMENTS WITH ARTICULATABLE END EFFECTORS AND MOVABLE FIRING BEAM SUPPORT ARRANGEMENTS, now U.S. Pat. No. 9,943,309;

U.S. patent application Ser. No. 14/575,154, entitled SURGICAL INSTRUMENTS WITH ARTICULATABLE END EFFECTORS AND IMPROVED FIRING BEAM SUPPORT ARRANGEMENTS, now U.S. Pat. No. 9,968,355;

U.S. patent application Ser. No. 14/574,493, entitled SURGICAL INSTRUMENT ASSEMBLY COMPRISING A FLEXIBLE ARTICULATION SYSTEM, now U.S. Pat. No. 9,987,000; and U.S. patent application Ser. No. 14/574,500, entitled SURGICAL INSTRUMENT ASSEMBLY COMPRISING A LOCKABLE ARTICULATION SYSTEM, now U.S. Pat. No. 10,117,649.

Applicant of the present application owns the following patent applications that were filed on Mar. 1, 2013 and which are each herein incorporated by reference in their respective entirety:

U.S. patent application Ser. No. 13/782,295, entitled ARTICULATABLE SURGICAL INSTRUMENTS WITH CONDUCTIVE PATHWAYS FOR SIGNAL COMMUNICATION, now U.S. Pat. No. 9,700,309;

U.S. patent application Ser. No. 13/782,323, entitled ROTARY POWERED ARTICULATION JOINTS FOR SURGICAL INSTRUMENTS, now U.S. Pat. No. 9,782,169;

U.S. patent application Ser. No. 13/782,338, entitled THUMBWHEEL SWITCH ARRANGEMENTS FOR SURGICAL INSTRUMENTS, now U.S. Patent Application Publication No. 2014/0249557;

U.S. patent application Ser. No. 13/782,499, entitled ELECTROMECHANICAL SURGICAL DEVICE WITH SIGNAL RELAY ARRANGEMENT, now U.S. Pat. No. 9,358,003;

U.S. patent application Ser. No. 13/782,460, entitled MULTIPLE PROCESSOR MOTOR CONTROL FOR MODULAR SURGICAL INSTRUMENTS, now U.S. Pat. No. 9,554,794;

U.S. patent application Ser. No. 13/782,358, entitled JOYSTICK SWITCH ASSEMBLIES FOR SURGICAL INSTRUMENTS, now U.S. Pat. No. 9,326,767;

U.S. patent application Ser. No. 13/782,481, entitled SENSOR STRAIGHTENED END EFFECTOR DURING REMOVAL THROUGH TROCAR, now U.S. Pat. No. 9,468,438;

U.S. patent application Ser. No. 13/782,518, entitled CONTROL METHODS FOR SURGICAL INSTRUMENTS WITH REMOVABLE IMPLEMENT PORTIONS, now U.S. Patent Application Publication No. 2014/0246475;

U.S. patent application Ser. No. 13/782,375, entitled ROTARY POWERED SURGICAL INSTRUMENTS WITH MULTIPLE DEGREES OF FREEDOM, now U.S. Pat. No. 9,398,911; and U.S. patent application Ser. No. 13/782,536, entitled SURGICAL INSTRUMENT SOFT STOP, now U.S. Pat. No. 9,307,986.

Applicant of the present application also owns the following patent applications that were filed on Mar. 14, 2013 and which are each herein incorporated by reference in their respective entirety:

U.S. patent application Ser. No. 13/803,097, entitled ARTICULATABLE SURGICAL INSTRUMENT COMPRISING A FIRING DRIVE, now U.S. Pat. No. 9,687,230;

U.S. patent application Ser. No. 13/803,193, entitled CONTROL ARRANGEMENTS FOR A DRIVE MEMBER OF A SURGICAL INSTRUMENT, now U.S. Pat. No. 9,332,987;

U.S. patent application Ser. No. 13/803,053, entitled INTERCHANGEABLE SHAFT ASSEMBLIES FOR USE WITH A SURGICAL INSTRUMENT, now U.S. Pat. No. 9,883,860

U.S. patent application Ser. No. 13/803,086, entitled ARTICULATABLE SURGICAL INSTRUMENT COMPRISING AN ARTICULATION LOCK, now U.S. Patent Application Publication No. 2014/0263541;

U.S. patent application Ser. No. 13/803,210, entitled SENSOR ARRANGEMENTS FOR ABSOLUTE POSITIONING SYSTEM FOR SURGICAL INSTRUMENTS, now U.S. Pat. No. 9,808,244;

U.S. patent application Ser. No. 13/803,148, entitled MULTI-FUNCTION MOTOR FOR A SURGICAL INSTRUMENT, now U.S. Pat. No. 10,470,762;

U.S. patent application Ser. No. 13/803,066, entitled DRIVE SYSTEM LOCKOUT ARRANGEMENTS FOR MODULAR SURGICAL INSTRUMENTS, now U.S. Pat. No. 9,629,623;

U.S. patent application Ser. No. 13/803,117, entitled ARTICULATION CONTROL SYSTEM FOR ARTICULATABLE SURGICAL INSTRUMENTS, now U.S. Pat. No. 9,351,726;

U.S. patent application Ser. No. 13/803,130, entitled DRIVE TRAIN CONTROL ARRANGEMENTS FOR MODULAR SURGICAL INSTRUMENTS, now U.S. Pat. No. 9,351,727; and U.S. patent application Ser. No. 13/803,159, entitled METHOD AND SYSTEM FOR OPERATING A SURGICAL INSTRUMENT, now U.S. Pat. No. 9,888,919.

Applicant of the present application also owns the following patent application that was filed on Mar. 7, 2014 and is herein incorporated by reference in its entirety:

U.S. patent application Ser. No. 14/200,111, entitled CONTROL SYSTEMS FOR SURGICAL INSTRUMENTS, now U.S. Pat. No. 9,629,629.

Applicant of the present application also owns the following patent applications that were filed on Mar. 26, 2014 and are each herein incorporated by reference in their respective entirety:

U.S. patent application Ser. No. 14/226,106, entitled POWER MANAGEMENT CONTROL SYSTEMS FOR SURGICAL INSTRUMENTS, now U.S. Patent Application Publication No. 2015/0272582;

U.S. patent application Ser. No. 14/226,099, entitled STERILIZATION VERIFICATION CIRCUIT, now U.S. Pat. No. 9,826,977;

U.S. patent application Ser. No. 14/226,094, entitled VERIFICATION OF NUMBER OF BATTERY EXCHANGES/PROCEDURE COUNT, now U.S. Patent Application Publication No. 2015/0272580;

U.S. patent application Ser. No. 14/226,117, entitled POWER MANAGEMENT THROUGH SLEEP OPTIONS OF SEGMENTED CIRCUIT AND WAKE UP CONTROL, now U.S. Pat. No. 10,013,049;

U.S. patent application Ser. No. 14/226,075, entitled MODULAR POWERED SURGICAL INSTRUMENT WITH DETACHABLE SHAFT ASSEMBLIES, now U.S. Pat. No. 9,743,929;

U.S. patent application Ser. No. 14/226,093, entitled FEEDBACK ALGORITHMS FOR MANUAL BAIL-OUT SYSTEMS FOR SURGICAL INSTRUMENTS, now U.S. Pat. No. 10,028,761;

U.S. patent application Ser. No. 14/226,116, entitled SURGICAL INSTRUMENT UTILIZING SENSOR ADAPTATION, now U.S. Patent Application Publication No. 2015/0272571;

U.S. patent application Ser. No. 14/226,071, entitled SURGICAL INSTRUMENT CONTROL CIRCUIT HAVING A SAFETY PROCESSOR, now U.S. Pat. No. 9,690,362;

U.S. patent application Ser. No. 14/226,097, entitled SURGICAL INSTRUMENT COMPRISING INTERACTIVE SYSTEMS, now U.S. Pat. No. 9,820,738;

U.S. patent application Ser. No. 14/226,126, entitled INTERFACE SYSTEMS FOR USE WITH SURGICAL INSTRUMENTS, now U.S. Pat. No. 10,004,497;

U.S. patent application Ser. No. 14/226,133, entitled MODULAR SURGICAL INSTRUMENT SYSTEM, now U.S. Patent Application Publication No. 2015/0272557;

U.S. patent application Ser. No. 14/226,081, entitled SYSTEMS AND METHODS FOR CONTROLLING A SEGMENTED CIRCUIT, now U.S. Pat. No. 9,804,618;

U.S. patent application Ser. No. 14/226,076, entitled POWER MANAGEMENT THROUGH SEGMENTED CIRCUIT AND VARIABLE VOLTAGE PROTECTION, now U.S. Pat. No. 9,733,663;

U.S. patent application Ser. No. 14/226,111, entitled SURGICAL STAPLING INSTRUMENT SYSTEM, now U.S. Pat. No. 9,750,499; and U.S. patent application Ser. No. 14/226,125, entitled SURGICAL INSTRUMENT COMPRISING A ROTATABLE SHAFT, now U.S. Pat. No. 10,201,364.

Applicant of the present application also owns the following patent applications that were filed on Sep. 5, 2014 and which are each herein incorporated by reference in their respective entirety:

U.S. patent application Ser. No. 14/479,103, entitled CIRCUITRY AND SENSORS FOR POWERED MEDICAL DEVICE, now U.S. Pat. No. 10,111,679;

U.S. patent application Ser. No. 14/479,119, entitled ADJUNCT WITH INTEGRATED SENSORS TO QUANTIFY TISSUE COMPRESSION, now U.S. Pat. No. 9,724,094;

U.S. patent application Ser. No. 14/478,908, entitled MONITORING DEVICE DEGRADATION BASED ON COMPONENT EVALUATION, now U.S. Pat. No. 9,737,301;

U.S. patent application Ser. No. 14/478,895, entitled MULTIPLE SENSORS WITH ONE SENSOR AFFECTING A SECOND SENSOR'S OUTPUT OR INTERPRETATION, now U.S. Pat. No. 9,757,128;

U.S. patent application Ser. No. 14/479,110, entitled POLARITY OF HALL MAGNET TO DETECT MIS-LOADED CARTRIDGE, now U.S. Pat. No. 10,016,199;

U.S. patent application Ser. No. 14/479,098, entitled SMART CARTRIDGE WAKE UP OPERATION AND DATA RETENTION, now U.S. Pat. No. 10,135,242;

U.S. patent application Ser. No. 14/479,115, entitled MULTIPLE MOTOR CONTROL FOR POWERED MEDICAL DEVICE, now U.S. Pat. No. 9,788,836; and U.S. patent application Ser. No. 14/479,108, entitled LOCAL DISPLAY OF TISSUE PARAMETER STABILIZATION, now U.S. Patent Application Publication No. 2016/0066913.

Applicant of the present application also owns the following patent applications that were filed on Apr. 9, 2014 and which are each herein incorporated by reference in their respective entirety:

U.S. patent application Ser. No. 14/248,590, entitled MOTOR DRIVEN SURGICAL INSTRUMENTS WITH LOCKABLE DUAL DRIVE SHAFTS, now U.S. Pat. No. 9,826,976;

U.S. patent application Ser. No. 14/248,581, entitled SURGICAL INSTRUMENT COMPRISING A CLOSING DRIVE AND A FIRING DRIVE OPERATED FROM THE SAME ROTATABLE OUTPUT, now U.S. Pat. No. 9,649,110;

U.S. patent application Ser. No. 14/248,595, entitled SURGICAL INSTRUMENT SHAFT INCLUDING SWITCHES FOR CONTROLLING THE OPERATION OF THE SURGICAL INSTRUMENT, now U.S. Pat. No. 9,844,368;

U.S. patent application Ser. No. 14/248,588, entitled POWERED LINEAR SURGICAL STAPLE/FASTENER, now U.S. Pat. No. 10,405,857;

U.S. patent application Ser. No. 14/248,591, entitled TRANSMISSION ARRANGEMENT FOR A SURGICAL INSTRUMENT, now U.S. Pat. No. 10,149,680;

U.S. patent application Ser. No. 14/248,584, entitled MODULAR MOTOR DRIVEN SURGICAL INSTRUMENTS WITH ALIGNMENT FEATURES FOR ALIGNING ROTARY DRIVE SHAFTS WITH SURGICAL END EFFECTOR SHAFTS, now U.S. Pat. No. 9,801,626;

U.S. patent application Ser. No. 14/248,587, entitled POWERED SURGICAL STAPLE/FASTENER, now U.S. Pat. No. 9,867,612;

U.S. patent application Ser. No. 14/248,586, entitled DRIVE SYSTEM DECOUPLING ARRANGEMENT FOR A SURGICAL INSTRUMENT, now U.S. Pat. No. 10,136,887; and U.S. patent application Ser. No. 14/248,607, entitled MODULAR MOTOR DRIVEN SURGICAL INSTRUMENTS WITH STATUS INDICATION ARRANGEMENTS, now U.S. Pat. No. 9,814,460.

Applicant of the present application also owns the following patent applications that were filed on Apr. 16, 2013 and which are each herein incorporated by reference in their respective entirety:

U.S. Provisional Patent Application Ser. No. 61/812,365, entitled SURGICAL INSTRUMENT WITH MULTIPLE FUNCTIONS PERFORMED BY A SINGLE MOTOR;

U.S. Provisional Patent Application Ser. No. 61/812,376, entitled LINEAR CUTTER WITH POWER;

U.S. Provisional Patent Application Ser. No. 61/812,382, entitled LINEAR CUTTER WITH MOTOR AND PISTOL GRIP;

U.S. Provisional Patent Application Ser. No. 61/812,385, entitled SURGICAL INSTRUMENT HANDLE WITH MULTIPLE ACTUATION MOTORS AND MOTOR CONTROL; and U.S. Provisional Patent Application Ser. No. 61/812,372, entitled SURGICAL INSTRUMENT WITH MULTIPLE FUNCTIONS PERFORMED BY A SINGLE MOTOR.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

A surgical stapling system can comprise a shaft and an end effector extending from the shaft. The end effector comprises a first jaw and a second jaw. The first jaw comprises a staple cartridge. The staple cartridge is insertable into and removable from the first jaw; however, other embodiments are envisioned in which a staple cartridge is not removable from, or at least readily replaceable from, the first jaw. The second jaw comprises an anvil configured to deform staples ejected from the staple cartridge. The second jaw is pivotable relative to the first jaw about a closure axis; however, other embodiments are envisioned in which the first jaw is pivotable relative to the second jaw. The surgical stapling system further comprises an articulation joint configured to permit the end effector to be rotated, or articulated, relative to the shaft. The end effector is rotatable about an articulation axis extending through the articulation joint. Other embodiments are envisioned which do not include an articulation joint.

The staple cartridge comprises a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities are arranged in six longitudinal rows. Three rows of staple cavities are positioned on a first side of a longitudinal slot and three rows of staple cavities are positioned on a second side of the longitudinal slot. Other arrangements of staple cavities and staples may be possible.

The staples are supported by staple drivers in the cartridge body. The drivers are movable between a first, or unfired position, and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions by a sled. The sled is movable between a proximal position adjacent the proximal end and a distal position adjacent the distal end. The sled comprises a plurality of ramped surfaces configured to slide under the drivers and lift the drivers, and the staples supported thereon, toward the anvil.

Further to the above, the sled is moved distally by a firing member. The firing member is configured to contact the sled and push the sled toward the distal end. The longitudinal slot defined in the cartridge body is configured to receive the firing member. The anvil also includes a slot configured to receive the firing member. The firing member further comprises a first cam which engages the first jaw and a second cam which engages the second jaw. As the firing member is advanced distally, the first cam and the second cam can control the distance, or tissue gap, between the deck of the staple cartridge and the anvil. The firing member also comprises a knife configured to incise the tissue captured intermediate the staple cartridge and the anvil. It is desirable for the knife to be positioned at least partially proximal to the ramped surfaces such that the staples are ejected ahead of the knife.

Figure 1:
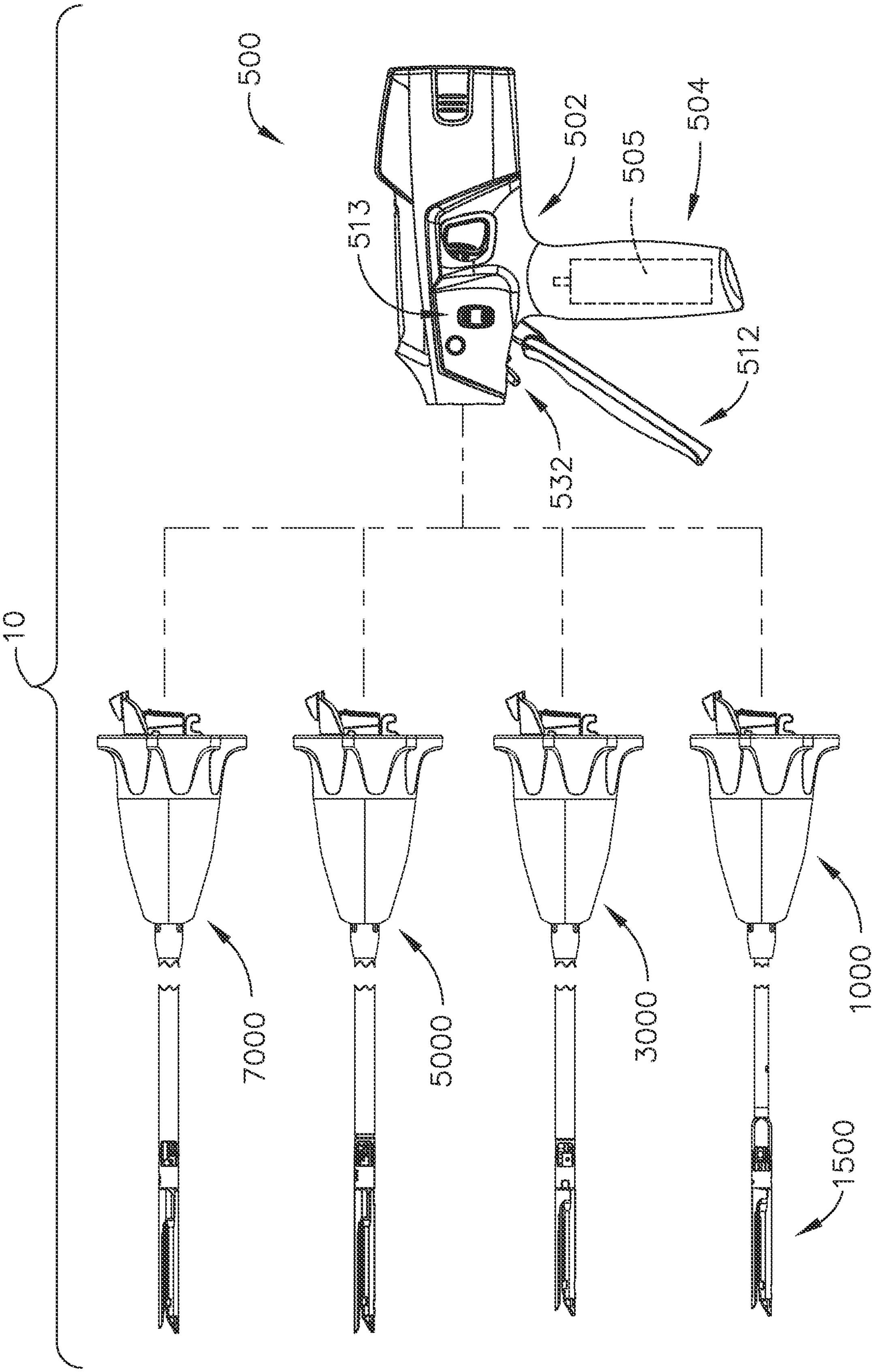
FIG. 1 is a side elevational view of a surgical system comprising a handle assembly and multiple interchangeable surgical tool assemblies that may be used therewith.

FIG. 1 depicts a motor-driven surgical system 10 that may be used to perform a variety of different surgical procedures. As can be seen in that Figure, one example of the surgical system 10 includes four interchangeable surgical tool assemblies 1000, 3000, 5000 and 7000 that are each adapted for interchangeable use with a handle assembly 500. Each interchangeable surgical tool assembly 1000, 3000, 5000 and 7000 may be designed for use in connection with the performance of one or more specific surgical procedures. In another surgical system embodiment, one or more of the interchangeable surgical tool assemblies 1000, 3000, 5000 and 7000 may also be effectively employed with a tool drive assembly of a robotically controlled or automated surgical system. For example, the surgical tool assemblies disclosed herein may be employed with various robotic systems, instruments, components and methods such as, but not limited to, those disclosed in U.S. Pat. No. 9,072,535, entitled SURGICAL STAPLING INSTRUMENTS WITH ROTATABLE STAPLE DEPLOYMENT ARRANGEMENTS, which is hereby incorporated by reference herein in its entirety.

Figure 2:
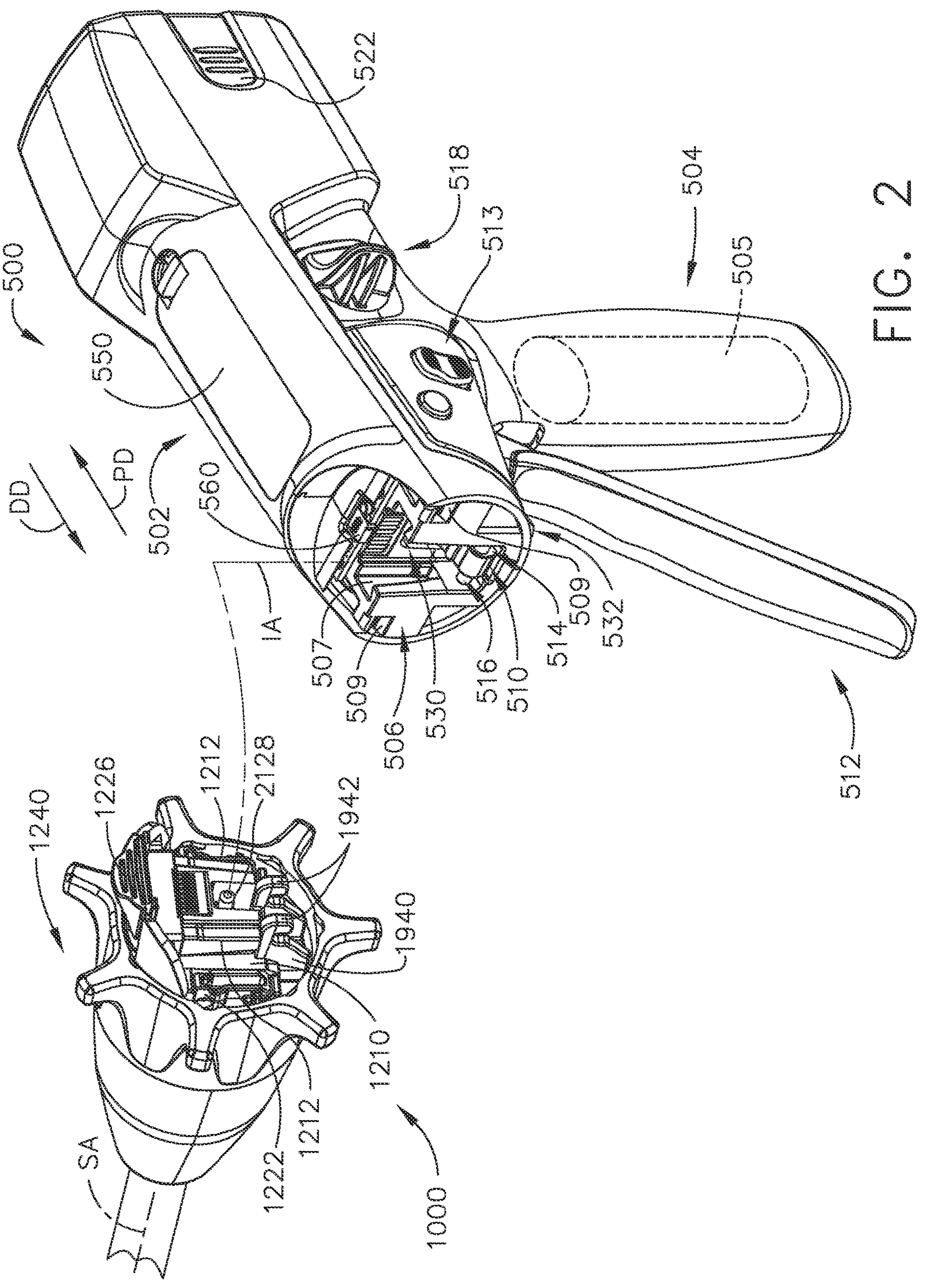
FIG. 2 is an exploded assembly view of portions of the handle assembly and one of the interchangeable surgical tool assemblies depicted in FIG. 1.

FIG. 2 illustrates attachment of an interchangeable surgical tool assembly 1000 to the handle assembly 500. It will be understood that any of the other interchangeable tool assemblies 3000, 5000, and 7000 may be coupled to the handle assembly 500 in a similar manner. The attachment arrangement and process depicted in FIG. 2 may also be employed in connection with attachment of any of the interchangeable surgical tool assemblies 1000, 3000, 5000 and 7000 to a tool drive portion or tool drive housing of a robotic system. The handle assembly 500 may comprise a handle housing 502 that includes a pistol grip portion 504 that can be gripped and manipulated by the clinician. As will be briefly discussed below, the handle assembly 500 operably supports a plurality of drive systems 510, 530 that are configured to generate and apply various control motions to corresponding portions of the interchangeable surgical tool assembly 1000, 3000, 5000 and/or 7000 that is operably attached thereto.

As can be seen in FIG. 2, the handle assembly 500 may further include a handle frame 506 that operably supports the plurality of drive systems. For example, the handle frame 506 can operably support a "first" or closure drive system, generally designated as 510, which may be employed to apply closing and opening motions to the interchangeable surgical tool assembly 1000, 3000, 5000 and 7000 that is operably attached or coupled to the handle assembly 500. In at least one form, the closure drive system 510 may include an actuator in the form of a closure trigger 512 that is pivotally supported by the handle frame 506. Such arrangement enables the closure trigger 512 to be manipulated by a clinician such that when the clinician grips the pistol grip portion 504 of the handle assembly 500, the closure trigger 512 may be easily pivoted from a starting or "unactuated" position to an "actuated" position and more particularly to a fully compressed or fully actuated position. In various forms, the closure drive system 510 further includes a closure linkage assembly 514 that is pivotally coupled to the closure trigger 512 or otherwise operably interfaces therewith. As will be discussed in further detail below, in the illustrated example, the closure linkage assembly 514 includes a transverse attachment pin 516 that facilitates attachment to a corresponding drive system on the surgical tool assembly. In use, to actuate the closure drive system 510, the clinician depresses the closure trigger 512 towards the pistol grip portion 504. As described in further detail in U.S. patent application Ser. No. 14/226,142, entitled SURGICAL INSTRUMENT COMPRISING A SENSOR SYSTEM, U.S. Patent Application Publication No. 2015/0272575, now U.S. Pat. No. 9,913,642, which is hereby incorporated by reference in its entirety herein, when the clinician fully depresses the closure trigger 512 to attain the full closure stroke, the closure drive system 510 is configured to lock the closure trigger 512 into the fully depressed or fully actuated position. When the clinician desires to unlock the closure trigger 512 to permit it to be biased to the unactuated position, the clinician simply activates a closure release button assembly 518 which enables the closure trigger to return to unactuated position. The closure release button assembly 518 may also be configured to interact with various sensors that communicate with a microprocessor 560 in the handle assembly 500 for tracking the position of the closure trigger 512. Further details concerning the configuration and operation of the closure release button assembly 518 may be found in U.S. Patent Application Publication No. 2015/0272575, now U.S. Pat. No. 9,913,642.

In at least one form, the handle assembly 500 and the handle frame 506 may operably support another drive system referred to herein as a firing drive system 530 that is configured to apply firing motions to corresponding portions of the interchangeable surgical tool assembly that is attached thereto. As was described in detail in U.S. Patent Application Publication No. 2015/0272575, now U.S. Pat. No. 9,913,642, the firing drive system 530 may employ an electric motor 505 that is located in the pistol grip portion 504 of the handle assembly 500. In various forms, the motor 505 may be a DC brushed driving motor having a maximum rotation of, approximately, 25,000 RPM, for example. In other arrangements, the motor 505 may include a brushless motor, a cordless motor, a synchronous motor, a stepper motor, or any other suitable electric motor. The motor 505 may be powered by a power source 522 that in one form may comprise a removable power pack. The power pack may support a plurality of Lithium Ion ("LI") or other suitable batteries therein. A number of batteries connected in series may be used as the power source 522 for the surgical system 10. In addition, the power source 522 may be replaceable and/or rechargeable.

The electric motor 505 is configured to axially drive a longitudinally movable drive member (not shown) in a distal and proximal directions depending upon the polarity of the motor. For example, when the motor is driven in one rotary direction, the longitudinally movable drive member will be axially driven in a distal direction "DD". When the motor 505 is driven in the opposite rotary direction, the longitudinally movable drive member will be axially driven in a proximal direction "PD". The handle assembly 500 can include a switch 513 which can be configured to reverse the polarity applied to the electric motor 505 by the power source 522 or otherwise control the motor 505. The handle assembly 500 can also include a sensor or sensors (not shown) that is configured to detect the position of the drive member and/or the direction in which the drive member is being moved. Actuation of the motor 505 can be controlled by a firing trigger 532 (FIG. 1) that is pivotally supported on the handle assembly 500. The firing trigger 532 may be pivoted between an unactuated position and an actuated position. The firing trigger 532 may be biased into the unactuated position by a spring or other biasing arrangement such that when the clinician releases the firing trigger 532, it may be pivoted or otherwise returned to the unactuated position by the spring or biasing arrangement. In at least one form, the firing trigger 532 can be positioned "outboard" of the closure trigger 512 as was discussed above. As discussed in U.S. Patent Application Publication No. 2015/0272575, now U.S. Pat. No. 9,913,642, the handle assembly 500 may be equipped with a firing trigger safety button (not shown) to prevent inadvertent actuation of the firing trigger 532. When the closure trigger 512 is in the unactuated position, the safety button is contained in the handle assembly 500 where the clinician cannot readily access it and move it between a safety position preventing actuation of the firing trigger 532 and a firing position wherein the firing trigger 532 may be fired. As the clinician depresses the closure trigger 512, the safety button and the firing trigger 532 pivot down wherein they can then be manipulated by the clinician.

In at least one form, the longitudinally movable drive member may have a rack of teeth (not shown) formed thereon for meshing engagement with a corresponding drive gear arrangement (not shown) that interfaces with the motor. Further details regarding those features may be found in U.S. Patent Application Publication No. 2015/0272575, now U.S. Pat. No. 9,913,642. At least one form also includes a manually-actuatable "bailout" assembly that is configured to enable the clinician to manually retract the longitudinally movable drive member should the motor 505 become disabled. The bailout assembly may include a lever or bailout handle assembly that is stored within the handle assembly 500 under a releasable door 550. See FIG. 2. The lever may be configured to be manually pivoted into ratcheting engagement with the teeth in the drive member. Thus, the clinician can manually retract the drive member by using the bailout handle assembly to ratchet the drive member in the proximal direction "PD". U.S. Pat. No. 8,608,045, entitled POWERED SURGICAL CUTTING AND STAPLING APPARATUS WITH MANUALLY RETRACTABLE FIRING SYSTEM, the entire disclosure of which is hereby incorporated by reference herein, discloses bailout arrangements and other components, arrangements and systems that may also be employed with any one of the various interchangeable surgical tool assemblies disclosed herein.

Figure 3:
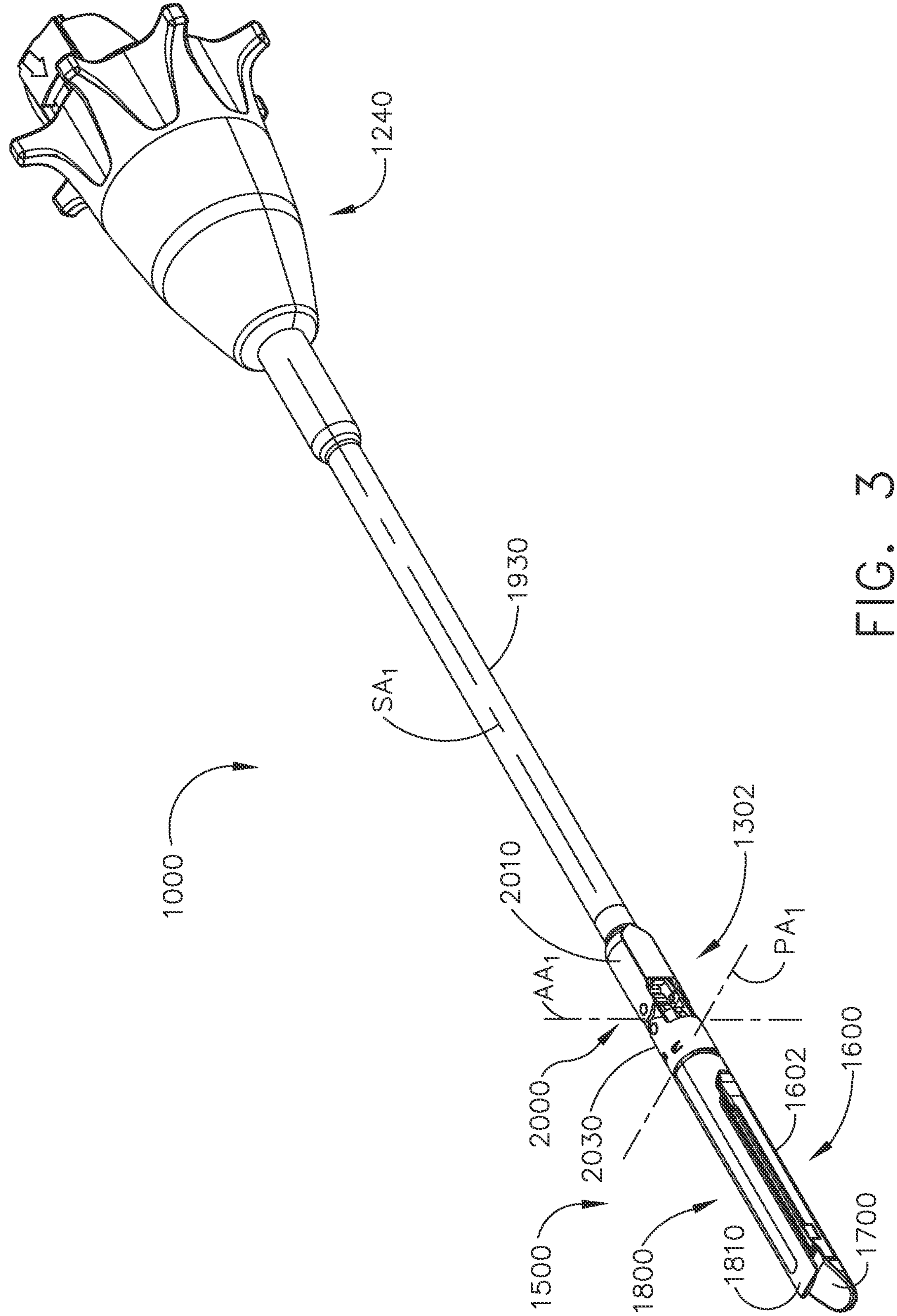
FIG. 3 is a perspective view of one of the interchangeable surgical tool assemblies depicted in FIG. 1.
Figure 4:
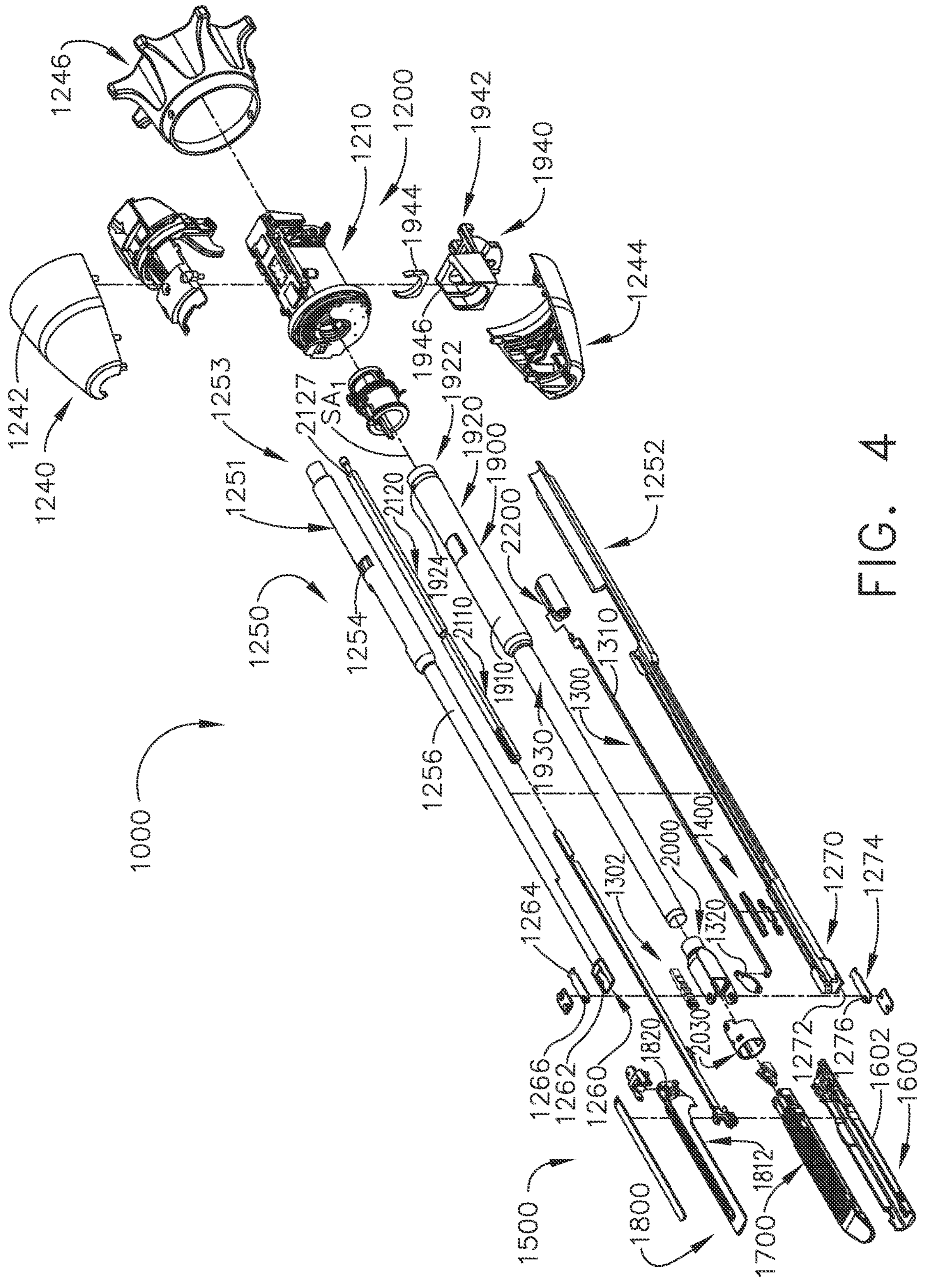
FIG. 4 is an exploded assembly view of the interchangeable surgical tool assembly of FIG. 3.

Turning now to FIGS. 3 and 4, the interchangeable surgical tool assembly 1000 includes a surgical end effector 1500 that comprises a first jaw 1600 and a second jaw 1800. In one arrangement, the first jaw comprises an elongate channel 1602 that is configured to operably support a surgical staple/fastener cartridge 1700 therein. The second jaw 1800 comprises an anvil 1810 that is pivotally supported relative to the elongate channel 1602. The interchangeable surgical tool assembly 1000 includes an articulation system 1300 that comprises an articulation joint 1302 and an articulation lock 1400 (FIGS. 4-6) which can be configured to releasably hold the surgical end effector 1500 in a desired articulated position relative to a shaft axis $SA_1$. Further details regarding the articulation system and articulation lock may be found in U.S. patent application Ser. No. 15/635,837, entitled SURGICAL INSTRUMENT COMPRISING AN ARTICULATION SYSTEM LOCKABLE TO A FRAME, filed on Jun. 28, 2017, now U.S. Patent Application Publication No. 2019/0000472, and hereby incorporated by reference herein in its entirety.

As can be further seen in FIGS. 4 and 7-9, the interchangeable surgical tool assembly 1000 includes a tool frame assembly 1200 that comprises a tool chassis 1210 that operably supports a nozzle assembly 1240 thereon. In one form, the nozzle assembly 1240 is comprised of nozzle portions 1242, 1244 as well as an actuator wheel portion 1246 that is configured to be coupled to the assembled nozzle portions 1242, 1244 by snaps, lugs, screws etc. The interchangeable surgical tool assembly 1000 includes a proximal closure assembly 1900 which is operably coupled to a distal closure assembly 2000 that is utilized to close and/or open the anvil 1810 of the surgical end effector 1500 as will be discussed in further detail below. In addition, the interchangeable surgical tool assembly 1000 includes a spine assembly 1250 that operably supports the proximal closure assembly 1900 and is coupled to the surgical end effector 1500. In various circumstances, for ease of assembly, the spine assembly 1250 may be fabricated from an upper spine segment 1251 and a lower spine segment 1252 that are interconnected together by snap features, adhesive, welding, etc. In assembled form, the spine assembly 1250 includes a proximal end 1253 that is rotatably supported in the tool chassis 1210. In one arrangement, for example, the proximal end 1253 of the spine assembly 1250 is attached to a spine bearing (not shown) that is configured to be supported within the tool chassis 1210. Such arrangement facilitates rotatable attachment of the spine assembly 1250 to the tool chassis 1210 such that the spine assembly 1250 may be selectively rotated about the shaft axis $SA_1$ relative to the tool chassis 1210. In particular, in one arrangement, for example, the proximal end 1253 of the spine assembly 1250 includes an upper lug seat 1254 (FIGS. 4, 5, 7, 8 and 10) and a lower lug seat (not shown) that are each configured to receive a corresponding nozzle lug 1245 extending inwardly from each of the nozzle portions 1242, 1244. Such arrangement facilitates rotation of the spine assembly 1250 about the shaft axis $SA_1$ by rotating the actuator wheel portion 1246 of the nozzle assembly 1240.

Figure 5:
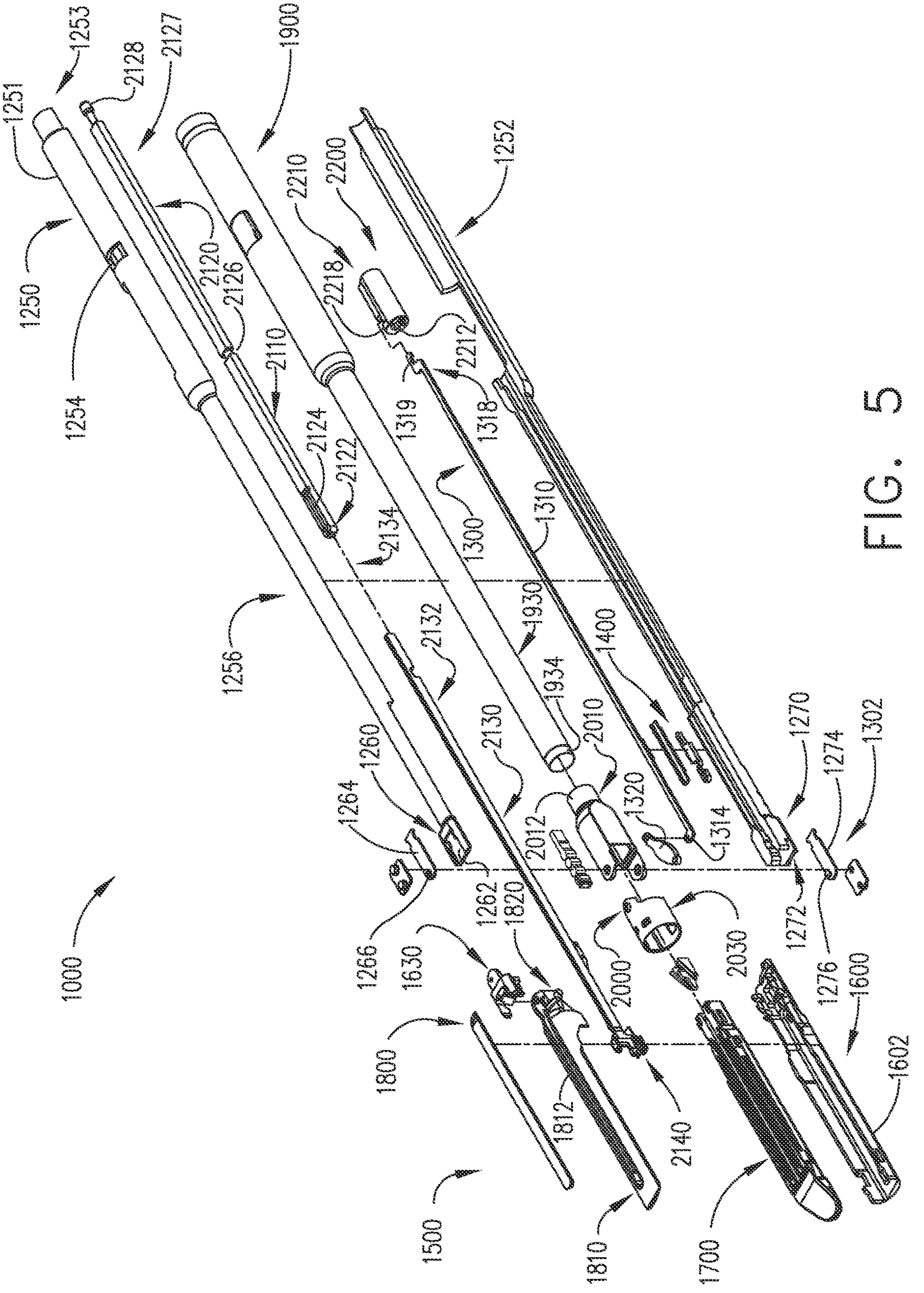
FIG. 5 is another exploded assembly view of a distal portion of the interchangeable surgical tool assembly of FIGS. 3 and 4.

As can be seen in FIGS. 4 and 5, spine assembly 1250 further includes an intermediate spine shaft segment 1256 that has a diameter that is less than the diameter of the proximal end 1253 of the spine assembly 1250. The intermediate spine shaft segment 1256 of the upper spine segment 1251 terminates in an upper lug mount feature 1260 and the intermediate spine shaft segment of the lower spine segment 1252 terminates in a lower lug mount feature 1270. As can be most particularly seen in FIG. 6, for example, the upper lug mount feature 1260 is formed with a lug slot 1262 therein that is adapted to mountingly support an upper mounting link 1264 therein. Similarly, the lower lug mount feature 1270 is formed with a lug slot 1272 therein that is adapted to mountingly support a lower mounting link 1274 therein. The upper mounting link 1264 includes a pivot socket 1266 therein that is offset from the shaft axis $SA_1$. The pivot socket 1266 is adapted to rotatably receive therein a pivot pin 1634 that is formed on a channel cap or anvil retainer 1630 that is attached to a proximal end portion 1610 of the elongate channel 1602. The lower mounting link 1274 includes lower pivot pin 1276 that adapted to be received within a pivot hole 1611 formed in the proximal end portion 1610 of the elongate channel 1602. See FIG. 6. The lower pivot pin 1276 as well as the pivot hole 1611 is offset from the shaft axis $SA_1$. The lower pivot pin 1276 is vertically aligned with the pivot socket 1266 to define an articulation axis $AA_1$ about which the surgical end effector 1500 may articulate relative to the shaft axis $SA_1$. Although the articulation axis $AA_1$ is transverse to the shaft axis $SA_1$, the articulation axis $AA_1$ is laterally offset therefrom and does not intersect the shaft axis $SA_1$.

Figure 6:
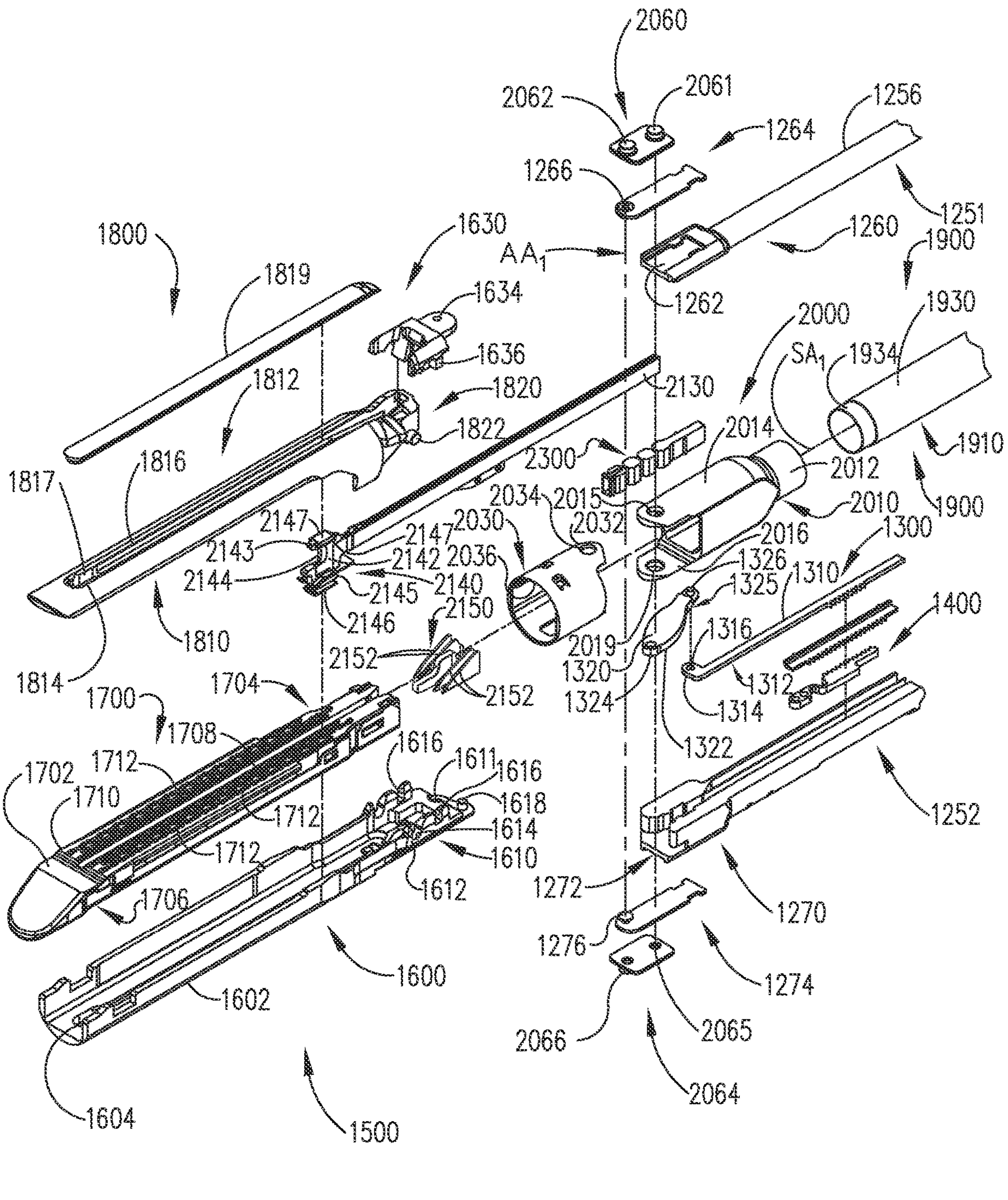
FIG. 6 is another exploded assembly view of a distal portion of the interchangeable surgical tool assembly of FIGS. 3-5.
Figure 15:
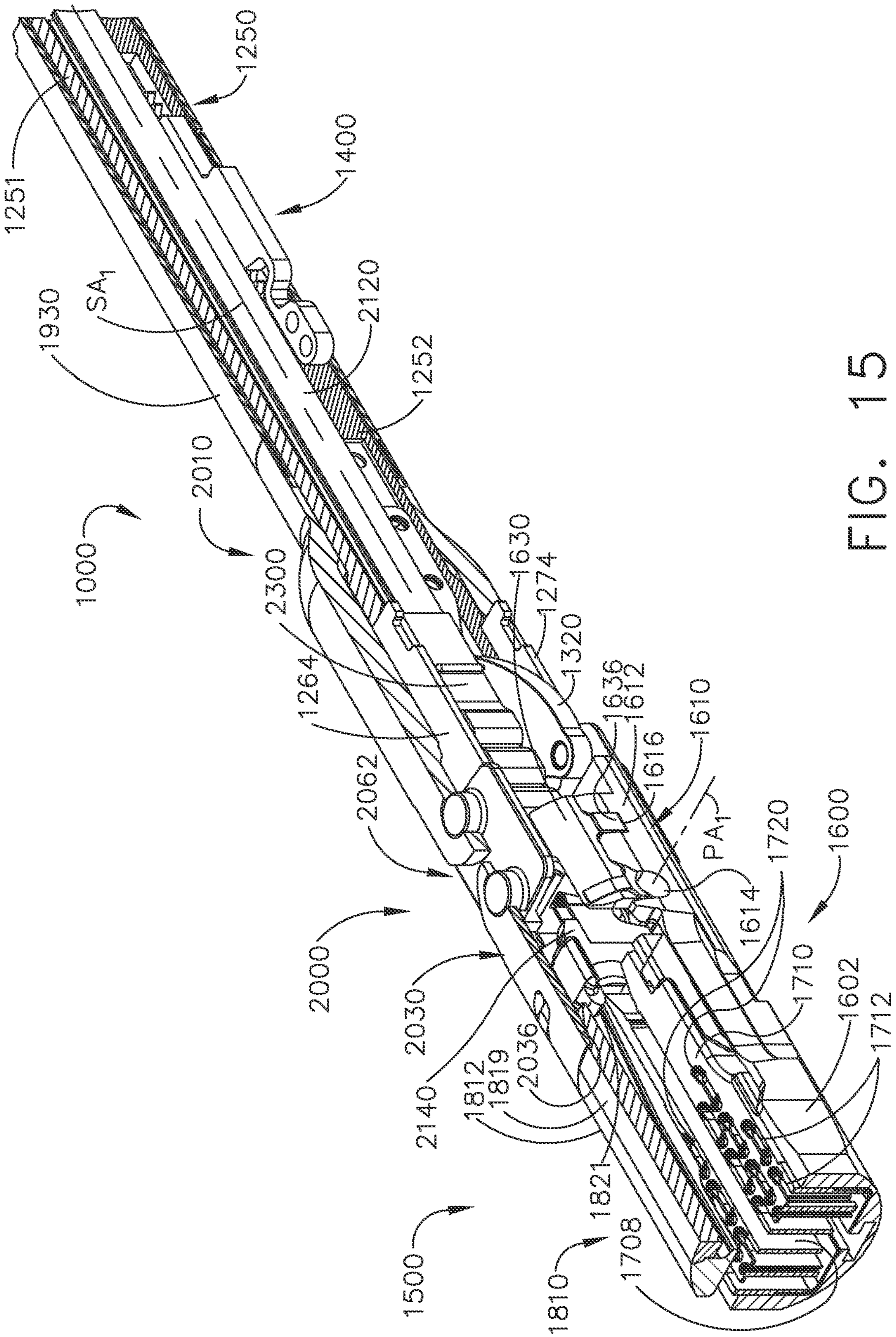
FIG. 15 is a cross-sectional perspective view of a distal portion of the interchangeable surgical tool assembly of FIGS. 3-14.

Referring now to FIGS. 6 and 15, the anvil 1810 in the illustrated example includes an anvil body 1812 that terminates in anvil mounting portion 1820. The anvil mounting portion 1820 is movably or pivotably supported on the elongate channel 1602 for selective pivotal travel relative thereto about a fixed anvil pivot axis $PA_1$ (FIG. 15) that is transverse to the shaft axis $SA_1$. In the illustrated arrangement, a pivot member or anvil trunnion 1822 extends laterally out of each lateral side of the anvil mounting portion 1820 to be received in a corresponding trunnion cradle 1614 formed in the upstanding walls 1612 of the proximal end portion 1610 of the elongate channel 1602. The anvil trunnions 1822 are pivotally retained in their corresponding trunnion cradle 1614 by the channel cap or anvil retainer 1630. The channel cap or anvil retainer 1630 includes a pair of attachment lugs 1636 that are configured to be retainingly received within corresponding lug grooves or notches 1616 formed in the upstanding walls 1612 of the proximal end portion 1610 of the elongate channel 1602.

In the illustrated example, the surgical end effector 1500 is selectively articulatable about the articulation axis $AA_1$ by the articulation system 1300. In one form, the articulation system 1300 includes proximal articulation driver 1310 that is pivotally coupled to an articulation link 1320. As can be most particularly seen in FIG. 6, an offset attachment lug 1314 is formed on a distal end 1312 of the proximal articulation driver 1310. A pivot hole 1316 is formed in the offset attachment lug 1314 and is configured to pivotally receive therein a proximal link pin 1326 formed on the proximal end 1325 of the articulation link 1320. A distal end 1322 of the articulation link 1320 includes a pivot hole 1324 that is configured to pivotally receive therein a channel pin 1618 formed on the proximal end portion 1610 of the elongate channel 1602. Thus, axial movement of proximal articulation driver 1310 will thereby apply articulation motions to the elongate channel 1602 to thereby cause the surgical end effector 1500 to articulate about the articulation axis $AA_1$ relative to the spine assembly 1250.

Figure 7:
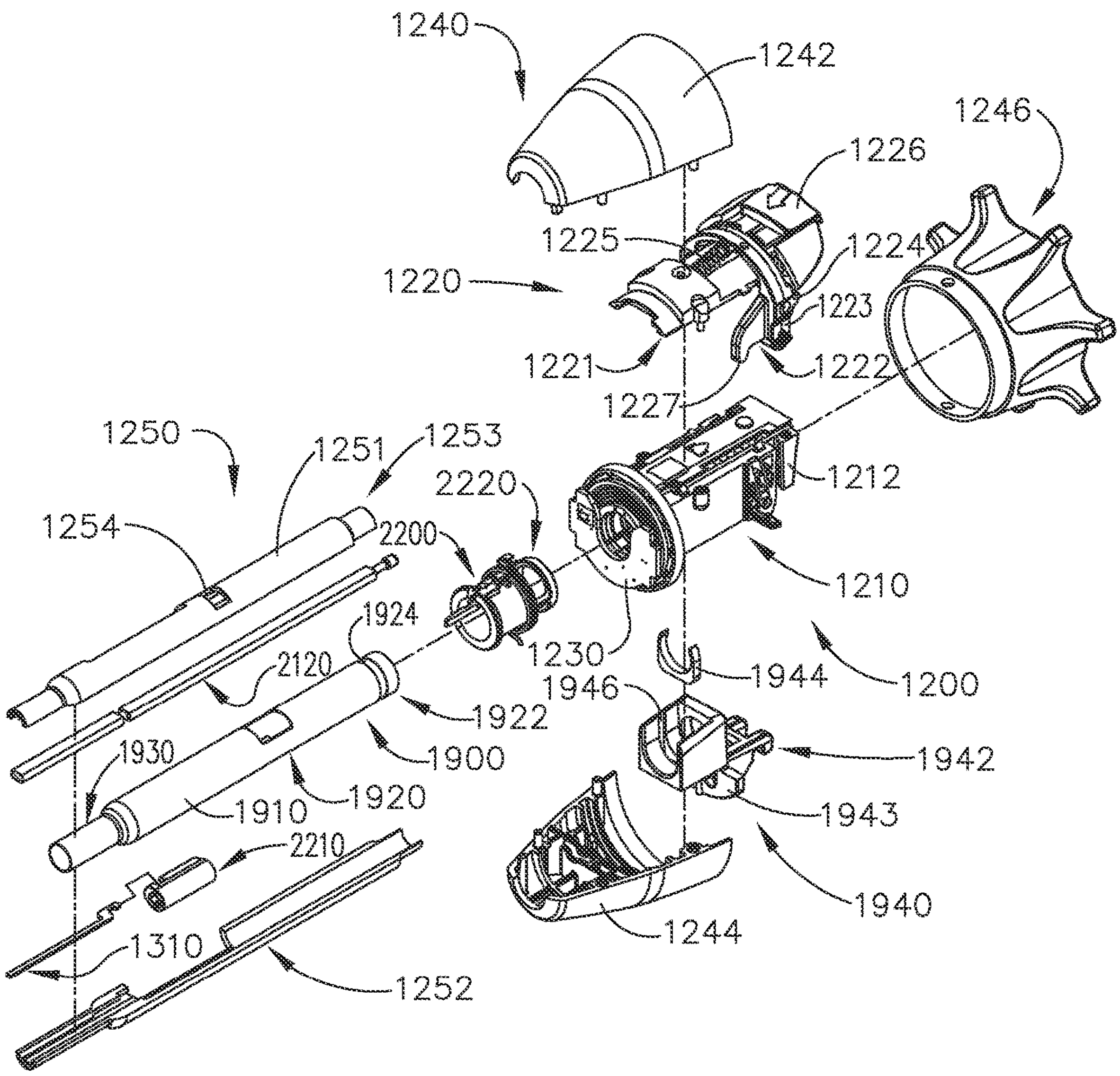
FIG. 7 is an exploded assembly view of a proximal portion of the interchangeable surgical tool assembly of FIGS. 3-6.
Figure 8:
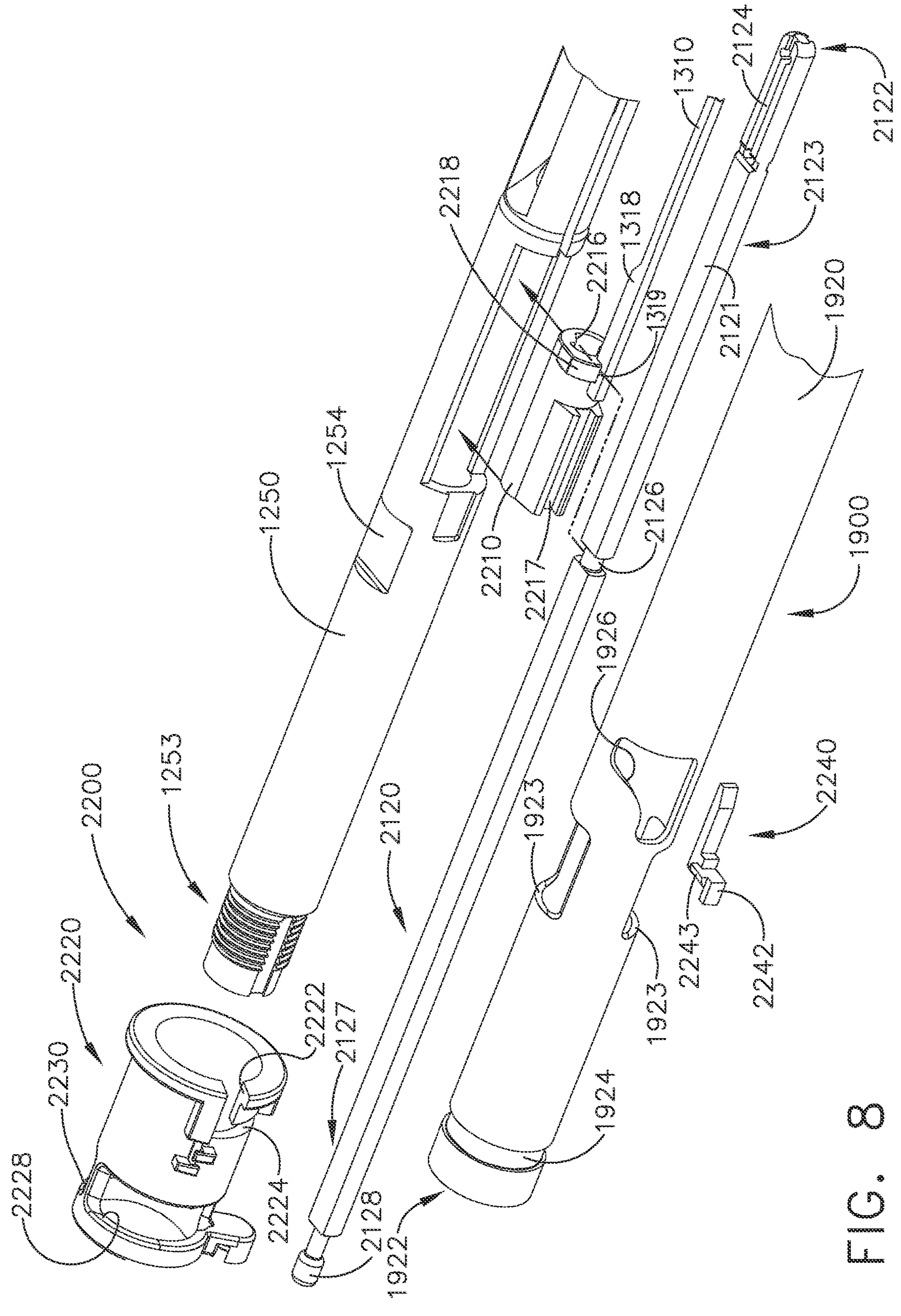
FIG. 8 is another exploded assembly view of a portion of the interchangeable surgical tool assembly of FIGS. 3-7.
Figure 9:
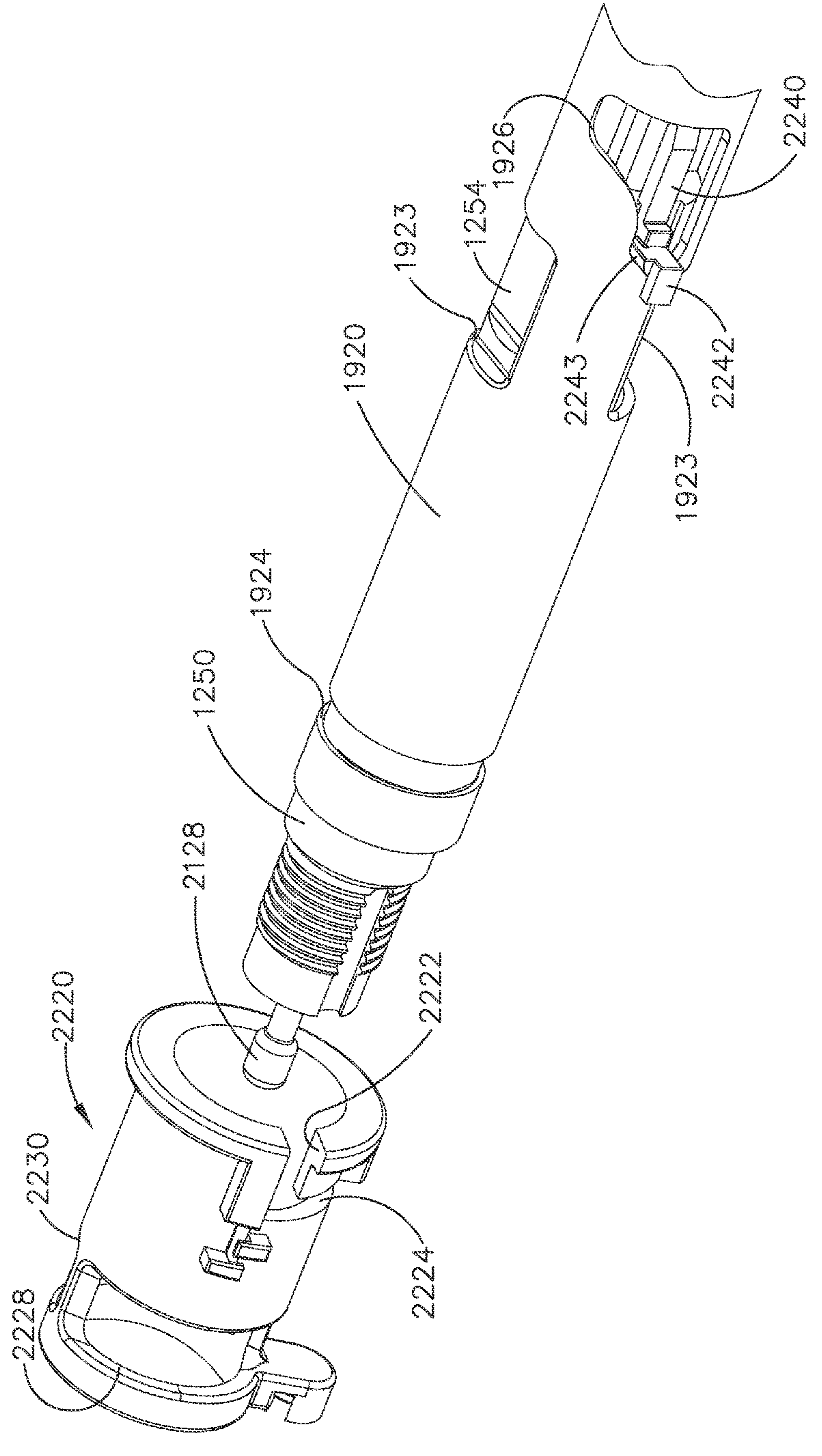
FIG. 9 is another exploded assembly view of a portion of the interchangeable surgical tool assembly of FIGS. 3-8.
Figure 10:
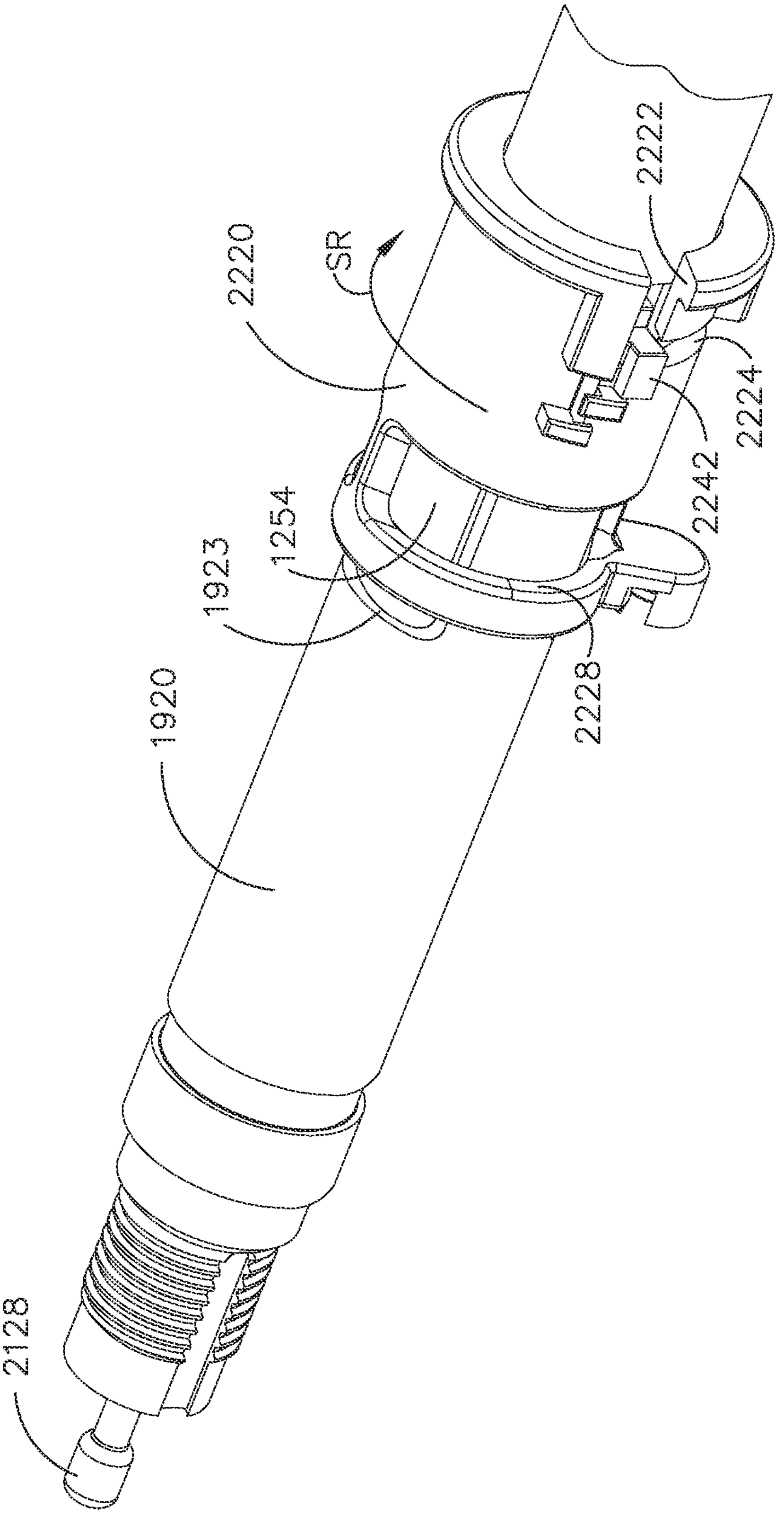
FIG. 10 is a perspective view of a proximal portion of the interchangeable surgical tool assembly of FIGS. 3-9.
Figure 11:
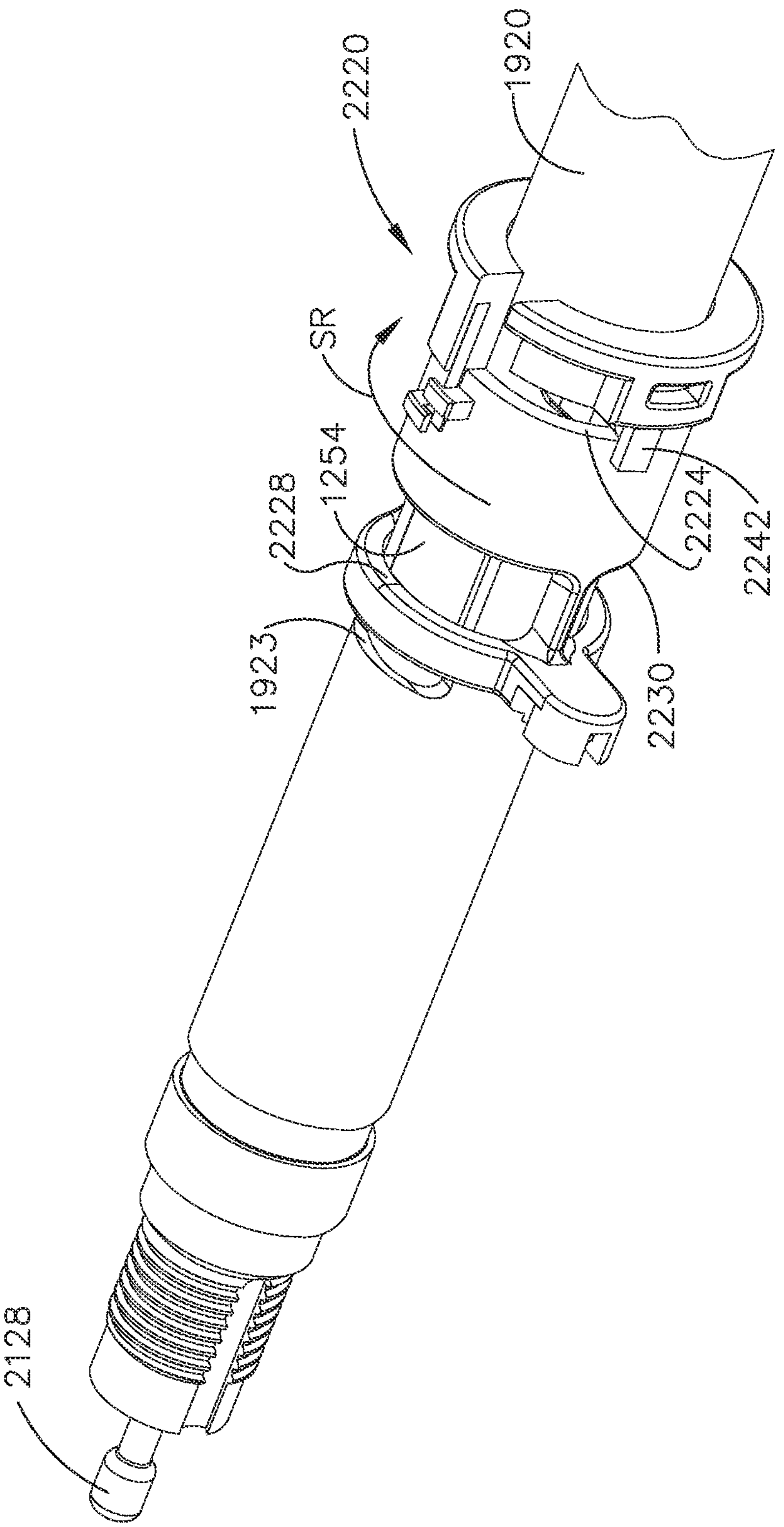
FIG. 11 is another perspective view of the proximal portion of the interchangeable surgical tool assembly of FIGS. 3-10.
Figure 12:
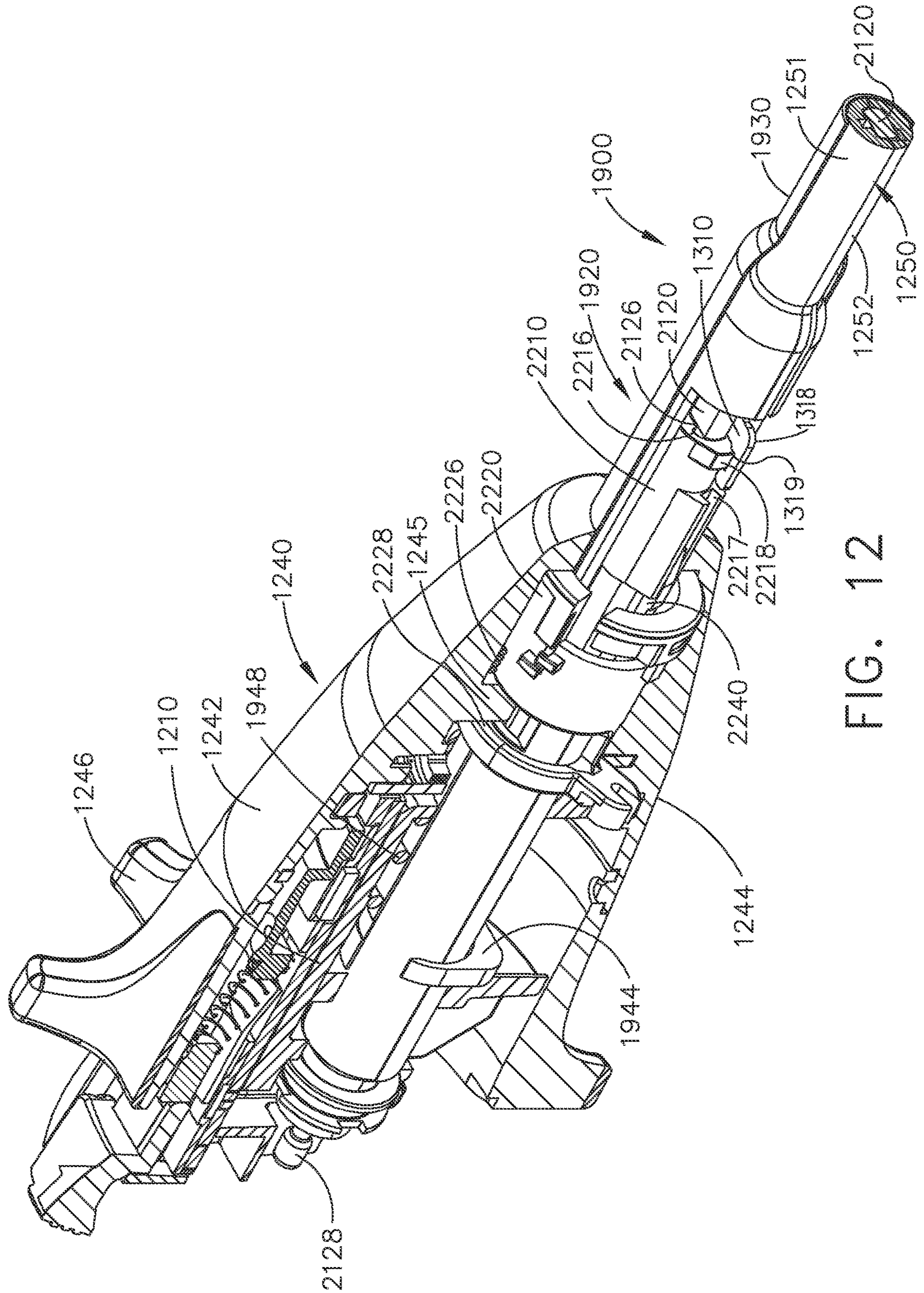
FIG. 12 is a cross-sectional perspective view of the proximal portion of the interchangeable surgical tool assembly of FIGS. 3-11.
Figure 13:
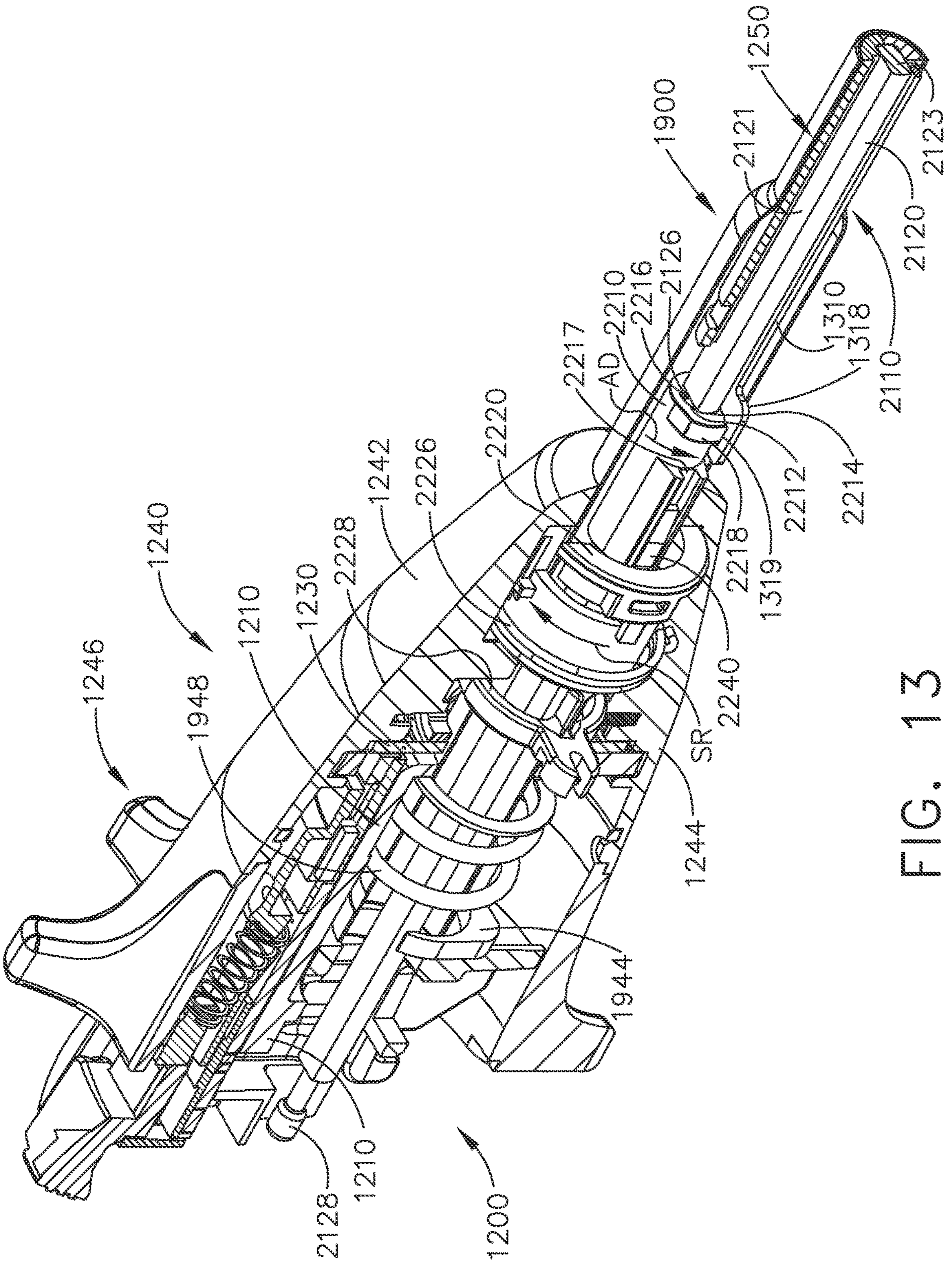
FIG. 13 is another cross-sectional perspective view of the proximal portion of the interchangeable surgical tool assembly of FIGS. 3-12.
Figure 14:
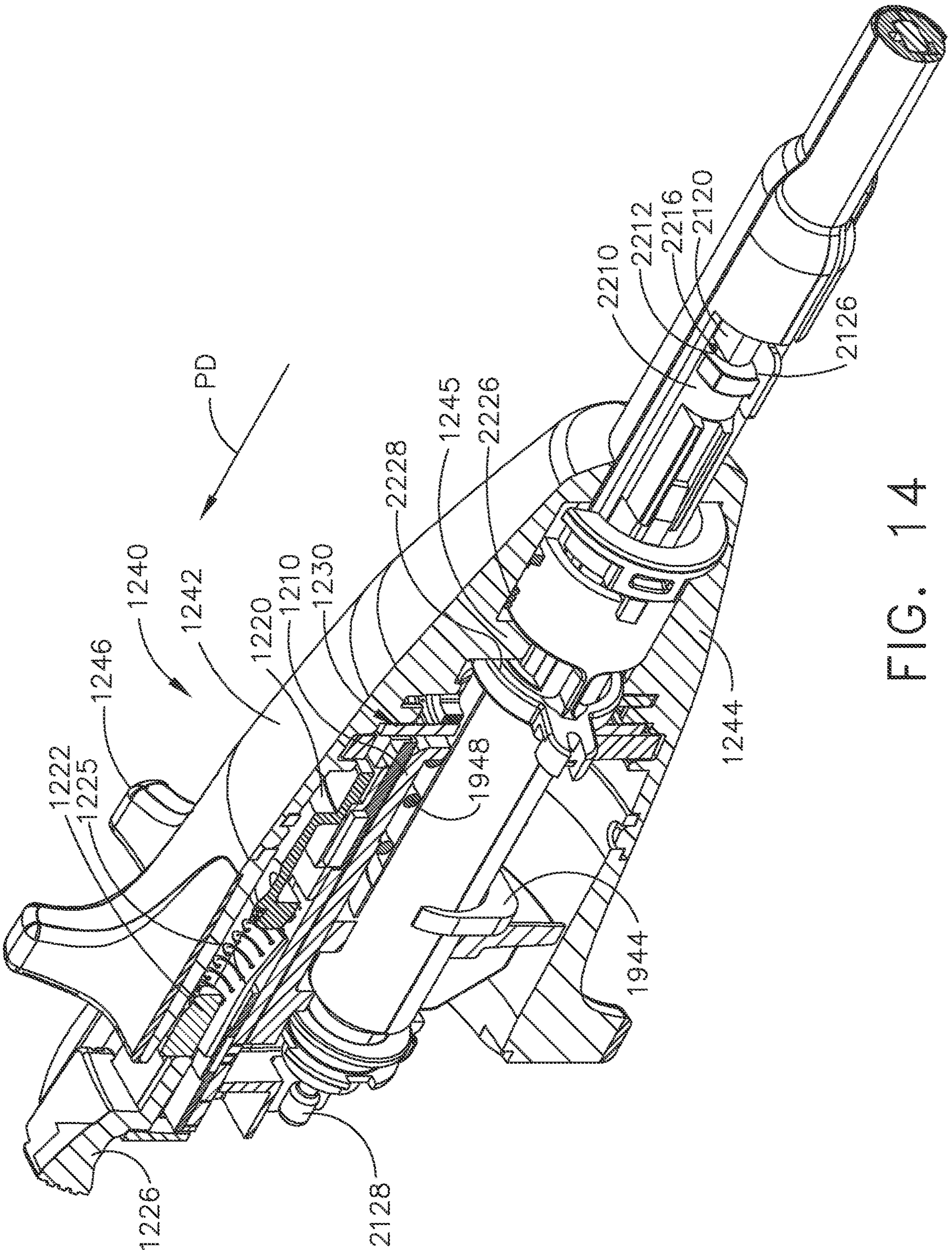
FIG. 14 is another cross-sectional perspective view of the proximal portion of the interchangeable surgical tool assembly of FIGS. 3-13.

Movement of the anvil 1810 relative to the elongate channel 1602 is effectuated by axial movement of the proximal closure assembly 1900 and the distal closure assembly 2000. Referring now to FIGS. 4 and 7, in the illustrated arrangement, the proximal closure assembly 1900 comprises a proximal closure tube 1910 that has a proximal closure tube portion 1920 and a distal portion 1930. The distal portion 1930 has a diameter that is less than the diameter of the proximal closure tube portion 1920. The proximal end 1922 of the proximal closure tube portion 1920 is rotatably supported in a closure shuttle 1940 that is slidably supported within the tool chassis 1210 such that it may be axially moved relative thereto. In one form, the closure shuttle 1940 includes a pair of proximally-protruding hooks 1942 that are configured for attachment to the attachment pin 516 that is attached to the closure linkage assembly 514 of the handle assembly 500. The proximal end 1922 of the proximal closure tube portion 1920 is coupled to the closure shuttle 1940 for relative rotation thereto. For example, a U-shaped connector 1944 is inserted into an annular slot 1924 in the proximal closure tube portion 1920 and is retained within vertical slots 1946 in the closure shuttle 1940. Such arrangement serves to attach the proximal closure assembly 1900 to the closure shuttle 1940 for axial travel therewith while enabling the proximal closure assembly 1900 to rotate relative to the closure shuttle 1940 about the shaft axis $SA_1$. A closure spring 1948 (FIGS. 12-14) extends over the proximal closure tube portion 1920 to bias the closure shuttle 1940 in the proximal direction PD which can serve to pivot the closure trigger 512 on the handle assembly 500 (FIG. 2) into the unactuated position when the interchangeable surgical tool assembly 1000 is operably coupled to the handle assembly 500.

Referring now to FIGS. 5 and 6, a distal portion 1930 of the proximal closure tube 1910 is attached to the distal closure assembly 2000. In the illustrated arrangement for example, the distal closure assembly 2000 includes an articulation connector 2010 that is coupled to a distal closure tube segment 2030. In the illustrated example, the distal closure tube segment 2030 has a diameter that is larger than the diameter of the distal portion 1930 of the proximal closure tube 1910. The articulation connector 2010 has a proximally extending end portion 2012 that is adapted to be received on a connection flange 1934 formed on the distal end of the distal portion 1930. The articulation connector 2010 may be retained on the connection flange 1934 by an appropriate fastener arrangement such as adhesive, welding, etc. The articulation connector 2010 includes upper and lower tangs 2014, 2016 protrude distally from a distal end of the articulation connector 2010 to be movably coupled to an end effector closure sleeve or distal closure tube segment 2030. The distal closure tube segment 2030 includes an upper tang 2032 and a lower tang (not shown) that protrude proximally from a proximal end thereof. An upper double pivot link 2060 includes proximal and distal pins 2061, 2062 that engage corresponding holes 2015, 2034 in the upper tangs 2014, 2032 of the articulation connector 2010 and distal closure tube segment 2030, respectively. Similarly, a lower double pivot link 2064 includes proximal and distal pins 2065, 2066 that engage corresponding holes 2019 in the lower tangs 2016 of the articulation connector 2010 and distal closure tube segment 2030, respectively. As will be discussed in further detail below, distal and proximal axial translation of the proximal closure assembly 1900 and distal closure assembly 2000 will result in the closing and opening of the anvil 1810 relative to the elongate channel 1602.

In at least one arrangement, the interchangeable surgical tool assembly 1000 further includes a firing system generally designated as 2100. In the illustrated example, the firing system 2100 includes a firing member assembly 2110 that is supported for axial travel within the spine assembly 1250. In the illustrated embodiment, the firing member assembly 2110 includes an intermediate firing shaft portion 2120 that is configured for attachment to a distal cutting portion or knife bar 2130. The firing member assembly 2110 may also be referred to herein as a "second shaft" and/or a "second shaft assembly". As can be seen in FIG. 5, the intermediate firing shaft portion 2120 may include a longitudinal slot 2124 in a distal end 2122 thereof which can be configured to receive a proximal end 2132 of the knife bar 2130. The longitudinal slot 2124 and the proximal end 2132 of the knife bar 2130 can be sized and configured to permit relative movement therebetween and can comprise a slip joint 2134. The slip joint 2134 can permit the intermediate firing shaft portion 2120 of the firing member assembly 2110 to be moved to articulate the end effector 1500 without moving, or at least substantially moving, the knife bar 2130. Once the end effector 1500 has been suitably oriented, the intermediate firing shaft portion 2120 can be advanced distally until a proximal sidewall of the longitudinal slot 2124 comes into contact with a portion of the knife bar 2130 to advance the knife bar 2130 and fire the surgical staple/fastener cartridge 1700 positioned within the elongate channel 1602. In the illustrated arrangement, a proximal end 2127 of the intermediate firing shaft portion 2120 has a firing shaft attachment lug 2128 formed thereon (FIG. 8) that is configured to be seated into an attachment cradle (not shown) that is on the distal end of the longitudinally movable drive member (not shown) of the firing drive system 530 within the handle assembly 500. Such arrangement facilitates the axial movement of the intermediate firing shaft portion 2120 upon actuation of the firing drive system 530.

Further to the above, the interchangeable tool assembly 1000 can include a shifter assembly 2200 which can be configured to selectively and releasably couple the proximal articulation driver 1310 to the firing system 2100. In one form, the shifter assembly 2200 includes a lock collar, or lock sleeve 2210, positioned around the intermediate firing shaft portion 2120 of the firing system 2100 wherein the lock sleeve 2210 can be rotated between an engaged position in which the lock sleeve 2210 couples the proximal articulation driver 1310 to the firing member assembly 2110 and a disengaged position in which the proximal articulation driver 1310 is not operably coupled to the firing member assembly 2110. When lock sleeve 2210 is in its engaged position, distal movement of the firing member assembly 2110 can move the proximal articulation driver 1310 distally and, correspondingly, proximal movement of the firing member assembly 2110 can move the proximal articulation driver 1310 proximally. When lock sleeve 2210 is in its disengaged position, movement of the firing member assembly 2110 is not transmitted to the proximal articulation driver 1310 and, as a result, the firing member assembly 2110 can move independently of the proximal articulation driver 1310. In various circumstances, the proximal articulation driver 1310 can be held in position by the articulation lock 1400 when the proximal articulation driver 1310 is not being moved in the proximal or distal directions by the firing member assembly 2110.

In the illustrated arrangement, the intermediate firing shaft portion 2120 of the firing member assembly 2110 is formed with two opposed flat sides 2121, 2123 with a drive notch 2126 formed therein. See FIG. 8. As can also be seen in FIG. 13, the lock sleeve 2210 comprises a cylindrical, or an at least substantially cylindrical, body that includes a longitudinal aperture 2212 that is configured to receive the intermediate firing shaft portion 2120 therethrough. The lock sleeve 2210 can comprise diametrically-opposed, inwardly-facing lock protrusions 2214, 2216 that, when the lock sleeve 2210 is in one position, are engagingly received within corresponding portions of the drive notch 2126 in the intermediate firing shaft portion 2120 and, when in another position, are not received within the drive notch 2126 to thereby permit relative axial motion between the lock sleeve 2210 and the intermediate firing shaft portion 2120.

Referring now to FIGS. 8 and 12-14, in the illustrated example, the lock sleeve 2210 further includes a lock member 2218 that is sized to be movably received within a notch 1319 in a proximal end 1318 of the proximal articulation driver 1310. Such arrangement permits the lock sleeve 2210 to slightly rotate into and out of engagement with the intermediate firing shaft portion 2120 while remaining in engagement with the notch 1319 in the proximal articulation driver 1310. For example, when the lock sleeve 2210 is in its engaged position, the lock protrusions 2214, 2216 are positioned within the drive notch 2126 in the intermediate firing shaft portion 2120 such that a distal pushing force and/or a proximal pulling force can be transmitted from the firing member assembly 2110 to the lock sleeve 2210. Such axial pushing or pulling motion is then transmitted from the lock sleeve 2210 to the proximal articulation driver 1310 to thereby articulate the surgical end effector 1500. In effect, the firing member assembly 2110, the lock sleeve 2210, and the proximal articulation driver 1310 will move together when the lock sleeve 2210 is in its engaged (articulation) position. On the other hand, when the lock sleeve 2210 is in its disengaged position, the lock protrusions 2214, 2216 are not received within the drive notch 2126 in the intermediate firing shaft portion 2120 and, as a result, a distal pushing force and/or a proximal pulling force may not be transmitted from the firing member assembly 2110 to the lock sleeve 2210 (and the proximal articulation driver 1310).

In the illustrated example, relative movement of the lock sleeve 2210 between its engaged and disengaged positions may be controlled by a shifter assembly 2200 that is interfaces with the proximal closure tube 1910 of the proximal closure assembly 1900. More specifically and with reference to FIGS. 8 and 9, the shifter assembly 2200 further includes a shifter key 2240 that is configured to be slidably received within a key groove 2217 formed in the outer perimeter of the lock sleeve 2210. Such arrangement enables the shifter key 2240 to move axially with respect to the lock sleeve 2210. Referring to FIGS. 8-11, the shifter key 2240 includes an actuator lug 2242 that extends through a cam slot or cam opening 1926 in the proximal closure tube portion 1920. See FIG. 9. A cam surface 2243 is also provided adjacent the actuator lug 2242 which is configured to cammingly interact with the cam opening 1926 so as to cause the shifter key 2240 to rotate in response to axial motion of the proximal closure tube portion 1920.

Also in the illustrated example, the shifter assembly 2200 further includes a switch drum 2220 that is rotatably received on a proximal end portion of the proximal closure tube portion 1920. As can be seen in FIGS. 10-14, the actuator lug 2242 extends through an axial slot segment 2222 in the switch drum 2220 and is movably received within an arcuate slot segment 2224 in the switch drum 2220. A switch drum torsion spring 2226 (FIGS. 12-14) is mounted on the switch drum 2220 and engages nozzle portion 1244 to apply a torsional bias or rotation (arrow SR in FIGS. 10 and 11) which serves to rotate the switch drum 2220 until the actuator lug 2242 reaches the end of the arcuate slot segment 2224. See FIGS. 11 and 12. When in this position, the switch drum 2220 may provide a torsional bias to the shifter key 2240 which thereby causes the lock sleeve 2210 to rotate into its engaged position with the intermediate firing shaft portion 2120. This position also corresponds to the unactuated configuration of the proximal closure assembly 1900. In one arrangement, for example, when the proximal closure assembly 1900 is in an unactuated configuration (anvil 1810 is in an open position spaced away from the surgical staple/fastener cartridge 1700) the actuator lug 2242 is located in the upper portion of the cam opening 1926 in the proximal closure tube portion 1920. When in that position, actuation of the intermediate firing shaft portion 2120 will result in the axial movement of the proximal articulation driver 1310. Once the user has articulated the surgical end effector 1500 to a desired orientation, the user may then actuate the proximal closure assembly 1900. Actuation of the proximal closure assembly 1900 will result in the distal travel of the proximal closure tube portion 1920 to ultimately apply a closing motion to the anvil 1810. This distal travel of the proximal closure tube portion 1920 will result in the cam opening 1926 cammingly interacting with the cam surface 2243 on the actuator lug 2242 to thereby cause the shifter key 2240 to rotate the lock sleeve 2210 in an actuation direction AD. Such rotation of the lock sleeve 2210 will result in the disengagement of the lock protrusions 2214, 2216 from the drive notch 2126 in the intermediate firing shaft portion 2120. When in such configuration, the firing drive system 530 may be actuated to actuate the intermediate firing shaft portion 2120 without actuating the proximal articulation driver 1310. Further details concerning the operation of the switch drum 2220 and lock sleeve 2210, as well as alternative articulation and firing drive arrangements that may be employed with the various interchangeable surgical tool assemblies described herein, may be found in U.S. patent application Ser. No. 13/803,086, now U.S. Patent Application Publication No. 2014/0263541, and U.S. patent application Ser. No. 15/019,196, now U.S. Pat. No. 10,413,291, the entire disclosures of which are hereby incorporated by reference herein.

Referring again to FIGS. 8-13, the switch drum 2220 can further comprise at least partially circumferential openings 2228, 2230 defined therein which can receive circumferential lugs/mounts 1245 that extend from the nozzle portions 1242, 1244 and permit relative rotation, but not translation, between the switch drum 2220 and the nozzle assembly 1240. The nozzle lugs 1245 extend through corresponding openings 1923 in the proximal closure tube portion 1920 to be seated in lug seats 1254 in the spine assembly 1250. See FIGS. 8 and 9. Such arrangement enables the user to rotate the spine assembly 1250 about the shaft axis by rotating the nozzle assembly 1240.

As also illustrated in FIGS. 7 and 12-14, the interchangeable tool assembly 1000 can comprise a slip ring assembly 1230 which can be configured to conduct electrical power to and/or from the surgical end effector 1500 and/or communicate signals to and/or from the surgical end effector 1500, back to a microprocessor 560 (FIG. 2) in the handle assembly 500 or robotic system controller, for example. Further details concerning the slip ring assembly 1230 and associated connectors may be found in U.S. patent application Ser. No. 13/803,086, now U.S. Patent Application Publication No. 2014/0263541, and U.S. patent application Ser. No. 15/019,196, now U.S. Pat. No. 10,413,291, which have each been herein incorporated by reference in their respective entirety as well as in U.S. patent application Ser. No. 13/800,067, entitled STAPLE CARTRIDGE TISSUE THICKNESS SENSOR SYSTEM, now U.S.

Patent Application Publication No. 2014/0263552, which is hereby incorporated by reference herein in its entirety. As also described in further detail in the aforementioned patent applications that have been incorporated by reference herein, the interchangeable surgical tool assembly 1000 can also comprise at least one sensor that is configured to detect the position of the switch drum 2220.

Referring again to FIG. 2, the tool chassis 1210 includes at least one, and preferably two, tapered attachment portions 1212 formed thereon that are adapted to be received within corresponding dovetail slots 507 formed within the distal end portion of the handle frame 506 of the handle assembly 500. Various interchangeable surgical tool assemblies employ a latch system 1220 for removably coupling the interchangeable surgical tool assembly 1000 to the handle frame 506 of the handle assembly 500. As can be seen in FIG. 7, for example, in at least one form, the latch system 1220 includes a lock member or lock yoke 1222 that is movably coupled to the tool chassis 1210. In the illustrated embodiment, for example, the lock yoke 1222 has a U-shape with two spaced downwardly extending legs 1223. The legs 1223 each have a pivot lug (not shown) formed thereon that are adapted to be received in corresponding holes formed in the tool chassis 1210. Such arrangement facilitates pivotal attachment of the lock yoke 1222 to the tool chassis 1210. The lock yoke 1222 may include two proximally protruding lock lugs 1224 that are configured for releasable engagement with corresponding lock detents or grooves 509 in the distal end of the handle frame 506 of the handle assembly 500. See FIG. 2. In various forms, the lock yoke 1222 is biased in the proximal direction by a spring or biasing member 1225. Actuation of the lock yoke 1222 may be accomplished by a latch button 1226 that is slidably mounted on a latch actuator assembly 1221 that is mounted to the tool chassis 1210. The latch button 1226 may be biased in a proximal direction relative to the lock yoke 1222. The lock yoke 1222 may be moved to an unlocked position by biasing the latch button 1226 in the distal direction which also causes the lock yoke 1222 to pivot out of retaining engagement with the distal end of the handle frame 506. When the lock yoke 1222 is in “retaining engagement” with the distal end of the handle frame 506, the lock lugs 1224 are retainingly seated within the corresponding lock detents or grooves 509 in the distal end of the handle frame 506.

In the illustrated arrangement, the lock yoke 1222 includes at least one and preferably two lock hooks 1227 that are adapted to contact corresponding lock lug portions 1943 that are formed on the closure shuttle 1940. When the closure shuttle 1940 is in an unactuated position, the lock yoke 1222 may be pivoted in a distal direction to unlock the interchangeable surgical tool assembly 1000 from the handle assembly 500. When in that position, the lock hooks 1227 do not contact the lock lug portions 1943 on the closure shuttle 1940. However, when the closure shuttle 1940 is moved to an actuated position, the lock yoke 1222 is prevented from being pivoted to an unlocked position. Stated another way, if the clinician were to attempt to pivot the lock yoke 1222 to an unlocked position or, for example, the lock yoke 1222 was inadvertently bumped or contacted in a manner that might otherwise cause it to pivot distally, the lock hooks 1227 on the lock yoke 1222 will contact the lock lug portions 1943 on the closure shuttle 1940 and prevent movement of the lock yoke 1222 to an unlocked position.

Referring again to FIG. 6, the knife bar 2130 may comprise a laminated beam structure that includes at least two beam layers. Such beam layers may comprise, for example, stainless steel bands that are interconnected by, for example, welding or pinning together at their proximal ends and/or at other locations along their length. In alternative embodiments, the distal ends of the bands are not connected together to allow the laminates or bands to splay relative to each other when the end effector is articulated. Such arrangement permits the knife bar 2130 to be sufficiently flexible to accommodate articulation of the end effector. Various laminated knife bar arrangements are disclosed in U.S. patent application Ser. No. 15/019,245, entitled SURGICAL INSTRUMENTS WITH CLOSURE STROKE REDUCTION ARRANGEMENTS, now U.S. Pat. No. 10,470,764, which is hereby incorporated by reference in its entirety. As can also be seen in FIG. 6, a firing shaft support assembly 2300 is employed to provide lateral support to the knife bar 2130 as it flexes to accommodate articulation of the surgical end effector 1500. Further details concerning the operation of the firing shaft support assembly 2300 and alternative knife bar support arrangements may be found in U.S. patent application Ser. No. 15/019,245, entitled SURGICAL INSTRUMENTS WITH CLOSURE STROKE REDUCTION ARRANGEMENTS, now U.S. Pat. No. 10,470,764, and U.S. patent application Ser. No. 15/019,220, entitled SURGICAL INSTRUMENT WITH ARTICULATING AND AXIALLY TRANSLATABLE END EFFECTOR, now U.S. Pat. No. 10,245,029, which are each hereby incorporated by reference herein in their respective entireties.

As can also be seen in FIG. 6, a firing member or knife member 2140 is attached to the distal end of the knife bar 2130. In one exemplary form, the firing member 2140 comprises a body portion 2142 that supports a knife or tissue cutting portion 2144. The body portion 2142 protrudes through an elongate slot 1604 in the elongate channel 1602 and terminates in a foot member 2146 that extends laterally on each side of the body portion 2142. As the firing member 2140 is driven distally through the surgical staple/fastener cartridge 1700, the foot member 2146 rides within a passage 1622 (FIG. 48) in the elongate channel 1602 that is located under the surgical staple/fastener cartridge 1700. In one arrangement, the body portion 2142 includes two laterally protruding central tabs 2145 that may ride above the central passage within the surgical staple/fastener cartridge 1700. See FIG. 6. The tissue cutting portion 2144 is disposed between a distally protruding top nose portion 2143. As can be further seen in FIG. 6, the firing member 2140 may further include two laterally extending top tabs, pins or anvil engagement features 2147. As the firing member 2140 is driven distally, a top portion of the body portion 2142 extends through a centrally disposed anvil slot 1814 and the anvil engagement features 2147 ride on corresponding anvil ledges 1816 formed on each side of the anvil slot 1814. In one arrangement, to facilitate assembly of the anvil 1810 and firing member 2140 arrangement, the top of the anvil body 1812 has an opening 1817 therein. Once the anvil 1810 is assembled onto the elongate channel 1602 and the firing member 2140 is installed, the opening 1817 is covered by an anvil cap 1819 that is affixed to the anvil body 1812 by welding or other suitable fastening means.

Returning to FIG. 6, the firing member 2140 is configured to operably interface with a sled assembly 2150 that is operably supported within a body 1702 of the surgical staple/fastener cartridge 1700. The sled assembly 2150 is slidably displaceable within the surgical staple/fastener cartridge body 1702 from a proximal starting position adjacent the proximal end 1704 of the cartridge body 1702 to an ending position adjacent a distal end 1706 of the cartridge body 1702. The cartridge body 1702 operably supports therein a plurality of staple drivers (not shown) that are aligned in rows on each side of a centrally disposed slot 1708. The centrally disposed slot 1708 enables the firing member 2140 to pass therethrough and cut the tissue that is clamped between the anvil 1810 and the surgical staple/fastener cartridge 1700. The drivers are associated with corresponding staple/fastener pockets 1712 that open through an upper deck surface 1710 of the cartridge body 1702. Each of the staple drivers supports one or more surgical staple/fastener or fastener (not shown) thereon. The sled assembly 2150 includes a plurality of sloped or wedge-shaped cams 2152 wherein each cam 2152 corresponds to a particular line of fasteners or drivers located on a side of the slot 1708.

Attachment of the interchangeable surgical tool assembly 1000 to the handle assembly 500 will now be described with reference to FIG. 2. To commence the coupling process, the clinician may position the tool chassis 1210 of the interchangeable surgical tool assembly 1000 above or adjacent to the distal end of the handle frame 506 such that the tapered attachment portions 1212 formed on the tool chassis 1210 are aligned with the dovetail slots 507 in the handle frame 506. The clinician may then move the surgical tool assembly 1000 along an installation axis IA that is perpendicular to the shaft axis $SA_1$ to seat the tapered attachment portions 1212 in "operable engagement" with the corresponding dovetail receiving slots 507 in the distal end of the handle frame 506. In doing so, the firing shaft attachment lug 2128 on the intermediate firing shaft portion 2120 will also be seated in the attachment cradle (not shown) in the longitudinally movable drive member (not shown) within the handle assembly 500 and the portions of attachment pin 516 on the closure link 514 will be seated in the corresponding hooks 1942 in the closure shuttle 1940. As used herein, the term "operable engagement" in the context of two components means that the two components are sufficiently engaged with each other so that upon application of an actuation motion thereto, the components may carry out their intended action, function and/or procedure.

During a typical surgical procedure, the clinician may introduce the surgical end effector 1500 into the surgical site through a trocar or other opening in the patient to access the target tissue. When doing so, the clinician typically axially aligns the surgical end effector 1500 along the shaft axis (unarticulated state). Once the surgical end effector 1500 has passed through the trocar port, for example, the clinician may need to articulate the end effector 1500 to advantageously position it adjacent the target tissue. This is prior to closing the anvil onto the target tissue, so the closure drive system 510 would remain unactuated. When in this position, actuation of the firing drive system 530 will result in the application of articulation motions to the proximal articulation driver 1310. Once the end effector has attained the desired articulated position, the firing drive system 530 is deactivated and the articulation lock 1400 may retain the surgical end effector 1500 in the articulated position. The clinician may then actuate the closure drive system 510 to close the anvil 1810 onto the target tissue. Such actuation of the closure drive system 510 may also result in the shifter assembly 2200 delinking the proximal articulation driver from the intermediate firing shaft portion 2120. Thus, once the target tissue has been captured in the surgical end effector 1500, the clinician may once again actuate the firing drive system 530 to axially advance the firing member 2140 through the surgical staple/fastener cartridge 1700 to cut the clamped tissue and fire the staples into the cut tissue. Other closure and firing drive arrangements, actuator arrangements (both handheld, manual and automated or robotic) may also be employed to control the axial movement of the closure system components, the articulation system components and/or the firing system components of the surgical tool assembly 1000 without departing from the spirit and scope of the various inventions disclosed herein.

Figure 16:
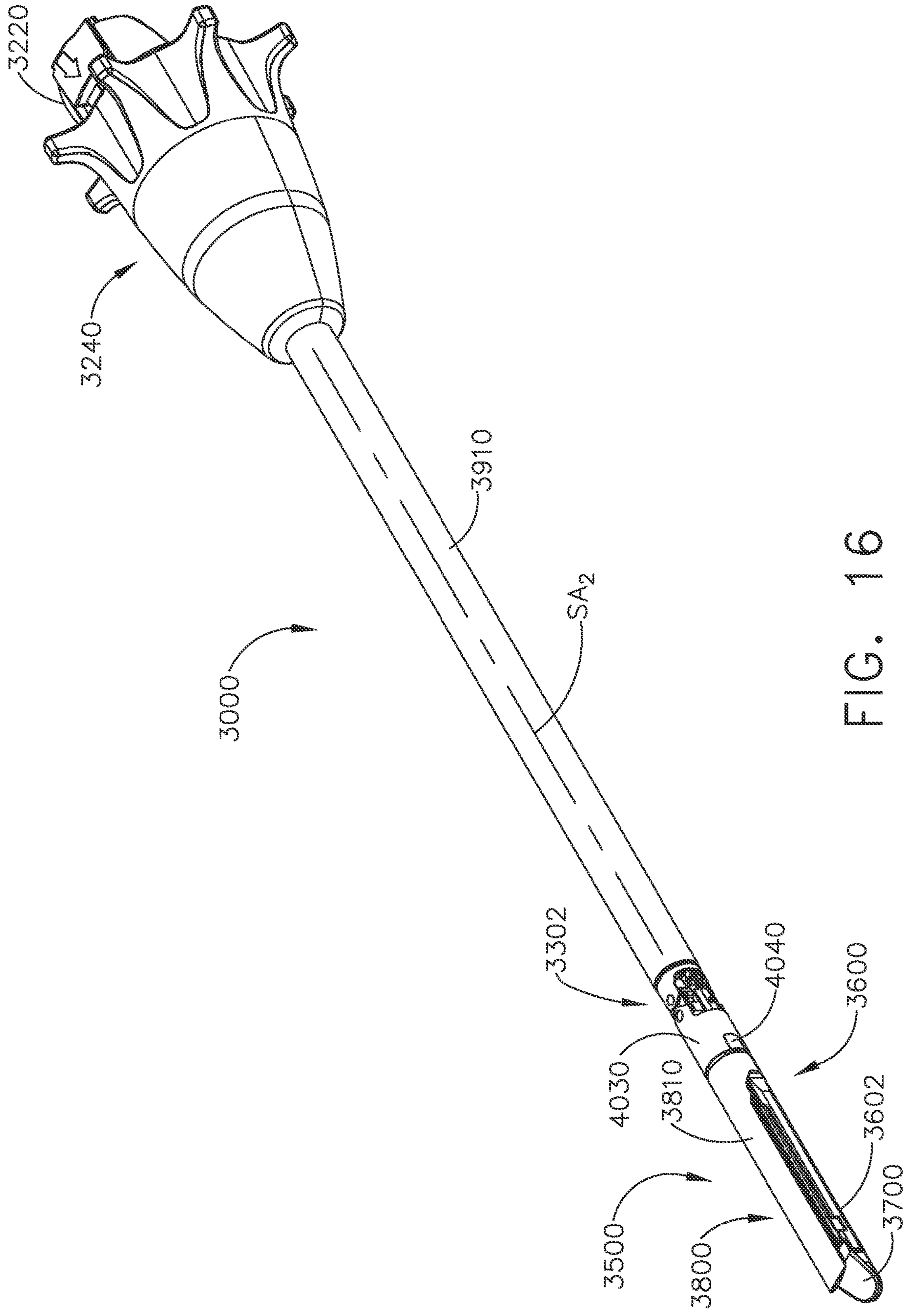
FIG. 16 is a perspective view of another one of the interchangeable surgical tool assemblies depicted in FIG. 1.
Figure 17:
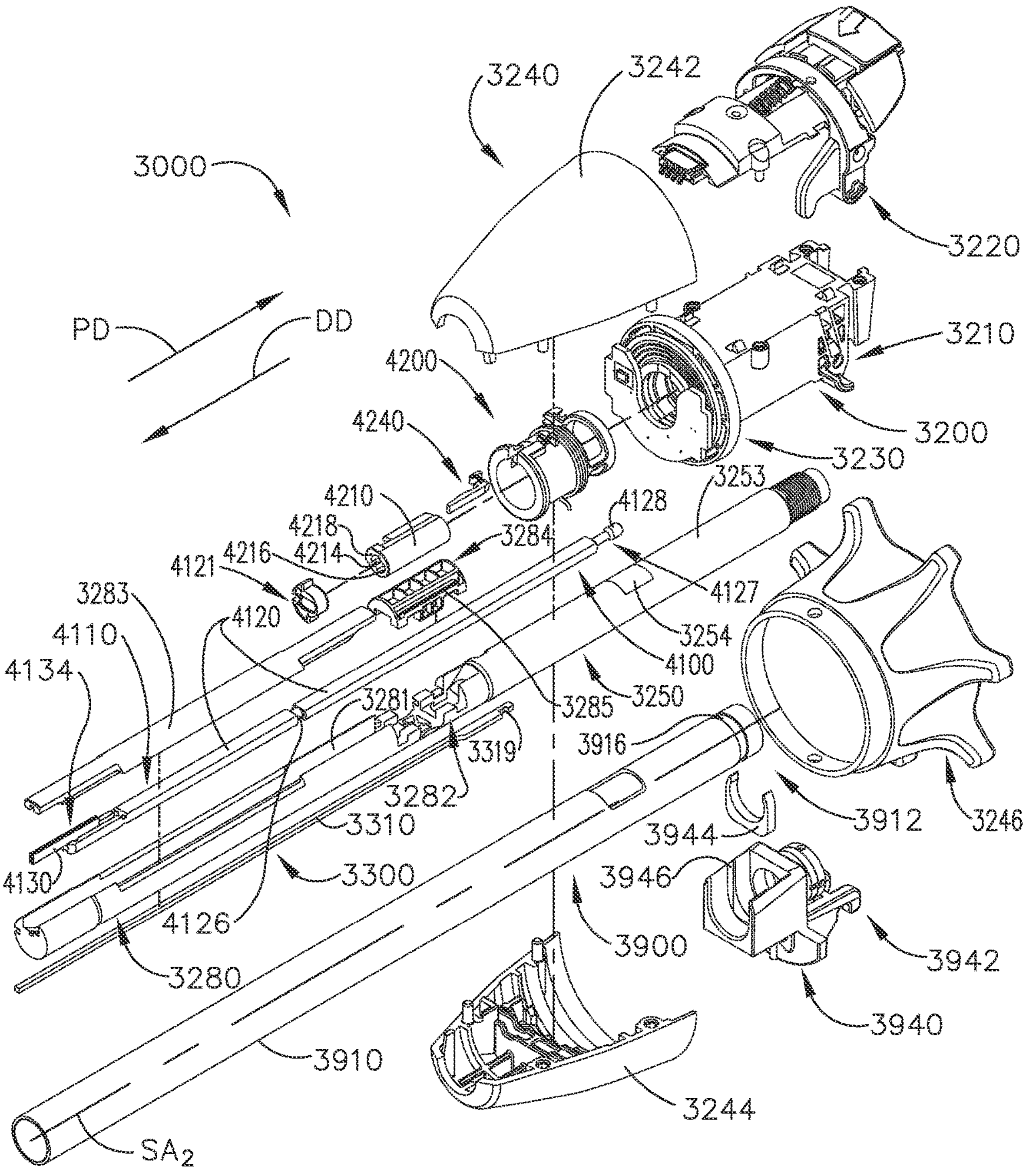
FIG. 17 is an exploded assembly view of a proximal portion of the interchangeable surgical tool assembly of FIG. 16.
Figure 18:
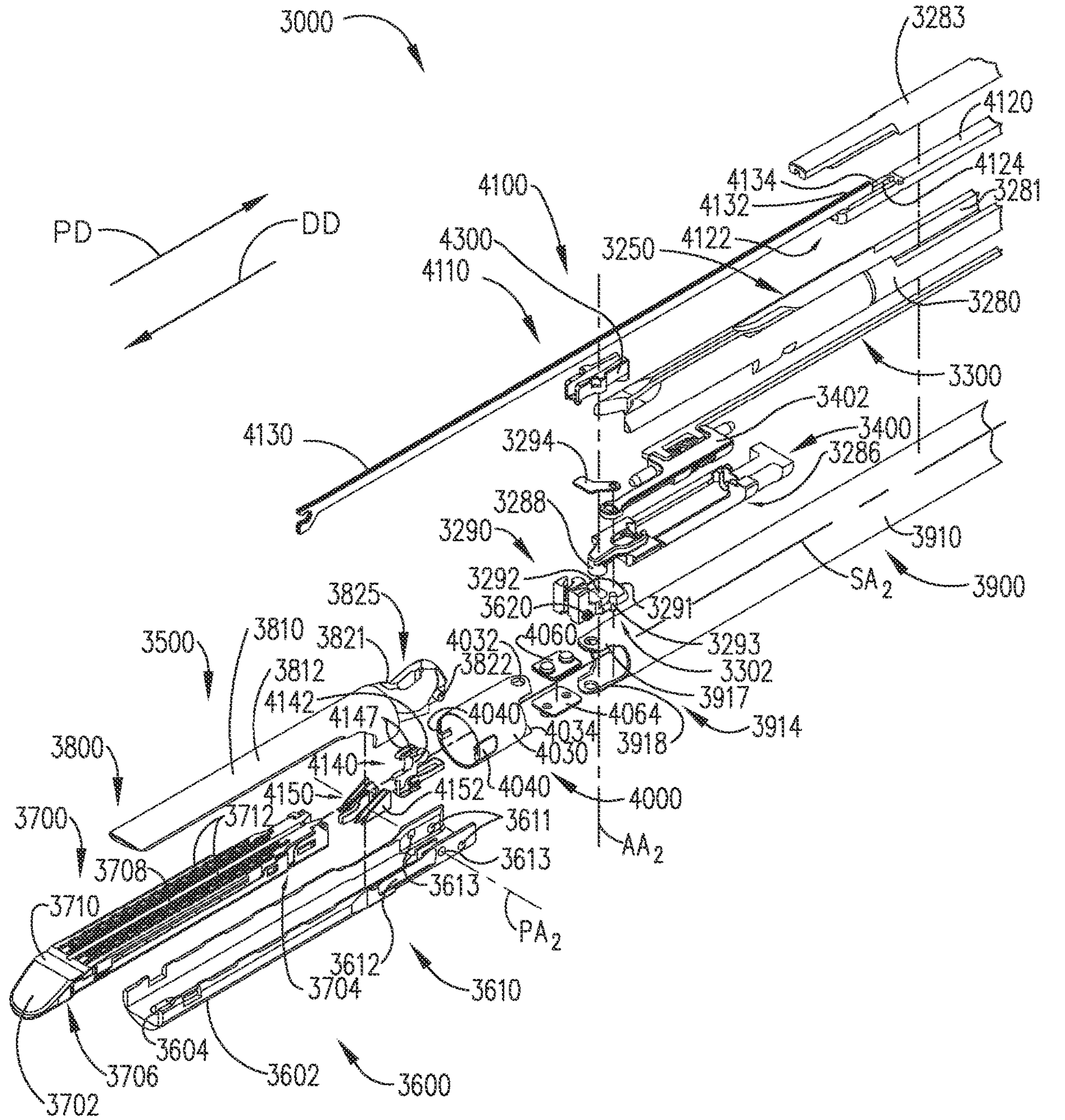
FIG. 18 is another exploded assembly view of a distal portion of the interchangeable surgical tool assembly of FIGS. 16 and 17.

Returning now to FIG. 1, the surgical system 10 illustrated in that Figure includes four interchangeable surgical tool assemblies 1000, 3000, 5000 and 7000 that may each be effectively employed with the same handle assembly 500 to perform different surgical procedures. Turning now to FIGS. 16-18, the interchangeable surgical tool assembly 3000 includes a surgical end effector 3500 that comprises a first jaw 3600 and a second jaw 3800. In one arrangement, the first jaw comprises an elongate channel 3602 that is configured to operably support a surgical staple/fastener cartridge 3700 therein. The second jaw 3800 comprises an anvil 3810 that is pivotally supported relative to the elongate channel 3602. The interchangeable surgical tool assembly 3000 includes an articulation system 3300 that comprises an articulation joint 3302 and an articulation lock 3400 which can be configured to releasably hold the surgical end effector 3500 in a desired articulated position relative to a shaft axis $SA_2$. Details regarding the construction and operation of the articulation lock 3400 as well as alternative lock configurations and operational details may be found in in U.S. patent application Ser. No. 13/803,086, entitled ARTICULATABLE SURGICAL INSTRUMENT COMPRISING AN ARTICULATION LOCK, now U.S. Patent Application Publication No. 2014/0263541, the entire disclosure of which is hereby incorporated by reference herein. Additional details concerning the articulation lock 3400 may also be found in U.S. patent application Ser. No. 15/019,196, filed Feb. 9, 2016, entitled SURGICAL INSTRUMENT ARTICULATION MECHANISM WITH SLOTTED SECONDARY CONSTRAINT, now U.S. Pat. No. 10,413,291, the entire disclosure of which is hereby incorporated by reference herein.

As can be seen in FIG. 17, the interchangeable surgical tool assembly 3000 includes a tool frame assembly 3200 that comprises a tool chassis 3210 that operably supports a nozzle assembly 3240 thereon. In one form, the nozzle assembly 3240 is comprised of nozzle portions 3242, 3244 as well as an actuator wheel portion 3246 that is configured to be coupled to the assembled nozzle portions 3242, 3244 by snaps, lugs, screws etc. The interchangeable surgical tool assembly 3000 includes a proximal closure assembly 3900 which is operably coupled to a distal closure assembly 4000 that is utilized to close and/or open the anvil 3810 of the surgical end effector 3500 as will be discussed in further detail below. In addition, the interchangeable surgical tool assembly 3000 includes an "elastic" spine assembly 3250 that operably supports the proximal closure assembly 3900 and is coupled to the surgical end effector 3500. One exemplary form of spine assembly 3250 is disclosed in U.S. patent application Ser. No. 15/385,911, entitled SURGICAL STAPLE/FASTENERS WITH INDEPENDENTLY ACTUATABLE CLOSING AND FIRING SYSTEMS, now U.S. Pat. No. 10,448,950, the entire disclosure of which is hereby incorporated by reference herein. For example, the spine assembly 3250 may comprise an elastic spine member that has a proximal end portion 3253 and a distal end portion 3280 that is separated from the proximal end portion 3253 of the elastic spine assembly 3250 by a stretch feature 3282 formed therebetween. In addition, a stretch limiting insert 3284 is retainingly supported between the distal end portion 3280 and the proximal end portion 3253. In various arrangements, the elastic spine assembly 3250 may be fabricated from, for example, suitable polymeric material, rubber, etc. which has a modulus of elasticity designated as $ME_1$ for reference purposes. The stretch limiting insert 3284 may have a modulus of elasticity designated as $ME_2$ for reference purposes. In various circumstances, the stretch limiting insert 3284 also includes a pair of stretch limiters 3285 (only one is shown in FIG. 17). The stretch limiter 3285 may have a modulus of elasticity for reference purposes of $ME_3$. In at least one arrangement, $ME_3<ME_2<ME_1$. Further details about at least one implementation of the elastic spine assembly 3250 and stretch limiting insert 3284 may be found in U.S. patent application Ser. No. 15/385,911, now U.S. Pat. No. 10,448,950.

In the illustrated arrangement, the distal end portion 3280 of the spine assembly 3250 has an opening 3281 therein for ease of assembly. A spine cap 3283 may be attached thereto to cover the opening 3281 after the various components have been assembled therein. In assembled form, the proximal end portion 3253 of the spine assembly 3250 is rotatably supported in the tool chassis 3210. In one arrangement, for example, the proximal end of the proximal end portion 3253 of the spine assembly 3250 is attached to a spine bearing (not shown) that is configured to be supported within the tool chassis 3210. Such arrangement facilitates rotatable attachment of the spine assembly 3250 to the tool chassis 3210 such that the spine assembly 3250 may be selectively rotated about a shaft axis $SA_2$ relative to the tool chassis 3210. In particular, in one arrangement, for example, the proximal end portion 3253 of the spine assembly 3250 includes two diametrically opposed lug seats 3254 (only one can be seen in FIG. 17) that are each configured to receive a corresponding nozzle lug (not shown) that extend inwardly from each of the nozzle portions 3242, 3244. Such arrangement facilitates rotation of the spine assembly 3250 about the shaft axis $SA_2$ by rotating the actuator wheel portion 3246 of the nozzle assembly 3240.

Referring now to FIG. 18, the distal end portion 3280 of the elastic spine assembly 3250 is attached to a distal frame segment 3286 that operably supports the articulation lock 3400 therein. The spine assembly 3250 is configured to, one, slidably support a firing member assembly 4110 therein and, two, slidably support the proximal closure tube 3910 which extends around the spine assembly 3250. The spine assembly 3250 can also be configured to slidably support a proximal articulation driver 3310. As can be seen in FIG. 18, the distal frame segment 3286 is pivotally coupled to the elongate channel 3602 by an end effector mounting assembly 3290. In one arrangement, for example, the distal end of the distal frame segment 3286 has a pivot pin 3288 formed thereon. The pivot pin 3288 is adapted to be pivotally received within a pivot hole 3292 formed in pivot base portion 3291 of the end effector mounting assembly 3290. The end effector mounting assembly 3290 is attached to a proximal end 3610 of the elongate channel 3602 by a spring pin 3620 or other suitable member that is received within mounting holes 3611 in the proximal end portion 3610. The pivot pin 3288 defines an articulation axis $AA_2$ that is transverse to the shaft axis $SA_2$. See FIG. 18. Such arrangement facilitates pivotal travel (i.e., articulation) of the surgical end effector 3500 about the articulation axis $AA_2$ relative to the elastic spine assembly 3250. The distal frame segment 3286 is further configured to support the articulation lock 3400 therein. Various articulation lock arrangements may be employed. At least one form of articulation lock 3400 is described in further detail in U.S. patent application Ser. No. 13/803,086, entitled ARTICULATABLE SURGICAL INSTRUMENT COMPRISING AN ARTICULATION LOCK, now U.S. Patent Application Publication No. 2014/0263541, the entire disclosure of which is hereby incorporated by reference herein. Additional details concerning the articulation lock may also be found in U.S. patent application Ser. No. 15/019,196, filed Feb. 9, 2016, entitled SURGICAL INSTRUMENT ARTICULATION MECHANISM WITH SLOTTED SECONDARY CONSTRAINT, now U.S. Pat. No. 10,413,291.

In the illustrated example, the surgical end effector 3500 is electively articulatable about the articulation axis $AA_2$ by the articulation system 3300. In one form, the articulation system 3300 includes the proximal articulation driver 3310 that operably interfaces with the articulation lock 3400. The articulation lock 3400 includes an articulation frame 3402 that is adapted to operably engage a drive pin 3293 on the pivot base portion 3291 of the end effector mounting assembly 3290. In addition, a cross link 3294 may be linked to the drive pin 3293 and articulation frame 3402 to assist articulation of the surgical end effector 3500. As indicated above, further details regarding the operation of the articulation lock 3400 and the articulation frame 3402 may be found in U.S. patent application Ser. No. 13/803,086, now U.S. Patent Application Publication No. 2014/0263541. Further details regarding the end effector mounting assembly and cross link 3294 may be found in U.S. patent application Ser. No. 15/019,245, filed Feb. 9, 2016, entitled SURGICAL INSTRUMENTS WITH CLOSURE STROKE REDUCTION ARRANGEMENTS, now U.S. Pat. No. 10,470,764, the entire disclosure of which is hereby incorporated by reference herein. As further described therein, as well as in other disclosures incorporated by reference herein, axial movement of proximal articulation driver 3310 will result in the engagement/disengagement of the articulation lock 3400 to thereby apply articulation motions to the elongate channel 3602 and thereby cause the surgical end effector 3500 to articulate about the articulation axis $AA_2$ relative to the spine assembly 3250.

The anvil 3810 in the illustrated example includes an anvil body 3812 that terminates in anvil mounting portion 3820. The anvil mounting portion 3820 is movably or pivotably supported on the elongate channel 3602 for selective pivotal travel relative thereto about a fixed anvil pivot axis $PA_2$ (FIG. 18) that is transverse to the shaft axis $SA_2$. In the illustrated arrangement, an anvil trunnion 3822 extends laterally out of each lateral side of the anvil mounting portion 3820 to be received in a corresponding trunnion pivot hole 3613 formed in the upstanding walls 3612 of the proximal end portion 3610 of the elongate channel 3602. Movement of the anvil 3810 relative to the elongate channel 3602 is effectuated by axial movement of the proximal closure assembly 3900 and the distal closure assembly 4000. In the illustrated arrangement, the proximal closure assembly 3900 comprises a proximal closure tube 3910 that has a proximal end 3912 and a distal end 3914. The proximal end 3912 is rotatably supported in a closure shuttle 3940 that is slidably supported within the tool chassis 3210 such that it may be axially moved relative thereto. In one form, the closure shuttle 3940 includes a pair of proximally-protruding hooks 3942 that are configured for attachment to the transverse attachment pin 516 that is attached to the closure linkage assembly 514 of the handle assembly 500. The proximal end 3912 is coupled to the closure shuttle 3940 for relative rotation thereto. For example, a U-shaped connector 3944 is inserted into an annular slot 3916 in the proximal end 3912 and is retained within vertical slots 3946 in the closure shuttle 3940. Such arrangement serves to attach the proximal closure assembly 3900 to the closure shuttle 3940 for axial travel therewith while enabling the proximal closure tube 3910 to rotate relative to the closure shuttle 3940 about the shaft axis $SA_2$. As was discussed above in connection with the interchangeable surgical tool assembly 1000, a closure spring (not shown) may extend over the proximal end 3912 of the proximal closure tube 3910 to bias the closure shuttle 3940 in the proximal direction PD which can serve to pivot the closure trigger 512 on the handle assembly 500 (FIG. 2) into the unactuated position when the interchangeable surgical tool assembly 3000 is operably coupled to the handle assembly 500 in the above described manner.

As can be seen in FIG. 18, the distal end 3914 of the proximal closure tube 3910 is attached to the distal closure assembly 4000. The distal end 3914 includes upper and lower tangs 3917, 3918 that are configured to be movably coupled to an end effector closure sleeve or distal closure tube segment 4030. The distal closure tube segment 4030 includes an upper tang 4032 and a lower tang 4034 that protrude proximally from a proximal end thereof. An upper double pivot link 4060 pivotally couples the upper tangs 3917 and 4032 and a lower double pivot link 4064 pivotally couples the lower tangs 3918 and 4034 together in the above-described manner. The distal advancement of the distal closure tube segment 4030 on the anvil mounting portion 3820 will result in closure or pivotal travel of the anvil 3810 towards the elongate channel 3602 about the fixed anvil pivot axis $PA_2$. In the illustrated arrangement, the distal closure tube segment 4030 also includes positive jaw or anvil opening features 4040 that are configured to coact with surfaces or ramp portions on the anvil mounting portion 3820 so as to cause the anvil 3810 to pivot from a closed position to an open position as the distal closure tube segment 4030 is moved proximally back to a starting position. Other embodiments may not employ the positive jaw opening features, but may rely on springs or other biasing arrangements to bias the anvil to the open position when the distal closure tube segment has been retracted to its proximal-most starting position. Further details regarding configurations and operation of the anvil opening features may be found in for example, U.S. patent application Ser. No. 15/385,911, entitled SURGICAL STAPLE/FASTENERS WITH INDEPENDENTLY ACTUATABLE CLOSING AND FIRING SYSTEMS, now U.S. Pat. No. 10,448, 950.

In the illustrated arrangement, the interchangeable surgical tool assembly 3000 further includes a firing system generally designated as 4100. In various instances, the firing system 4100 includes a firing member assembly 4110 that is supported for axial travel within the spine assembly 3250. In the illustrated embodiment, the firing member assembly 4110 includes an intermediate firing shaft portion 4120 that is configured for attachment to a distal cutting portion or knife bar 4130. A support bushing arrangement 4121 may be employed to support the intermediate firing shaft portion 4120 within the spine assembly 3250. The firing member assembly 4110 may also be referred to herein as a "second shaft" and/or a "second shaft assembly". As can be seen in FIG. 18, the intermediate firing shaft portion 4120 may include a longitudinal slot 4124 in a distal end 4122 thereof which can be configured to receive a proximal end 4132 of the knife bar 4130. The longitudinal slot 4124 and the proximal end 4132 of the knife bar 4130 can be sized and configured to permit relative movement therebetween and can comprise a slip joint 4134. The slip joint 4134 can permit the intermediate firing shaft portion 4120 of the firing member assembly 4110 to be moved to articulate the end effector 3500 without moving, or at least substantially moving, the knife bar 4130 as was discussed above. In the illustrated arrangement, a proximal end 4127 of the intermediate firing shaft portion 4120 has a firing shaft attachment lug 4128 formed thereon that is configured to be seated into the attachment cradle (not shown) that is on the distal end of the longitudinally movable drive member (not shown) of the firing drive system 530 within the handle assembly 500 as was discussed above. Such arrangement facilitates the axial movement of the intermediate firing shaft portion 4120 upon actuation of the firing drive system 530. Other attachment configurations may also be employed to couple the intermediate firing shaft portion 4120 to other firing drive arrangements (e.g., manually actuated, robotic, etc.).

Further to the above, the interchangeable tool assembly 3000 can include a shifter assembly 4200 which can be configured to selectively and releasably couple the proximal articulation driver 3310 to the firing member assembly 4110 in the manner described above. In one form, the shifter assembly 4200 includes a lock collar, or lock sleeve 4210, positioned around the intermediate firing shaft portion 4120 of the firing member assembly 4110 wherein the lock sleeve 4210 can be rotated between an engaged position in which the lock sleeve 4210 couples the proximal articulation driver 3310 to the firing member assembly 4110 and a disengaged position in which the proximal articulation driver 3310 is not operably coupled to the firing member assembly 4110. As was discussed above, the intermediate firing shaft portion 4120 of the firing member assembly 4110 is formed with a drive notch 4126. The lock sleeve 4210 comprises a cylindrical, or an at least substantially cylindrical, body that includes a longitudinal aperture 4212 that is configured to receive the intermediate firing shaft portion 4120 therethrough. The lock sleeve 4210 can comprise diametrically-opposed, inwardly-facing lock protrusions 4214, 4216 that, when the lock sleeve 4210 is in one position, are engagingly received within corresponding portions of the drive notch 4126 in the intermediate firing shaft portion 4120 and, when in another position, are not received within the drive notch 4126 to thereby permit relative axial motion between the lock sleeve 4210 and the intermediate firing shaft 4120 as was discussed in further detail above. The lock sleeve 4210 further includes a lock member 4218 that is sized to be movably received within a notch 3319 in a proximal end of the proximal articulation driver 3310. When the lock sleeve 4210 is in its engaged position, the lock protrusions 4214, 4216 are positioned within the drive notch 4126 in the intermediate firing shaft portion 4120 such that a distal pushing force and/or a proximal pulling force can be transmitted from the firing member assembly 4110 to the lock sleeve 4210. Such axial pushing or pulling motion is then transmitted from the lock sleeve 4210 to the proximal articulation driver 3310 to thereby articulate the surgical end effector 3500.

As was discussed above, in the illustrated example, relative movement of the lock sleeve 4210 between its engaged and disengaged positions may be controlled by the shifter assembly 4200 that interfaces with the proximal closure tube 3910 of the proximal closure assembly 3900. The shifter assembly 4200 further includes a shifter key 4240 that is configured to be slidably received within a key groove (similar to the key groove 2217 illustrated in FIG. 8) formed in the outer perimeter of the lock sleeve 4210. Such arrangement enables the shifter key 4240 to move axially with respect to the lock sleeve 4210. Operation of the shifter assembly 4200 may be identical to the operation of the shifter assembly 2200 which was described in further detail above and which will not be repeated again for brevity. Further details, alternative arrangements and drive configurations that may be employed are disclosed in other arrangements that may be employed are disclosed in U.S. patent application Ser. No. 15/385,911, entitled SURGICAL STAPLE/FASTENERS WITH INDEPENDENTLY ACTUATABLE CLOSING AND FIRING SYSTEMS, now U.S. Pat. No. 10,448,950, U.S. patent application Ser. No. 13/803,086, now U.S. Patent Application Publication No. 2014/0263541, and U.S. patent application Ser. No. 15/019,196, now U.S. Pat. No. 10,413,291, the as well as other disclosures that have been incorporated herein.

The interchangeable tool assembly 3000 can comprise a slip ring assembly 3230 which can be configured to conduct electrical power to and/or from the surgical end effector 3500 and/or communicate signals to and/or from the surgical end effector 3500, back to a microprocessor 560 in the handle assembly 500 or robotic system controller, for example as was discussed above. Further details concerning the slip ring assembly 3230 and associated connectors may be found in U.S. patent application Ser. No. 13/803,086, now U.S. Patent Application Publication No. 2014/0263541, and U.S. patent application Ser. No. 15/019,196 now U.S. Pat. No. 10,413,291, which have each been herein incorporated by reference in their respective entirety as well as in U.S. patent application Ser. No. 13/800,067, entitled STAPLE CARTRIDGE TISSUE THICKNESS SENSOR SYSTEM, now U.S. Patent Application Publication No. 2014/0263552, which is hereby incorporated by reference herein in its entirety.

The illustrated interchangeable surgical tool assembly 3000 also employs a latch system 3220 for removably coupling the interchangeable surgical tool assembly 3000 to the handle frame 506 of the handle assembly 500, for example. The latch system 3220 may be identical to the latch system 1220 described in detail above. The knife bar 4130 may comprise a laminated beam structure that includes at least two beam layers. Such beam layers may comprise, for example, stainless steel bands that are interconnected by, for example, welding or pinning together at their proximal ends and/or at other locations along their length. In alternative embodiments, the distal ends of the bands are not connected together to allow the laminates or bands to splay relative to each other when the end effector is articulated. Such arrangement permits the knife bar 4130 to be sufficiently flexible to accommodate articulation of the end effector. Various laminated knife bar arrangements are disclosed in U.S. patent application Ser. No. 15/019,245, entitled SURGICAL INSTRUMENTS WITH CLOSURE STROKE REDUCTION ARRANGEMENTS, now U.S. Pat. No. 10,470,764, which is hereby incorporated by reference in its entirety. As can also be seen in FIG. 18, a firing shaft support assembly 4300 is employed to provide lateral support to the knife bar 4130 as it flexes to accommodate articulation of the surgical end effector 3500. Further details concerning the operation of the firing shaft support assembly 4300 and alternative knife bar support arrangements may be found in U.S. patent application Ser. No. 15/019,245, entitled SURGICAL INSTRUMENTS WITH CLOSURE STROKE REDUCTION ARRANGEMENTS, now U.S. Pat. No. 10,470,764, and U.S. patent application Ser. No. 15/019,220, entitled SURGICAL INSTRUMENT WITH ARTICULATING AND AXIALLY TRANSLATABLE END EFFECTOR, now U.S. Pat. No. 10,245,029, which are each hereby incorporated by reference herein in their respective entireties.

As can also be seen in FIG. 18, a firing member or knife member 4140 is attached to the distal end of the knife bar 4130. The firing member 4140 is configured to operably interface with a sled assembly 4150 that is operably supported within the body 3702 of the surgical staple/fastener cartridge 3700. The sled assembly 4150 is slidably displaceable within the surgical staple/fastener cartridge body 3702 from a proximal starting position adjacent the proximal end 3704 of the cartridge body 3702 to an ending position adjacent a distal end 3706 of the cartridge body 3702. The cartridge body 3702 operably supports therein a plurality of staple drivers (not shown) that are aligned in rows on each side of a centrally disposed slot 3708. The centrally disposed slot 3708 enables the firing member 4140 to pass therethrough and cut the tissue that is clamped between the anvil 3810 and the staple cartridge 3700. The drivers are associated with corresponding staple pockets 3712 that open through the deck surface 3710 of the cartridge body 3702. Each of the staple drivers supports one or more surgical staple/fastener or fastener (not shown) thereon. The sled assembly 4150 includes a plurality of sloped or wedge-shaped cams 4152 wherein each cam 4152 corresponds to a particular line of fasteners or drivers located on a side of the slot 3708.

Figure 49:
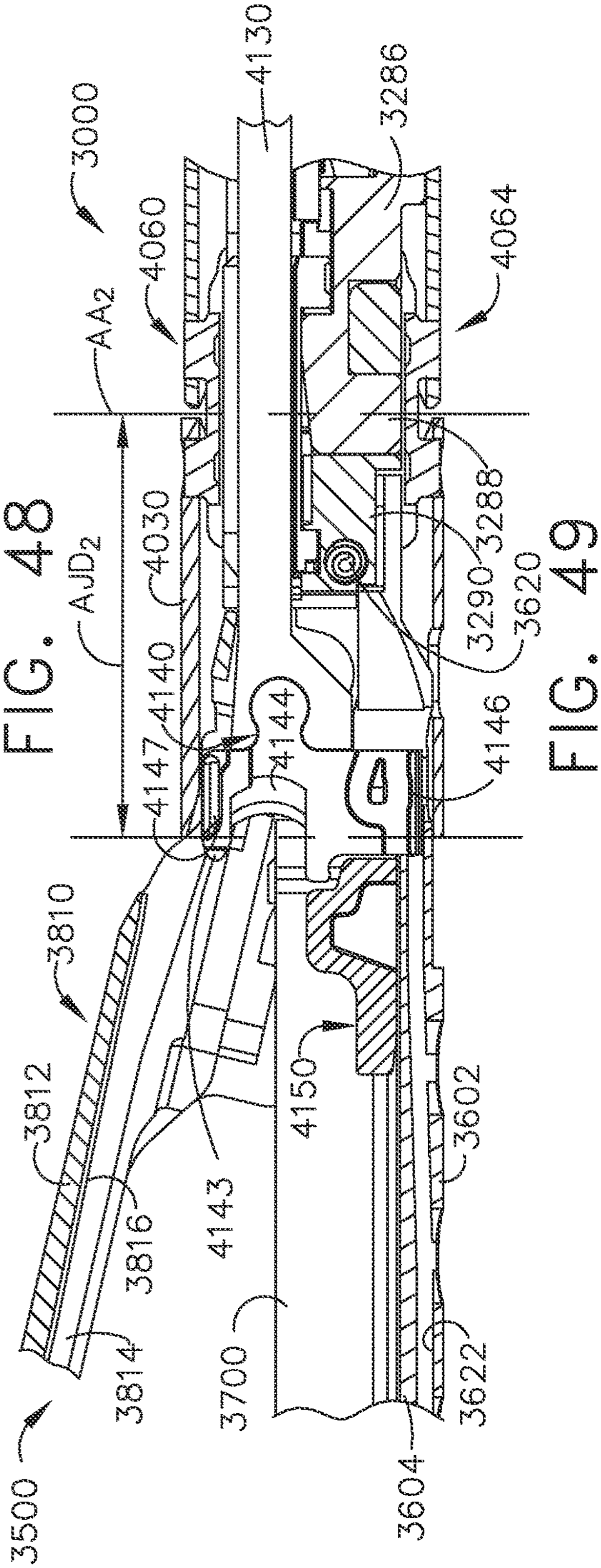
FIG. 49 is a partial cross-sectional view of the anvil mounting portion and elongate channel of the interchangeable surgical tool assembly of FIG. 16 with the anvil in a fully open position.

In one exemplary form, the firing member 4140 comprises a body portion 4142 that supports a knife or tissue cutting portion 4144. See FIG. 49. The body portion 4142 protrudes through an elongate slot 3604 in the elongate channel 3602 and terminates in a foot member 4146 that extends laterally on each side of the body portion 4142. As the firing member 4140 is driven distally through the surgical staple/fastener cartridge 3700, the foot member 4146 rides within a passage 3622 in the elongate channel 3602 that is located under the surgical staple/fastener cartridge 3700. The tissue cutting portion 4144 is disposed between a distally protruding top nose portion 4143. As can be further seen in FIG. 18, the firing member 4140 may further include two laterally extending top tabs, pins or anvil engagement features 4147. As the firing member 4140 is driven distally, a top portion of the body portion 4142 extends through a centrally disposed anvil slot 3814 and the anvil engagement features 4147 ride on corresponding ledges 3816 formed on each side of the anvil slot 3814. Further details concerning the firing member 4140, sled assembly 4150 and their various alternatives as well as examples of their operation will be discussed in further detail below and may also be found in U.S. patent application Ser. No. 15/385,911, entitled SURGICAL STAPLE/FASTENERS WITH INDEPENDENTLY ACTUATABLE CLOSING AND FIRING SYSTEMS, now U.S. Pat. No. 10,448,950. The interchangeable surgical tool assembly 3000 may be to the handle assembly 500 in the manner as described above with respect to the interchangeable surgical tool assembly 1000.

Figure 19:
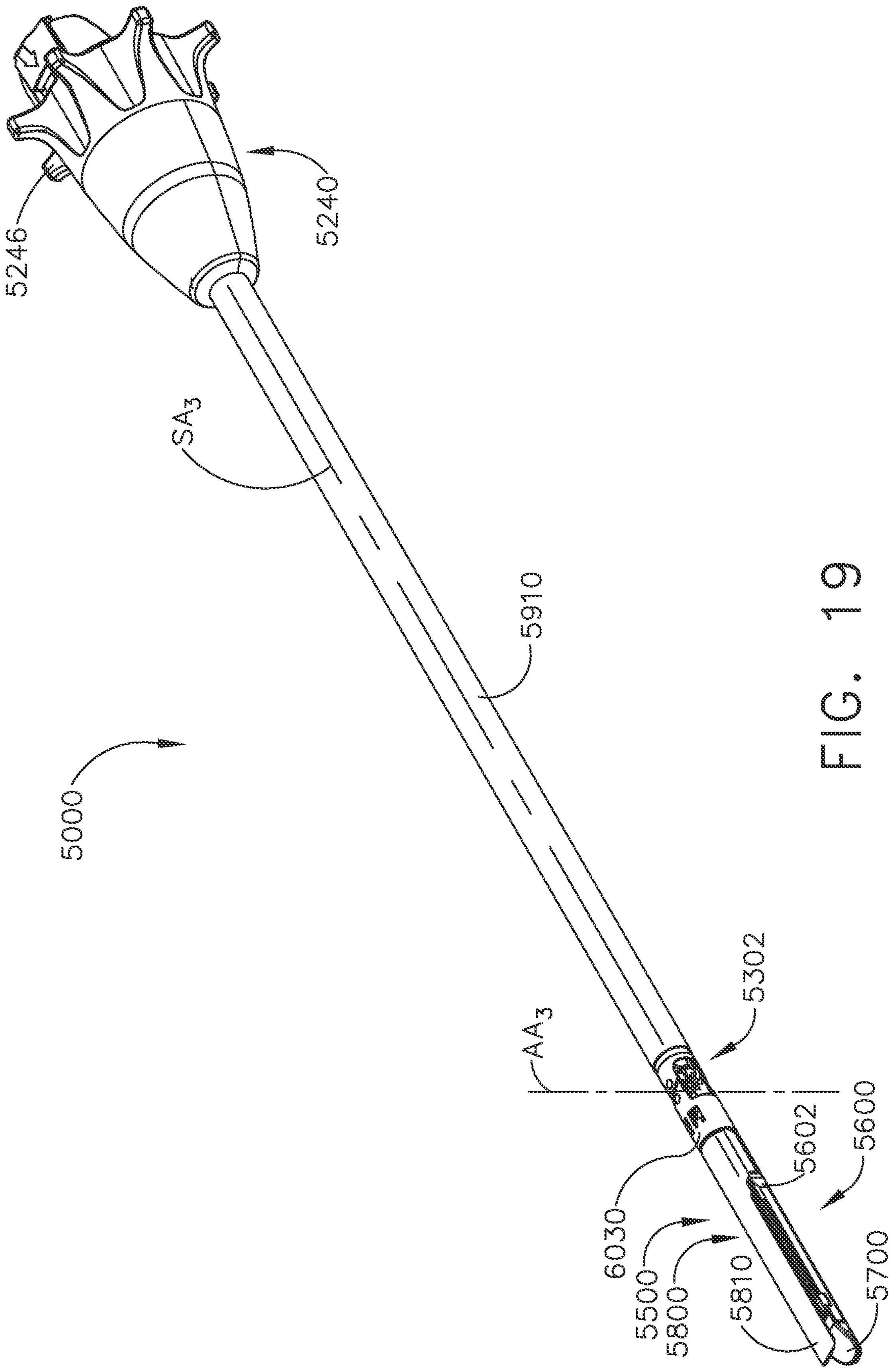
FIG. 19 is a perspective view of another one of the interchangeable surgical tool assemblies depicted in FIG. 1.
Figure 20:
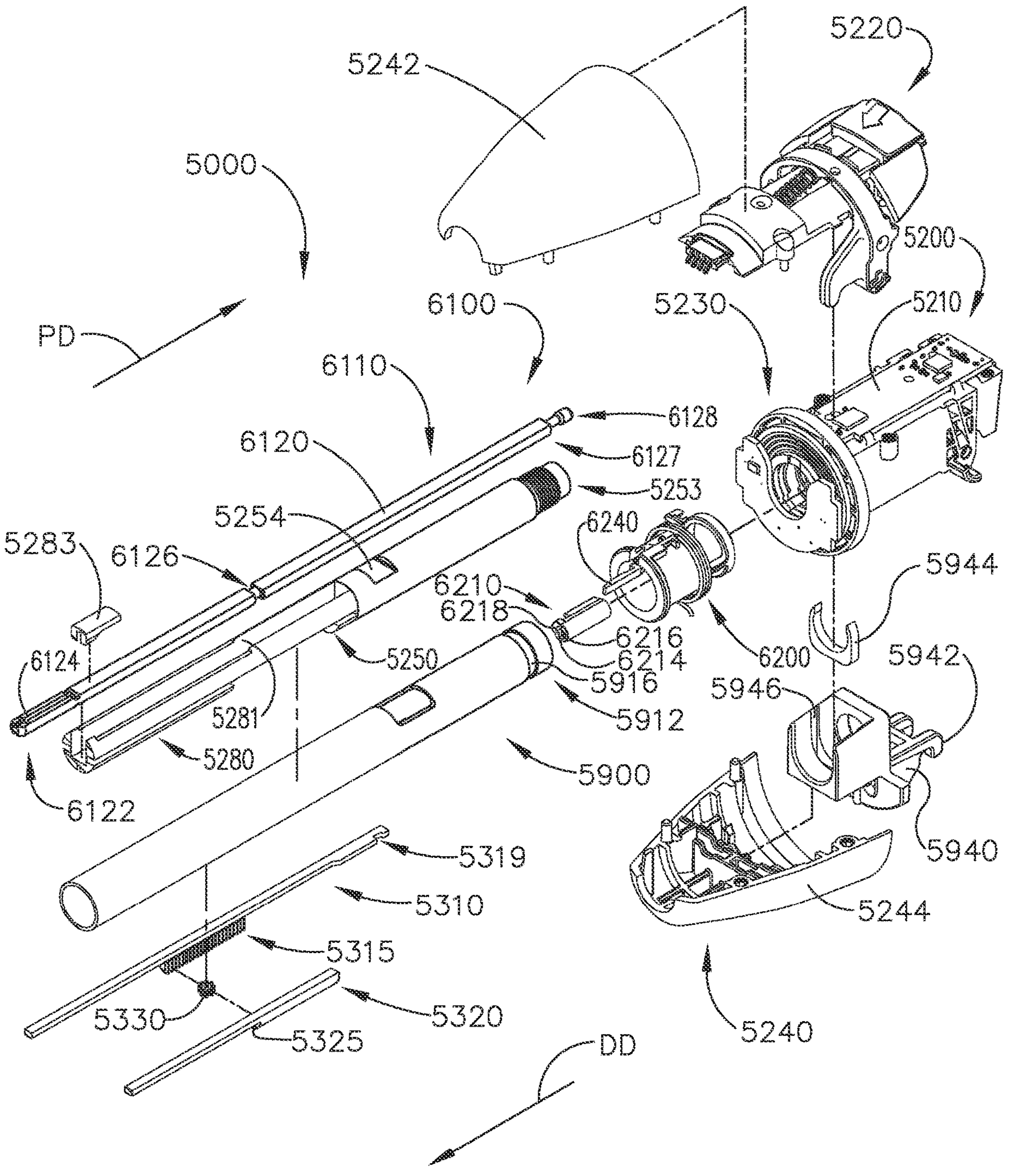
FIG. 20 is an exploded assembly view of a proximal portion of the interchangeable surgical tool assembly of FIG. 19.
Figure 21:
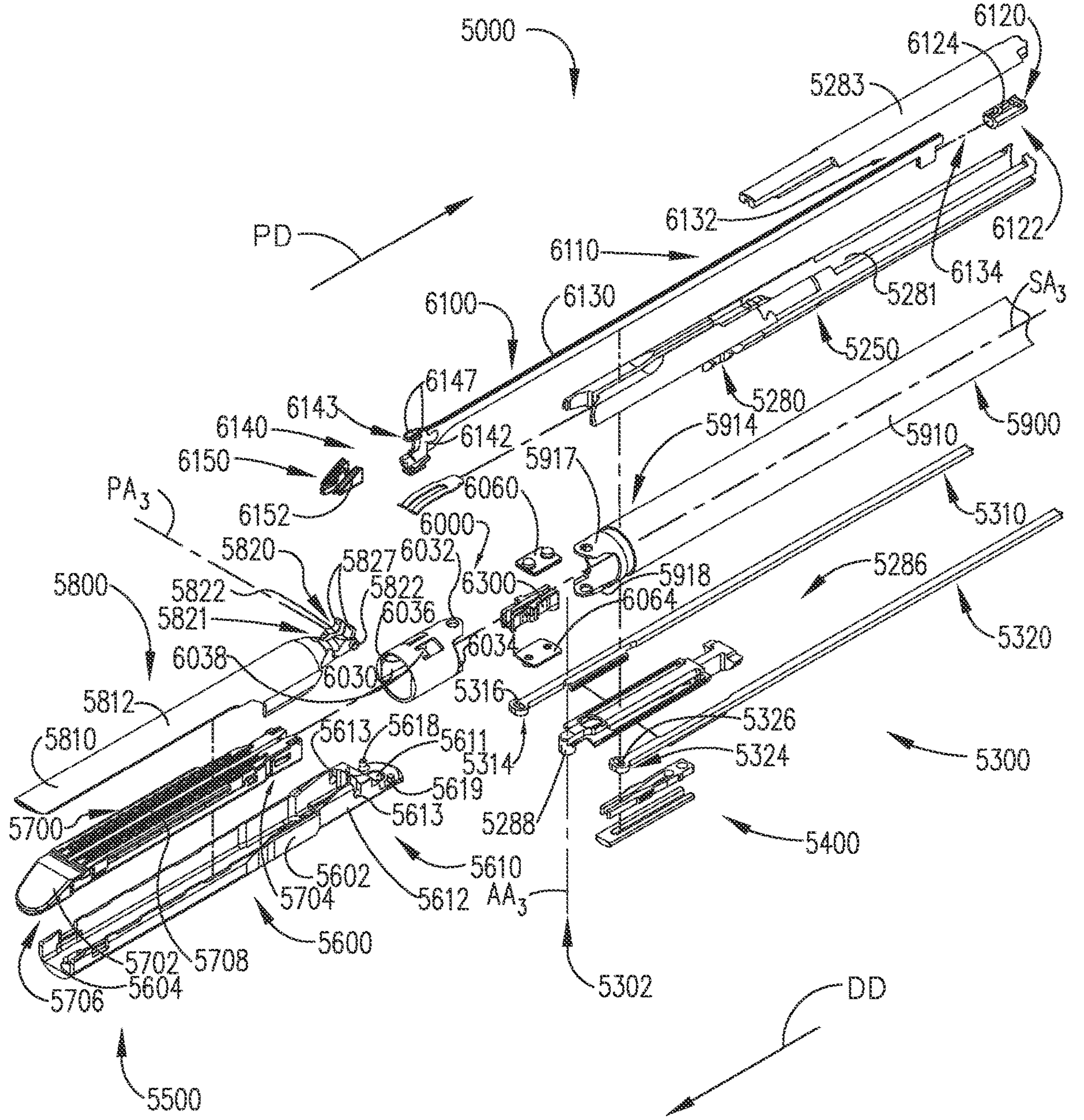
FIG. 21 is another exploded assembly view of a distal portion of the interchangeable surgical tool assembly of FIGS. 19 and 20.

Returning again to FIG. 1, as was discussed above, the surgical system 10 illustrated in that Figure includes four interchangeable surgical tool assemblies 1000, 3000, 5000 and 7000 that may each be effectively employed with the same handle assembly 500 to perform different surgical procedures. Turning now to FIGS. 19-21, the interchangeable surgical tool assembly 5000 includes a surgical end effector 5500 that comprises a first jaw 5600 and a second jaw 5800. In one arrangement, the first jaw comprises an elongate channel 5602 that is configured to operably support a surgical staple/fastener cartridge 5700 therein. The second jaw 5800 comprises an anvil 5810 that is movably supported relative to the elongate channel 5602. The interchangeable surgical tool assembly 5000 includes an articulation system 5300 that comprises an articulation joint 5302 and an articulation lock 5400 which can be configured to releasably hold the surgical end effector 5500 in a desired articulated position relative to a shaft axis $SA_3$. Details regarding the construction and operation of the articulation lock 5400 as well as alternative lock configurations and operational details may be found in in U.S. patent application Ser. No. 15/385,894, entitled SHAFT ASSEMBLY COMPRISING A LOCK OUT, now U.S. Pat. No. 10,492,785, the entire disclosure of which is hereby incorporated by reference herein. Alternative articulation lock arrangements may also be found in U.S. patent application Ser. No. 13/803,086, entitled ARTICULATABLE SURGICAL INSTRUMENT COMPRISING AN ARTICULATION LOCK, now U.S. Patent Application Publication No. 2014/0263541 and U.S. patent application Ser. No. 15/019,196, filed Feb. 9, 2016, entitled SURGICAL INSTRUMENT ARTICULATION MECHANISM WITH SLOTTED SECONDARY CONSTRAINT, now U.S. Pat. No. 10,413,291, the entire disclosures of each such reference being hereby incorporated by reference herein.

As can be seen in FIG. 20, the interchangeable surgical tool assembly 5000 includes a tool frame assembly 5200 that comprises a tool chassis 5210 that operably supports a nozzle assembly 5240 thereon. In one form, the nozzle assembly 5240 is comprised of nozzle portions 5242, 5244 as well as an actuator wheel portion 5246 that is configured to be coupled to the assembled nozzle portions 5242, 5244 by snaps, lugs, screws etc. The interchangeable surgical tool assembly 5000 includes a proximal closure assembly 5900 which is operably coupled to a distal closure assembly 6000 that is utilized to close and/or open the anvil 5810 of the surgical end effector 5500 as will be discussed in further detail below. In addition, the interchangeable surgical tool assembly 5000 includes a spine assembly 5250 that operably supports the proximal closure assembly 5900 and is coupled to the surgical end effector 5500. In the illustrated arrangement, the spine assembly 5250 includes a distal end portion 5280 that has an opening 5281 therein for ease of assembly. A spine cap 5283 may be attached thereto to cover the opening 5281 after the various components have been assembled therein. In assembled form, a proximal end portion 5253 of the spine assembly 5250 is rotatably supported in the tool chassis 5210. In one arrangement, for example, the proximal end of the proximal end portion 5253 of the spine assembly 5250 is attached to a spine bearing (not shown) that is configured to be supported within the tool chassis 5210. Such arrangement facilitates rotatable attachment of the spine assembly 5250 to the tool chassis 5210 such that the spine assembly 5250 may be selectively rotated about the shaft axis $SA_3$ relative to the tool chassis 5210. In particular, in one arrangement, for example, the proximal end portion 5253 of the spine assembly 5250 includes two diametrically opposed lug seats 5254 (only one can be seen in FIG. 20) that are each configured to receive a corresponding nozzle lug (not shown) that extend inwardly from each of the nozzle portions 5242, 5244. Such arrangement facilitates rotation of the spine assembly 5250 about the shaft axis $SA_3$ by rotating the actuator wheel portion 5246 of the nozzle assembly 5240.

Referring now to FIG. 21, the distal end portion 5280 of the spine assembly 5250 is attached to a distal frame segment 5286 that operably supports the articulation lock 5400 therein. The spine assembly 5250 is configured to, one, slidably support a firing member assembly 6110 therein and, two, slidably support a proximal closure tube 5910 which extends around the spine assembly 5250. The spine assembly 5250 can also be configured to slidably support a first articulation driver 5310 and a second articulation driver 5320. As can be seen in FIG. 21, the distal frame segment 5286 is pivotally coupled to a proximal end 5610 of the elongate channel 5602. In one arrangement, for example, the distal end of the distal frame segment 5286 has a pivot pin 5288 formed thereon. The pivot pin 5288 is adapted to be pivotally received within a pivot hole 5611 formed in the proximal end portion 5610 of the elongate channel 5602. The pivot pin 5288 defines an articulation axis $AA_3$ that is transverse to the shaft axis $SA_3$. See FIG. 21. Such arrangement facilitates pivotal travel (i.e., articulation) of the surgical end effector 5500 about the articulation axis $AA_3$ relative to the spine assembly 5250. The distal frame segment 5286 is further configured to support the articulation lock 5400 therein.

In the illustrated arrangement, a distal end 5314 of the first articulation driver 5310 is formed with a loop 5316 that is adapted to receive a first articulation pin 5618 therein that is formed on the proximal end portion 5610 of the elongate channel 5602. Similarly, a distal end 5324 of the second articulation driver 5320 has a loop 5326 that is adapted to receive a second articulation pin 5619 therein that is formed on the proximal end portion 5610 of the elongate channel 5602. In one arrangement, for example, the first articulation driver 5310 further comprises a proximal rack of teeth 5315 that is in meshing engagement with an idler gear 5330 rotatably supported in the spine assembly 5250. Similarly the second articulation driver 5320 further comprises a proximal rack of teeth 5325 that is in meshing engagement with the idler gear 5330. Thus, in such arrangement, movement of the first articulation driver 5310 in the distal direction DD will result in movement of the second articulation driver 5320 in the proximal direction PD. Movement of the first articulation driver 5310 in the proximal direction PD will result in the movement of the second articulation driver 5320 in the distal direction DD. Thus, such movement of the first and second articulation drivers 5310, 5320 will provide simultaneously pushing and pulling motions to the surgical end effector 5500 to articulate the surgical end effector about the articulation axis $AA_3$.

The anvil 5810 in the illustrated example includes an anvil body 5812 that terminates in anvil mounting portion 5820. The anvil mounting portion 5820 is movably supported on the elongate channel 5602 for selective pivotal and vertical travel relative thereto. In the illustrated arrangement, an anvil trunnion 5822 extends laterally out of each lateral side of the anvil mounting portion 5820 to be received in a corresponding "open-ended" vertical cradle 5613 formed in upstanding walls 5612 of the proximal end portion 5610 of the elongate channel 5602. Movement of the anvil 5810 relative to the elongate channel 5602 is effectuated by axial movement of the proximal closure assembly 5900 and the distal closure assembly 6000. In the illustrated arrangement, the proximal closure assembly 5900 comprises the proximal closure tube 5910 that has a proximal end 5912 and a distal end 5914. The proximal end 5912 is rotatably supported in a closure shuttle 5940 that is slidably supported within the tool chassis 5210 such that it may be axially moved relative thereto. In one form, the closure shuttle 5940 includes a pair of proximally-protruding hooks 5942 that are configured for attachment to the transverse attachment pin 516 that is attached to the closure linkage assembly 514 of the handle assembly 500. The proximal end 5912 of the proximal closure tube 5910 is coupled to the closure shuttle 5940 for relative rotation thereto. For example, a U-shaped connector 5944 is inserted into an annular slot 5916 in the proximal end 5912 and is retained within vertical slots 5946 in the closure shuttle 5940. Such arrangement serves to attach the proximal closure assembly 5900 to the closure shuttle 5940 for axial travel therewith while enabling the proximal closure tube 5910 to rotate relative to the closure shuttle 5940 about the shaft axis $SA_3$. As was discussed above in connection with the interchangeable surgical tool assembly 1000, a closure spring (not shown) may extend over the proximal end 5912 of the proximal closure tube 5910 to bias the closure shuttle 5940 in the proximal direction PD which can serve to pivot the closure trigger 512 on the handle assembly 500 (FIG. 2) into the unactuated position when the interchangeable surgical tool assembly 5000 is operably coupled to the handle assembly 500 in the above described manner.

As can be seen in FIG. 21, the distal end 5914 of the proximal closure tube 5910 is attached to the distal closure assembly 6000. The distal end 5914 includes upper and lower tangs 5917, 7918 that are configured to be movably coupled to an end effector closure sleeve or distal closure tube segment 6030. The distal closure tube segment 6030 includes an upper tang 6032 and a lower tang 6034 that protrude proximally from a proximal end thereof. An upper double pivot link 6060 pivotally couples the upper tangs 5917 and 6032 and a lower double pivot link 6064 pivotally couples the lower tangs 5918 and 6034 together in the above-described manner. The distal closure tube segment 6030 includes an internal cam surface 6036 that is configured to cammingly engage an anvil cam surface 5821 on the anvil mounting portion 5820. The distal advancement of the distal closure tube segment 6030 on the anvil mounting portion 5820 will result in closure or pivotal travel of the anvil 5810 towards the elongate channel 5602. In the illustrated arrangement, upstanding anvil tabs 5827 are formed on the anvil mounting portion 5820 and are configured to be contacted by two positive jaw opening tabs 6038 that extend inwardly within the distal closure tube segment 6030. Each positive jaw opening tab 6038 is configured to engage a corresponding one of the anvil tabs 5827 to pivot the anvil 5810 to an open position when the distal closure tube segment 6030 is axially moved in the proximal direction PD.

In the illustrated arrangement, the interchangeable surgical tool assembly 5000 further includes a firing system generally designated as 6100. In various instances, the firing system 6100 includes the firing member assembly 6110 that is supported for axial travel within the spine assembly 5250. In the illustrated embodiment, the firing member assembly 6110 includes an intermediate firing shaft portion 6120 that is configured for attachment to a distal cutting portion or knife bar 6130. The firing member assembly 6110 may also be referred to herein as a "second shaft" and/or a "second shaft assembly". As can be seen in FIG. 21, the intermediate firing shaft portion 6120 may include a longitudinal slot 6124 in a distal end 6122 thereof which can be configured to receive a proximal end 6132 of the knife bar 6130. The longitudinal slot 6124 and the proximal end 6132 of the knife bar 6130 can be sized and configured to permit relative movement therebetween and can comprise a slip joint 6134. The slip joint 6134 can permit the intermediate firing shaft portion 6120 of the firing member assembly 6110 to be moved to articulate the end effector 5500 without moving, or at least substantially moving, the knife bar 6130 as was discussed above. In the illustrated arrangement, a proximal end 6127 of the intermediate firing shaft portion 6120 has a firing shaft attachment lug 6128 formed thereon that is configured to be seated into an attachment cradle (not shown) that is on the distal end of the longitudinally movable drive member (not shown) of the firing drive system 530 within the handle assembly 500 as was discussed above. Such arrangement facilitates the axial movement of the intermediate firing shaft portion 6120 upon actuation of the firing drive system 530. Other attachment configurations may also be employed to couple the intermediate firing shaft portion to other firing drive arrangements (e.g., manually actuated, robotic, etc.).

Further to the above, the interchangeable tool assembly 5000 can include a shifter assembly 6200 which can be configured to selectively and releasably couple the first articulation driver 5310 to the firing member assembly 6110 in the manner described above. In one form, the shifter assembly 6200 includes a lock collar, or lock sleeve 6210, positioned around the intermediate firing shaft portion 6120 of the firing member assembly 6110 wherein the lock sleeve 6210 can be rotated between an engaged position in which the lock sleeve 6210 couples the first articulation driver 5310 to the firing member assembly 6110 and a disengaged position in which the first articulation driver 5310 is not operably coupled to the firing member assembly 6110. As was discussed above, the intermediate firing shaft portion 6120 of the firing member assembly 6110 is formed with a drive notch 6126. The lock sleeve 6210 comprises a cylindrical, or an at least substantially cylindrical, body that includes a longitudinal aperture that is configured to receive the intermediate firing shaft portion 6120 therethrough. The lock sleeve 6210 can comprise diametrically-opposed, inwardly-facing lock protrusions 6214, 6216 that, when the lock sleeve 6210 is in one position, are engagingly received within corresponding portions of the drive notch 6126 in the intermediate firing shaft portion 6120 and, when in another position, are not received within the drive notch 6126 to thereby permit relative axial motion between the lock sleeve 6210 and the intermediate firing shaft 6120 as was discussed in further detail above. The lock sleeve 6210 further includes a lock member 6218 that is sized to be movably received within a notch 5319 in a proximal end of the first articulation driver 5310. When the lock sleeve 6210 is in its engaged position, the lock protrusions 6214, 6216 are positioned within the drive notch 6126 in the intermediate firing shaft portion 6120 such that a distal pushing force and/or a proximal pulling force can be transmitted from the firing member assembly 6110 to the lock sleeve 6210. Such axial pushing or pulling motion is then transmitted from the lock sleeve 6210 to the first articulation driver 5310. Axial movement of the first articulation driver 5310 results in the axial movement of the second articulation driver 5320 in an opposite direction to thereby articulate the surgical end effector 5500.

As was discussed above, in the illustrated example, relative movement of the lock sleeve 6210 between its engaged and disengaged positions may be controlled by the shifter assembly 6200 that interfaces with the proximal closure tube 5910 of the proximal closure assembly 5900. The shifter assembly 6200 further includes a shifter key 6240 that is configured to be slidably received within a key groove (similar to the key groove 2217 illustrated in FIG. 8) formed in the outer perimeter of the lock sleeve 6210. Such arrangement enables the shifter key 6240 to move axially with respect to the lock sleeve 6210. Operation of the shifter assembly 6200 may be identical to the operation of the shifter assembly 2200 which was described in further detail above and which will not be repeated again for brevity. Further details, alternative arrangements and drive configurations that may be employed are disclosed in Other arrangements that may be employed are disclosed in U.S. patent application Ser. No. 15/385,911, entitled SURGICAL STAPLE/FASTENERS WITH INDEPENDENTLY ACTUATABLE CLOSING AND FIRING SYSTEMS, now U.S. Pat. No. 10,448,950, U.S. patent application Ser. No. 13/803,086, now U.S. Patent Application Publication No. 2014/0263541, and U.S. patent application Ser. No. 15/019,196, now U.S. Pat. No. 10,413,291, the as well as other disclosures that have been incorporated herein.

The interchangeable tool assembly 5000 can comprise a slip ring assembly 5230 which can be configured to conduct electrical power to and/or from the surgical end effector 5500 and/or communicate signals to and/or from the surgical end effector 5500, back to a microprocessor 560 in the handle assembly 500 or robotic system controller, for example as was discussed above. Further details concerning the slip ring assembly 5230 and associated connectors may be found in U.S. patent application Ser. No. 13/803,086, now U.S. Patent Application Publication No. 2014/0263541, and U.S. patent application Ser. No. 15/019,196, now U.S. Pat. No. 10,413,291, which have each been herein incorporated by reference in their respective entirety as well as in U.S. patent application Ser. No. 13/800,067, entitled STAPLE CARTRIDGE TISSUE THICKNESS SENSOR SYSTEM, now U.S. Patent Application Publication No. 2014/0263552, which is hereby incorporated by reference herein in its entirety.

The illustrated interchangeable surgical tool assembly 5000 also employs a latch system 5220 for removably coupling the interchangeable surgical tool assembly 5000 to the handle frame 506 of the handle assembly 500, for example. The latch system 5220 may be identical to the latch system 1220 described in detail above. The knife bar 6130 may comprise a laminated beam structure that includes at least two beam layers. Such beam layers may comprise, for example, stainless steel bands that are interconnected by, for example, welding or pinning together at their proximal ends and/or at other locations along their length. In alternative embodiments, the distal ends of the bands are not connected together to allow the laminates or bands to splay relative to each other when the end effector is articulated. Such arrangement permits the knife bar 6130 to be sufficiently flexible to accommodate articulation of the end effector. Various laminated knife bar arrangements are disclosed in U.S. patent application Ser. No. 15/019,245, entitled SURGICAL INSTRUMENTS WITH CLOSURE STROKE REDUCTION ARRANGEMENTS, now U.S. Pat. No. 10,470,764, which is hereby incorporated by reference in its entirety. As can also be seen in FIG. 21, a firing shaft support assembly 6300 is employed to provide lateral support to the knife bar 6130 as it flexes to accommodate articulation of the surgical end effector 5500. Further details concerning the operation of the firing shaft support assembly 6300 and alternative knife bar support arrangements may be found in U.S. patent application Ser. No. 15/019,245, entitled SURGICAL INSTRUMENTS WITH CLOSURE STROKE REDUCTION ARRANGEMENTS, now U.S. Pat. No. 10,470,764, and U.S. patent application Ser. No. 15/019,220, entitled SURGICAL INSTRUMENT WITH ARTICULATING AND AXIALLY TRANSLATABLE END EFFECTOR, now U.S. Pat. No. 10,245,029, which are each hereby incorporated by reference herein in their respective entireties.

Figure 50:
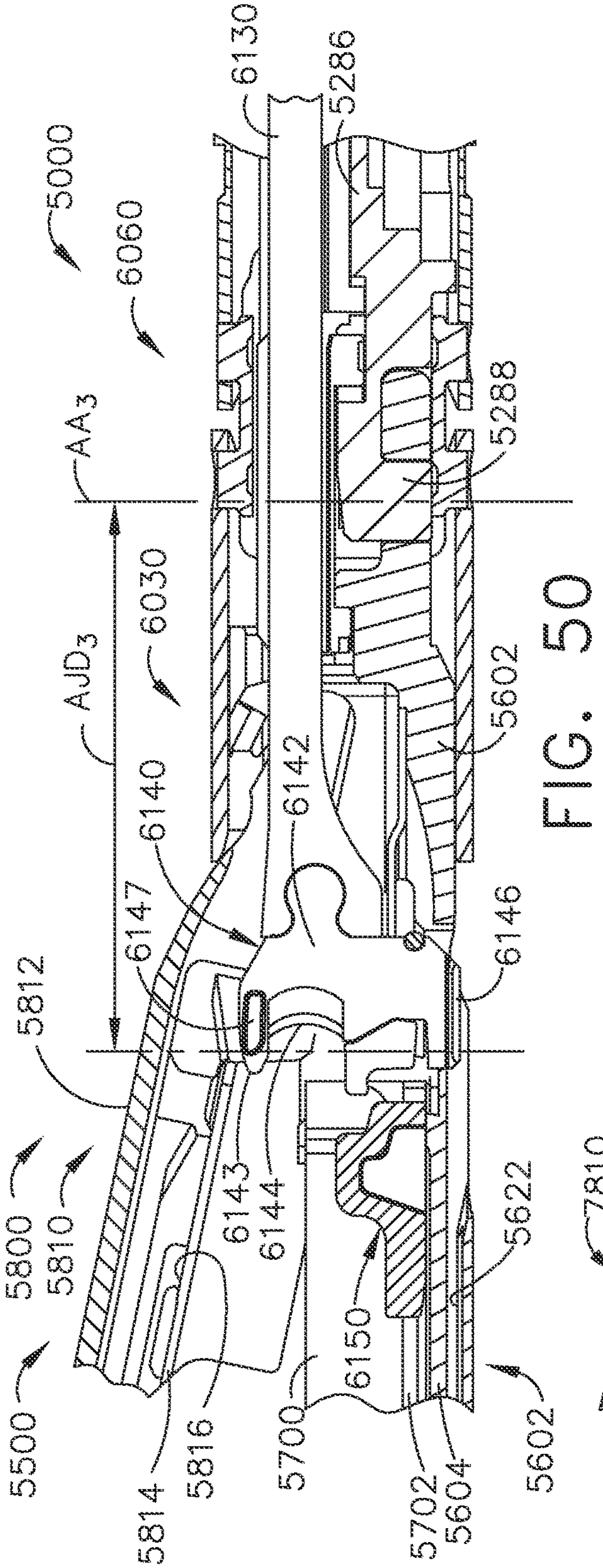
FIG. 50 is a partial cross-sectional view of the anvil mounting portion and elongate channel of the interchangeable surgical tool assembly of FIG. 19 with the anvil in a fully open position.

As can also be seen in FIGS. 21 and 50, a firing member or knife member 6140 is attached to the distal end of the knife bar 6130. The firing member 6140 is configured to operably interface with a sled assembly 6150 that is operably supported within the body 5702 of the surgical staple/fastener cartridge 5700. The sled assembly 6150 is slidably displaceable within the surgical staple/fastener cartridge body 5702 from a proximal starting position adjacent a proximal end 5704 of the cartridge body 5702 to an ending position adjacent a distal end 5706 of the cartridge body 5702. The cartridge body 5702 operably supports therein a plurality of staple drivers (not shown) that are aligned in rows on each side of a centrally disposed slot 5708. The centrally disposed slot 5708 enables the firing member 6140 to pass therethrough and cut the tissue that is clamped between the anvil 5810 and the staple cartridge 5700. The drivers are associated with corresponding staple pockets that open through the upper deck surface of the cartridge body 5702. Each of the staple drivers supports one or more surgical staple/fastener or fastener (not shown) thereon. The sled assembly includes a plurality of sloped or wedge-shaped cams 6152 wherein each cam corresponds to a particular line of fasteners or drivers located on a side of the slot 5708.

In one exemplary form, the firing member 6140 comprises a body portion 6142 that supports a knife or tissue cutting portion 6144. See FIG. 50. The body portion 6142 protrudes through an elongate slot 5604 in the elongate channel 5602 and terminates in a foot member 6146 that extends laterally on each side of the body portion 6142. As the firing member 6140 is driven distally through the surgical staple/fastener cartridge 5700, the foot member 6146 rides within a passage 5622 in the elongate channel 5602 that is located under the surgical staple/fastener cartridge 5700. The tissue cutting portion 6144 is disposed between a distally protruding top nose portion 6143. As can be further seen in FIGS. 21 and 50, the firing member 6140 may further include two laterally extending top tabs, pins or anvil engagement features 6147. As the firing member 6140 is driven distally, a top portion of the body portion 6142 extends through a centrally disposed anvil slot 5814 and the anvil engagement features 6147 ride on corresponding ledges 5816 formed on each side of the anvil slot 5814. Further details concerning the firing member 6140, sled assembly 6150, and their various alternatives as well as examples of their operation will be discussed in further detail below and may also be found in U.S. patent application Ser. No. 15/385,911, entitled SURGICAL STAPLE/FASTENERS WITH INDEPENDENTLY ACTUATABLE CLOSING AND FIRING SYSTEMS, now U.S. Pat. No. 10,448,950. The interchangeable surgical tool assembly 5000 may be operably coupled to the handle assembly 500 in the manner as described above with respect to the interchangeable surgical tool assembly 1000.

Figure 22:
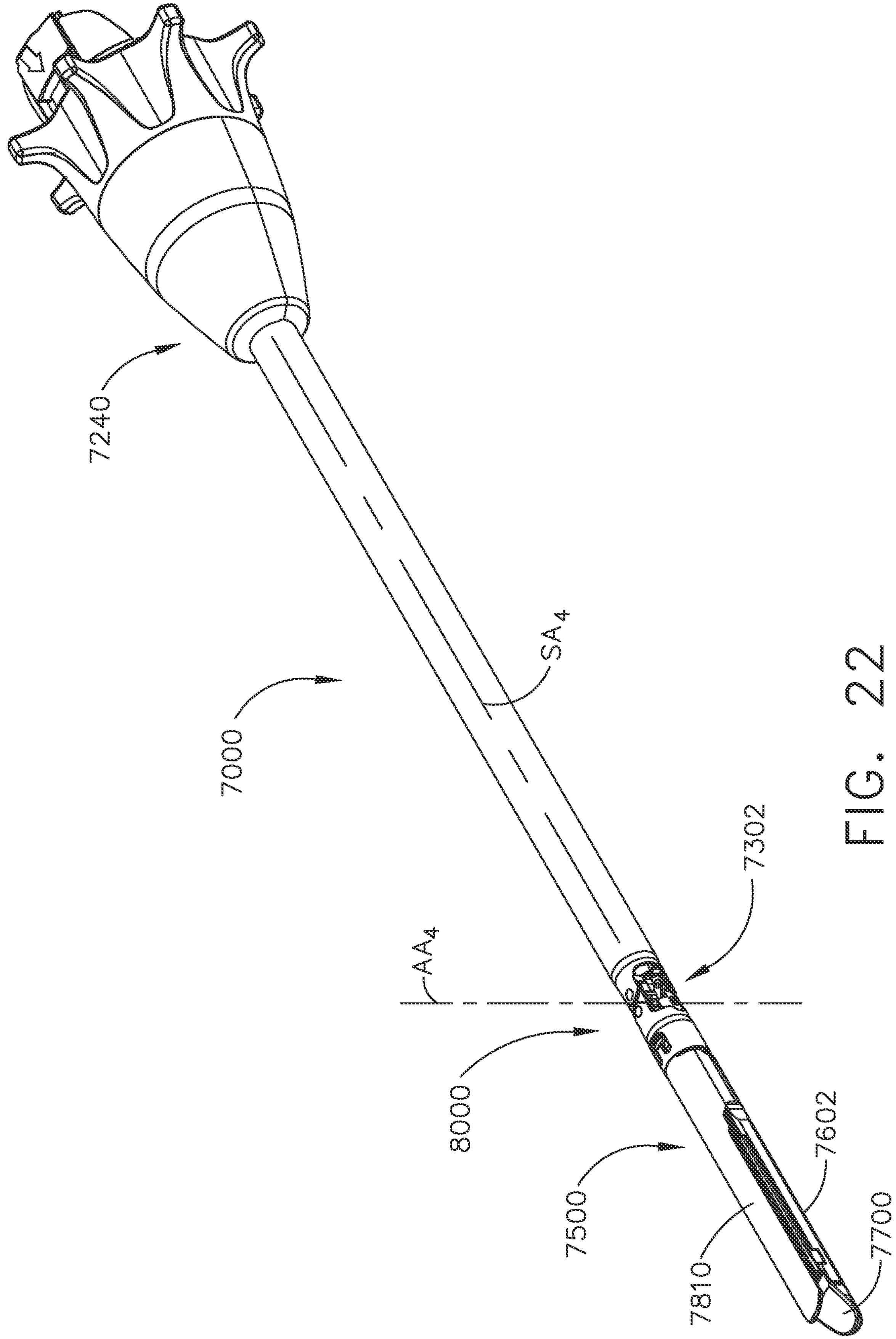
FIG. 22 is a perspective view of another one of the interchangeable surgical tool assemblies depicted in FIG. 1.
Figure 23:
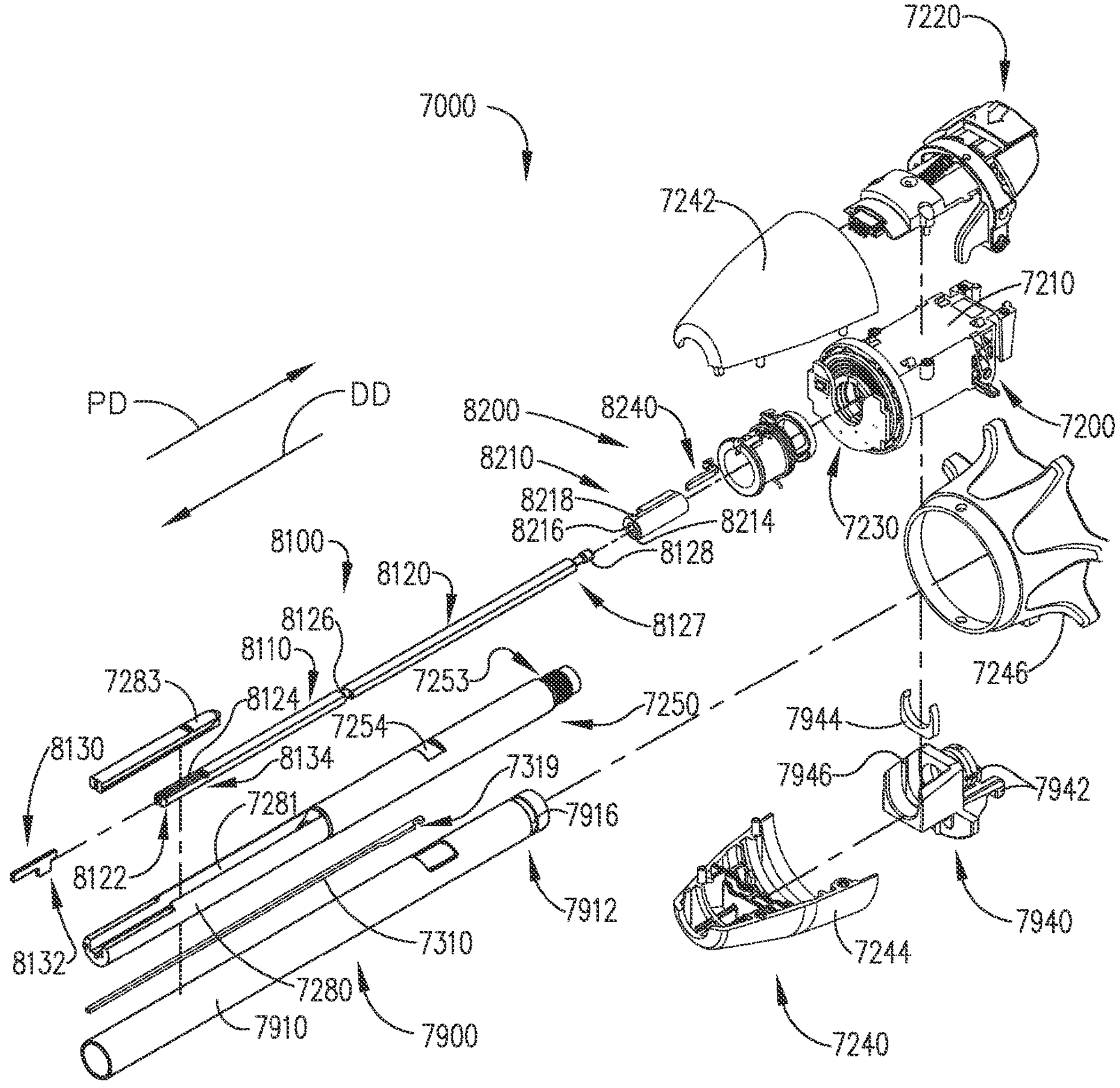
FIG. 23 is an exploded assembly view of a proximal portion of the interchangeable surgical tool assembly of FIG. 22.
Figure 24:
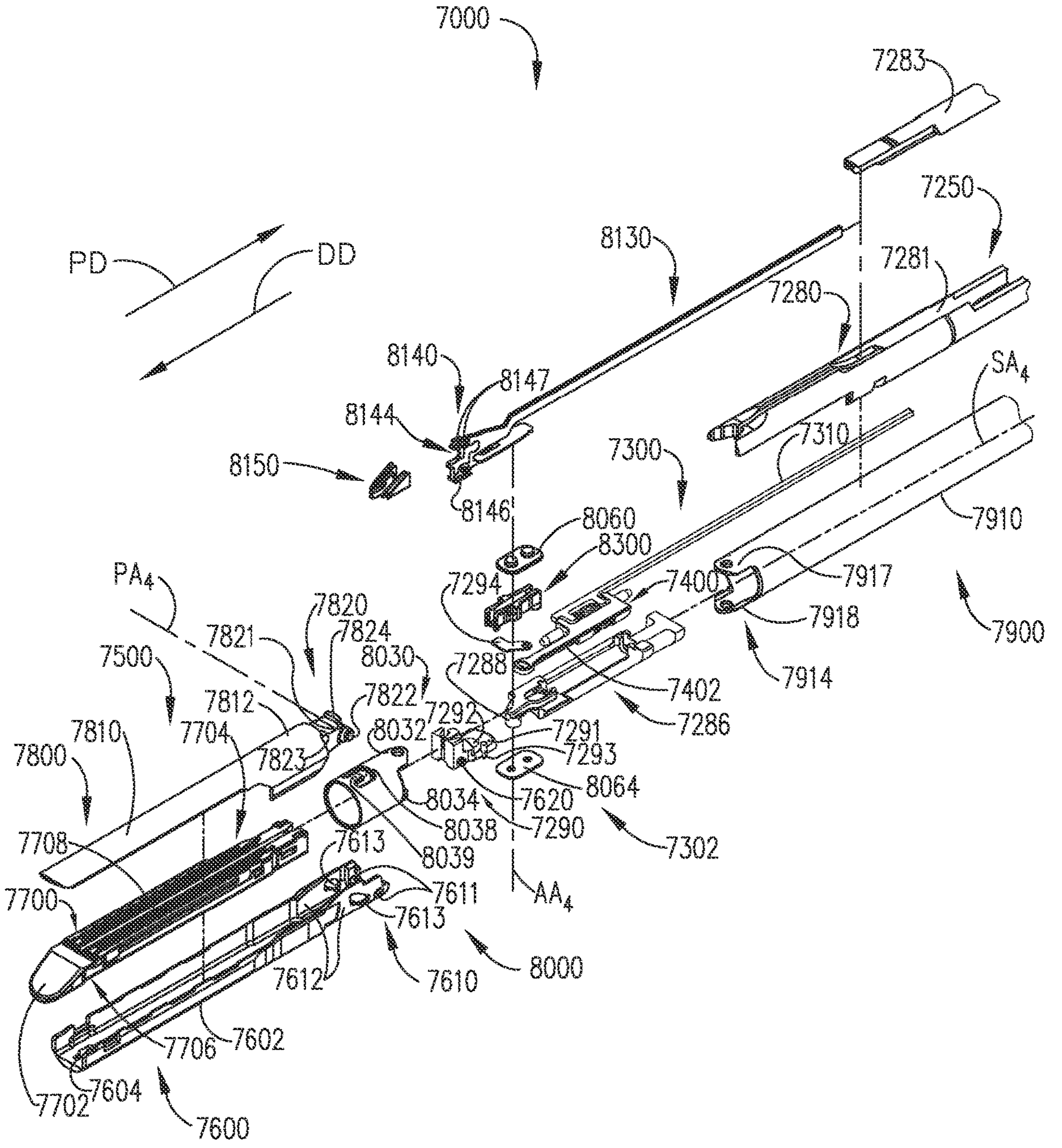
FIG. 24 is another exploded assembly view of a distal portion of the interchangeable surgical tool assembly of FIGS. 22 and 23.

Returning again to FIG. 1, as was discussed above, the surgical system 10 illustrated in that Figure includes four interchangeable surgical tool assemblies 1000, 3000, 5000 and 7000 that may each be effectively employed with the same handle assembly 500 to perform different surgical procedures. Turning now to FIGS. 22-24, the interchangeable surgical tool assembly 7000 includes a surgical end effector 7500 that comprises a first jaw 7600 and a second jaw 7800. In one arrangement, the first jaw comprises an elongate channel 7602 that is configured to operably support a surgical staple/fastener cartridge 7700 therein. The second jaw 7800 comprises an anvil 7810 that is movably supported relative to the elongate channel 7602. The interchangeable surgical tool assembly 7000 includes an articulation system 7300 that comprises an articulation joint 7302 and an articulation lock 7400 which can be configured to releasably hold the surgical end effector 7500 in a desired articulated position relative to a shaft axis $SA_4$. Details regarding the construction and operation of the articulation lock 7400 as well as alternative lock configurations and operational details may be found in in U.S. patent application Ser. No. 13/803,086, entitled ARTICULATABLE SURGICAL INSTRUMENT COMPRISING AN ARTICULATION LOCK, now U.S. Patent Application Publication No. 2014/0263541, the entire disclosure of which is hereby incorporated by reference herein. Additional details concerning the articulation lock 7400 and/or alternative articulation lock arrangements may also be found in U.S. patent application Ser. No. 15/019,196, filed Feb. 9, 2016, entitled SURGICAL INSTRUMENT ARTICULATION MECHANISM WITH SLOTTED SECONDARY CONSTRAINT, now U.S. Pat. No. 10,413,291, the entire disclosure of which is hereby incorporated by reference herein.

As can be seen in FIG. 24, the interchangeable surgical tool assembly 7000 includes a tool frame assembly 7200 that comprises a tool chassis 7210 that operably supports a nozzle assembly 7240 thereon. In one form, the nozzle assembly 7240 is comprised of nozzle portions 7242, 7244 as well as an actuator wheel portion 7246 that is configured to be coupled to the assembled nozzle portions 7242, 7244 by snaps, lugs, screws etc. The interchangeable surgical tool assembly 7000 includes a proximal closure assembly 7900 which is operably coupled to a distal closure assembly 8000 that is utilized to close and/or open the anvil 7810 of the surgical end effector 7500 as will be discussed in further detail below. In addition, the interchangeable surgical tool assembly 7000 includes a spine assembly 7250 that operably supports the proximal closure assembly 7900 and is coupled to the surgical end effector 3500. In the illustrated arrangement, the spine assembly 7250 includes a distal end portion 7280 that has an opening 7281 therein for ease of assembly. A spine cap 7283 may be attached thereto to cover the opening 7281 after the various components have been assembled therein. In assembled form, a proximal end portion 7253 of the spine assembly 7250 is rotatably supported in the tool chassis 7210. In one arrangement, for example, the proximal end of the proximal end portion 7253 of the spine assembly 7250 is attached to a spine bearing (not shown) that is configured to be supported within the tool chassis 7210. Such arrangement facilitates rotatable attachment of the spine assembly 7250 to the tool chassis 7210 such that the spine assembly 7250 may be selectively rotated about the shaft axis $SA_4$ relative to the tool chassis 7210. In particular, in one arrangement, for example, the proximal end portion 7253 of the spine assembly 7250 includes two diametrically opposed lug seats 7254 (only one can be seen in FIG. 23) that are each configured to receive a corresponding nozzle lug (not shown) that extend inwardly from each of the nozzle portions 7242, 7244. Such arrangement facilitates rotation of the spine assembly 7250 about the shaft axis $SA_4$ by rotating the actuator wheel portion 7246 of the nozzle assembly 7240.

Referring now to FIG. 24, the distal end portion 7280 of the spine assembly 7250 is attached to a distal frame segment 7286 that operably supports the articulation lock 7400 therein. The spine assembly 7250 is configured to, one, slidably support a firing member assembly 8110 therein and, two, slidably support a proximal closure tube 7910 which extends around the spine assembly 7250. The spine assembly 7250 can also be configured to slidably support a proximal articulation driver 7310. As can be seen in FIG. 24, the distal frame segment 7286 is pivotally coupled to the elongate channel 7602 by an end effector mounting assembly 7290. In one arrangement, for example, the distal end of the distal frame segment 7286 has a pivot pin 7288 formed thereon. The pivot pin 7288 is adapted to be pivotally received within a pivot hole 7292 formed in pivot base portion 7291 of the end effector mounting assembly 7290. The end effector mounting assembly 7290 is attached to a proximal end portion 7610 of the elongate channel 7602 by a spring pin 7620 or other suitable member that is received within mounting holes 7611 in the proximal end portion 7610. The pivot pin 7288 defines an articulation axis $AA_4$ that is transverse to the shaft axis $SA_4$. See FIG. 24. Such arrangement facilitates pivotal travel (i.e., articulation) of the surgical end effector 7500 about the articulation axis $AA_4$ relative to the spine assembly 7250. The distal frame segment 7286 is further configured to support the articulation lock 7400 therein. Various articulation lock arrangements may be employed. At least one form of articulation lock 7400 is described in further detail in U.S. patent application Ser. No. 13/803,086, entitled ARTICULATABLE SURGICAL INSTRUMENT COMPRISING AN ARTICULATION LOCK, now U.S. Patent Application Publication No. 2014/0263541, the entire disclosure of which is hereby incorporated by reference herein. Additional details concerning the articulation lock may also be found in U.S. patent application Ser. No. 15/019,196, filed Feb. 9, 2016, entitled SURGICAL INSTRUMENT ARTICULATION MECHANISM WITH SLOTTED SECONDARY CONSTRAINT, now U.S. Pat. No. 10,413,291.

In the illustrated example, the surgical end effector 7500 is electively articulatable about the articulation axis $AA_4$ by the articulation system 7300. In one form, the articulation system 7300 includes the proximal articulation driver 7310 that operably interfaces with the articulation lock 7400. The articulation lock 7400 includes an articulation frame 7402 that is adapted to operably engage a drive pin 7293 on the pivot base portion 7291 of the end effector mounting assembly 7290. In addition, a cross link 7294 may be linked to the drive pin 7293 and articulation frame 7402 to assist articulation of the surgical end effector 7500. As indicated above, further details regarding the operation of the articulation lock 7400 and the articulation frame 7402 may be found in U.S. patent application Ser. No. 13/803,086, now U.S. Patent Application Publication No. 2014/0263541. Further details regarding the end effector mounting assembly and cross link 7294 may be found in U.S. patent application Ser. No. 15/019,245, filed Feb. 9, 2016, entitled SURGICAL INSTRUMENTS WITH CLOSURE STROKE REDUCTION ARRANGEMENTS, now U.S. Pat. No. 10,470,764, the entire disclosure of which is hereby incorporated by reference herein. As further described therein, as well as in other disclosures incorporated by reference herein, axial movement of proximal articulation driver 7310 will result in the engagement/disengagement of the articulation lock 7400 to thereby apply articulation motions to the elongate channel 7602 and thereby cause the surgical end effector 7500 to articulate about the articulation axis $AA_4$ relative to the spine assembly 7250.

The anvil 7810 in the illustrated example includes an anvil body 7812 that terminates in anvil mounting portion 7820. The anvil mounting portion 7820 is movably supported on the elongate channel 7602 for selective pivotal and axial travel relative thereto. In the illustrated arrangement, an anvil trunnion 7822 extends laterally out of each lateral side of the anvil mounting portion 7820 to be received in a corresponding "kidney-shaped" opening 7613 formed in upstanding walls 7612 of the proximal end portion 7610 of the elongate channel 7602. Movement of the anvil 7810 relative to the elongate channel 7602 is effectuated by axial movement of the proximal closure assembly 7900 and the distal closure assembly 8000. In the illustrated arrangement, the proximal closure assembly 7900 comprises the proximal closure tube 7910 that has a proximal end 7912 and a distal end 7914. The proximal end 7912 is rotatably supported in a closure shuttle 7940 that is slidably supported within the tool chassis 7210 such that it may be axially moved relative thereto. In one form, the closure shuttle 7940 includes a pair of proximally-protruding hooks 7942 that are configured for attachment to the transverse attachment pin 516 that is attached to the closure linkage assembly 514 of the handle assembly 500. The proximal end 7912 of the proximal closure tube 7910 is coupled to the closure shuttle 7940 for relative rotation thereto. For example, a U-shaped connector 7944 is inserted into an annular slot 7916 in the proximal end 7912 of the proximal closure tube 7910 and is retained within vertical slots 7946 in the closure shuttle 7940. Such arrangement serves to attach the proximal closure assembly 7900 to the closure shuttle 7940 for axial travel therewith while enabling the proximal closure tube 7910 to rotate relative to the closure shuttle 7940 about the shaft axis $SA_4$. As was discussed above in connection with the interchangeable surgical tool assembly 1000, a closure spring (not shown) may extend over the proximal end 7912 of the proximal closure tube 7910 to bias the closure shuttle 7940 in the proximal direction PD which can serve to pivot the closure trigger 512 on the handle assembly 500 (FIG. 2) into the unactuated position when the interchangeable surgical tool assembly 7000 is operably coupled to the handle assembly 500 in the above described manner.

As can be seen in FIG. 24, the distal end 7914 of the proximal closure tube 3910 is attached to the distal closure assembly 8000. The distal end 7914 includes upper and lower tangs 7917, 7918 that are configured to be movably coupled to an end effector closure sleeve or distal closure tube segment 8030. The distal closure tube segment 8030 includes an upper tang 8032 and a lower tang 8034 that protrude proximally from a proximal end thereof. An upper double pivot link 8060 pivotally couples the upper tangs 7917 and 8032 and a lower double pivot link 8064 pivotally couples the lower tangs 7918 and 8034 together in the above-described manner. The distal advancement of the distal closure tube segment 8030 on the anvil mounting portion 7820 will result in closure or pivotal travel of the anvil 7810 towards the elongate channel 7602. In the illustrated arrangement, an upstanding anvil tab 7824 is formed on the anvil mounting portion 7820 and extends into a horseshoe-shaped opening 8038. Opening 8038 defines an opening tab 8039 configured to operably interface with the anvil tab 7824 as the distal closure tube is retracted in the distal direction. Such interaction between the opening tab 8039 and the anvil tab 7824 applies an opening motion to the anvil 7810 to thereby cause the anvil 7810 to move to an open position.

In the illustrated arrangement, the interchangeable surgical tool assembly 7000 further includes a firing system generally designated as 8100. In various instances, the firing system 8100 includes the firing member assembly 8110 that is supported for axial travel within the spine assembly 7250. In the illustrated embodiment, the firing member assembly 8110 includes an intermediate firing shaft portion 8120 that is configured for attachment to a distal cutting portion or knife bar 8130. The firing member assembly 8110 may also be referred to herein as a "second shaft" and/or a "second shaft assembly". As can be seen in FIG. 24, the intermediate firing shaft portion 8120 may include a longitudinal slot 8124 in a distal end 8122 thereof which can be configured to receive a proximal end 8132 of the knife bar 8130. The longitudinal slot 8124 and the proximal end 8132 of the knife bar 8130 can be sized and configured to permit relative movement therebetween and can comprise a slip joint 8134. The slip joint 8134 can permit the intermediate firing shaft portion 8120 of the firing member assembly 8110 to be moved to articulate the end effector 7500 without moving, or at least substantially moving, the knife bar 8130 as was discussed above. In the illustrated arrangement, a proximal end 8127 of the intermediate firing shaft portion 8120 has a firing shaft attachment lug 8128 formed thereon that is configured to be seated into an attachment cradle (not shown) that is on the distal end of the longitudinally movable drive member (not shown) of the firing drive system 530 within the handle assembly 500 as was discussed above. Such arrangement facilitates the axial movement of the intermediate firing shaft portion 8120 upon actuation of the firing drive system 530. Other attachment configurations may also be employed to couple the intermediate firing shaft portion to other firing drive arrangements (e.g., manually actuated, robotic, etc.).

Further to the above, the interchangeable tool assembly 7000 can include a shifter assembly 8200 which can be configured to selectively and releasably couple the proximal articulation driver 7310 to the firing member assembly 8110 in the manner described above. In one form, the shifter assembly 8200 includes a lock collar, or lock sleeve 8210, positioned around the intermediate firing shaft portion 8120 of the firing member assembly 8110 wherein the lock sleeve 8210 can be rotated between an engaged position in which the lock sleeve 8210 couples the proximal articulation driver 7310 to the firing member assembly 8110 and a disengaged position in which the proximal articulation driver 7310 is not operably coupled to the firing member assembly 8110. As was discussed above, the intermediate firing shaft portion 8120 of the firing member assembly 8110 is formed with a drive notch 8126. The lock sleeve 8210 comprises a cylindrical, or an at least substantially cylindrical, body that includes a longitudinal aperture that is configured to receive the intermediate firing shaft portion 8120 therethrough. The lock sleeve 8210 can comprise diametrically-opposed, inwardly-facing lock protrusions 8214, 8216 that, when the lock sleeve 8210 is in one position, are engagingly received within corresponding portions of the drive notch 8126 in the intermediate firing shaft portion 8120 and, when in another position, are not received within the drive notch 8126 to thereby permit relative axial motion between the lock sleeve 8210 and the intermediate firing shaft 8120 as was discussed in further detail above. The lock sleeve 8210 further includes a lock member 8218 that is sized to be movably received within a notch 7319 in a proximal end of the proximal articulation driver 7310. When the lock sleeve 8210 is in its engaged position, the lock protrusions 8214, 8216 are positioned within the drive notch 7126 in the intermediate firing shaft portion 8120 such that a distal pushing force and/or a proximal pulling force can be transmitted from the firing member assembly 8110 to the lock sleeve 8210. Such axial pushing or pulling motion is then transmitted from the lock sleeve 8210 to the proximal articulation driver 7310 to thereby articulate the surgical end effector 7500.

As was discussed above, in the illustrated example, relative movement of the lock sleeve 8210 between its engaged and disengaged positions may be controlled by the shifter assembly 8200 that interfaces with the proximal closure tube 7910 of the proximal closure assembly 7900. The shifter assembly 8200 further includes a shifter key 8240 that is configured to be slidably received within a key groove (similar to the key groove 2217 illustrated in FIG. 8) formed in the outer perimeter of the lock sleeve 8210. Such arrangement enables the shifter key 8240 to move axially with respect to the lock sleeve 8210. Operation of the shifter assembly 8200 may be identical to the operation of the shifter assembly 2200 which was described in further detail above and which will not be repeated again for brevity. Further details, alternative arrangements and drive configurations that may be employed are disclosed in Other arrangements that may be employed are disclosed in U.S. patent application Ser. No. 15/385,911, entitled SURGICAL STAPLE/FASTENERS WITH INDEPENDENTLY ACTUATABLE CLOSING AND FIRING SYSTEMS, now U.S. Pat. No. 10,448,950, U.S. patent application Ser. No. 13/803,086, now U.S. Patent Application Publication No. 2014/0263541, and U.S. patent application Ser. No. 15/019,196, now U.S. Pat. No. 10,413,291, the as well as other disclosures that have bee incorporated herein.

The interchangeable tool assembly 7000 can comprise a slip ring assembly 7230 which can be configured to conduct electrical power to and/or from the surgical end effector 7500 and/or communicate signals to and/or from the surgical end effector 7500, back to a microprocessor 560 in the handle assembly 500 or robotic system controller, for example as was discussed above. Further details concerning the slip ring assembly 7230 and associated connectors may be found in U.S. patent application Ser. No. 13/803,086, now U.S. Patent Application Publication No. 2014/0263541, and U.S. patent application Ser. No. 15/019,196, now U.S. Pat. No. 10,413,291, which have each been herein incorporated by reference in their respective entirety as well as in U.S. patent application Ser. No. 13/800,067, entitled STAPLE CARTRIDGE TISSUE THICKNESS SENSOR SYSTEM, now U.S. Patent Application Publication No. 2014/0263552, which is hereby incorporated by reference herein in its entirety.

The illustrated interchangeable surgical tool assembly 7000 also employs a latch system 7220 for removably coupling the interchangeable surgical tool assembly 7000 to the handle frame 506 of the handle assembly 500, for example. The latch system 7220 may be identical to the latch system 1220 described in detail above. The knife bar 8130 may comprise a laminated beam structure that includes at least two beam layers. Such beam layers may comprise, for example, stainless steel bands that are interconnected by, for example, welding or pinning together at their proximal ends and/or at other locations along their length. In alternative embodiments, the distal ends of the bands are not connected together to allow the laminates or bands to splay relative to each other when the end effector is articulated. Such arrangement permits the knife bar 8130 to be sufficiently flexible to accommodate articulation of the end effector. Various laminated knife bar arrangements are disclosed in U.S. patent application Ser. No. 15/019,245, entitled SURGICAL INSTRUMENTS WITH CLOSURE STROKE REDUCTION ARRANGEMENTS, now U.S. Pat. No. 10,470,764, which is hereby incorporated by reference in its entirety. As can also be seen in FIG. 24, a firing shaft support assembly 8300 is employed to provide lateral support to the knife bar 8130 as it flexes to accommodate articulation of the surgical end effector 7500. Further details concerning the operation of the firing shaft support assembly 8300 and alternative knife bar support arrangements may be found in U.S. patent application Ser. No. 15/019,245, entitled SURGICAL INSTRUMENTS WITH CLOSURE STROKE REDUCTION ARRANGEMENTS, now U.S. Pat. No. 10,470,764, and U.S. patent application Ser. No. 15/019,220, entitled SURGICAL INSTRUMENT WITH ARTICULATING AND AXIALLY TRANSLATABLE END EFFECTOR, now U.S. Pat. No. 10,245,029, which are each hereby incorporated by reference herein in their respective entireties.

As can also be seen in FIG. 24, a firing member or knife member 8140 is attached to the distal end of the knife bar 8130. The firing member 8140 is configured to operably interface with a sled assembly 8150 that is operably supported within the body 7702 of the surgical staple/fastener cartridge 7700. See FIG. 51. The sled assembly 8150 is slidably displaceable within the surgical staple/fastener cartridge body 7702 from a proximal starting position adjacent a proximal end 7704 of the cartridge body 7702 to an ending position adjacent a distal end 7706 of the cartridge body 7702. The cartridge body 7702 operably supports therein a plurality of staple drivers (not shown) that are aligned in rows on each side of a centrally disposed slot 7708. The centrally disposed slot 7708 enables the firing member 8140 to pass therethrough and cut the tissue that is clamped between the anvil 7810 and the staple cartridge 7700. The drivers are associated with corresponding staple pockets that open through the upper deck surface of the cartridge body 7702. Each of the staple drivers supports one or more surgical staple/fastener or fastener (not shown) thereon. The sled assembly includes a plurality of sloped or wedge-shaped cams wherein each cam corresponds to a particular line of fasteners or drivers located on a side of the slot 7708.

In one exemplary form, the firing member 8140 comprises a body portion 8142 that supports a knife or tissue cutting portion 8144. See FIG. 51. The body portion 8142 protrudes through an elongate slot 7604 in the elongate channel 7602 and terminates in a foot member 8146 that extends laterally on each side of the body portion 8142. As the firing member 8140 is driven distally through the surgical staple/fastener cartridge 7700, the foot member 8146 rides within a passage 7622 in the elongate channel 7602 that is below the staple cartridge 7700. The tissue cutting portion 8144 is disposed between a distally protruding top nose portion 8143. As can be further seen in FIG. 24, the firing member 8140 may further include two laterally extending top tabs, pins or anvil engagement features 8147. As the firing member 8140 is driven distally, a top portion of the body portion 8142 extends through a centrally disposed anvil slot 7814 and the anvil engagement features 8147 ride on corresponding ledges 7816 formed on each side of the anvil slot 7814. Further details concerning the firing member 8140, sled assembly 8150, and their various alternatives as well as examples of their operation will be discussed in further detail below and may also be found in U.S. patent application Ser. No. 15/385,911, entitled SURGICAL STAPLE/FASTENERS WITH INDEPENDENTLY ACTUATABLE CLOSING AND FIRING SYSTEMS, now U.S. Pat. No. 10,448,950. The interchangeable surgical tool assembly 7000 may be operably coupled to the handle assembly 500 in the manner as described above with respect to the interchangeable surgical tool assembly 1000.

As can be appreciated from the foregoing descriptions, the interchangeable surgical tool assemblies described herein may be actuated by the same handle assembly, robotic system or other automated actuation system. All of the above described interchangeable surgical tool assemblies comprise surgical cutting and fastening instruments that have somewhat similar closure and firing components. However, the closure and firing systems and components of each of these tool assemblies have differences that may seem somewhat subtle at first blush, but, as will be further discussed below, such differences can result in significant improvements in the material composition, design, construction, manufacture and use of such tools. As will become apparent as the present Detailed Description proceeds, the interchangeable surgical tool assembly 1000 contains subtle design differences when compared to the other interchangeable surgical tool assemblies 3000, 5000, 7000 described herein that can result in significant improvements in the overall functionality, reliability, and cost of the tool assembly. Moreover, we have discovered that, in some cases, a synergistic effect exists between certain component arrangements employed by the tool assembly 1000 which can further enhance the overall efficiency and functionality of the tool assembly 1000. In order to better understand these differences and improvements, certain components and systems of each of the tool assemblies 1000, 3000, 5000, 7000 will now be further described and compared to each other below.

For example, each of the interchangeable surgical tool assemblies 1000, 3000, 5000, 7000 must be able to apply a sufficient amount of closure force to cause the jaws to sufficiently clamp the target tissue so as to permit the firing member to properly treat the clamped tissue upon actuation of the firing drive system. For example, in the illustrated assemblies, the respective closure system components must be able to clamp the anvil and surgical staple/fastener cartridge onto the target tissue to enable the firing member to properly sever the clamped tissue and eject lines of staples or fasteners on each side of the tissue cut line. Depending upon the thickness and composition of the target tissue, significant closure forces and firing forces are often required. Thus, the closure and firing drive systems in the handle assembly housing, robotic housing, etc. must be able to generate such forces of sufficient magnitude (through the use of a motor or manually generated motion, for example) to sufficiently close the jaws and fire the firing member through the clamped tissue. Such procedures further require that the components within the interchangeable shaft assemblies to be sufficiently robust to accommodate the magnitudes of the forces being transmitted therethrough. In the past, the magnitudes of such forces often dictated that the closure system components, as well as the firing system components, be fabricated from metal or other suitable materials with relatively large cross-sectional thicknesses and of substantial reinforced configurations.

The tissue loads encountered during the clamping process typically create a large "moment" about the anvil pivot axis PA. The closure system components must be designed to counteract such moment. In various circumstances, for example, a moment about the anvil pivot axis PA in the opposite direction is needed. To maximize the efficiency of the system (e.g., minimize the magnitude of the force applied), the largest practical moment arm is desired. However, as will be further discussed below, there are trade-offs with other design variables when seeking to establish a large counter moment. For example, there is a balance between the distance from the articulation joint to the first staple and the length of the moment arm for a closure system where the firing and closing systems are separate and distinct. The larger the moment arm of the closure system, the more efficiently it handles clamp loads and tissue compression. However, the distance between the articulation joint and the first staple may have a large impact on the access of the surgical end effector as it is positioned into tight spaces within a laparoscopic environment.

Figure 25:
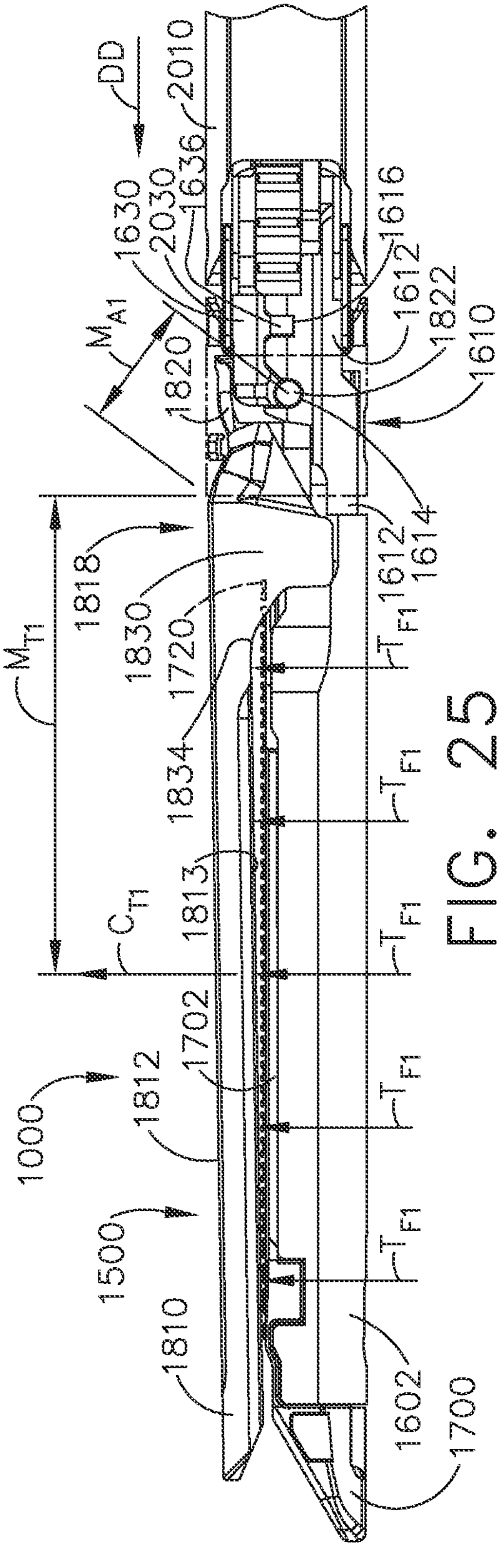
FIG. 25 is a side elevational view of a distal portion of the interchangeable surgical tool assembly of FIG. 3 with the anvil thereof in a fully closed position.

FIGS. 25-32 illustrate exemplary moment arms for each of the surgical end effectors 1500, 3500, 5500, 7500. Turning first to FIG. 25, as was described above, the anvil trunnions 1822 extend laterally out of each lateral side of the anvil mounting portion 1820 to be received in a corresponding trunnion cradle 1614 formed in the upstanding walls 1612 of the proximal end portion 1610 of the elongate channel 1602. The anvil trunnions 1822 are pivotally retained in their corresponding trunnion cradle 1614 by the channel cap or anvil retainer 1630. The channel cap 1630 includes a pair of attachment lugs 1636 that are configured to be retainingly received within corresponding lug grooves or notches 1616 formed in the upstanding walls 1612 of the proximal end portion 1610 of the elongate channel 1602. Such arrangement constrains the anvil 1810 to only pivot about the pivot axis $PA_1$ (see FIG. 3). Under such arrangement, the anvil mounting portion 1820 does not move axially or vertically. As the distal closure tube segment 2030 is advanced in the distal direction DD under a horizontal closure force $F_{H1}$ (FIG. 26), the interaction between an internal cam surface 2036 on the distal closure tube segment 2030 and an anvil cam surface 1821 on the anvil mounting portion 1820 results in the application of a closure force $F_{C1}$ to the anvil cam surface 1821. The closure force $F_{C1}$ comprises the resultant force of the horizontal closure force $F_{H1}$ and a vertical closure force $F_{V1}$ and is essentially "normal to" or perpendicular to the cam surface 1821 on the anvil mounting portion 1820. See FIG. 26. $M_{A1}$ represents a closure moment arm from the anvil pivot axis $PA_1$ (coincident with the center of anvil trunnions 1822) to the point of contact between the internal cam surface 2036 on the distal closure tube segment 2030 and the anvil cam surface 1821 on the anvil mounting portion 1820 when the anvil 1810 has been pivoted to the fully closed position. In one example, the closure moment arm $M_{A1}$ may be approximately 0.415 inches, for example. $M_{A1} \times F_{C1}$=a closure moment $C_{M1}$ that is applied to the anvil mounting portion 1820.

Figure 26:
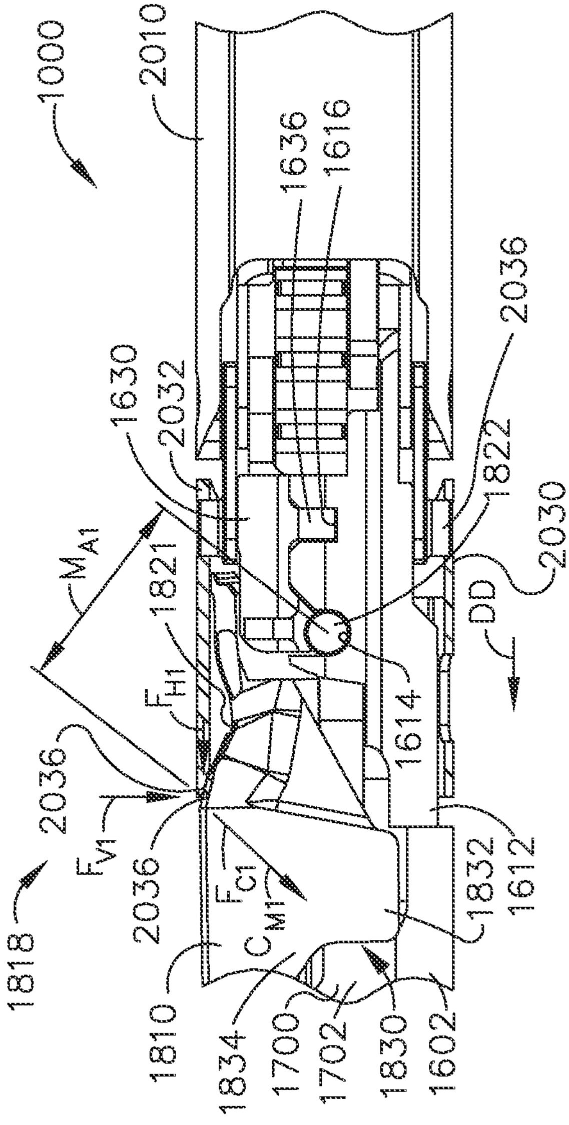
FIG. 26 is an enlarged side elevational view of the anvil mounting portion and elongate channel of the interchangeable surgical tool assembly of FIG. 25.

To ensure that the each side of the tissue cut line is fastened with staples or fasteners extending from the proximal end to the distal end of the tissue cutline, a proximal end portion 1818 of the anvil body 1812 is formed with two tissue stop formations or tissue locating features 1830 that extend downwardly from each lateral side of the anvil body 1812 (only one tissue stop formation 1830 may be seen in FIGS. 25 and 26). When the anvil 1810 is opened to receive the target tissue between the underside of the anvil and the cartridge deck surface, the downwardly extending tissue stop 1830 serve to prevent the target tissue from extending proximally past the proximal most staples/fasteners in the surgical staple/fastener cartridge 1700. If the tissue were to extend proximally beyond the proximal most staples/fasteners, that portion of tissue may be severed by the firing member during the firing process and may not be fastened which may lead to catastrophic results. The downwardly extending tissue stops 1830 may prevent this from happening. In the embodiment depicted in FIG. 26, for example, the proximal-most staple/fastener pockets 1720 are shown in phantom lines relative to the tissue stops 1830. As can be seen in that Figure, the tissue stop 1830 has a downwardly extending portion 1832 and a chamfered portion 1834. The target tissue is contacted by the portions 1832, 1834 to prevent the target tissue from extending proximally beyond the proximal most staples/fasteners that are supported in the proximal most staple/fastener pockets 1720 in the staple/fastener cartridge body 1702.

Returning again to FIG. 25, as the anvil 1810 is pivoted closed onto the target tissue (not shown) that is positioned between the underside or tissue contacting surface 1813 of the anvil body 1812, the tissue applies tissue forces $T_{F1}$ to the underside 1813 of the anvil body 1812 which cause the anvil 1810 to experience a tissue counter moment $C_{T1}$ that must be overcome by the closure moment $C_{M1}$ established by the closure system components. The example depicted in FIG. 25 illustrates equally distributed tissue forces $T_{F1}$ on the anvil 1810 and a tissue moment arm $M_{T1}$ established by the clamped tissue (the clamped tissue is not shown in FIG. 25 for clarity purposes). As can be seen in that Figure, in that example, the tissue moment arm $M_{T1}$ is considerably longer than the closure moment arm $M_{A1}$ (i.e., $M_{T1}>M_{A1}$).

Figure 27:
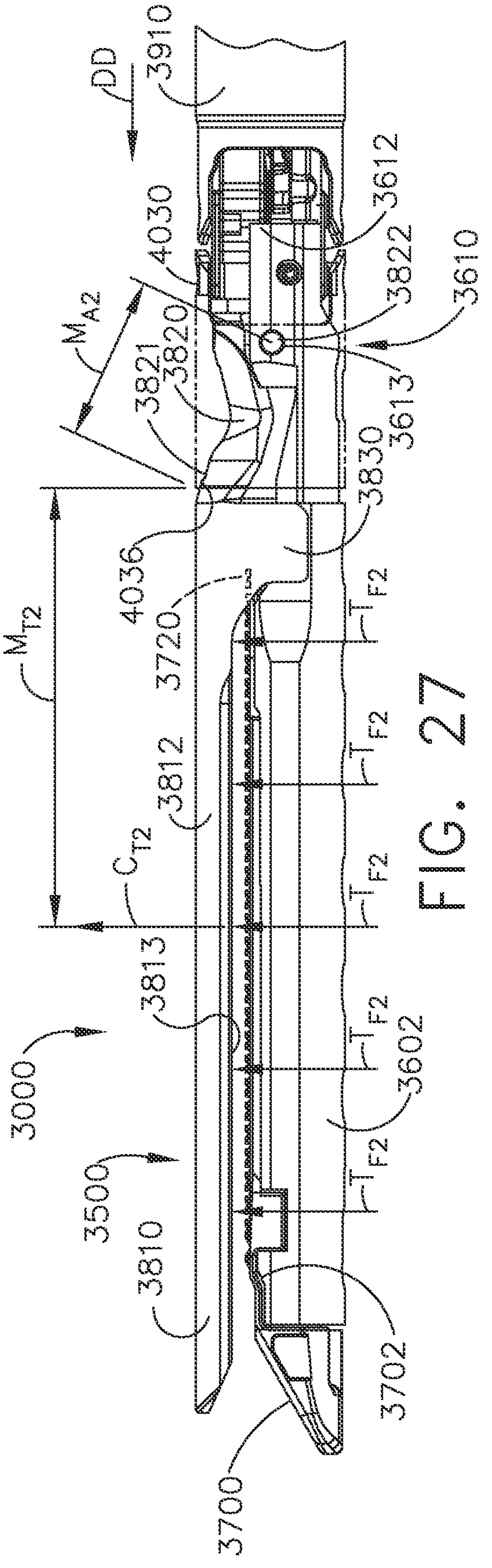
FIG. 27 is a side elevational view of a distal portion of the interchangeable surgical tool assembly of FIG. 16 with the anvil thereof in a fully closed position.
Figure 28:
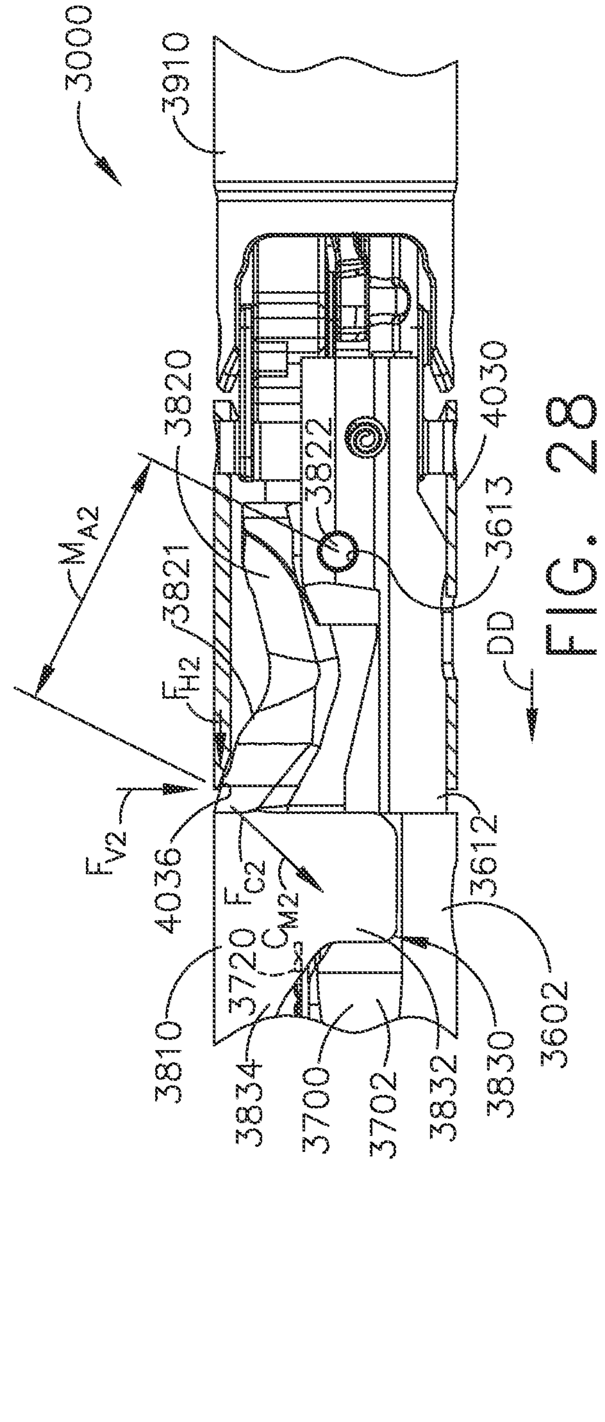
FIG. 28 is an enlarged side elevational view of the anvil mounting portion and elongate channel of the interchangeable surgical tool assembly of FIG. 27.

Turning next to FIGS. 27 and 28, as was described above, the anvil trunnions 3822 of the anvil 3810 of the interchangeable surgical tool assembly 3000 extend laterally out of each lateral side of the anvil mounting portion 3820 to be received in corresponding trunnion holes 3613 formed in the upstanding walls 3612 of the proximal end portion 3610 of the elongate channel 3602. Such arrangement constrains the anvil 3810 to only pivot about the anvil pivot axis $PA_2$ (see FIG. 18). Under such arrangement, the anvil mounting portion 3820 does not move axially or vertically. As the distal closure tube segment 4030 is advanced in the distal direction DD under a horizontal closure force $F_{H2}$ (FIG. 28), the interaction between an internal cam surface 4036 on the distal closure tube segment 4030 and an anvil cam surface 3821 on the anvil mounting portion 3820 results in the application of a closure force $F_{C2}$ to the anvil cam surface 3821. The closure force $F_{C2}$ comprises the resultant force of the horizontal closure force $F_{H2}$ and a vertical closure force $F_{V2}$ and is essentially "normal to" or perpendicular to the anvil cam surface 3821 on the anvil mounting portion 3820. See FIG. 28. $M_{A2}$ represents the closure moment arm from the anvil pivot axis $PA_2$ (center of anvil trunnions 3822) to the point of contact between the internal cam surface 4036 on the distal closure tube 4030 and the anvil cam surface 3821 on the anvil mounting portion 3820 when the anvil 3810 has been pivoted to the fully closed position. In one example, closure moment arm $M_{A2}$ may be approximately 0.539 inches, for example. $M_{A2} \times F_{C2}$=a closure moment $C_{M2}$ that is applied to the anvil mounting portion 3820.

In the example depicted in FIGS. 27 and 28, the anvil body 3812 is formed with two tissue stop formations or tissue locating features 3830 that extend downwardly from each lateral side of the anvil body 3812 (only one tissue stop formation 3830 may be seen in FIGS. 27 and 28). When the anvil 3810 is opened to receive the target tissue between the underside of the anvil and the cartridge deck surface, the downwardly extending tissue stop formations 3830 serve to prevent the target tissue from extending proximally past the proximal most staples/fasteners in the surgical staple/fastener/fastener cartridge 3700. In the embodiment depicted in FIG. 28, for example, the proximal-most staple pockets 3720 are shown in phantom lines relative to the tissue stop formations 3830. As can be seen in that Figure, the tissue stop formation 3830 has a downwardly extending portion 3832 and a chamfered portion 3834. The target tissue is contacted by the portions 3832, 3834 to prevent the target tissue from extending proximally beyond the proximal most staples/fasteners that are supported in the proximal-most staple/fastener pockets 3720 in the staple/fastener cartridge body 3702.

Returning again to FIG. 27, as the anvil 3810 is pivoted closed onto the target tissue (not shown) that is positioned between the underside or tissue contacting surface 3813 of the anvil body 3812, the tissue applies tissue forces $T_{F2}$ to the underside 3813 of the anvil body 3812 which cause the anvil 3810 to experience a tissue counter moment $C_{T2}$ that must be overcome by the closure moment $C_{M2}$ established by the closure system components. The example depicted FIG. 27 illustrates equally distributed tissue forces $T_{F2}$ on the anvil 3810 and a tissue moment arm $M_{T2}$ established by the clamped tissue (the clamped tissue is not shown in FIG. 27 for clarity purposes). As can be seen in that Figure, in that example, the tissue moment arm $M_{T2}$ is considerably longer than the closure moment arm $M_{A2}$ (i.e., $M_{T2}>M_{A2}$).

Figure 29:
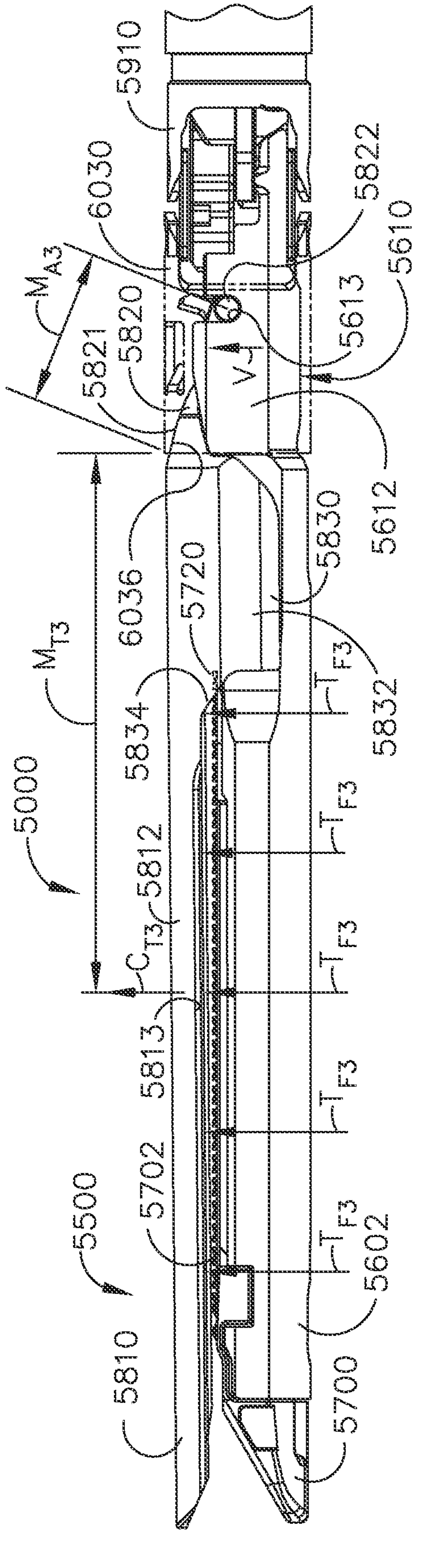
FIG. 29 is a side elevational view of a distal portion of the interchangeable surgical tool assembly of FIG. 19 with the anvil thereof in a fully closed position.
Figure 30:
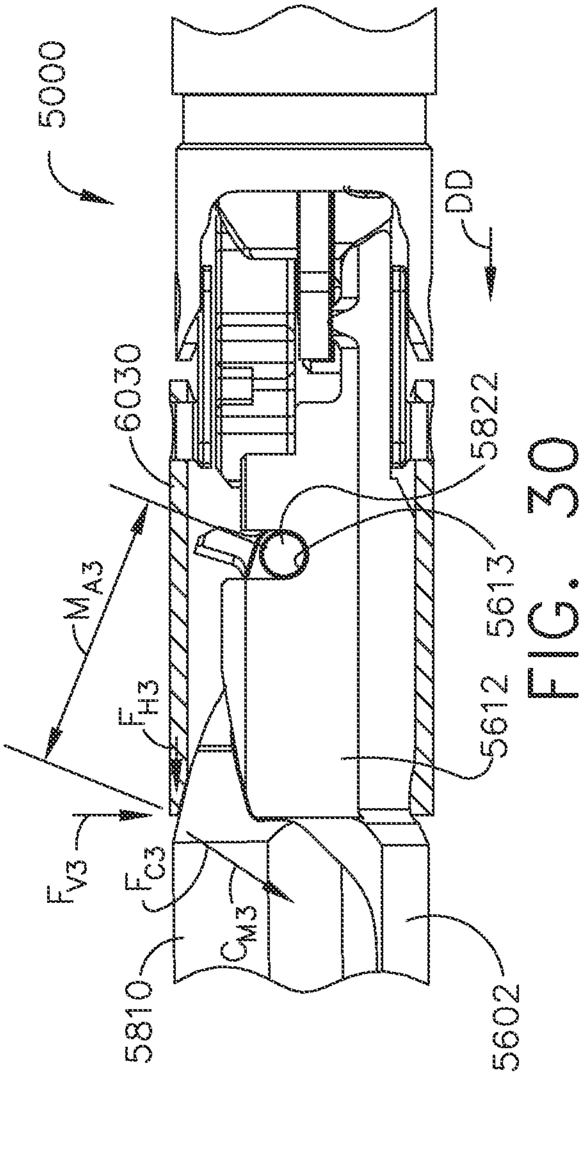
FIG. 30 is an enlarged side elevational view of the anvil mounting portion and elongate channel of the interchangeable surgical tool assembly of FIG. 29.

Turning next to FIGS. 29 and 30, as was described above, the anvil trunnions 5822 of the anvil 5810 of the interchangeable surgical tool assembly 5000 extend laterally out of each lateral side of the anvil mounting portion 5820 to be received in the corresponding "open-ended" vertical cradle 5613 formed in the upstanding walls 5612 of the proximal end portion 5610 of the elongate channel 5602. In this arrangement, the anvil trunnions 5822 are free to pivot within their respective cradles 5613 as the distal closure tube segment 6030 cammingly contacts the anvil cam surface 5821 on the anvil mounting portion 5820. Under such arrangement, the anvil 5810 does not move axially, but the anvil trunnions 5822 are free to move vertically (arrow V) within their respective cradles 5613. As the distal closure tube segment 6030 is advanced in the distal direction DD under the horizontal closure force $F_{H3}$ (FIG. 30), the interaction between an internal cam surface 6036 on the distal closure tube segment 6030 and the anvil cam surface 5821 on the anvil mounting portion 5820 results in the application of a closure force $F_{C3}$ to the anvil cam surface 5821. The closure force $F_{C3}$ comprises the resultant force of the horizontal closure force $F_{H3}$ and a vertical closure force $F_{V3}$ and is essentially "normal to" or perpendicular to the anvil cam surface 5821 on the anvil mounting portion 5820. See FIG. 30. $M_{A3}$ represents the closure moment arm from the anvil pivot axis $PA_3$ (coincident with the center of anvil trunnions 5822) to the point of contact between the internal cam surface 6036 on the distal closure tube 6030 and the anvil cam surface 5821 on the anvil mounting portion 5820 when the anvil 5810 has been pivoted to the closed position. In one example, closure moment arm $M_{A3}$ may be approximately 0.502 inches, for example. $M_{A3} \times F_{C3}$=a closure moment $C_{M3}$ that is applied to the anvil mounting portion 5820.

In the example depicted in FIGS. 29 and 30, the anvil body 5812 is formed with two tissue stop formations or tissue locator features 5830 that extend downwardly from each lateral side of the anvil body 5812 (only one tissue stop formation 5830 may be seen in FIGS. 29 and 30). When the anvil 5810 is opened to receive the target tissue between the underside of the anvil and the cartridge deck surface, the downwardly extending tissue stop formations 5830 serve to prevent the target tissue from extending proximally past the proximal most staples/fasteners in the surgical staple/fastener cartridge 5700. In the embodiment depicted in FIG. 29, for example, the proximal-most staple/fastener pockets 5720 are shown in phantom lines relative to the tissue stop formations 5830. As can be seen in that Figure, the tissue stop formation 5830 has a downwardly extending portion 5832 and a chamfered portion 5834. The target tissue is contacted by the portions 5832, 5834 to prevent the target tissue from extending proximally beyond the proximal most staples/fasteners that are supported in the proximal-most staple/fastener pockets 5720 in the staple/fastener cartridge body 5702.

Returning again to FIG. 29, as the anvil 5810 is pivoted closed onto the target tissue (not shown) that is positioned between the underside 5813 of the anvil body 5812, the tissue applies tissue forces $T_{F3}$ to the underside or tissue contacting surface 5813 of the anvil body 5812 which cause the anvil 5810 to experience a tissue counter moment $C_{T3}$ that must be overcome by the closure moment $C_{M3}$ established by the closure system components. The example depicted in FIG. 29 illustrates equally distributed tissue forces $T_{F3}$ on the anvil 5810 and a tissue moment arm $M_{T3}$ established by the clamped tissue (the clamped tissue is not shown in FIG. 29 for clarity purposes). As can be seen in that Figure, in that example, the tissue moment arm $M_{T3}$ is considerably longer than the closure moment arm $M_{A3}$ (i.e., $M_{T3}>M_{A3}$).

Figure 31:
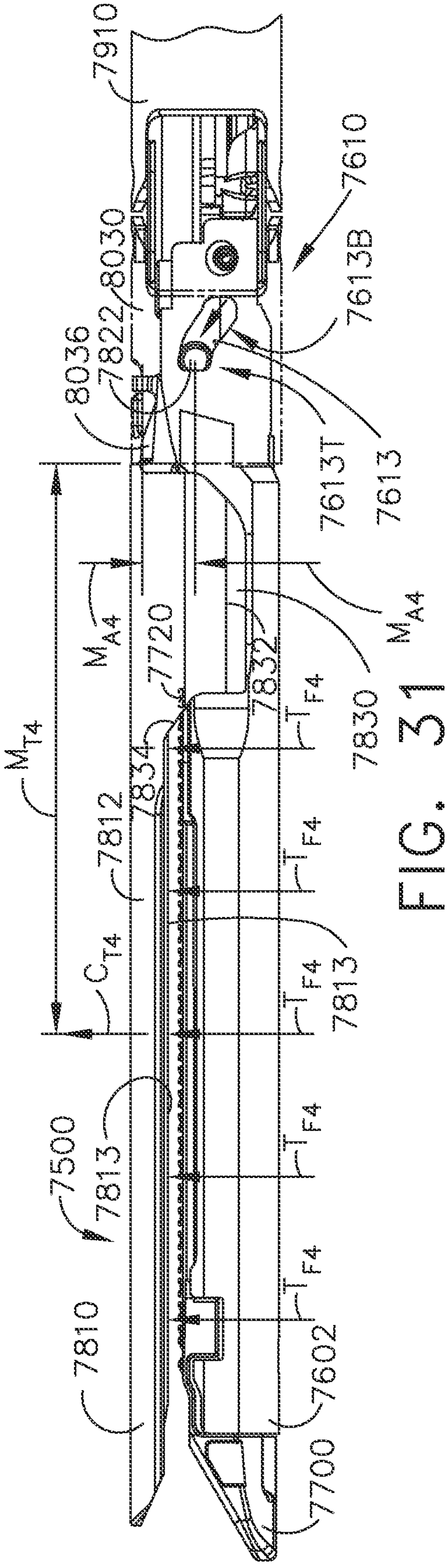
FIG. 31 is a side elevational view of a distal portion of the interchangeable surgical tool assembly of FIG. 22 with the anvil thereof in a fully closed position.
Figure 32:
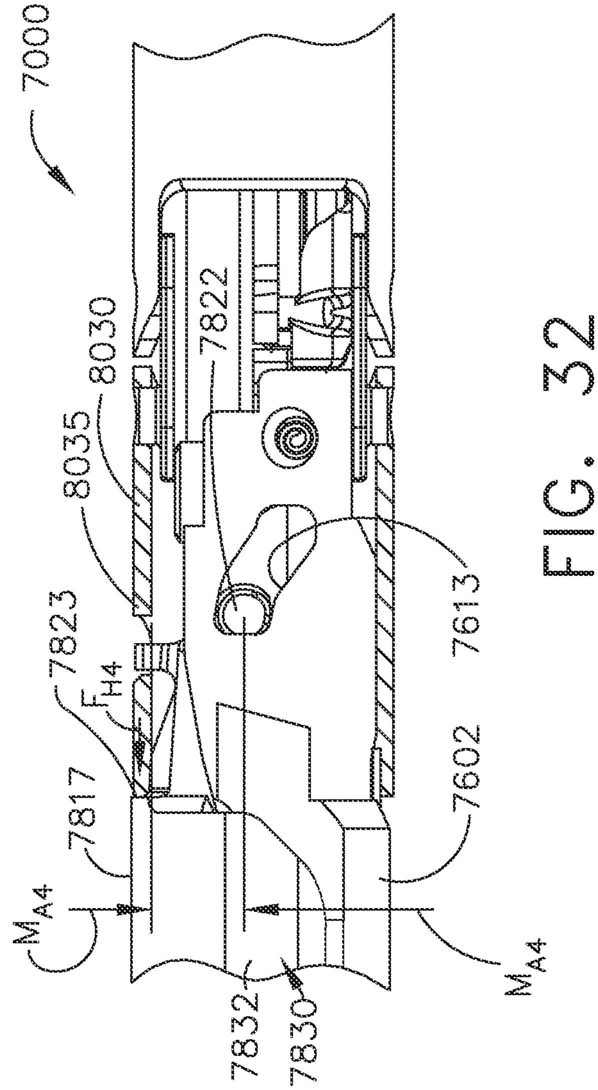
FIG. 32 is an enlarged side elevational view of the anvil mounting portion and elongate channel of the interchangeable surgical tool assembly of FIG. 31.

Turning now to FIGS. 31 and 32, as was described above, the anvil trunnions 7822 of the anvil 7810 of the interchangeable surgical tool assembly 7000 extend laterally out of each lateral side of the anvil mounting portion 7820 to be received in the corresponding "kidney-shaped" opening 7613 formed in the upstanding walls 7612 of the proximal end portion 7610 of the elongate channel 7602. When the anvil 7810 is in a "fully" open position, the anvil trunnions 7822 may generally be located in the bottom portion 76136 of the kidney slot 7613. The anvil 7810 can be moved to a closed position by distally advancing the distal closure tube segment 8030 in the distal direction DD so that the internal cam surface 8036 on the distal end 8035 of the distal closure tube segment 8030 rides up an anvil cam surface 7821 that is formed on the anvil mounting portion 7820 of the anvil 7810. As the internal cam surface 8036 on the distal end 8035 of the distal closure tube segment 8030 is distally advanced along the anvil cam surface 7821 on the anvil mounting portion 7820 under the horizontal closure force $F_{H4}$ (FIG. 32), the distal closure tube segment 8030 causes the body portion 7812 of the anvil 7810 to pivot and move axially relative to the surgical staple/fastener cartridge 7700 as the anvil trunnions 7822 move upwardly and distally in the kidney slots 7613. When the distal closure tube segment 8030 reaches the end of its closure stroke, the distal end 8035 of the distal closure tube segment 8030 abuts/contacts an abrupt anvil ledge 7823 and serves to position the anvil 7810 so that the forming pockets (not shown) in the underside or tissue contacting surface 7813 of the body portion 7812 are properly aligned with the staples/fasteners in the staple/fastener cartridge 7700. The anvil ledge 7823 is defined between the anvil cam surface 7821 on the anvil mounting portion 7820 and the anvil body portion 7812. Stated another way, in this arrangement, the anvil cam surface 7821 does not extend to an outermost surface 7817 of the anvil body 7812. When in that position, the anvil trunnions 7822 are located at top portions 7613T of the kidney slots 7613. $M_{A4}$ represents the moment arm from the anvil pivot axis $PA_4$ (coincident with the center of the anvil trunnions 7822) when the trunnions 7822 are located in the top portions 7613T of the kidney slots 7613 as shown. In one example, the moment arm $M_{A4}$ may be approximately 0.184 inches, for example. $M_{A4} \times F_{H4}$=a closure moment $C_{M4}$ that is applied to the anvil mounting portion 7820.

In the example depicted in FIGS. 31 and 32, the anvil body 7812 is formed with two tissue stop formations or tissue locator formations 7830 that extend downwardly from each lateral side of the anvil body 7812 (only one tissue stop formation 7830 may be seen in FIGS. 31 and 32). When the anvil 7810 is opened to receive the target tissue between the underside of the anvil and the cartridge deck surface, the downwardly extending tissue stop formations 7830 serve to prevent the target tissue from extending proximally past the proximal most staples/fasteners in the surgical staple/fastener cartridge 7700. In the embodiment depicted in FIG. 31, for example, the proximal most staple/fastener pockets 7720 are shown in phantom lines relative to the tissue stop formations 7830. As can be seen in that Figure, the tissue stop formation 7830 has a downwardly extending portion 7832 and a chamfered portion 7834. The target tissue is contacted by the portions 7832, 7834 to prevent the target tissue from extending proximally beyond the proximal most staples/fasteners that are supported in the proximal most staple/fastener pockets 7720 in the staple/fastener cartridge body 7702.

Returning again to FIG. 31, as the anvil 7810 is pivoted closed onto the target tissue (not shown) that is positioned between the underside or tissue contacting surface 7813 of the anvil body portion 7812, the tissue applies tissue forces $T_{F4}$ to the underside 7813 of the anvil body 7812 which cause the anvil 7810 to experience a tissue counter moment $C_{T4}$ that must be overcome by a closure moment $C_{M4}$ established by the closure system components. The example depicted FIG. 31 illustrates equally distributed tissue forces $T_{F4}$ on the anvil 7810 and a tissue moment arm $M_{T4}$ established by the clamped tissue (the clamped tissue is not shown in FIG. 31 for clarity purposes). As can be seen in that Figure, in that example, the tissue moment arm $M_{T4}$ is considerably longer than the closure moment arm $M_{A4}$ (i.e., $M_{T4}>M_{A4}$).

The illustrated exemplary interchangeable surgical tool assemblies 1000, 3000, 5000, 7000 comprise surgical stapling devices that employ "separate and distinct" closure and firing systems. That is, the closure system employed to close the jaws is separately actuatable from the firing system used to drive the firing member through the surgical staple/fastener cartridge to cut and fasten tissue. These separate and distinct closure and firing systems may be distinguishable from those surgical stapling instruments wherein actuation of the firing system to advance the firing member is required to move the jaws from an open position to a closed position. As will be discussed in further detail below, however, the firing members of some of the interchangeable surgical tool assemblies disclosed herein may also apply additional closure motions to the anvil as the firing member is fired (i.e., distally advanced through the surgical end effector). As can be seen from reference to FIGS. 25-32, in the illustrated examples, $M_{A2}>M_{A3}>M_{A1}>M_{A4}$. FIGS. 25, 27, 29 and 31 also illustrate the resistive forces established by the tissue during the closure process. $T_F$ represents the force generated by the tissue when the tissue is clamped between the anvil and the staple cartridge. These forces establish a "counter" moment $C_T$ that is applied to the anvil about the point/area where the distal closure tube segment is in camming contact with the anvil cam surface on the anvil mounting portion. In these illustrated examples, the tissue moment arm for each surgical instrument (tool assembly) is generally larger than the closure moment arm for that instrument. It may be appreciated from the difference between a typical tissue moment arm encountered when clamping tissue between the anvil and the surgical staple/fastener cartridge and the closure moment arm of the instrument results in the need for sufficient closure forces to be applied by the distal closure tube segment to the anvil in order to sufficiently close the anvil onto the tissue. Thus, the distal closure tube segment must be sufficiently strong and robust to handle the considerable stresses formed therein during the closure process. To establish a stress state in the distal closure tube segment that more closely resembles a "hoop stress" state instead of a "ring stress" state, the sidewalls of the distal closure tube segment may be thickened so as to contact the side walls and anvil mounting portions of the corresponding elongate channel. Such arrangement may also add strength to the overall hoop-like structure of the tube. Maximizing the thickness on the anvil side of the distal closure tube segment may also improve the strength of the tube segment (hoop) while allowing room for a large bearing or cam surface to cam the anvil downward towards the cartridge. U.S. patent application Ser. No. 15/385,911, entitled SURGICAL STAPLE/FASTENERS WITH INDEPENDENTLY ACTUATABLE CLOSING AND FIRING SYSTEMS, now U.S. Pat. No. 10,448,950, discloses several distal closure tube segment configurations which may be employed in the various interchangeable surgical tool assemblies disclosed herein.

Figure 33:
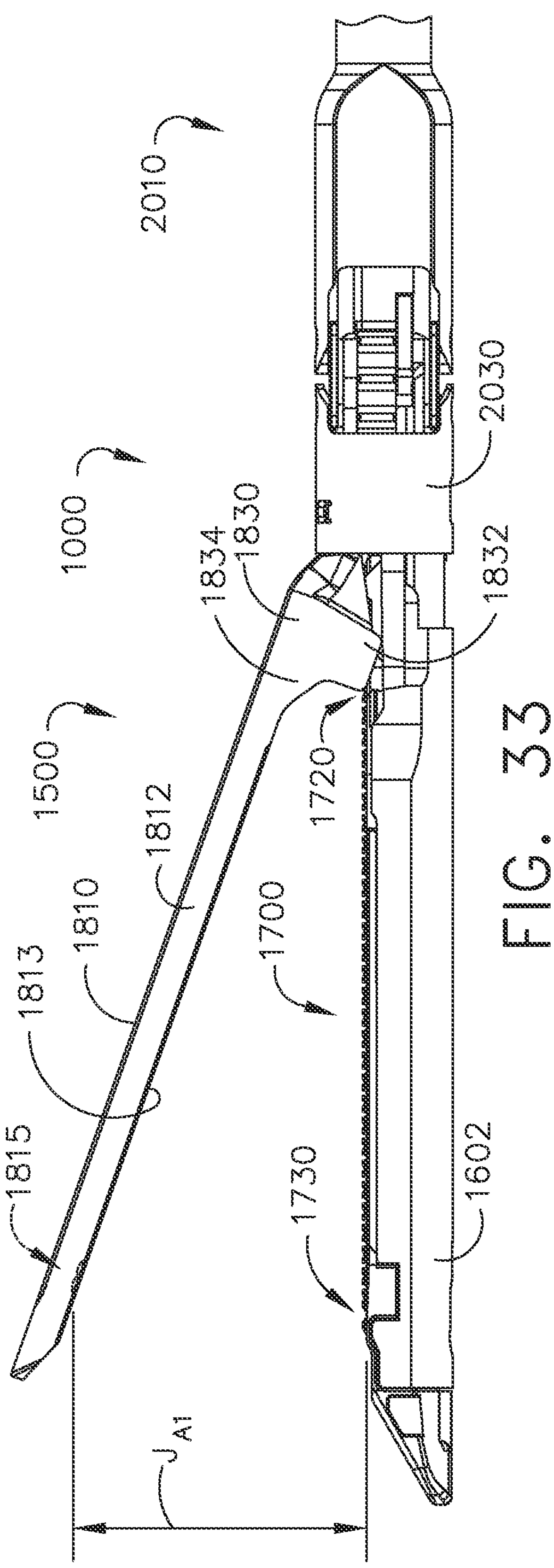
FIG. 33 is a side elevational view of a distal portion of the interchangeable surgical tool assembly of FIG. 3 with the anvil thereof in a fully open position.
Figure 34:
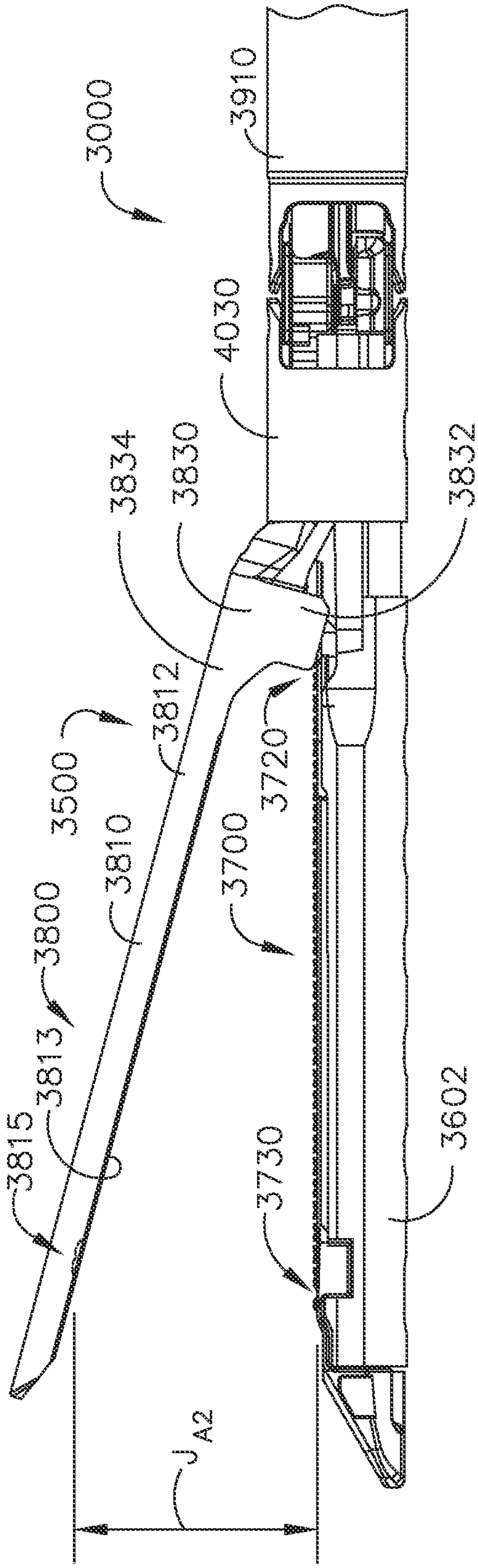
FIG. 34 is a side elevational view of a distal portion of the interchangeable surgical tool assembly of FIG. 16 with the anvil thereof in a fully open position.
Figure 35:
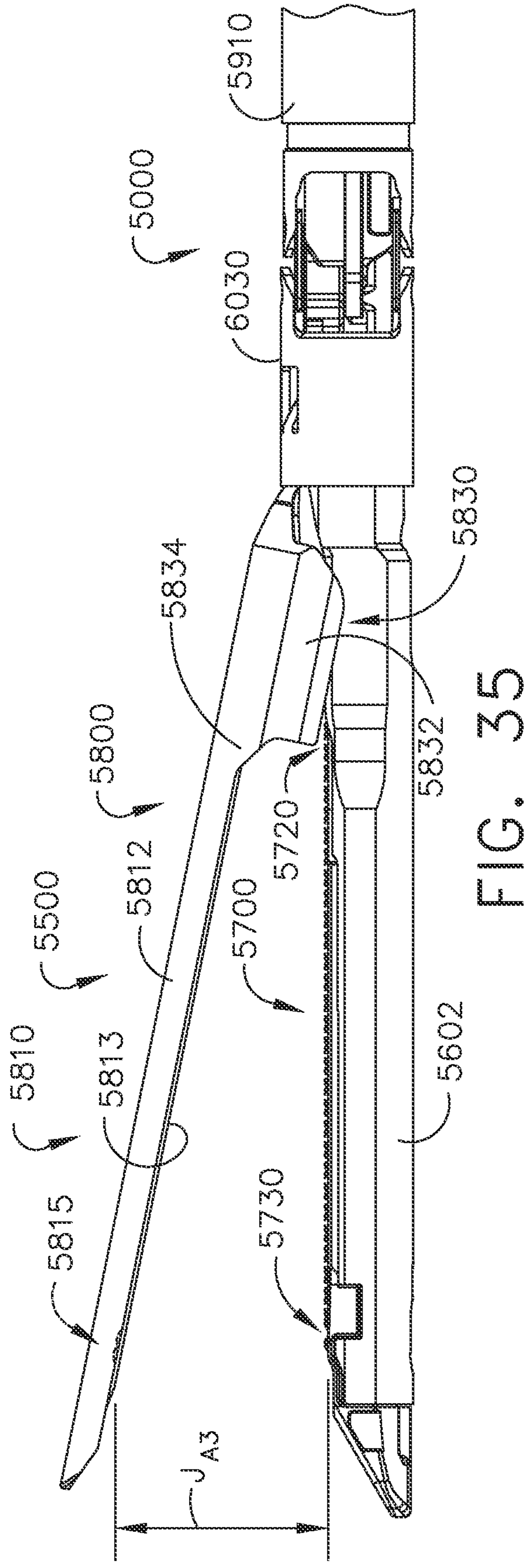
FIG. 35 is a side elevational view of a distal portion of the interchangeable surgical tool assembly of FIG. 19 with the anvil thereof in a fully open position.
Figure 36:
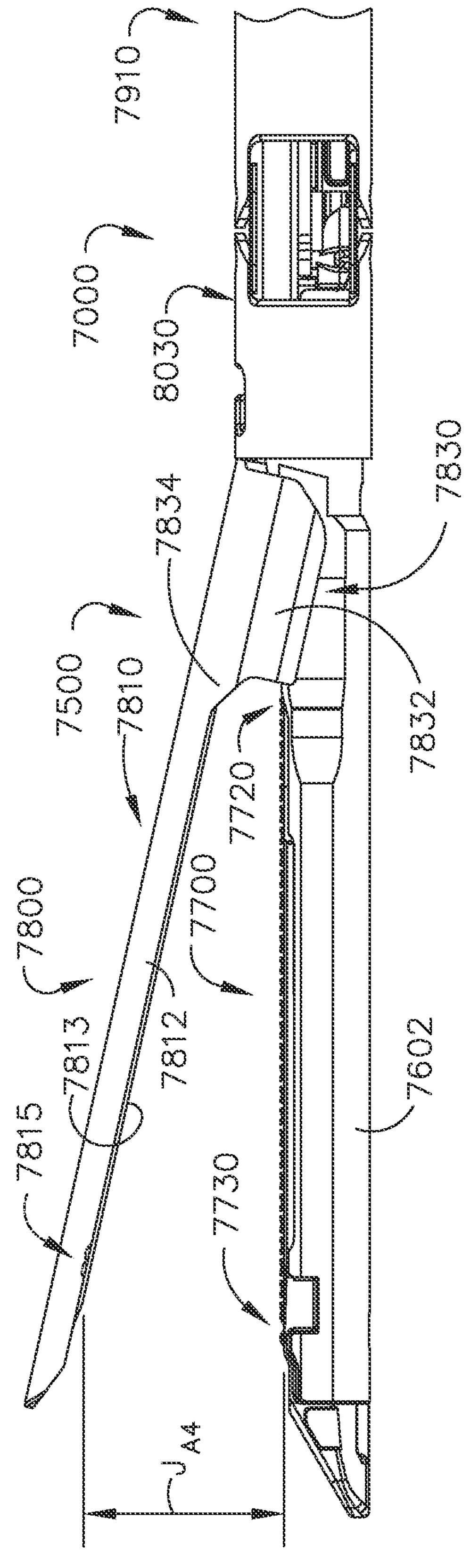
FIG. 36 is a side elevational view of a distal portion of the interchangeable surgical tool assembly of FIG. 22 with the anvil thereof in a fully open position.

The forgoing discussion and comparisons may illustrate that closure system designs that have large closure moment arms may lead to improved efficiencies of the closure system components and can reduce the amount of closure forces that are required to achieve full anvil closure onto the tissue. However, as noted above, there may be tradeoffs with other design variables when attempting to maximize the closure moment arm. For example, another desirable attribute relates to "jaw aperture". "Jaw aperture" may refer to a distance JA which is measured from the middle of a distalmost staple or fastener center along a line that is perpendicular to the corresponding distalmost staple forming pocket on the underside or tissue contact surface of the anvil body portion. FIG. 33 illustrates the jaw aperture $J_{A1}$ for the surgical end effector 1500. In the illustrated example, the distalmost staple/fastener pockets 1730 contain the distalmost staples or fasteners (not shown) therein. Each distalmost staple or fastener corresponds to a distalmost staple/fastener forming pocket 1815 (shown in phantom in FIG. 33) that is formed in the underside or tissue contacting surface 1813 of the anvil body 1812. The distance $J_{A1}$ between the distalmost staple/fastener pocket 1730 and the corresponding distalmost staple/fastener forming pocket 1815 is the "jaw aperture" for the surgical end effector 1500. In at least one embodiment, for example, $J_{A1}$ is approximately 1.207 inches. FIG. 34 illustrates the jaw aperture $J_{A2}$ for the surgical end effector 3500. In the illustrated example, the distalmost staple/fastener pockets 3730 contain the distalmost staples or fasteners (not shown) therein. Each distalmost staple or fastener corresponds to a distalmost staple/fastener forming pocket 3815 that is formed in the underside or tissue contact surface 3813 of the anvil body 3812. The distance $J_{A2}$ between the distalmost staple/fastener pocket 3730 and the corresponding distalmost staple/fastener forming pocket 3815 is the "jaw aperture" for the surgical end effector 3500. In at least one embodiment, for example, $J_{A2}$ is approximately 0.781 inches. FIG. 35 illustrates the jaw aperture $J_{A3}$ for the surgical end effector 5500. In the illustrated example, the distalmost staple/fastener pockets 5730 contain the distalmost staples/fasteners (not shown therein). Each distalmost staple/fastener corresponds to a distalmost staple/fastener forming pocket 5815 that is formed in the underside or tissue contact surface 5813 of the anvil body 5812. The distance $J_{A3}$ between the distalmost staple/fastener pocket 5730 and the corresponding distalmost staple/fastener forming pocket 5815 is the "jaw aperture" for the surgical end effector 5500. In at least one embodiment, for example, $J_{A3}$ is approximately 0.793 inches. FIG. 36 illustrates the jaw aperture $J_{A4}$ for the surgical end effector 7500. In the illustrated example, the distalmost staple/fastener pockets 7730 contain the distalmost staples or fasteners (not shown) therein. Each distalmost staple or fastener corresponds to a distalmost staple/fastener forming pocket 7815 that is formed in the underside or tissue contact surface 7813 of the anvil body 7812. The distance $J_{A4}$ between the distalmost staple/fastener pocket 7730 and the corresponding distalmost staple/fastener forming pocket 7815 is the "jaw aperture" for the surgical end effector 7500. In at least one embodiment, for example, $J_{A4}$ is approximately 0.717 inches. Thus, for these examples, $J_{A1}>J_{A3}>J_{A2}>J_{A4}$. As such, comparatively, surgical end effector 1500 has the greatest jaw aperture.

Figure 37:
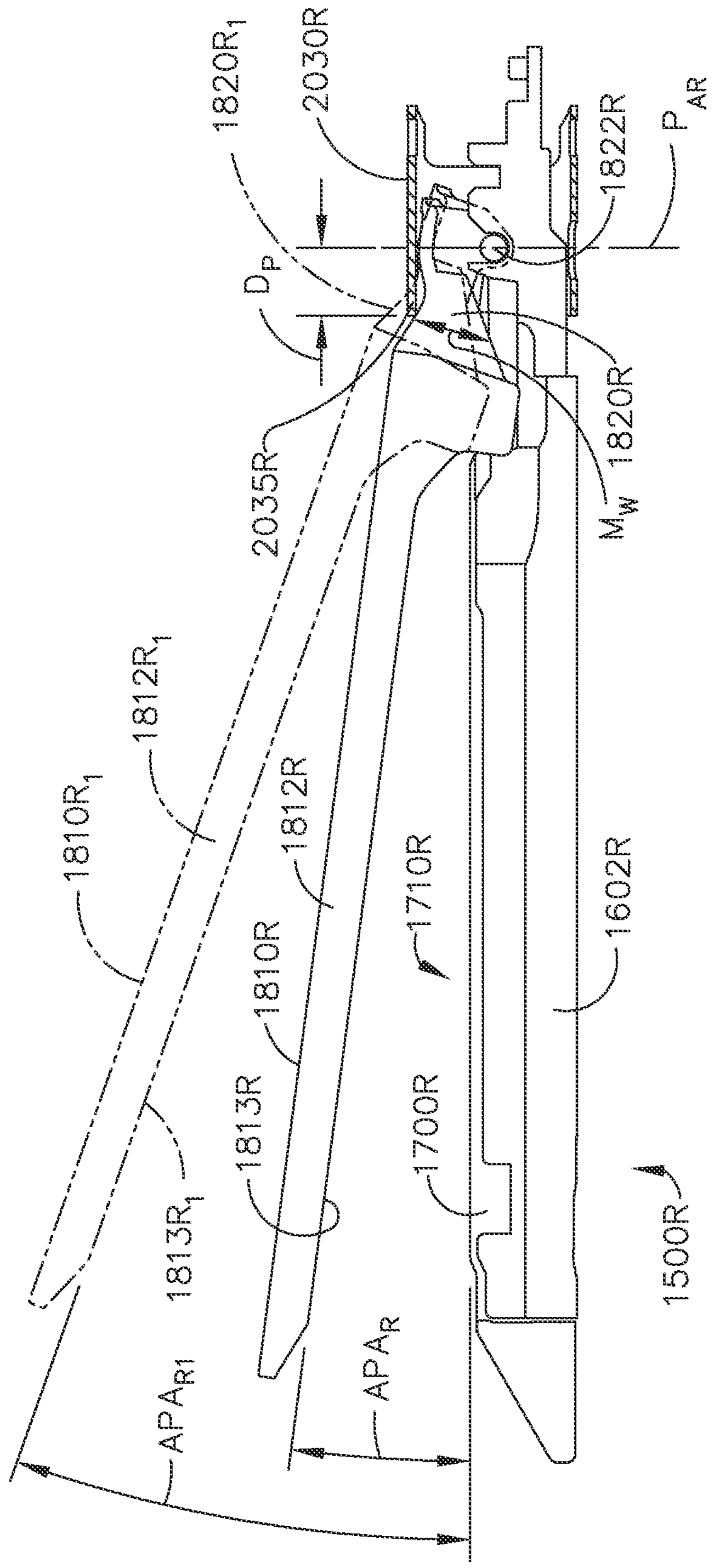
FIG. 37 is a side elevational view of a distal portion of another interchangeable surgical tool assembly with the anvil thereof shown in one open position in solid lines and another open position in phantom lines.

In those surgical end effector designs that employ separate and distinct closure and firing systems that utilize an axially movable closure ring or distal closure tube segment such as the examples described above, the interrelationships between the anvil or jaw pivot axis PA and the distal end of the distal closure tube segment as well as the robustness of the anvil mounting portion may determine the magnitude of the jaw aperture that is attainable for each specific end effector design. These interrelationships may be better appreciated from reference to FIG. 37, for example. FIG. 37 depicts a surgical end effector 1500R that employs an anvil 1810R that has an anvil mounting portion 1820R that is shown in solid lines. The anvil mounting portion 1820R includes anvil trunnions 1822R that define a reference pivot axis $P_{AR}$ about which the anvil mounting portion 1820R may pivot relative to an elongate channel 1602R. The surgical end effector 1500R also employs a distal closure tube segment 2030R that has a distal end 2035R that is configured to cammingly contact the anvil mounting portion 1820R in the various manners discussed above. A surgical staple/fastener cartridge 1700R is supported in the elongate channel 1602R and has a cartridge deck surface or tissue contact surface 1710R. FIG. 37 depicts a distance DP between the reference pivot axis $P_{AR}$ and the distal end 2035R of the distal closure tube segment 2030R. FIG. 37 illustrates the anvil 1810R in solid lines. The anvil body 1812R is in its maximum open position when the distal closure tube segment 2030R is in its proximal most starting position relative to the anvil mounting portion 1820R. The maximum aperture angle $APA_R$ for that configuration is approximately ten degrees, for example. This aperture angle $APA_R$ is typical for many end effector arrangements. In another end effector arrangement, the aperture angle is 12.25 degrees. In one arrangement, for example, DP may be approximately 0.200 inches. To attain a larger aperture angle $APA_{R1}$ of, for example, twenty-two degrees, if the relationship between the distal end 2035R of the distal closure tube segment 2030R and the reference pivot axis $P_{AR}$ remains unchanged, then a cross-sectional width $M_W$ of an anvil mounting portion 1820$R_1$ must undesirably be decreased. The anvil 1810$R_1$ is illustrated in phantom lines. As can be seen in that Figure, an abrupt ledge must be formed between the anvil body 1812$R_1$ and the anvil mounting portion 1820$R_1$ such that the cross-sectional width thereof is reduced. The aperture angle $APA_{R1}$ is measured from the underside 1813$R_1$ of the anvil body 1812$R_1$ and the deck surface 1710R of the surgical staple/fastener cartridge 1700R. Such reduction in robustness of the anvil mounting portion of the anvil may lead to reduced anvil reliability and is less desirable than anvils that have anvil mounting portions with larger cross-sectional profiles.

Figure 38:
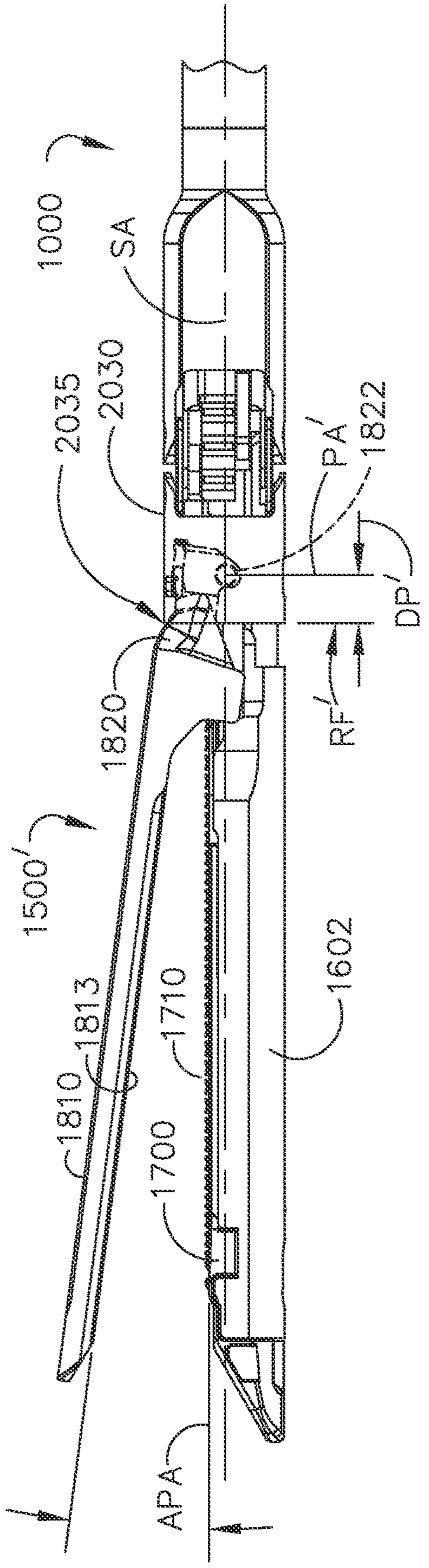
FIG. 38 is a side elevational view of a distal portion of another interchangeable surgical tool assembly with the anvil thereof in an open position.
Figure 39:
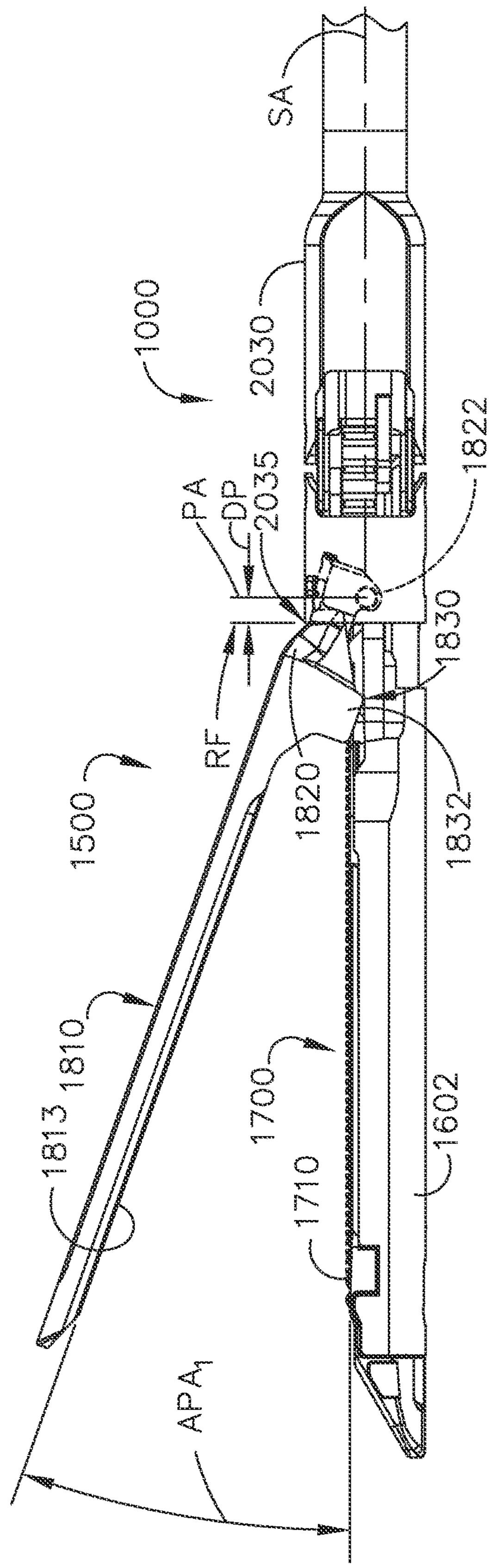
FIG. 39 is a side elevational view of a distal portion of the interchangeable surgical tool assembly of FIG. 3 with the anvil thereof in a fully open position.

Referring now to FIGS. 38 and 39, increases in jaw aperture (or aperture angle) may be more easily achieved as the pivot or pivot axis PA moves closer to the distal end of the starting or proximal position of the distal closure tube segment. FIG. 38 illustrates a surgical end effector 1500' that is substantially similar to surgical end effector 1500, except for the location of the pivot axis PA' relative to the distal end 2035 of the distal closure tube segment 2030. As can be seen in that Figure, the distance between the pivot axis PA' and the distal end 2035 of the distal closure tube segment 2030 when the distal closure tube segment 2030 is in its proximal-most starting position is represented by DP' and the aperture angle is APA. Stated another way, when the distal closure tube segment 2030 is in its starting position that corresponds with the fully open position of the anvil 1810, the distal end 2035 thereof is on a reference plane RF that is perpendicular to said shaft axis SA. The distance between the pivot axis PA' and the reference plane RF' measured along a line that is perpendicular to the reference plane RF' and extends through the pivot axis PA' is DP'. In at least one arrangement, DP' is approximately 0.200 inches and the aperture angle APA may be approximately 10°.

FIG. 38 illustrates the aperture angle APA of a surgical end effector 1500' with a distance DP' between the reference pivot axis PA' and the distal end 2035 of the distal closure tube segment 2030. Turning next to FIG. 39, as can be seen in that Figure, the distance DP between the pivot axis PA and the reference plane RF upon which the distal end 2035 of the distal closure tube segment 2030 is located when the distal closure tube segment 2030 is in its proximal most starting position is less than distance DP' and the aperture angle $APA_1$ is greater than APA. For example, in at least one embodiment, the distance DP is approximately 0.090 inches and the aperture angle $APA_1$ is approximately twenty two degrees. Thus, by moving the pivot axis PA closer to the distal end of the distal closure tube segment when the distal closure tube segment is in its proximal most starting position, the jaw aperture may be significantly increased without the need to reduce the cross-sectional width of the anvil mounting position. This may represent a significant improvement over other surgical end effector arrangements.

In various circumstances, the center of the anvil trunnions 1822 may ideally be located between 0.010-0.060 inches from the distal end 2035 of the distal closure tube segment 2030 when the distal closure tube segment is in the starting (proximal most) position. A maximum distance for large jaw aperture applications may be, for example, 0.090 inches. As can also be seen in FIG. 39, when the anvil 1810 is in its fully open position as shown, the downwardly extending portion 1832 of the tissue stop 1830 generally stops at the staple cartridge deck surface 1710 to prevent any proximal movement of the target tissue during clamping.

Figure 40:
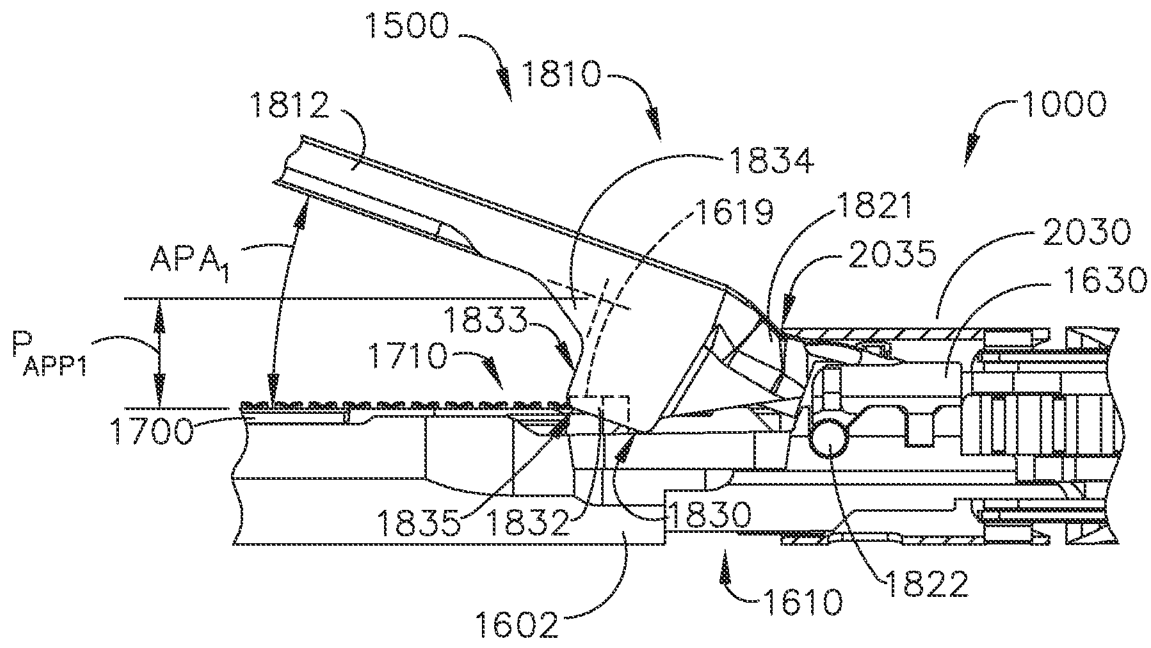
FIG. 40 is an enlarged side elevational view of the anvil mounting portion and elongate channel of the interchangeable surgical tool assembly of FIG. 39.
Figure 41:
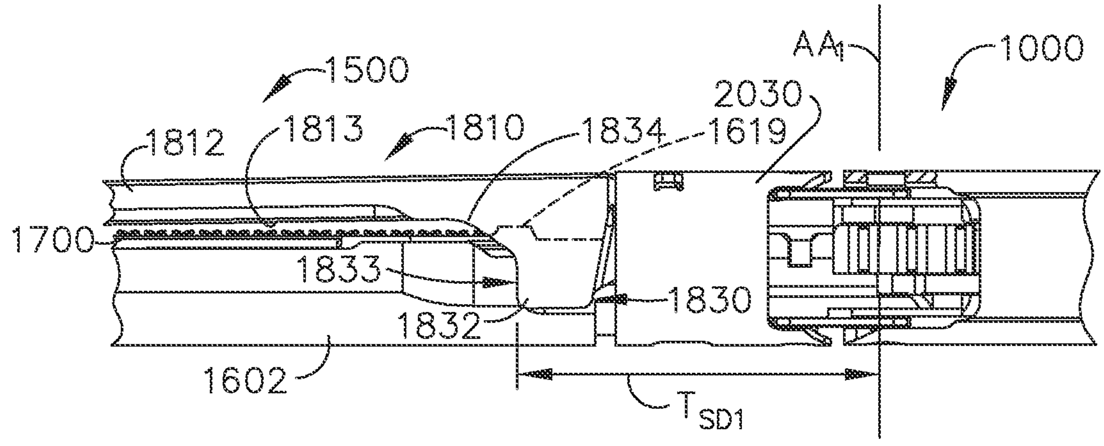
FIG. 41 is a side elevational view of a distal portion of the interchangeable surgical tool assembly of FIGS. 39 and 40 with the anvil thereof in a fully closed position.

FIGS. 40 and 41 illustrate tissue stop or tissue locator arrangements 1830 employed on one form of the surgical end effector 1500. As indicated above, the tissue stops 1830 comprise a downwardly extending portion 1832 and a chamfered portion 1834. The downwardly extending portion 1832 comprises a distal edge 1833 that terminates in a distal corner portion 1835. FIG. 40 illustrates the anvil 1810 in its fully open position. The underside 1813 of the anvil body 1812 is positioned at an aperture angle $APA_1$. In at least one arrangement, the aperture angle $APA_1$ is greater than 12.25 degrees (12.25°) and may be as large as eighteen degrees (18°). When in that fully open position, the surgical end effector 1500 may further have a proximal aperture $P_{APP1}$ that in at least one arrangement may be approximately 0.254 inches, for example. The proximal aperture defines how much tissue can be positioned between the proximal portions of the jaws (anvil and cartridge). A large proximal aperture may be most advantageous, for example, when cutting and fastening lung tissue which may be partially inflated when being introduced between the anvil and cartridge. The proximal aperture may be measured from the center of the proximal most fastener pocket or pocket pair directly vertical to the underside or tissue contact surface on the anvil body.

When the anvil 1810 is in the fully opened position as shown in FIG. 40, the distal corner 1835 does not extend above the cartridge deck surface 1710 so as to prevent tissue from moving proximal to the proximal most staples in the proximal most staple pockets 1720. In at least one embodiment, an upstanding channel stop portion 1619 may extend upwardly from the side walls of the elongate channel 1602 so as to coincide with each corresponding tissue stop 1830 to further prevent any proximal infiltration of tissue between the tissue stop 1830 and the channel stop portion 1619. FIG. 41 illustrates the anvil 1810 in a fully closed position. When in that position, the distal edges 1833 of the tissue stops 1830 are approximately aligned or coincident with the locations of the proximal most staples/fasteners in the staple/fastener cartridge 1700. The distance from the articulation axis $AA_1$ to the proximal most staples/fasteners is identified as $T_{SD1}$. In one arrangement, $T_{SD1}$ is approximately 1.044 inches, for example. When the anvil 1810 is fully closed, the tissue stops 1830 may be sized and shaped relative to the proximal end portion 1610 of the elongate channel 1602 so as to facilitate easy insertion through a correspondingly sized standard trocar. In at least one example, the tissue stops 1830 of the anvil 1810 are sized and shaped relative to the elongate channel 1602 so as to permit the surgical end effector 1500 to be inserted through a conventional 12 mm trocar.

Figure 42:
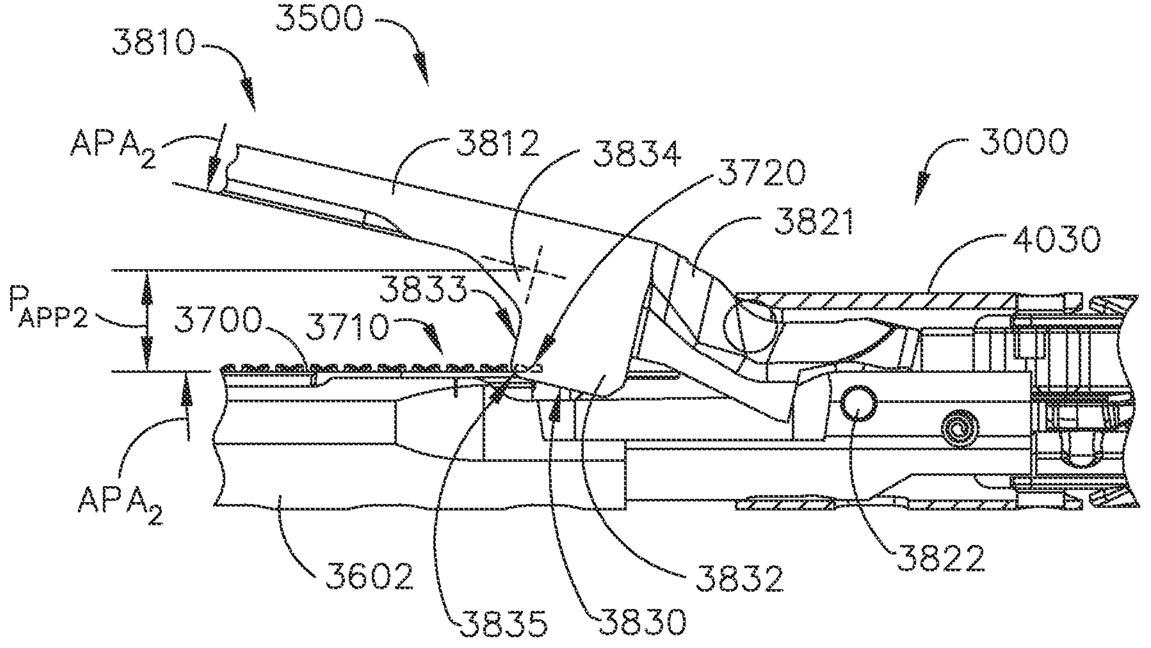
FIG. 42 is an enlarged side elevational view of the anvil mounting portion and elongate channel of the interchangeable surgical tool assembly of FIG. 16 with the anvil thereof in a fully open position.
Figure 43:
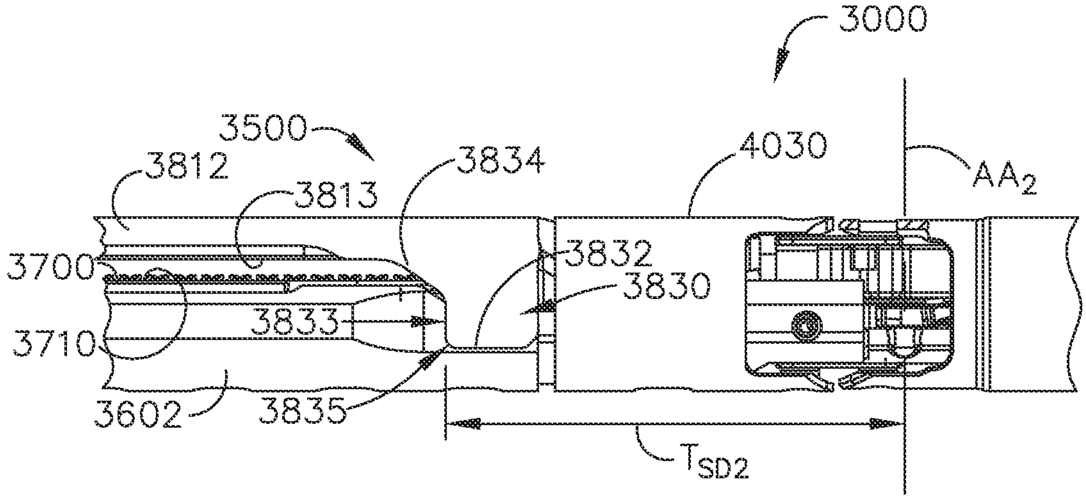
FIG. 43 is a side elevational view of a distal portion of the interchangeable surgical tool assembly of FIG. 42 with the anvil thereof in a fully closed position.

FIGS. 42 and 43 illustrate tissue stop arrangements 3830 employed on one form of the surgical end effector 3500. As indicated above, the tissue stops 3830 comprise a downwardly extending portion 3832 and a chamfered portion 3834. The downwardly extending portion 3832 comprises a distal edge 3833 that terminates in a distal corner portion 3835. FIG. 42 illustrates the anvil 3810 in its fully open position. The underside 3813 of the anvil body 3812 is positioned at an aperture angle $APA_2$. In at least one arrangement, the aperture angle $APA_2$ is approximately thirteen and one half degrees (13.5°). When in that fully open position, the surgical end effector 3500 may further have a proximal aperture $P_{APP2}$ that in at least one arrangement may be approximately 0.242 inches, for example. When the anvil 3810 is in the fully opened position as shown in FIG. 42, the distal corner 3835 does not extend above the cartridge deck surface 3710 so as to prevent tissue from moving proximal to the proximal most staples/fasteners in the proximal most staple/fastener pockets 3720. FIG. 43 illustrates the anvil 3810 in a fully closed position. When in that position, the distal edges 3833 of the tissue stops 3830 are approximately aligned or coincident with the locations of the proximal most staples/fasteners in the staple/fastener cartridge 3700. The distance from the articulation axis $AA_2$ to the proximal most staples/fasteners is identified as $T_{SD2}$. In one arrangement, $T_{SD2}$ is approximately 1.318 inches, for example.

Figure 44:
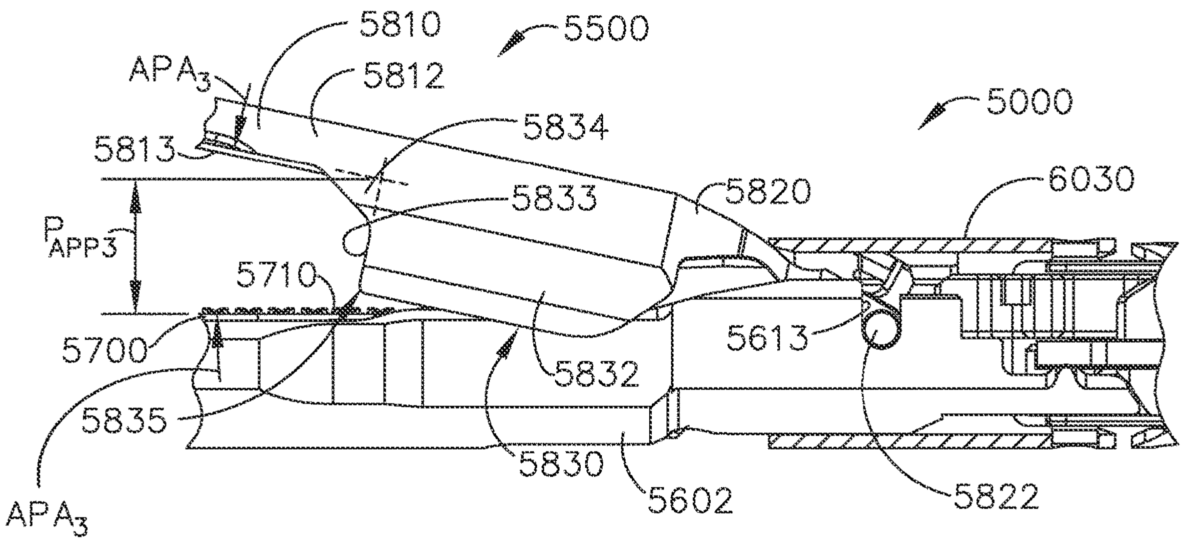
FIG. 44 is an enlarged side elevational view of the anvil mounting portion and elongate channel of the interchangeable surgical tool assembly of FIG. 19 with the anvil thereof in a fully open position.
Figure 45:
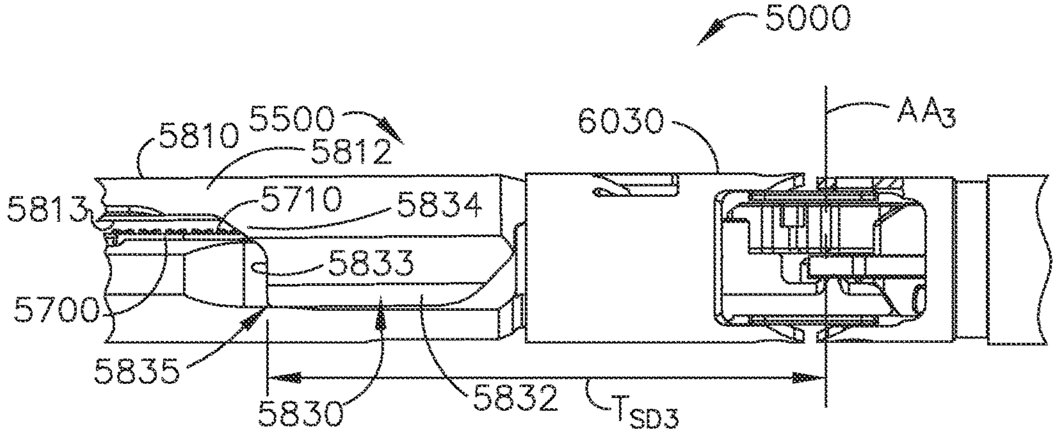
FIG. 45 is a side elevational view of a distal portion of the interchangeable surgical tool assembly of FIG. 44 with the anvil thereof in a fully closed position.

FIGS. 44 and 45 illustrate tissue stop arrangements 5830 employed on one form of the surgical end effector 5500. As indicated above, the tissue stops 5830 comprise a downwardly extending portion 5832 and a chamfered portion 5834. The downwardly extending portion 5832 comprises a distal edge 5833 that terminates in a distal corner portion 5835. FIG. 44 illustrates the anvil 5810 in its fully open position. The underside 5813 of the anvil body 5812 is positioned at an aperture angle $APA_3$. In at least one arrangement, the aperture angle $APA_3$ is approximately eight degrees (8°). When in that fully open position, the surgical end effector 5500 may further have a proximal aperture $P_{APP3}$ that in at least one arrangement may be approximately 0.226 inches, for example. When the anvil 5810 is in the fully opened position as shown in FIG. 44, the distal corner 3835 extends slightly above the cartridge deck surface 5710. FIG. 45 illustrates the anvil 5810 in a fully closed position. When in that position, the distal edges 5833 of the tissue stops 5830 are approximately aligned or coincident with the locations of the proximal most staples/fasteners in the staple/fastener cartridge 5700. The distance from the articulation axis $AA_3$ to the proximal most staples/fasteners is identified as $T_{SD3}$. In one arrangement, $T_{SD3}$ is approximately 1.664 inches, for example.

Figure 46:
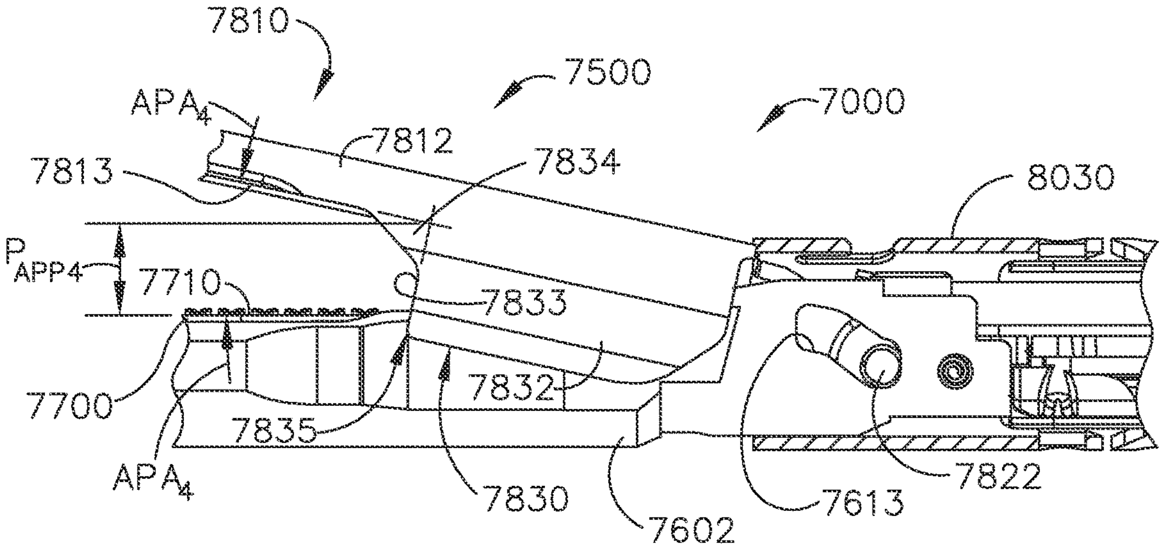
FIG. 46 is an enlarged side elevational view of the anvil mounting portion and elongate channel of the interchangeable surgical tool assembly of FIG. 22 with the anvil thereof in a fully open position.
Figure 47:
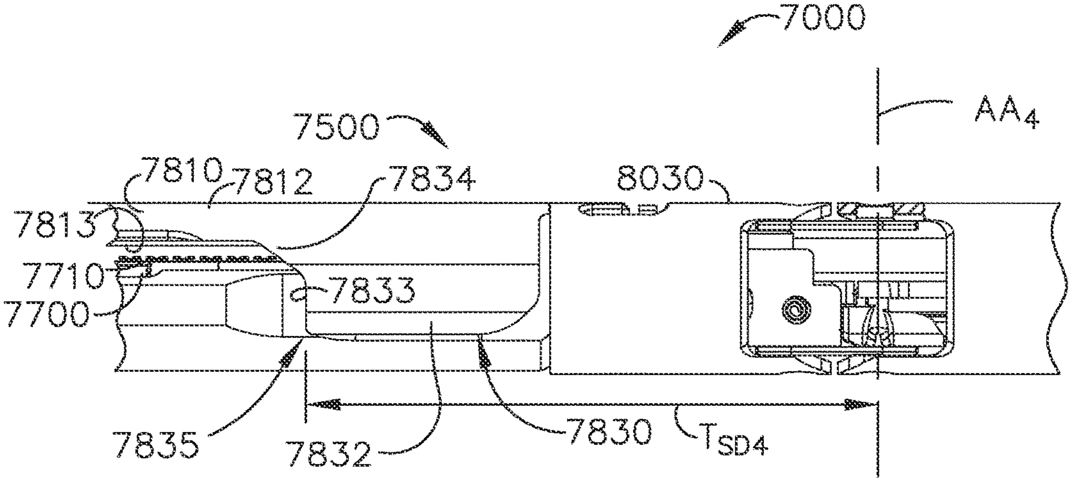
FIG. 47 is a side elevational view of a distal portion of the interchangeable surgical tool assembly of FIG. 46 with the anvil thereof in a fully closed position.

FIGS. 46 and 47 illustrate tissue stop arrangements 7830 employed on one form of the surgical end effector 7500. As indicated above, the tissue stops 7830 comprise a downwardly extending portion 7832 and a chamfered portion 7834. The downwardly extending portion 7832 comprises a distal edge 7833 that terminates in a distal corner portion 7835. FIG. 46 illustrates the anvil 7810 in its fully open position. The underside 7813 of the anvil body portion 7812 is positioned at an aperture angle $APA_4$. In at least one arrangement, the aperture angle $APA_4$ is approximately ten degrees (10°). When in that fully open position, the surgical end effector 7500 may further have a proximal aperture $P_{APP4}$ that in at least one arrangement may be approximately 0.188 inches, for example. When the anvil 7810 is in the fully opened position as shown in FIG. 46, the distal corner portion 7835 extends slightly below the cartridge deck surface 7710 so as to prevent tissue from getting proximal to the proximal most staples/fasteners in the proximal most staple pockets 7720. FIG. 47 illustrates the anvil 7810 in a fully closed position. When in that position, the distal edges 7833 of the tissue stops 7830 is approximately aligned or coincident with the locations of the proximal most staples/fasteners in the staple/fastener cartridge 7700. The distance from the articulation axis $AA_4$ to the proximal most staples/fasteners is identified as $T_{SD4}$. In one arrangement, $T_{SD4}$ is approximately 1.686 inches, for example.

Figure 48:
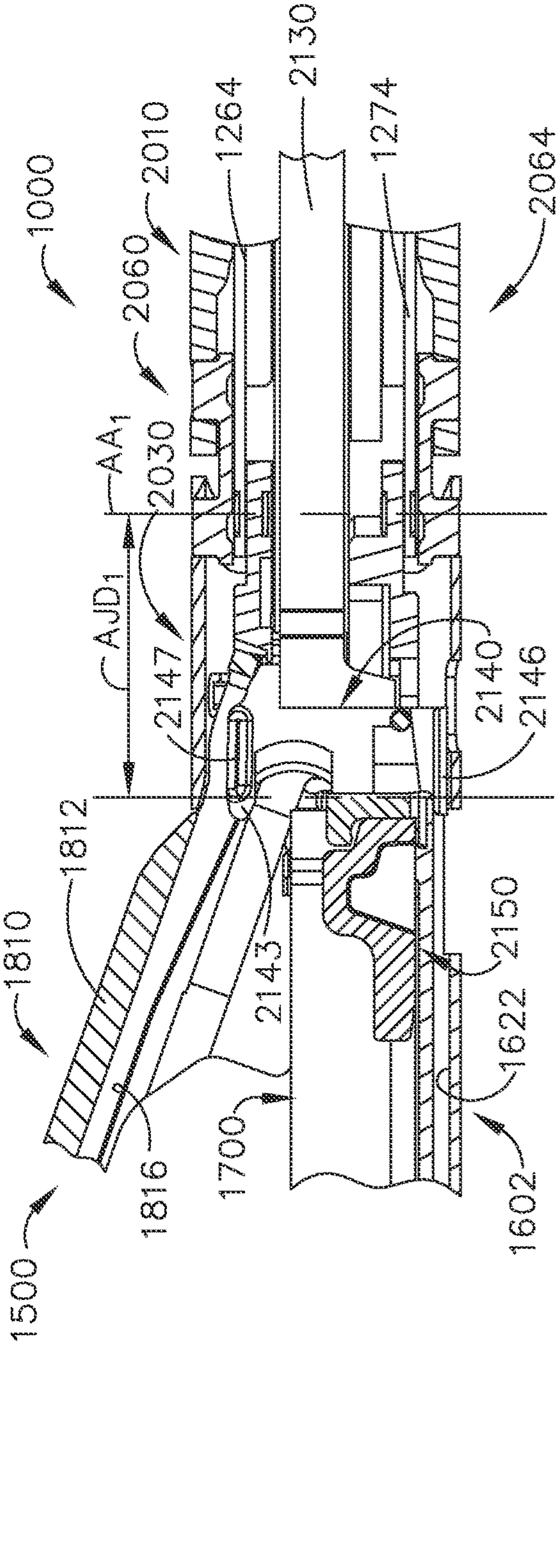
FIG. 48 is a partial cross-sectional view of the anvil mounting portion and elongate channel of the interchangeable surgical tool assembly of FIG. 3 with the anvil in a fully open position.
Figure 51:
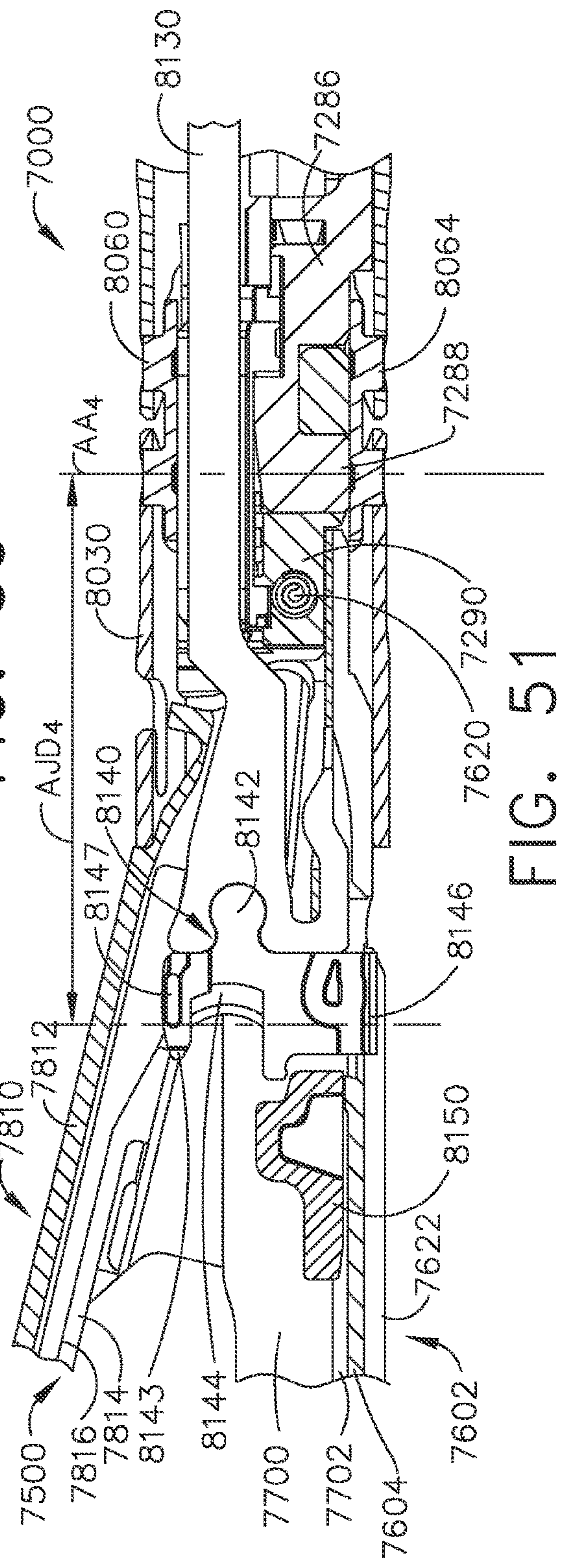
FIG. 51 is a partial cross-sectional view of the anvil mounting portion and elongate channel of the interchangeable surgical tool assembly of FIG. 22 with the anvil in a fully open position.

In various circumstances, the relationships of the firing member to the articulation axis AA as well as to the jaw pivot axis PA about which the anvil pivots may bear upon the length of the articulation joint arrangement. Of course, longer articulation joint arrangements may detrimentally affect the end effector's maneuverability within tight spaces and also limit the magnitude of the jaw aperture that may ultimately be obtained by the end effector. FIG. 48 illustrates the surgical end effector 1500 in a fully open position. That is, the anvil 1810 has been pivoted to its fully open position and the firing member 2140 is in its home or starting position. The distance between the distal end of each of the anvil engagement features 2147 and the articulation axis $AA_1$ is represented by $AJD_1$. In at least one example, $AJD_1$ is approximately 0.517 inches. By way of comparison and turning to FIG. 49, the distance $AJD_2$ from the distal end of each of the anvil engagement features 4147 and the articulation axis $AA_2$ is, in at least one example, is approximately 0.744 inches. Referring to FIG. 50, the distance $AJD_3$ from the distal end of each of the anvil engagement features 6147 and the articulation axis $AA_3$ is, in at least one example, is approximately 1.045 inches. Turning to FIG. 51, the distance $AJD_4$ from the distal end of each of the anvil engagement features 8147 and the articulation axis $AA_4$ is, in at least one example, is approximately 1.096 inches. Thus, as can be seen from this comparison, the articulation joint arrangement (as measured by distances $AJD_1$, $AJD_2$, $AJD_3$, $AJD_4$) of the surgical end effector 1500 is more compact and thus may be more maneuverable than the surgical end effectors 3500, 5500 and 7500 in at least some surgical applications.

Figures 52, 53:
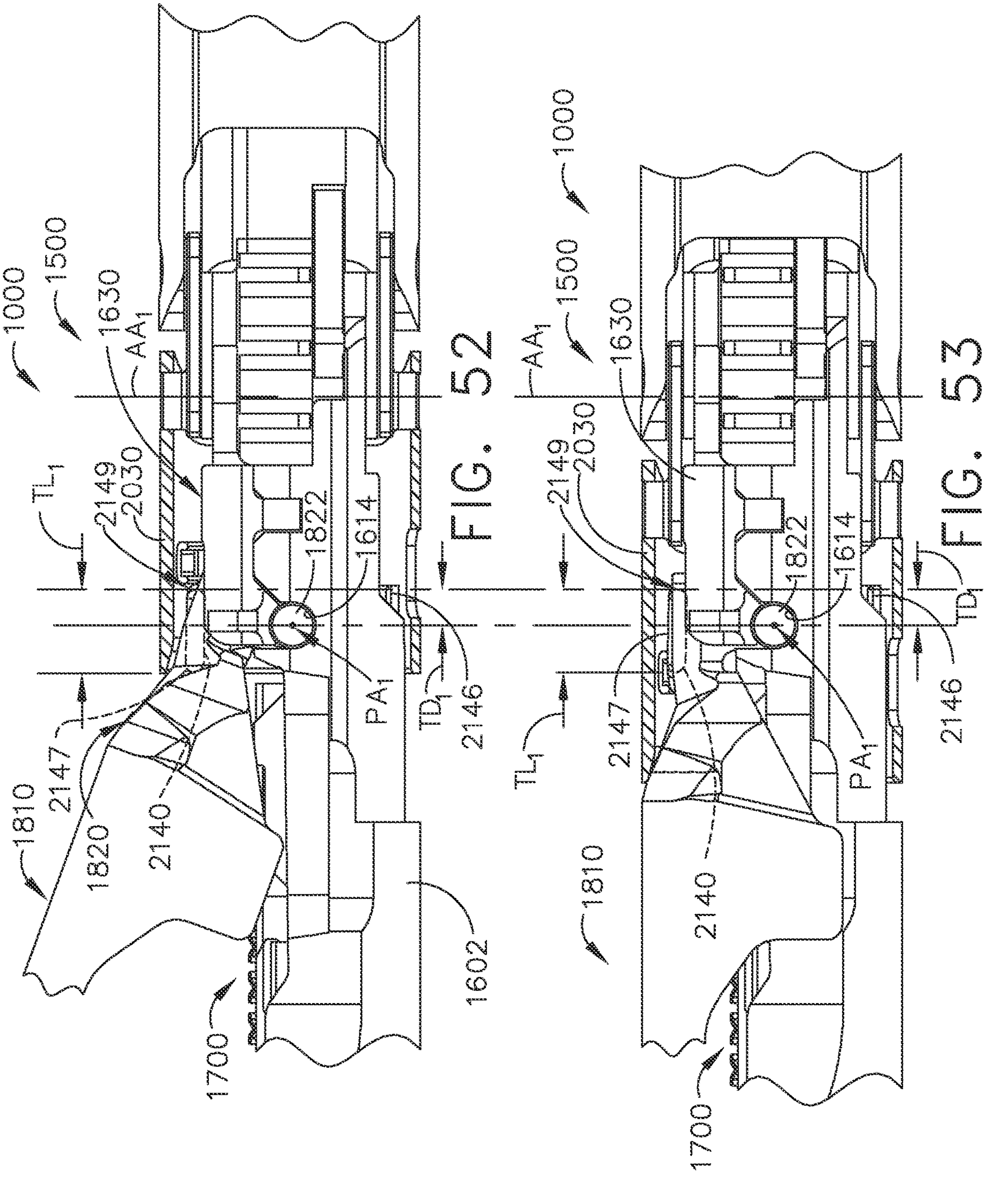
FIG. 52 is another partial cross-sectional view of a portion of the interchangeable surgical tool assembly of FIG. 3 with the anvil of the surgical end effector thereof in a fully open position.
FIG. 53 is another partial cross-sectional view of a portion of the interchangeable surgical tool assembly of FIG. 52 with the anvil in a fully closed position.

Another factor that may affect the length of the joint arrangement relates to the location of the firing member relative to the anvil pivot axis PA about which the anvil pivots. For example, FIG. 52 illustrates the anvil 1810 of surgical end effector 1500 in its fully open position. When in that position, the firing member 2140 is in its parked or "starting position". As can be seen in that Figure, one useful metric for comparing the "compactness" of the articulation joint arrangement is the proximal tab distance $TD_1$ between the proximal end 2149 of each of the top anvil engagement features 2147 and the anvil pivot axis $PA_1$. In at least one preferred arrangement, the proximal tab distance $TD_1$ is approximately greater than thirty-five percent (35%) of the overall length $TL_1$ of each of the anvil engagement features 2147 when the anvil 1810 is in a fully open position and the firing member 2140 is in its proximal most or starting position. Stated another way, when the anvil 1810 and the firing member 2140 are in the above described positions, at least 35% of each of the anvil engagement features 2147 extends proximally past the anvil pivot axis $PA_1$. FIG. 53 illustrates the end effector 1500 with the anvil 1810 in the closed position and the firing member 2140 in its proximal most or starting position. As can be seen in that Figure, at least 35% of each of the anvil engagement features 2147 extends proximally past the anvil pivot axis $PA_1$.

Figure 54:
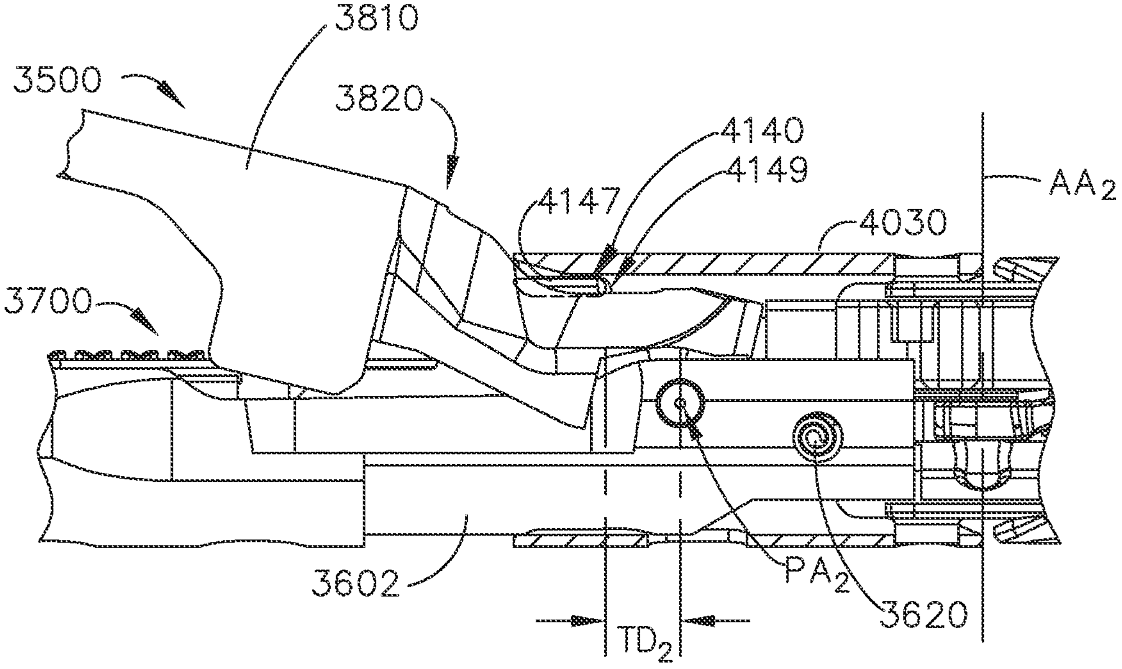
FIG. 54 is another partial cross-sectional view of a portion of the interchangeable surgical tool assembly of FIG. 16 wherein the anvil is in a fully open position.
Figure 55:
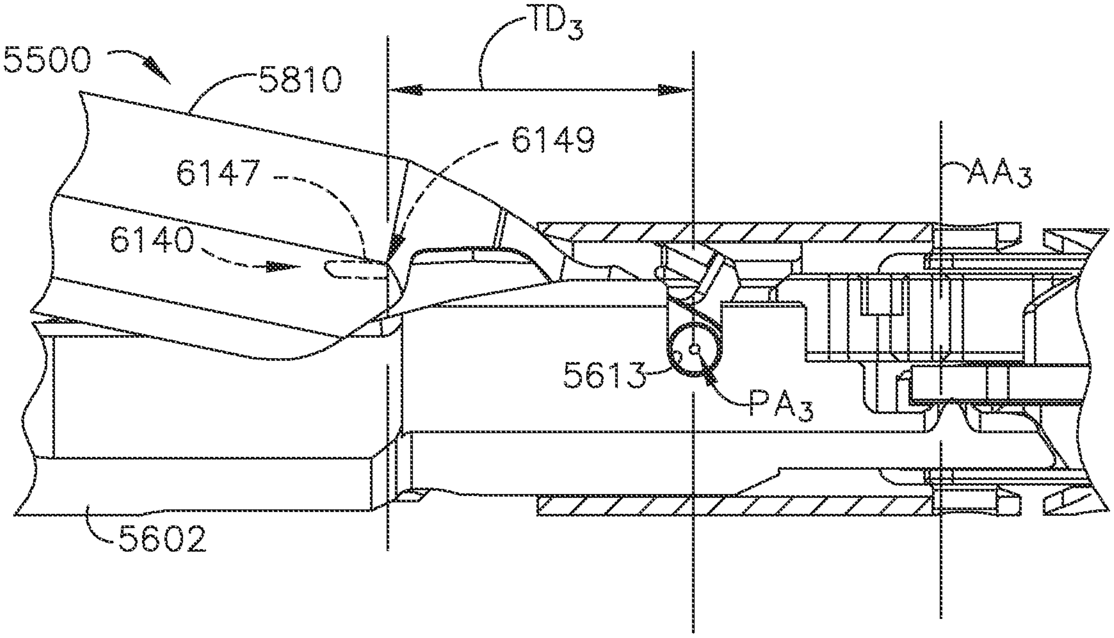
FIG. 55 is another partial cross-sectional view of a portion of the interchangeable surgical tool assembly of FIG. 19 wherein the anvil is in a fully open position.
Figure 56:
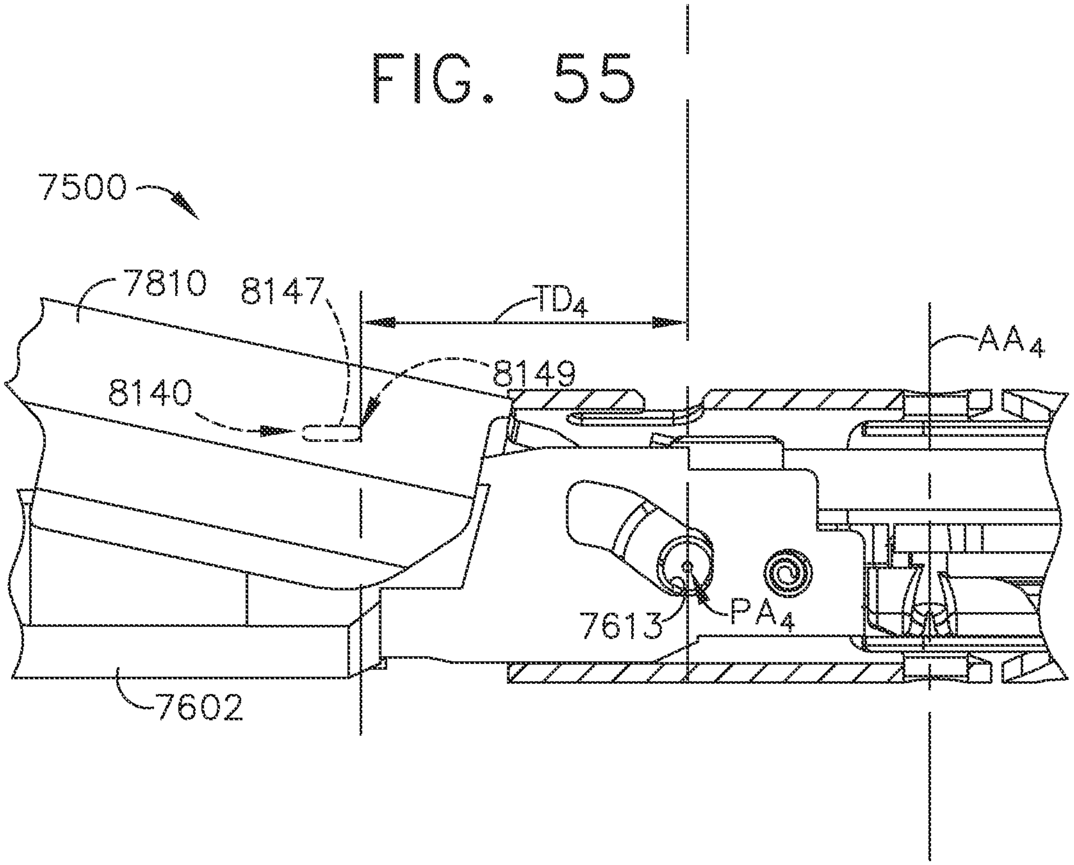
FIG. 56 is another partial cross-sectional view of a portion of the interchangeable surgical tool assembly of FIG. 22 wherein the anvil is in a fully open position.

FIG. 54 illustrates the position of the firing member 4140 of the surgical end effector 3500 when the anvil 3810 is in its fully open position and the firing member 4140 is in its proximal most or starting position. As can be seen in that Figure, each of the anvil engagement features 4147 are completely distal to the anvil pivot axis $PA_2$ thereby resulting in a longer articulation joint arrangement. Thus, the distance $TD_2$, is the distal distance between the proximal ends 4149 of the anvil engagement features 4147 and the anvil pivot axis $PA_2$. FIG. 55 illustrates the position of the firing member 6140 of the surgical end effector 5500 when the anvil 5810 is in its fully open position and the firing member 6140 is in its proximal most or starting position. As can be seen in that Figure, each of the anvil engagement features 6147 are completely distal to the anvil pivot axis $PA_3$ thereby resulting in a longer articulation joint arrangement. Thus, the distance $TD_3$, is the distal distance between the proximal ends 6149 of the anvil engagement features 6147 and the anvil pivot axis $PA_3$. FIG. 56 illustrates the position of the firing member 8140 of the surgical end effector 7500 when the anvil 7810 is in its fully open position and the firing member 8140 is in its proximal-most or starting position. As can be seen in that Figure, each of the anvil engagement features 8147 are completely distal to the anvil pivot axis $PA_4$ thereby resulting in a longer articulation joint arrangement. Thus, the distance $TD_4$, is the distal distance between the proximal ends 8149 of the anvil engagement features 8147 and the anvil pivot axis $PA_4$. For comparison purposes, the surgical end effector 1500 is the only surgical end effector wherein a portion of the anvil engagement features on the firing member extend proximally past the anvil pivot axis when the firing member is in its proximal most or starting position. The anvil engagement features of each of the firing members of the surgical end effectors 3500, 5500 and 7500 are completely distal to their respective anvil pivot axes when the firing members are in their proximal most or starting position. Taking this comparison further, for example, the surgical end effector 1500 is the only surgical end effector wherein at least thirty-five percent (35%) of the anvil engagement features reside between the anvil pivot axis and the articulation axis when the firing member is in its starting position and the anvil is fully opened. Similar comparisons may be drawn from comparing the same distances between the location of the lower channel engagement features on the firing member to the jaw pivot axis when the firing member is in its proximal most starting position.

Another metric that may be used to assess the compactness of the articulation joint arrangement may comprise comparing the ratio between the distance from the articulation axis to the distal end of the anvil engagement features on the firing member (distances $AJD_1$, $AJD_2$, $AJD_3$, $AJD_4$—FIGS. 48-51) relative to the distance from the articulation axis to the distal edge of the tissue stops or the proximal most staple/fastener (distances $TSD_1$, $T_{SD2}$, $T_{SD3}$, $T_{SD4}$—FIGS. 41, 43, 45, 47) for each end effector. For example, in a preferred arrangement, AJD/TSD<0.500. The ratio of AJD/TSD may be referred to herein as the "compactness ratio" of that particular surgical end effector. In one arrangement, for example, for end effector 1500, $AJD_1/TSD_1$=0.517 inches/1.044 inches=0.495. In one illustrated example for end effector 3500, $AJD_2/TSD_2$=0.744 inches/1.318 inches=0.564. In one illustrated example for end effector 5500, $AJD_3/TSD_3$=1.045 inches/1.664 inches=0.628. In one illustrated arrangement, $AJD_4/TSD_4$=1.096 inches/1.686 inches=0.650. Thus, in at least one preferred arrangement wherein the articulation joint arrangement is the most compact, has the largest jaw aperture and is the most maneuverable, the ratio between the distance from the articulation axis to the proximal end of the anvil engagement features on the firing member and the distance from the articulation axis to the distal edge of the tissue stops or the proximal most staple/fastener is approximately less than 0.500.

Figure 57:
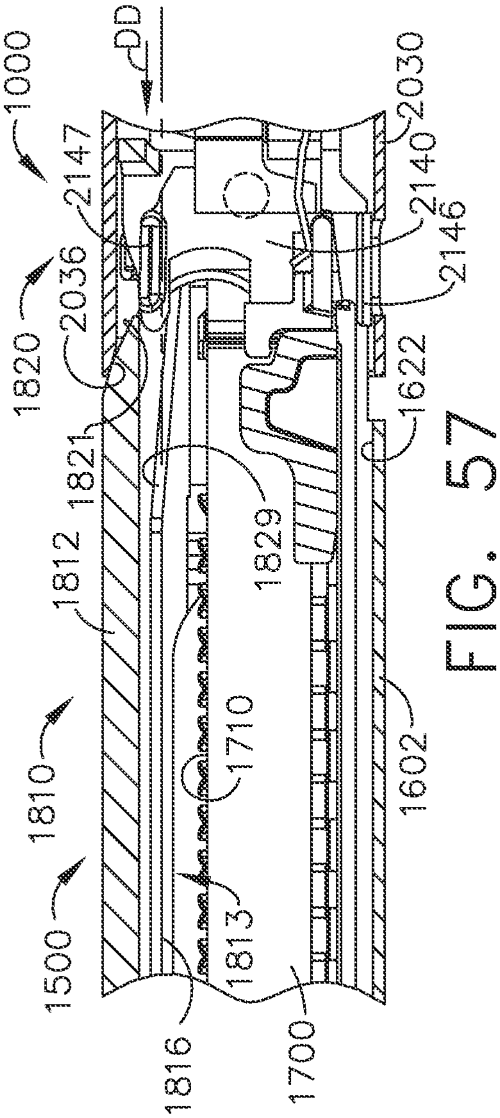
FIG. 57 is another partial cross-sectional view of a portion of the interchangeable surgical tool assembly of FIG. 3 wherein the firing member thereof is in a starting position.
Figure 58:
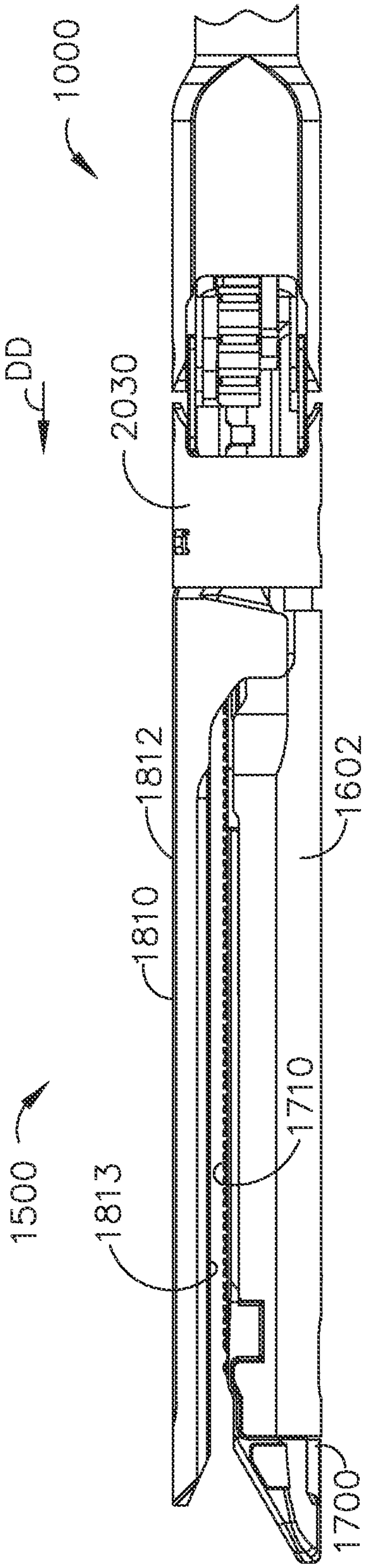
FIG. 58 is a side elevational view of the surgical end effector of FIG. 57 with the anvil in a fully closed position.
Figure 59:
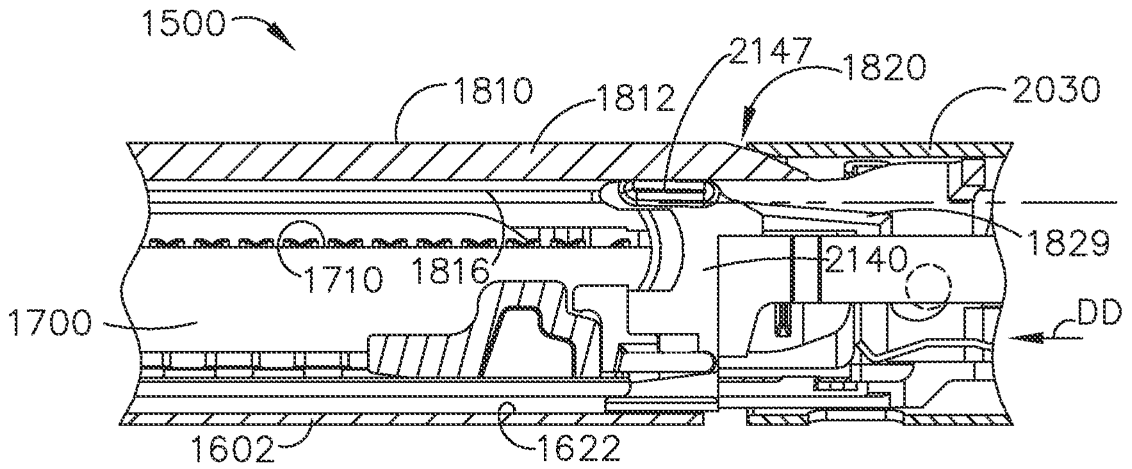
FIG. 59 is another partial cross-sectional view of the portion of the surgical end effector of FIGS. 57 and 58 wherein the firing member is in initial engagement with the anvil thereof.
Figure 61:
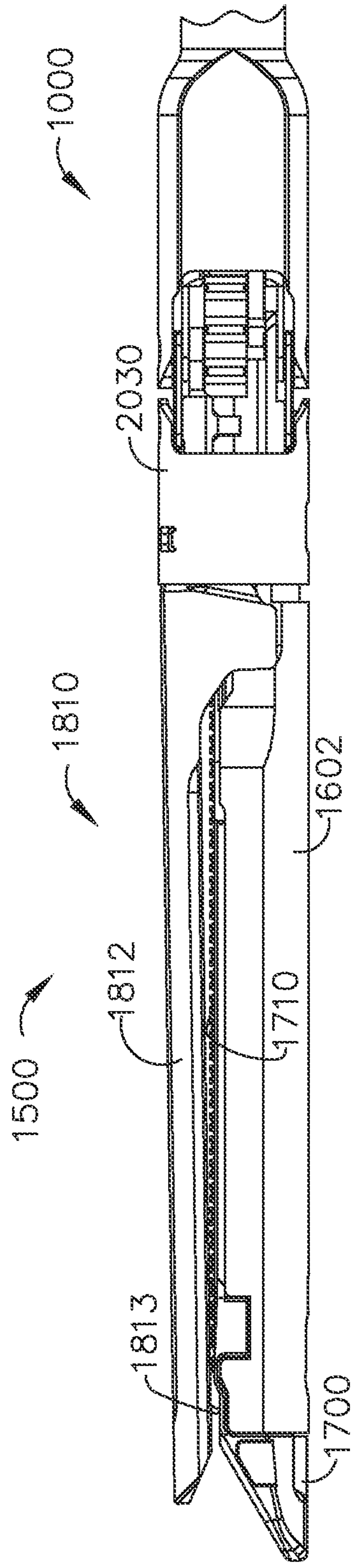
FIG. 61 is another side elevational view of the surgical end effector of FIGS. 57-60 with the anvil in an over closed position.

FIGS. 57-61 illustrate a progressive closure arrangement for moving the anvil 1810 of the surgical end effector 1500 from a fully open position to a closed position and then to an over closed position. FIGS. 57 and 58 illustrate the anvil 1810 in a closed position. In both of those Figures, the distal closure tube segment 2030 has been advanced in the distal direction DD to its fully closed position. As was discussed above, the interaction between an internal cam surface 2036 on the distal closure tube segment 2030 and an anvil cam surface 1821 on the anvil mounting portion 1820 causes the anvil 1810 to pivot to the closed position. As can be seen in FIG. 58, the staple forming underside or tissue contacting surface 1813 of the anvil body 1812 may be relatively parallel and spaced relative to the cartridge deck surface 1710 of the surgical staple/fastener cartridge. When in that initial closed position, the firing member 2140 is in its starting position as can be seen in FIG. 57. When in that position, the anvil engagement features 2147 of the firing member 2140 have not engaged the anvil 1810 but are in substantial horizontal alignment with the ledges 1816 formed in the anvil 1810. In at least one arrangement, a ramp segment 1829 is formed proximal to each of the horizontal anvil ledges 1816. FIG. 59 illustrates the position of the firing member 2140 after it has been distally advanced to a point wherein the anvil engagement features 2147 have initially engaged the horizontal anvil ledges 1816 on the anvil 1810 and FIG. 61 illustrates the position of the firing member 2140 and the anvil 1810 such that the anvil engagement features are in full engagement with the anvil ledges 1816 to apply an "overclosure" force to the anvil 1810 as the firing member 2140 continues to be distally advanced. In at least one arrangement as illustrated in FIG. 61, for example, when the anvil 1810 is in the over closed position (with no tissue being clamped between the anvil and the cartridge), the distal portion of the anvil 1810 will contact with the cartridge deck surface 1710. As a result of such configuration, the force required to distally advance the firing member from its starting position to its ending position within the end effector may generally be less than other surgical end effector arrangements that do not employ such progressive closure arrangements.

Figure 62:
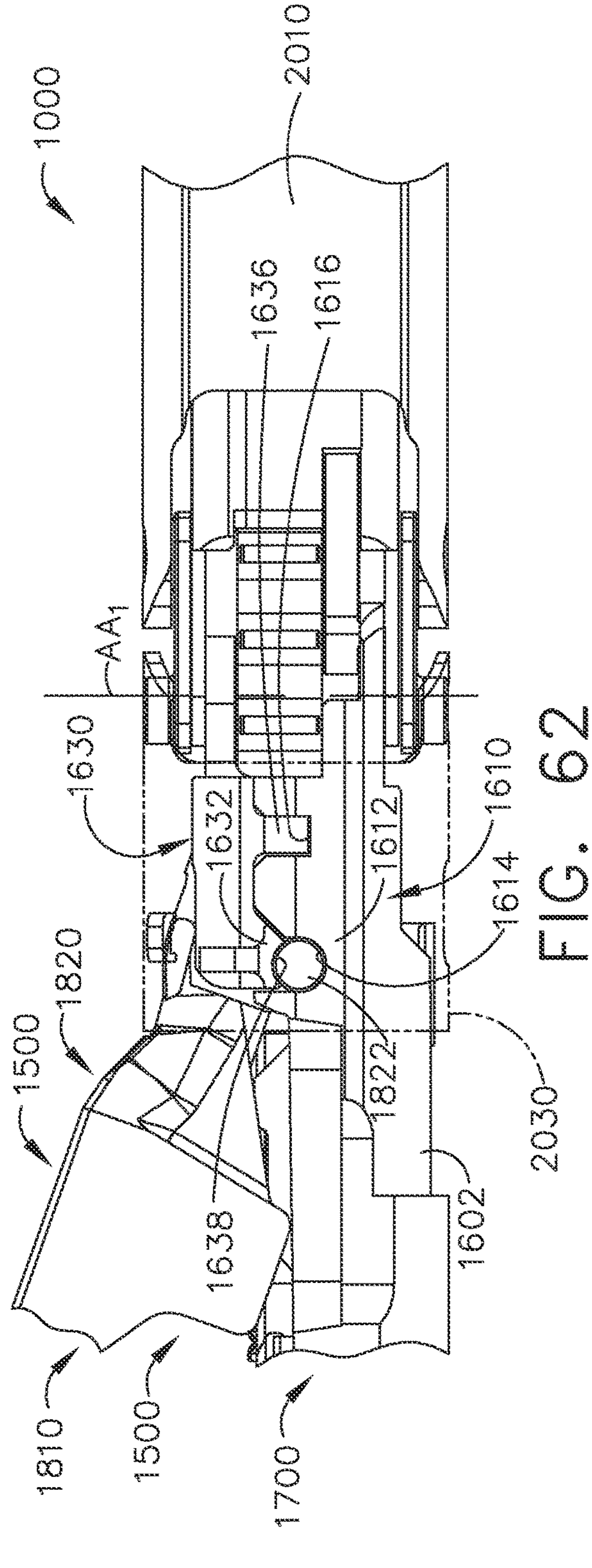
FIG. 62 is a partial side elevational view of the surgical end effector of the interchangeable surgical tool assembly of FIG. 3 in a fully open position with the distal closure tube segment shown in phantom to illustrate the anvil retaining member.
Figure 63:
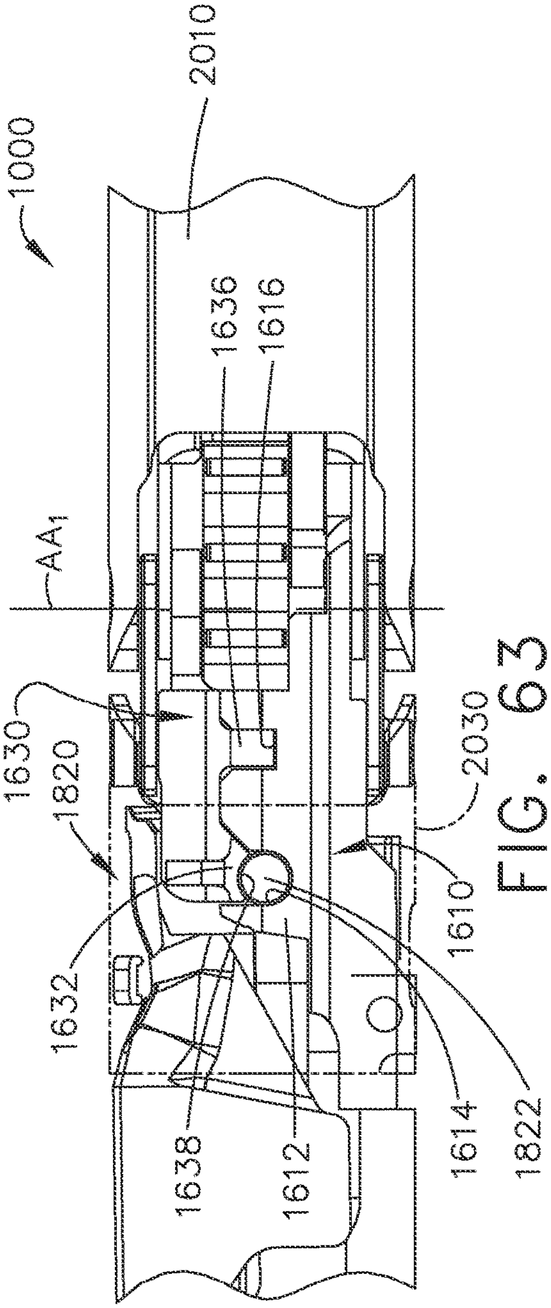
FIG. 63 is another partial side elevational view of the surgical end effector of FIG. 62 with the anvil in a fully closed position.

FIG. 62 illustrates the anvil 1810 of the surgical end effector 1500 in a fully opened position. As was discussed above, each of the anvil trunnions 1822 are received in a corresponding trunnion cradle 1614 that is formed in the upstanding walls 1612 of the proximal end portion 1610 of the elongate channel 1602. The anvil trunnions 1822 are pivotally retained in their corresponding trunnion cradle 1614 by the channel cap or anvil retainer 1630. The channel cap 1630 includes a pair of attachment lugs 1636 that are configured to be retainingly received within corresponding lug grooves or notches 1616 formed in the upstanding walls 1612 of the proximal end portion 1610 of the elongate channel 1602. During a portion of the closure stroke for the anvil 1810 on thick tissue, counterforces established during the tissue clamping process seek to push the anvil trunnions 1822 out of their respective trunnion cradles 1614. The channel cap 1630 includes a pair of slot cap portions 1632 that correspond to each trunnion cradle 1614. When the channel cap 1630 is installed onto the proximal end portion 1610 of the elongate channel 1602, each slot cap portion 1632 serves to retain the anvil trunnions 1822 within their respective trunnion cradles 1614 during the closure process. As can be seen in FIGS. 62 and 63, each slot cap portion 1632 may have an arcuate bottom portion 1638 that is configured to pivotally receive the corresponding anvil trunnion 1822. Each slot cap 1632 may have a wedge shape to completely block the open end of the trunnion cradles 1614. Such channel cap arrangement 1630 may facilitate ease of assembly of the anvil 1810 to the elongate channel 1602. Once the anvil trunnions 1822 have been placed into their respective trunnion cradles 1614, the channel cap 1630 may then be installed as shown. In at least one arrangement, the distal closure tube segment 2030 serves to retain the channel cap 1630 in position which serves to prevent the anvil trunnions 1822 from moving vertically in their respective trunnion cradles 1614 during closure as shown in FIG. 63. In another arrangement, the attachment lugs 1636 may be frictionally retained within their respective notches 1616 or otherwise be retained therein by adhesive or other fastening means.

The four interchangeable tool assemblies 1000, 3000, 5000 and 7000 employ different jaw opening configurations to facilitate moving the anvil from a closed position to a fully open position. For example, the distal closure tube segment 4030 of the interchangeable tool assembly 3000 includes positive jaw or anvil opening features 4040 that correspond to each of the sidewalls of the distal closure tube segment 4030 and protrude inwardly therefrom. The positive anvil opening features 4040 extend inwardly through corresponding openings in the transitional sidewalls and may be welded to the distal closure tube segment 4030. In this arrangement, the positive anvil opening features are axially aligned with each other and are configured to operably interface with corresponding opening ramps formed on the undersides of the anvil mounting portion 3820. When the anvil 3810 and the distal closure tube segment 4030 are in their fully closed positions, each of the positive anvil opening features 4040 is located in a cavity that is established between the anvil opening ramps and the bottom portion of the elongate channel 3602. When in that position, the positive anvil opening features 4040 do not contact the anvil mounting portion 3820 or at least may not apply any significant opening motions or forces thereto. When the distal closure tube segment 4030 is moved in the proximal direction, the anvil opening features 4040 are brought into contact with the anvil opening ramps to cause the anvil 3810 to pivot to an open position. Further details regarding the positive anvil opening features 4040 may be found in U.S. patent application Ser. No. 15/385,911, entitled SURGICAL STAPLE/FASTENERS WITH INDEPENDENTLY ACTUATABLE CLOSING AND FIRING SYSTEMS, now U.S. Pat. No. 10,448,950.

With regard to the surgical end effector 5500 of tool assembly 5000, the distal closure tube segment 6030 includes two inwardly extending positive anvil opening tabs 6038 that may be punched into the wall of the distal closure tube segment 6030. See FIG. 21. In the illustrated arrangement, the tabs 6038 are axially aligned with each other and are configured to contact corresponding upstanding anvil tails 5827 formed on the anvil mounting portion 5820. When the distal closure tube segment 6030 is moved in the proximal direction, the anvil opening features 6038 are brought into contact with the anvil tails 5827 to cause the anvil 5810 to pivot to an open position.

With regard to the surgical end effector 7500 of the tool assembly 7000, a positive anvil opening motion is applied to the anvil 7810 by the distal closure tube segment 8030 when the distal closure tube segment 8030 is moved proximally. As was discussed above, an upstanding anvil tab 7824 is formed on the anvil mounting portion 7820 and extends into the horseshoe-shaped opening 8038 in the distal closure tube segment 8030. See FIG. 24. Opening 8038 defines an opening tab 8039 that is configured to operably interface with the anvil tab 7824 as the distal closure tube segment 8030 is retracted in the distal direction. Such interaction between the opening tab 8039 and the anvil tab 7824 applies an opening motion to the anvil 7810 to thereby cause the anvil 7810 to move to an open position.

Figure 64:
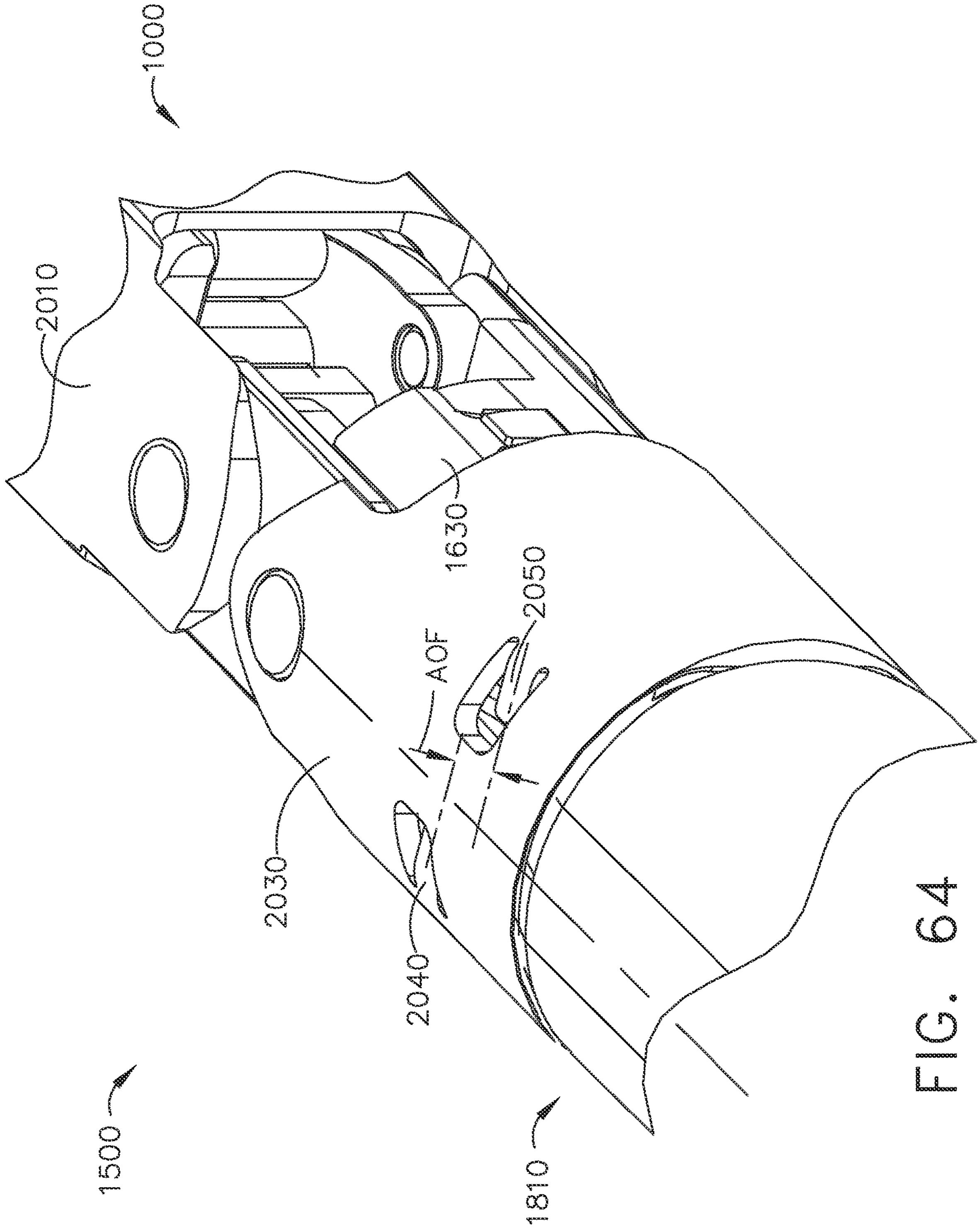
FIG. 64 is a partial perspective view of a distal closure tube segment of the interchangeable surgical tool assembly of FIG. 3 with the anvil in a fully closed position.
Figure 65:
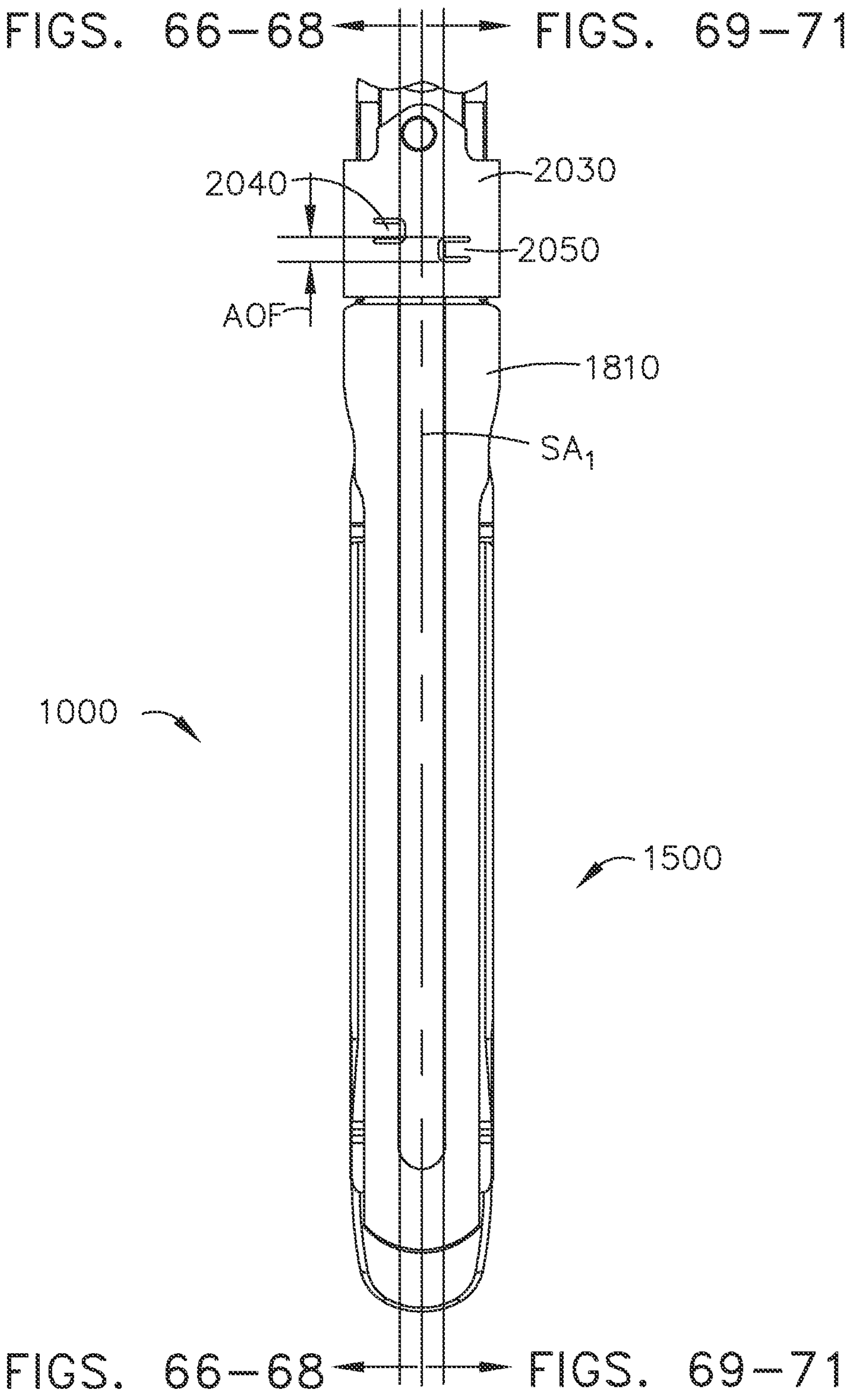
FIG. 65 is a top plan view of the distal closure tube segment and anvil of FIG. 64.
Figure 66:
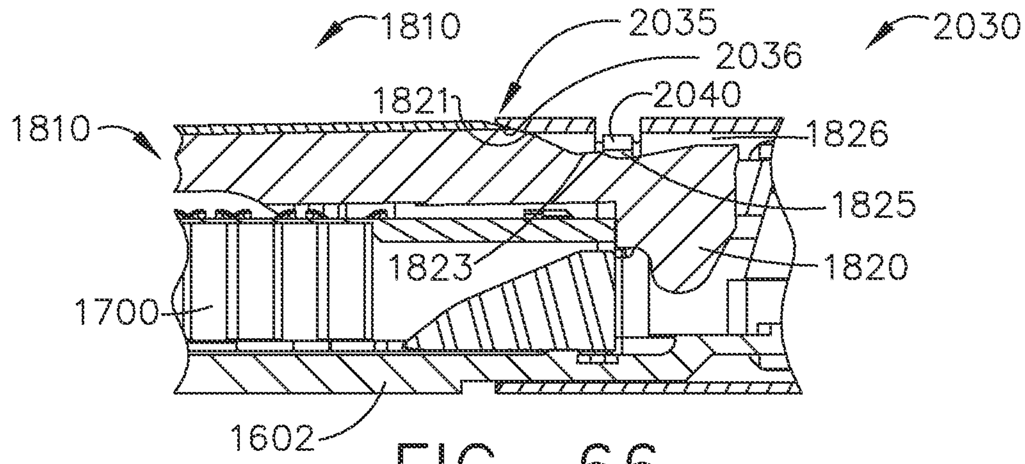
FIG. 66 is a partial cross-sectional view of the anvil and distal closure tube segment of FIGS. 64 and 65 illustrating the position of a proximal jaw opening feature when the anvil is in a fully closed position.
Figure 67:
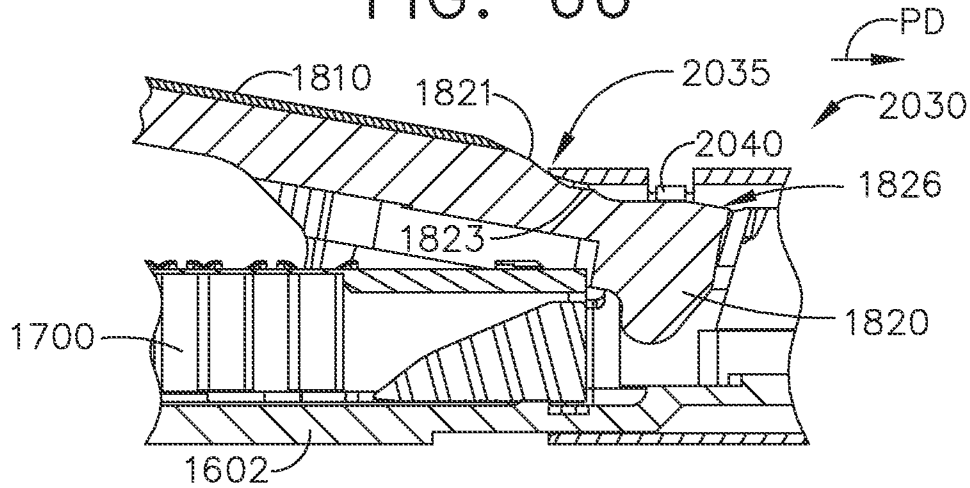
FIG. 67 is another partial cross-sectional view of a portion of the anvil and distal closure tube segment of FIGS. 64-66 illustrating the position of the proximal jaw opening feature when the anvil is between the fully open and fully closed positions.

With regard to surgical end effector 1500 of the interchangeable tool assembly 1000, in the illustrated example, the distal closure tube segment 2030 employs two axially offset, proximal and distal positive jaw opening features 2040 and 2050 as illustrated in FIGS. 64-77. As can be seen in FIGS. 64 and 65, the proximal positive jaw opening feature 2040 is axially proximal to the distal positive jaw opening feature 2050 by an axial offset distance AOF. In FIG. 65, the proximal positive jaw opening feature 2040 is located on the right side (as viewed by a user of the tool assembly) of the shaft axis $SA_1$. FIGS. 66, 72 and 73 illustrate the position of the proximal positive jaw opening feature 2040 when the anvil 1810 is in the closed position. As can be most particularly seen in FIG. 66, when in that position, the proximal positive jaw opening feature 2040 is in a right side or first relieved area 1825 formed in the anvil mounting portion 1820. FIGS. 69, 72 and 73 illustrate the position of the distal positive jaw opening feature 2050 when the anvil 1810 is in the closed position. As can be most particularly seen in FIG. 69, when in that position, the distal positive jaw opening feature is in contact with a stepped portion 1823 of the anvil cam surface 1821.

Figure 70:
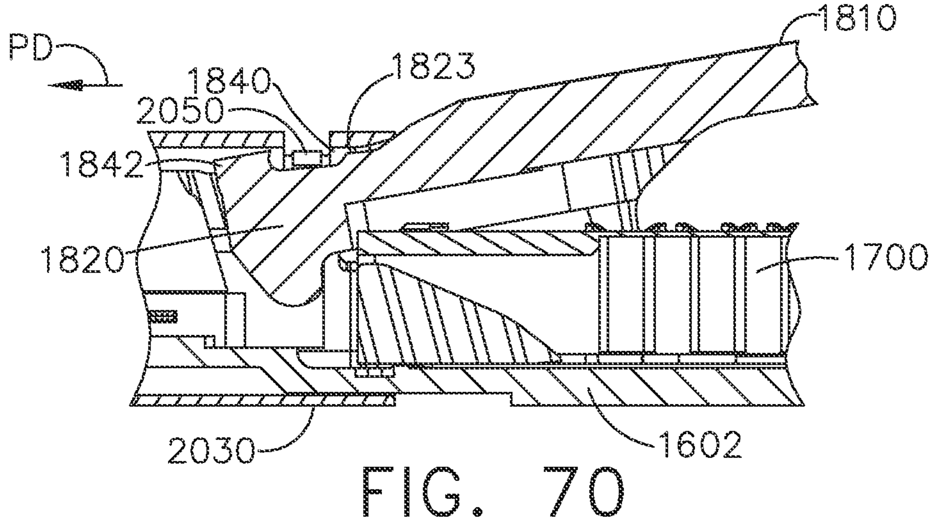
FIG. 70 is a partial cross-sectional view of the anvil and distal closure tube segment of FIGS. 64-69 illustrating the position of the distal jaw opening feature when the anvil is between the fully open and fully closed positions.
Figure 74:
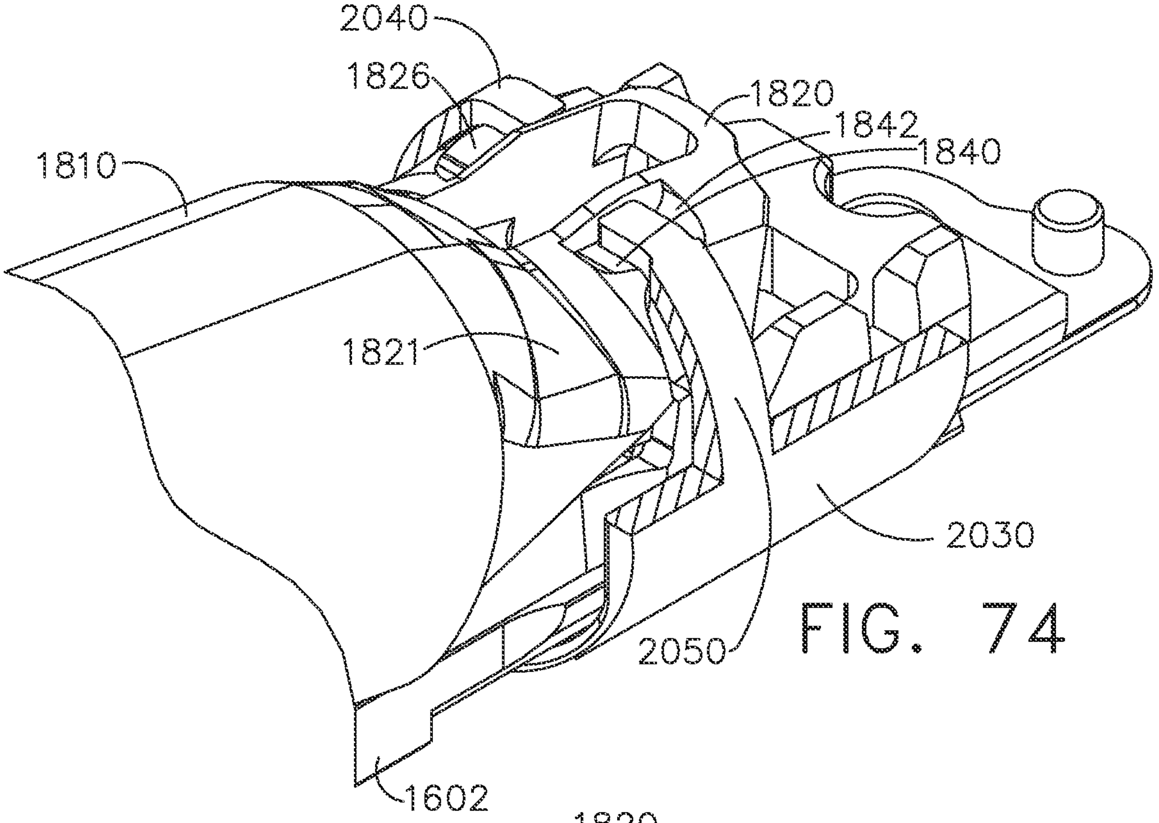
FIG. 74 is a partial left side perspective view of the anvil and distal closure tube segment of FIGS. 64-73 with the anvil in a partially open position.
Figure 75:
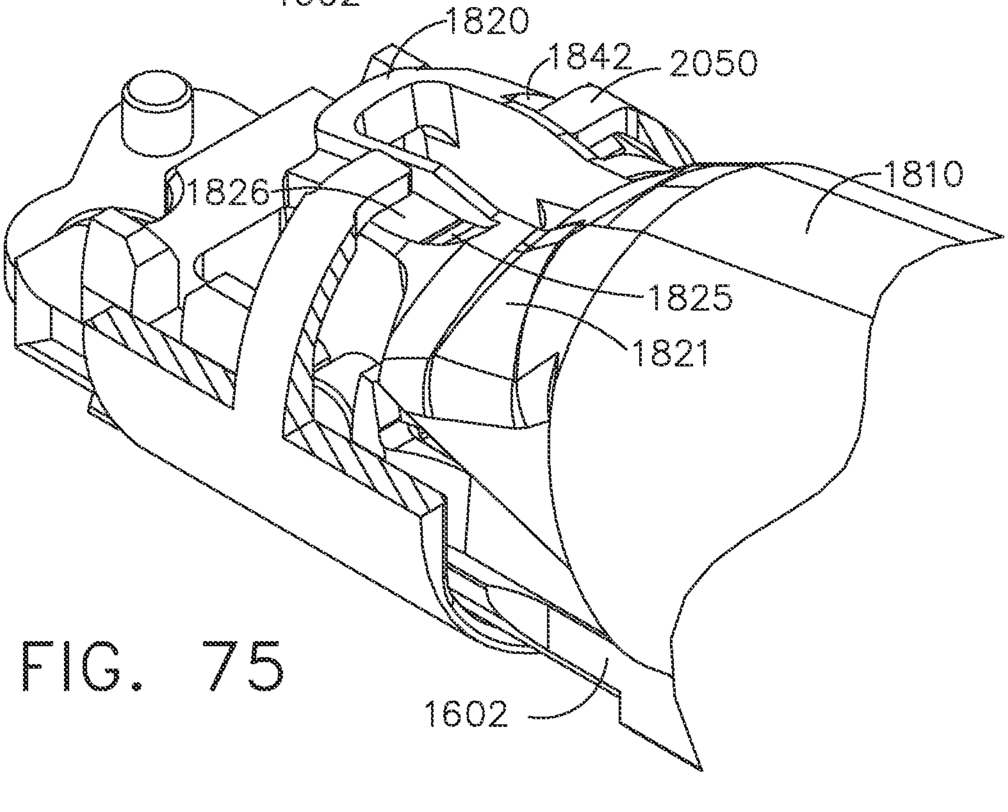
FIG. 75 is a partial right side perspective view of the anvil and distal closure tube segment of FIGS. 64-74 with the anvil in a partially open position.
Figure 76:
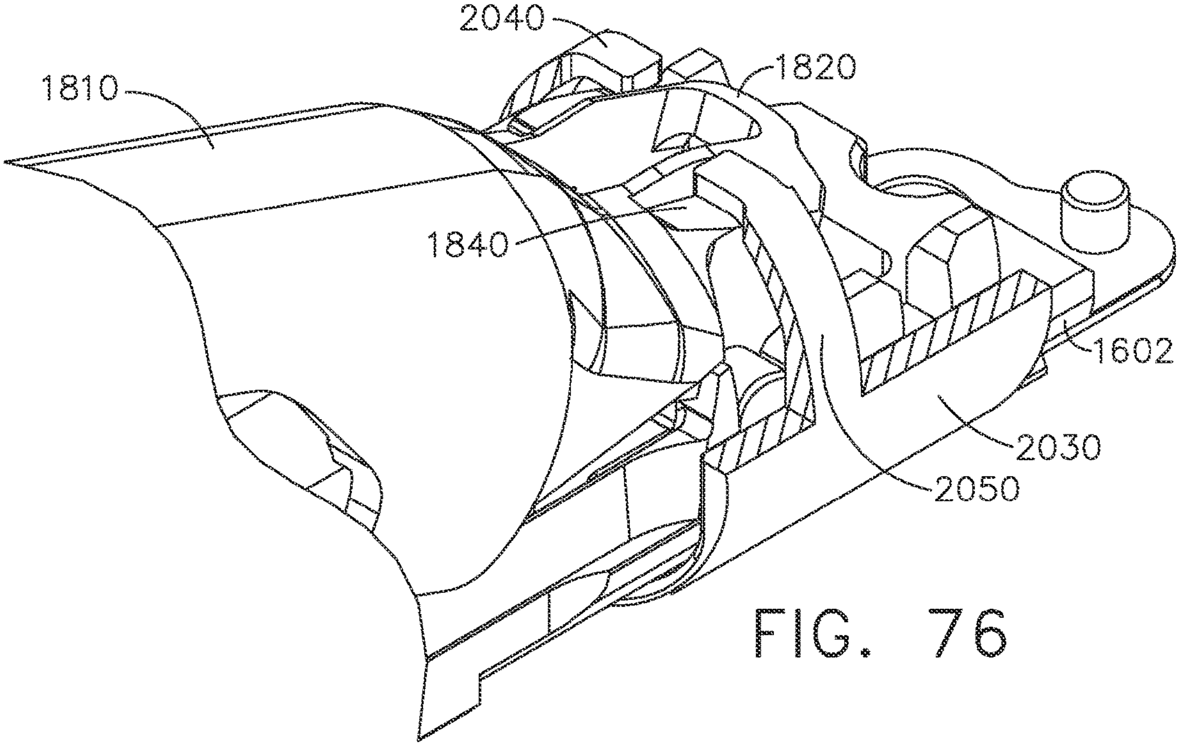
FIG. 76 is a partial left side perspective view of the anvil and distal closure tube segment of FIGS. 64-75 with the anvil in a fully open position.
Figure 77:
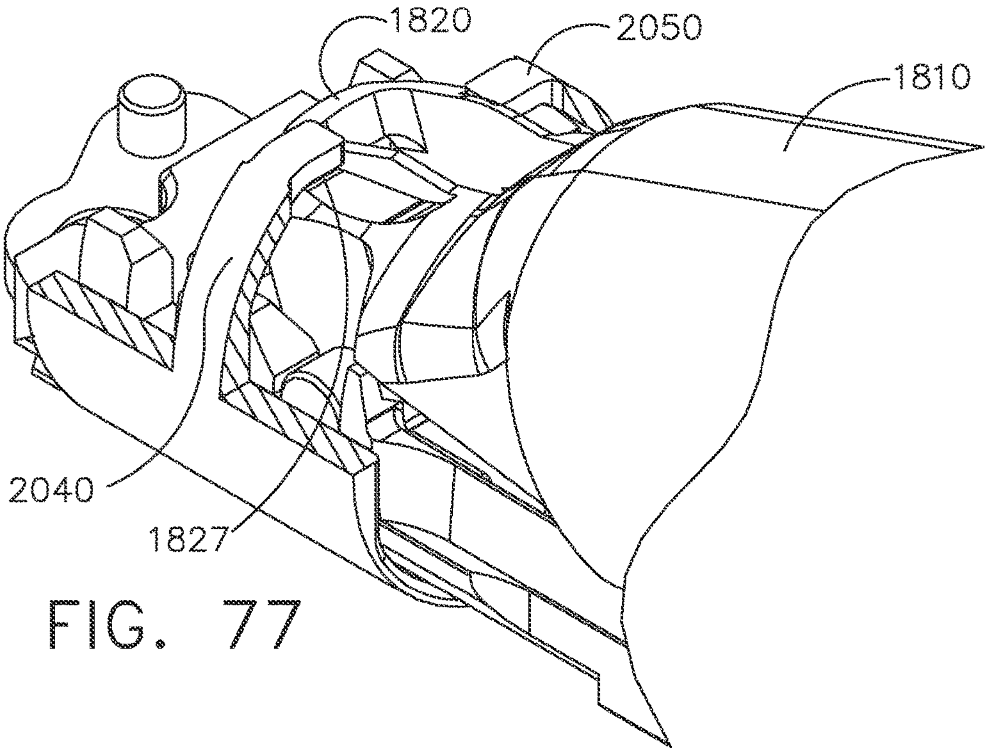
FIG. 77 is a partial right side perspective view of the anvil and distal closure tube segment of FIGS. 64-76 with the anvil in a fully open position.

To commence the opening process, the jaw closure system is actuated to move the distal closure tube segment 2030 in the proximal direction PD. As the distal closure tube segment 2030 is moved in the proximal direction PD, the proximal positive jaw opening feature 2040 contacts a first or right side jaw opening cam surface 1826 and begins to apply a jaw opening motion to the anvil 1810. See FIGS. 67, 74 and 75. As can be seen in FIGS. 70, 74 and 75, during this proximal movement of the distal closure tube segment 2030, the distal positive jaw opening feature 2050 is axially movable within a second or left relief area 1840 formed in the anvil mounting portion 1820. Thus, while the proximal positive jaw opening feature 2040 is applying a first or initial opening motion to the anvil mounting portion 1820, the distal positive jaw opening feature 2050 is not applying any significant opening motion to the anvil 1810. Further proximal motion of the distal closure tube segment 2030 will result in the distal positive jaw opening feature 2050 contacting a left anvil open tab 1842 and the proximal positive jaw opening feature 2040 disengaging the jaw opening cam surface 1826. Thus, the proximal positive jaw opening feature 2040 has disengaged the anvil mounting portion 1820 and is not applying any further opening motion thereto while the distal positive jaw opening feature 2050 is applying a second jaw opening motion to the anvil mounting portion 1820 to pivot the anvil 1810 to a fully open position illustrated in FIGS. 68, 71, 76 and 77.

Figure 78:
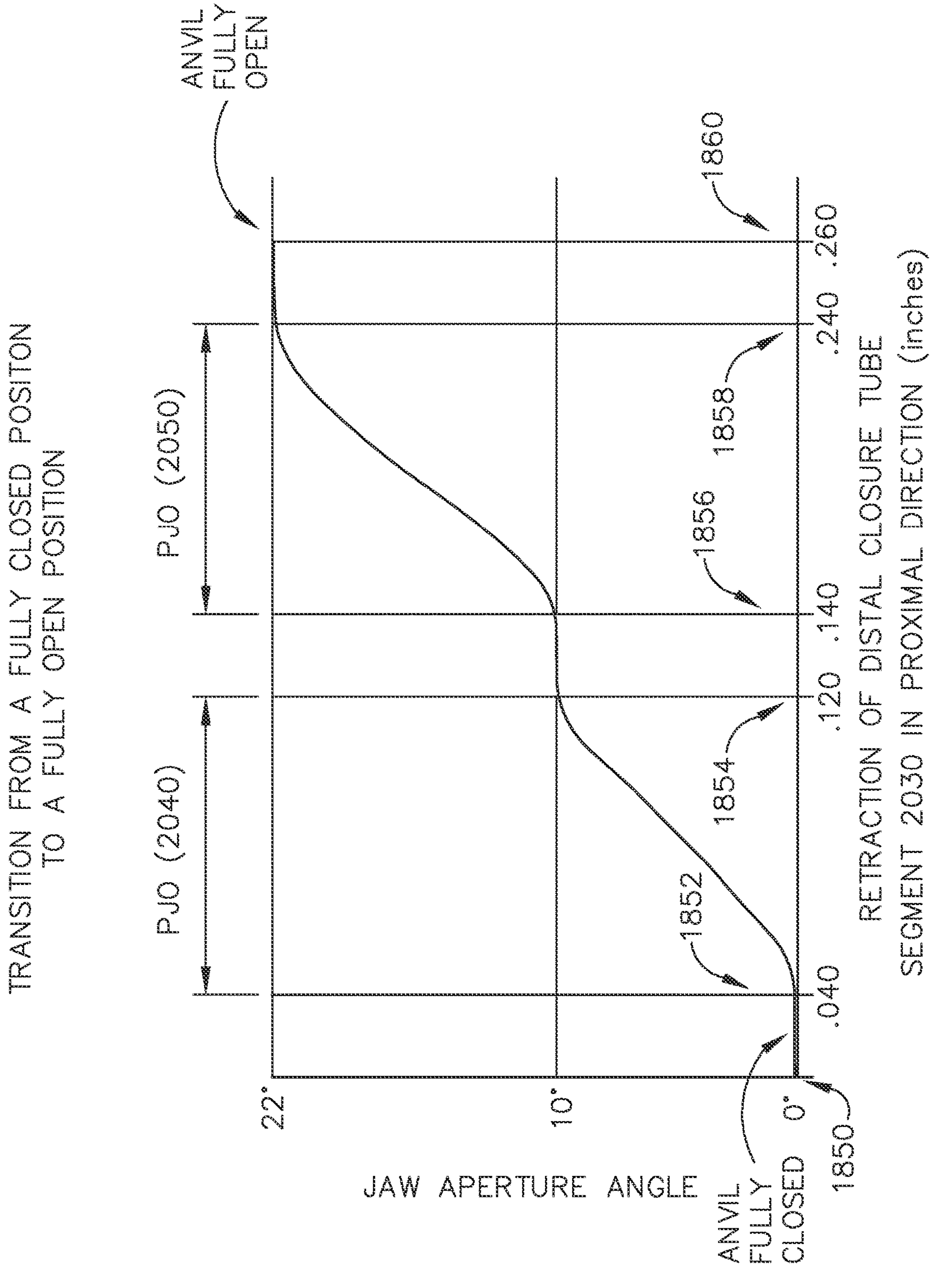
FIG. 78 is a graphical comparison between the jaw aperture angle and retraction of the distal closure tube segment of FIGS. 64-77.

FIG. 78 depicts the anvil or jaw opening process employed by the interchangeable tool assembly 1000 in graphical form. As can be seen in that Figure, the left or vertical axis of the graph represents the amount of jaw aperture from about 0° to about 22° (“anvil aperture angle”) and the bottom or horizontal axis represents the approximate proximal axial travel of the distal closure tube segment 2030 from a position wherein the anvil is fully closed to a position wherein the anvil is fully open. As indicated above, the “anvil aperture angle” or “jaw aperture angle” may represent the angle between the cartridge deck surface or tissue contacting surface on the surgical fastener cartridge or “first jaw” and the fastener forming surface or tissue contacting surface on the anvil or “second jaw”. When the anvil is fully closed, the anvil aperture angle may be approximately 0°, for example. In the illustrated arrangement, the distal closure tube segment 2030 can move proximally from a first position (1850 on the graph) that corresponds to the fully closed position a proximal distance of, for example, about 0.040 inches to a first intermediate position (1852 on the graph) before the proximal positive jaw opening feature 2040 begins to apply a first jaw opening motion to the anvil 1810. As the distal closure tube segment 2030 continues to move proximally from the first intermediate position 1852 to a second intermediate position (1854 on the graph) a further proximal distance of, for example, about 0.040 inches to about 0.120 inches, the proximal positive jaw opening feature 2040 moves the anvil 1810 through an anvil aperture angle from 0° to about 10°. While the distal closure tube segment 2030 continues to travel proximally from the second intermediate position 1854 to a third intermediate position (1856 on the graph) a further proximal distance (from about 0.120 inches to about 0.140 inches), the anvil remains at about a 10° anvil aperture angle. Further proximal movement of the distal closure tube segment 2030 from the third intermediate position 1856 to a fourth intermediate position (1858 on the graph) a proximal distance (from about 0.140 inches to about 0.240 inches), the distal positive jaw opening feature 2050 begins to apply a second jaw opening motion to the anvil 1810. As the distal closure tube segment 2030 continues to move proximally from the third intermediate position 1856 to a fourth intermediate position (1858 on the graph) a further proximal distance (from, for example, about 0.140 inches to about 0.240 inches), the distal positive jaw opening feature 2050 moves the anvil 1810 relative to the elongate channel 1602 such that the anvil aperture angle increases from about 10° to about 22°, for example. While the distal closure tube segment 2030 continues to travel proximally from the fourth intermediate position 1858 to a final proximal position (1860 on the graph) a further proximal distance (from about 0.240 inches to about 0.260 inches, for example), the anvil 1810 remains at a fully open position with an anvil aperture angle of approximately 22°.

Figure 68:
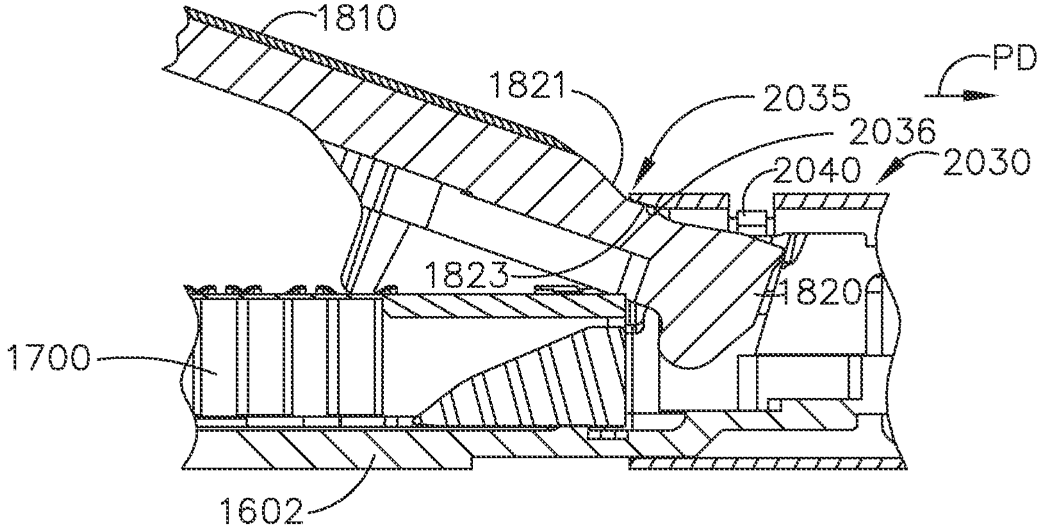
FIG. 68 is another partial cross-sectional view of a portion of the anvil and distal closure tube segment of FIGS. 64-67 illustrating the position of the proximal jaw opening feature when the anvil is in the fully open position.
Figure 69:
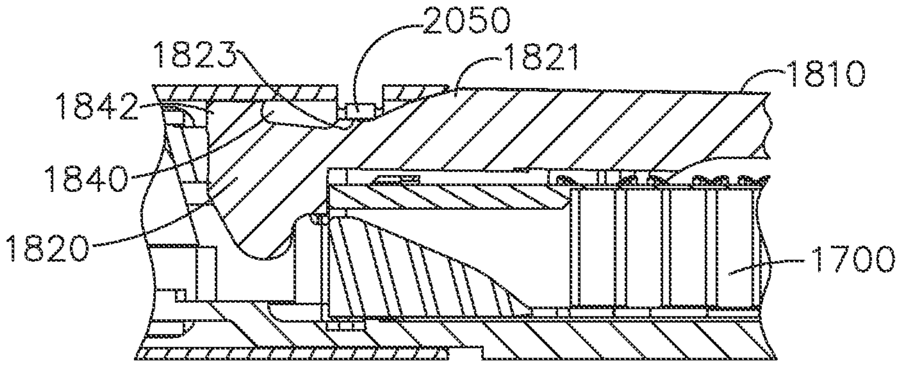
FIG. 69 is a partial cross-sectional view of the anvil and distal closure tube segment of FIGS. 64-68 illustrating the position of a distal jaw opening feature when the anvil is in a fully closed position.
Figure 71:
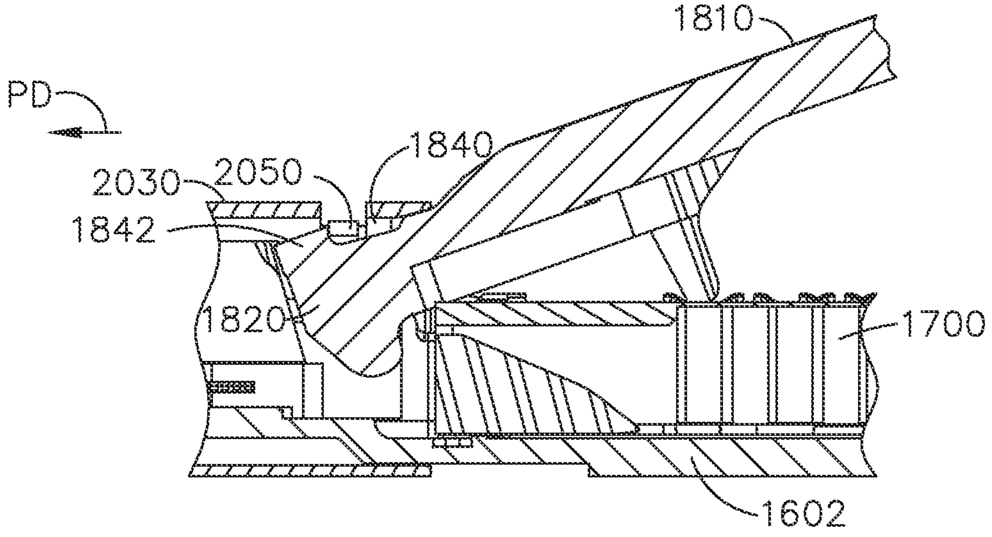
FIG. 71 is another partial cross-sectional view of a portion of the anvil and distal closure tube segment of FIGS. 64-70 illustrating the position of the distal jaw opening feature when the anvil is in the fully open position.
Figure 72:
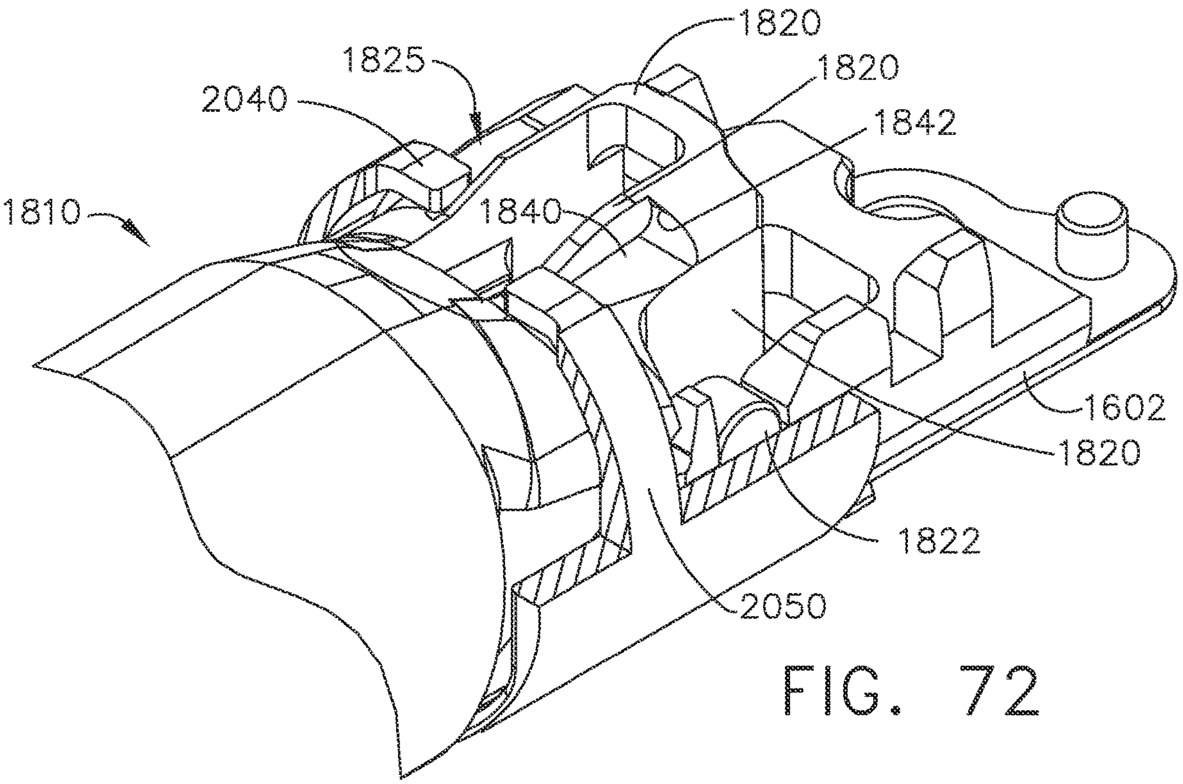
FIG. 72 is a partial left side perspective view of the anvil and distal closure tube segment of FIGS. 64-71 with the anvil in a fully closed position.
Figure 73:
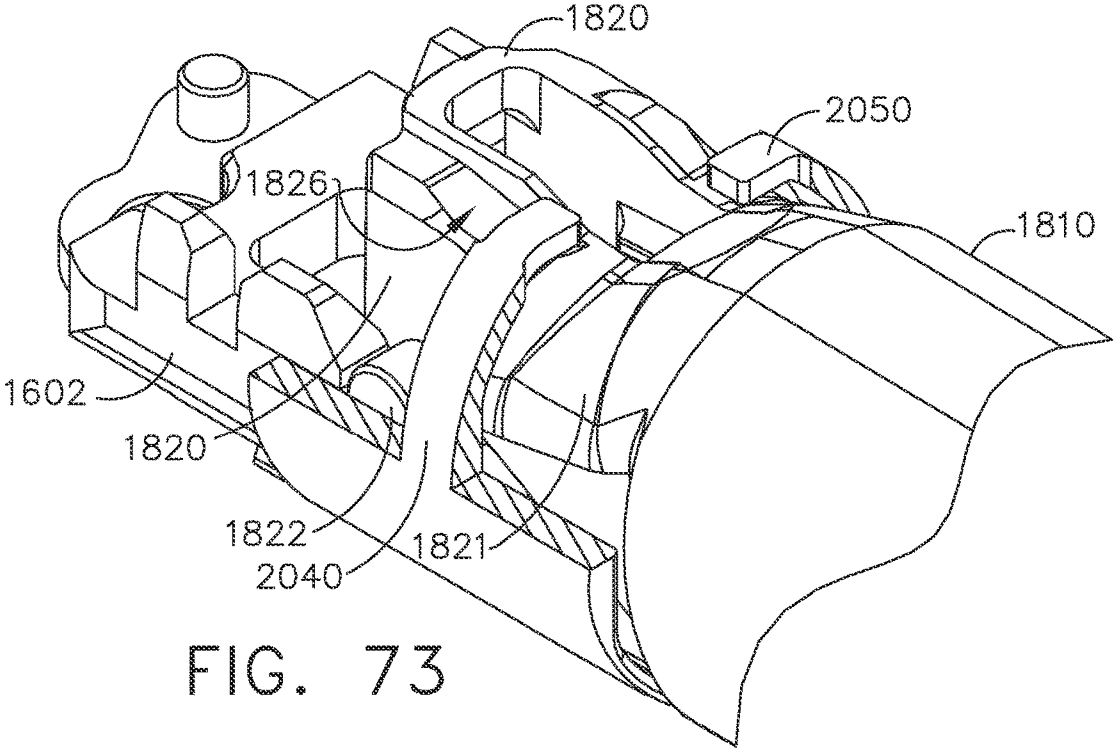
FIG. 73 is a partial right side perspective view of the anvil and distal closure tube segment of FIGS. 64-72 with the anvil in a fully closed position.

The closure process of the illustrated example of the interchangeable tool assembly 1000 may be understood from reference to FIGS. 67-69 and 70-72, as well as FIG. 78. FIGS. 68 and 71 illustrate the anvil 1810 in its fully open position. As can be seen in those Figures, the proximal positive jaw opening feature 2040 is out of contact with the anvil mounting portion 1820 and the distal positive jaw opening feature 2050 is in contact with the left anvil open tab 1842. When the anvil closure process is commenced, the closure drive system is actuated to move the distal closure tube segment 2030 in the distal direction DD. As the distal closure tube segment moves from the final proximal position 1860 to the fourth intermediate position 1858 (FIG. 78), the anvil 1810 remains in its fully open position. Thus, once the closure process is commenced, in at least one example, the distal closure tube segment 2030 may move distally a first or initial predetermined axial closure distance before the anvil 1810 begins to move. Stated another way, the distal closure tube segment may move the first predetermined axial closure distance before any closure motion is applied to the anvil 1810. In at least one example, the first or initial predetermined closure distance may be approximately 0.020 inches. As the distal closure tube segment 2030 continues to move distally through an intermediate axial closure distance, the distal end 2035 of the distal closure tube segment 2030 begins to contact the anvil cam surface 1821 on the anvil mounting portion 1820 (FIGS. 67 and 70) until the internal cam surface 2036 on the distal closure tube segment 2030 begins to cammingly contact the anvil cam surface 1821. As the internal cam surface 2036 travels up the anvil cam surface 1821, the anvil 1810 is pivoted to the fully closed position. The anvil cam surface 1821 and the internal cam surface 2036 may be configured to permit further distal travel of the distal closure tube segment 2030 from, for example, first intermediate point or position 1852 to the first position 1850 (FIG. 78). Thus, in at least one example, the distal closure tube segment 2030 may move distally a final predetermined axial closure distance during the closing process after the anvil 1810 has attained its fully closed position. In at least one example, the final predetermined axial closure distance may be approximately 0.040 inches.

In those surgical stapling devices that employ a firing member assembly that comprises a firing member that has a tissue cutting surface, it may be desirable for the firing system and portions of the end effector to be configured in such a way so as to prevent the inadvertent advancement of the firing member unless an unspent staple cartridge is properly supported in the end effector. If, for example, no staple cartridge is present at all and the firing member is distally advanced through the end effector, the tissue would be severed, but not stapled. Similarly, if a spent staple cartridge (i.e., a staple cartridge wherein at least some of the staples have already been fired therefrom) is present in the end effector and the firing member is advanced, the tissue would be severed, but may not be completely stapled, if at all. It will be appreciated that such occurrences could lead to undesirable catastrophic results during the surgical procedure. U.S. Pat. No. 6,988,649 entitled SURGICAL STAPLING INSTRUMENT HAVING A SPENT CARTRIDGE LOCKOUT, U.S. Pat. No. 7,044,352 entitled SURGICAL STAPLING INSTRUMENT HAVING A SINGLE LOCKOUT MECHANISM FOR PREVENTION OF FIRING, U.S. Pat. No. 7,380,695 entitled SURGICAL STAPLING INSTRUMENT HAVING A SINGLE LOCKOUT MECHANISM FOR PREVENTION OF FIRING, U.S. Patent Application Publication No. 2016/0367247, entitled SURGICAL STAPLING INSTRUMENTS WITH LOCKOUT ARRANGEMENTS FOR PREVENTING FIRING SYSTEM ACTUATION WHEN A CARTRIDGE IS SPENT OR MISSING, now U.S. Pat. No. 10,154,841, and U.S. patent application Ser. No. 15/385,958, entitled SURGICAL INSTRUMENTS WITH LOCKOUT ARRANGEMENTS FOR PREVENTING FIRING SYSTEM ACTUATION UNLESS AN UNSPENT STAPLE CARTRIDGE IS PRESENT, now U.S. Pat. No. 10,639,034, each disclose various firing member lockout arrangements. Each of those references is hereby incorporated by reference in its entirety herein.

Referring to FIGS. 60A-60I, there is shown a surgical end effector 9010 that comprises a portion of a surgical tool assembly 9000 that comprises a first jaw 9020 and a second jaw 9120. In the illustrated arrangement, for example, the first jaw 9020 comprises an elongate channel 9022 that is configured to removably and operably support a surgical staple cartridge 9600 therein. The elongate channel 9022 is attached to an elongate shaft assembly 9300 of the surgical tool assembly. In the arrangement depicted in FIGS. 60C and 60D, for example, the elongate channel 9022 is pivotally coupled to a spine assembly 9310 of the elongate shaft assembly 9300 for selective articulation relative thereto. See FIGS. 60D, 60E, 60H and 60I. The elongate shaft assembly 9300 may define a shaft axis SA. The second jaw 9120 comprises an anvil 9122 that is movably supported on the elongate channel 9022 and which is movable between open and closed positions by the closure system 9400. The anvil 9122 includes an anvil body 9124 and an anvil mounting portion 9126 that is pivotally supported for pivotal travel relative to the proximal end 9024 of the elongate channel 9022. The closure system 9400 may include, for example, an axially movable distal closure tube segment 9410 that is configured to cammingly engage a cam surface 9128 on the anvil mounting portion 9126 when the distal closure tube segment 9410 is axially advanced in the distal direction DD. The distal closure tube segment 9410 may also be configured to apply opening motions to the anvil mounting portion 9126 when the distal closure tube segment 9410 is moved in the proximal direction PD. See FIGS. 60C and 60D.

The surgical tool assembly 9000 further includes a firing system 9500 that, in the illustrated arrangement, comprises a firing member assembly 9510 that is configured to receive firing motions from a firing control system supported in a housing of a handheld control system or a robotic control system, for example. In the illustrated embodiment, one form of firing member assembly 9510 comprises a first firing member element 9520 that consists of a firing member body 9522 that supports a tissue cutting surface or blade 9524 thereon. The firing member body 9522 is coupled to a firing bar or knife bar 9530 that operably interfaces with corresponding portions of the firing system 9500 to receive the firing motions from the firing control system. The firing member body 9522 may include second jaw or anvil engagement features 9526 that may comprise laterally extending tab features configured to be received within corresponding second jaw passages or slots 9125 in the anvil body 9124. In addition, the firing member body 9522 may further include first jaw or channel engagement features or a foot 9528 that is configured to be received in corresponding first jaw passages or slots or openings 9023 in the elongate channel 9022.

The staple cartridge 9600 comprises a cartridge body 9602. See FIGS. 60H and 60I. The cartridge body 9602 includes a proximal end 9604, a distal end (not shown), and a deck 9606 extending between the proximal end and the distal end. In use, the staple cartridge 9600 is positioned on a first side of the tissue to be stapled and the anvil 9122 is positioned on a second side of the tissue. The anvil 9122 is moved toward the staple cartridge 9600 to compress and clamp the tissue against the deck 9606. Thereafter, staples or fasteners removably stored in the cartridge body 9602 can be deployed into the tissue. The cartridge body 9602 includes staple or fastener cavities (not shown) defined therein wherein staples or fasteners (not shown) are removably stored in the staple cavities. The staple cavities may be arranged in longitudinal rows. In one arrangement, for example, three rows of staple cavities are positioned on a first side of a longitudinal slot and three rows of staple cavities are positioned on a second side of the longitudinal slot. The longitudinal slot is configured to axially receive the first firing member element 9520 therethrough. Other arrangements of staple/fastener cavities and staples or fasteners may be possible.

Figure 60:
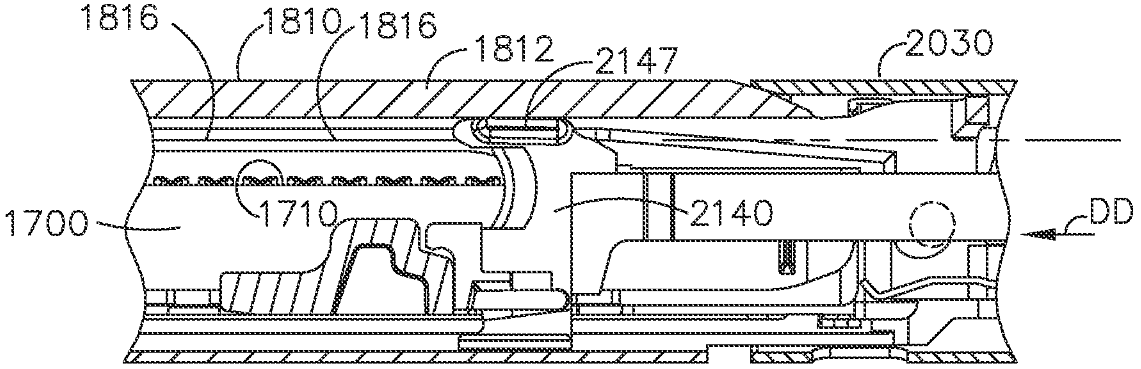
FIG. 60 is another partial cross-sectional view of the surgical end effector of FIGS. 57 and 58 after the firing member thereof has been distally advanced during the firing process.
Figure 60A:
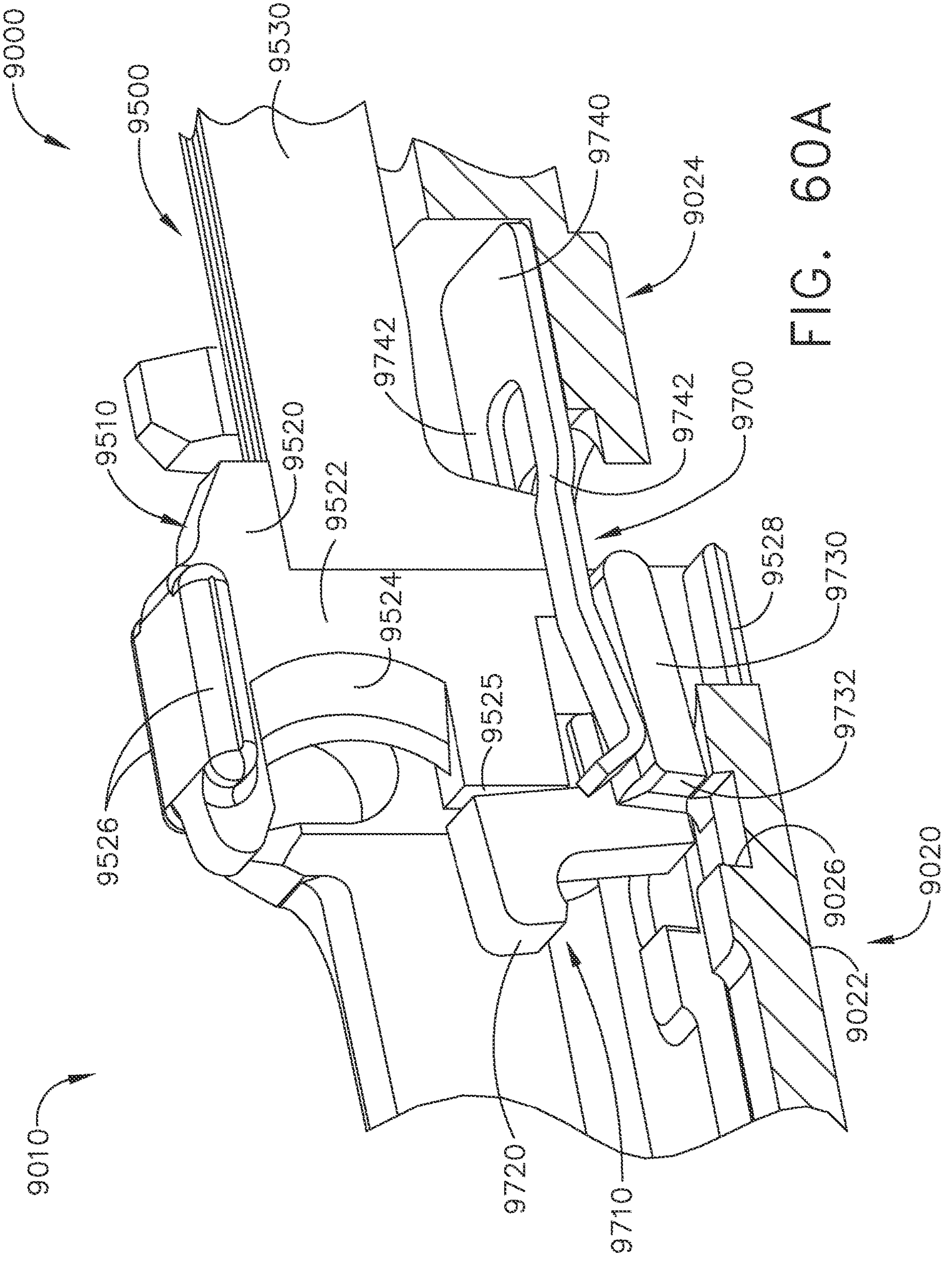
FIG. 60A is a perspective view of a portion of a firing member assembly of surgical stapling instrument that includes a first firing member element and a second firing member element that is movable relative to the first firing member element between a locked and an unlocked position.
Figure 60B:
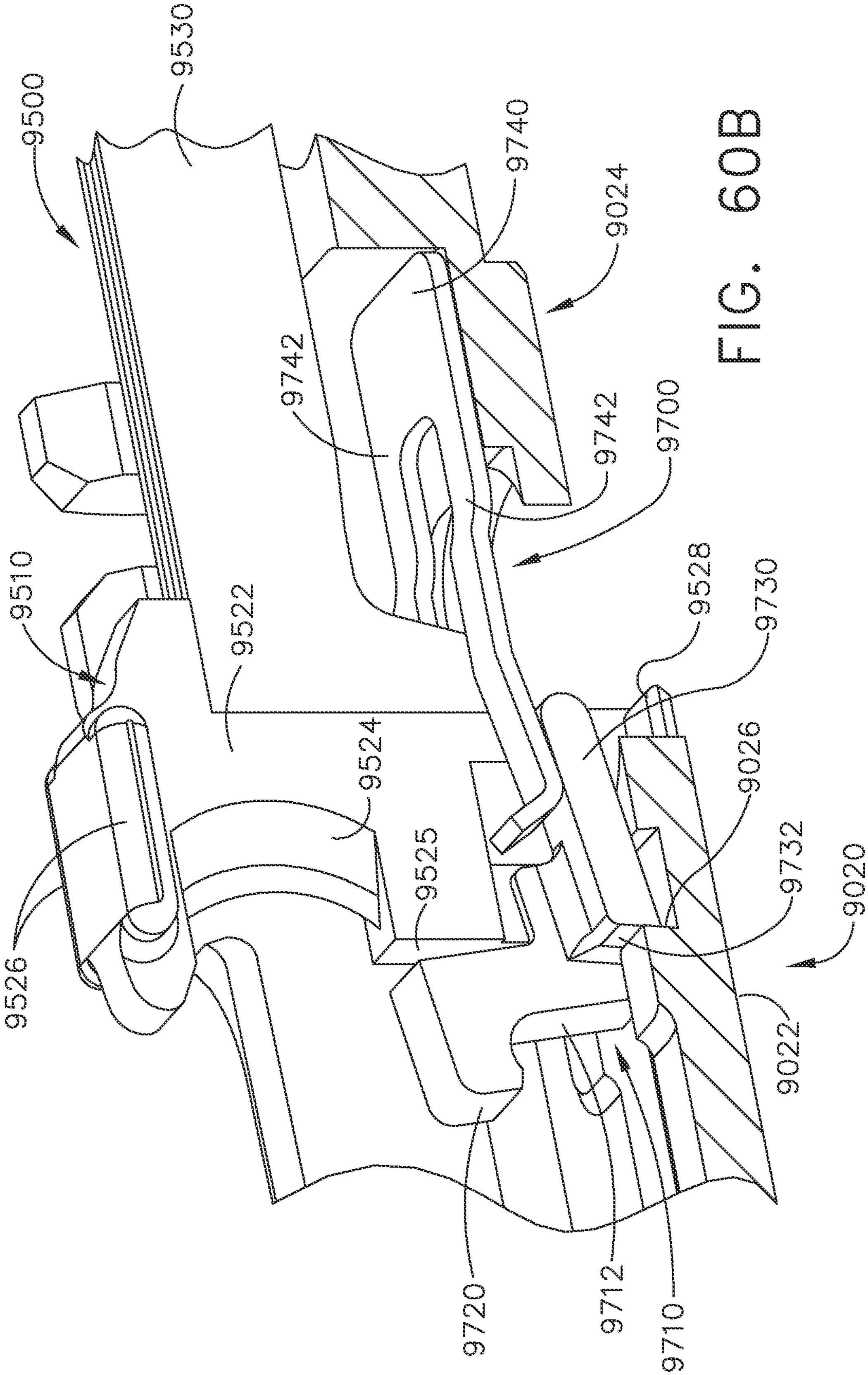
FIG. 60B is another perspective view of the firing member assembly of FIG. 60A with the second firing member element in the locked position.
Figure 60C:
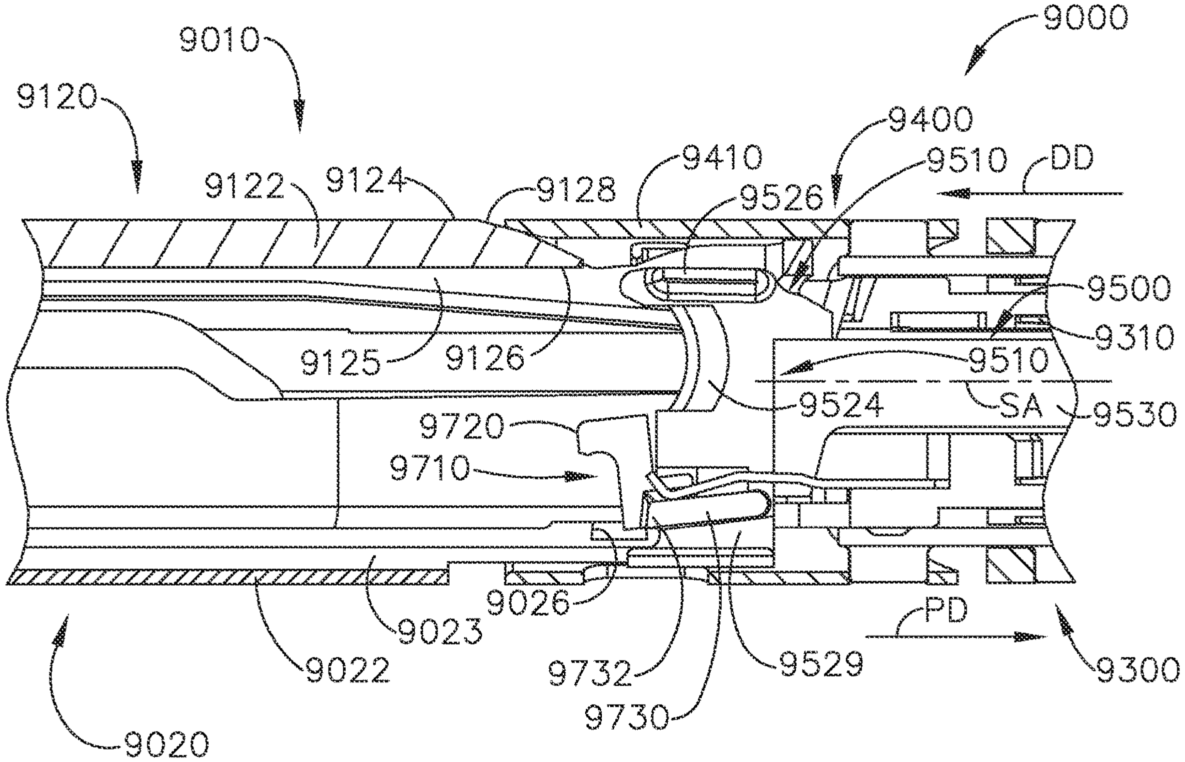
FIG. 60C is a cross-sectional elevational view of the surgical stapling instrument of FIG. 60A with the firing member assembly in a starting position.
Figure 60D:
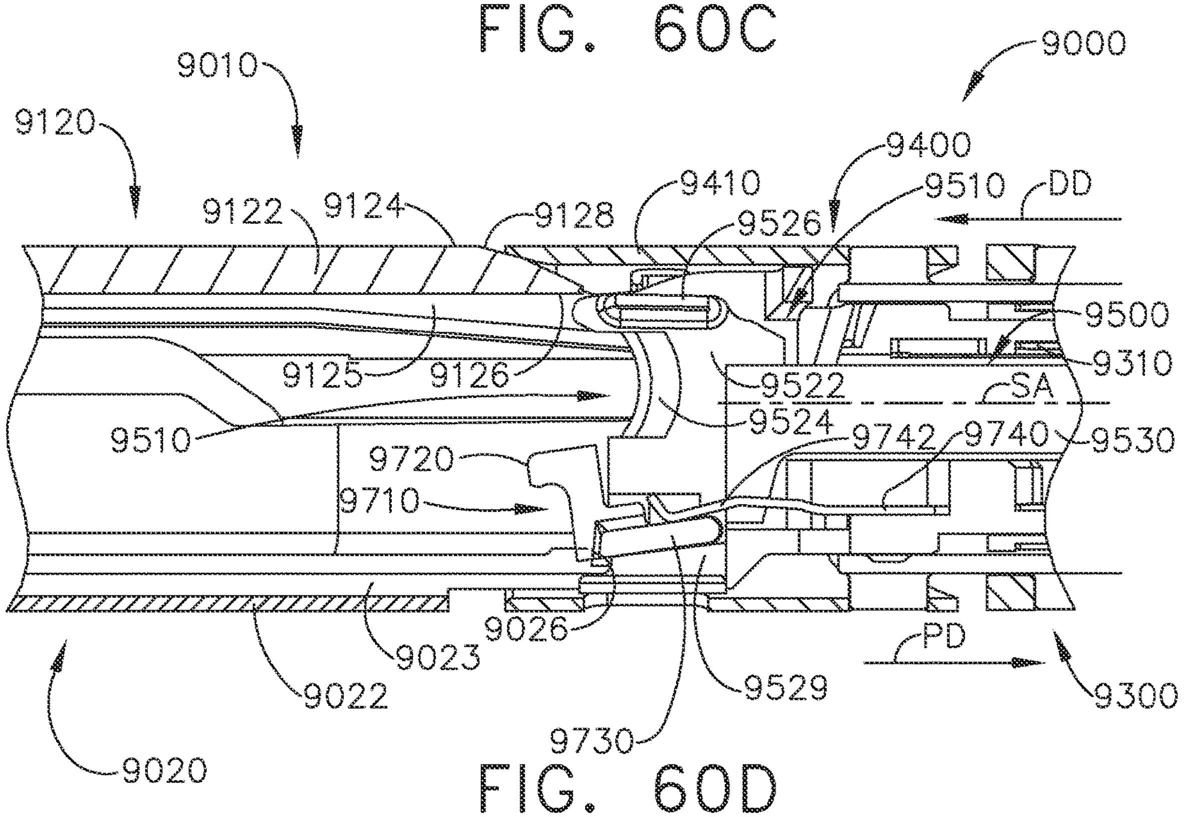
FIG. 60D is another cross-sectional view of the surgical stapling instrument of FIG. 60C illustrated in a locked out configuration.

The staples or fasteners are supported by staple drivers (not shown) that are movably supported in the cartridge body 9602. The drivers are movable between a first, or unfired position, and a second, or fired, position to eject the staples or fasteners from the cavities. The drivers are retained in the cartridge body 9602 by a retainer (not shown) which extends around the bottom of the cartridge body 9602 and includes resilient members configured to grip the cartridge body and hold the retainer to the cartridge body. The drivers are movable between their unfired positions and their fired positions by a sled 9610. The sled 9610 is movable between a proximal, or "unfired" position adjacent the proximal end 9604 and a distal or "fired" position adjacent the distal end (after firing). As can be seen in FIG. 60G, the sled 9610 comprises a plurality of ramped or cam surfaces 9620 that are configured to slide under the drivers and lift the drivers, and the staples or fasteners supported thereon, toward the anvil. An "unfired", "unspent", "fresh" or "new" staple cartridge 9600 means herein that the staple cartridge 9600 has all of its staples or fasteners in their "ready-to-be-fired positions". When in that position, the sled assembly 9610 is located in its starting or "unfired" position. The new staple cartridge 9600 is seated within the elongate channel 9022 and may be retained therein by snap features on the cartridge body 9602 that are configured to retainingly engage corresponding portions of the elongate channel 9022. FIGS. 60G and 60H illustrate a portion of the surgical end effector 9010 with a new or unfired surgical staple cartridge 9600 seated therein. As can be seen in FIGS. 60G and 60H, the sled 9610 is in the unfired position. To prevent the firing system 9500 from being activated and, more precisely, to prevent the first firing member element 9520 from being distally driven through the surgical end effector 9010 unless an unfired or new surgical staple cartridge 9600 has been properly seated within the elongate channel 9022, the illustrated surgical tool assembly 9000 employs a firing member lockout system generally designated as 9700.

Figure 60E:
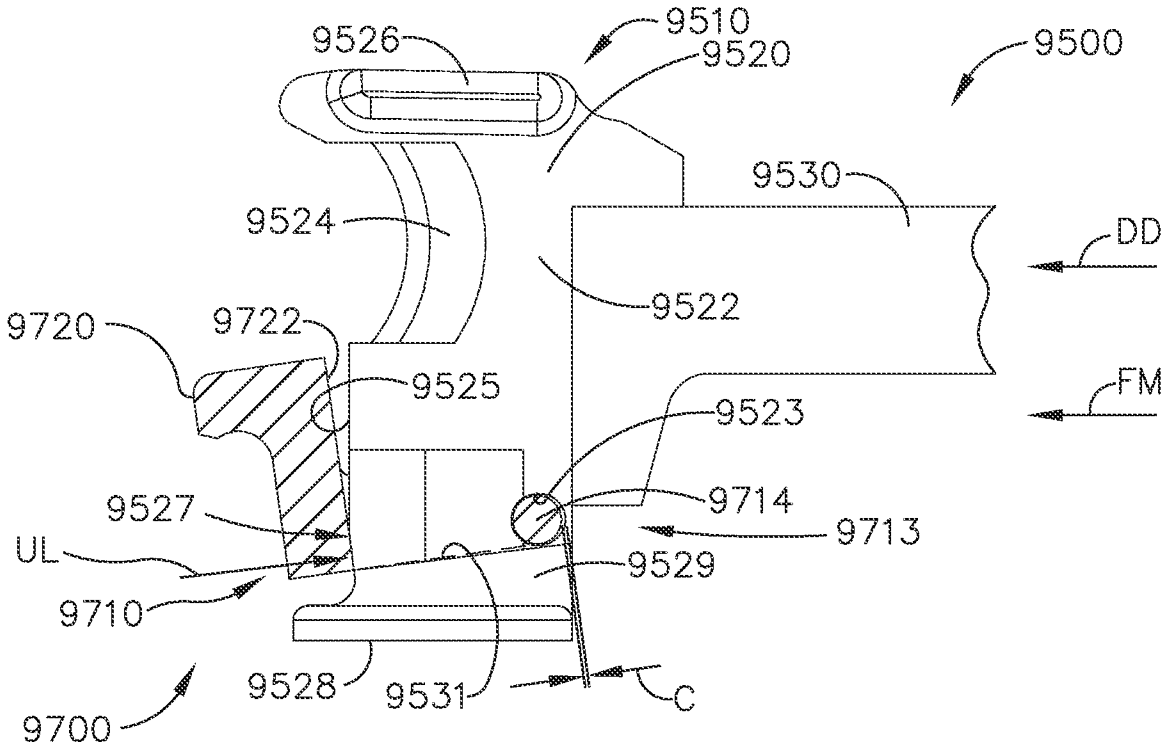
FIG. 60E is a side view of a firing member assembly with the second firing member element in a lockout orientation.
Figure 60F:
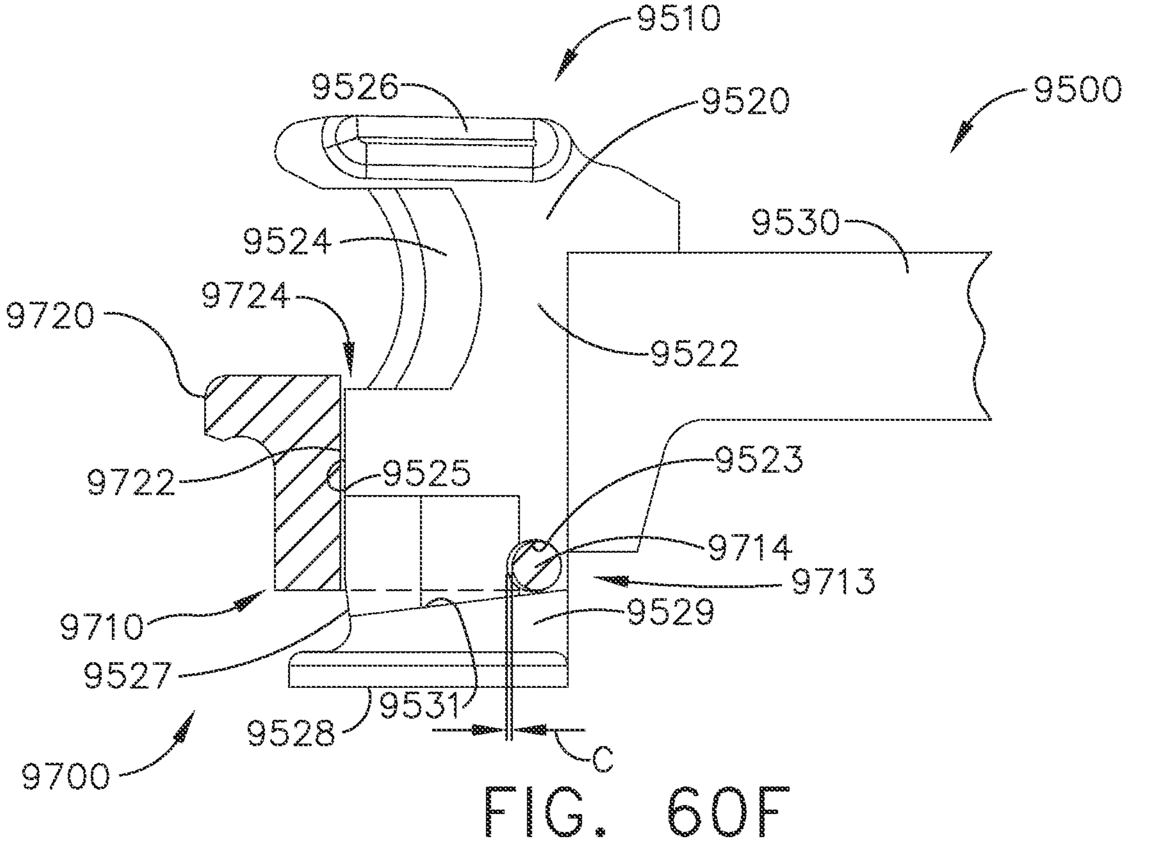
FIG. 60F is another side view of the firing member assembly of FIG. 60E with the second firing member element illustrated in an unlocked or firing orientation.
Figure 60G:
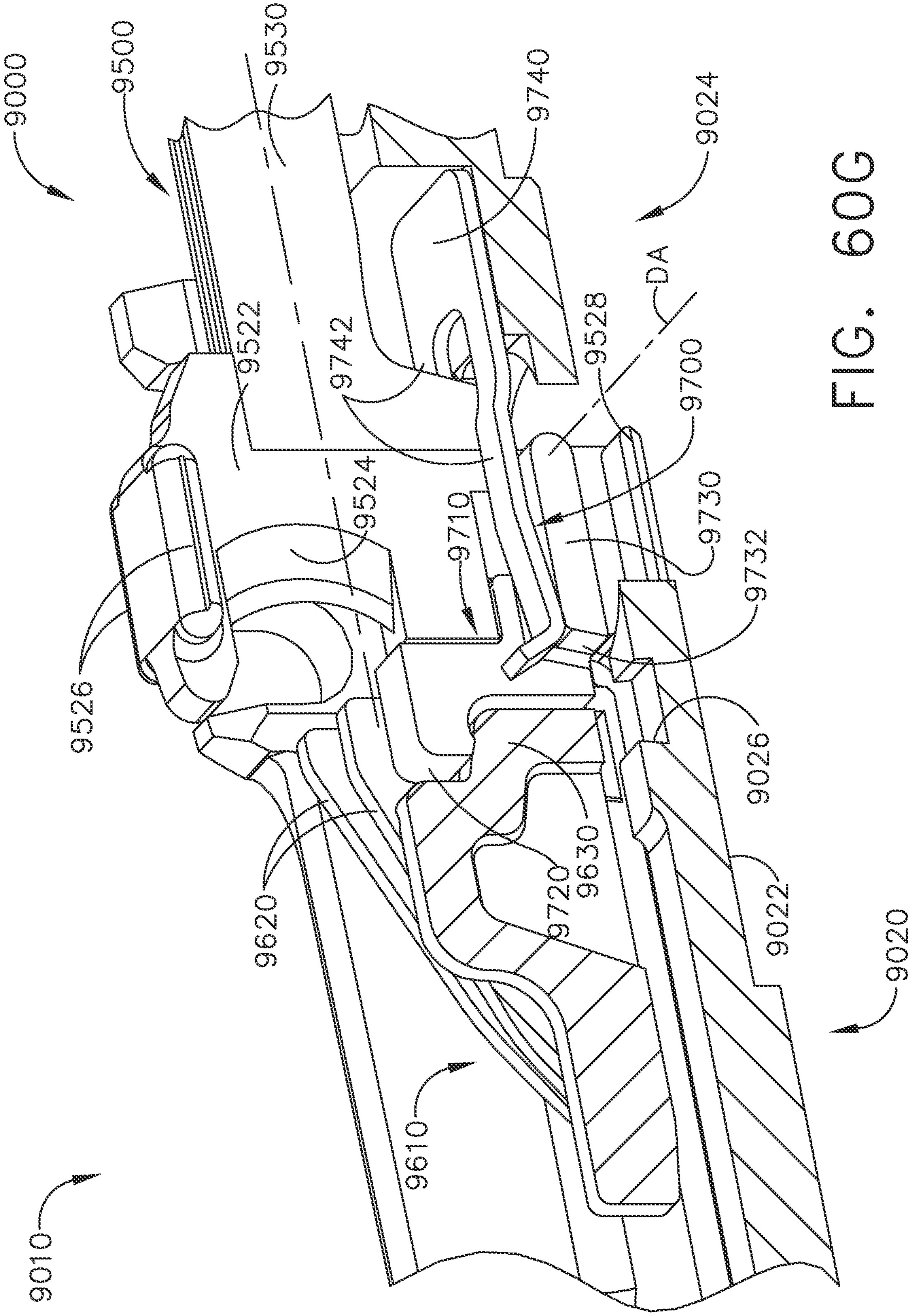
FIG. 60G is another partial perspective view of the surgical stapling instrument of FIG. 60A illustrated in an unlocked configuration.
Figure 60H:
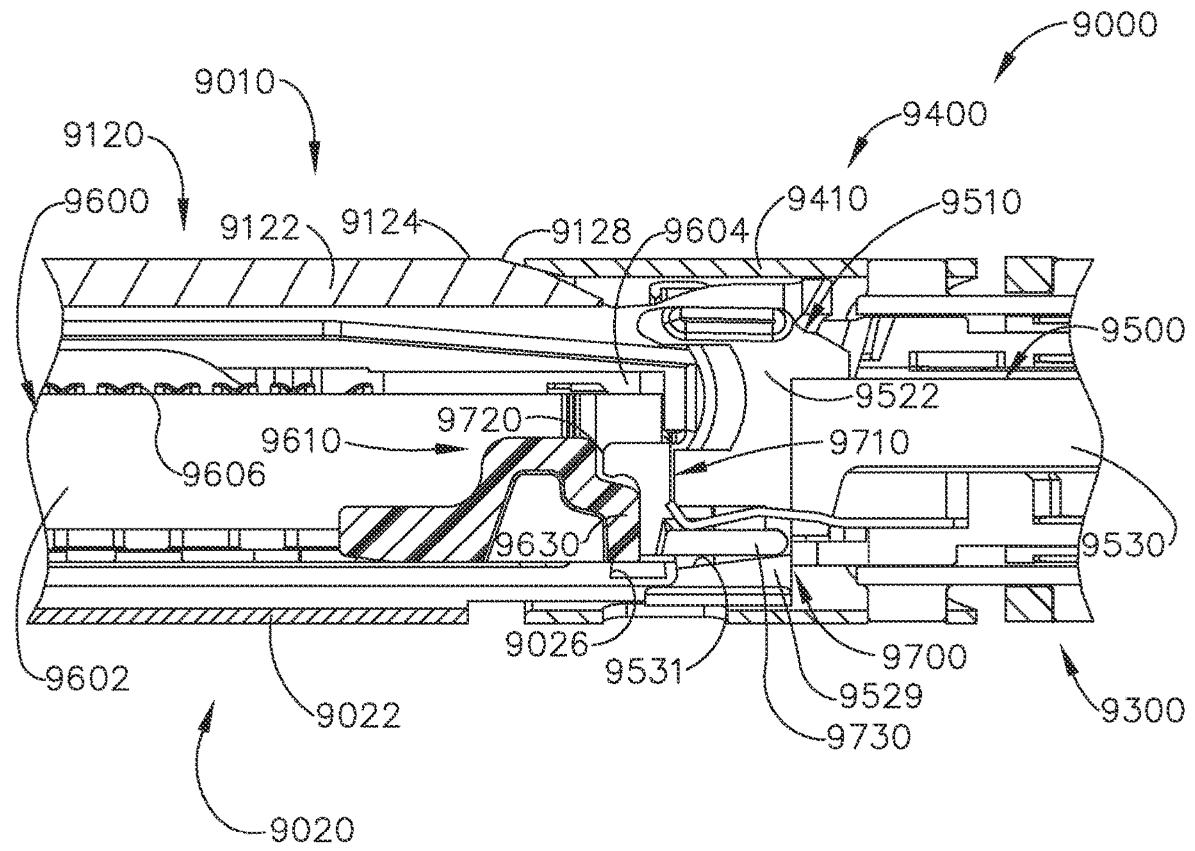
FIG. 60H is a cross-sectional view of the surgical stapling instrument of FIG. 60A with an unfired surgical fastener cartridge operably supported in an elongate channel thereof and with the firing member assembly illustrated in a starting position.

Referring now to FIGS. 60E and 60F, in one form, the firing member lockout system 9700 comprises a second firing member element or tippable element 9710 that comprises a sled engaging portion 9720. In the illustrated arrangement, the second firing member element 9710 is pivotally coupled to the firing member body 9522 by an attachment joint 9713 in the form of, for example, a pivot member or members 9714 that are pivotally received in corresponding pivot holes 9523 provided in the firing member body 9522 for pivotal travel relative thereto about a pivot axis PA that is transverse to the shaft axis SA. Such arrangement facilitates pivotal travel of the second firing member element 9710 relative to the firing member body 9522 between a locked position (FIG. 60E) and an unlocked position (FIG. 60F). In the illustrated example, the firing member body 9522 comprises a distal surface 9525 that is approximately perpendicular to the channel engagement features 9528 and a lockout surface 9527 that is angled relative to the distal surface 9525. In addition, one or more support ramps 9529 are formed on the firing member body 9522 that serve to define corresponding landing surfaces 9531 for receiving the second firing member element 9710 when in the locked configuration. See FIG. 60E.

As can be seen in FIG. 60F, when the second firing member element 9710 is in the unlocked position, a space, generally indicated as 9724, is provided between a proximal surface 9722 of the second firing member element 9710 and the distal surface 9525 of the firing member body 9522. Thus, when in the unlocked position, the proximal surface 9722 of the second firing member element 9710 is not in contact with the distal surface 9525 of the firing member body 9522. Referring now to FIGS. 60A-60D, the second firing member element 9710 further comprises at least one lockout-engaging portion 9730 that includes an angled lock end 9732 that is configured to engage a corresponding lock-out notch 9026 that is formed in the elongate channel 9022 when the second firing member element 9710 is in the locked position. In one embodiment, for example, the second firing member element 9710 includes two lockout-engaging portions 9730. As can also be seen in FIGS. 60A-60D, a lockout spring or biasing member 9740 is mounted in the proximal end 9024 of the elongate channel

9022 and includes two spring arms 9742 that each correspond to a lockout-engaging portion 9730. The spring arms 9742 serve to bias the second firing member element 9710 into the locked position as shown in FIGS. 60B-60D.

Figure 60I:
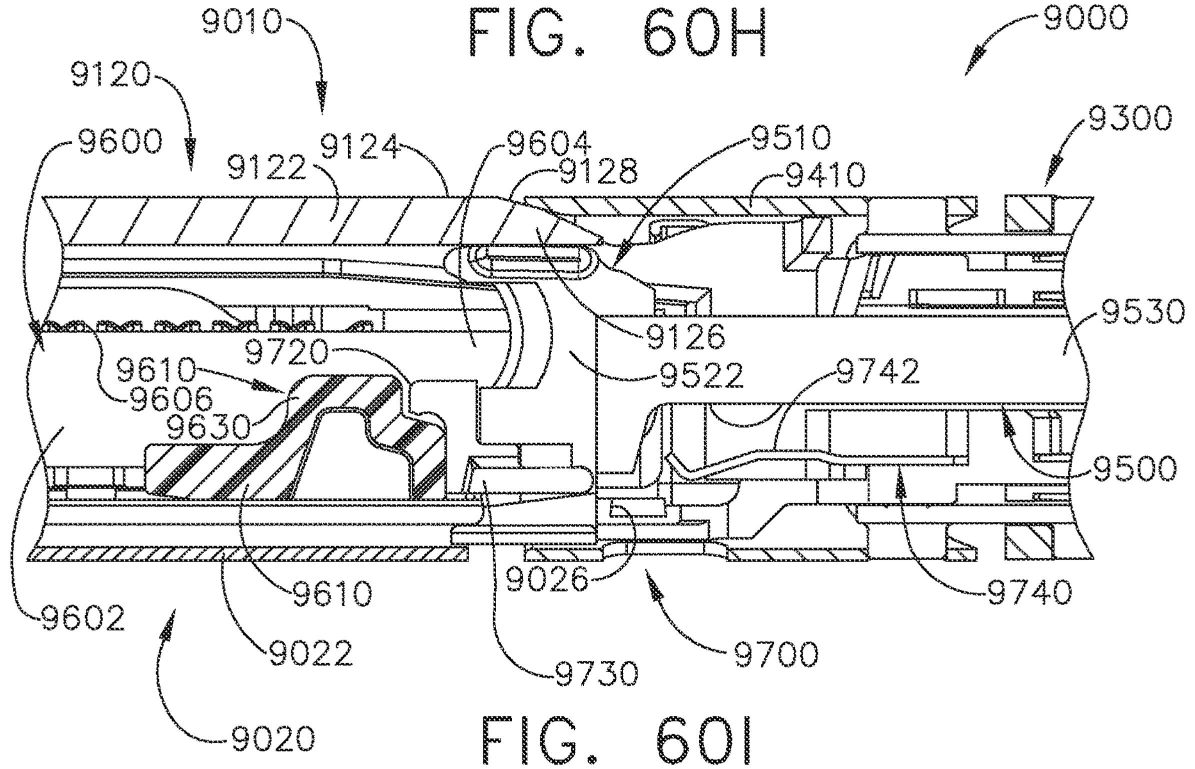
FIG. 60I is another cross-sectional view of the surgical stapling instrument of FIG. 60H with the firing member assembly illustrated in a partially-fired configuration.

Turning now to FIGS. 60G-60I, the sled 9610 comprises an unlocking portion 9630 that is configured to engage the sled engaging portion 9720 on the second firing member element 9710 when the sled 9610 is in the unfired position. Such arrangement serves to pivot the second firing member element 9710 into the unlocked position. When in the unlocked position, the angled lock end 9732 of each lockout-engaging portion 9730 is pivoted out of the corresponding lock-out notch 9026 in the elongate channel 9022 so that the firing member assembly 9510 may be fired or distally advanced through the staple cartridge. If the staple cartridge that has been loaded into the elongate channel 9022 was previously fired or even partially fired, the sled 9610 will not be in the unfired position so as to pivot the second firing member element 9710 into the unlocked position. In such instance therefor, the clinician will be unable to distally advance or fire the firing member assembly 9510. When in the unlocked position, actuation of the firing system 9500 will result in the distal travel of the firing member assembly 9510. As indicated above, when the firing member assembly 9510 is driven distally, the second firing member element 9710 is in contact with the firing member body 9522 through the pivot members 9714. However, when the second firing member element 9710 is pivoted into the locked position (FIG. 60E), a portion of the proximal surface 9722 is in abutting contact with the angled lockout surface 9527 on the firing member body 9522. In addition, as can be most particularly seen in FIGS. 60E and 60F, the pivot hole 9523 in the firing member body 9522 is sized relative to the corresponding pivot member 9714 to provide clearance C therebetween so that the load is transferred through the second firing member element directly to the firing member body 9522 and not through the pivot members 9714. As can be seen in FIG. 60E, the angled lockout surface 9527 facilitates pivotal travel of the sled engaging portion 9720 into the locked position. When the second firing member element 9720 is in the locked position, should the clinician inadvertently apply a firing motion FM to the firing member assembly 9510 in the distal direction DD, the engagement between the second firing member element 9720 and the lock-out notch 9026 in the elongate channel 9022 will prevent the distal advancement of the firing member assembly 9510 and cause a resultant unlocking load force UL to be applied to the second firing member element 9720. This unlocking load force UL will be applied to the angled lockout surface 9527 on the firing member body 9522 and will not be applied to the pivot members 9714. Such arrangement avoids loading or stressing the pivot members 9714 should the clinician inadvertently attempt to advance the firing member assembly 9510 when in the locked position. Thus, this configuration may prevent the pivot members 9714 from shearing off during such attempted advancement of the firing member assembly 9510.

Thus, the foregoing firing member assembly 9510 and firing member lockout assembly 9700 may provide several advantages. For example, as was discussed above, the distal surface 9525 on the firing member body 9522 carries the load during firing and avoids transferring such load to the pivot members that attach the second firing member element 9710 to the first firing member element 9520. When in the lockout state or locked position, the load is carried by the angled lock ends 9732 on the lockout engaging portions 9730. Such arrangement also avoids the need for the firing member assembly 9510 or more precisely the first firing member element 9520 from moving vertically which may inadvertently lead to misalignment with the anvil and elongate channel when moved into an unlocked state for firing. Moreover, because the first firing member element 9520 does not move vertically, the anvil engagement features as well as the channel engagement features may be advantageously shaped and designed to obtain desirable engagement with the anvil and channel during firing. The design and shape of the firing member body may also afford a large surface area for attachment to the knife bar by, for example, welding. For example, the distal end of the knife bar may be attached to the firing member body by a butt weld and a laser weld from both sides to interconnect the laminates forming the knife bar at the distal end. Such weld configuration may be more longitudinally compact than prior weld configurations and can lead to superior joint length. Other advantages may also be enjoyed from the foregoing firing member and lockout system arrangements.

Figure 79A:
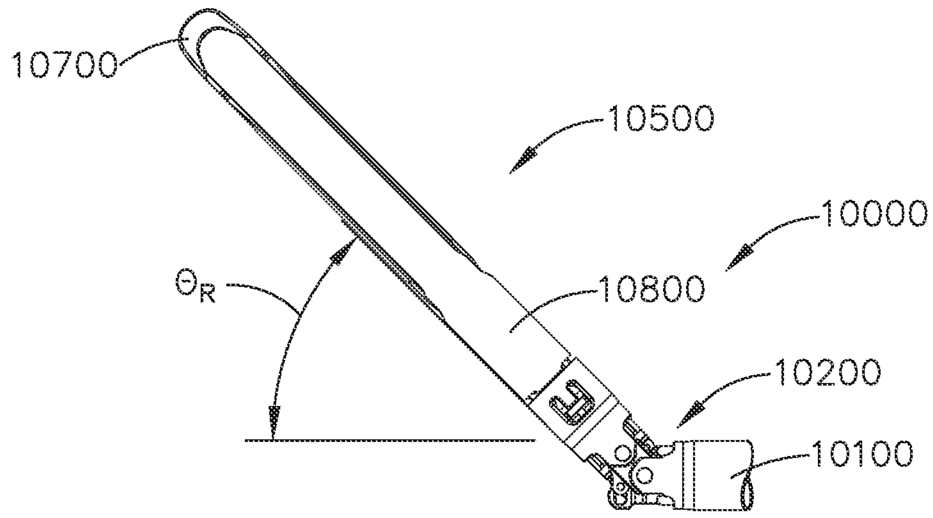
FIG. 79A is a partial plan view of the end effector of FIG. 79 illustrating the end effector articulated in a first direction.
Figure 79:
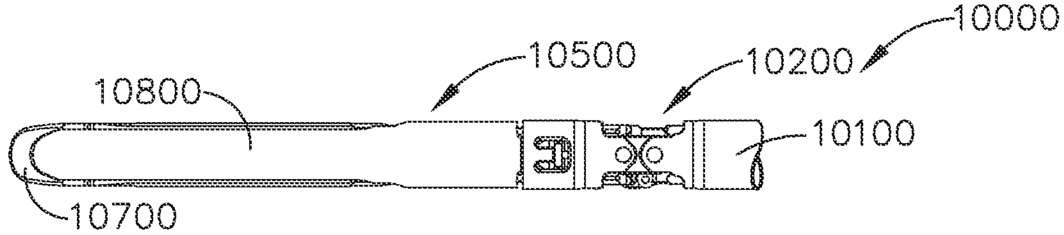
FIG. 79 is a partial plan view of an end effector of a surgical instrument in accordance with at least one embodiment.
Figure 79B:
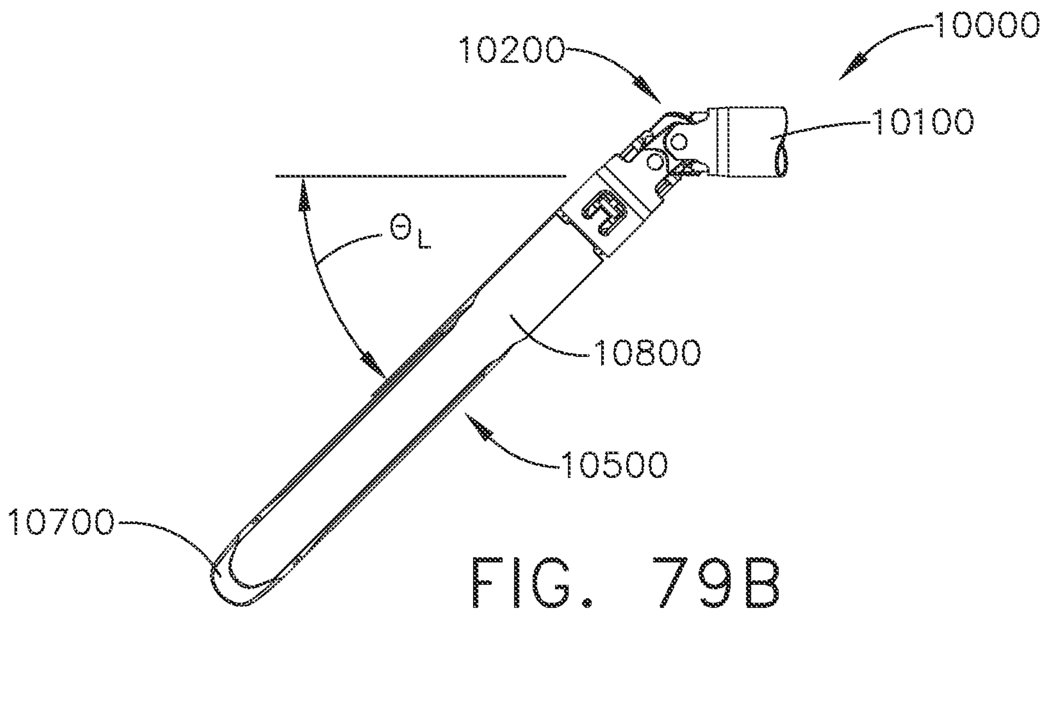
FIG. 79B is a partial plan view of the end effector of FIG. 79 illustrating the end effector articulated in a second direction.

An end effector 10500 of a surgical instrument 10000 is illustrated in FIGS. 79-79B. The end effector 10500 comprises a cartridge jaw 10600 (FIG. 81) including a staple cartridge 10700 and, in addition, an anvil 10800 configured to deform staples ejected from the staple cartridge 10700. In use, the anvil 10800 is rotatable between an open, unclamped position and a closed, clamped position; however, the cartridge jaw 10600 can be rotatable toward the anvil 10800 in other embodiments. The surgical instrument 10000 further comprises a shaft 10100 wherein the end effector 10500 is rotatably connected to the shaft 10100 about an articulation joint 10200. In use, the end effector 10500 is rotatable about the articulation joint 10200 between a fully-articulated right position (FIG. 79A), indicated by angle $\theta_R$, and a fully-articulated left position (FIG. 79B), indicated by angle $\theta_L$—and/or any suitable position there between. As discussed in greater detail below, the angles $\theta_R$ and $\theta_L$ are limited by the design of the articulation drive system of the surgical instrument 10000. In at least one instance the angles $\theta_R$ and $\theta_L$ are limited to approximately 45 degrees with respect to the unarticulated position of the end effector 10500 (FIG. 79).

Figure 81:
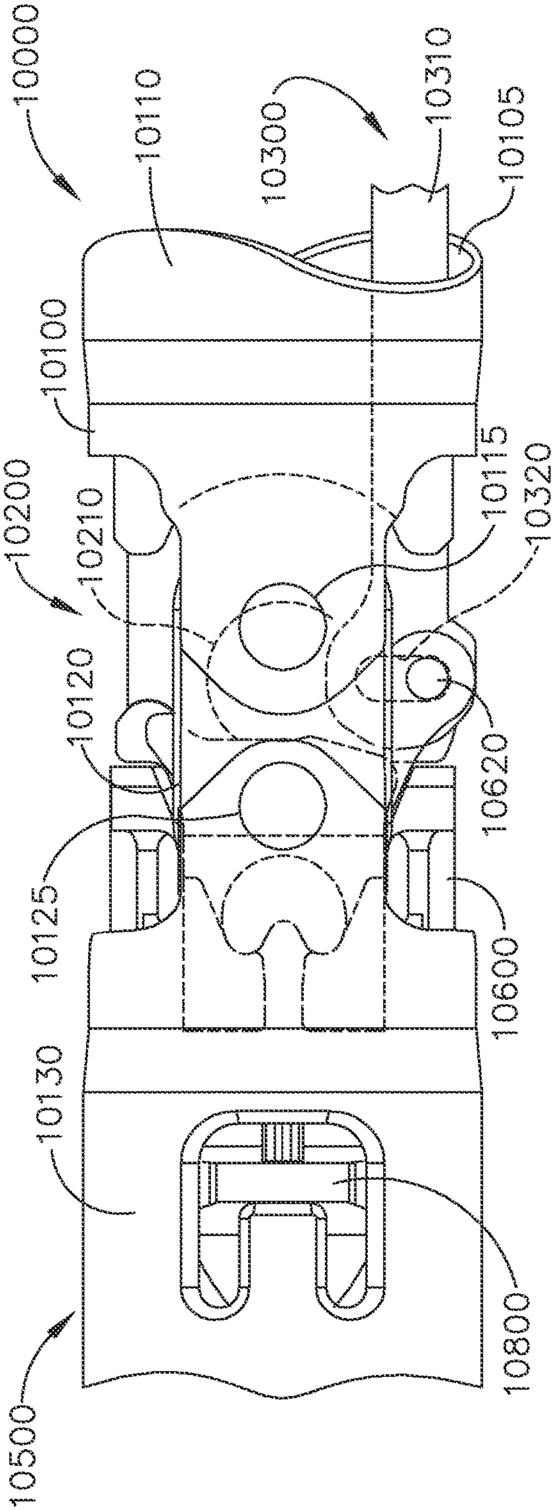
FIG. 81 is a partial plan view of the end effector of FIG. 79.

Referring to FIG. 81, the shaft 10100 of the surgical instrument 10000 comprises an outer closure tube including an outer housing 10110 which is movable distally to engage the anvil 10800 and move the anvil 10800 toward the staple cartridge 10700. The shaft 10100 further comprises a distal housing portion 10130 rotatably connected to the outer housing 10110 by two connector plates 10120 positioned on opposite sides of the articulation joint 10200. Each connector plate 10120 is connected to the outer housing 10110 at a pivot 10115 and, similarly, to the distal housing portion 10130 at a pivot 10125. The connector plates 10120 permit the closure tube to slide relative to the articulation joint 10200 when the end effector 10500 is in an articulated position and, as a result, the anvil 10800 can be opened and closed while the end effector 10500 is in an articulated position. Further to the above, the distal housing 10130 comprises an opening defined therein configured to receive a tab extending from the proximal end of the anvil 10800—a sidewall of which is configured to engage the tab and transfer a proximal, or opening motion, of the closure tube to the anvil 10800.

Figure 80A:
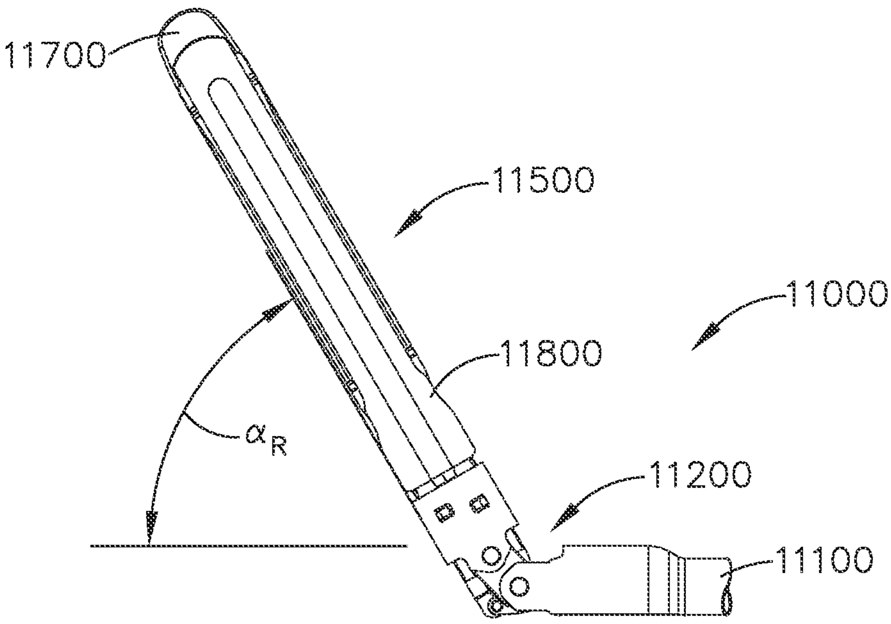
FIG. 80A is a partial plan view of the end effector of FIG. 80 illustrating the end effector articulated in a first direction.
Figure 80:
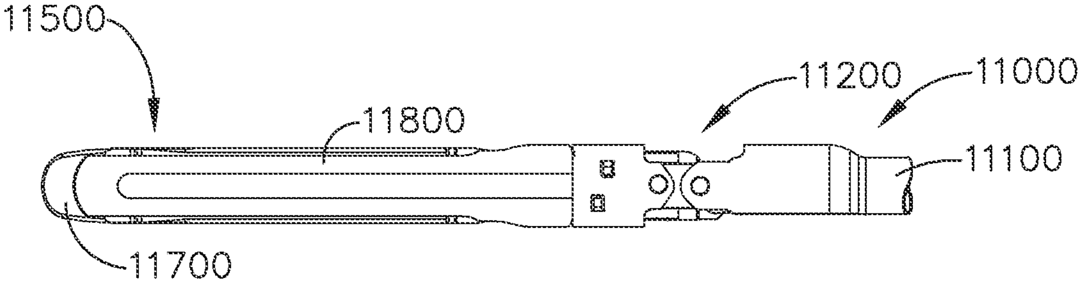
FIG. 80 is a partial plan view of an end effector of a surgical instrument in accordance with at least one embodiment.
Figure 80B:
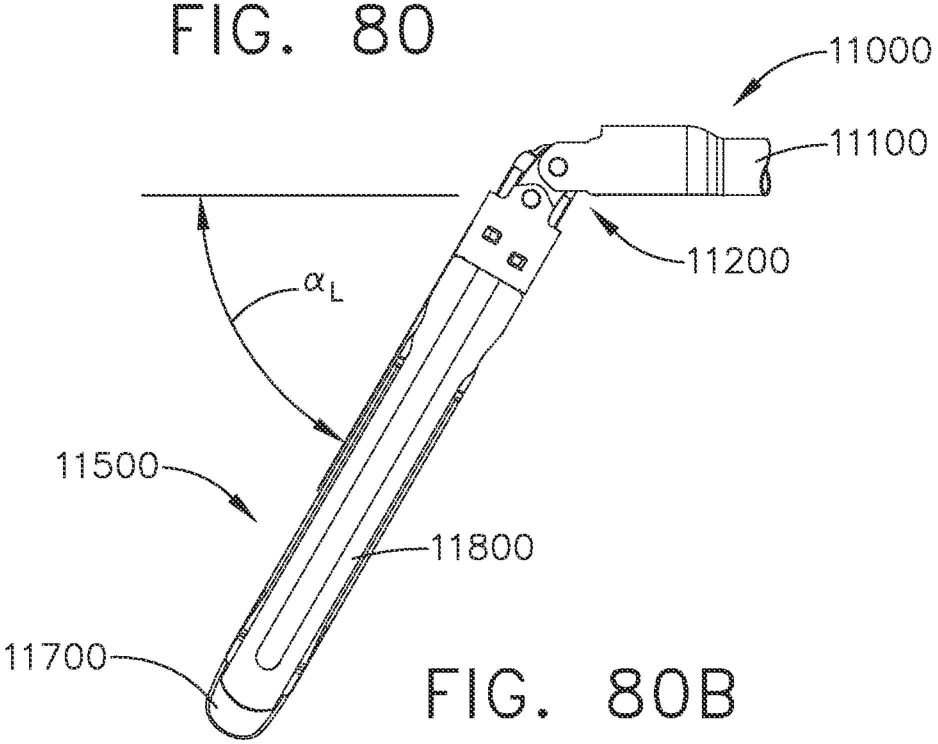
FIG. 80B is a partial plan view of the end effector of FIG. 80 illustrating the end effector articulated in a second direction.

An end effector 11500 of a surgical instrument 11000 is illustrated in FIGS. 80-80B. The end effector 11500 comprises a cartridge jaw 11600 (FIG. 82) including a staple cartridge 11700 and, in addition, an anvil 11800 configured to deform staples ejected from the staple cartridge 11700. In use, the anvil 11800 is rotatable between an open, unclamped position and a closed, clamped position; however, embodiments are envisioned in which the cartridge jaw 11600 is movable relative to the anvil 11800. The surgical instrument 11000 further comprises a shaft 11100 wherein the end effector 11500 is rotatably connected to the shaft 11100 about an articulation joint 11200. In use, the end effector 11500 is rotatable about the articulation joint 11200 between a fully-articulated right position (FIG. 80A), indicated by angle $\alpha_R$, and a fully-articulated left position (FIG. 80B), indicated by angle $\alpha_L$—and/or any suitable position there between. Although the angles $\alpha_R$ and $\alpha_L$ are ultimately limited by the design of the articulation drive system of the surgical instrument 11000, the angles $\alpha_R$ and $\alpha_L$ are larger. In at least one instance the angles $\alpha_R$ and $\alpha_L$ are approximately 60 degrees with respect to the unarticulated position of the end effector 11500 (FIG. 80), for example.

Figure 82:
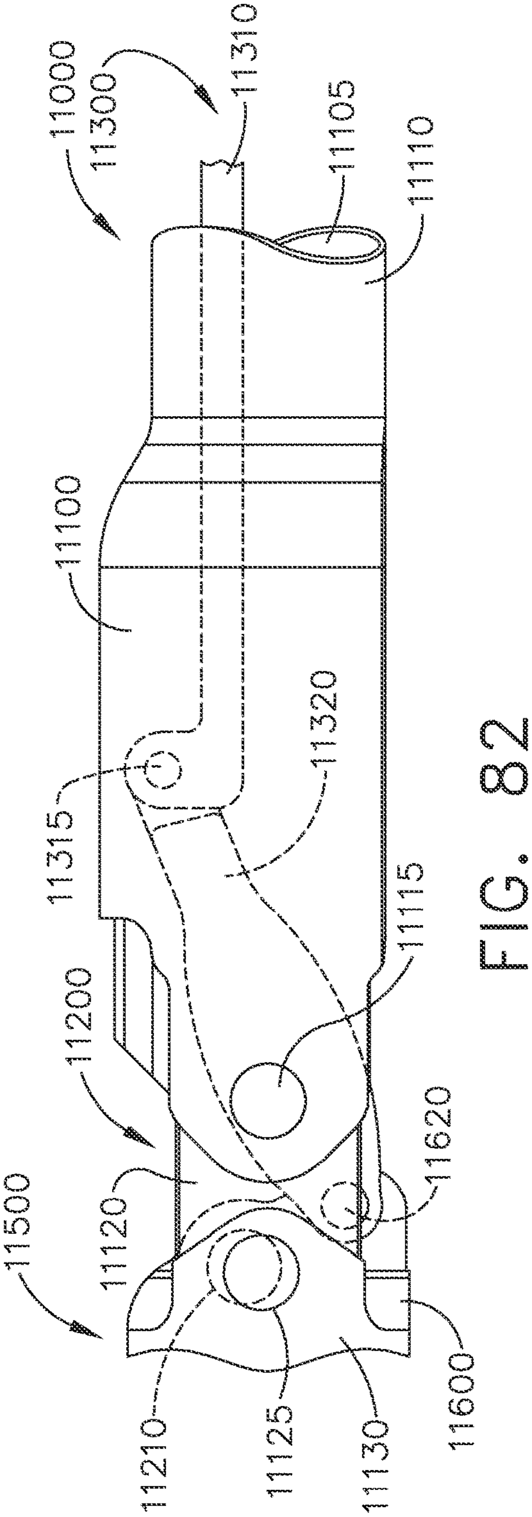
FIG. 82 is a partial plan view of the end effector of FIG. 80.

Referring to FIG. 82, the shaft 11100 of the surgical instrument 11000 comprises an outer closure tube including an outer housing 11110 which is movable distally to engage the anvil 11800 and move the anvil 11800 toward the staple cartridge 11700. The shaft 11100 further comprises a distal housing 11130 rotatably connected to the outer housing 11110 by two connector plates 11120 positioned on opposite sides of the articulation joint 11200. Each connector plate 11120 is connected to the outer housing 11110 at a pivot 11115 and, similarly, to the distal housing 11130 at a pivot 11125. Similar to the above, the connector plates 11120 permit the closure tube to slide relative to the articulation joint 11200 when the end effector 11500 is in an articulated position wherein, as a result, the anvil 11800 can be opened and closed while the end effector 11500 is in an articulated position. Further to the above, the distal housing 11130 comprises an opening defined therein configured to receive a tab extending from the proximal end of the anvil 11800—a sidewall of which is configured to engage the tab and transfer a proximal, or opening, motion of the closure tube to the anvil 11800.

Referring again to FIG. 81, the surgical instrument 10000 further comprises an articulation drive system 10300 including an articulation drive actuator 10310 extending through an interior aperture 10105 defined within the closure tube 10110 of the shaft 10100. The articulation drive actuator 10310 comprises a distal end operably engaged with the cartridge jaw 10600 of the end effector 10500. More specifically, the distal end of the articulation drive actuator 10310 comprises an opening, or slot, 10320 defined therein and the cartridge jaw 10600 comprises a pin 10620 extending into the slot 10320. When the articulation drive actuator 10310 is pushed distally, the end effector 10500 is driven to the right (FIG. 79A) about a fixed axis defined by a pivot 10210 which rotatably connects the cartridge jaw 10600 to a frame of the shaft 10100. Correspondingly, the end effector 10500 is rotated to the left (FIG. 79B) about the pivot 10210 when the articulation drive actuator 10310 is pulled proximally.

Referring again to FIG. 82, the surgical instrument 11000 further comprises an articulation drive system 11300 including an articulation drive actuator 11310 extending through an interior aperture 11105 defined within the closure tube 11110. The articulation drive system 11300 further comprises an articulation link 11320 rotatably coupled to a distal end of the articulation drive actuator 11310 about a pin 11315. Similarly, the articulation link 11320 is rotatably coupled to the cartridge jaw 11600 about a drive pin 11620 which extends through an aperture defined in the articulation link 11320. When the articulation drive actuator 11310 is pushed distally, the end effector 11500 is driven to the right (FIG. 80A) about a fixed axis defined by a pivot 11210 which rotatably connects the cartridge jaw 11600 to a frame of the shaft 11100. Correspondingly, the end effector 11500 is rotated to the left (FIG. 80B) about the pivot 11210 when the articulation drive actuator 11310 is pulled proximally.

Figure 84:
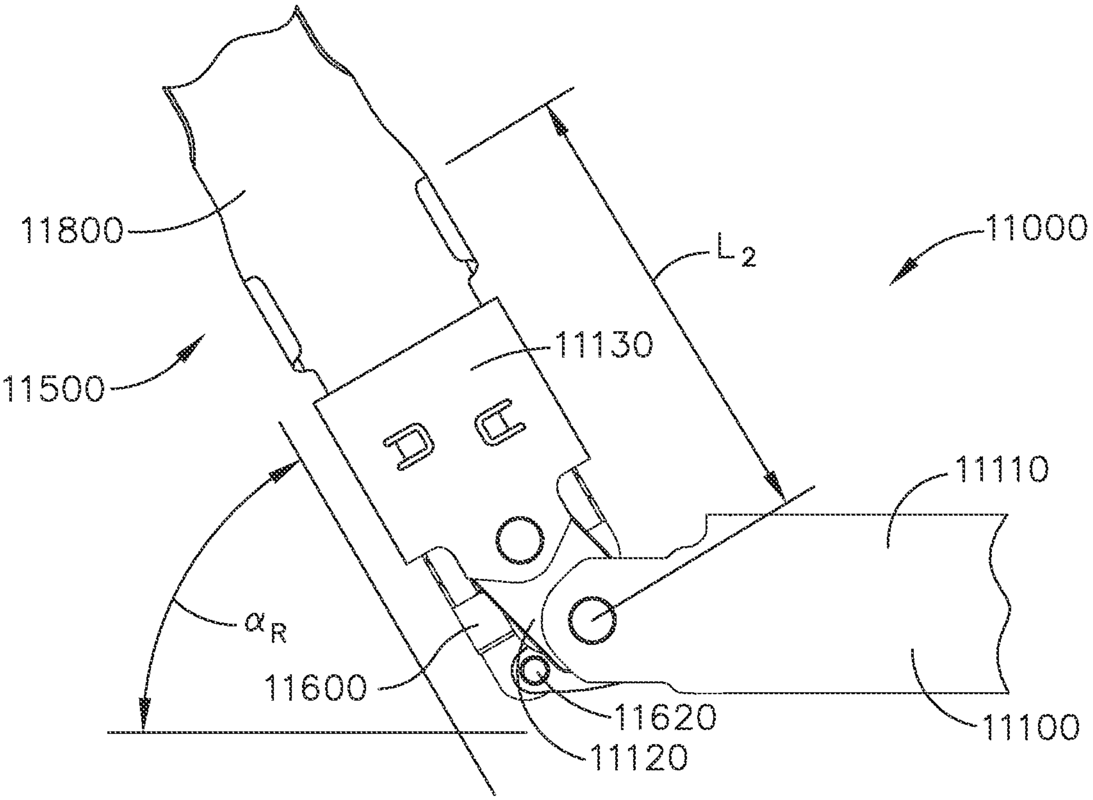
FIG. 84 is a partial plan view of the end effector of FIG. 80 in an articulated position.
Figure 83:
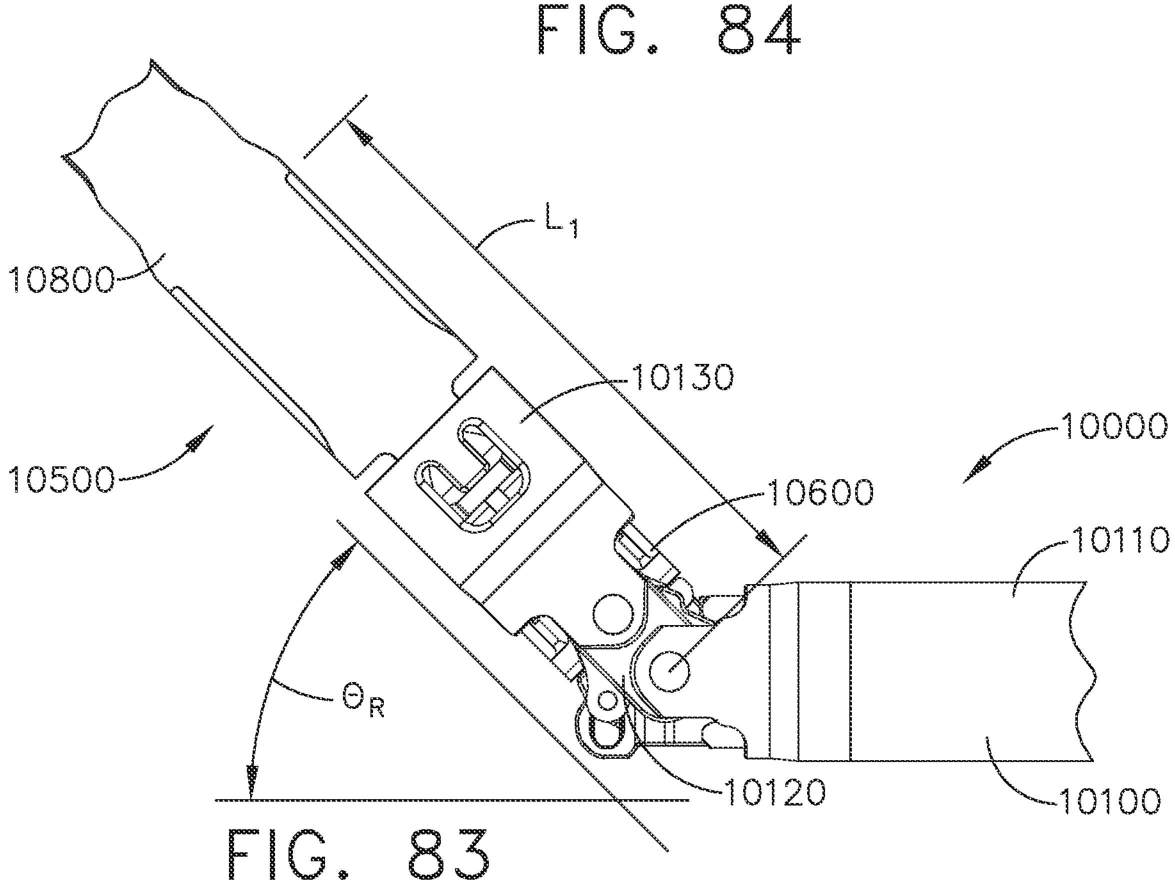
FIG. 83 is a partial plan view of the end effector of FIG. 79 in an articulated position.
Figure 85:
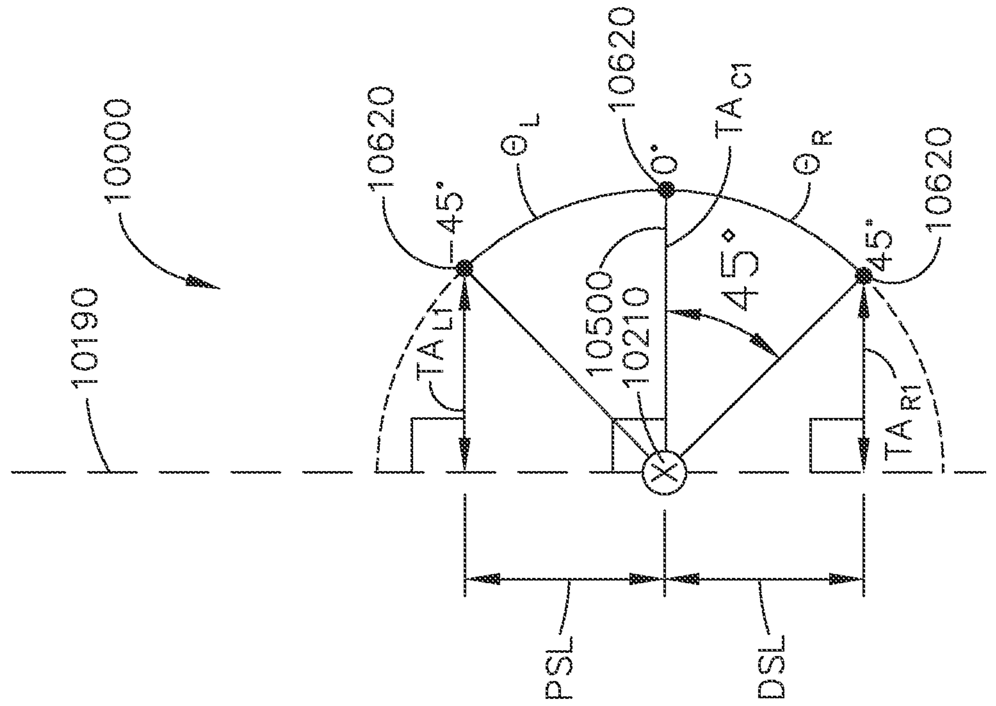
FIG. 85 is a schematic illustrating an articulation range of the end effector of FIG. 79.
Figure 86:
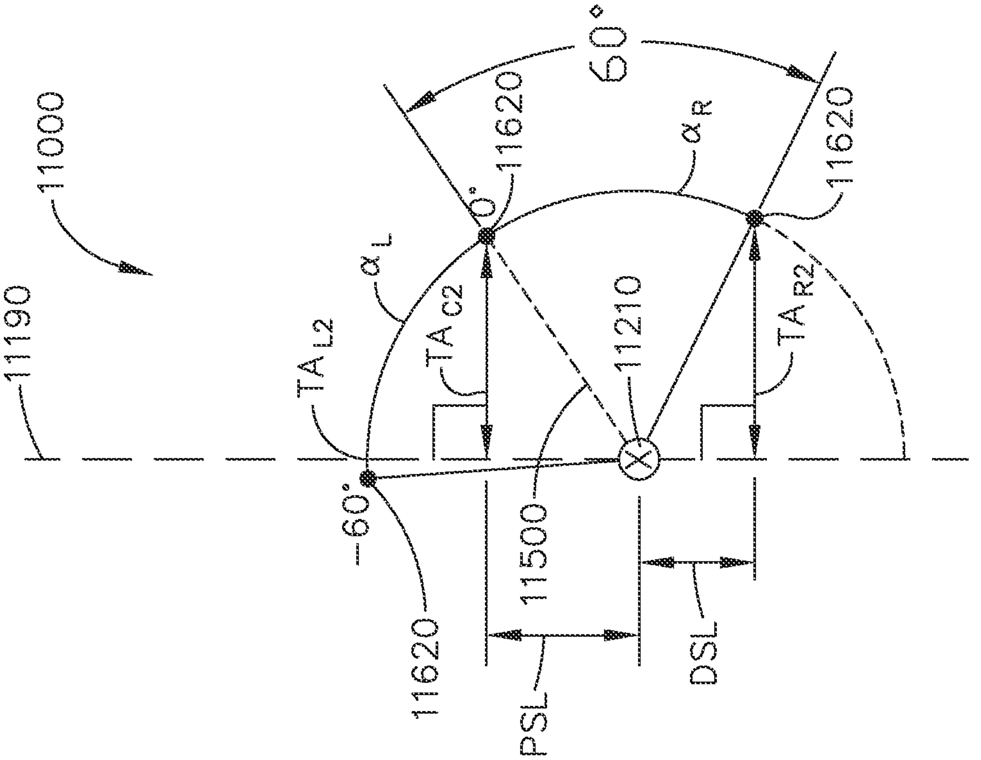
FIG. 86 is a schematic illustrating an articulation range of the end effector of FIG. 80.

Further to the above, the articulation link 11320 of the articulation system 11300 allows the end effector 11500 to be articulated through a larger range of articulation angles than the end effector 10500 for a given, or equal, stroke length of the articulation actuators 10310 and 11310. A side-by-side comparison of the end effectors 10500 and 11500 is provided in FIGS. 83 and 84 illustrating the end effectors 10500 and 11500 in their fully right-articulated configurations—and also illustrating that the end effector 11500 can be articulated further to the right than the end effector 10500. A similar comparison can be made showing the end effectors 10500 and 11500 in their fully left-articulated configurations. Moreover, FIG. 85 depicts the full articulation range of the end effector 10500 while FIG. 86 depicts the full articulation range of the end effector 11500.

Figure 94:
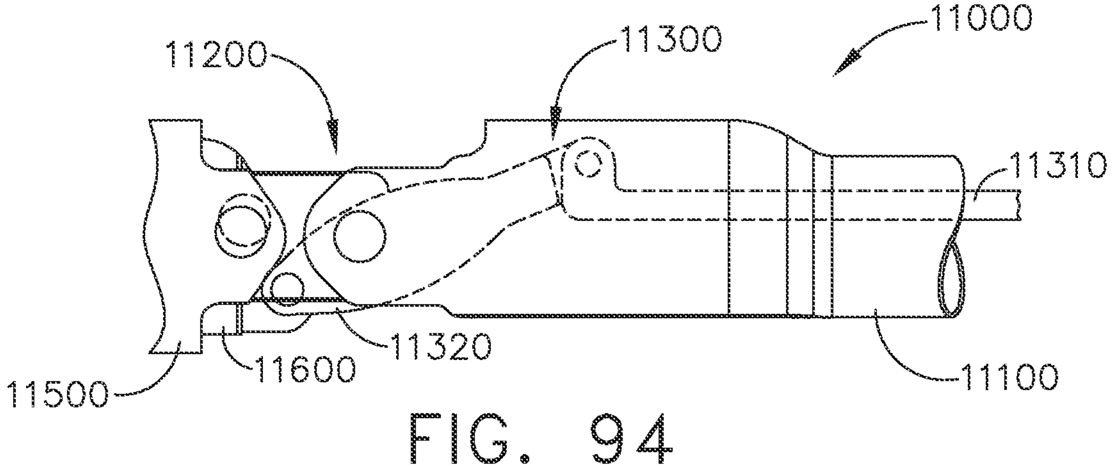
FIG. 94 is a partial plan view of the end effector of FIG. 80 illustrated in an unarticulated configuration.
Figure 94A:
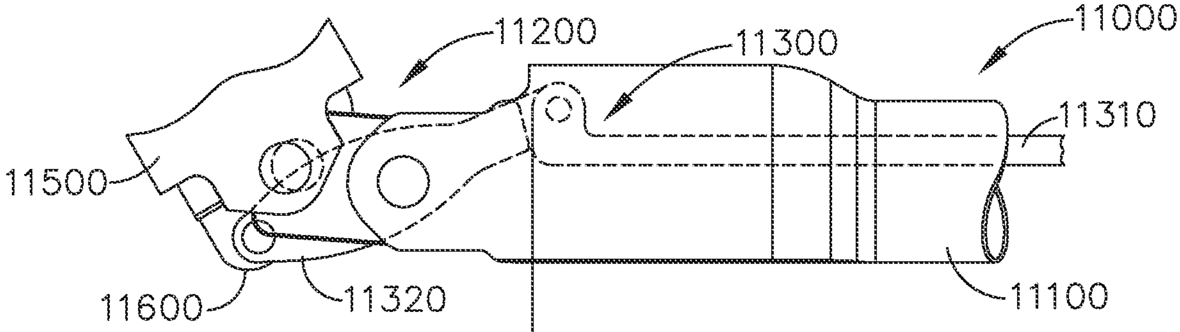
FIG. 94A is a partial plan view of the end effector of FIG. 80 illustrated in a fully-right articulated configuration.
Figure 94B:
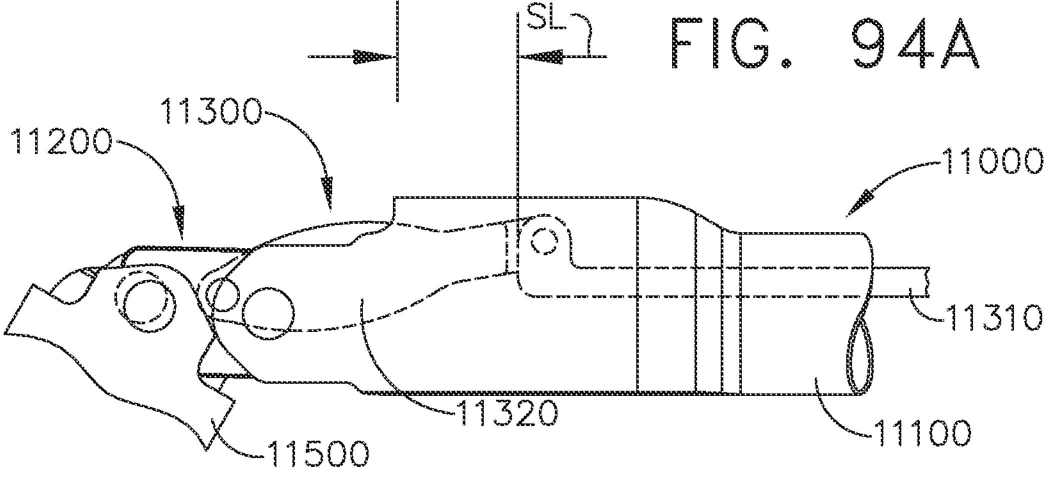
FIG. 94B is a partial plan view of the end effector of FIG. 80 illustrated in a fully-left articulated configuration.
Figure 95:
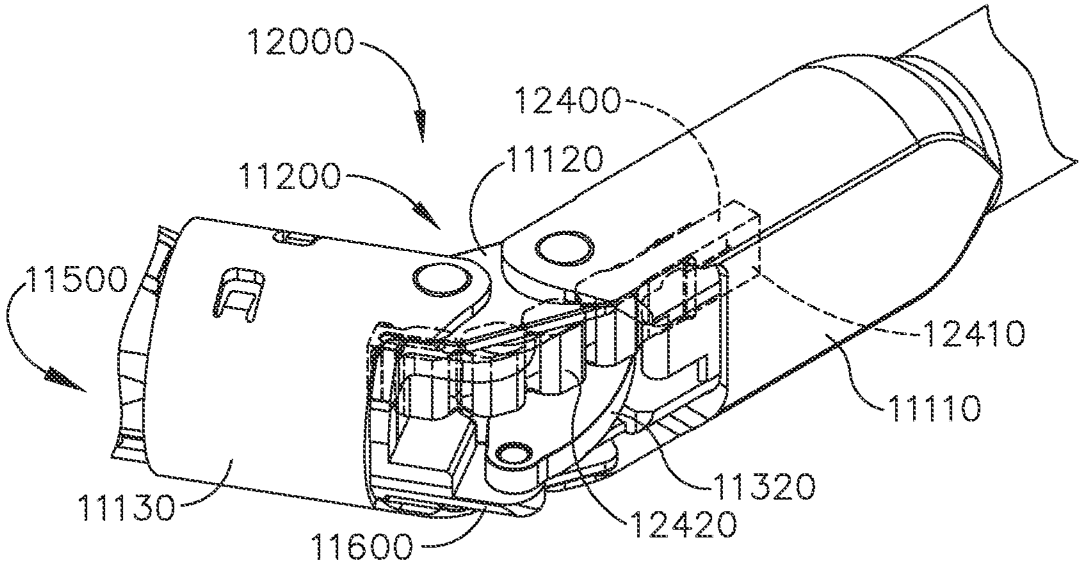
FIG. 95 is a partial perspective view of an end effector in accordance with at least one embodiment.
Figure 96:
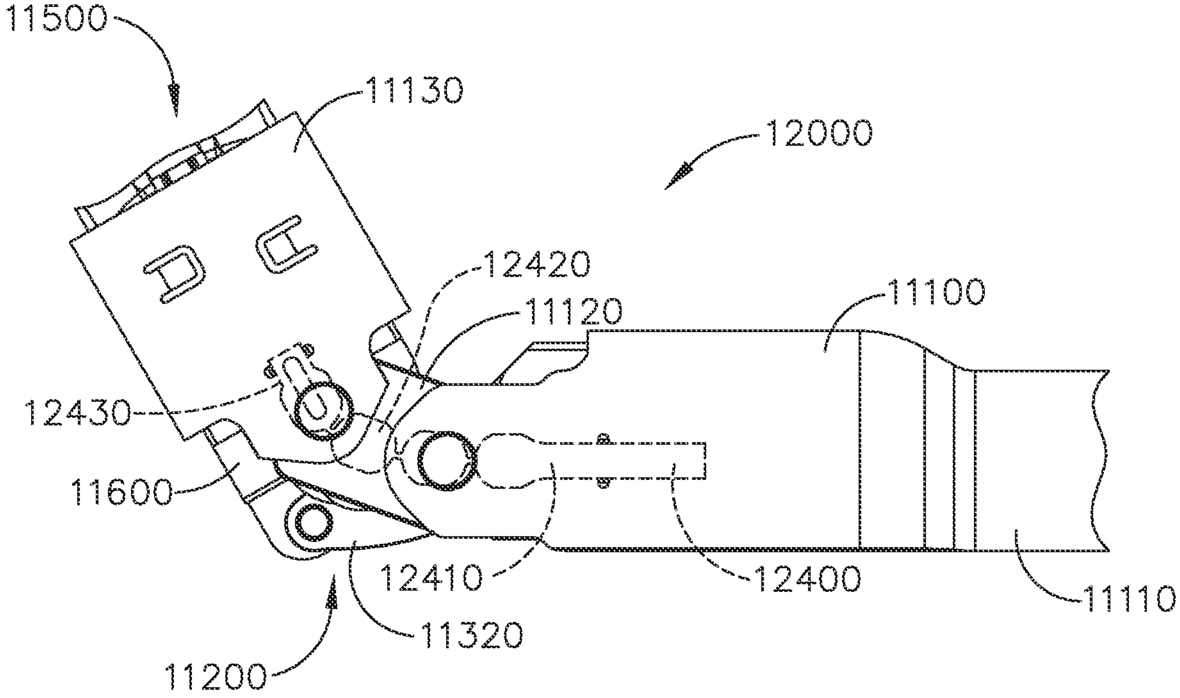
FIG. 96 is a partial plan view of the end effector of FIG. 95.

Referring again to FIG. 85, the articulation actuator 10310 of the surgical instrument 10000 is advanced a distal stroke length (DSL) with respect to its unarticulated position to fully articulate the end effector 10500 to the right. Correspondingly, the articulation actuator 10310 is retracted a proximal stroke length (PSL) with respect to its unarticulated position to fully articulate the end effector 10500 to the left. The distal stroke length (DSL) and the proximal stroke length (PSL) of the articulation actuator 10310 are equal, or at least substantially equal. Referring now to FIG. 86, the articulation actuator 11310 is advanced a distal stroke length (DSL) with respect to its unarticulated position to fully articulate the end effector 11500 to the right. Correspondingly, the articulation actuator 11310 is retracted a proximal stroke length (PSL) with respect to its unarticulated position to fully articulate the end effector 11500 to the left. The distal stroke length (DSL) and the proximal stroke length (PSL) of the articulation actuator 11310 are not equal—instead, the distal stroke length (DSL) is shorter than the proximal stroke length (PSL). In other embodiments, the proximal stroke length (DSL) is shorter than the distal stroke length (PSL). In any event, referring now to FIGS. 94-94B, the combination of the proximal stroke length (PSL) and the distal stroke length (DSL) equals the entire stroke length (SL).

Further to the above, the articulation actuator 10310 is configured to apply a torque to the first jaw 10600 of the end effector 10500 via the pin 10620 to rotate the end effector 10500 about the articulation joint 10200. Referring again to FIG. 85, a lateral torque arm defined between the pivot joint 10210 of the articulation joint 10200 and the pin 10620 has a length $TA_{C1}$ when the end effector 10500 is in its unarticulated position. The length $TA_{C1}$ is measured in an orthogonal direction with respect to a longitudinal axis 10190 extending through the articulation pivot joint 10210. Similarly, the lateral torque arm defined between the pivot joint 10210 and the pin 10620 has a length $TA_{R1}$ when the end effector 10500 is fully articulated to the right and, similarly, a length $TA_{L1}$ when the end effector 10500 is fully articulated to the left—both lengths of which are measured orthogonally with respect to the longitudinal axis 10190. Notably, the lengths $TA_{R1}$ and $TA_{L1}$, and the torque arms which they define, are equal, or at least substantially equal. Moreover, the lengths $TA_{R1}$ and $TA_{L1}$ are less than the unarticulated lateral torque arm length $TA_{C1}$. Thus, the largest torque arm, or mechanical advantage, of the articulation system 10300 exists when the end effector 10500 is in its unarticulated position.

In at least one instance, the arm length $TA_{C1}$ is approximately 0.180", the arm length $TA_{R1}$ is approximately 0.130", and the arm length $TA_{L1}$ is approximately 0.130", for example.

Figure 91:
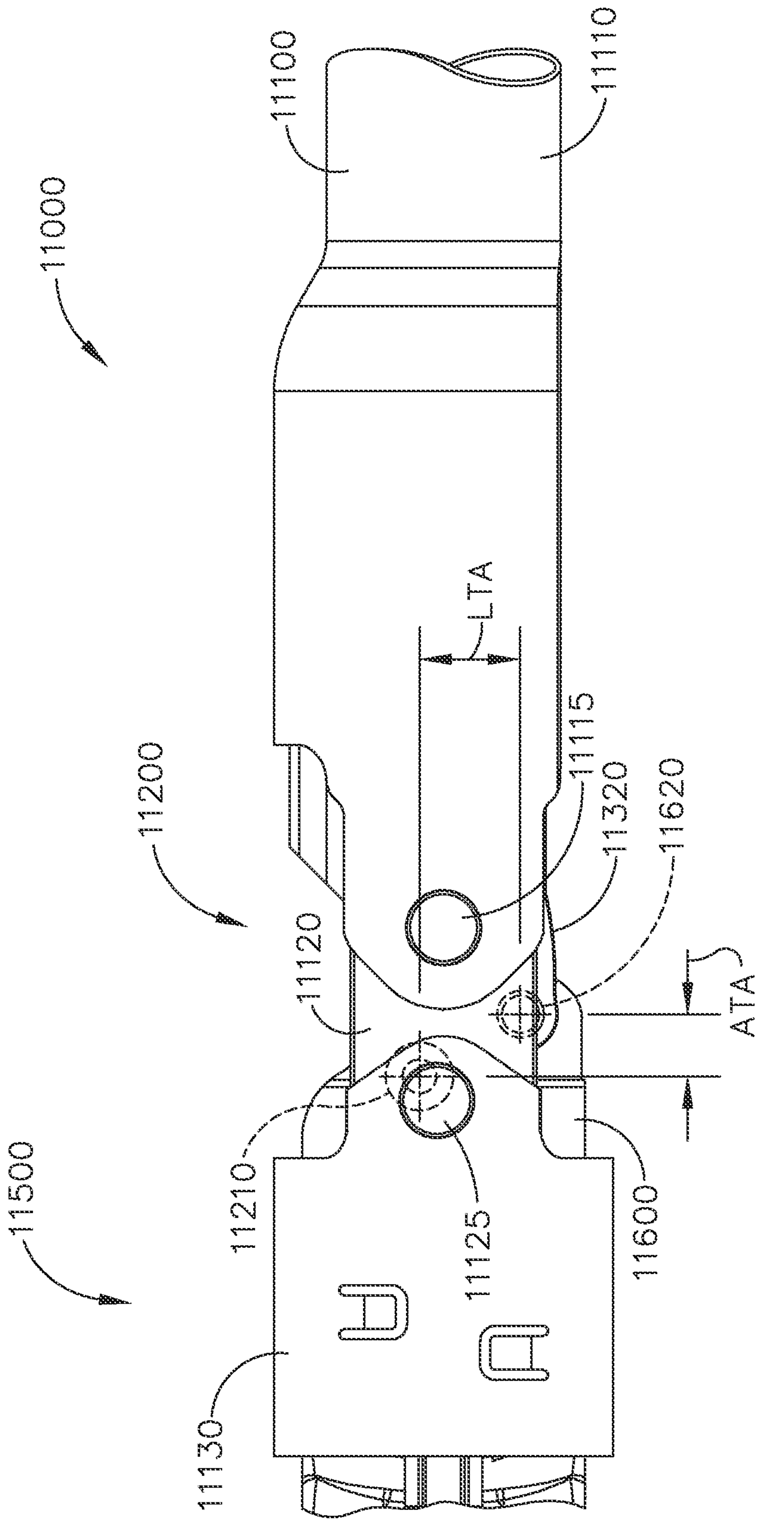
FIG. 91 is a partial plan view of the end effector of FIG. 80 illustrated in an unarticulated configuration.
Figure 92:
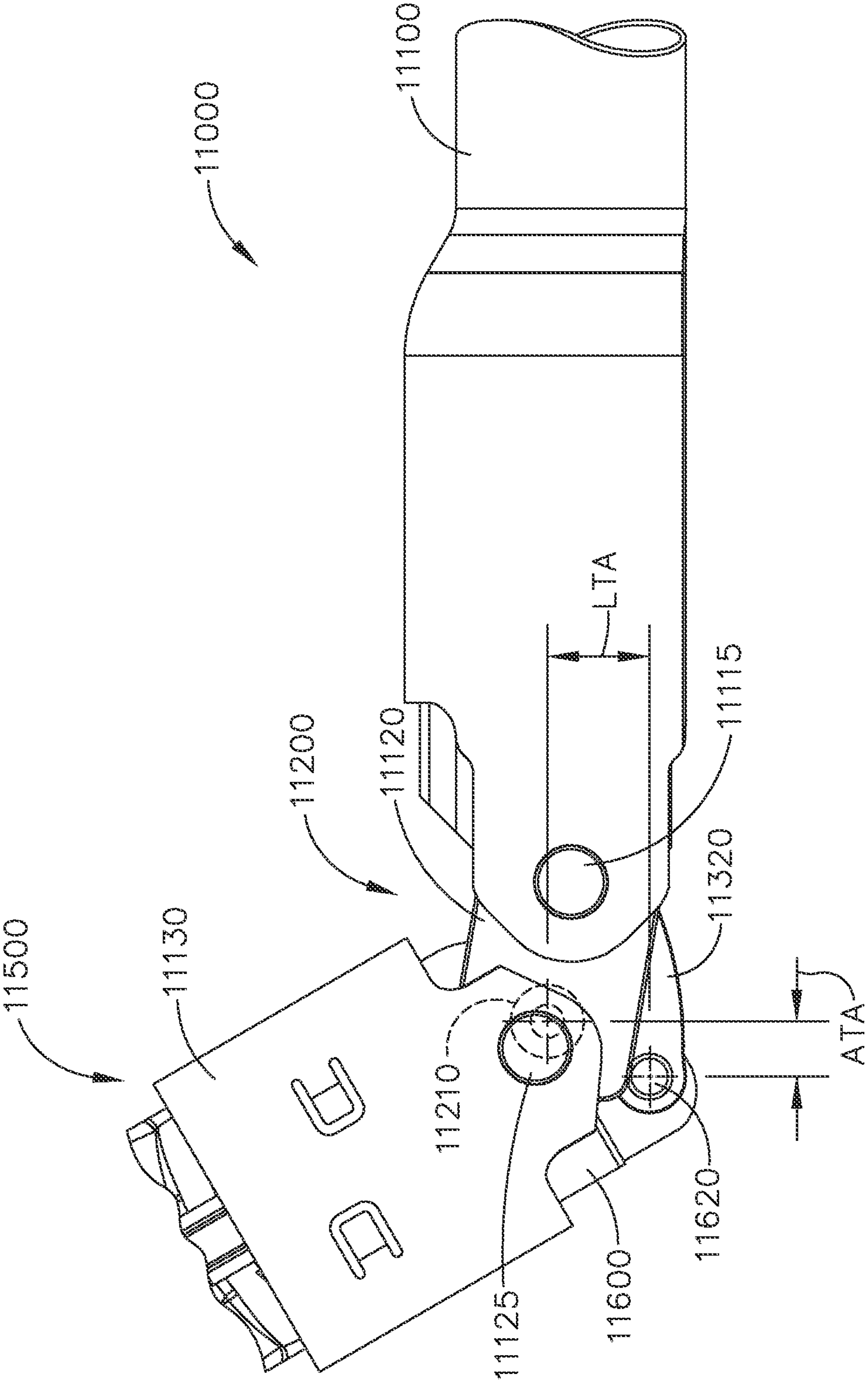
FIG. 92 is a partial plan view of the end effector of FIG. 80 illustrated in an articulated configuration.
Figure 93A:
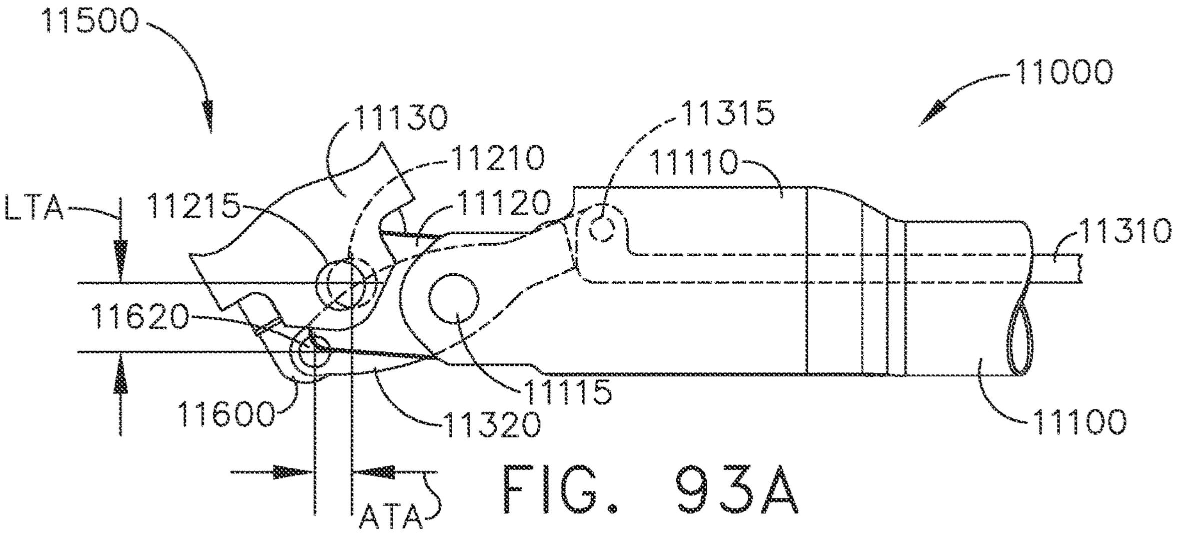
FIG. 93A is a partial plan view of the end effector of FIG. 80 illustrated in a fully-right articulated configuration.
Figure 93:
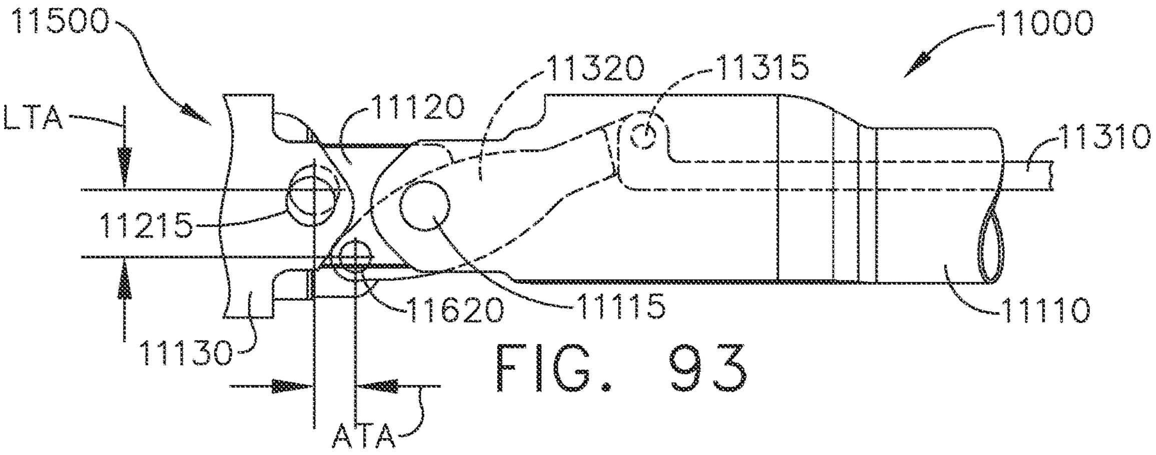
FIG. 93 is a partial plan view of the end effector of FIG. 80 illustrated in an unarticulated configuration.
Figure 93B:
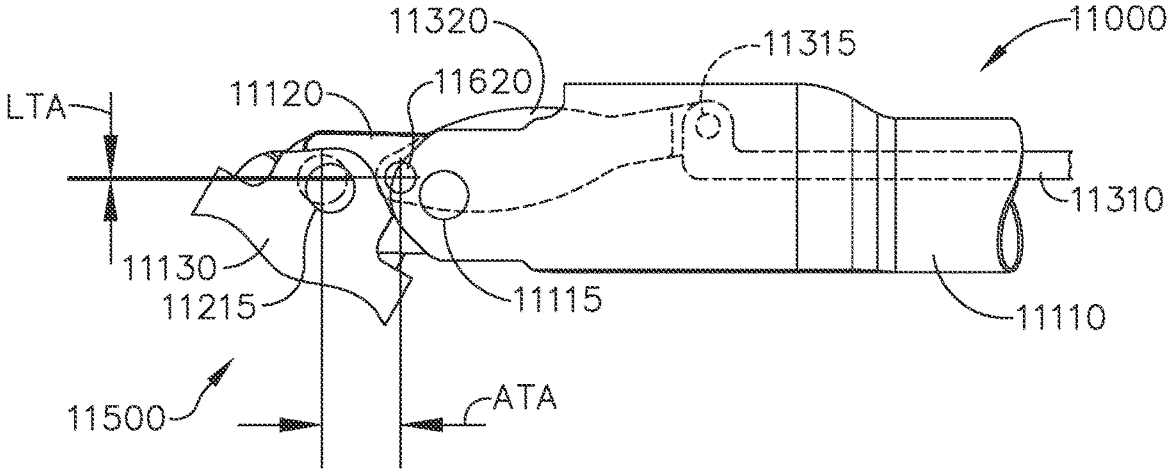
FIG. 93B is a partial plan view of the end effector of FIG. 80 illustrated in a fully-left articulated configuration.

Further to the above, the articulation actuator 11310 of the surgical instrument 11000 is configured to apply a torque to the first jaw 11600 of the end effector 11500 via the pin 11620 to rotate the end effector 11500 about the articulation joint 11200. Referring to FIGS. 86, 91, and 93, a lateral torque arm (LTA) defined between the pivot joint 11210 of the articulation joint 11200 and the pin 11620 is defined by a length $TA_{C2}$ when the end effector 11500 is in its unarticulated position. The length $TA_{C2}$ is measured in an orthogonal direction with respect to a longitudinal axis 11190 extending through the articulation pivot joint 11210. Notably, the longitudinal axis 11190 is offset and parallel with respect to the centerline of the shaft 11100, as discussed in greater detail below in connection with FIG. 88. Similar to the above, the lateral torque arm defined between the pivot joint 11210 and the pin 11620 is defined by a length $TA_{R2}$ when the end effector 11500 is fully articulated to the right (FIG. 93A) and, similarly, a length $TA_{L2}$ when the end effector 11500 is fully articulated to the left (FIG. 93B)—both lengths of which are measured orthogonally with respect to the longitudinal axis 11190. Notably, the length $TA_{R2}$ is larger than the unarticulated lateral torque arm length $TA_{C1}$ and the length $TA_{L2}$ is shorter than the unarticulated lateral torque arm length $TA_{C1}$ Moreover, the lengths $TA_{R2}$ and $TA_{L2}$, and the torque arms which they define, are not equal. Instead, the right-articulated torque arm length $TA_{R2}$ is considerably larger than the left-articulated torque arm length $TA_{L2}$. In fact, the right-articulated torque arm length $TA_{R2}$ and the left-articulated torque arm length $TA_{L2}$ extend in different directions. Such an arrangement provides for a larger pushing torque arm as compared to a smaller pulling torque arm. In various instances, as a result, the retraction pulling force applied by the articulation actuator 11310 to articulate the end effector 11500 to the left (FIG. 93B) may be, or may need to be, larger than the distal pushing force to articulate the end effector 11500 to the right (FIGS. 92 and 93A). Advantageously, the articulation actuator 11310 can accommodate such a larger pulling force as the articulation actuator 11310 is not subject to buckling failure when being pulled.

In at least one instance, the arm length $TA_{C2}$ is approximately 0.149", the arm length $TA_{R2}$ is approximately 0.154", and the arm length $TA_{L2}$ is approximately 0.015", for example.

Further to the above, the surgical instrument 11000 is configured and arranged to provide a large torque to the end effector 11500 while, at the same time, providing a large articulation range, or sweep, in response to a short articulation stroke. To wit, several design ratios for these relationships can be established and used to design the surgical instrument 11000. For instance, a first ratio comprises the fully-right articulated torque arm length (TA) divided by the full articulation stroke length (SL) of the articulation actuator 11310. The value of this first ratio is unitless. In at least one instance, the fully-right articulated torque arm length (TA) is 0.154" and the full articulation stroke length (SL) is 0.275", resulting in a ratio value of 0.56, for example. Larger ratio values for the first ratio indicate more efficient articulation systems. In various instances, the value for the first ratio is less than 1.0, but can be more than 1.0. In at least one instance, the fully-right articulated torque arm length (TA) is 2.79 mm and the full articulation stroke length (SL) is 11.43 mm, resulting in a ratio value of 0.24, for example.

The examples provided above for the first ratio were based on the torque arm length (TA) when the end effector 11500 is in its fully-right articulated position. This particular position of the end effector 11500 is notable because the articulation actuator 11310 is in compression and can undergo buckling when the load transmitted there through is excessive. That said, the first ratio could also be used to analyze any suitable position of the end effector 11500 such as its unarticulated position and its fully-left articulated position, for example. In at least one instance, the unarticulated torque arm length (TA) is 6.17 mm, resulting in a ratio value of 0.54 for a stroke length (SL) of 11.43 mm, for example. Also, in at least one instance, the fully-left articulated torque arm length (TA) is 1.41 mm, resulting in a ratio value of 0.12 for a stroke length (SL) of 11.43 mm, for example.

A second ratio includes the arc length in which the drive pin 11620 is swept through when the end effector 11500 is articulated between its fully-right articulated position and its fully-left articulated position, i.e., its arc length sweep (ALS). More specifically, the second ratio comprises the arc length sweep (ALS) of the drive pin 11620 divided by the full articulation stroke length (SL) of the articulation actuator 11310. The value of this second ratio is unitless. In at least one instance, the arc length sweep (ALS) of the drive pin 11620 is 0.387" and the full articulation stroke length (SL) is 0.275", resulting in a ratio value of 1.41, for example. In at least one instance, the arc length sweep (ALS) is 0.444" and the full articulation stroke length (SL) is 0.306", resulting in a ratio value of 1.45, for example. In at least one instance, the arc length sweep (ALS) is 12.94 mm and the full articulation stroke length (SL) is 11.43 mm, resulting in a ratio value of 1.13, for example. Larger ratio values for the second ratio indicate more efficient articulation systems. In various instances, the value for the second ratio is more than 1.0, such as between 1.0 and 3.0, for example. In at least one instance, the second ratio value is approximately 2.0, for example. In certain instances, the value for the second ratio is about 1.1, but between 0.9 and 1.3, for example.

A third ratio comprises the sum of the fully-right articulated torque arm length (TA) and the arc length sweep (ALS) of the drive pin 11620 divided by the full articulation stroke length (SL). The value of this third ratio is unitless. In at least one instance, the fully-right articulated torque arm length (TA) is 0.154", the arc length sweep (ALS) of the drive pin 11620 is 0.387", and the full articulation stroke length (SL) is 0.275", resulting in a ratio value of 1.97, for example. In at least one instance, the fully-right articulated torque arm length (TA) is 2.79 mm, the arc length sweep (ALS) of the drive pin 11620 is 12.94 mm, and the full articulation stroke length (SL) is 11.43 mm, resulting in a ratio value of 1.38, for example. Larger ratio values for the third ratio indicate more efficient articulation systems. In various instances, the value for the third ratio is more than 1.0, such as between 1.0 and 3.0, for example. In at least one instance, the third ratio value is approximately 2.0 or more than 2.0, for example.

Similar to the above, the third ratio could be used to evaluate the articulation system when the end effector 11500 is in any suitable position, such as its unarticulated and fully-left articulated positions, for example.

A fourth ratio comprises the product of the fully-right articulated torque arm length (TA) and the arc length sweep (ALS) of the drive pin 11620 divided by the full articulation stroke length (SL). The value of this fourth ratio is not unitless and is, instead, measured in distance. In at least one instance, the fully-right articulated torque arm length (TA) is 0.154", the arc length sweep (ALS) of the drive pin 11620 is 0.387", and the full articulation stroke length (SL) is 0.275", resulting in a ratio value of 0.217", for example. This value can be made unitless by dividing it by the stroke length (SL) once again resulting in a value of 0.79. In at least one instance, the fully-right articulated torque arm length (TA) is 2.79 mm, the arc length sweep (ALS) of the drive pin 11620 is 12.94 mm, and the full articulation stroke length (SL) is 11.43 mm, resulting in a ratio value of 3.15 mm, for example. In certain instances, the value for the fourth ratio is about 3.1 mm, but between 0.9 mm and 5.4 mm, for example. Similar to the above, this value can be made unitless by dividing it by the stroke length (SL) once again resulting in a value of 0.28. Larger ratio values for the fourth ratio indicate more efficient articulation systems.

Similar to the above, the fourth ratio could be used to evaluate the articulation system when the end effector 11500 is in any suitable position, such as its unarticulated and fully-left articulated positions, for example.

Figure 87:
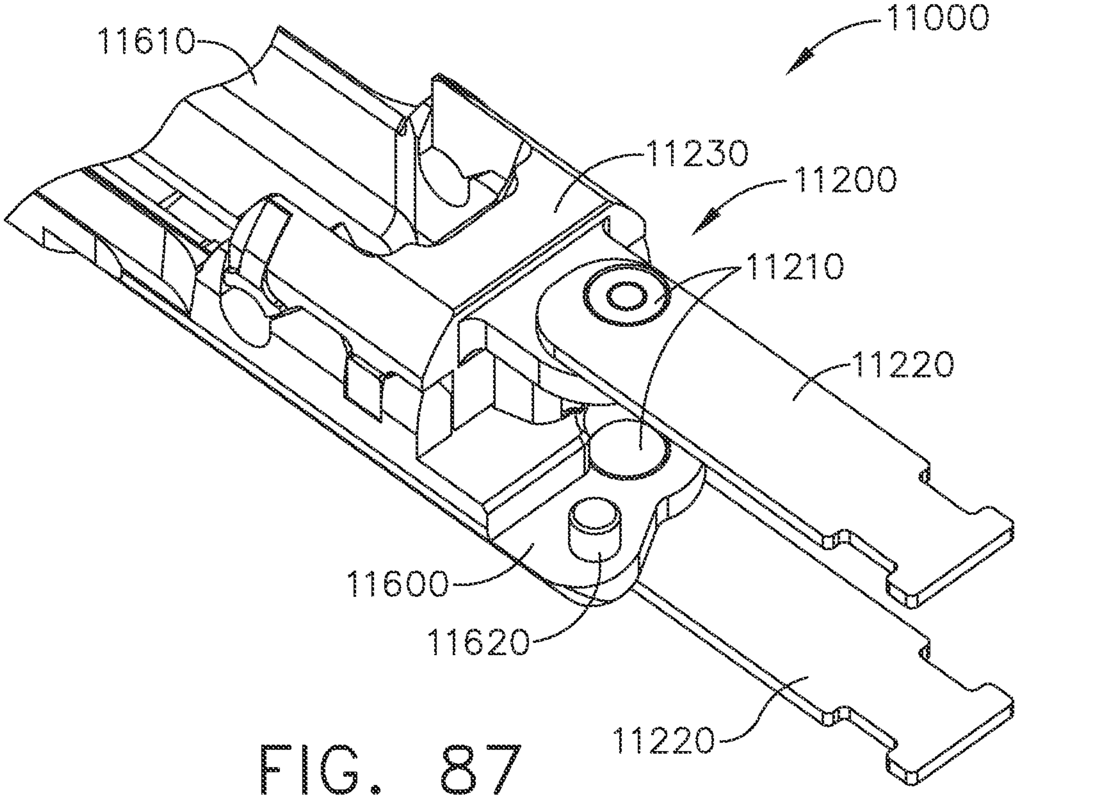
FIG. 87 is a partial perspective view of the end effector of FIG. 80 illustrated with some components removed.
Figure 88:
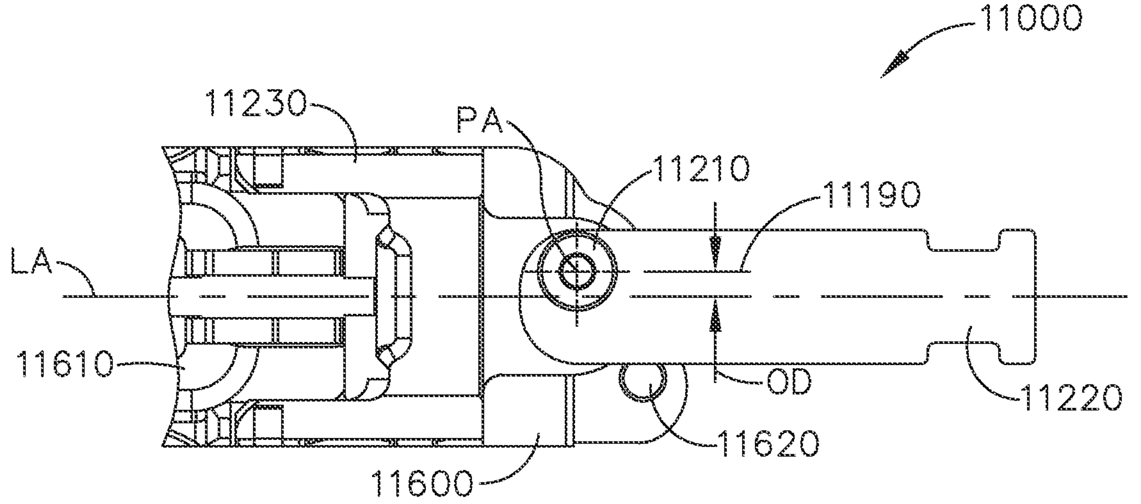
FIG. 88 is a partial plan view of the end effector of FIG. 80 illustrated with some components removed.

As discussed above, the end effector 11500 is rotatably mounted to the shaft 11100 about a fixed pivot 11210 of the articulation joint 11200. Referring now to FIGS. 87 and 88, the shaft 11100 comprises distal mounting tabs 11220 which extend from and are fixedly mounted to the frame, or spine, of the shaft 11100. A first distal mounting tab 11220 is mounted to the first jaw 11600, which comprises a lower frame portion, and a second distal mounting tab 11220 is mounted to an upper frame portion 11230. The interconnection between the mounting tabs 11220 and the first jaw 11600 and upper frame portion 11230 defines the fixed pivot 11210. As also discussed above, the fixed axis pivot 11210 is laterally offset with respect to a central longitudinal axis LA of the shaft 11100 by an offset distance OD. In at least one instance, the fixed axis pivot 11210 is laterally offset by approximately 0.036", for example. Moreover, referring to FIGS. 91-93B, the pin 11620 is longitudinally offset with respect to the fixed pivot 11210 which creates a longitudinal, or axial, torque arm (ATA).

Figure 89A:
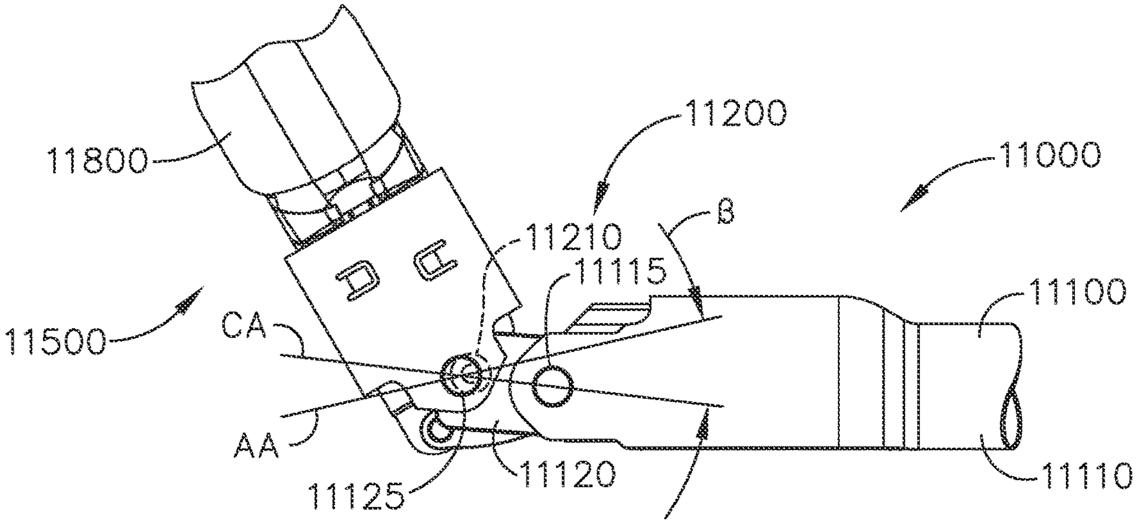
FIG. 89A is a partial plan view of the end effector of FIG. 80 illustrated in an open, fully-right articulated configuration.

As discussed above, the closure tube of the shaft 11100 is movable distally to engage the anvil jaw 11800 of the end effector 11500 and move the anvil jaw 11800 toward a staple cartridge 11700 positioned in the cartridge jaw 11600. Stated another way, the closure tube is configured to move the anvil 11800 from an open position (FIGS. 89-89B) to a closed position (FIGS. 90-90B) to clamp the tissue of a patient against the staple cartridge 11700. In such instances, the closure tube, comprising the housing 11110, the connector plates 11120, and the distal housing 11130, are slid distally with respect to the articulation joint 11200 during a closure stroke. When the end effector 11500 is in an open, unarticulated configuration, referring now to FIG. 89, the connector plates 11120 extend in a direction which is slightly transverse to the central longitudinal axis LA of the shaft 11100. More specifically, an axis CA extending between the joints 11115 and 11125 is slightly transverse with respect to the central longitudinal axis LA of the shaft 11100 when the end effector 11500 is in an open, unarticulated configuration. When the end effector 11500 is articulated relative to the right (FIG. 89A) or the right (FIG. 89B), the orientation of the axis CA relative to the central longitudinal axis LA can change.

In various instances, further to the above, the orientation of the axis CA will change relative to a longitudinal axis extending between the proximal end and the distal end of the end effector 11500. In at least one instance, the axis CA is transverse to such a longitudinal end effector axis except in one configuration in which the axis CA will be parallel to the longitudinal end effector axis.

Figure 89:
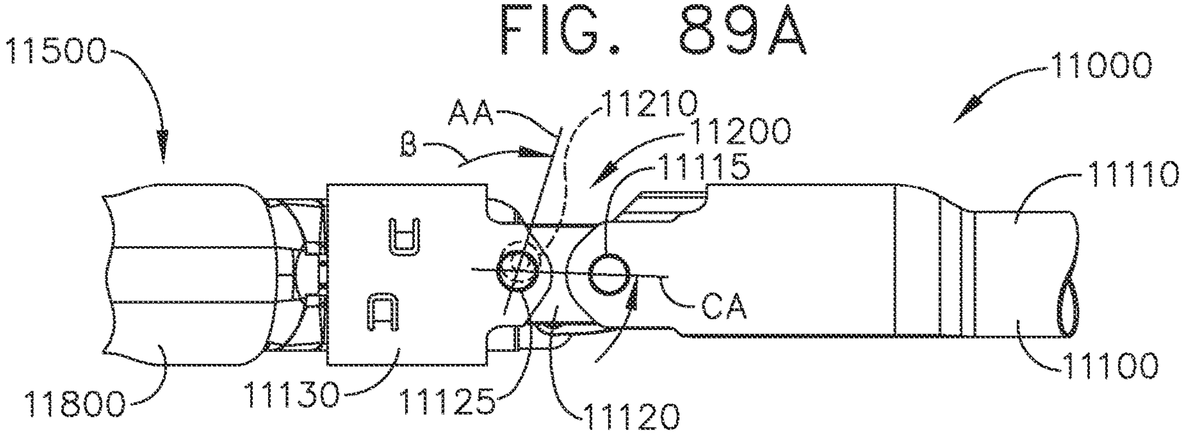
FIG. 89 is a partial plan view of the end effector of FIG. 80 illustrated in an open, unarticulated configuration.
Figure 89B:
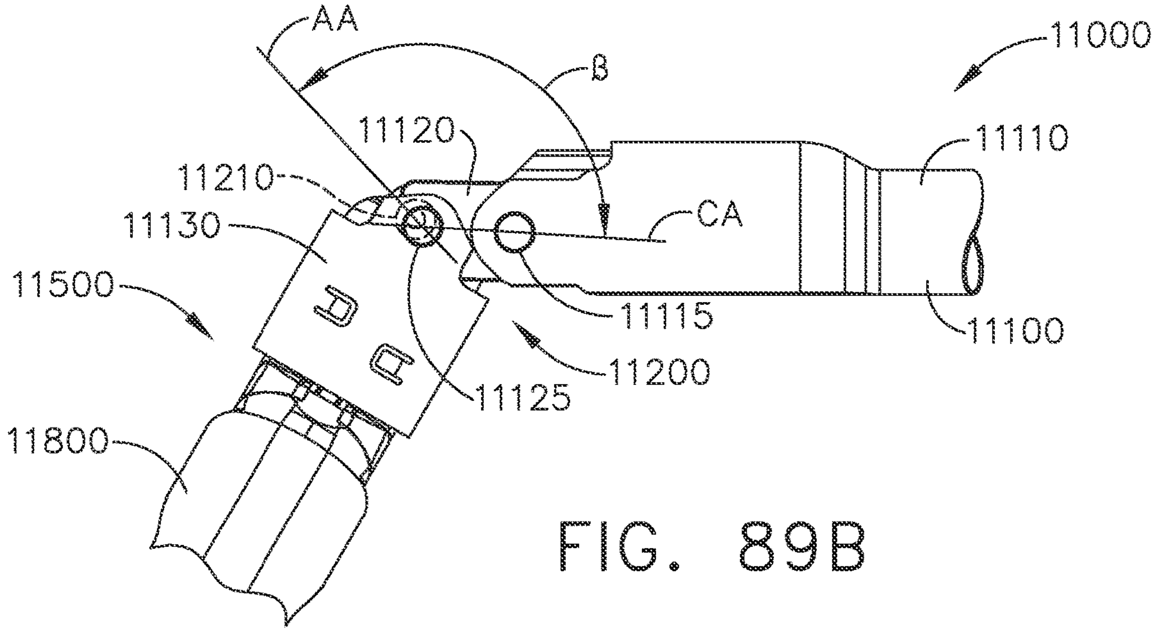
FIG. 89B is a partial plan view of the end effector of FIG. 80 illustrated in an open, fully-left articulated configuration.

Further to the above, the orientation of an axis AA defined between the articulation pivot 11210 and the distal pivot 11125 of the connector plates 11120 changes as the end effector 11500 is articulated. Referring to FIG. 89, the axis AA extends at an angle β with respect to the axis CA when the end effector 11500 is in an open, unarticulated configuration. When the end effector 11500 is articulated into an open, right configuration (FIG. 89A), the angle β decreases. When the end effector 11500 is articulated into an open, left configuration (FIG. 89B), the angle β increases. At no point, however, is the axis AA collinear with or parallel to the axis CA when the open end effector 11500 is articulated. Instead, the axis AA is transverse to the axis CA when the end effector 11500 is articulated in an open configuration.

Figure 90A:
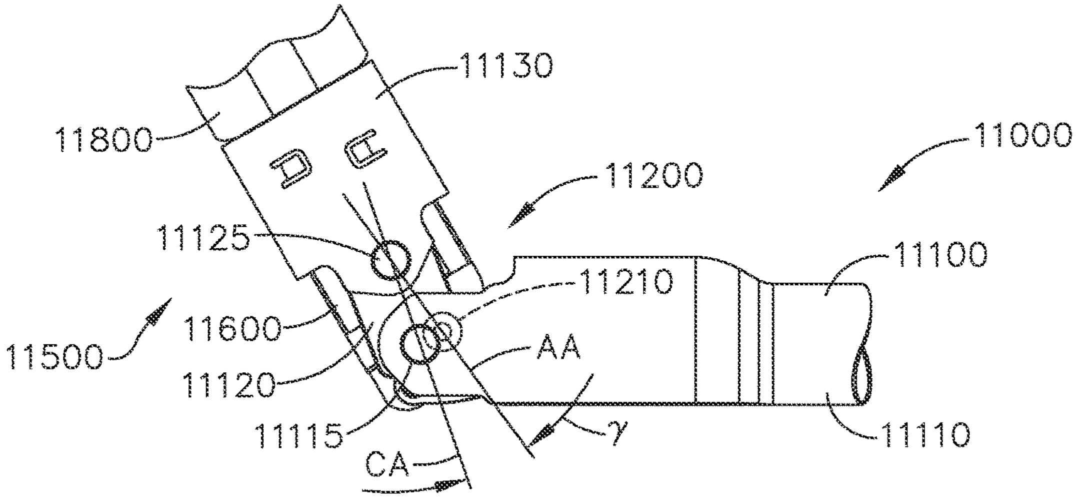
FIG. 90A is a partial plan view of the end effector of FIG. 80 illustrated in a closed, fully-right articulated configuration.
Figure 90:
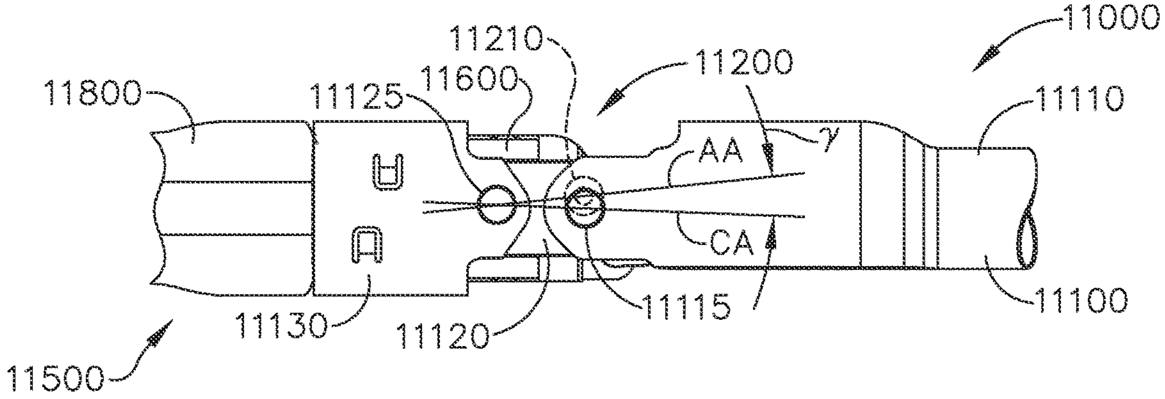
FIG. 90 is a partial plan view of the end effector of FIG. 80 illustrated in a closed, unarticulated configuration.
Figure 90B:
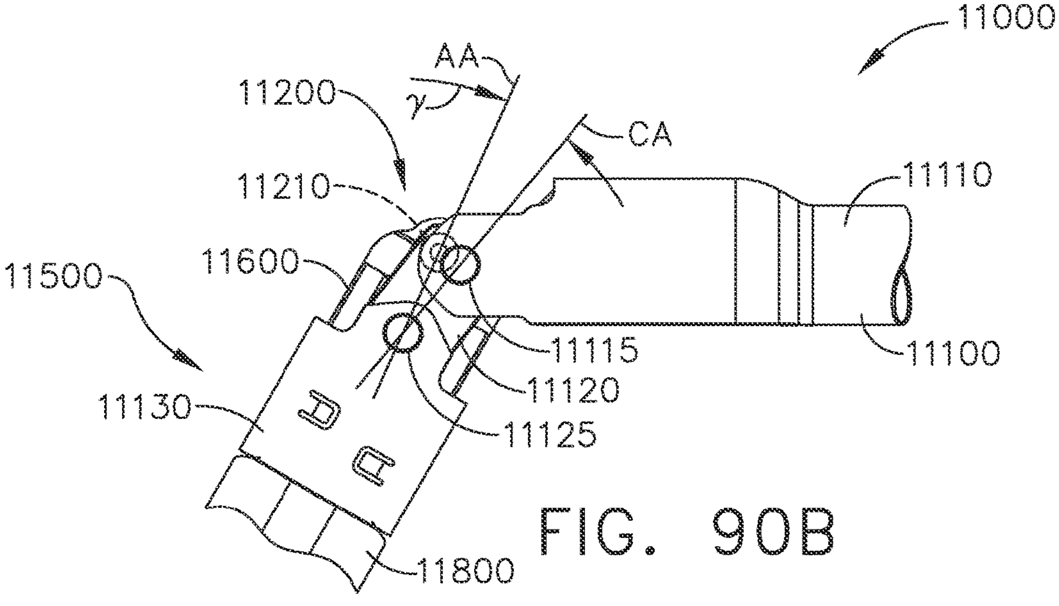
FIG. 90B is a partial plan view of the end effector of FIG. 80 illustrated in a closed, fully-left articulated configuration.

Referring to FIG. 90, the axis AA extends at an angle γ with respect to the axis CA when the end effector 11500 is in a closed, unarticulated configuration. When the end effector 11500 is articulated into a closed, right configuration (FIG. 90A), the angle γ increases. When the end effector 11500 is articulated into a closed, left configuration (FIG. 90B), the angle δ also increases. At no point, however, is the axis AA collinear with the axis CA when the end effector 11500 is articulated in a closed configuration, and/or any other configuration between an open configuration and a closed configuration. Instead, the axis AA is transverse to the axis CA when the end effector 11500 is articulated in a closed configuration and/or any other configuration between an open configuration and a closed configuration.

Referring again to FIGS. 83 and 84, the design of the surgical instrument 11000 can shorten the end effector 11500 as compared to the end effector 10500. Also, the distance between the articulation joint 10200 and the proximal end of the staple line that is applied to the tissue of a patient by the end effector 10500 is a distance L1—while the distance between the articulation joint 11200 and the proximal end of the staple line that is applied by the end effector 11500 is a distance L2, which is shorter than the distance L1.

Turning now to FIGS. 103-108, the surgical instrument 11000 further comprises an articulation lock 11400 configured to selectively lock the articulation drive system 11300 and the end effector 11500 in position. The articulation lock 11400 comprises a distal end 11402 mounted to a frame 11180 of the shaft 11100. More particularly, the shaft frame 11180 comprises pins, or projections, 11182 closely received and/or pressed within apertures defined in the distal end 11402. The articulation lock 11400 further comprises a proximal end 11404 configured to move relative to the distal end 11402. In at least one respect, the articulation lock 11400 comprises a cantilever beam where the distal end 11402 comprises a fixed end and the proximal end 11404 comprises a free end. The proximal end 11404 is positioned in a cavity 11184 defined in the shaft frame 11180 and is configured to move laterally toward and away from the articulation drive actuator 11310, as described in greater detail below.

Figure 104:
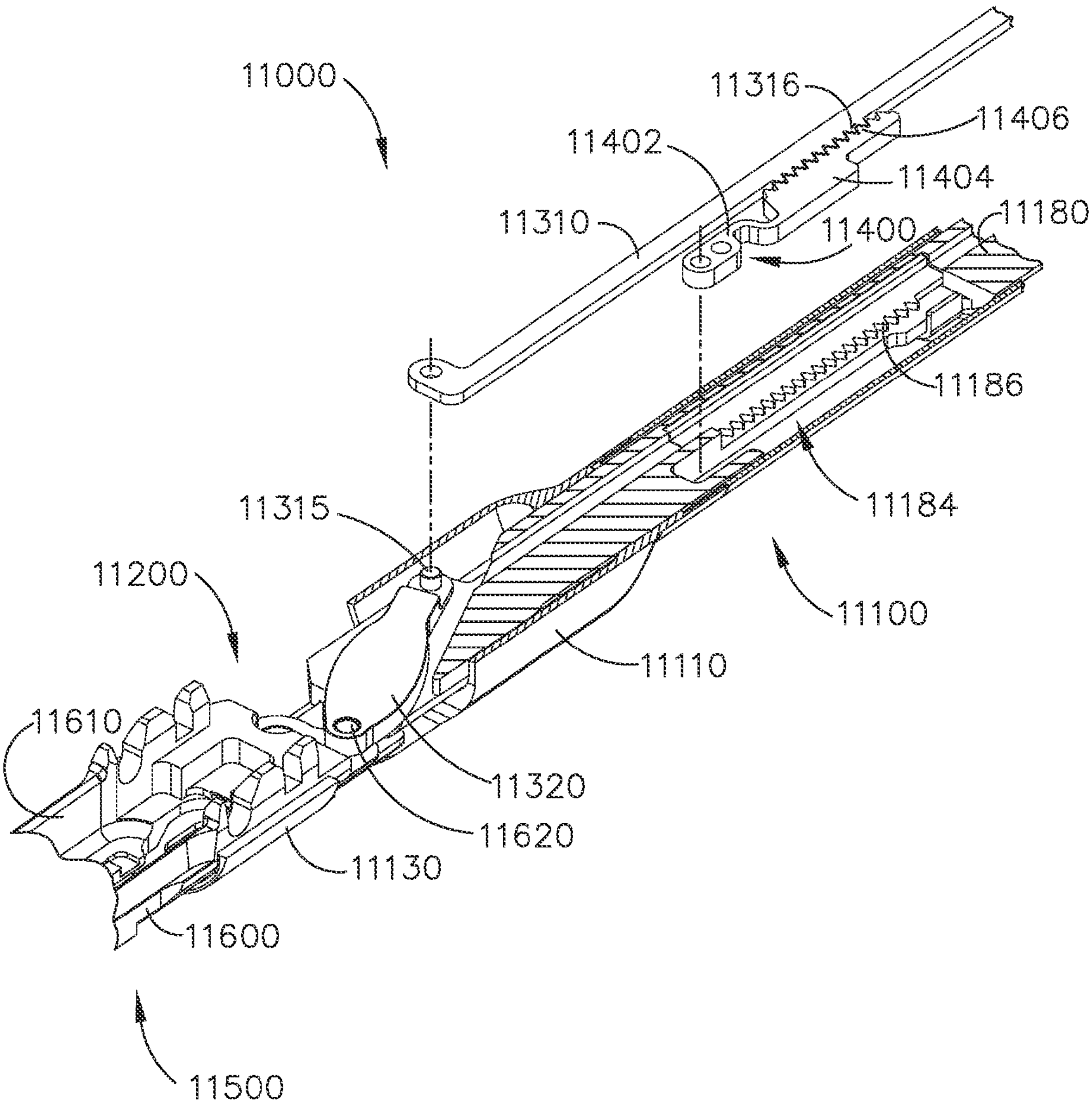

Further to the above, the proximal end 11404 of the articulation lock 11400 comprises one or more teeth 11406 defined thereon which are configured to engage the articulation drive actuator 11310. As illustrated in FIG. 103, the teeth 11406 are arranged in a longitudinal array; however, any suitable arrangement may be used. The articulation drive actuator 11310 comprises a longitudinal array of teeth 11316 defined thereon which are configured to be engaged by the articulation lock teeth 11406. Referring to FIG. 104, the shaft frame 11180 further comprises a longitudinal array of teeth 11186 defined therein which are also configured to be engaged by the articulation lock teeth 11406. When the articulation lock 11400 is in a fully-locked state, as described in greater detail below, the articulation lock teeth 11406 are engaged with the drive actuator teeth 11316 and the shaft frame teeth 11186 such that the articulation lock 11400 locks the articulation drive actuator 11310 to the shaft frame 11180 and prevents, or at least inhibits, relative movement between the articulation drive actuator 11310 and the shaft frame 11180.

Figure 105:
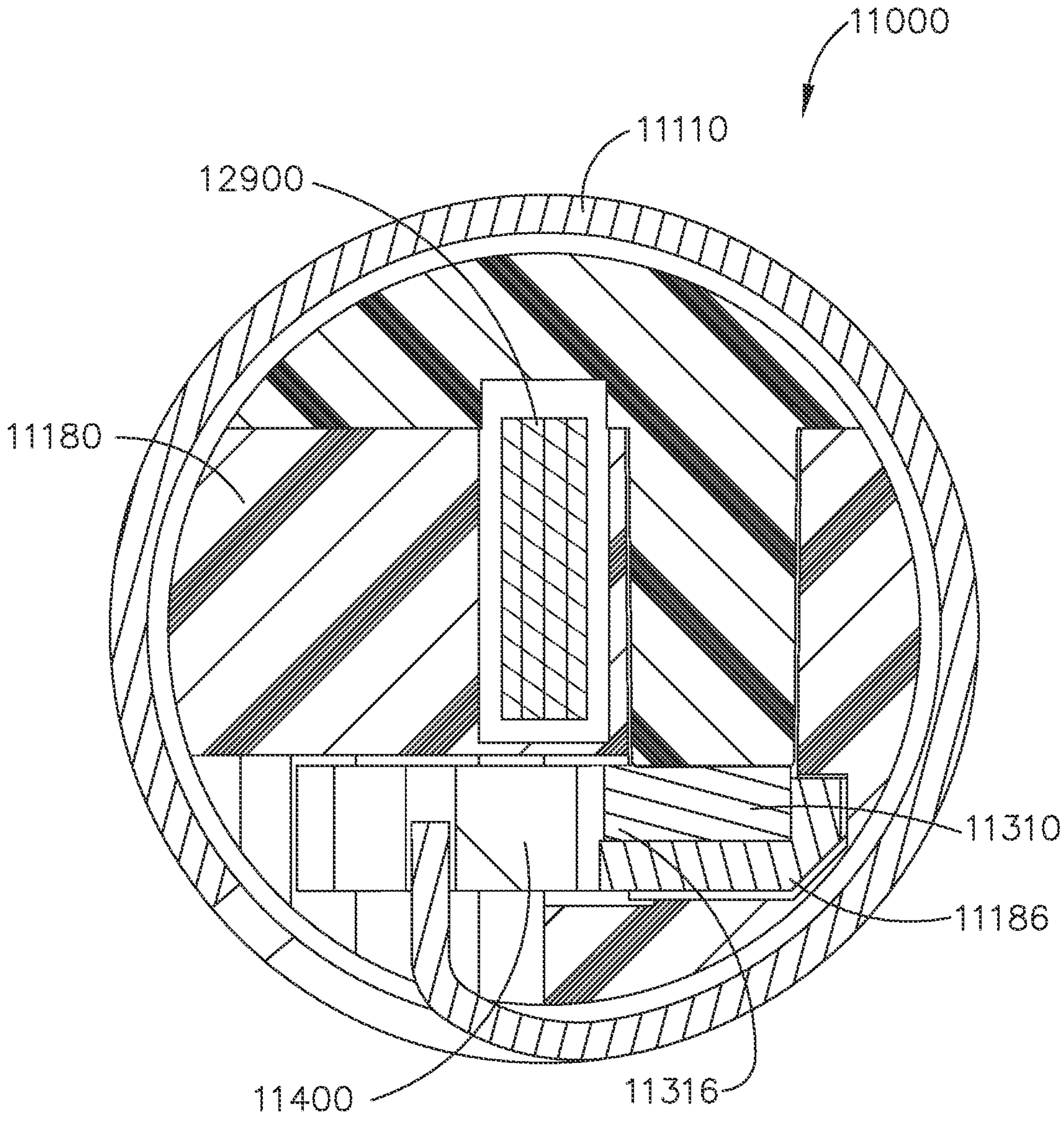

Further to the above, the articulation lock 11400 is configurable in three states—a self-locked state, an unlocked state, and a fully-locked state. When the articulation lock 11400 is in a self-locked stated, referring to FIG. 106, the teeth 11406 of the articulation lock 11400 are engaged with the drive actuator teeth 11316 and the shaft frame teeth 11186. In such instances, the articulation lock 11400 can resist some force transmitted through the articulation drive actuator 11310; however, proximal and/or distal movement of the articulation drive actuator 11310 can overcome the holding force of the articulation lock 11400 and displace the articulation lock 11400 into its unlocked configuration, as illustrated in FIG. 107. In such instances, the articulation lock 11400 can flex or deflect laterally away from the drive actuator 11310. The articulation lock 11400 comprises a spring member 11403 extending between the distal portion 11402 and the proximal portion 11404 which is configured to resiliently return, or at least bias, the articulation lock toward its self-locked configuration (FIG. 105). As a result, the articulation drive system 11300 can lock and unlock itself as a result of its own motion and articulate the end effector 11500 unless the articulation lock 11400 is placed in its fully-locked position, as discussed below.

As discussed further above, the shaft 11100 of the surgical instrument 11000 comprises a closure tube 11110 that is advanced distally during a closure stroke to close the end effector 11500. Prior to the closure stroke, the articulation lock 11400 is movable between its self-locked and unlocked configurations to permit the end effector 11500 to be articulated by the articulation drive system 11300. During the closure stroke, however, the closure tube 11110 is configured to engage the articulation lock 11400 and place or hold the articulation lock 11400 in its fully-locked configuration. More specifically, the closure tube 11110 comprises a projection, or tab, 11118 configured to engage a cam surface 11408 defined on the back side of the articulation lock 11400 and prevent the articulation lock teeth 11406 from becoming demeshed from the drive actuator teeth 11316 and the shaft frame teeth 11186. When the closure tube 11110 is retracted proximally to open the end effector 11500, the tab 11118 disengages from the articulation lock 11400 and the articulation lock 11400 is free to move between its self-locked and unlocked positions, as discussed above, so that the end effector 11500 can be articulated once again.

The surgical instrument 11000 described above is further illustrated in FIGS. 143-145. The surgical instrument 11000 comprises a shaft 11100 which is configured for use with a trocar having a passageway defined therein. The surgical instrument shaft 11100 comprises different diameters at different points along the length of the surgical instrument shaft 11100. Among other things, the surgical instrument shaft 11100 comprises a central region 11160 comprising a smaller diameter than any other region of the surgical instrument shaft 11000. This geometry of the surgical instrument shaft 11100 provides significant advantages over previous designs and solves a long felt problem associated with the use of a trocar. Typically, when a surgical instrument is used in combination with a trocar during a surgical procedure, the surgical procedure is limited by the range of angles the instrument can take as a result of constrictions created by the trocar passageway. The configuration of the surgical instrument shaft 11100 is an improvement over existing shaft configurations because it increases the range of angles that a surgical instrument can take relative to the longitudinal axis of a trocar. As a result, the user of the surgical instrument 11000 can manipulate the surgical instrument 11000 in a variety of angles relative to the longitudinal axis of the trocar due to the smaller diameter of the central region 11160 of the surgical instrument shaft 11100.

Referring to FIGS. 143 and 144, the surgical instrument shaft further 11100 comprises a proximal region 11150 and a distal region 11170. The proximal region 11150 of the surgical instrument shaft 11000 is located adjacent to a nozzle assembly 11140 of the shaft 11100. The distal region 11170 is located closest to the end effector 11500. The proximal region 11150 of the surgical instrument shaft comprises a first diameter, and the central region 11160 comprises a second diameter. The distal region 11170 further comprises a third diameter. The first diameter of the proximal region 11150 is different than the second diameter of the central region 11160. Similarly, the second diameter of the central region 11160 is different than the third diameter of the distal region 11170. The first diameter of the proximal region 11150 is different than the third diameter of the distal region 11170; however, embodiments are envisioned in which the first diameter and the third diameter are the same.

Further to the above, the proximal region 11150 defines a central longitudinal axis. The central region 11160 extends along the central longitudinal axis and is centered with respect to the central longitudinal axis. The proximal region 11150 and the central region 11160 each define a circular profile, although they can comprise any suitable configuration. The distal region 11170 is not centered with respect to the central longitudinal axis. Instead, the distal region 11170 is offset laterally with respect to the central longitudinal axis. Moreover, more of the cross-section and/or perimeter of the distal region 11170 is positioned on a first side of the central longitudinal axis than a second side. In at least one instance, the distal region 11170 comprises an enlargement extending to one side of the central longitudinal axis. Additionally, the distal region 11170 does not define a circular profile.

Still referring to FIGS. 143 and 144, the central region 11160 comprises a second width that is smaller than the first width of the proximal region 11150. The central region further comprises a second width which is smaller than the third width of the distal region 11170. The proximal region 11150 further comprises a different width than the width of the distal region 11170. For example, the width of the proximal region 11150 is smaller than the width of the distal region 11170, but is still larger than the width of the central region 11160. Similarly, the width of the proximal region 11150 is larger than the width of the distal region 11170 and the width of the central region 11160. In other instances, the proximal region 11150 and the distal region 11170 comprise approximately the same width.

Referring to FIGS. 143-145, the surgical instrument shaft 11100 of the surgical instrument 11000 is configured to fit through a 12 mm trocar, for example. In at least one such instance, the central region 11160 of the surgical instrument shaft 11100 comprises a maximum diameter of approximately 9 mm. Such a diameter of the central region 11160 provides for a wider range of angles that the shaft 11100 can take relative to the centerline of the trocar. Also, such an arrangement can reduce the possibility of causing intercostal nerve damage associated with placing the surgical instrument shaft 11100 between the ribs of a patient during certain surgical procedures. The distal region 11170 of the surgical instrument shaft 11100 is configured to fit through a 12 mm trocar, and comprises one or more flat sides 11172 in order to provide for an increased level of access during procedures which require a high level of articulation. Other embodiments are envisioned in which the shaft 11100 is inserted through a 8 mm trocar and/or a 5 mm trocar, for example.

The proximal region 11150 comprises a stepped down, or tapered, region near the proximal end of the surgical instrument shaft 11100, where the surgical instrument shaft 11100 transitions from the proximal region 11150 to the central region 11160. The central region 11160 further comprises a stepped up, or tapered, region near the distal end of the surgical instrument shaft 11100, where the surgical instrument shaft 11100 transitions from the central region 11160 to the distal region 11170.

Still referring to FIGS. 143 and 144, the proximal region 11150 comprises a first circumference, the central region 11160 comprises a second circumference, and the distal region 11170 comprises a third circumference. The circumference of the proximal region 11150 is different than the circumference of the central region 11160, owing to the difference in diameters of such portions of the surgical instrument shaft 11100. Similarly, the circumference of the central region 11160 and the circumference of the distal region 11170 are different. The circumference of the proximal region 11150 and the circumference of the distal region 11170 are the same, but can be different in other embodiments.

Referring again to FIGS. 143 and 144, the surgical instrument shaft 11100 comprises a single, formed piece of material, although the surgical instrument shaft 11100 can comprise multiple pieces of material that are combined to form a single, cohesive surgical instrument shaft in other instances. The pieces of material can be assembled using any appropriate process. The surgical instrument shaft 11100 is configured to operate with a variety of surgical arrangements not limited to the surgical stapling instruments described above. The surgical instrument shaft 11100 can be used with other surgical instruments having articulatable end effectors. The other surgical instruments can include, for example, ultrasonic surgical devices, clip appliers, and fastener appliers. In addition, the surgical instrument shaft 11100 is configured for use with any surgical instrument wherein use of a trocar passageway is appropriate.

Further to the above, the outer tube 11110 of the shaft 11100 comprises a proximal end 11150 and a longitudinal portion 11160 comprising a diameter, or width, which is narrower than the diameter, or width, of the proximal end 11150. That said, the surgical instrument 11000 is configured and arranged to provide a large torque to the end effector 11500 while, at the same time, the longitudinal portion 11160 comprises a narrow diameter. To wit, at least one design ratio for this relationship can be established and used to design the surgical instrument 11000. For instance, one ratio comprises the diameter of the longitudinal portion 11160 (D) divided by the fully-right articulated torque arm length (TA). The value of this ratio is unitless. In at least one instance, the diameter of the longitudinal portion 11160 (D) is 0.316" and the torque arm length (TA) is 0.154", resulting in a ratio value of 2.06, for example. Smaller values for this ratio indicate more efficient articulation systems. In various instances, the value for this ratio is less than 2.0, such as between 1.0 and 2.0, for example. In at least one instance, the ratio value is between 2.0 and 3.0, for example. In certain instances, the ratio value is smaller than 3.38, for example.

Further to the above, the outer tube 11110 of the shaft 11100 comprises a longitudinal portion 11160 and an enlarged distal end 11170 (FIG. 143). Referring again to FIG. 103, the entirety of the articulation lock 11400 is positioned in the longitudinal portion 11160 and not the enlarged distal end 11170. Embodiments are envisioned, however, in which at least a portion of the articulation lock 11400 is positioned in the enlarged distal end 11170. In at least one such instance, the articulation lock 11400 is mounted to the shaft frame such that the distal end 11402 of the articulation lock 11400 is in the enlarged distal end 11170 of the outer tube 11110. In certain instances, the articulation lock 11400 is re-arranged such that the movable end of the articulation lock 11400 is positioned in the enlarged distal end 11170 of the outer tube 11110. In various instances, the entirety of the articulation lock 11400 is positioned in the enlarged distal end 11170.

Turning now to FIG. 109, a surgical instrument 14000 comprises a shaft 14100, an end effector 11500, and, in addition, an articulation drive system including an articulation drive actuator 14310 configured to articulate the end effector 11500. The shaft 14100 comprises an articulation lock system configured to selectively lock the articulation drive actuator 14310 and the end effector 14500 in position. The articulation lock system comprises an articulation lock 14400 including proximal end and distal ends mounted to a frame 14180 of the shaft 14100. In at least one respect, the articulation lock 14400 comprises a beam fixedly and/or simply-supported at both ends. The articulation lock 14400 further comprises an intermediate portion 14404 positioned in a cavity 14184 defined in the shaft frame 14180 which is configured to move laterally toward and away from an articulation drive actuator 14310 of the articulation drive system 14300. Similar to the above, the articulation lock 14400 comprises one or more spring portions 14403 configured to permit the articulation lock 14400 to flex toward and away from the articulation drive actuator 14310.

Further to the above, the intermediate portion 14404 of the articulation lock 14400 comprises one or more teeth 14406 defined thereon which are configured to engage the articulation drive actuator 14310. The teeth 14406 are arranged in a longitudinal array; however, any suitable arrangement may be used. The articulation drive actuator 14310 comprises a longitudinal array of teeth 14316 defined thereon which are configured to be engaged by the articulation lock teeth 14406. The articulation lock system further comprises a lock plate 14420 slidably positioned in the shaft cavity 14184 which includes a longitudinal array of teeth 14226 defined therein which are also configured to be engaged by the articulation lock teeth 14406. When the articulation lock 14400 is in a fully-locked state, as described in greater detail below, the articulation lock teeth 14406 are engaged with the drive actuator teeth 14316 and the lock plate teeth 14226 such that the articulation lock 14400 locks the articulation drive actuator 14310 in position and prevents, or at least inhibits, relative movement between the articulation drive actuator 14310 and the shaft frame 14180.

The lock plate 14420 comprises a shoulder 14424 which is positioned under the articulation drive actuator 14310. The lock plate teeth 14426 are defined on a lateral edge of the shoulder 14424 and are substantially aligned with the teeth 14316 defined in the articulation drive actuator 14310. In at least one instance, the articulation drive actuator teeth 14316 are aligned along a first teeth axis and the lock plate teeth 14406 are defined along a second teeth axis which is parallel, or at least substantially parallel, to the first teeth axis. In various instances, the drive actuator teeth 14316 are defined in a plane which is parallel to a plane including the lock plate teeth 14406. Such arrangements permit the articulation lock 14400 to simultaneously engage the lock plate 14420 and the articulation drive actuator 14310. Although the first teeth axis and the second teeth axis are parallel to a longitudinal axis of the shaft 14100, embodiments are envisioned in which the first teeth axis and the second teeth axis are skew or transverse with respect to the longitudinal axis of the shaft 14100.

Referring again to FIG. 109, the lock plate 14420 is slidable longitudinally within the cavity 14184; however, the longitudinal movement of the lock plate 14420 is limited by proximal and distal end walls 14427. As a result, the lock plate 14420 can float within the shaft cavity 14184 between the end walls 14427. In various instances, the lock plate teeth 14426 may not be completely aligned with the drive actuator teeth 14316 when the articulation lock 14400 engages the teeth 14426 and 14316. In such instances, the lock plate 14420 can move longitudinally, to a certain degree, such that the lock plate teeth 14426 are aligned with the drive actuator teeth 14316. In various instances, the lock plate 14420 can move in response to a locking force applied thereto by the articulation lock 14400. In at least one instance, the lock plate 14420 can be permitted to move distally one tooth pitch distance and proximally one tooth pitch distance with respect to its centered position, for example, wherein a tooth pitch distance is the distance between the peaks of adjacent lock teeth 14426 of the lock plate 14420. In other instances, the lock plate 14420 can be permitted to move distally ¼ of a tooth pitch distance and proximally ¼ of a tooth pitch distance with respect to its centered position, for example. In various instances, the lock plate 14420 can be permitted to move proximally and distally more than one toot pitch distance.

Further to the above, the articulation lock 14400 is configurable in three states—a self-locked state, an unlocked state, and a fully-locked state. When the articulation lock 14400 is in a self-locked stated, the teeth 14406 of the articulation lock 14400 are engaged with the drive actuator teeth 14316 and the shaft frame teeth 14186. In such instances, the articulation lock 14400 can resist some force transmitted through the articulation drive actuator 14310; however, proximal and/or distal movement of the articulation drive actuator 14310 can overcome the holding force of the articulation lock 14400 and displace the articulation lock 14400 into its unlocked configuration. In such instances, the articulation lock 14400 can flex or deflect laterally away from the drive actuator 14310 so that the end effector 11500 can be articulated. Similar to the above, the spring members 14403 of the articulation lock 14400 can resiliently return, or at least bias, the articulation lock 14400 toward its self-locked configuration. As a result, the articulation drive system can lock and unlock itself as a result of its own motion unless it is placed in its fully-locked position, as discussed below.

Similar to the above, the shaft 14100 of the surgical instrument 14000 comprises a closure tube that is advanced distally during a closure stroke to close the end effector 11500. Prior to the closure stroke, the articulation lock 14400 is movable between its self-locked and unlocked configurations to permit the end effector 11500 to be articulated by the articulation drive system. During the closure stroke, the closure tube is configured to engage the articulation lock 14400 and place, block, and/or hold the articulation lock 14400 in its fully-locked configuration. More specifically, the closure tube comprises a cam 14118 configured to engage a cam surface 14405 defined on the back side of the articulation lock 14400 and prevent the articulation lock teeth 14406 from becoming de-meshed from the drive actuator teeth 14316 and the shaft frame teeth 14186. The cam 14118 comprises an angled surface 14115 which engages a corresponding angled surface defined on the cam surface 14405, although any suitable arrangement could be used. When the closure tube is retracted proximally to permit the end effector 11500 to be opened, the tab 14118 disengages from the articulation lock 14400 and the articulation lock 14400 is free to move between its self-locked and unlocked positions, as discussed above, so that the end effector 11500 can be articulated once again.

When the articulation lock 14400 is moved into its fully-locked configuration by the closure tube, referring again to FIG. 109, the articulation lock 14400 pushes the lock plate 14420 against a lateral sidewall 14183 of the shaft cavity 14184. In fact, the articulation lock 14400 engages the lock plate 14420 with sufficient force to pin the lock plate 14420 against the sidewall 14183 such that the lock plate 14420 cannot move, or at least substantially move, longitudinally with respect to the shaft frame 14180. The lock plate 14420 comprises one or more projections 14422 extending therefrom which are configured to dig into, bite, and/or deflect the sidewall 14183 of the shaft cavity 14184 when the lock plate 14420 is pushed against the sidewall 14183 to prevent, or at least reduce the possibility of, the lock plate 14420 from moving longitudinally relative to the shaft frame 14180.

Further to the above, the shaft frame 14180 comprises one or more cavities, or openings, defined therein which are configured to permit and/or facilitate the deflection of the sidewall 14183. For example, as illustrated in FIG. 109, the shaft frame 14180 comprises cavities 14182 defined therein which are aligned, or at least substantially aligned, with the projections 14422. When the lock plate 14420 is displaced laterally by the closure tube, as discussed above, the sidewall 14183 elastically displaces into the cavities 14182 and the lock plate 14420 is locked in position. In such instances, the engagement between the shaft frame 14180 and the lock plate 14420 prevents the articulation drive actuator 14310 from being moved longitudinally and locks the end effector 11500 in position. When the closure tube is retracted and disengaged from the articulation lock 14400, the sidewall 14183 can return to its unflexed state and displace the lock plate 14420 laterally. At such point, the lock plate 14420 is unlocked and the end effector 11500 can be articulated, as outlined above.

A surgical instrument 15000 is illustrated in FIGS. 110-112 and is similar to the surgical instrument 14000 in many respects, most of which will not be repeated herein for the sake of brevity. Among other things, the surgical instrument 15000 comprises a shaft, an end effector 11500, and an articulation drive system including an articulation drive actuator 14310. The surgical instrument 15000 further comprises an articulation locking system including an articulation lock 15400 which is, similar to the above, movable between a self-locking position, an unlocked position, and a fully-locked position. The articulation locking system further comprises a lock plate 15420 which is similar to the lock plate 14420 in many respects. For instance, the lock plate 15420 is movable laterally into engagement with the wall 14183. Also, for instance, the lock plate 15420 is movable longitudinally to float into a suitable locked position in which an array of teeth 15426 defined on the lock plate 15420 are meshed with the teeth 14406 of the articulation lock 15400, as depicted in FIG. 111. That said, the shaft of the surgical instrument 15000 further comprises a distal spring 15429 positioned intermediate the lock plate 15420 and a distal end wall 15427 defined in the shaft frame and, in addition, a proximal spring 15429 positioned intermediate the lock plate 15420 and a proximal end wall 15427 defined in the shaft frame. The springs 15429 are configured to position the lock plate 15420 in a centered, or balanced, position between the end walls 15427, which is illustrated in FIG. 110. Such a centered position creates a proximal gap (PG) and a distal gap (DG) between the end walls 15427 and the lock plate 15420 which are equal, or at least substantially equal, to one another. That said, the springs 15429 may experience different deflections or loading when the lock plate 15420 seats itself into meshing engagement with the articulation lock 15400, as illustrated in FIG. 112, which may create unequal gaps PG and DG.

A surgical instrument 16000 is illustrated in FIGS. 113-115 and is similar to the surgical instruments 14000 and 15000 in many respects, most of which will not be repeated herein for the sake of brevity. Among other things, the surgical instrument 16000 comprises a shaft, an end effector 11500, and an articulation drive system including an articulation driver 16310. Referring primarily to FIG. 113, the surgical instrument 16000 further comprises an articulation locking system including an articulation lock 16400 which is, similar to the above, configurable in a self-locking configuration, an unlocked configuration, and a fully-locked configuration. The articulation locking system further comprises a lock plate 16420 which is similar to the lock plate 14420 in many respects. For instance, the lock plate 16420 is movable laterally into engagement with the wall 14183, as illustrated in FIG. 114. Also, for instance, the lock plate 16420 is movable longitudinally to float into a suitable locked position in which teeth 16426 of the lock plate 16420 are meshed with the teeth 16406 of the articulation lock 16400, as depicted in FIG. 115. Moreover, the teeth 16406 of the articulation lock 16400, the teeth 16426 of the lock plate 16420, and the lock teeth 16316 of the articulation driver 16310 are configured and arranged to provide a plurality of positions, or permutations of positions, in which the articulation lock 16400 can lock the articulation driver 16310 to the lock plate 16420. For instance, the articulation lock system has reached a fully-locked configuration in a set of positions illustrated in FIG. 114 and a fully-locked configuration in a different set of positions illustrated in FIG. 115.

The above-discussed adaptability of the articulation locking system can be achieved via the tooth pitches of the articulation lock teeth 16406, the articulation driver teeth 16316, and the lock plate teeth 16426. For instance, referring primarily to FIG. 113, the articulation lock teeth 16406 are set at a first pitch 16407, the articulation driver teeth 16316 are set at a second pitch 16317, and the lock plate teeth 16426 are set at a third pitch 16427. The first pitch is different than the second pitch and the third pitch—the second pitch is different than the first pitch and the third pitch—and the third pitch is different than the first pitch and the second pitch, although embodiments are envisioned in which two of the first pitch, the second pitch, and the third pitch are the same. Referring again to FIG. 113, the third pitch 16427 of the lock plate teeth 16426 is larger than the second pitch 16317 of the articulation driver teeth 16316, and the second pitch 16317 is larger than the first pitch 16407 of the articulation lock teeth 16406, although any suitable arrangement can be used.

A surgical instrument 17000 is illustrated in FIGS. 116-119 and is similar to the surgical instrument 11000 in many respects, most of which will not be repeated herein for the sake of brevity. The surgical instrument 17000 comprises a shaft, an end effector 11500 rotatably connected to the shaft about an articulation joint 11200, and an articulation drive system configured to articulate the end effector 11500 about the articulation joint 11200. Similar to the above, the articulation drive system comprises an articulation link 17320 rotatably mounted to the jaw 11600 about a pin 11620 and an articulation driver 17310 rotatably mounted to the articulation link 17320 about a pin 17315. The surgical instrument 17000 further comprises an articulation lock 17400 movably mounted to a shaft frame of the surgical instrument 17000 which is movable between an unlocked position and a locked position. The articulation lock 17400 comprises a distal end 17402 fixedly mounted to the shaft frame and a proximal end 17404 slidably mounted to the shaft frame. More specifically, the shaft frame comprises a pin extending into an aperture defined in the distal end 17402 of the articulation lock 17400 and a guide projection 17114 extending into an elongate aperture defined in the proximal end 17404. In certain instances, the shaft frame can comprise two or more pins extending into apertures defined in the distal end 17402 of the articulation lock 17400 to fix the distal end 17402 to the shaft frame and prevent the distal end 17402 from rotating relative to the shaft frame. As a result of the above, at least the proximal end 17404 of the articulation lock 17400 is movable relative to the shaft frame to engage the articulation driver 17310 and lock the articulation system and end effector 11500 in position.

Further to the above, the articulation driver 17310 comprises a longitudinal rack of teeth 17316 defined thereon and the articulation lock 17400 comprises a longitudinal rack of teeth 17406 defined thereon. When the articulation lock 17400 is in its unlocked position, as illustrated in FIGS. 116-117, the teeth 17406 of the articulation lock 17400 are not engaged with the teeth 17316 of the articulation driver 17310. In such instances, the articulation driver 17310 can move freely relative to the articulation lock 17400 to articulate the end effector 11500. When the articulation lock 17400 is in a partially-locked position, as illustrated in FIG. 118, the articulation lock teeth 17406 are partially engaged with the articulation driver teeth 17316. In such instances, the proximal and distal movement of the articulation driver 17310 is impeded by the articulation lock 17400; however, the articulation driver 17310 can still move relative to the articulation lock 17400 to articulate the end effector 11500. When the articulation lock 17400 is in a fully-locked position, as illustrated in FIG. 119, the articulation lock teeth 17406 are fully engaged with the articulation driver teeth 17316. In such instances, the proximal and distal movement of the articulation driver 17310, and the articulation of the end effector 11500, is prevented by the articulation lock 17400.

Further to the above, the surgical instrument 17000 does not include a biasing member configured to move the articulation lock 17400 toward the articulation driver 17310 other than a closure member, or tube, 17110. The closure tube 17110 is configured to engage the articulation lock 17400 and move the articulation lock 17400 from its unlocked position (FIG. 117) to its partially-locked (FIG. 118) and fully-locked positions (FIG. 119). Similar to the above, the closure tube 17110 comprises a cam 17118 configured to engage a cam surface defined on the articulation lock 17400, although other arrangements can be used. The closure tube 17110 is configured to move the articulation lock 17400 between its unlocked position and its partially-locked position when the closure tube 17110 is moved distally through a partial closing stroke (PCS) which at least partially closes the end effector 11500. In such instances, the end effector 11500 of the surgical instrument 17000 can be used to grasp the tissue of a patient, for example. The closure tube 17110 is configured to move the articulation lock 17400 into its fully-locked position when the closure tube 17110 is moved distally through a full closing stroke (FCS) which completely closes the end effector 11500. In such instances, the end effector 11500 of the surgical instrument 17000 can be used to fully clamp the tissue of a patient, for example.

As discussed above, the locking force applied to the articulation driver 17310 by the articulation lock 17400 increases as the closure tube 17110 is advanced distally. Stated another way, the articulation locking force is a function of the closure tube 17110 stroke. Further to the above, turning now to FIG. 120, the locking force between the articulation driver 17310 and the articulation lock 17400 is represented by line 17101. As illustrated in FIG. 120, the articulation lock teeth 17406 become initially engaged with the articulation driver teeth 17316 during the partial closure stroke. In at least one instance, such initial engagement of the teeth 17406 and 17316 occurs after approximately 0.050" of closure stroke of the closure tube 17110, although any suitable distance can be used. Notably, such initial engagement of the teeth 17406 and 17316 does not necessarily coincide with the end of the partial closing stroke; rather, it can occur at some point during the partial closure stroke (PCS). It also occurs at some point during the full closure stroke (FCS). Such an initial engagement, however, does not comprise a locking force couple. Instead, a locking force couple between the teeth 17406 and 17316 is only established at some during the full closing stroke (FCS). In at least one instance, the full closing stroke (FCS) has a length of approximately 0.260", for example.

A surgical instrument 18000 is illustrated in FIGS. 121-123 and is similar to the surgical instruments 11000 and 17000 in many respects, most of which will not be repeated herein for the sake of brevity. The surgical instrument 18000 comprises a shaft, an end effector 11500 rotatably connected to the shaft about an articulation joint, and an articulation system configured to articulate the end effector 11500. The shaft comprises a frame 18180 including first and second longitudinal racks of teeth 18186 which are parallel, or at least substantially parallel, to one another, although the racks of teeth 18186 can extend transversely to one another. The surgical instrument 18000 further comprises an articulation lock 18400 and a closure member including a cam 18118. The articulation lock 18400 includes a first lock arm 18410 configured to engage the first longitudinal rack of teeth 18186 and a second lock arm 18420 configured to engage the second longitudinal rack of teeth 18186. Referring primarily to FIGS. 122 and 123, the first lock arm 18410 comprises a first cam surface 18415 defined thereon and the second lock arm 18420 comprises a second cam surface 18425 defined thereon which are configured to be contacted by the cam 18118 during a closure stroke of the closure member and displaced or flexed outwardly into a fully-locked engagement with the longitudinal racks of teeth 18186. Moreover, one or both of the lock arms 18410 and 18420 also engage the articulation system to lock the end effector 11500 in place when the lock arms 18410 and 18420 are displaced outwardly into engagement with the shaft frame 18180.

Once displaced or flexed into their fully-locked states, the lock arms 18410 and 18420 define a longitudinal slot 18430 there between which is configured to permit the cam 18118 to pass thereby during the remainder of the closure stroke, for example. Moreover, in such instances, the cam 18118 wedges the articulation lock 18400 into engagement with the frame 18180 and securely holds the lock arms 18410 and 18420 in their fully-locked positions.

In at least one alternative embodiment, further to the above, the first lock arm 18410 of the articulation lock 18400 can be configured to engage the shaft frame 18180 of the surgical instrument 18000 while the second lock arm 18420 of the articulation lock 18400 can be configured to engage the articulation system of the surgical instrument 18000.

A surgical instrument 19000 is illustrated in FIGS. 124-128 and is similar to the surgical instrument 11000 in many respects, most of which will not be repeated herein for the sake of brevity. The surgical instrument 19000 comprises a shaft 19100 including a closure member 19110, an end effector 11500 rotatably connected to the shaft 19100 about an articulation joint 11200, and an articulation drive system 19300 including an articulation driver 19310 configured to articulate the end effector 11500 about the articulation joint 11200. Referring primarily to FIG. 124, the surgical instrument 19000 further comprises an articulation lock 19400 configured to selectively engage the articulation drive system 19300 and lock the end effector 11500 in position. The shaft 19100 further comprises a frame 19180 and the articulation lock 19400 is movably mounted to the frame 19180 between an unlocked position (FIG. 124), a partially-locked position (FIG. 126), and a locked position (FIG. 127). As described in greater detail below, the articulation lock 19400 is movable laterally toward the articulation driver 19310 to bring the articulation lock 19400 into close approximation with the articulation driver 19310 (FIG. 126) and, also, transversely into interference with the articulation driver 19310 (FIG. 127).

Further to the above, the shaft frame 19180 comprises a proximal guide post 19182 and a distal guide post 19184. The proximal guide post 19182 extends into a lateral elongate slot defined in a proximal end 19402 of the articulation lock 19400 and, similarly, the distal guide post 19184 extends into a lateral elongate slot defined in a distal end 19404 of the articulation lock 19400. The lateral elongate slots permit the articulation lock 19400 to move laterally toward and away from the articulation driver 19310, as outlined above. The lateral elongate slots also define the lateral path of the articulation lock 19400 and prevent, or at least substantially prevent, longitudinal movement of the articulation lock 19400 relative to the shaft frame 19180. As a result, the elongate slots of the articulation lock 19400 can guide the articulation lock 19400 between an unlocked position (FIG. 124) in which the lock teeth 19406 of the articulation lock 19400 are not engaged with a longitudinal rack of teeth 19316 defined on the articulation driver 19310, a partially-locked position (FIG. 126) in which the lock teeth 19406 are partially engaged with the teeth 19316, and a fully-locked position (FIG. 127) in which the lock teeth 19406 are fully engaged with the teeth 19316.

Further to the above, the articulation lock 19400 further comprises a longitudinal cam slot 19408 defined therein and the closure member 19110 comprises a cam pin 19188 positioned in the cam slot 19408. When the closure member 19110 is in an unactuated, or open, position (FIG. 124), the cam pin 19188 is positioned in a proximal portion 19408*a* of the cam slot 19408. When the closure member 19110 is moved distally into a partially-actuated, or partially-closed, position, as illustrated in FIG. 125, the cam pin 19188 is moved into a central portion 19408*b* of the cam slot 19408. In such instances, the cam pin 19188 displaces the articulation lock 19400 toward the articulation driver 19310. In such instances, however, the teeth 19406 of the articulation lock 19400 may not be engaged with the teeth 19316 of the articulation driver 19310 and, as a result, the articulation driver 19310 can still be moved to articulate the end effector 11500 relative to the shaft 19100. As a result, the end effector 11500 can be articulated when the closure stroke of the closure member 19110 has only been partially completed.

When the closure member 19110 is moved further distally, as illustrated in FIG. 126, the cam pin 19188 is moved into a distal portion 19408*c* of the cam slot 19408. In such instances, the cam pin 19188 displaces the articulation lock 19400 into close approximation with the articulation driver 19310 and into partial intermeshment with the teeth 19316 of the articulation driver 19310. That said, such partial intermeshment between the teeth 19406 and 19316 can only resist a certain amount of force transmitted through the articulation driver 19310 and such resistance can be overcome to move the articulation driver 19310 relative to the articulation lock 19400 and articulate the end effector 11500.

Further to the above, the articulation lock 19400 is not transversely lifted or lowered relative to the shaft frame 19180 during the partial closure stroke of the closure member 19110 (FIGS. 124-126). Rather, the articulation lock 19400 is lifted upwardly such that teeth 19406 of the articulation lock 19400 fully engage the teeth 19316 of the articulation driver 19310 and lock the articulation driver 19310 in position during the final or last portion of the closure stroke of the closure member 19110, as illustrated in FIG. 127. The articulation lock 19400 is moved upwardly by a different cam pin extending from the closure member 19110, i.e., cam pin 19189 which engages the articulation lock 19400 at the end of the closure stroke of the closure member 19110. Notably, the cam pin 19189 is not engaged with the articulation lock 19400 at the beginning of the closure stroke or during the partial closure stroke of the closure member 19110. At most, the cam pin 19189 may slidingly touch the bottom of the articulation lock 19400 during the partial closure stroke. That said, referring primarily to FIG. 128, the articulation lock 19400 comprises a cut-out, or recess, 19409 defined therein which provides clearance between the cam pin 19189 and the articulation lock 19400 during the partial closure stroke. That said, the cam pin 19189 comes into contact with the articulation lock 19400 when the cam pin 19189 reaches the end of the recess 19409 and, in such instances, drives the articulation lock 19400 transversely upwardly such that the lock teeth 19406 interferingly engage with the teeth 19316 of the articulation driver 19310 and the articulation lock 19400 is placed in its fully-locked position, as illustrated in FIG. 127. At such point, the articulation driver 19310 is locked in position and cannot be moved longitudinally to articulate the end effector 11500.

Referring again to FIG. 128, the teeth 19316 of the articulation driver 19310 are angled, or tilted, relative to the longitudinal axis of the shaft 19100. The lock teeth 19406 of the articulation lock 19400 are not angled, or are angled at a different orientation than the teeth 19316. As a result, the lock teeth 19406 of the articulation lock 19400 can be partially engaged with the teeth 19316 of the articulation driver 19310 when the articulation lock 19400 is in its lowered position (FIG. 126) and fully engaged with the teeth 19316 when the articulation lock 19400 is in its raised position (FIG. 127).

In order to unlock the articulation system 19300 of the surgical instrument 19000, the closure member 19110 must be retracted to disengage the cam pin 19189 from the articulation lock 19400 so that the articulation lock 19400 can return to its lowered position. Once the cam pin 19189 has been disengaged from the articulation lock 19400, the proximal retraction of the cam pin 19188 can drive the articulation lock 19400 downwardly as the cam pin 19188 is pulled proximally through cam slot 19408. Moreover, the cam pin 19188 can displace the articulation lock 19400 away from the articulation driver 19310 when it is pulled proximally. In various embodiments, the shaft 19110 can comprise one or more biasing members, such as springs, for example, configured to bias or push the articulation lock 19400 downwardly to quickly reset the articulation lock to an unlocked position.

A surgical instrument 20000 is illustrated in FIGS. 129-131 and is similar to the surgical instruments 11000, 17000, 18000, and 19000 in many respects, most of which will not be repeated herein for the sake of brevity. The surgical instrument 20000 comprises a shaft including a closure tube 20110, an end effector 11500 rotatably mounted to the shaft about an articulation joint 11200, and an articulation system configured to articulation the end effector 11500 relative to the shaft. Similar to the above, the articulation system comprises an articulation link 20320 rotatably pinned to the end effector 11500 and, in addition, an articulation actuator 20310 rotatably pinned to the articulation link 20320. In use, the articulation actuator 20310 is moved proximally and/or distally to drive the articulation link 20320 and articulate the end effector 11500. The surgical instrument 20000 further comprises an articulation lock system comprising an articulation lock gear 20400 rotatably mounted to a frame of the shaft about a fixed axis. The articulation lock gear 20400 comprises an annular array of teeth 20406 which is meshingly engaged with a longitudinal array of teeth 20316 defined on the articulation actuator 20310. As a result, referring generally to FIG. 129, the articulation lock gear 20400 will rotate in response to the proximal and/or distal movement of the articulation actuator 20310 until the articulation lock gear 20400 is locked in position by the closure tube 20110, as illustrated in FIG. 131.

Further to the above, the articulation lock system further comprises lock arms 20405 extending from the shaft frame into a central aperture defined in the articulation lock gear 20400 and, when the closure tube 20110 is moved distally during a closure stroke to close the end effector 11500, a cam, or wedge, 20118 of the closure tube 20110 is configured to engage the lock arms 20405 and splay the lock arms 20405 outwardly into engagement with the articulation lock gear 20400. Once the lock arms 20405 are engaged with the articulation lock gear 20400, the lock arms 20405 can prevent the rotation of the articulation lock gear 20400 and, also, the longitudinal movement of the articulation actuator 20310. In such instances, the lock arms 20405 can prevent, or at least substantially prevent, the articulation of the end effector 11500 until the wedge 20118 of the closure tube 20110 is retracted proximally during an opening stroke and the lock arms 20405 resiliently return to their unflexed, or unlocked, configurations.

Further to the above, the articulation system of the surgical instrument 20000 can be placed in an unlocked configuration (FIG. 129), a partially-locked configuration (FIG. 130), and a fully-locked configuration (FIG. 131). The articulation system can be placed in its partially-locked configuration (FIG. 130) when the closure tube 20110 is advanced distally through a partial closing stroke (PCS). In such instances, the end effector 11500 is at least partially closed but can still be articulated even though the lock arms 20405 may be partially engaged with the articulation lock gear 20400. More particularly, the articulation lock gear 20400 can still rotate despite drag created by the partial engagement of the lock arms 20405 against the articulation lock gear 20400. In at least one instance, the PCS is approximately 0.050", for example. The articulation system can be placed in its fully-locked configuration (FIG. 131) when the closure tube 20110 is advanced distally through a full closure stroke (FCS). In such instances, the end effector 11500 is completely closed and cannot be articulated until the articulation system is returned to its partially-locked and/or unlocked configurations.

A surgical instrument 21000 is illustrated in FIGS. 132-134 and is similar to the surgical instruments 11000, 17000, 18000, 19000, and 20000 in many respects, most of which will not be repeated herein for the sake of brevity. The surgical instrument 21000 comprises a shaft including a closure member 21110, an end effector 11500 rotatably mounted to the shaft about an articulation joint 11200, and an articulation system including an articulation actuator 21130 configured to articulate the end effector 11500 relative to the shaft. The surgical instrument 21000 further comprises an articulation lock system comprising an articulation lock gear 21400 rotatably mounted to a frame of the shaft about a fixed axis. The articulation lock gear 21400 comprises an annular array of teeth 21406 which is meshingly engaged with a longitudinal array of teeth 21316 defined on the articulation actuator 21310. As a result, referring generally to FIG. 132, the articulation lock gear 21400 rotates in response to the proximal and/or distal longitudinal movement of the articulation actuator 21310 until, as described in greater detail below, the articulation lock gear 21400 is locked in position by the closure member 21110 (FIG. 134).

Further to the above, the articulation lock system of the surgical instrument 21000 further comprises a movable lock element 21405 which is slidably mounted to the shaft frame. More specifically, referring primarily to FIG. 132, the lock element 21405 comprises a guide projection 21402 extending therefrom which extends into a lateral elongate slot 21403 defined in the shaft frame which is configured to permit the lock element 21405 to slide laterally toward and/or away from the articulation driver 21310. Moreover, referring primarily to FIG. 133, the lock element 21405 slides laterally within an aperture defined in the articulation lock gear 21400 between an unlocked position (FIG. 132) and a locked position (FIG. 134). The lock element 21405 comprises an annular array of lock teeth 21407 and the articulation lock gear 21400 comprises an annular array of lock teeth 21408 defined around the inner aperture thereof and, when the lock element 21405 is in its unlocked position (FIG. 132), the lock teeth 21407 of the lock element 21405 are not engaged with the lock teeth 21408 of the articulation lock gear 21400. When the lock element 21405 is in its locked position (FIG. 134), the lock teeth 21407 of the lock element 21405 are engaged with the lock teeth 21408 of the articulation lock gear 21400 such that the articulation lock gear 21400 cannot rotate and, as a result, the articulation actuator 21300 is prevented from being moved longitudinally to articulate the end effector 11500.

FIGS. 132-134 illustrate the distal progression of the closure member 21110 during a closure stroke. FIG. 132 illustrates the closure member 21110 in an unactuated, or open, position. In such a position, the closure member 21110 is not engaged with the lock element 21405. FIG. 133 illustrates the closure member 21110 in a partially closed position in which the closure member 21110 has at least partially closed the end effector 11500. In such a position, a cam surface 21115 of the closure member 21110 has engaged the lock element 21405. In at least one instance, the closure member 21110 moves distally approximately 0.050" from its open position (FIG. 132) to its partially closed position (PCP) (FIG. 133). FIG. 134 illustrates the closure member 21110 in a fully closed position (FCP) in which the closure member 21110 has completely closed the end effector 11500. In such a position, the cam surface 21115 has moved by the lock element 21405 and the lock element 21405 has been displaced by the full thickness of the closure member 21110.

In view of the above, a surgical instrument can include an articulation lock system configured to prevent the end effector of the surgical instrument from being articulated and/or unintentionally back-driven by a load, or torque, applied to the end effector. At least a portion of the articulation lock system can be moved into engagement with an articulation drive system of the surgical instrument to prevent the articulation of the end effector. In at least one instance, an articulation lock can be integral to the articulation drive system, as described in greater detail below.

Referring to FIGS. 135-137, a surgical instrument 22000 comprises a shaft and an articulation drive system 22300 which is configured to articulate an end effector, such as an end effector 11500, for example, of the surgical instrument 22000 relative to the shaft. The articulation drive system 22300 comprises an articulation driver 22310 and a pinion gear 22320. The articulation driver 22310 comprises a longitudinal rack of teeth 22316 defined thereon which is operably meshed with teeth 22326 of the pinion gear 22320. When the articulation driver 22310 is translated distally, the pinion gear 22320 is rotated in a first direction. Correspondingly, the pinion gear 22320 is rotated in a second direction when the articulation driver 22310 is translated proximally. The pinion gear 22320 comprises a bevel gear 22330 fixedly mounted thereto such that the bevel gear 22330 rotates with the pinion gear 22320 about a common axis of rotation. The combined assembly of the pinion gear 22320 and the bevel gear 22330 is rotatably mounted in the shaft of the surgical instrument 22000.

Further to the above, teeth 22336 of the bevel gear 22330 are meshingly engaged with the teeth 22346 of a bevel gear 22340 which is rotatably mounted about a rotatable threaded articulation lead screw 22350. More specifically, the bevel gear 22340 comprises a nut portion which includes an at least partially threaded aperture which is threadably engaged with the articulation lead screw 22350. When the bevel gear 22340 is rotated in a first direction by the articulation driver 22310 via the bevel gear 22330, the bevel gear 22340 rotates the articulation lad screw 22350 in a first direction. Correspondingly, the bevel gear 22340 rotates the articulation lead screw 22350 in a second direction when the bevel gear 22340 is rotated in a second direction. Moreover, the end effector 11500 is rotated in a first direction when the articulation lead screw 22350 is rotated in its first direction and, correspondingly, in a second direction when the threaded articulation driver shaft 22350 is rotated in its second direction.

Further to the above, the pitch of the threads on the threaded articulation lead screw 22350 can be selected to prevent back-driving within the articulation drive system 22300. Stated another way, a steep pitch of the threads defined on the articulation lead screw 22350 would be able to resist a force and/or torque transmitted proximally from the end effector 11500 through the articulation drive system 22300 and, as a result, can prevent the end effector 11500 from being unintentionally articulated. As such, the thread pitch can serve as an articulation lock integral to the articulation drive system 22300. In at least one instance, the articulation lead screw comprises an ACME lead screw, for example.

Referring to FIGS. 138-142, a surgical instrument 23000 comprises a shaft and an articulation drive system 23300 which is configured to articulate an end effector, such as an end effector 11500, for example, of the surgical instrument 23000 relative to the shaft. The articulation drive system 23300 comprises an articulation driver 23310 and a pinion gear 23320. The articulation driver 23310 comprises a longitudinal rack of teeth 23316 defined thereon which is operably meshed with the teeth 23326 of the pinion gear 23320. When the articulation driver 23310 is translated distally, the pinion gear 23320 is rotated in a first direction. Correspondingly, the pinion gear 23320 is rotated in a second direction when the articulation driver 23310 is translated proximally. The pinion gear 23320 comprises a worm gear 23330 fixedly mounted thereto such that the worm gear 23330 rotates with the pinion gear 23320 about a common axis of rotation. The combined assembly of the pinion gear 23320 and the worm gear 23330 is rotatably mounted in the shaft of the surgical instrument 23000.

Further to the above, teeth 23336 of the worm gear 23330 are meshingly engaged with the teeth 23346 of a worm 23340 which is rotatably mounted to the shaft frame. The worm 23340 comprises a pinion gear 23350 fixedly mounted thereto such that the pinion gear 23350 rotates with the worm 23340 about a common axis of rotation. The pinion gear 23350 is operably engaged with a translatable articulation output driver 23360. More specifically, the pinion gear 23350 comprises teeth 23356 which are meshingly engaged with a rack of teeth 23366 defined on the output driver 23360. When the worm 23340 is rotated in a first direction by the articulation driver 23310 via the worm gear 23330, the pinion gear 23350 drives the output driver 23360 distally. Correspondingly, the worm 23340 and the pinion gear 23350 drive the output driver 23360 proximally when the worm 23340 is rotated in a second direction by the worm gear 23330. Moreover, the end effector 11500 is rotated in a first direction when the output driver 23350 is driven distally by the articulation drive system 23330 and in a second direction when the output driver 23350 is driven proximally by the articulation drive system 23330.

Further to the above, the pitch of the threads on the worm 23340 can be selected to prevent back-driving within the articulation drive system 23300. Stated another way, a steep pitch of the threads defined on the worm 23340, for instance, would be able to resist a force and/or torque transmitted proximally from the end effector 11500 through the articulation drive system 23300 and can prevent the end effector 11500 from being unintentionally articulated. As such, the thread pitch can serve as an articulation lock integral to the articulation drive system 23300.

A surgical instrument 12000, illustrated in FIGS. 95-97B, is similar to the surgical instrument 11000 in several respects, many of which will not be repeated herein in the interest of brevity. In addition to a shaft 11100, an end effector 11500, and an articulation joint 11200, the surgical instrument 12000 further comprises a staple firing system 12900, for example, including a firing bar 12910 extending through the articulation joint 11200. In use, the firing bar 12910 is translatable distally to perform a staple firing stroke and retractable proximally after at least a portion of the staple firing stroke has been completed. The firing bar 12910 extends through a channel, or slot, 11190 defined in the frame 11180 of the shaft 11100 which is configured to closely receive and/or guide the firing bar 12910 as the firing bar 12910 moves relative to the shaft 11100. Similarly, the end effector 11500 comprises a channel, or slot, 11590 defined in the frame 11580 of the end effector 11500 which is also configured to closely receive and/or guide the firing bar 12910 as the firing bar 12910 moves relative to the end effector 11500

Figure 97A:
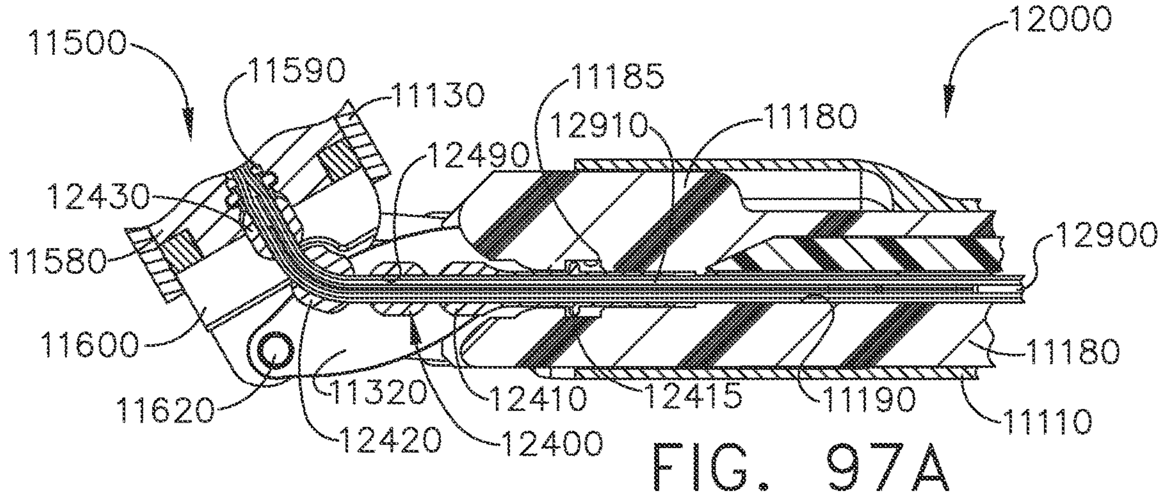
FIG. 97 is a cross-sectional view of the end effector of FIG. 95 illustrated in an unarticulated configuration.
Figure 97:
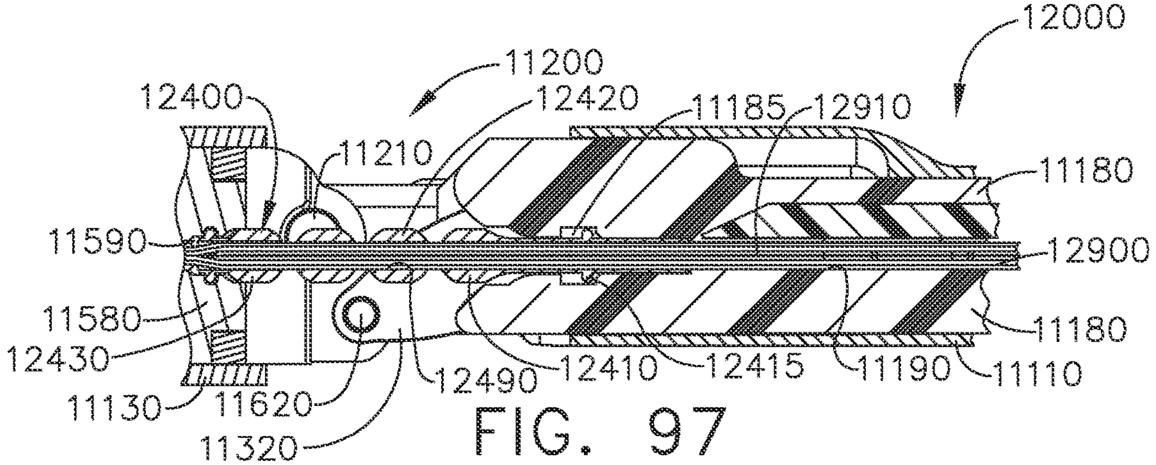
Figure 97B:
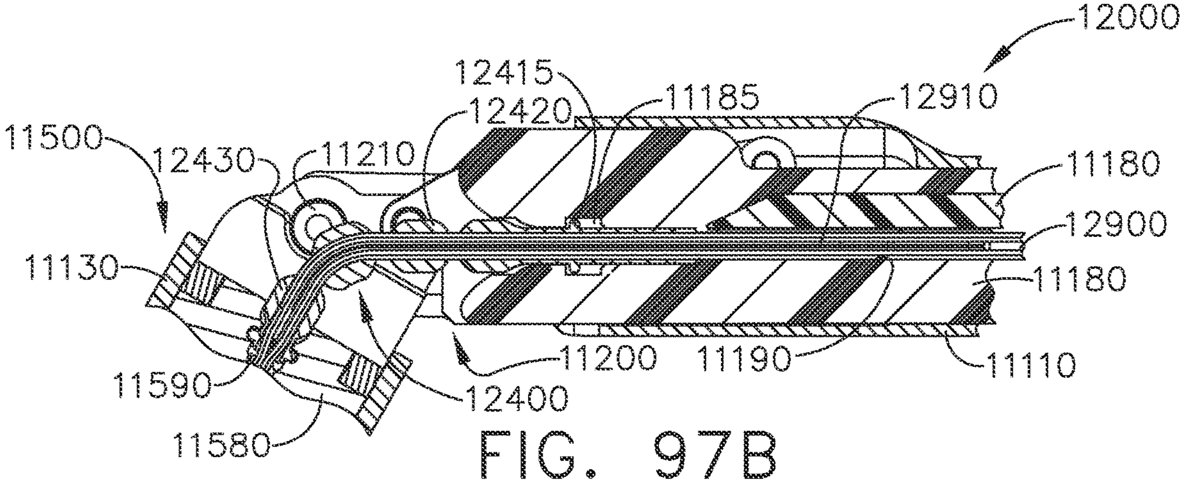
Figure 98:
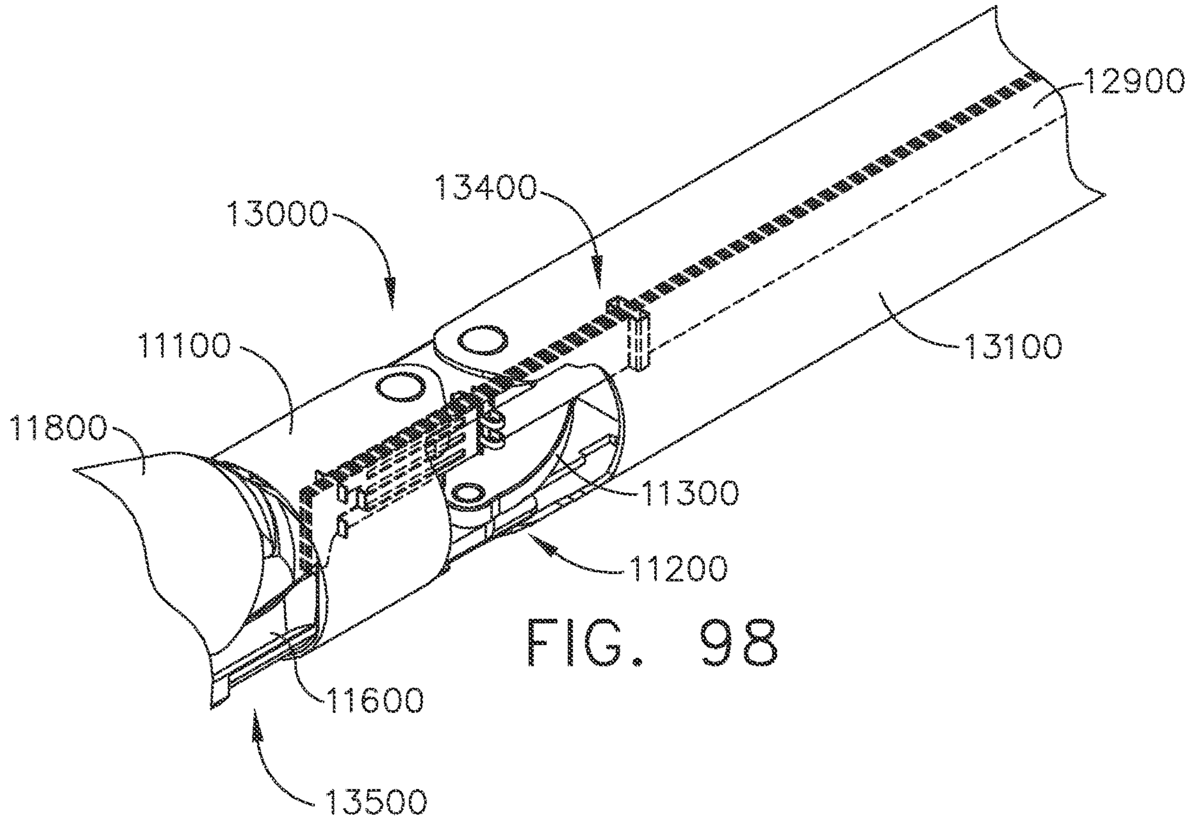
Figure 99:
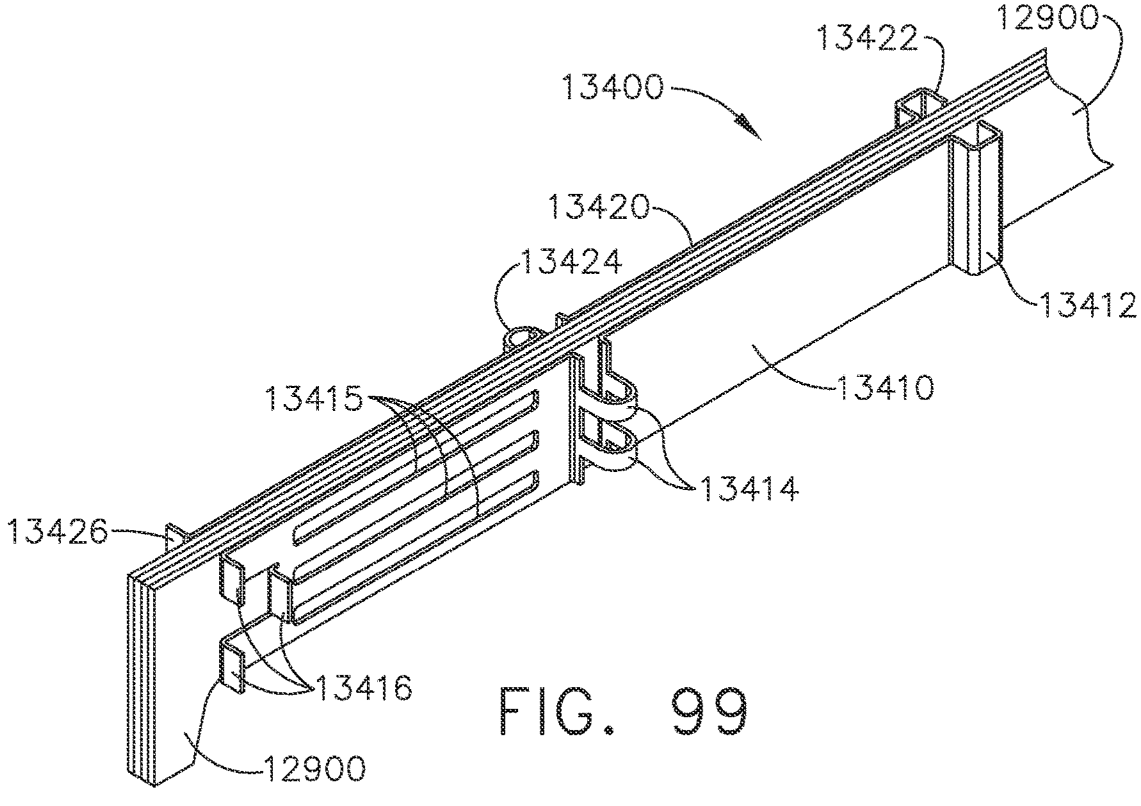
Figure 100:
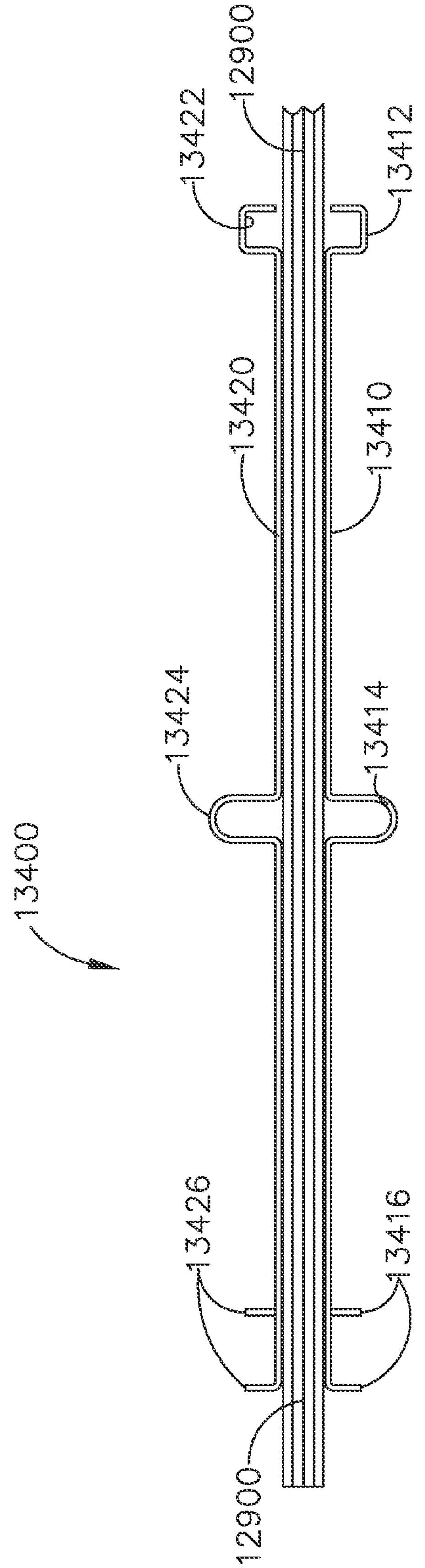
Figure 101:
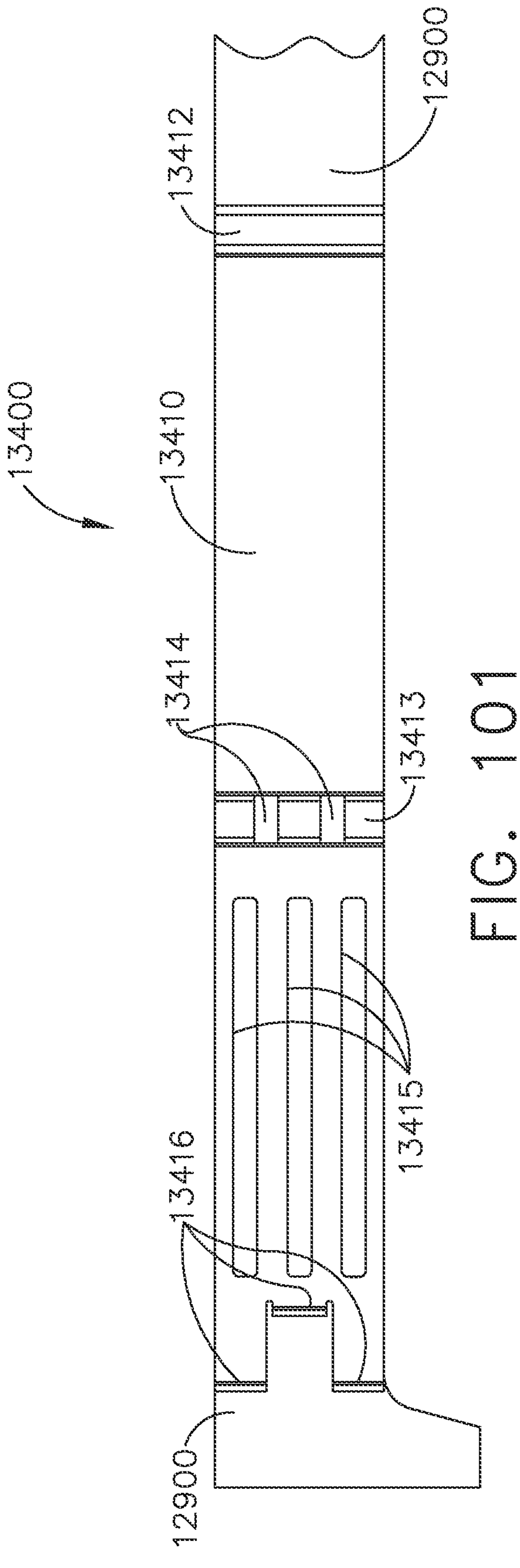

Further to the above, the channels 11190 and 11590 do not extend into the articulation joint 11200 and, without more, the firing bar 12910 may be unsupported within the articulation joint 11200. When the end effector 11500 is in an unarticulated configuration (FIG. 97), the firing bar 12910 is unlikely to buckle within the articulation joint 11120 during the staple firing stroke—however, the likelihood of the firing bar 12910 buckling laterally during the staple firing stroke increases when the end effector 11500 is in an articulated configuration (FIGS. 97A and 97B). To reduce the possibility of such buckling, the surgical instrument 12000 further comprises a firing bar support 12400 configured to support the firing bar 12910. The firing bar support 12400 comprises a proximal portion 12410 connected to the shaft frame 11180, a distal portion 12430 connected to the end effector frame 11580, and an intermediate portion 12420 extending between the proximal portion 12410 and the distal portion 12430. The portions 12410, 12420, and 12430 of the firing bar support 12400 are integrally formed; however, other embodiments are envisioned in which the portions 12410, 12420, and 12430 are assembled to one another and/or comprise separate components.

Further to the above, the distal portion 12430 of the firing bar support 12400 is fixedly mounted to the end effector frame 11580 and does not move, or at least substantially move, relative to the end effector frame 11580. The intermediate portion 12420 of the firing bar support 12400 comprises one or more portions having a reduced cross-section which, among other things, allows the firing bar support 12400 to flex within the articulation joint 11200 when the end effector 11500 is articulated. The proximal portion 12410 of the firing bar support 12400 is slideably mounted to the shaft frame 11180 such that the firing bar support 12400 can translate relative to the shaft frame 11180 when the end effector 11500 is articulated. That said, the proximal portion 12410 of the firing bar support 12400 comprises a proximal head 12415 that is slideable within a chamber, or cavity, 11185 defined within the shaft frame 11180 which can limit the travel of the firing bar support 12400. Embodiments are envisioned, however, without such a travel constraint. In any event, the proximal portion 12410, intermediate portion 12420, and distal portion 12430 of the firing bar support 12400 co-operatively define a channel, or slot, 12490 which is configured to support the firing bar 12910—especially within the articulation joint 11200—and reduce the possibility of the firing bar 12910 buckling during the staple firing stroke, for instance.

In various instances, the firing bar 12910 is comprised of a plurality of parallel, or at least substantially parallel, layers. The layers are affixed to a distal cutting member and can partially translate or slide longitudinally relative to one another—especially within the articulation joint 11200. Each such layer is configured to transmit a load in the same direction, i.e., proximally or distally, even though such layers can move, or slide, relative to one another. Further to the above, such layers may splay laterally relative to one another—especially within the articulation joint 11200—when the end effector 11500 has been articulated. The intermediate portion 12420 of the firing bar support 12400 comprises a plurality of connected control elements which can at least reduce, if not prevent, the relative lateral splay of the firing bar layers. Alternatively, as mentioned above, one or more of the control elements can be unconnected to one another.

In addition to or in lieu of the firing bar support 12400, the surgical instrument 12000 comprises one or more dividers which separate and control the layers of the firing bar 12910. Referring to FIGS. 97-97B, the shaft 11110 comprises a divider 12920 positioned within the layers of the firing bar 12910. Two layers of the firing bar 12910 are positioned on one side of the divider 12920 while two layers are positioned on the other side of the divider 12920, although any suitable arrangement can be used. The divider 12920 prevents half of the layers of the firing bar 12910 from splaying outwardly when the end effector 11500 is articulated. Stated another way, the divider 12920 prevents the two right-most firing bar layers from splaying to the left when the end effector 11500 is articulated to the right (FIG. 97A) and, similarly, the divider 12920 prevents the two left-most firing bar layers from splaying to the right when the end effector 11500 is articulated to the left (FIG. 97B). The divider 12920 extends through the articulation joint 11200 and the firing bar support 12400 and into the end effector 11500 and can bend when the end effector 11500 is articulated. Accordingly, in such instances, the divider 12920 is flexible. The divider 12920 is mounted to the frame 11180 of the shaft 11110 and does not move relative to the frame 11180; however, embodiments are envisioned in which the divider 12920 is not mounted to the frame 11180 and can float within the firing bar layers.

Figure 102A:
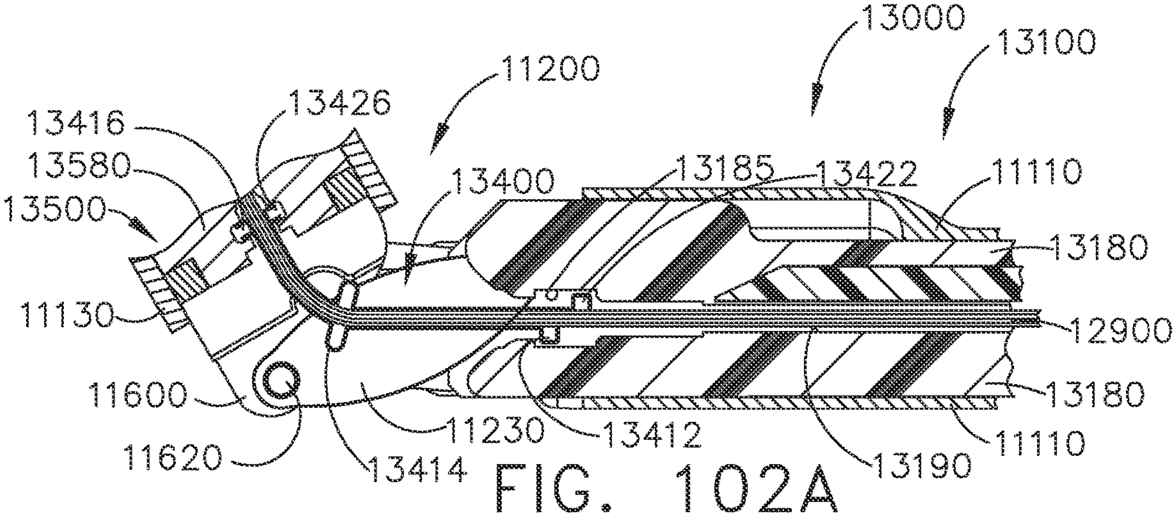
Figure 102:
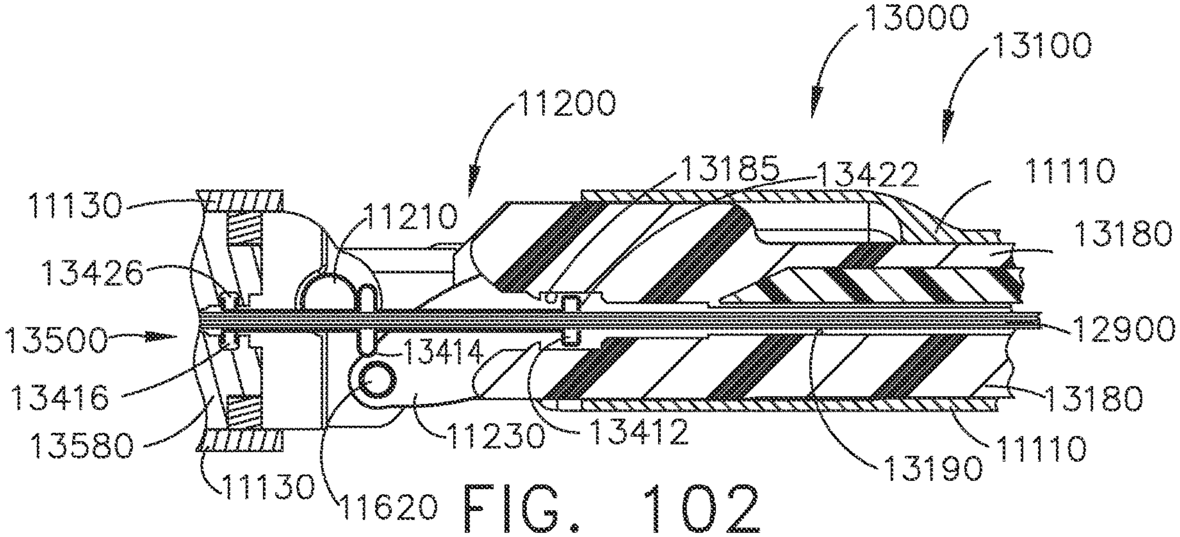
Figure 102B:
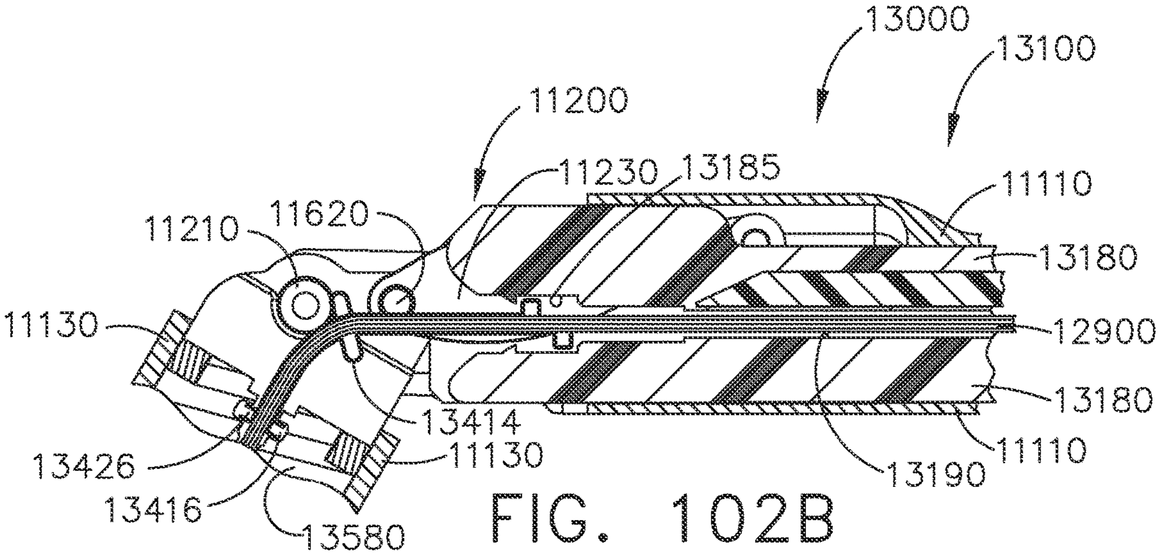

A surgical instrument 13000, illustrated in FIGS. 98-102B, is similar to the surgical instruments 11000 and 12000 in several respects, many of which will not be repeated herein in the interest of brevity. In addition to a shaft 13100, an end effector 13500, and an articulation joint 11200, the surgical instrument 13000 further comprises a staple firing system 12900, for example, including a firing bar 12910 extending through the articulation joint 11200. In use, the firing bar 12910 is translatable distally to perform a staple firing stroke and retractable proximally after at least a portion of the staple firing stroke has been completed. Referring primarily to FIGS. 102-102B, the firing bar 12910 extends through a channel, or slot, 13190 defined in the frame 13180 of the shaft 13100 which is configured to closely receive and/or guide the firing bar 12190 as the firing bar 12910 moves relative to the shaft 11100. Similarly, the end effector 13500 comprises a channel, or slot, defined in the frame 13580 of the end effector 13500 which is also configured to closely receive and/or guide the firing bar 12190 as the firing bar 12910 moves relative to the end effector 13500

When the end effector 13500 is in an unarticulated configuration (FIG. 102), further to the above, the firing bar 12910 is unlikely to buckle within the articulation joint 11120 during the staple firing stroke—however, the likelihood of the firing bar 12910 buckling laterally during the staple firing stroke increases when the end effector 13500 is in an articulated configuration (FIGS. 102A and 102B). To reduce the possibility of such buckling, the surgical instrument 13000 further comprises a firing bar support 13400 configured to support the firing bar 12190. The firing bar support 13400 comprises a first lateral plate 13410 and a second lateral plate 13420. The lateral plates 13410 and 13420 are positioned on opposite sides of the firing bar 12910. Each lateral plate 13410, 13420 comprises a proximal portion connected to the shaft frame 13180, a distal portion connected to the end effector frame 13580, and an intermediate portion extending between the proximal portion and the distal portion. The portions of each plate 13410, 13420 are integrally formed; however, other embodiments are envisioned in which the portions are assembled to one another and/or comprise separate components.

Further to the above, the first lateral plate 13410 comprises a distal portion 13416 which is fixedly mounted to the end effector frame 13580 and does not move, or at least substantially move, relative to the end effector frame 13580. Similarly, the second lateral plate 13420 comprises a distal portion 13426 which is fixedly mounted to the end effector frame 13580 and does not move, or at least substantially move, relative to the end effector frame 13580. The first lateral plate 13410 comprises a proximal portion 13412 which is slideably mounted to the shaft frame 13180 such that the first lateral plate 13410 can translate relative to the shaft frame 13180 when the end effector 13500 is articulated. The proximal portion 13412 comprises a head that is slideable within a chamber, or cavity, 13185 defined within the shaft frame 13180 which can limit the travel of the firing bar support 13400. Similarly, the second lateral plate 13420 comprises a proximal portion 13422 which is slideably mounted to the shaft frame 13180 such that the firing bar support 13400 can translate relative to the shaft frame 13180 when the end effector 13500 is articulated. The proximal portion 13422 comprises a head that is slideable within the chamber 13185 defined within the shaft frame 13180 which can also limit the travel of the firing bar support 13400.

The first lateral plate 13410 comprises a flexible portion 13414 positioned in the articulation joint 11200 which permits the distal portion 13416 of the first lateral plate 13410 to flex relative to the proximal portion 13412 and accommodate the articulation of the end effector 13500. The flexible portion 13414 extends laterally from the first lateral plate 13410 and comprises a hinge including gaps 13413 defined therein which permit rotation within the first lateral plate 13410. In addition to or in lieu of the above, the first lateral plate 13410 comprises longitudinal openings 13415 defined therein which permit the first lateral plate 13410 to flex within the end effector 13500 and accommodate the articulation of the end effector 13500. The first lateral plate 13410 can comprise any suitable number and configuration of openings and/or recesses defined therein at any suitable location which are configured to permit the first lateral plate 13410 to flex during the articulation of the end effector 13500. Similarly, the second lateral plate 13412 comprises a flexible portion 13424 positioned in the articulation joint 11200 which permits the distal portion 13426 of the second lateral plate 13420 to flex relative to the proximal portion 13422 and accommodate the articulation of the end effector 13500. The flexible portion 13424 extends laterally from the first lateral plate 13420 and comprises a hinge including gaps defined therein which permit rotation within the second lateral plate 13420. In addition to or in lieu of the above, the second lateral plate 13420 comprises longitudinal openings defined therein which permit the second lateral plate 13420 to flex within the end effector 13500 and accommodate the articulation of the end effector 13500. The second lateral plate 13420 can comprise any suitable number and configuration of openings and/or recesses defined therein at any suitable location which are configured to permit the second lateral plate 13420 to flex during the articulation of the end effector 13500.

Further to the above, the lateral plates 13410 and 13420 are flexible and can resiliently return to their unflexed configurations when the end effector 13500 is returned to its unarticulated configuration. In various instances, the lateral plates 13410 and 13420 comprise springs which resiliently bias the end effector 13500 into its unarticulated configuration.

A firing member 24900 is illustrated in FIGS. 146 and 147 and can be used with any of the surgical stapling instruments disclosed herein. The firing member 24900 comprises a firing bar 24910 which, similar to the above, comprises a plurality of layers. More specifically, the firing bar 24910 comprises two exterior layers 24911 and two interior layers 24912. The firing member 24900 further comprises a distal cutting member 24920 which includes a tissue cutting edge 24926. The distal cutting member 24920 further comprises a first cam 24922 configured to engage a first jaw of an end effector and a second cam 24924 configured to engage a second jaw of the end effector. That said, embodiments are envisioned in which the distal cutting member 24920 is configured to only engage one jaw of an end effector or, alternatively, neither jaw of an end effector.

The layers 24911 and 24912 of the firing bar 24910 are welded to the distal cutting member 24920 at welds 24930. As illustrated in FIG. 147, a first weld 24930 is present on a first side of the firing member 24900 and a second weld 24930 is present on a second side of the firing member 24900. The first weld 24930 penetrates a first exterior layer 24911 and the adjacent interior layer 24912. In various instances, the first weld 24930 penetrates entirely through the adjacent interior layer 24912 and/or also penetrates into the other interior layer 24912. The second weld 24930 penetrates a second exterior layer 24911 and the adjacent interior layer 24912. In various instances, the second weld 24930 penetrates entirely through the adjacent interior layer 24912 and/or also penetrates into the other interior layer 24912.

Referring primarily to FIG. 146, each weld 24930 of the firing member 24900 comprises a weld line which is configured to securely hold the firing bar 24910 to the cutting member 24920 and, at the same time, provide a flexible connection there between. Each weld 24930 comprises a butt weld 24931 connecting the cutting member 24920 to the distal ends of the plates 24911 and 24912 and is placed in tension and/or compression when a longitudinal firing force is transmitted through the firing member 24900. The butt weld is orthogonal to, or at least substantially orthogonal to, a longitudinal firing axis (FA) of the firing member 24900. The butt weld 24931 can comprise any suitable configuration, such as a square, closed square, single-bevel, double-bevel, single-J, double-J, single-V, double-V, single-U, double-U, flange, flare, and/or tee configuration, for example.

Further to the above, each weld 24930 further comprises a distal hook weld portion 24932 and a proximal hook weld portion 24933. Each hook weld portion 24932 and 24933 comprises a longitudinal portion which is aligned with, or is parallel to, the longitudinal firing axis (FA) of the firing member 24900 and is placed in shear when a longitudinal firing force is transmitted through the firing member 24900. In addition, each hook weld portion 24932 and 24933 comprises a butt portion which is orthogonal, or at least substantially orthogonal, to the longitudinal firing axis (FA) and is placed in tension and/or compression when a longitudinal firing force is transmitted through the firing member 24900. Notably, each set of hook weld portions 24932 and 24933 comprises an interlocking connection between the firing bar 24910 and the cutting member 24920 which can transmit a flow of stress there between without failing and/or yielding unsuitably.

Each weld 24930 is generally L-shaped, for example; however, the welds 24930 can comprise any suitable configuration.

Although the surgical instruments 10000, 11000, 12000, 13000, 14000, 15000, 16000, 17000, 18000, 19000, 20000, 21000, 22000, and 23000 are surgical staplers, their designs can be readily adapted to other surgical instruments having articulatable end effectors, among others. Such other surgical instruments can include, for example, clip appliers, fastener appliers, and/or surgical instruments capable of delivering electrical and/or vibrational energy to tissue.

FIG. 149 depicts a surgical staple cartridge 25100 comprising an elongate nose 25150 located at a distal end thereof, generally denoted as 25102. The elongate nose 25150 has a base 25152 that is defined by a first length 25154 extending a distance between the end of the staple line 25056 and a distal tip 25142 of the staple cartridge 25100. The distal tip 25142 is formed at an angle σ from the base 25152 of the staple cartridge 25100. The distal tip 25142 on the staple cartridge 25100 is pointed and configured to serve as a parking area for a wedge sled, not shown, of the firing system upon the completion of a staple firing stroke.

In an effort to shorten the overall length of the staple cartridge without sacrificing length of stapled tissue, the surgical staple cartridge 25200 depicted in FIG. 148 comprises a cartridge body 25210 including a shortened nose 25250 located at a distal end thereof, generally denoted as 25202. The shortened nose 25250 has a base 25252 that is defined by a second length 25254 extending a distance between the end of the staple line 25056 and a blunted distal tip 25242 of the staple cartridge 25200. The second length 25254 of the shortened nose 25250 is minimized by blunting the parking area for the wedge sled 25270 (See FIG. 152). While the blunt, shortened nose 25250 of the staple cartridge 25200 in FIG. 148 still provides a parking area for the wedge sled, additional accommodations for storage may have to be made, as will be discussed below. The blunted distal tip 25242 is formed at an angle γ from the base 25252 of the staple cartridge 25200.

Upon comparing the staple cartridges 25200 and 25100 depicted in FIGS. 148 and 149, respectively, the reader should recognize that the second length 25254 is shorter than the first length 25154. As a result, the length of the staple cartridge 25200 beyond the end of the staple line 25056 is minimized to allow for improved spatial access within a surgical site, among other things. The shortened nose 25250 also prevents the blunted distal tip 25242 from puncturing a seal on a trocar system, as discussed further below. Furthermore, one will recognize the angle γ of the blunted distal tip 25242 of the staple cartridge 25200 with respect to the base 25252 is greater than the angle σ of the pointed distal tip 25142 of the staple cartridge 25100 with respect to the base 25152. For example, the blunted distal tip 25242 can extend at an angle of approximately 45-50 degrees with respect to the base 25252 of the staple cartridge 25200, while the pointed distal tip 25142 can extend at an angle of approximately 30 degrees with respect to the base 25152 of the staple cartridge 25100. The steeper angle of the blunted distal tip 25242 provides increased stability throughout distal regions of the structure of the staple cartridge 25200.

FIG. 152 is a plan view of the staple cartridge 25200. The cartridge body 25210 of the staple cartridge 25200 comprises an elongate slot 25230 that extends from a proximal end 25204 of the staple cartridge 25200 toward the distal, shortened nose 25250. A plurality of staple cavities 25220 are formed within the cartridge body 25210. Staple cavities 25220 extend between the proximal end 25204 and the distal end 25202 of the staple cartridge 25200. The staple cavities 25220 are arranged in six laterally-spaced longitudinal rows 25221, 25222, 25223, 25224, 25225, 25226, with three rows on each side of the elongate slot 25230. Removably positioned within the staple cavities 25220 are staples 25260.

FIG. 150 illustrates one embodiment of a triple staple driver 25240 within the staple cartridge 25200 for supporting and driving three staples 25260. The staple driver 25240 comprises a first driver portion 25342, a second driver portion 25344, and a third driver portion 25346. A central base member 25348 connects the first driver portion 25342 and the third driver portion 25346 to the second driver portion 25344. The first driver portion 25342 is positioned at least partially distal to the second driver portion 25344. Additionally, the third driver portion 25346 is positioned at least partially distal to the second driver portion 25344. A plurality of first staple drivers 25240 are slidably mounted within corresponding staple cavities 25220 from the three longitudinal rows 25221, 25222, 25223 on one side of the elongate slot 25230. In other words, each first staple driver 25240 is configured to support three staples 25260: a staple 25260 stored within a staple cavity 25220 in the first longitudinal row 25221; a staple 25260 stored within a staple cavity 25220 in the second longitudinal row 25222; and a staple 25260 stored within a staple cavity 25220 in the third longitudinal row 25223. Due to the distal position of the first driver portion 25342 and the third driver portion 25346 relative to the second driver portion 25344, the staples 25260 are fired in a reverse arrow configuration. As shown in FIG. 152, the last staples 25260 in the first longitudinal row 25221 and the third longitudinal row 25223 are closer to the shortened nose 25250 of the staple cartridge 25200 than the last staple 25260 in the second longitudinal row 25222.

On the other side of the elongate slot 25230, a plurality of second staple drivers are mounted within corresponding staple cavities 25220 in the three longitudinal rows 25224, 25225, 25226. Similar to the staple driver 25240, the second staple drivers each comprise a first driver portion 25342, a second driver portion 25344, and a third driver portion 25346. A central base member 25348 connects the first driver portion 25342 and the third driver portion 25346 to the second driver portion 25344. The first driver portion 25342 is positioned at least partially distal to the second driver portion 25344. Additionally, the third driver portion 25346 is positioned at least partially distal to the second driver portion 25344. As the staple driver 25240 above, each second staple driver is configured to support three staples 25260: a staple 25260 stored within a staple cavity 25220 in the fourth longitudinal row 25224, a staple 25260 stored within a staple cavity 25220 in the fifth longitudinal row 25225, and a staple 25260 stored within a staple cavity 25220 in the sixth longitudinal row 25226. Due to the distal position of the first driver portion 25342 and the third driver portion 25346 relative to the second driver portion 25344, the staples 25260 are fired in a reverse arrow configuration. As shown in FIG. 152, the last staples 25260 in the fourth longitudinal row 25224 and the sixth longitudinal row 25226 are closer to the shortened nose 25250 of the staple cartridge 25200 than the last staple 25260 in the fifth longitudinal row 25225.

The first driver portion 25342 of the staple driver 25240 has a first forward support column 25352 and a first rearward support column 25354 protruding upward from a first driver portion base. The first forward support column 25352 and the first rearward support column 25354 are spaced from each other and collectively form a first staple cradle for supporting a staple 25260 in an upright position (i.e., the prongs of the staple facing the anvil). Similarly, the second driver portion 25344 has a second forward support column 25362 and a second rearward support column 25364 protruding upward from a second driver portion base. The second forward support column 25362 and the second rearward support column 25364 are spaced from each other and collectively form a second staple cradle for supporting a staple 25260 in an upright position (i.e., the prongs of the staple facing the anvil). The third driver portion 25346 has a third forward support column 25372 and a third rearward support column 25374 protruding upward from a third driver portion base. The third forward support column 25372 and the third rearward support column 25374 are spaced from each other and collectively form a third staple cradle for supporting a staple 25260 in an upright position (i.e., the prongs of the staple facing the anvil).

The center of mass of the first and third driver portions 25342, 25346 is represented by the dashed line D-D. Similarly, the dashed line P-P represents the center of mass of the second driver portion 25344. The combined center of mass of the triple staple driver 25240 is represented in FIGS. 150 and 151 as dashed line C-C. As such, staple driver 25240 is less likely to roll forward. Notably, C-C is closer to D-D than P-P which makes the staple driver 25240 very stable.

As discussed above, the central base member 25348 of the staple driver 25240, depicted in FIG. 151, attaches the first driver portion 25342 and the third driver portion 25346 to the second driver portion 25344. The central base member 25348 extends laterally between the proximal ends of the first and third rearward support columns 25354, 25374 on the first and third driver portions 25342, 25346, respectively, and the proximal end of the second forward support column 25362 on the second driver portion 25344. As can be seen in FIG. 153, the central base member 25348 has an angled rearwardly facing edge 25349 adapted to be engaged by a wedge sled 25270, as will be discussed in further detail below. Due to the extension of the central base member 25348 between all three driver portions 25342, 25344, 25346, the midpoint of the rearwardly facing edge 25349 may be bifurcated into a portion which is closer to the first portion 25342 and a portion which is closer to the third portion 25346. Such an arrangement can balance moments created during the firing and formation of the staples 25260 stored within the staple cavities 25220.

Referring primarily to FIG. 152, each staple cavity 25220 defined in the cartridge body 25210 of the staple cartridge 25200 comprises a proximal wall 25264 and a distal wall 25262. The reverse arrow orientation formed by the arrangement of the first, second, and third driver portions 25342, 25344, 25346 of the triple staple driver 25240 discussed above, reduces forward and/or lateral roll of the staple driver 25240 during a staple firing stroke. In various instances, the distal end of the first forward support column 25352 and the distal end of the third forward support column 25372 are pushed into the distal walls 25262 of their respective staple cavities 25220, which stabilize the driver 25240. Thus, when the sled 25270 (FIG. 152) lifts the staple driver 25240 upwardly during the staple firing stroke, two distal walls 25262 of the staple cavities 25220 provide an opposing force against the forward support columns 25352, 25372, preventing any unwanted movement or rolling of the staple driver 25240.

As illustrated in FIGS. 150-153, the elongate slot 25230 of the staple cartridge 25200 is configured to receive a portion of a firing assembly 25280. The firing assembly 25280 is configured to push the sled 25270 distally to eject the staples 25260 stored within the staple cavities 25220 and deform the staples 25260 against an anvil positioned opposite the staple cartridge 25200. More specifically, a coupling member 25282 pushes the wedge sled 25270 of the staple cartridge 25200 distally. The wedge sled 25270 has four rails, two inner rails 25272 and two outer rails 25274 which are connected to each other by a central member 25276. One inner rail 25272 and one outer rail 25274 are positioned on one side of the elongate slot 25230, while the other inner rail 25272 and the other outer rail 26274 are positioned on the opposite side of the elongate slot 25230. When driven distally, the inner rails 25272 pass through inner channels 25212 defined within the cartridge body 25210 and engage the rearwardly facing edge 25349 of the drivers 25240 supporting the staples 25260 to cause the firing of the staples toward the anvil. Likewise, the outer rails 25274 pass through outer channels 25214 defined within the cartridge body 25210 and engage portions of the drivers 25240 supporting the staples 25260 to push the staples toward the anvil. Distal movement of the wedge sled 25270 causes the rails 25272, 25274 to make contact with the rearwardly facing edges 25349 of the staple drivers 25240, pushing drivers 25240 upwards to eject the staples 25260 from the staple cartridge 25200 into tissue captured between the staple cartridge 25200 and an opposing anvil. The coupling member 25282 also comprises a cutting edge 25284 which incises the tissue as the coupling member 25282 is advanced distally to eject the staples 25260 from the cartridge body 25210.

Referring again to FIG. 150, the positioning of the first, second, and third driver portions 25342, 25344, 25346 of the staple driver 25240 between or adjacent an inner rail 25272 and an outer rail 25274 of the wedge sled 25270 provides increased lateral stability. Two rails, one inner rail 25272 and one outer rail 25274, straddle the staple driver 25240, providing increased support and stability of throughout a firing stroke. In addition to providing enhanced stability to the staple driver 25240, another benefit of having a staple driver 25240 spanning across two rails 25272, 25274 of a wedge sled 25270 is a reduced force required to perform a firing stroke. The required force is decreased as there is less deflection and loss within the system. Additionally, the additional drive surface provided by the rearwardly facing edge 25349 allows for the rails 25272, 25274 of the wedge sled 25270 to extend at a steeper angle from the base 25278 of the wedge sled 25270. The steeper angle of the wedge sled 25270 allows for an overall decrease in the length of the base 25278 of the wedge sled 25270, further contributing to the reduction in length of the shortened nose 25250 of the staple cartridge 25200. Upon the completion of the staple firing stroke, referring again to FIG. 152, the wedge sled 25270 of the firing assembly 25280 is parked within the shortened nose 25250 of the staple cartridge 25200.

FIG. 152 depicts the wedge sled 25270 of the firing assembly 25280 parked in the shortened nose 25250 upon the completion of the staple firing stroke. The shortened nose 25250 comprises a plurality of openings 25292, 25294 at the distal end of the shortened nose 25250 to receive the four rails 25272, 25274. The shortened nose 25250 further comprises an opening 25296 configured to receive the central sled member 25276 of the wedge sled 25270. Thus, portions of the rails 25272, 25274 and central sled member 25276 of the wedge sled 25270 are exposed at the distal end 25202 of the staple cartridge 25200. The openings 25292, 25294 are continuations of the channels 25212, 25214 within which the rails 25272, 25274 of the wedge sled 25270 slidably travel. Two inner openings 25292 are configured to receive the two inner rails 25272 of the wedge sled 25270, while two outer openings 25294 are configured to receive the two outer rails 25274 of the wedge sled 25270. A central opening 25296 in the center of the distal portion 25202 of the shortened nose 25250 is configured to receive the central member 25276 of the wedge sled 25270. The openings 25292, 25294, 25296 at the distal end 25202 of the shortened nose 25250 allow for the staple firing stroke to be completed and for the wedge sled 25270 to be parked in a shortened distal end.

Referring again to FIG. 152, the staple cartridge 25200 further includes projections 25262 extending around the proximal and distal ends of the staple cavities 25220. The projections 25262 in the first longitudinal row 25221 are shown to be singular, while the projections in the second and third longitudinal rows 25222, 25223 are shown to be connected. The projections 25262 are configured to provide additional support to the staples 25260 as they are fired upwardly out of their staple cavities 25220. Furthermore, the projections 25264 formed on the distalmost staple cavity 25220 are ramped to control the flow of tissue into the end effector. A more detailed discussion of the projections can be found in U.S. Patent Application Publication No. 2015/0297228, entitled FASTENER CARTRIDGES INCLUDING EXTENSIONS HAVING DIFFERENT CONFIGURATIONS, filed on Jun. 30, 2014, the entire disclosure of which is incorporated by reference.

FIG. 154 illustrates some of the advantages gained by using the shortened staple cartridge 25200 from FIG. 148 instead of the elongate staple cartridge 25100 from FIG. 149. Both staple cartridges are suitable for various surgical procedures, including, for example, Low Anterior Resection Surgery (LAR). LAR is a common treatment for colorectal cancer, for example. Such procedures require precise dissection and sealing of tissue deep within the pelvic cavity of a patient. As will be discussed in more detail below, the shortened length of the staple cartridge 25200, owing to the shortened nose 25250 in FIG. 148, among other things, allows the end effector of the surgical instrument to gain greater access to tissue within the pelvic cavity. The reader should understand that the staple cartridges described herein can be used in various surgical treatments and are not to be limited by the specific procedures discussed herein.

Further to the above, the short staple cartridge 25200 is part of a first end effector 25202 on a first surgical instrument 25201 which also includes an anvil 25203. The first surgical instrument 25201 further comprises a first shaft 25206 that is rotatably connected to the first end effector 25202. The first end effector 25202 is articulatable about an articulation joint 25208 positioned intermediate the first end effector 25202 and the first shaft 25206. The first end effector 25202 is capable of being articulated to an angle $\alpha$ with respect to the first shaft 25206. Similarly, the elongate staple cartridge 25100 is part of a second end effector 25102 on a second surgical instrument 25101 which also includes an anvil 25103. Also, the second surgical instrument 25101 further comprises a second shaft 25106 that is rotatably connected to the second end effector 25102. The second end effector 25102 is articulatable about an articulation joint 25108 positioned intermediate the second end effector 25102 and the second shaft 25106. The second end effector 25102 is capable of being articulated to an angle β with respect to the second shaft 25106.

Further to the above, in use, a clinician inserts the end effector 25202 through a cannula, or trocar, and into a patient when the end effector 25202 is in its unarticulated condition. Once through the trocar, the end effector 25202 can be articulated as illustrated in FIG. 154. At such point, the shaft 25206 can be moved to position the end effector 25202 in the pelvic cavity. Similar steps would be used to position the end effector 25102.

The first end effector 25202 is able to reach a distance $X_1$ from the pelvic floor within the pelvic cavity during a LAR procedure. The second end effector 25102 is able to reach a distance $X_2$ from the pelvic floor within the pelvic cavity during a LAR procedure. Distance $X_1$ is shorter than distance $X_2$, allowing the first surgical instrument 25201 to be placed deeper into the pelvic cavity than the second surgical instrument 25101, giving the surgeon the capability to, among other things, target, access, and remove a greater array of diseased tissue from the colon. Additionally, the articulation capabilities of the first surgical instrument 25201 allow deeper access to tissue within the surgical site while inflicting minimal trauma to surrounding tissue. The first end effector 25202 is able to be articulated to a greater degree than the second end effector 25102, as β is larger than α. For example, the first end effector 25202 may be articulated to an angle 115 degrees from the first shaft 25206, while the second end effector 25102 may only be articulated to an angle 135 degrees from the second shaft 25106.

As illustrated in FIG. 154, the staple cartridge 25100 and the anvil 25103 of the end effector 25102 have approximately the same length, but the staple cartridge 25100 is noticeably longer than the anvil 25103. Comparatively, the staple cartridge 25200 and the anvil 25203 of the end effector 25202 are substantially the same length, if not the same length. In any event, the difference in length between the staple cartridge 25200 and the anvil 25203 of the end effector 25202, if any, is much smaller than the end effector 25102.

An extreme difference between the distal end of a staple cartridge and a distal end of an anvil can cause damage to a trocar when the end effector is inserted there through. Referring to FIG. 155, an end effector 25810 comprises a distal end 25802, an anvil 25820, and a staple cartridge 25830. The staple cartridge 25830 has a blunt, shortened nose 25840 similar to the shortened nose 25250 on the staple cartridge 25200 in FIG. 148. As can be seen in FIGS. 155 and 156, the anvil 25820 has a protective tip 25822 thereon. The protective tip 25822 is sized and positioned on the anvil 25820 in a way that causes the anvil 25820 to be shorter in length than the staple cartridge 25830. Thus, the shortened nose 25840 of the staple cartridge 25830 extends distally relative to the anvil 25820. The protective tip 25822 may be integrally formed (molded, machined, etc.) on the distal end 25802 of the anvil 25820 or it may comprise a separate piece configured to receive a complementary portion of the anvil. A more extensive discussion of protective tips can be found U.S. Patent Application Publication No. 2008/0169328, entitled IMPROVED BUTTRESS MATERIAL FOR USE WITH A SURGICAL STAPLER, the entire disclosure of which is hereby incorporated by reference in its entirety.

As can be seen in FIGS. 155 and 156, the protective tip 25822 of the anvil 25820 has a first curved, or angled, outer surface 25824 and a second curved, or angled, outer surface 25826 configured to form a stubby distal end on the anvil 25820. The first angled outer surface 25824 extends downwardly from a top surface 25828 of the anvil 25820 at a first angle ϕ. The second angled outer surface 25826 extends downwardly from the first angled outer surface 25824 toward the staple cartridge 25830 at a second angle θ. The second angle θ is greater than the first angle ϕ. Various embodiments are envisions in which angle θ is approximately 90 degrees, for example. Other embodiments of the protective tip 25822 are envisioned having only one of either a first angled outer surface 25824 or a second angled outer surface 25826. The first angled outer surface 25824 serves to deflect a centering ring of a trocar seal assembly during the insertion of the end effector 25810 through the trocar. When the second angle θ gets farther from 90 degrees, and/or when the first and second curved outer surfaces 25824, 25826 are not continuous, the anvil 25820 might pierce through a trocar seal or can displace the centering ring of a trocar seal system, as will be discussed in greater detail below.

A protective tip can be attached to an anvil in any suitable manner. FIGS. 157-162 illustrate exemplary embodiments of separately formed protective tips 25922, 26022, and various methods for their attachment to an anvil. As depicted in FIGS. 157-159, a distal portion of an anvil 25920 comprises an attachment feature including attachment members 25927, 25929 which are configured to retainingly mate with complementary retention channels 25926, 25928 formed in the protective tip 25922. More specifically, a central retention channel 25928 is formed within the protective tip 25922 to receive a central attachment member 25929 of the anvil 25920. A pair of side retention channels 25296 is formed within the protective tip 25922 to receive a pair of corresponding side attachment members 25927 on the anvil 25920. FIG. 159 is a cross-sectional view of the anvil 25920 of FIG. 157 taken along the line 159-159 in FIG. 158 in a disassembled configuration showing the alignment of the retention channels 25926, 25928 with their respective attachment members 25927, 25929. An elongate slot 25994 extends longitudinally from the proximal end 25904 of the anvil 25920 toward the distal end 25902 of the anvil 25920. The elongate slot 25994 is configured to receive a portion of the firing assembly discussed herein.

In addition, or in the alternative, to the above, the protective tip 25922 may be secured to the anvil 25920 using rivets 25924. As shown in FIG. 159, a through-hole 25925 extends through the central retention channel 25928 of the protective tip 25922. A through-hole 25925 also extends through the central attachment member 25929 of the anvil 25920 so that when the protective tip 25922 is attached to the anvil 25920, the through-holes 25925 line up to facilitate the insertion of a rivet 25924 therein. FIG. 158 is a cross-sectional view of the anvil 25920 of FIG. 157 taken along line 158-158 in FIG. 157 in a disassembled configuration illustrating a rivet assembly for removably affixing the protective tip 25922 to the anvil 25920. In addition, or in the alternative, to the above, the protective tip 25922 may be affixed to the anvil 25920 by adhesives such as, for example, cyanoacrylates, light-curable acrylics, polyurethanes, silicones, epoxies, and/or ultra-violet curable adhesives such as HENKEL LOCTITE®. In any event, a combination of attachment members and retention channels may be provided on the anvil 25920 and the protective tip 25922. Still other forms of attachments and attachment arrangements may be used to affix the protective tip 25922 to the anvil 25920.

FIGS. 160-162 illustrate another embodiment of a tip attachment arrangement. A distal portion of an anvil 26020 comprises attachment members 26027 configured to retainingly mate with complementary retention channels 26026 defined in the protective tip 26022. In addition, a central retention channel 26028 defined within the protective tip 26022 is configured to receive a central attachment member 26029 of the anvil 26020. FIG. 161 is a cross-sectional view of the anvil 26020 of FIG. 160 taken along the line 161-161 in FIG. 160 in a disassembled configuration showing the alignment of the retention channels 26026, 26028 with their respective attachment members 26027, 26029. FIG. 162 is a cross-sectional view of the anvil 26020 of FIG. 160 taken along the line 162-162 in FIG. 160 in an assembled configuration. The protective tip 26022 is secured to the anvil 26020 using a compression fit. The central attachment member 26029 is press-fit into the central retention channel 26028, remaining in place due to the geometry of the central retention channel 26028. The central attachment member 26029 of the anvil 26020 in FIG. 161 has a trapezoidal shape that is mimicked by the central retention channel 26028. An elongate slot 26094 extends longitudinally from a proximal end 26004 of the anvil 26020 toward the distal end 26002 of the anvil 26020. The elongate slot 26094 is configured to receive a portion of the firing assembly discussed herein.

In addition, or in the alternative, to the above, the protective tip 26022 may be affixed to the anvil 26020 by adhesives such as, for example, cyanoacrylates, light-curable acrylics, polyurethanes, silicones, epoxies, and/or ultraviolet curable adhesives such as HENKEL LOCTITE®, for example. In various embodiments, a combination of attachment members and retention channels may be provided on the anvil 26020 and the protective tip 26022. Still other forms of attachments and attachment arrangements may be used to affix the protective tip 26022 to the anvil 26020. FIGS. 160-162 further illustrate means for assisting a user in attaching the protective tip 26022 to the anvil 26020. FIG. 160 illustrates the protective tip 26022 removably positioned within a temporary holder 26030. In order to releasably affix the protective tip 26022 to the anvil 26020, the user presses the temporary holder 26030 and the anvil 26020 together. The temporary holder 26030 may provide an additional sterilization barrier to the protective tip 26022 while the protective tip 26022 is affixed to the anvil 26020. Furthermore, the temporary holder 26030 provides the user with an object that is more substantial to hold onto while attaching the protective tip 26022 to the anvil 26020, as the protective tip 26022 may be small in size. It is envisioned that the temporary holder 26030 can be used across various embodiments of protective tips, including the other embodiments disclosed herein.

Various protective anvil tips have been described and depicted herein as being used in connection with a linear end effector. Those of ordinary skill in the art will readily appreciate, however, that the protective anvil tips described herein may be used in connection with a variety of different end effector configurations such as curved end effectors and other types of end effectors without departing from the spirit and scope of the present disclosure. Thus, the protective tip described above should not be limited solely to use in connection with linear end effectors and/or staplers.

FIGS. 163-169 illustrate an exemplary practical application of the various end effectors described herein when they are inserted through a trocar seal system prior to being introduced into a surgical site. The trocar seal system 27040 of FIGS. 163-169 comprises a housing 27042 configured to support a floating seal assembly 27050 and a central opening 27044 configured to receive a surgical instrument. The floating seal assembly 27050 comprises a first seal door 27052 and a second seal door 27054 that work together to prohibit gas from escaping from an insufflated cavity in a patient during a surgical procedure. The floating seal assembly 27050 further comprises a centering ring 27058 which is configured to guide a surgical instrument through the central opening 27044 of the trocar seal system 27040. The floating seal assembly 27050 is attached to the housing 27042 of the trocar seal system 27040 through an annular resilient member 27056.

FIG. 163 depicts an end effector 27000 comprising an anvil 27010 and a staple cartridge 27020. The staple cartridge 27020 comprises a blunt, shortened nose 27022, similar to the shortened nose 25250 depicted on the staple cartridge 25200 in FIG. 148. The distal end 27202 of the anvil 27010 is pointed and does not have a protective tip, such as that shown in FIG. 155. As can be seen in FIG. 163, the anvil 27010 is shorter in length than the staple cartridge 27020. In other words, the shortened nose 27022 of the staple cartridge 27020 extends longitudinally beyond the distal end 27002 of the anvil 27010. Prior to inserting the end effector 27000 through the trocar seal system 27040, the first seal door 27052 and the second seal door 27054 extend inwardly to prevent gas from escaping from the surgical site. FIG. 164 depicts the end effector 27000 of FIG. 163 partially inserted into the trocar seal system 27040. The shortened nose 27022 of the staple cartridge 27020 is the first component of the end effector 27000 to come into contact with the first and second seal doors 27052, 27054 of the trocar seal system 27040, tilting the floating seal assembly 27050 to one side. Due to its blunt shape, the shortened nose 27022 does not damage the second seal door 27054 despite exerting a force on it.

FIG. 165 depicts the end effector 27000 of FIGS. 163 and 164 when the end effector 27000 has been further introduced into the central opening 27044 of the trocar seal system 27040. After the initial contact of the shortened staple cartridge nose 27022 with the trocar seal system 27040, the pointed distal end 27002 of the anvil 27010 contacts the first seal door 27052 of the trocar seal system 27040. In various instances, the pointed distal end 27002 of the anvil 27010 can rupture the first seal door 27052 of the trocar seal system 27040, as the contact between the shortened nose 27022 and the second seal door 27054 has already shifted the position of the floating seal assembly 27050 laterally. As illustrated in FIG. 166, had the distal end 27002 of the anvil 27010 comprised a protective tip 27012 similar to the protective tip 25822 shown in FIG. 155, the risk of rupturing the first seal door 27052 would have been reduced. The risk of rupture decreases with the use of a protective tip 27012 on the anvil 27010, as the first seal door 27052 will smoothly stretch around the protective tip 27012. Moreover, the same length of the cartridge and the anvil reduces, or prevents, the pre-shifting of the floating seal assembly.

FIG. 167 depicts an end effector 27100 comprising an anvil 27110 and a staple cartridge 27120. The staple cartridge 27120 comprises a pointy, elongate nose 27122, similar to the elongate nose 25150 depicted on the staple cartridge 25100 in FIG. 149. The distal end 27102 of the anvil 27110 is pointed and does not have a protective tip, such as that shown in FIG. 155. The anvil 27110 is shorter in length than the staple cartridge 27120. In other words, the elongate nose 27122 of the staple cartridge 27120 extends longitudinally beyond the distal end 27102 of the anvil 27110. Prior to the insertion the end effector 27100 through the trocar seal system 27040, the first seal door 27052 and the second seal door 27054 of the trocar seal system 27040 extend inwardly to prevent gas from escaping the surgical site. FIG. 168 depicts the end effector 27100 of FIG. 167 when the end effector 27100 is initially inserted into the trocar seal system 27040. The elongate nose 27122 of the staple cartridge 27120 is the first component of the end effector 27100 to come into contact with the first and second seal doors 27052, 27054 of the trocar seal system 27040, tilting, or pre-shifting, the floating seal assembly 27050 to one side as discussed above.

FIG. 169 depicts the end effector 27100 of FIGS. 167 and 168 when the end effector 27100 has been further introduced into the central opening 27044 of the trocar seal system 27040. After the initial contact of the elongate nose 27122 of the staple cartridge 27120, the pointed distal end 27102 of the anvil 27110 contacts the first seal door 27052 of the trocar seal system 27040. In various instances, the pointed distal end 27102 of the anvil 27110 may rupture the first seal door 27052 of the trocar seal system 27040, as the contact between the elongate nose 27122 and the second seal door 27054 displaced the position of the floating seal assembly 27050.

As discussed herein, a first staple cartridge can comprise a first cartridge length and a second staple cartridge can comprise a second cartridge length which is different than the first cartridge length. In various instances, an end effector of a surgical stapling instrument can comprise a cartridge jaw configured to receive the first staple cartridge and, in the alternative, the second staple cartridge. Stated another way, the cartridge jaw is configured to receive the first staple cartridge and the second staple cartridge, but not at the same time. The first staple cartridge and the second staple cartridge each comprise a proximal end which is aligned with a proximal cartridge jaw datum when it is positioned in the cartridge jaw. When the first cartridge length is longer than the second cartridge length, for instance, the distal end of the first staple cartridge would be positioned further away from the proximal cartridge jaw datum than the distal end of the second staple cartridge. The reader should understand that the second cartridge length can be longer than the first cartridge length in other instances.

Further to the above, the end effector comprises an anvil jaw movable relative to the cartridge jaw between an open, or unclamped, position, and a closed, or clamped, position. In alternative embodiments, the cartridge jaw is movable relative to the anvil jaw. In either event, the anvil jaw comprises a distal anvil end which is supported by the first staple cartridge and the second staple cartridge, depending on which staple cartridge is positioned in the cartridge jaw. The distal anvil end is supported at a first location on the first cartridge jaw and at a second location on the second cartridge jaw. In various instances, the first location and the second location may not be the same distance from the proximal cartridge jaw datum. In some instances, however, they can be the same distance from the proximal cartridge jaw datum. Moreover, in various instances, the first location is located a first distance away from the distal end of the first staple cartridge while the second location is located a second, or different, distance away from the distal end of the second staple cartridge. In use, the tissue of a patient will be positioned between the anvil jaw and the cartridge jaw but, nonetheless, the support locations of the staple cartridges will still support the anvil jaw, or the clamping load applied by the anvil jaw.

In various instances, further to the above, the distal anvil end can extend distally beyond the distal end of the first staple cartridge when the end effector is in a clamped configuration and the first staple cartridge is positioned in the cartridge jaw and, similarly, the distal anvil end can extend distally beyond the distal end of the second staple cartridge when the end effector is in a clamped configuration and the second staple cartridge is positioned in the cartridge jaw. However, when the first cartridge length is longer than the second cartridge length, in various instances, the distal anvil tip can extend distally beyond the distal end of the second staple cartridge but not extend distally beyond the distal end of the first staple cartridge. In such instances, the anvil jaw can be longer than the second staple cartridge when the second staple cartridge is positioned in the cartridge jaw but shorter than the first staple cartridge when the first staple cartridge is positioned in the cartridge jaw. In some instances, the anvil jaw is the same length as the first staple cartridge or the second staple cartridge.

Further to the above, the anvil jaw will deflect when it is moved into its clamped position. Owing to the different cartridge lengths of the staple cartridges, the deflection of the anvil jaw may be different depending on which staple cartridge is positioned in the cartridge jaw. As a result, the staple forming gap between the anvil jaw and the staple drivers of the first cartridge jaw can be different than the staple forming gap between the anvil jaw and the staple drivers of the second cartridge jaw. In some instances, the difference in staple forming gap is negligible, and the staples ejected from the first staple cartridge and the second staple cartridge will be formed to the same, or at least suitable, heights and sufficiently staple the tissue captured between the anvil jaw and the cartridge jaw. In such instances, the unformed height of the staples in the first staple cartridge can be the same as the unformed height of the staples in the second staple cartridge. In other instances, the unformed height of the staples in the first staple cartridge is different than the unformed height of the staples in the second staple cartridge. In such instances, taller staples can be used in the first staple cartridge and shorter staples can be used in the second staple cartridge, for example, depending on the anticipated deflection and/or orientation of the anvil jaw when clamped against the first and second staple cartridges. In at least one such instance, each of the staples in the first staple cartridge has an unformed height in a first unformed height range and each of the staples in the second staple cartridge has an unformed height in a second unformed height range. In some instances, the first unformed height range is completely different than the second unformed height range while, in other instances, the first unformed height range partially overlaps the second unformed height range.

As discussed above, the first staple cartridge and the second staple cartridge are selectively positioned in the cartridge jaw of the end effector and, further to the above, the cartridge jaw further comprises a bottom support or surface configured to support the staple cartridges when they are seated in the cartridge jaw. Such a support can comprise a vertical datum. In various instances, the first support location on the first staple cartridge and the second support location on the second staple cartridge, discussed above, are the same vertical distance from the vertical datum of the cartridge jaw. The vertical distance is measured orthogonally from the vertical datum, but can be measured in any suitable manner. In other instances, the first support location on the first staple cartridge has a different vertical height than the second support location on the second staple cartridge. In such instances, the orientation and/or deflection of the anvil jaw when the anvil jaw is in its clamped position can be different as a result of the first support location and the second support location having different vertical heights. Such different vertical heights can occur when the distal end, or nose, of the first staple cartridge is different than the distal end of the second staple cartridge, among other reasons.

Many of the surgical instrument systems described herein are motivated by an electric motor; however, the surgical instrument systems described herein can be motivated in any suitable manner. In various instances, the surgical instrument systems described herein can be motivated by a manually-operated trigger, for example. In certain instances, the motors disclosed herein may comprise a portion or portions of a robotically controlled system. Moreover, any of the end effectors and/or tool assemblies disclosed herein can be utilized with a robotic surgical instrument system. U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, for example, discloses several examples of a robotic surgical instrument system in greater detail.

The surgical instrument systems described herein have been described in connection with the deployment and deformation of staples; however, the embodiments described herein are not so limited. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue.

The entire disclosures of:

- U.S. Pat. No. 5,403,312, entitled ELECTROSURGICAL HEMOSTATIC DEVICE, which issued on Apr. 4, 1995;
- U.S. Pat. No. 7,000,818, entitled SURGICAL STAPLING INSTRUMENT HAVING SEPARATE DISTINCT CLOSING AND FIRING SYSTEMS, which issued on Feb. 21, 2006;
- U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;
- U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;
- U.S. Pat. No. 7,670,334, entitled SURGICAL INSTRUMENT HAVING AN ARTICULATING END EFFECTOR, which issued on Mar. 2, 2010;
- U.S. Pat. No. 7,753,245, entitled SURGICAL STAPLING INSTRUMENTS, which issued on Jul. 13, 2010;
- U.S. Pat. No. 8,393,514, entitled SELECTIVELY ORIENTABLE IMPLANTABLE FASTENER CARTRIDGE, which issued on Mar. 12, 2013;
- U.S. patent application Ser. No. 11/343,803, entitled SURGICAL INSTRUMENT HAVING RECORDING CAPABILITIES, now U.S. Pat. No. 7,845,537;
- U.S. patent application Ser. No. 12/031,573, entitled SURGICAL CUTTING AND FASTENING INSTRUMENT HAVING RF ELECTRODES, filed Feb. 14, 2008;
- U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;
- U.S. patent application Ser. No. 12/235,782, entitled MOTOR-DRIVEN SURGICAL CUTTING INSTRUMENT, now U.S. Pat. No. 8,210,411;
- U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;
- U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009, now U.S. Pat. No. 8,220,688;
- U.S. patent application Ser. No. 12/893,461, entitled STAPLE CARTRIDGE, filed Sep. 29, 2012, now U.S. Pat. No. 8,733,613;
- U.S. patent application Ser. No. 13/036,647, entitled SURGICAL STAPLING INSTRUMENT, filed Feb. 28, 2011, now U.S. Pat. No. 8,561,870;
- U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;
- U.S. patent application Ser. No. 13/524,049, entitled ARTICULATABLE SURGICAL INSTRUMENT COMPRISING A FIRING DRIVE, filed on Jun. 15, 2012, now U.S. Pat. No. 9,101,358;
- U.S. patent application Ser. No. 13/800,025, entitled STAPLE CARTRIDGE TISSUE THICKNESS SENSOR SYSTEM, filed on Mar. 13, 2013, now U.S. Pat. No. 9,345,481;
- U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552;
- U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and
- U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

Although various devices have been described herein in connection with certain embodiments, modifications and variations to those embodiments may be implemented. Particular features, structures, or characteristics may be combined in any suitable manner in one or more embodiments. Thus, the particular features, structures, or characteristics illustrated or described in connection with one embodiment may be combined in whole or in part, with the features, structures or characteristics of one ore more other embodiments without limitation. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, a device can be reconditioned for reuse after at least one use. Reconditioning can include any combination of the steps including, but not limited to, the disassembly of the device, followed by cleaning or replacement of particular pieces of the device, and subsequent reassembly of the device. In particular, a reconditioning facility and/or surgical team can disassemble a device and, after cleaning and/or replacing particular parts of the device, the device can be reassembled for subsequent use. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices disclosed herein may be processed before surgery. First, a new or used instrument may be obtained and, when necessary, cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, and/or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta radiation, gamma radiation, ethylene oxide, plasma peroxide, and/or steam.

While this invention has been described as having exemplary designs, the present invention may be further modified within the spirit and scope of the disclosure. This application is therefore intended to cover any variations, uses, or adaptations of the invention using its general principles.

Any patent, publication, or other disclosure material, in whole or in part, that is said to be incorporated by reference herein is incorporated herein only to the extent that the incorporated materials do not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A modular surgical instrument, comprising:

an end effector, comprising:

a first jaw; and a second jaw rotatable relative to the first jaw between an open position and a closed position;

a shaft;

a closure tube slideable relative to the shaft between a proximal position and a distal position, wherein the second jaw is rotatable toward the closed position based on the closure tube moving toward the distal position, and wherein the closure tube comprises a cam;

an articulation joint, wherein the end effector is rotatable relative to the shaft about the articulation joint;

an articulation driver configured to rotate the end effector about the articulation joint, wherein the articulation driver comprises first teeth;

an articulation lock comprising a cam surface and second teeth, wherein the articulation lock is rotatable relative to the articulation driver between:

a first position in which the second teeth are demeshed from the first teeth and the articulation driver is permitted to rotate the end effector about the articulation joint; and a second position in which the second teeth are meshed with the first teeth and the articulation driver is prevented from rotating the end effector about the articulation joint;

wherein the cam is configured to engage the cam surface of the articulation lock and rotate the articulation lock toward the second position based on the closure tube moving toward the distal position.

2. The modular surgical instrument of claim 1, further comprising an articulation link operably coupling the articulation driver and the end effector.

3. The modular surgical instrument of claim 2, wherein the shaft defines a longitudinal axis, wherein the articulation link is operably coupled to the articulation driver on a first side of the longitudinal axis, and wherein the articulation link is operably coupled to the end effector on a second side of the longitudinal axis.

4. The modular surgical instrument of claim 1, wherein the closure tube comprises:

a proximal closure tube portion; and a distal closure tube portion pivotable relative to the proximal closure tube portion.

5. The modular surgical instrument of claim 4, further comprising plates operably coupling the proximal closure tube portion and the distal closure tube portion.

6. The modular surgical instrument of claim 4, wherein the distal closure tube portion comprises opening tabs configured to positively transition the second jaw toward the open position based on the closure tube moving toward the proximal position through an opening stroke.

7. The modular surgical instrument of claim 6, wherein the opening stroke comprises a first stroke portion and a second stroke portion, and wherein the opening tabs comprise:

a first opening tab is configured to positively transition the second jaw from the closed position toward a partially-opened position based on the closure tube moving through the first stroke portion; and a second opening tab is configured to positively transition the second jaw from the partially-opened position toward the open position based on the closure tube moving through the second stroke portion.

8. The modular surgical instrument of claim 7, wherein the first opening tab and the second opening tab are axially offset.

9. The modular surgical instrument of claim 7, wherein the opening stroke further comprises a third stroke portion intermediate the first stroke portion and the second stroke portion, and wherein the first opening tab and the second opening tab abstain from transitioning the second jaw toward the open position based on the closure tube moving through the third stroke portion.

10. The modular surgical instrument of claim 1, wherein a first aperture is defined in the articulation lock, wherein the shaft comprises a projection extending into the first aperture to guide the rotation of the articulation lock.

11. The modular surgical instrument of claim 10, wherein a second aperture is defined in the articulation lock, wherein the shaft comprises a pin extending into the second aperture.

12. The modular surgical instrument of claim 11, wherein the articulation lock comprises a proximal end and a distal end, wherein the first aperture is defined in the proximal end, and wherein the second aperture is defined in the distal end.

13. The modular surgical instrument of claim 1, wherein the first teeth comprise a first longitudinal rack of teeth, and wherein the second teeth comprise a second longitudinal rack of teeth.

* * * * *